(12) United States Patent
Madden et al.

(10) Patent No.: US 8,623,859 B2
(45) Date of Patent: Jan. 7, 2014

(54) BRADYKININ B1 ANTAGONISTS

(75) Inventors: James Madden, Workingham (GB); David James Hallett, Marlow (GB); Alastair Parkes, Reading (GB); Ali Raoof, Didcot (GB); Xiaolu Wang, Hamburg (DE)

(73) Assignee: Evotec AG, Hamburg (DE)

( * ) Notice: Subject to any disclaimer, the term of this patent is extended or adjusted under 35 U.S.C. 154(b) by 0 days.

(21) Appl. No.: 13/059,659

(22) PCT Filed: Aug. 10, 2009

(86) PCT No.: PCT/EP2009/060339
§ 371 (c)(1),
(2), (4) Date: Apr. 14, 2011

(87) PCT Pub. No.: WO2010/020556
PCT Pub. Date: Feb. 25, 2010

(65) Prior Publication Data
US 2011/0201589 A1 Aug. 18, 2011

(30) Foreign Application Priority Data
Aug. 22, 2008 (EP) .................................. 08162822

(51) Int. Cl.
A61K 31/341 (2006.01)
A61K 31/4523 (2006.01)
A61K 31/4525 (2006.01)
A61K 31/18 (2006.01)
C07C 311/13 (2006.01)
C07D 307/38 (2006.01)

(52) U.S. Cl.
USPC ........ 514/210.2; 514/471; 514/317; 514/608; 514/252.13; 544/159; 544/360; 544/374; 546/192; 546/207; 546/208; 546/209; 549/429; 549/473; 564/84

(58) Field of Classification Search
USPC ...................... 549/429; 564/84; 514/471, 608
See application file for complete search history.

(56) References Cited

U.S. PATENT DOCUMENTS

| 2005/0038099 A1 | 2/2005 | Tung et al. |
| 2005/0234044 A1 | 10/2005 | Groneberg et al. |

FOREIGN PATENT DOCUMENTS

| WO | WO 99/26923 A1 | 6/1999 |
| WO | WO 03/024955 A2 | 3/2003 |
| WO | WO 03/078398 A1 | 9/2003 |
| WO | WO 2005/004810 A3 | 1/2005 |
| WO | WO 2005/042489 A1 | 5/2005 |
| WO | WO 2005/097765 A1 | 10/2005 |
| WO | WO 2006/132837 A1 | 12/2006 |
| WO | WO 2008/125570 A1 | 10/2008 |
| WO | WO 2009152824 A1 * | 12/2009 |

OTHER PUBLICATIONS

U.S. Appl. No. 61/061,789, filed Jun. 16, 2008.*
Campos et al., "Non-Peptide Antagonists for Kinin B1 Receptors: New Insights into Their Therapeutic Potential for the Management of Inflammation and Pain", Trends in Pharmacological Sciences, vol. 27, No. 12, pp. 646-651, 2006.
Chen et al., "Targeting the Bradykinin B1 Receptor to Reduce Pain", Expert Opin. Ther. Targets, vol. 11, No. 1, pp. 21-35, 2007.
Choong et al., "Identification of Potent and Selective Small-Molecule Inhibitors of Caspase-3 through the Use of Extended Tethering and Structure-Based Drug Design", J. Med. Chem., vol. 45, pp. 5005-5022, 2002.
Ferreira et al., "Evidence for the Participation of Kinins in Freund's Adjuvant-Induced Inflammatory and Nociceptive Responses in Kinin B1 and B2 Receptor Knockout Mice", Neuropharmacology, vol. 41, pp. 1006-1012, 2001.
Ferreira et al., "Reduced Nerve Injury-Induced Neuropathic Pain in Kinin B1 Receptor Knock-Out Mice", The Journal of Neuroscience, vol. 25, No. 9, pp. 2405-2412, Mar. 2, 2005.
Fox et al., "Antihyperalgesic Activity of a Novel Nonpeptide Bradykinin B1 Receptor Antagonist in Transgenic Mice Expressing the Human B1 Receptor", British Journal of Pharmacology, vol. 144, pp. 889-899, 2005.
Gougat et al., "SSR240612 . . . Biochemical and Pharmacological", The Journal of Pharmacology and Experimental Therapeutics, vol. 309, No. 2, pp. 661-669, 2004.
Hawkinson et al., "Pharmacological, Pharmacokinetic, and Primate Analgesic Efficacy Profile of the Novel Bradykinin B1 Receptor Antagonist ELN441958", The Journal of Pharmacology and Experimental Therapeutics, vol. 322, No. 2, pp. 619-630, 2007.
Leeb-Lundberg et al., "International Union of Pharmacology. XLV. Classification of the Kinin Receptor Family: from Molecular Mechanisms to Pathophysiological Consequences", The American Society for Pharmacology and Experimental Therapeutics, vol. 57, No. 1, pp. 27-77, 2005.

(Continued)

Primary Examiner — Yong Chu
(74) Attorney, Agent, or Firm — Birch, Stewart, Kolasch & Birch, LLP

(57) ABSTRACT

The invention relates to compounds of formula (I) wherein $R^1$, $R^{1a}$, $R^{1b}$, $R^2$, $R^3$ and X, $X^1$, $X^2$, $X^3$ have the meaning as cited in the description and the claims. Said compounds are useful as Bradykinin B1 antagonists. The invention also relates to pharmaceutical compositions, the preparation of such compounds as well as the production and use as medicament.

(I)

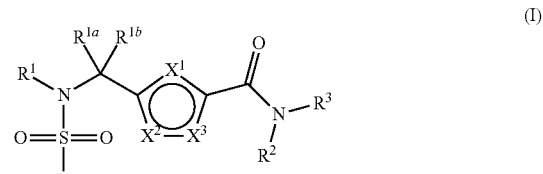

17 Claims, No Drawings

(56) References Cited

OTHER PUBLICATIONS

McEachern et al., "Expression Cloning of a Rat B2 Bradykinin Receptor", Proc. Natl. Acad. Sci. USA, vol. 88, pp. 7724-7728, Sep. 1991.

Menke et al., "Expression Cloning of a Human B1 Bradykinin Receptor", The Journal of Biological Chemistry, vol. 269, No. 34, pp. 21583-21586, Aug. 26, 1994.

Moreau et al., "The Kallikrein-Kinin System: Current and Future Pharmacological Targets", Journal of Pharmacological Sciences, vol. 99, pp. 6-38, 2005.

Phagoo et al., "Bradykinin B1 Receptor Up-Regulation . . . in Human Lungs Fibroblasts", The Journal of Pharmacology and Experimental Therapeutics, vol. 298, pp. 77-85, 2001.

* cited by examiner

BRADYKININ B1 ANTAGONISTS

The present invention relates to Bradykinin B1 antagonists, pharmaceutical compositions thereof, the preparation of such compounds as well as the production and use as medicament, especially for treatment of inflammation-related disorders including inflammatory pain, and neuropathic pain.

The patient populations for nociceptive pain and neuropathic pain are large, and are driven by separate disease trends that necessitate pain relief. Across the seven major markets in 2005 it was estimated that 170.1 million suffered from nociceptive pain and 37.6 million individuals suffered from neuropathic pain. Unfortunately, current treatments for pain are only partially effective, and many cause life-style altering, debilitating, and/or dangerous side effects. For example, non-steroidal anti-inflammatory drugs (NSAIDS) such as aspirin, ibuprofen, and indomethacin are moderately effective against inflammatory pain but they are also renally toxic, and high doses tend to cause gastrointestinal irritation, ulceration, bleeding, confusion and increased cardiovascular risk. Notably, Vioxx was withdrawn from the market in 2004, due to a risk of myocardial infarction and stroke. Patients treated with opioids frequently experience confusion and constipation, and long-term opioid use is associated with tolerance and dependence. Local anaesthetics such as lidocaine and mixelitine simultaneously inhibit pain and cause loss of normal sensation. In addition, when used systemically, local anaesthetics are associated with adverse cardiovascular effects. Thus, there is currently an unmet need in the treatment of chronic pain.

Kinins are proinflammatory peptides that mediate vascular and pain responses to tissue injury, with functions in cardiovascular homeostasis, contraction or relaxation of smooth muscle, inflammation and nociception. They exert most of their effects by interacting with two classes of G-protein-coupled receptors called Bradykinin receptor 1 and 2 (B1 and B2). The classification of the kinin receptors was originally achieved by means of pharmacological studies originally carried out at the end of the 1970s. During the 1990s, the existence of kinin B1 and B2 receptors was further confirmed through cloning and genetic deletion studies (McEachern et al. 1991; Menke et al. 1994). The past 30 years of research on the kinin system has indicated that both B1 and B2 receptors are involved in pain and inflammation (for reviews see Leeb-Lundberg et al. 2005; Moreau et al. 2005; Chen and Johnson 2007).

It has been demonstrated that B2 receptors are widely expressed in a constitutive manner throughout most mammalian tissues. In contrast, B1 receptors are not constitutively expressed to a great extent under normal conditions, but are up-regulated under different inflammatory conditions such as asthma, arthritis and osteoarthritis, sepsis and type-1 diabetes, as well as by some neuropathological diseases such as epilepsy, stroke and multiple sclerosis. Therefore, B1 receptors have been suggested to have a pivotal role in several chronic diseases involving inflammation, inflammatory pain and neuropathic pain (Campos et al. 2006). The contribution of B1 receptor activation in inflammation and pain processes is supported by the demonstration that B1 receptor knockout mice have a largely decreased response to nociceptive and pro-inflammatory stimuli (Ferreira et al. 2001; Ferreira et al. 2005). The therapeutic interest of B1 receptor blockage is supported further by the pharmacological properties of B1 antagonists in many inflammatory and neuropathic pain models (Gougat et al. 2004; Fox et al. 2005). The fact that B1 receptor expression is induced under disease conditions clearly raises the possibility that therapeutic use of B1 receptor antagonists should be devoid of undesired side effects.

The development of non-peptide B1 antagonists with long-lasting efficacy and oral bioavailability, which would represent a new treatment paradigm for inflammation and pain, should clearly be advantageous over the existing treatment strategies. Such agents are provided in the present invention.

Bradykinin antagonists are described in WO-A 2006/132837, US-A 2005/234044 and Expert Opin. Ther. Targets 11 (2007), 21-35.

However there is a continuing need for new compounds useful as Bradykinin B1 antagonists.

Thus, an object of the present invention is to provide a new class of compounds as Bradykinin B1 antagonists which may be effective in the treatment of B1 receptor related diseases.

Accordingly, the present invention provides compounds of formula (I)

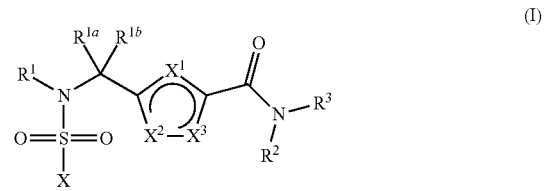

or a pharmaceutically acceptable salt, prodrug or metabolite thereof, wherein

X is phenyl or a 5- or 6-membered aromatic heterocycle, wherein X is substituted with $R^4$ and is optionally substituted with one or more $R^5$, which are the same or different;

$R^4$; $R^5$ are independently selected from the group consisting of halogen; CN; $C(O)OR^6$; $OR^6$; $C(O)N(R^6R^{6a})$; $S(O)_2N(R^6R^{6a})$; $S(O)N(R^6R^{6a})$; $S(O)_2R^6$; $N(R^6)S(O)_2N(R^{6a}R^{6b})$; $SR^6$; $N(R^6R^{6a})$; $NO_2$; $OC(O)R^6$; $N(R^6)C(O)R^{6a}$; $N(R^6)S(O)_2R^{6a}$; $N(R^6)S(O)R^{6a}$; $N(R^6)C(O)N(R^{6a}R^{6b})$; $N(R^6)C(O)OR^{6a}$; $OC(O)N(R^6R^{6a})$; $C(O)R^6$; $C_{1-6}$ alkyl; $C_{2-6}$ alkenyl; $C_{2-6}$ alkynyl; and T, wherein $C_{1-6}$ alkyl; $C_{2-6}$ alkenyl; and $C_{2-6}$ alkynyl are optionally substituted with one or more $R^7$, which are the same or different;

Optionally, $R^4$ and $R^5$ or two adjacent $R^5$ are joined together with the atoms to which they are attached to form benzo; or a 5- or 6-membered aromatic heterocycle; wherein benzo; and the 5- or 6-membered aromatic heterocycle are optionally substituted with one or more $R^8$, which are the same or different;

$R^8$ is halogen; CN; $C(O)OR^6$; $OR^6$; $C(O)N(R^6R^{6a})$; $S(O)_2N(R^6R^{6a})$; $S(O)N(R^6R^{6a})$; $S(O)_2R^6$; $N(R^6)S(O)_2N(R^{6a}R^{6b})$; $SR^6$; $N(R^6R^{6a})$; $NO_2$; $OC(O)R^6$; $N(R^6)C(O)R^{6a}$; $N(R^6)S(O)_2R^{6a}$; $N(R^6)S(O)R^{6a}$; $N(R^6)C(O)N(R^{6a}R^{6b})$; $N(R^6)C(O)OR^{6a}$; $OC(O)N(R^6R^{6a})$; $C(O)R^6$; $C_{1-6}$ alkyl; $C_{2-6}$ alkenyl; $C_{2-6}$ alkynyl; or T, wherein $C_{1-6}$ alkyl; $C_{2-6}$ alkenyl; and $C_{2-6}$ alkynyl are optionally substituted with one or more $R^7$, which are the same or different;

$R^6$, $R^{6a}$, $R^{6b}$ are independently selected from the group consisting of H; T; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^9$, which are the same or different;

$R^7$, $R^9$ are independently selected from the group consisting of halogen; $C(O)R^{10}$; CN; $C(O)OR^{10}$; $OR^{10}$; $C(O)N(R^{10}R^{10a})$; $S(O)_2N(R^{10}R^{10a})$; $S(O)N(R^{10}R^{10a})$; $S(O)_2R^{10}$; $N(R^{10})S(O)_2N(R^{10a}R^{10b})$; $SR^{10}$; $N(R^{10}R^{10a})$; $NO_2$; OC(O)

$R^{10}$; $N(R^{10})C(O)R^{10a}$; $N(R^{10})S(O)_2R^{10a}$; $N(R^{10})S(O)R^{10a}$; $N(R^{10})C(O)N(R^{10a}R^{10b})$; $N(R^{10})C(O)OR^{10a}$; $OC(O)N(R^{10}R^{10a})$; and $T^1$;

$R^{10}$, $R^{10a}$, $R^{10b}$ are independently selected from the group consisting of H; $T^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{11}$, which are the same or different;

$R^{11}$ is halogen; $C(O)R^{12}$; CN; $C(O)OR^{12}$; $OR^{12}$; $C(O)N(R^{12}R^{12a})$; $S(O)_2N(R^{12}R^{12a})$; $S(O)N(R^{12}R^{12a})$; $S(O)_2R^{12}$; $N(R^{12})S(O)_2N(R^{12a}R^{12b})$; $SR^{12}$; $N(R^{12}R^{12a})$; $NO_2$; $OC(O)R^{12}$; $N(R^{12})C(O)R^{12a}$; $N(R^{12})S(O)_2R^{12a}$; $N(R^{12})S(O)R^{12a}$; $N(R^{12})C(O)N(R^{12a}R^{12b})$; $N(R^{12})C(O)OR^{12a}$; or $OC(O)N(R^{12}R^{12a})$;

$R^{12}$, $R^{12a}$, $R^{12b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

T, $T^1$ are independently selected from the group consisting of phenyl; naphthyl; indenyl; indanyl; tetralinyl; decalinyl; adamantyl; $C_{3-7}$ cycloalkyl; 4 to 7 membered heterocyclyl; and 8 to 11 membered heterobicyclyl, wherein T, $T^1$ are optionally substituted with one or more $R^{13}$, which are the same or different;

$R^{13}$ is halogen; CN; $C(O)R^{14}$; $COOR^{14}$; $OR^{14}$; $C(O)N(R^{14}R^{14a})$; $S(O)_2N(R^{14}R^{14a})$; $S(O)N(R^{14}R^{14a})$; $S(O)_2R^{14}$; $N(R^{14})S(O)_2N(R^{14a}R^{14b})$; $SR^{14}$; $N(R^{14}R^{14a})$; $NO_2$; $OC(O)R^{14}$; $N(R^{14})C(O)R^{14a}$; $N(R^{14})S(O)_2R^{14a}$; $N(R^{14})S(O)R^{14a}$; $N(R^{14})C(O)N(R^{14a}R^{14b})$; $N(R^{14})C(O)OR^{14a}$; $OC(O)N(R^{14}R^{14a})$; oxo (=O), where the ring is at least partially saturated; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^{14}$, $R^{14a}$; $R^{14b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^1$ is H; $T^2$; $C_{1-8}$ alkyl; $C_{2-8}$ alkenyl; and $C_{2-8}$ alkynyl, wherein $C_{1-8}$ alkyl; $C_{2-8}$ alkenyl; and $C_{2-8}$ alkynyl are optionally substituted with one or more $R^{15}$, which are the same or different;

$R^{15}$ is halogen; $C(O)R^{16}$; CN; $C(O)OR^{16}$; $OR^{16}$; $C(O)N(R^{16}R^{16a})$; $S(O)_2N(R^{16}R^{16a})$; $S(O)N(R^{16}R^{16a})$; $S(O)_2R^{16}$; $N(R^{16})S(O)_2N(R^{16a}R^{16b})$; $SR^{16}$; $N(R^{16}R^{16a})$; $NO_2$; $OC(O)R^{16}$; $N(R^{16})C(O)R^{16a}$; $N(R^{16})S(O)_2R^{16a}$; $N(R^{16})S(O)R^{16a}$; $N(R^{16})C(O)N(R^{16a}R^{16b})$; $N(R^{16})C(O)OR^{16a}$; $OC(O)N(R^{16}R^{16a})$; or cyclopropyl;

$R^{16}$, $R^{16a}$, $R^{16b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$T^2$ is phenyl; $C_{3-7}$ cycloalkyl; or 4 to 7 membered heterocyclyl, wherein $T^2$ is optionally substituted with one or more $R^{17}$, which are the same or different;

$R^{17}$ is halogen; CN; $C(O)R^{18}$; $C(O)OR^{18}$; $OR^{18}$; $C(O)N(R^{18}R^{18a})$; $S(O)_2N(R^{18}R^{18a})$; $S(O)N(R^{18}R^{18a})$; $S(O)_2R^{18}$; $N(R^{18})S(O)_2N(R^{18a}R^{18b})$; $SR^{18}$; $N(R^{18}R^{18a})$; $NO_2$; $OC(O)R^{18}$; $N(R^{18})C(O)R^{18a}$; $N(R^{18})S(O)_2R^{18a}$; $N(R^{18})S(O)R^{18a}$; $N(R^{18})C(O)N(R^{18a}R^{18b})$; $N(R^{18})C(O)OR^{18a}$; $OC(O)N(R^{18}R^{18a})$; oxo (=O), where the ring is at least partially saturated; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^{18}$, $R^{18a}$, $R^{18b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^{1a}$, $R^{1b}$ are independently selected from the group consisting of H; $C_{1-4}$ alkyl, wherein $C_{1-4}$ alkyl is optionally substituted with one or more halogen, which are the same or different;

$X^1$, $X^2$, $X^3$ are independently selected from the group consisting of O; S; N; $N(R^{1c})$; and $C(R^{1c})$, provided that at least one of $X^1$, $X^2$, $X^3$ is other than $C(R^{1c})$;

$R^{1c}$ is H; or $CH_3$;

$R^2$ is H; $C_{1-4}$ alkyl; $C_{2-4}$ alkenyl; or $C_{2-4}$ alkynyl, wherein $C_{1-4}$ alkyl; $C_{2-4}$ alkenyl; and $C_{2-4}$ alkynyl are optionally substituted with one or more halogen, which are the same or different;

$R^3$ is $T^3$; $CH_2$-$T^3$; $CH(CH_3)T^3$; $CH_2$—$CH_2$-$T^3$; $CH_2$—$CH(T^3)_2$; or $C_{1-8}$ alkyl, wherein $C_{1-8}$ alkyl is substituted with one or more $R^{19}$, which are the same or different;

Optionally, $R^2$, $R^3$ are joined to form, together with the nitrogen atom to which they are attached, a ring, wherein the ring is a saturated 4 to 7 membered heterocycle; or a saturated 8 to 11 membered heterobicycle, wherein the ring contains said nitrogen atom and optionally one or more further heteroatoms, which are the same or different, and, wherein the ring is optionally substituted with one or more $R^{20}$, which are the same or different;

$R^{19}$ is halogen; $C(O)R^{21}$; CN; $C(O)OR^{21}$; $OR^{21}$; $C(O)N(R^{21}R^{21a})$; $S(O)_2N(R^{21}R^{21a})$; $S(O)N(R^{21}R^{21a})$; $S(O)_2R^{21}$; $N(R^{21})S(O)_2N(R^{21a}R^{21b})$; $SR^{21}$; $N(R^{21}R^{21a})$; $NO_2$; $OC(O)R^{21}$; $N(R^{21})C(O)R^{21a}$; $N(R^{21})S(O)_2R^{21a}$; $N(R^{21})S(O)R^{21a}$; $N(R^{21})C(O)N(R^{21a}R^{21b})$; $N(R^{21})C(O)OR^{21a}$; or $OC(O)N(R^{21}R^{21a})$.

$R^{21}$, $R^{21a}$, $R^{21b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$T^3$ is phenyl; naphthyl; indenyl; indanyl; tetralinyl; decalinyl; adamantyl; $C_{3-7}$ cycloalkyl; 4 to 7 membered heterocyclyl; or 8 to 11 membered heterobicyclyl, wherein $T^3$ is optionally substituted with one or more $R^{22}$, which are the same or different;

$R^{20}$, $R^{22}$ are independently selected from the group consisting of halogen; CN; $C(O)OR^{23}$; $OR^{23}$; $C(O)N(R^{23}R^{23a})$; $C(NR^{23b})N(R^{23}R^{23a})$; $C(NR^{23b})N(R^{23})OR^{23a}$; $S(O)_2N(R^{23}R^{23a})$; $S(O)N(R^{23}R^{23a})$; $S(O)_2R^{23}$; $N(R^{23})S(O)_2N(R^{23a}R^{23b})$; $SR^{23}$; $N(R^{23}R^{23a})$; $NO_2$; $OC(O)R^{23}$; $N(R^{23})C(O)R^{23a}$; $N(R^{23})S(O)_2R^{23a}$; $N(R^{23})S(O)R^{23a}$; $N(R^{23})C(O)N(R^{23a}R^{23b})$; $N(R^{23})C(NR^{23c})N(R^{23a}R^{23b})$; $N(R^{23})C(O)OR^{23a}$; $OC(O)N(R^{23}R^{23a})$; oxo (=O), where the ring is at least partially saturated; $C(O)R^{23}$; $C_{1-10}$ alkyl; $C_{2-10}$ alkenyl; $C_{2-10}$ alkynyl; and $T^4$, wherein $C_{1-10}$ alkyl; $C_{2-10}$ alkenyl; and $C_{2-10}$ alkynyl are optionally substituted with one or more $R^{24}$, which are the same or different;

$R^{23}$, $R^{23a}$, $R^{23b}$, $R^{23c}$ are independently selected from the group consisting of H; $T^4$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{25}$, which are the same or different;

$R^{24}$, $R^{25}$ are independently selected from the group consisting of halogen; CN; $C(O)R^{26}$; $C(O)OR^{26}$; $OR^{26}$; $C(O)R^{26}$; $C(O)N(R^{26}R^{26a})$; $S(O)_2N(R^{26}R^{26a})$; $S(O)N(R^{26}R^{26a})$;

$S(O)_2R^{26}$; $N(R^{26})S(O)_2N(R^{26a}R^{26b})$; $SR^{26}$; $N(R^{26}R^{26a})$; $OC(O)R^{26}$; $N(R^{26})C(O)R^{26a}$; $N(R^{26})SO_2R^{26a}$; $N(R^{26})S(O)R^{26a}$; $N(R^{26})C(O)N(R^{26a}R^{26})$; $N(R^{26})C(O)OR^{26a}$; $OC(O)N(R^{26}R^{26a})$; $C_{1-6}$ alkyl; $C_{2-6}$ alkenyl; $C_{2-6}$ alkynyl and $T^4$, wherein $C_{1-6}$ alkyl; $C_{2-6}$ alkenyl; and $C_{2-6}$ alkynyl are optionally substituted with one or more $R^{27}$, which are the same or different;

$R^{26}$, $R^{26a}$, $R^{26b}$ are independently selected from the group consisting of H; $T^4$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{28}$, which are the same or different;

$R^{27}$, $R^{28}$ are independently selected from the group consisting of halogen; CN; $C(O)OR^{29}$; $OR^{29}$; $C(O)R^{29}$; $C(O)N(R^{29}R^{29a})$; $S(O)_2N(R^{29}R^{29a})$; $S(O)N(R^{29}R^{29a})$; $S(O)_2R^{29}$; $N(R^{29})S(O)_2N(R^{29a}R^{29b})$; $SR^{29}$; $N(R^{29}R^{29a})$; $NO_2$; $OC(O)R^{29}$; $N(R^{29})C(O)R^{29a}$; $N(R^{29})SO_2R^{29a}$; $N(R^{29})S(O)R^{29a}$; $N(R^{29})C(O)N(R^{29a}R^{29b})$; $N(R^{29})C(O)OR^{29a}$; $OC(O)N(R^{29}R^{29a})$; $C_{1-6}$ alkyl; $C_{2-6}$ alkenyl; $C_{2-6}$ alkynyl; and $T^4$, wherein $C_{1-6}$ alkyl; $C_{2-6}$ alkenyl; and $C_{2-6}$ alkynyl are optionally substituted with one or more $R^{30}$, which are the same or different;

$R^{29}$, $R^{29a}$, $R^{29b}$ are independently selected from the group consisting of H; $C_{1-6}$ alkyl; $C_{2-6}$ alkenyl; $C_{2-6}$ alkynyl; and $T^4$, wherein $C_{1-6}$ alkyl; $C_{2-6}$ alkenyl; and $C_{2-6}$ alkynyl are optionally substituted with one or more $R^{31}$, which are the same or different;

$T^4$ is phenyl; naphthyl; indenyl; indanyl; tetralinyl; decalinyl; adamantyl; $C_{3-7}$ cycloalkyl; 4 to 7 membered heterocyclyl; and 8 to 11 membered heterobicyclyl, wherein $T^4$ is optionally substituted with one or more $R^{32}$, which are the same or different;

$R^{32}$ is halogen; CN; $C(O)OR^{33}$; $OR^{33}$; $C(O)N(R^{33}R^{33a})$; $C(NR^{33b})N(R^{33}R^{33a})$; $C(NR^{33b})N(R^{33})OR^{33a}$; $S(O)_2N(R^{33}R^{33a})$; $S(O)N(R^{33}R^{33a})$; $S(O)_2R^{33}$; $N(R^{33})S(O)_2N(R^{33a}R^{33b})$; $SR^{33}$; $N(R^{33}R^{33a})$; $NO_2$; $OC(O)R^{33}$; $N(R^{33})C(O)R^{33a}$; $N(R^{33})S(O)_2R^{33a}$; $N(R^{33})S(O)R^{33a}$; $N(R^{33})C(O)N(R^{33a}R^{33b})$; $N(R^{33})C(NR^{33c})N(R^{33a}R^{33b})$; $N(R^{33})C(O)OR^{33a}$; $OC(O)N(R^{33}R^{33a})$; oxo (=O), where the ring is at least partially saturated; $C(O)R^{33}$; $T^5$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{34}$, which are the same or different;

$R^{33}$, $R^{33a}$, $R^{33b}$, $R^{33c}$ are independently selected from the group consisting of H; $T^5$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same of different;

$R^{30}$; $R^{31}$; $R^{34}$ are independently selected from the group consisting of halogen; CN; $C(O)OR^{35}$; $OR^{35}$; $C(O)R^{35}$; $C(O)N(R^{35}R^{35a})$; $S(O)_2N(R^{35}R^{35a})$; $S(O)N(R^{35}R^{35a})$; $S(O)_2R^{35}$; $N(R^{35})S(O)_2N(R^{35a}R^{35b})$; $SR^{35}$; $N(R^{35}R^{35a})$; $NO_2$; $OC(O)R^{35}$; $N(R^{35})C(O)R^{35a}$; $N(R^{35})SO_2R^{35a}$; $N(R^{35})S(O)R^{35a}$; $N(R^{35})C(O)N(R^{35a}R^{35b})$; $N(R^{35})C(O)OR^{35a}$; $OC(O)N(R^{35}R^{35a})$; $T^5$; $C_{1-6}$ alkyl; $C_{2-6}$ alkenyl; $C_{2-6}$ alkynyl, wherein $C_{1-6}$ alkyl; $C_{2-6}$ alkenyl; and $C_{2-6}$ alkynyl are optionally substituted with one or more halogen, which are the same of different;

$R^{35}$, $R^{35a}$, $R^{35b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same of different;

$T^5$ is phenyl; $C_{3-7}$ cycloalkyl; or 4 to 7 membered heterocyclyl, wherein $T^5$ is optionally substituted with one or more $R^{36}$, which are the same or different;

$R^{36}$ is independently selected from the group consisting of halogen; CN; $C(O)OR^{37}$; $OR^{37}$; $C(O)N(R^{37}R^{37a})$; $C(NR^{37b})N(R^{37}R^{37a})$; $C(NR^{37b})N(R^{37})OR^{37a}$; $S(O)_2N(R^{37}R^{37a})$; $S(O)N(R^{37}R^{37a})$; $S(O)_2R^{37}$; $N(R^{37})S(O)_2N(R^{37a}R^{37b})$; $SR^{37}$; $N(R^{37}R^{37a})$; $NO_2$; $OC(O)R^{37}$; $N(R^{37})C(O)R^{37a}$; $N(R^{37})S(O)_2R^{37a}$; $N(R^{37})S(O)R^{37a}$; $N(R^{37})C(O)N(R^{37a}R^{37b})$; $N(R^{37})C(NR^{37c})N(R^{37a}R^{37b})$; $N(R^{37})C(O)OR^{37a}$; $OC(O)N(R^{37}R^{37a})$; oxo (=O), where the ring is at least partially saturated; $C(O)R^{37}$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^{37}$, $R^{37a}$, $R^{37b}$, $R^{37c}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same of different.

In case a variable or substituent can be selected from a group of different variants and such variable or substituent occurs more than once the respective variants can be the same or different.

Within the meaning of the present invention the terms are used as follows:

"Alkyl" means a straight-chain or branched saturated aliphatic acyclic hydrocarbon chain. Each hydrogen of an alkyl carbon may be replaced by a substituent.

"Alkenyl" means a straight-chain or branched hydrocarbon chain that contains at least one carbon-carbon double bond. Each hydrogen of an alkenyl carbon may be replaced by a substituent.

"Alkynyl" means a straight-chain or branched hydrocarbon chain that contains at least one carbon-carbon triple bond. Each hydrogen of an alkynyl carbon may be replaced by a substituent.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl, tert-butyl, or e.g. —$CH_2$—, —$CH_2$—$CH_2$—, —$CH(CH_3)$—, —$C(CH_2)$—, —$CH_2$—$CH_2$—$CH_2$—, —$CH(C_2H_5)$—, —$CH(CH_3)_2$—, when two moieties of a molecule are linked by the alkyl group. Each hydrogen of a $C_{1-4}$ alkyl carbon may be replaced by a substituent.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent.

"$C_{1-8}$ alkyl" means an alkyl chain having 1 to 8 carbon atoms, e.g. if present at the end of a molecule: $C_{1-4}$ alkyl, $C_{1-6}$ alkyl, methyl, ethyl, n-propyl, isopropyl, n-butyl, isobutyl, sec-butyl; tert-butyl, n-pentyl, n-hexyl, n-heptyl, n-octyl, or e.g. —$CH_2$—, —$CH_2$—$CH_2$—, —$CH(CH_3)$—, —$C(CH_2)$—, —$CH_2$—$CH_2$—$CH_2$—, —$CH(C_2H_5)$—, —$CH(CH_3)_2$—, when two moieties of a molecule are linked by the alkyl group. Each hydrogen of a $C_{1-8}$ alkyl carbon may be replaced by a substituent.

"$C_{1-10}$ alkyl" means an alkyl chain having 1 to 10 carbon atoms, e.g. if present at the end of a molecule: $C_{1-4}$ alkyl, $C_{1-6}$ alkyl, $C_{1-8}$ alkyl, methyl, ethyl, n-propyl, isopropyl, n-butyl, isobutyl, sec-butyl; tert-butyl, n-pentyl, n-hexyl, n-heptyl, n-octyl, n-nonyl, n-hexyl or e.g. —$CH_2$—, —$CH_2$—$CH_2$—, —$CH(CH_3)$—, —$C(CH_2)$—, —$CH_2$—$CH_2$—$CH_2$—, —$CH(C_2H_5)$—, —$CH(CH_3)_2$—, when two moieties of a molecule are linked by the alkyl group. Each hydrogen of a $C_{1-10}$ alkyl carbon may be replaced by a substituent.

"$C_{2-4}$ alkenyl" means an alkenyl chain having 2 to 4 carbon atoms, e.g. if present at the end of a molecule: —CH=CH$_2$, —CH=CH—CH$_3$, —CH$_2$—CH=CH$_2$, —CH=CH—CH$_2$—CH$_3$, —CH=CH—CH=CH$_2$, or e.g. —CH=CH—, when two moieties of a molecule are linked by the alkyl group. Each hydrogen of a $C_{2-4}$ alkenyl carbon may be replaced by a substituent.

"$C_{2-6}$ alkenyl" means an alkenyl chain having 2 to 6 carbon atoms, e.g. if present at the end of a molecule: $C_{2-4}$ alkenyl, —CH=CH$_2$, —CH=CH—CH$_3$, —CH$_2$—CH=CH$_2$, —CH=CH—CH$_2$—CH$_3$, —CH=CH—CH=CH$_2$, or e.g. —CH=CH—, when two moieties of a molecule are linked by the alkyl group. Each hydrogen of a $C_{2-6}$ alkenyl carbon may be replaced by a substituent.

"$C_{2-8}$ alkenyl" means an alkenyl chain having 2 to 8 carbon atoms, e.g. if present at the end of a molecule: $C_{2-4}$ alkenyl, $C_{2-6}$ alkenyl, —CH=CH$_2$, —CH=CH—CH$_3$, —CH$_2$—CH=CH$_2$, —CH=CH—CH$_2$—CH$_3$, —CH=CH—CH=CH$_2$, or e.g. —CH=CH—, when two moieties of a molecule are linked by the alkyl group. Each hydrogen of a $C_{2-8}$ alkenyl carbon may be replaced by a substituent.

"$C_{2-10}$ alkenyl" means an alkenyl chain having 2 to 10 carbon atoms, e.g. if present at the end of a molecule: $C_{2-4}$ alkenyl, $C_{2-6}$ alkenyl, $C_{2-8}$ alkenyl, —CH=CH$_2$, —CH=CH—CH$_3$, —CH$_2$—CH=CH$_2$, —CH=CH—CH$_2$—CH$_3$, —CH=CH—CH=CH$_2$, or e.g. —CH=CH—, when two moieties of a molecule are linked by the alkyl group. Each hydrogen of a $C_{2-8}$ alkenyl carbon may be replaced by a substituent.

"$C_{2-4}$ alkynyl" means an alkynyl chain having 2 to 4 carbon atoms, e.g. if present at the end of a molecule: —C≡CH, —CH$_2$—C≡CH, CH$_2$—CH$_2$—C≡CH, CH$_2$—C≡C—CH$_3$, or e.g. —C≡C— when two moieties of a molecule are linked by the alkyl group. Each hydrogen of a $C_{2-4}$ alkynyl carbon may be replaced by a substituent.

"$C_{2-6}$ alkynyl" means an alkynyl chain having 2 to 6 carbon atoms, e.g. if present at the end of a molecule: $C_{2-4}$ alkynyl, —C≡CH, —CH$_2$—C≡CH, CH$_2$—CH$_2$—C≡CH, CH$_2$—C≡C—CH$_3$, or e.g. —C≡C— when two moieties of a molecule are linked by the alkyl group. Each hydrogen of a $C_{2-6}$ alkynyl carbon may be replaced by a substituent.

"$C_{2-8}$ alkynyl" means an alkynyl chain having 2 to 8 carbon atoms, e.g. if present at the end of a molecule: $C_{2-4}$ alkynyl, $C_{2-6}$ alkynyl, —C≡CH, —CH$_2$—C≡CH, CH$_2$—CH$_2$—C≡CH, CH$_2$—C≡C—CH$_3$, or e.g. —C≡C— when two moieties of a molecule are linked by the alkyl group. Each hydrogen of a $C_{2-8}$ alkynyl carbon may be replaced by a substituent.

"$C_{2-10}$ alkynyl" means an alkynyl chain having 2 to 10 carbon atoms, e.g. if present at the end of a molecule: $C_{2-4}$ alkynyl, $C_{2-6}$ alkynyl, $C_{2-8}$ alkynyl, —C≡CH, —CH$_2$—C≡CH, CH$_2$—CH$_2$—C≡CH, CH$_2$—C≡C—CH$_3$, or e.g. —C≡C— when two moieties of a molecule are linked by the alkyl group. Each hydrogen of a $C_{2-10}$ alkynyl carbon may be replaced by a substituent.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Each hydrogen of a cycloalkyl carbon may be replaced by a substituent.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydro furan, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, pyridine, pyridazine, pyrazine, pyrimidine, piperazine, piperidine, morpholine, tetrazole, triazole, triazolidine, tetrazolidine, diazepane, azepine or homopiperazine. The term "saturated" means a fully saturated ring, e.g. azetidine, oxetane, thietane, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, tetrahydropyran, piperidine, morpholine, triazolidine, tetrazolidine, diazepane, or homopiperazine.

"8 to 11 membered heterobicyclyl" or "8 to 11 membered heterobicycle" means a heterocyclic system of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 8 to 11 membered heterobicycle are indole, indo line, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 8 to 11 membered heterobicycle also includes spiro structures of two rings like 1,4-dioxa-8-azaspiro[4.5]decane or bridged heterocycles like 8-aza-bicyclo[3.2.1]octane. The term "saturated" means a fully saturated ring, e.g. decahydroquinoline, decahydroisoquinoline, 1,4-dioxa-8-azaspiro[4.5]decane or 8-aza-bicyclo[3.2.1]octane.

"5 to 6 membered aromatic heterocyclyl" or "5 to 6 membered aromatic heterocycle" means a heterocycle derived from cyclopentadienyl or benzene, where at least one carbon atom is replaced by a heteoatom selected from the group consisting of sulfur (including —S(O)—, —S(O)$_2$—), oxygen and nitrogen (including =N(O)—). Examples for such heterocycles are furan, thiophene, pyrrole, imidazole, pyrazole, oxazole, isoxazole, thiazole, isothiazole, thiadiazole, pyranium, pyridine, pyridazine, pyrimidine, triazole, tetrazole.

Preferred compounds of formula (I) are those compounds in which one or more of the residues contained therein have the meanings given below, with all combinations of preferred substituent definitions being a subject of the present invention. With respect to all preferred compounds of the formulas (I) the present invention also includes all tautomeric and stereoisomeric forms and mixtures thereof in all ratios, and their pharmaceutically acceptable salts as well as their isotopic derivatives.

In preferred embodiments of the present invention, the substituents $R^1$ to $R^5$ and $X^1$ to $X^4$ of the formula (I) independently have the following meaning. Hence, one or more of the substituents $R^1$, $R^{1a}$, $R^{1b}$, $R^2$, $R^3$ and X, $X^1$, $X^2$, $X^3$ can have the preferred or more preferred meanings given below.

Preferably, X is phenyl; or thiophene, wherein X is substituted with $R^4$ and is optionally substituted with one or more $R^5$, which are the same or different. More preferably, X is phenyl, wherein X is substituted with $R^4$ and is optionally substituted with one or more $R^5$, which are the same or different. Preferably, X is substituted with $R^4$, $R^4$ and $R^5$, or $R^4$ and 2 $R^5$, which are the same or different.

Preferably, X is substituted in 2-position relative to the sulfonamide group in formula (I) with $R^4$ and is optionally substituted with one or more $R^5$, which are the same or different.

Preferably, two adjacent $R^5$ are joined together with the atoms to which they are attached to form benzo and wherein benzo is optionally substituted with one or more $R^8$, which are the same or different.

Preferably, $R^4$, $R^5$, $R^8$ are independently selected from the group consisting of $CH_3$; $CF_3$; $CH_2CH_3$; $CH_2OH$; $OCH_3$; Cl; Br; and phenyl. Preferably, $R^4$, $R^5$, $R^8$ are independently selected from the group consisting of $CH_3$; $CH_2CH_3$; $OCH_3$; Cl; Br; and phenyl. More preferably, $R^4$, $R^5$, $R^8$ are independently selected from the group consisting of $CH_3$; $CH_2CH_3$; $OCH_3$; Cl; and Br.

Preferably, $R^1$ is methyl; ethyl; isopropyl; cyclopropyl; cyclobutyl; phenyl; or cyclopropylmethyl. More preferably, $R^1$ is methyl; or cyclopropyl. Even more preferably, $R^1$ is methyl.

Preferably, $R^{1a}$, $R^{1b}$ are independently selected from the group consisting of H; and methyl. More preferably, $R^{1a}$, $R^{1b}$ are H.

Preferably, one of $X^1$, $X^2$, $X^3$ is O; or S and the other are independently selected from the group consisting of N; and $C(R^{1c})$. Preferably, all of $X^1$, $X^2$, $X^3$ are other than $C(R^{1c})$.

Preferably, $X^1$, $X^2$, $X^3$ are chosen to give one of the formulae (Ia) to (Im)

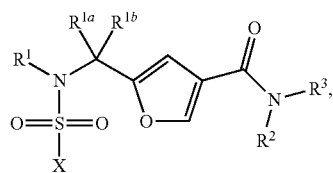
(Ia)

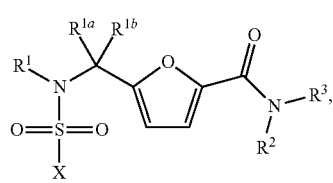
(Ib)

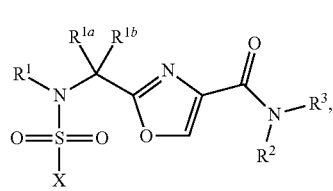
(Ic)

-continued

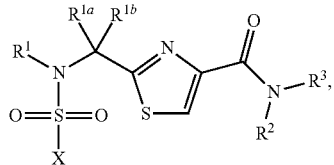
(Id)

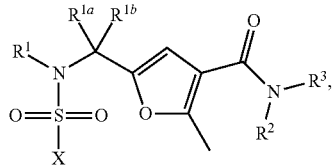
(Ie)

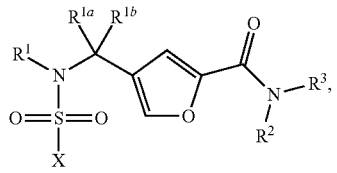
(If)

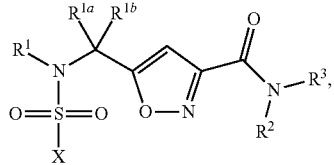
(Ig)

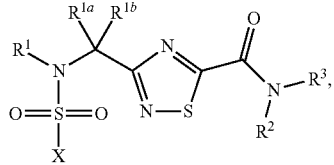
(Ih)

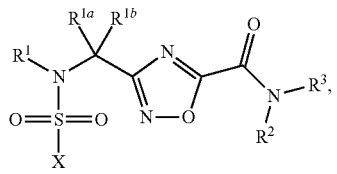
(Ii)

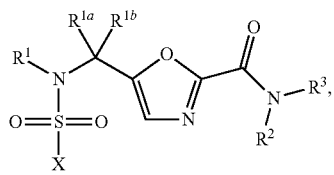
(Ij)

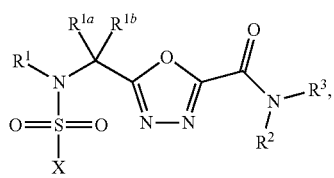
(Ik)

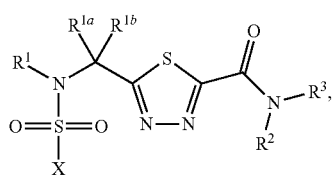
(IL)

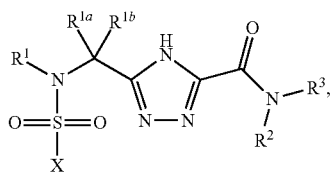

wherein X, $R^1$, $R^{1a}$, $R^{1b}$, $R^2$, $R^3$ have the meaning as indicated above. More preferred are formulae (Ia), (Ib), (Ic), (Ie), (If), (Ig), (Ih), (Ii), (Ij), (Ik), (IL), (Im). More preferred are formulae (Ia) to (IL). More preferred are formulae (Ia) to (Ii). More preferred are (Ia), (Ib), (Ic), (Ie), (If), (Ig), (Ih), (Ii). More preferred are formulae (Ig), (Ih), (Ii), (Ij), (Ik), (IL). More preferred are formulae (Ia), (Ib), (Ic), (Id). Even more preferred is formula (Ia). Even more preferred are formulae (Ij) and (Ik). Also most preferred are formulae (Ic) and (Ik).

Preferably, $R^2$ is H; or $CH_3$.

Preferably, $R^2$, $R^3$ are joined to form a ring selected from the group consisting of piperidine; piperazine; morpholine; 2,8-diazaspiro[4.5]decane; pyrrolidine; and diazepane, wherein the ring is optionally substituted with one or more $R^{20}$, which are the same or different.

Preferably, $R^3$ is $CH_2$-$T^3$; $CH_2$—$CH(CH_3)$-$T^3$ or $CH_2$—$CH_2$-$T^3$. More preferably, $R^3$ is $CH_2$-$T^3$; or $CH_2$—$CH_2$-$T^3$.

Preferably, $T^3$ is phenyl; or pyridine.

Preferably, $R^{20}$, $R^{22}$ are independently selected from the group consisting of CN; C(O)N($R^{23}R^{23a}$); C($NR^{23b}$)N($R^{23}R^{23a}$); C($NR^{23b}$)N($R^{23}$)O$R^{23a}$; N($R^{23}R^{23a}$); N($R^{23}$)C(O)N($R^{23a}R^{23b}$); C(O)$R^{23}$; N($R^{23}$)C($NR^{23c}$)N($R^{23a}R^{23b}$); $C_{1-6}$ alkyl; and $T^4$, wherein $C_{1-6}$ alkyl is optionally substituted with one or more $R^{24}$, which are the same or different.

Preferably, one of $R^{22}$, $R^{23}$, $R^{23a}$, $R^{23b}$, $R^{23c}$, $R^{24}$, $R^{25}$, $R^{26}$, $R^{27}$, $R^{28}$, $R^{29}$, $R^{29a}$, $R^{29b}$ is $T^4$.

Preferably, one of $R^{23}$, $R^{23a}$, $R^{23b}$, $R^{23c}$ is $T^4$.

Preferably, $R^{24}$ is $T^4$.

Preferably, $T^4$ is selected from the group consisting of pyrrole; pyrrolidine; imidazole; 4,5-dihydroimidazole; oxazolidine; tetrahydrofuran; pyridine; piperidine; morpholine; pyrimidine; and 3,4,5,6-tetrahydropyrimidine, and wherein $T^4$ is optionally substituted with one or more $R^{32}$, which are the same or different.

Preferably, $R^{32}$ is $C_{1-4}$ alkyl; oxo (=O), where the ring is at least partially saturated; $NH_2$; F; or C(O)$CF_3$.

Preferably, $R^{33}$, $R^{33a}$, $R^{33b}$, $R^{33c}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same of different.

Preferably, $R^{30}$; $R^{31}$; $R^{34}$ are independently selected from the group consisting of halogen; CN; C(O)O$R^{35}$; O$R^{35}$; C(O)$R^{35}$; C(O)N($R^{35}R^{35a}$); S(O)$_2$N($R^{35}R^{35a}$); S(O)N($R^{35}R^{35a}$); S(O)$_2R^{35}$; N($R^{35}$)S(O)$_2$N($R^{35a}R^{35b}$); S$R^{35}$; N($R^{35}R^{35a}$); $NO_2$; OC(O)$R^{35}$; N($R^{35}$)C(O)$R^{35a}$; N($R^{35}$)SO$_2R^{35a}$; N($R^{35}$)S(O)$R^{35a}$; N($R^{35}$)C(O)N($R^{35a}R^{35b}$); N($R^{35}$)C(O)O$R^{35a}$; OC(O)N($R^{35}R^{35a}$); $C_{1-6}$ alkyl; $C_{2-6}$ alkenyl; $C_{2-6}$ alkynyl, wherein $C_{1-6}$ alkyl; $C_{2-6}$ alkenyl; and $C_{2-6}$ alkynyl are optionally substituted with one or more halogen, which are the same of different.

Compounds of the formula (I) in which some or all of the above-mentioned groups have the preferred or more preferred meanings are also an object of the present invention.

Preferred specific compounds of the present invention are selected from the group consisting of 4-Methoxy-N,2,6-trimethyl-N-[(4-{[4-(1-methylpiperidin-4-yl)piperazin-1-yl]carbonyl}furan-2-yl)methyl]benzene-sulfonamide N-[4-(1H-imidazol-1-yl)benzyl]-5-({[(4-methoxy-2,6-dimethylphenyl)sulfonyl](methyl)amino}methyl)-N-methyl-furan-3-carboxamide 5-({[(4-methoxy-2,6-dimethylphenyl)sulfonyl](methyl)amino}methyl)-N-(1,2,2,6,6-pentamethylpiperidin-4-yl)furan-3-carboxamide N-{2-[4-(4,5-dihydro-1H-imidazol-2-yl)phenyl]ethyl}-5-({[(4-methoxy-2,6-dimethylphenyl)sulfonyl](methyl)amino}methyl)furan-3-carboxamide N-{2-[4-(4,5-dihydro-1H-imidazol-2-yl)phenyl]ethyl}-5-({[(4-methoxy-2,6-dimethylphenyl)sulfonyl](methyl)amino}methyl)-N-methylfuran-3-carboxamide N-[4-(4,5-dihydro-1H-imidazol-2-yl)benzyl]-5-({[(4-methoxy-2,6-dimethylphenyl)sulfonyl](methyl)amino}methyl)furan-3-carboxamide 5-({[(4-methoxy-2,6-dimethylphenyl)sulfonyl](methyl)amino}methyl)-N-{2-[4-(4-methyl-4,5-dihydro-1H-imidazol-2-yl)phenyl]ethyl}furan-3-carboxamide 5-({[(4-methoxy-2,6-dimethylphenyl)sulfonyl](methyl)amino}methyl)-N-methyl-N-[3-(pyrrolidin-1-ylmethyl)benzyl]furan-3-carboxamide 5-({[(4-methoxy-2,6-dimethylphenyl)sulfonyl](methyl)amino}methyl)-N-methyl-N-[4-(pyrrolidin-1-ylmethyl)benzyl]furan-3-carboxamide 5-({[(4-methoxy-2,6-dimethylphenyl)sulfonyl](methyl)amino}methyl)-N-methyl-N-[4-(1,4,5,6-tetrahydropyrimidin-2-yl)benzyl]furan-3-carboxamide 5-({[(4-methoxy-2,6-dimethylphenyl)sulfonyl](methyl)amino}methyl)-N-[3-(pyrrolidin-1-ylmethyl)benzyl]furan-3-carboxamide 2-({4-[({5-({[(4-methoxy-2,6-dimethylphenyl)sulfonyl](methyl)amino}methyl)furan-3-yl]carbonyl}amino)methyl]phenyl}amino)-1-methylpyridinium iodide 2-({4-[2-({[5-({[(4-methoxy-2,6-dimethylphenyl)sulfonyl](methyl)amino}methyl)furan-3-yl]carbonyl}amino)ethyl]phenyl}amino)-1-methylpyridinium iodide N-{4-[(4-aminopyrimidin-2-yl)amino]benzyl}-5-({[(4-methoxy-2,6-dimethylphenyl)sulfonyl](methyl)amino}methyl)furan-3-carboxamide 4-bromo-2-ethyl-N-methyl-N-[(4-{[4-(3-pyrrolidin-1-yl-propyl)-1,4-diazepan-1-yl]carbonyl}furan-2-yl)methyl]benzenesulfonamide 5-({[(4-bromo-2-ethylphenyl)sulfonyl](methyl)amino}methyl)-N-[3-(pyrrolidin-1-ylmethyl)benzyl]furan-3-carboxamide 2,6-dichloro-N-methyl-N-{[4-({4-[(1-methylpiperidin-4-yl)methyl]piperazin-1-yl}carbonyl)furan-2-yl]methyl}benzenesulfonamide 2,6-dichloro-N-methyl-N-[(4-{[4-(2-pyridin-4-ylethyl)piperazin-1-yl]carbonyl}furan-2-yl)methyl]benzenesulfonamide 5-({[(4-bromo-2,6-dichlorophenyl)sulfonyl](methyl)amino}methyl)-N-[4-(4,5-dihydro-1H-imidazol-2-yl)benzyl]-N-methylfuran-3-carboxamide 5-({[(4-chloro-2,5-dimethylphenyl)sulfonyl](methyl)amino}methyl)-N-[4-(4,5-dihydro-1H-imidazol-2-yl)benzyl]-N-methylfuran-3-carboxamide 5-({[(2,4-dichlorophenyl)sulfonyl](methyl)amino}methyl)-N-[4-(4,5-dihydro-1H-imidazol-2-yl)benzyl]-N-methyl-furan-3-carboxamide 5-({[(2,4-dichlorophenyl)sulfonyl](methyl)amino}methyl)-N-{2-[4-(4,5-dihydro-1H-imidazol-2-yl)phenyl]ethyl}-N-methylfuran-3-carboxamide 5-({[(2,6-dichlorophenyl)sulfonyl](methyl)amino}methyl)-N-[4-(4,5-dihydro-1H-imidazol-2-yl)benzyl]-N-methylfuran-3-carboxamide 5-({[(4-bromo-2,6-dichlorophenyl)sulfonyl](methyl)amino}methyl)-N-{2-[4-(4,5-dihydro-1H-imidazol-2-yl)phenyl]ethyl}-N-methylfuran-3-carboxamide 5-({[(4-bromo-2,6-dichlorophenyl)sulfonyl](methyl)amino}methyl)-N-{2-[4-(4,5-dihydro-1H-imidazol-2-yl)phenyl]ethyl}furan-3-carboxamide 5-({[(2,6-dichlorophenyl)sulfonyl](methyl)amino}methyl)-N-[4-(4,5-dihydro-1H-imidazol-2-yl)benzyl]furan-3-carboxamide 5-({[(4-bromo-2,6-dichlorophenyl)sulfonyl](methyl)amino}methyl)-N-[4-(pyrrolidin-1-ylmethyl)benzyl]furan-3-carboxamide 5-({[(4-chloro-2,5-dimethylphenyl)sulfonyl](methyl)amino}methyl)-N-{2-[4-(4,5-dihydro-1H-imidazol-2-yl)phenyl]ethyl}-N-methylfuran-3-carboxamide N-[4-(4,5-dihydro-1H-imidazol-2-yl)benzyl]-5-({[(4-methoxy-2,6-dimethylphenyl)sulfonyl](methyl)amino}methyl)-N-methylfuran-3-carboxamide N-{[4-({3-[4-(4,5-dihydro-1H-imidazol-2-yl)phenyl]piperidin-1-yl}carbonyl)furan-2-yl]methyl}-4-methoxy-N,2,6-trimethylbenzenesulfonamide 4-methoxy-N,2,6-trimethyl-N-{[4-({4-[(1-methylpiperidin-3-yl)methyl]piperazin-1-yl}carbonyl)furan-2-yl]methyl}benzenesulfonamide 4-methoxy-N,2,6-trimethyl-N-{[4-({4-[(1-methylpiperidin-4-yl)methyl]piperazin-1-yl}carbonyl)furan-2-yl]methyl}benzenesulfonamide 4-methoxy-N,2,6-trimethyl-N-[(4-{[4-(2-pyridin-4-ylethyl)piperazin-1-yl]carbonyl}furan-2-yl)methyl]benzenesulfonamide 4-methoxy-N,2,6-trimethyl-N-[(4-{[4-(pyridin-4-ylmethyl)piperazin-1-yl]carbonyl}furan-2-yl)methyl]benzenesulfonamide 4-methoxy-N,2,6-trimethyl-N-[(4-{[4-(2-morpholin-4-ylethyl)piperazin-1-yl]carbonyl}furan-2-yl)methyl]benzenesulfonamide N-(2-{4-[(3aR,7aR)-3a,4,5,6,7,7a-hexahydro-1H-benzimidazol-2-yl]phenyl}ethyl)-5-({[(4-methoxy-2,6-dimethylphenyl)sulfonyl](methyl)amino}methyl)furan-3-carboxamide 5-({[(4-methoxy-2,6-dimethylphenyl)sulfonyl](methyl)amino}methyl)-N-[4-(pyrrolidin-1-ylmethyl)benzyl]furan-3-carboxamide 5-({[(4-methoxy-2,6-dimethylphenyl)sulfonyl](methyl)amino}methyl)-N-methyl-N-(4-pyrimidin-5-ylbenzyl)furan-3-carboxamide 4-methoxy-N,2,6-trimethyl-N-[(4-{[4-(2-pyrrolidin-1-ylethyl)piperazin-1-yl]carbonyl}furan-2-yl)methyl]benzenesulfonamide N-[4-(5,5-dimethyl-1,4,5,6-tetrahydropyrimidin-2-yl)benzyl]-5-({[(4-methoxy-2,6-dimethylphenyl)sulfonyl](methyl)amino}methyl)-N-methylfuran-3-carboxamide 4-methoxy-N,2,6-trimethyl-N-[(4-{[4-(pyrrolidin-1-ylmethyl)piperidin-1-yl]carbonyl}furan-2-yl)methyl]benzenesulfonamide 5-({[(4-methoxy-2,6-dimethylphenyl)sulfonyl](methyl)amino}methyl)-N-[2-(4-{[(2-methylpropyl)amino]methyl}phenyl)ethyl]furan-3-carboxamide 5-({[(4-methoxy-2,6-dimethylphenyl)sulfonyl](methyl)amino}methyl)-N-methyl-N-[4-(1-methyl-1H-imidazol-2-yl)benzyl]furan-3-carboxamide N-(2-{4-[(2-aminopyrimidin-2-yl)amino]phenyl}ethyl)-5-({[(4-methoxy-2,6-dimethylphenyl)sulfonyl](methyl)amino}methyl)furan-3-carboxamide N-(2-{4-[(2-aminopyrimidin-4-yl)amino]phenyl}ethyl)-5-({[(4-methoxy-2,6-dimethylphenyl)sulfonyl](methyl)amino}methyl)furan-3-carboxamide 5-({[(4-methoxy-2,6-dimethylphenyl)sulfonyl](methyl)amino}methyl)-N-{2-[4-(pyrrolidin-1-ylmethyl)phenyl]ethyl}furan-3-carboxamide N-{2-[4-(4,5-dihydro-1H-imidazol-2-yl)phenyl]ethyl}-5-({ethyl[(4-methoxy-2,6-dimethylphenyl)sulfonyl]amino}methyl)-N-methylfuran-3-carboxamide N-{2-[4-(4,5-dihydro-1H-imidazol-2-yl)phenyl]ethyl}-5-({[(4-methoxy-2,6-dimethylphenyl)sulfonyl](1-methylethyl)amino}methyl)-N-methylfuran-3-carboxamide 5-({(Cyclopropylmethyl)[(4-methoxy-2,6-dimethylphenyl)sulfonyl]amino}methyl)-N-{2-[4-(4,5-dihydro-1H-imidazol-2-yl)phenyl]ethyl}furan-3-carboxamide N-[4-(4,5-dihydro-1H-imidazol-2-yl)benzyl]-5-({[(4-methoxy-2,6-dimethylphenyl)sulfonyl](phenyl)amino}methyl)-N-methylfuran-3-carboxamide 5-({Cyclobutyl[(4-methoxy-2,6-dimethylphenyl)sulfonyl]amino}methyl)-N-{2-[4-(4,5-dihydro-1H-imidazol-2-yl)phenyl]ethyl}-N-methylfuran-3-carboxamide 5-({Cyclopropyl[(4-methoxy-2,6-dimethylphenyl)sulfonyl]amino}methyl)-N-{2-[4-(4,5-dihydro-1H-imidazol-2-yl)phenyl]ethyl}furan-3-carboxamide N-cyclopropyl-4-methoxy-2,6-dimethyl-N-[(4-{[4-(1-methylpiperidin-4-yl)piperazin-1-yl]carbonyl}furan-2-yl)methyl]benzenesulfonamide 5-({Cyclopropyl[(4-methoxy-2,6-dimethylphenyl)sulfonyl]amino}methyl)-N-[3-(pyrrolidin-1-ylmethyl)benzyl]furan-3-carboxamide 5-({Cyclopropyl[(4-methoxy-2,6-dimethylphenyl)sulfonyl]amino}methyl)-N-methyl-N-[3-(pyrrolidin-1-ylmethyl)benzyl]furan-3-carboxamide 5-({Cyclopropyl[(4-methoxy-2,6-dimethylphenyl)sulfonyl]amino}methyl)-N-[4-(pyrrolidin-1-ylmethyl)benzyl]furan-3-carboxamide 5-({Cyclopropyl[(4-methoxy-2,6-dimethylphenyl)sulfonyl]amino}methyl)-N-methyl-N-[4-(pyrrolidin-1-ylmethyl)benzyl]furan-3-carboxamide N-[4-(4,5-dihydro-1H-imidazol-2-yl)benzyl]-5-({[(4-methoxy-2,6-dimethylphenyl)sulfonyl](methyl)amino}methyl)-N,2-dimethylfuran-3-carboxamide N-{2-[4-(4,5-dihydro-1H-imidazol-2-yl)phenyl]ethyl}-5-({[(4-methoxy-2,6-dimethylphenyl)sulfonyl](methyl)amino}methyl)-N,2-dimethylfuran-3-carboxamide N-{2-[4-(4,5-dihydro-1H-imidazol-2-yl)phenyl]ethyl}-5-({[(4-methoxy-2,6-dimethylphenyl)sulfonyl](methyl)amino}methyl)-2-methylfuran-3-carboxamide 4-Methoxy-N,2,6-trimethyl-N-[(5-{[4-(1-methylpiperidin-4-yl)piperazin-1-yl]carbonyl}furan-2-yl)methyl]benzenesulfonamide N-{2-[4-(4,5-dihydro-1H-imidazol-2-yl)phenyl]ethyl}-3-({[(4-methoxy-2,6-dimethylphenyl)sulfonyl](methyl)amino}methyl)-1,2,4-thiadiazole-5-carboxamide N-{2-[4-(4,5-dihydro-1H-imidazol-2-yl)phenyl]ethyl}-3-({[(4-methoxy-2,6-dimethylphenyl)sulfonyl](methyl)amino}methyl)-1,2,4-oxadiazole-5-carboxamide 4-Methoxy-N,2,6-trimethyl-N-[(3-{[4-(1-methylpiperidin-4-yl)piperazin-1-yl]carbonyl}isoxazol-5-yl)methyl]benzenesulfonamide 4-Methoxy-N,2,6-trimethyl-N-[(4-{[4-(1-methylpiperidin-4-yl)piperazin-1-yl]carbonyl}-1,3-oxazol-2-yl)methyl]benzenesulfonamide N-{2-[4-(4,5-dihydro-1H-imidazol-2-yl)phenyl]ethyl}-2-({[(4-methoxy-2,6-dimethylphenyl)sulfonyl](methyl)amino}methyl)-1,3-oxazole-4-carboxamide N-[4-(4,5-dihydro-1H-imidazol-2-yl)benzyl]-2-({[(4-methoxy-2,6-dimethylphenyl)sulfonyl](methyl)amino}methyl)-1,3-oxazole-4-carboxamide N-{2-[4-(4,5-dihydro-1H-imidazol-2-yl)phenyl]ethyl}-2-({[(4-methoxy-2,6-dimethylphenyl)sulfonyl](methyl)amino}methyl)-N-methyl-1,3-oxazole-4-carboxamide N-[4-(4,5-dihydro-1H-imidazol-2-yl)benzyl]-2-({[(4-methoxy-2,6-dimethylphenyl)sulfonyl](methyl)amino}methyl)-N-methyl-1,3-oxazole-4-carboxamide 2({[(4-Methoxy-2,6-dimethylphenyl)sulfonyl](methyl)amino}methyl)-N-methyl-N-[4-(pyrrolidin-1-ylmethyl)benzyl]-1,3-oxazole-4-carboxamide 2-({[(4-Methoxy-2,6dimethylphenyl)sulfonyl](methyl)amino}methyl)-N-[4-(pyrrolidin-1-ylmethyl)benzyl]-1,3-oxazole-4-carboxamide 2-({[(4-Methoxy-2,6-dimethylphenyl)sulfonyl](methyl)amino}methyl)-N-methyl-N-[3-(pyrrolidin-1-ylmethyl)benzyl]-1,3-oxazole-4-carboxamide 2-({[(4-Methoxy-2,6-dimethylphenyl)sulfonyl](methyl)amino}methyl)-N-[3-(pyrrolidin-1-ylmethyl)benzyl]-1,3-oxazole-4-carboxamide 2-({Cyclopropyl[(4-methoxy-2,6-dimethylphenyl)sulfonyl]amino}methyl)-N-methyl-N-[4-(pyrrolidin-1-ylmethyl)benzyl]-1,3-oxazole-4-carboxamide 2-({Cyclopropyl[(4-methoxy-2,6-dimethylphenyl)sulfonyl]amino}methyl)-N-[4-(pyrrolidin-1-ylmethyl)benzyl]-1,3-oxazole-4-carboxamide 2-({Cyclopropyl[(4-methoxy-2,6-dimethylphenyl)sulfonyl]amino}methyl)-N-methyl-N-[3-(pyrrolidin-1-ylmethyl)benzyl]-1,3-oxazole-4-carboxamide 2-({Cyclopropyl[(4-methoxy-2,6-dimethylphenyl)sulfonyl]amino}methyl)-N-[3-(pyrrolidin-1-ylmethyl)benzyl]-1,3-oxazole-4-carboxamide 2-({Cyclopropyl[(4-methoxy-2,6-dimethylphenyl)sulfonyl]amino}methyl)-N-{2-[4-(4,5-dihydro-1H-imidazol-2-yl)phenyl]ethyl}-N-methyl-1,3-oxazole-4-carboxamide N-{2-[4-(4,5-dihydro-1H-imidazol-2-yl)phenyl]ethyl}-2-({[(4-methoxy-2,6-dimethylphenyl)sulfonyl](methyl)amino}methyl)-N-methyl-1,3-thiazole-4-carboxamide N-[4-(4,5-dihydro-1H-imidazol-2-yl)benzyl]-2-({[(4-methoxy-2,6-dimethylphenyl)sulfonyl](methyl)amino}methyl)-N-methyl-1,3-thiazole-4-carboxamide 5-({cyclopropyl[(4-methoxy-2,6-dimethylphenyl)sulfonyl]amino}methyl)-N-[4-(4,5-dihydro-1H-imidazol-2-yl)benzyl]furan-3-carboxamide trifluoroacetate 5-({cyclopropyl[(4-methoxy-2,6-dimethylphenyl)sulfonyl]amino}methyl)-N-[4-(4,5-dihydro-1H-imidazol-2-yl)benzyl]-N-methylfuran-3-carboxamide trifluoroacetate 5-({cyclopropyl[(4-methoxy-2,6-dimethylphenyl)sulfonyl]amino}methyl)-N-{2-[4-(4,5-dihydro-1H-imidazol-2-yl)phenyl]ethyl}-N-methylfuran-3-carboxamide trifluoroacetate N-{2-[4-(4,5-dihydro-1H-imidazol-2-yl)phenyl]ethyl}-5-(1-{[(4-methoxy-2,6-dimethylphenyl)sulfonyl](methyl)amino}ethyl)furan-3-carboxamide trifluoroacetamide N-{2-[4-(4,5-dihydro-1H-imidazol-2-yl)phenyl]ethyl}-5-{[{[2-(hydroxymethyl)-4-methoxy-6-methylphenyl]sulfonyl}(methyl)amino]methyl}furan-3-carboxamide trifluoroacetate N-{2-[4-(4,5-dihydro-1H-imidazol-2-yl)phenyl]ethyl}-5-({[(4-hydroxy-2,6-dimethylphenyl)sulfonyl](methyl)amino}methyl)-N-methylfuran-3-carboxamide, trifluoroacetate 5-({[(4-methoxy-2,6-dimethylphenyl)sulfonyl](methyl)amino}methyl)-N-methyl-N-[4-(1-pyrrolidin-1-ylethyl)benzyl]furan-3-carboxamide trifluoroacetate N-cyclopropyl-4-methoxy-2,6-dimethyl-N-{[4-({4-[(1-methylpiperidin-4-yl)methyl]piperazin-1-yl}carbonyl)furan-2-yl]methyl}benzenesulfonamide 5-({[(4-methoxy-2,6-dimethylphenyl)sulfonyl](methyl)amino}methyl)-N-{1-[4-(pyrrolidin-1-ylmethyl)phenyl]ethyl}furan-3-carboxamide N-(1-{4-[(3-hydroxypyrrolidin-1-yl)methyl]phenyl}ethyl)-5-({[(4-methoxy-2,6-dimethylphenyl)sulfonyl](methyl)amino}methyl)furan-3-carboxamide N-[2-(4-{[(3S)-3-(dimethylamino)pyrrolidin-1-yl]methyl}phenyl)ethyl]-5-({[(4-methoxy-2,6-dimethylphenyl)sulfonyl](methyl)amino}methyl)furan-3-carboxamide, trifluoroacetate N-[4-(5,5-Dimethyl-4,5-dihydro-1H-imidazol-2-yl)benzyl]-5-({[(4-methoxy-2,6-dimethylphenyl)sulfonyl](methyl)amino}methyl)furan-3-carboxamide trifluoroacetate N-{2-[4-(5,5-Dimethyl-4,5-dihydro-1H-imidazol-2-yl)phenyl]ethyl}-5-({[(4-methoxy-2,6-dimethylphenyl)sulfonyl](methyl)amino}methyl)furan-3-carboxamide trifluoroacetate 4-Methoxy-N,2,6-trimethyl-N-{[4-({3-[4-(pyrrolidin-1-ylmethyl)phenyl]piperidin-1-yl}carbonyl)furan-2-yl]methyl}benzenesulfonamide trifluoroacetamide 5-({[(4-methoxy-2,6-dimethylphenyl)sulfonyl](methyl)amino}methyl)-N-(4-{[(pyridin-4-ylmethyl)amino]methyl}benzyl)furan-3-carboxamide trifluoroacetate N-[4-(azetidin-1-ylmethyl)benzyl]-5-({[(4-methoxy-2,6-dimethylphenyl)sulfonyl](methyl)amino}methyl)furan-3-carboxamide trifluoroacetate 5-({[(4-Methoxy-2,6-dimethylphenyl)sulfonyl](methyl)amino}methyl)-N-methyl-N-{2-[4-(1-methyl-4,5-dihydro-1H-imidazol-2-yl)phenyl]ethyl}furan-3-carboxamide trifluoroacetamide 5-({[(4-methoxy-2,6-dimethylphenyl)sulfonyl](methyl)amino}methyl)-N-{4-[(2-methylpiperidin-1-yl)methyl]benzyl}furan-3-carboxamide trifluoroacetate 5-({[(4-Methoxy-2,6-dimethylphenyl)sulfonyl](methyl)amino}methyl)-N-[4-(piperidin-1-ylmethyl)benzyl]furan-3-carboxamide trifluoroacetate N-[4-(Azepan-1-ylmethyl)benzyl]-5-({[(4-methoxy-2,6-dimethylphenyl)sulfonyl](methyl)amino}methyl)furan-3-carboxamide trifluoroacetate 5-({Ethyl[(4-methoxy-2,6-dimethylphenyl)sulfonyl]amino}methyl)-N-methyl-N-[4-(pyrrolidin-1-ylmethyl)benzyl]furan-3-carboxamide trifluoroacetate N-[4-(4,5-Dihydro-1H-imidazol-2-yl)benzyl]-5-({ethyl[(4-methoxy-2,6-dimethylphenyl)sulfonyl]amino}methyl)-N-methylfuran-3-carboxamide trifluoroacetate N-{2-[4-(4,5-Dihydro-1H-imidazol-2-yl)phenyl]ethyl}-5-({ethyl[(4-methoxy-2,6-dimethylphenyl)sulfonyl]amino}methyl)furan-3-carboxamide trifluoroacetate N-Cyclopropyl-4-methoxy-2,6-dimethyl-N-{[4-({4-[(1-methylpiperidin-4-yl)methyl]piperazin-1-yl}carbonyl)furan-2-yl]methyl}benzenesulfonamide trifluoroacetate N-cyclopropyl-4-methoxy-2,6-dimethyl-N-{[4-({4-[(1-methylpiperidin-3-yl)methyl]piperazin-1-yl}carbonyl)furan-2-yl]methyl}benzenesulfonamide trifluoroacetate N-cyclopropyl-4-methoxy-2,6-dimethyl-N-[(4-{[4-(8-methyl-8-azabicyclo[3.2.1]oct-3-yl)piperazin-1-yl]carbonyl}furan-2-yl)methyl]benzenesulfonamide trifluoroacetate N-Cyclopropyl-4-methoxy-2,6-dimethyl-N-[(4-{[4-(1,2,2,6,6-pentamethylpiperidin-4-yl)piperazin-1-yl]carbonyl}furan-2-yl)methyl]benzenesulfonamide trifluoroacetate N-Cyclopropyl-4-methoxy-2,6-dimethyl-N-[(4-{[4-(2-piperidin-1-ylethyl)piperazin-1-yl]carbonyl}furan-2-yl)methyl]benzenesulfonamide trifluoroacetate N-Cyclopropyl-4-methoxy-2,6-dimethyl-N-[(4-{[4-(2-pyridin-4-ylethyl)piperazin-1-yl]carbonyl}furan-2-yl)methyl]benzenesulfonamide trifluoroacetate N-Cyclopropyl-4-methoxy-2,6-dimethyl-N-[(4-{[4-(pyridin-3-ylmethyl)piperazin-1-yl]carbonyl}furan-2-yl)methyl]benzenesulfonamide trifluoroacetate N-Cyclopropyl-4-methoxy-2,6-dimethyl-N-[(4-{[4-(2-pyrrolidin-1-ylethyl)piperazin-1-yl]carbonyl}furan-2-yl)methyl]benzenesulfonamide trifluoroacetate 5-({Cyclopropyl[(4-methoxy-2,6-dimethylphenyl)sulfonyl]amino}methyl)-N-[2-(4-ethylpiperazin-1-yl)ethyl]furan-3-carboxamide trifluoroacetate N-Cyclopropyl-4-methoxy-2,6-dimethyl-N-[(4-{[4-(2-pyridin-2-ylethyl)piperazin-1-yl]carbonyl}furan-2-yl)methyl]benzenesulfonamide trifluoroacetate N-Cyclopropyl-4-methoxy-2,6-dimethyl-N-[(4-{[4-(3-pyrrolidin-1-ylpropyl)piperazin-1-yl]carbonyl}furan-2-yl)methyl]benzenesulfonamide trifluoroacetate N-Cyclopropyl-4-methoxy-2,6-dimethyl-N-[(4-{[4-(3-pyrrolidin-1-ylpropyl)-1,4-diazepan-1-yl]carbonyl}furan-2-yl)methyl]benzenesulfonamide trifluoroacetate 2-(4-{[5-({Cyclopropyl[(4-methoxy-2,6-dimethylphenyl)sulfonyl]amino}methyl)furan-3-yl]carbonyl}piperazin-1-yl)-N-pyridin-3-ylacetamide trifluoroacetate N-Cyclopropyl-N-{[4-({4-[3-(dimethylamino)propyl]piperazin-1-yl}carbonyl)furan-2-yl]methyl}-4-methoxy-2,6-dimethylbenzenesulfonamide trifluoroacetate N-Cyclopropyl-4-methoxy-2,6-dimethyl-N-[(4-{[4-(4-methylpiperazin-1-yl)piperidin-1-yl]carbonyl}furan-2-yl)methyl]benzenesulfonamide trifluoroacetate N-Cyclopropyl-4-methoxy-2,6-dimethyl-N-[(4-{[4-(2-pyrrolidin-1-ylethyl)piperidin-1-yl]carbonyl}furan-2-yl)methyl]benzenesulfonamide trifluoroacetate 5-({[(2,6-Dichlorophenyl)sulfonyl](ethyl)amino}methyl)-N-methyl-N-[4-(pyrrolidin-1-ylmethyl)benzyl]furan-3-carboxamide trifluoroacetate 5-({[(2,6-Dichlorophenyl)sulfonyl](ethyl)amino}methyl)-N-{2-[4-(4,5-dihydro-1H-imidazol-2-yl)phenyl]ethyl}furan-3-carboxamide trifluoroacetate 5-({[(4-Bromo-2,6-dichlorophenyl)sulfonyl](cyclopropyl)amino}methyl)-N-[4-(4,5-dihydro-1H-imidazol-2-yl)benzyl]-N-methylfuran-3-carboxamide trifluoroacetate 5-({[(4-Bromo-2,6-dichlorophenyl)sulfonyl](cyclopropyl)amino}methyl)-N-{2-[4-(4,5-dihydro-1H-imidazol-2-yl)phenyl]ethyl}-N-methylfuran-3-carboxamide trifluoroacetate 4-Bromo-2,6-dichloro-N-cyclopropyl-N-{[4-({3-[4-(pyrrolidin-1-ylmethyl)phenyl]piperidin-1-yl}carbonyl)furan-2-yl]methyl}benzenesulfonamide trifluoroacetate N-{4-[(4-Hydroxypiperidin-1-yl)methyl]benzyl}-5-({[(4-methoxy-2,6-dimethylphenyl)sulfonyl](methyl)amino}methyl)-N-methylfuran-3-carboxamide 5-({[(4-Methoxy-2,6-dimethylphenyl)sulfonyl](methyl)amino}methyl)-N-{4-[(4-methoxypiperidin-1-yl)methyl]benzyl}-N-methylfuran-3-carboxamide N-{4-[(3-Hydroxyazetidin-1-yl)methyl]benzyl}-5-({[(4-methoxy-2,6-dimethylphenyl)sulfonyl](methyl)amino}methyl)-N-methylfuran-3-carboxamide 5-({[(4-Methoxy-2,6-dimethylphenyl)sulfonyl](methyl)amino}methyl)-N-{4-[(3-methoxypyrrolidin-1-yl)methyl]benzyl}-N-methylfuran-3-carboxamide 5-({[(4-Methoxy-2,6-dimethylphenyl)sulfonyl](methyl)amino}methyl)-N-{4-[(3-methoxypiperidin-1-yl)methyl]benzyl}-N-methylfuran-3-carboxamide 1-(4-{[{[5-({[(4-Methoxy-2,6-dimethylphenyl)sulfonyl](methyl)amino}methyl)furan-3-yl]carbonyl}(methyl)amino]methyl}benzyl)-N,N-dimethylpyrrolidine-3-carboxamide N-(4-{[3-(Acetylamino)pyrrolidin-1-yl]methyl}benzyl)-5-({[(4-methoxy-2,6-dimethylphenyl)sulfonyl](methyl)amino}methyl)-N-methylfuran-3-carboxamide N-{4-[(3-Methoxyazetidin-1-yl)methyl]benzyl}-5-({[(4-methoxy-2,6-dimethylphenyl)sulfonyl](methyl)amino}methyl)-N-methylfuran-3-carboxamide N-{4-[(3-Hydroxypiperidin-1-yl)methyl]benzyl}-5-({[(4-methoxy-2,6-dimethylphenyl)sulfonyl](methyl)amino}methyl)-N-methylfuran-3-carboxamide N-{4-[(3-Hydroxypyrrolidin-1-yl)methyl]benzyl}-5-({[(4-methoxy-2,6-dimethylphenyl)sulfonyl](methyl)amino}methyl)-N-methylfuran-3-carboxamide N-(4-{[3-(Dimethylamino)pyrrolidin-1-yl]methyl}benzyl)-5-({[(4-methoxy-2,6-dimethylphenyl)sulfonyl](methyl)amino}methyl)-N-methylfuran-3-carboxamide 5-({[(4-Methoxy-2,6-dimethylphenyl)sulfonyl](methyl)amino}methyl)-N-methyl-N-{[5-(pyrrolidin-1-ylmethyl)-1,3,4-thiadiazol-2-yl]methyl}furan-3-carboxamide 5-({[(4-Methoxy-2,6-dimethylphenyl)sulfonyl](methyl)amino}methyl)-N-methyl-N-{[4-(pyrrolidin-1-ylmethyl)-1,3-thiazol-2-yl]methyl}furan-3-carboxamide 5-({Cyclopropyl[(4-methoxy-2,6-dimethylphenyl)sulfonyl]amino}methyl)-N-{4-[(4-hydroxypiperidin-1-yl)methyl]benzyl}-N-methylfuran-3-carboxamide 5-({Cyclopropyl[(4-methoxy-2,6-dimethylphenyl)sulfonyl]amino}methyl)-N-(4-{[3-(dimethylamino)pyrrolidin-1-yl]methyl}benzyl)-N-methylfuran-3-carboxamide 5-({Cyclopropyl[(4-methoxy-2,6-dimethylphenyl)sulfonyl]amino}methyl)-N-{4-[(3-hydroxypyrrolidin-1-yl)methyl]benzyl}-N-methylfuran-3-carboxamide 5-({Cyclopropyl[(4-methoxy-2,6-dimethylphenyl)sulfonyl]amino}methyl)-N-{4-[(3-hydroxypiperidin-1-yl)methyl]benzyl}-N-methylfuran-3-carboxamide 5-({Cyclopropyl[(4-methoxy-2,6-dimethylphenyl)sulfonyl]amino}methyl)-N-{4-[(4-methoxypiperidin-1-yl)methyl]benzyl}-N-methylfuran-3-carboxamide 5-({Cyclopropyl[(4-methoxy-2,6-dimethylphenyl)sulfonyl]amino}methyl)-N-{4-[(3-methoxypiperidin-1-yl)methyl]benzyl}-N-methylfuran-3-carboxamide 5-({Cyclopropyl[(4-methoxy-2,6-dimethylphenyl)sulfonyl]amino}methyl)-N-{4-[(3-methoxypyrrolidin-1-yl)methyl]benzyl}-N-methylfuran-3-carboxamide N-(4-{[3-(Acetylamino)pyrrolidin-1-yl]methyl}benzyl)-5-({cyclopropyl[(4-methoxy-2,6-dimethylphenyl)sulfonyl]amino}methyl)-N-methylfuran-3-carboxamide 1-(4-{[{[5-({Cyclopropyl[(4-methoxy-2,6-dimethylphenyl)sulfonyl]amino}methyl)furan-3-yl]carbonyl}(methyl)amino]methyl}benzyl)-N,N-dimethylpyrrolidine-3-carboxamide 5-({Cyclopropyl[(4-methoxy-2,6-dimethylphenyl)sulfonyl]amino}methyl)-N-{4-[(3-hydroxyazetidin-1-yl)methyl]benzyl}-N-methylfuran-3-carboxamide 5-({Cyclopropyl[(4-methoxy-2,6-dimethylphenyl)sulfonyl]amino}methyl)-N-{4-[(3-methoxyazetidin-1-yl)methyl]benzyl}-N-methylfuran-3-carboxamide N-Ethyl-5-({[(4-methoxy-2,6-dimethylphenyl)sulfonyl](methyl)amino}methyl)-N-[4-(pyrrolidin-1-ylmethyl)benzyl]furan-3-carboxamide trifluoroacetate N-[2-Fluoro-5-(pyrrolidin-1-ylmethyl)benzyl]-5-({[(4-methoxy-2,6-dimethylphenyl)sulfonyl](methyl)amino}methyl)furan-3-carboxamide trifluoroacetate N-[3-Fluoro-4-(pyrrolidin-1-ylmethyl)benzyl]-5-({[(4-methoxy-2,6-dimethylphenyl)sulfonyl](methyl)amino}methyl)furan-3-carboxamide trifluoroacetate 5-({Cyclopropyl[(4-methoxy-2,6-dimethylphenyl)sulfonyl]amino}methyl)-N-[2-fluoro-5-(pyrrolidin-1-ylmethyl)benzyl]furan-3-carboxamide trifluoroacetate 5-({Cyclopropyl[(4-methoxy-2,6-dimethylphenyl)sulfonyl]amino}methyl)-N-[3-fluoro-4-(pyrrolidin-1-ylmethyl)benzyl]furan-3-carboxamide trifluoroacetate N-[3-Fluoro-5-(pyrrolidin-1-ylmethyl)benzyl]-5-({[(4-methoxy-2,6-dimethylphenyl)sulfonyl](methyl)amino}methyl)furan-3-carboxamide trifluoroacetate N-[2-Fluoro-5-(pyrrolidin-1-ylmethyl)benzyl]-5-({[(4-methoxy-2,6-dimethylphenyl)sulfonyl](methyl)amino}methyl)-N-methylfuran-3-carboxamide trifluoroacetate N-[3-Fluoro-4-(pyrrolidin-1-ylmethyl)benzyl]-5-({[(4-methoxy-2,6-dimethylphenyl)sulfonyl](methyl)amino}methyl)-N-methylfuran-3-carboxamide trifluoroacetate N-[3-Fluoro-5-(pyrrolidin-1-ylmethyl)benzyl]-5-({[(4-methoxy-2,6-dimethylphenyl)sulfonyl](methyl)amino}methyl)-N-methylfuran-3-carboxamide trifluoroacetate 2-({[(4-Methoxy-2,6-dimethylphenyl)sulfonyl](methyl)amino}methyl)-N-methyl-N-{4-[(1-oxidopyrrolidin-1-yl)methyl]benzyl}-1,3-oxazole-4-carboxamide trifluoroacetate 2-({Cyclopropyl[(4-methoxy-2,6-dimethylphenyl)sulfonyl]amino}methyl)-N-(2-piperidin-3-ylethyl)-1,3-oxazole-4-carboxamide 2-({Cyclopropyl[(4-methoxy-2,6-dimethylphenyl)sulfonyl]amino}methyl)-N-methyl-N-{[2-(pyrrolidin-1-ylmethyl)-1,3-thiazol-4-yl]methyl}-1,3-oxazole-4-carboxamide N-Cyclopropyl-4-methoxy-2,6-dimethyl-N-({4-[(4-pyridin-4-ylpiperazin-1-yl)carbonyl]-1,3-oxazol-2-yl}methyl)benzenesulfonamide trifluoroacetate N-Cyclopropyl-4-methoxy-2,6-dimethyl-N-[(4-{[4-(pyridin-4-ylmethyl)piperazin-1-yl]carbonyl}-1,3-oxazol-2-yl)methyl]benzenesulfonamide trifluoroacetate N-Cyclopropyl-4-methoxy-2,6-dimethyl-N-[(4-{[4-(pyridin-3-ylmethyl)piperazin-1-yl]carbonyl}-1,3-oxazol-2-yl)methyl]benzenesulfonamide trifluoroacetate 4-Methoxy-N,2,6-trimethyl-N-[(4-{[4-(2-pyrrolidin-1-ylethyl)piperazin-1-yl]carbonyl}-1,3-oxazol-2-yl)methyl]benzenesulfonamide N-Cyclopropyl-4-methoxy-2,6-dimethyl-N-[(4-{[4-(1-methylpiperidin-4-yl)piperazin-1-yl]carbonyl}-1,3-oxazol-2-yl)methyl]benzenesulfonamide N-{4-[(4-Hydroxypiperidin-1-yl)methyl]benzyl}-2-({[(4-methoxy-2,6-dimethylphenyl)sulfonyl](methyl)amino}methyl)-N-methyl-1,3-oxazole-4-carboxamide 2-({[(4-Methoxy-2,6-dimethylphenyl)sulfonyl](methyl)amino}methyl)-N-{4-[(4-methoxypiperidin-1-yl)methyl]benzyl}-N-methyl-1,3-oxazole-4-carboxamide 2-({[(4-Methoxy-2,6-dimethylphenyl)sulfonyl](methyl)amino}methyl)-N-{4-[(3-methoxypiperidin-1-yl)methyl]benzyl}-N-methyl-1,3-oxazole-4-carboxamide 2-({[(4-Methoxy-2,6-dimethylphenyl)sulfonyl](methyl)amino}methyl)-N-{4-[(3-methoxypyrrolidin-1-yl)methyl]benzyl}-N-methyl-1,3-oxazole-4-carboxamide N-(4-{[3-(Acetylamino)pyrrolidin-1-yl]methyl}benzyl)-2-({[(4-methoxy-2,6-dimethylphenyl)sulfonyl](methyl)amino}methyl)-N-methyl-1,3-oxazole-4-carboxamide N-(4-{[3-(Dimethylcarbamoyl)pyrrolidin-1-yl]methyl}benzyl)-2-({[(4-methoxy-2,6-dimethylphenyl)sulfonyl](methyl)amino}methyl)-N-methyl-1,3-oxazole-4-carboxamide N-{4-[(3-Hydroxyazetidin-1-yl)methyl]benzyl}-2-({[(4-methoxy-2,6-dimethylphenyl)sulfonyl](methyl)amino}methyl)-N-methyl-1,3-oxazole-4-carboxamide N-{4-[(3-Methoxyazetidin-1-yl)methyl]benzyl}-2-({[(4-methoxy-2,6-dimethylphenyl)sulfonyl](methyl)amino}methyl)-N-methyl-1,3-oxazole-4-carboxamide 4-Methoxy-N,2,6-trimethyl-N-[(4-{[4-(3-pyrrolidin-1-ylpropyl)piperazin-1-yl]carbonyl}-1,3-oxazol-2-yl)methyl]benzenesulfonamide 4-Methoxy-N,2,6-trimethyl-N-{[4-({4-[(1-methylpiperidin-4-yl)methyl]piperazin-1-yl}carbonyl)-1,3-oxazol-2-yl]methyl}benzenesulfonamide 2-({Cyclopropyl[(4-methoxy-2,6-dimethylphenyl)sulfonyl]amino}methyl)-N-{4-[(3-hydroxypyrrolidin-1-yl)methyl]benzyl}-N-methyl-1,3-oxazole-4-carboxamide N-(4-{[3-(Dimethylamino)pyrrolidin-1-yl]methyl}benzyl)-2-({[(4-methoxy-2,6-dimethylphenyl)sulfonyl](methyl)amino}methyl)-N-methyl-1,3-oxazole-4-carboxamide N-{4-[(3-Hydroxypyrrolidin-1-yl)methyl]benzyl}-2-({[(4-methoxy-2,6-dimethylphenyl)sulfonyl](methyl)amino}methyl)-N-methyl-1,3-oxazole-4-carboxamide N-{4-[(3-Hydroxypiperidin-1-yl)methyl]benzyl}-2-({[(4-methoxy-2,6-dimethylphenyl)sulfonyl](methyl)amino}methyl)-N-methyl-1,3-oxazole-4-carboxamide 2-({Cyclopropyl[(4-methoxy-2,6-dimethylphenyl)sulfonyl]amino}methyl)-N-{4-[(3-hydroxypiperidin-1-yl)methyl]benzyl}-N-methyl-1,3-oxazole-4-carboxamide 2-({Cyclopropyl[(4-methoxy-2,6-dimethylphenyl)sulfonyl]amino}methyl)-N-{4-[(4-hydroxypiperidin-1-yl)methyl]benzyl}-N-methyl-1,3-oxazole-4-carboxamide 2-({Cyclopropyl[(4-methoxy-2,6-dimethylphenyl)sulfonyl]amino}methyl)-N-{4-[(3-methoxypyrrolidin-1-yl)methyl]benzyl}-N-methyl-1,3-oxazole-4-carboxamide 2-({Cyclopropyl[(4-methoxy-2,6-dimethylphenyl)sulfonyl]amino}methyl)-N-{4-[(4-methoxypiperidin-1-yl)methyl]benzyl}-N-methyl-1,3-oxazole-4-carboxamide 2-({Cyclopropyl[(4-methoxy-2,6-dimethylphenyl)sulfonyl]amino}methyl)-N-{4-[(3-methoxypiperidin-1-yl)methyl]benzyl}-N-methyl-1,3-oxazole-4-carboxamide N-(4-{[3-(Acetylamino)pyrrolidin-1-yl]methyl}benzyl)-2-({cyclopropyl[(4-methoxy-2,6-dimethylphenyl)sulfonyl]amino}methyl)-N-methyl-1,3-oxazole-4-carboxamide 2-({Cyclopropyl[(4-methoxy-2,6-dimethylphenyl)sulfonyl]amino}methyl)-N-(4-{[3-(dimethylcarbamoyl)pyrrolidin-1-yl]methyl}benzyl)-N-methyl-1,3-oxazole-4-carboxamide 2-({Cyclopropyl[(4-methoxy-2,6-dimethylphenyl)sulfonyl]amino}methyl)-N-{4-[(3-methoxyazetidin-1-yl)methyl]benzyl}-N-methyl-1,3-oxazole-4-carboxamide 2-({Cyclopropyl[(4-methoxy-2,6-dimethylphenyl)sulfonyl]amino}methyl)-N-{4-[(3-hydroxyazetidin-1-yl)methyl]benzyl}-N-methyl-1,3-oxazole-4-carboxamide 2-({Cyclopropyl[(4-methoxy-2,6-dimethylphenyl)sulfonyl]amino}methyl)-N-{4-[(3,4-dihydroxypyrrolidin-1-yl)methyl]benzyl}-N-methyl-1,3-oxazole-4-carboxamide 2-({Cyclopropyl[(4-methoxy-2,6-dimethylphenyl)sulfonyl]amino}methyl)-N-(4-{[3-(dimethylamino)pyrrolidin-1-yl]methyl}benzyl)-N-methyl-1,3-oxazole-4-carboxamide N-Cyclopropyl-4-methoxy-2,6-dimethyl-N-{[4-({4-[(1-methylpiperidin-4-yl)methyl]piperazin-1-yl}carbonyl)-1,3-oxazol-2-yl]methyl}benzenesulfonamide trifluoroacetate trifluoroacetate N-Cyclopropyl-4-methoxy-2,6-dimethyl-N-{[4-({4-[(1-methylpiperidin-3-yl)methyl]piperazin-1-yl}carbonyl)-1,3-oxazol-2-yl]methyl}benzenesulfonamide trifluoroacetate N-Cyclopropyl-4-methoxy-2,6-dimethyl-N-[(4-{[4-(2-pyrrolidin-1-ylethyl)piperidin-1-yl]carbonyl}-1,3-oxazol-2-yl)methyl]benzenesulfonamide trifluoroacetate N-Cyclopropyl-4-methoxy-2,6-dimethyl-N-[(4-{[4-(2-piperidin-1-ylethyl)piperazin-1-yl]carbonyl}-1,3-oxazol-2-yl)methyl]benzenesulfonamide trifluoroacetate N-Cyclopropyl-4-methoxy-2,6-dimethyl-N-[(4-{[4-(2-pyrrolidin-1-ylethyl)piperazin-1-yl]carbonyl}-1,3-oxazol-2-yl)methyl]benzenesulfonamide trifluoroacetate N-Cyclopropyl-N-{[4-({4-[3-(dimethylamino)propyl]piperazin-1-yl}carbonyl)-1,3-oxazol-2-yl]methyl}-4-methoxy-2,6-dimethylbenzenesulfonamide trifluoroacetate N-Cyclopropyl-4-methoxy-2,6-dimethyl-N-[(4-{[4-(3-pyrrolidin-1-ylpropyl)piperazin-1-yl]carbonyl}-1,3-oxazol-2-yl)methyl]benzenesulfonamide trifluoroacetate 2-({Cyclopropyl[(4-methoxy-2,6-dimethylphenyl)sulfonyl]amino}methyl)-N-{4-[(3-hydroxy-3-methylpyrrolidin-1-yl)methyl]benzyl}-N-methyl-1,3-oxazole-4-carboxamide 2-({Cyclopropyl[(4-methoxy-2,6-dimethylphenyl)sulfonyl]amino}methyl)-N-methyl-N-{[5-(pyrrolidin-1-ylmethyl)-1,3,4-thiadiazol-2-yl]methyl}-1,3-oxazole-4-carboxamide trifluoroacetate 2-({Cyclopropyl[(4-methoxy-2,6-dimethylphenyl)sulfonyl]amino}methyl)-N-methyl-N-{[4-(pyrrolidin-1-ylmethyl)-1,3-thiazol-2-yl]methyl}-1,3-oxazole-4-carboxamide trifluoroacetate 2-({[(4-Methoxy-2,6-dimethylphenyl)sulfonyl](methyl)amino}methyl)-N-methyl-N-{[5-(pyrrolidin-1-ylmethyl)-1,3,4-thiadiazol-2-yl]methyl}-1,3-oxazole-4-carboxamide trifluoroacetate 2-({[(4-Methoxy-2,6-dimethylphenyl)sulfonyl](methyl)amino}methyl)-N-methyl-N-{[4-(pyrrolidin-1-ylmethyl)-1,3-thiazol-2-yl]methyl}-1,3-oxazole-4-carboxamide trifluoroacetate 2-({Cyclopropyl[(4-methoxy-2,6-dimethylphenyl)sulfonyl]amino}methyl)-N-methyl-N-{[6-(pyrrolidin-1-ylmethyl)pyridin-3-yl]methyl}-1,3-oxazole-4-carboxamide N-Cyclopropyl-N-{[4-({4-[4-(dimethylamino)butyl]piperazin-1-yl}carbonyl)-1,3-oxazol-2-yl]methyl}-4-methoxy-2,6-dimethylbenzenesulfonamide trifluoroacetate N-Cyclopropyl-4-methoxy-2,6-dimethyl-N-{[4-(octahydro-2H-pyrrolo[3,4-c]pyridin-2-ylcarbonyl)-1,3-oxazol-2-yl]methyl}benzenesulfonamide N-Cyclopropyl-4-methoxy-2,6-dimethyl-N-[(4-{[5-(1-methylpiperidin-4-yl)octahydro-2H-pyrrolo[3,4-c]pyridin-2-yl]carbonyl}-1,3-oxazol-2-yl)methyl]benzenesulfonamide trifluoroacetate N-[(4-{[5-(1-Azabicyclo[2.2.2]oct-3-yl)octahydro-2H-pyrrolo[3,4-c]pyridin-2-yl]carbonyl}-1,3-oxazol-2-yl)methyl]-N-cyclopropyl-4-methoxy-2,6-dimethylbenzenesulfonamide trifluoroacetate N-Cyclopropyl-4-methoxy-2,6-dimethyl-N-{[4-({3-[methyl(1-methylpiperidin-4-yl)amino]pyrrolidin-1-yl}carbonyl)-1,3-oxazol-2-yl]methyl}benzenesulfonamide trifluoroacetate N-Cyclopropyl-4-methoxy-N-{[4-({5-[(6-methoxypyridin-3-yl)methyl]hexahydropyrrolo[3,4-c]pyrrol-2(1H)-yl}carbonyl)-1,3-oxazol-2-yl]methyl}-2,6-dimethylbenzenesulfonamide trifluoroacetate N-Cyclopropyl-4-methoxy-N-{[4-({5-[(6-methoxypyridin-3-yl)methyl]octahydro-2H-pyrrolo[3,4-c]pyridin-2-yl}carbonyl)-1,3-oxazol-2-yl]methyl}-2,6-dimethylbenzenesulfonamide trifluoroacetate N-Cyclopropyl-4-methoxy-2,6-dimethyl-N-{[4-({5-[(6-pyrrolidin-1-ylpyridin-3-yl)methyl]octahydro-2H-pyrrolo[3,4-c]pyridin-2-yl}carbonyl)-1,3-oxazol-2-yl]methyl}benzenesulfonamide trifluoroacetate N-Cyclopropyl-4-methoxy-N-({4-[(3-{[(6-methoxypyridin-3-yl)methyl](methyl)amino}pyrrolidin-1-yl)carbonyl]-1,3-oxazol-2-yl}methyl)-2,6-dimethylbenzenesulfonamide trifluoroacetate 2-({Cyclopropyl[(2,6-dichlorophenyl)sulfonyl]amino}methyl)-N-{2-[4-(4,5-dihydro-1H-imidazol-2-yl)phenyl]ethyl}-N-methyl-1,3-oxazole-4-carboxamide trifluoroacetate 2-({Cyclopropyl[(2,4-dichlorophenyl)sulfonyl]amino}methyl)-N-{2-[4-(4,5-dihydro-1H-imidazol-2-yl)phenyl]ethyl}-N-methyl-1,3-oxazole-4-carboxamide trifluoroacetate 2-({Cyclopropyl[(2,4,6-trichlorophenyl)sulfonyl]amino}methyl)-N-{2-[4-(4,5-dihydro-1H-imidazol-2-yl)phenyl]ethyl}-N-methyl-1,3-oxazole-4-carboxamide trifluoroacetate 2-({Cyclopropyl[(2,4,6-trichlorophenyl)sulfonyl]amino}methyl)-N-methyl-N-[4-(pyrrolidin-1-ylmethyl)benzyl]-1,3-oxazole-4-carboxamide trifluoroacetate 2-({[(4-Chloro-2,5-dimethylphenyl)sulfonyl](cyclopropyl)amino}methyl)-N-{2-[4-(4,5-dihydro-1H-imidazol-2-yl)phenyl]ethyl}-N-methyl-1,3-oxazole-4-carboxamide trifluoroacetate 2-({[(4-Chloro-2,5-dimethylphenyl)sulfonyl](cyclopropyl)amino}methyl)-N-methyl-N-[4-(pyrrolidin-1-ylmethyl)benzyl]-1,3-oxazole-4-carboxamide trifluoroacetate 2-({[(2-Chloro-6-methylphenyl)sulfonyl](cyclopropyl)amino}methyl)-N-{2-[4-(4,5-dihydro-1H-imidazol-2-yl)phenyl]ethyl}-N-methyl-1,3-oxazole-4-carboxamide trifluoroacetate 2-({[(2-Chloro-6-methylphenyl)sulfonyl](cyclopropyl)amino}methyl)-N-methyl-N-[4-(pyrrolidin-1-ylmethyl)benzyl]-1,3-oxazole-4-carboxamide trifluoroacetate 2-[(Cyclopropyl{[2-(trifluoromethyl)phenyl]sulfonyl}amino)methyl]-N-{2-[4-(4,5-dihydro-1H-imidazol-2-yl)phenyl]ethyl}-N-methyl-1,3-oxazole-4-carboxamide trifluoroacetate 2-[(Cyclopropyl{[2-(trifluoromethyl)phenyl]sulfonyl}amino)methyl]-N-methyl-N-[4-(pyrrolidin-1-ylmethyl)benzyl]-1,3-oxazole-4-carboxamide trifluoroacetate N-Cyclopropyl-N-{[4-({4-hydroxy-4-[(4-methylpiperazin-1-yl)methyl]piperidin-1-yl}carbonyl)-1,3-oxazol-2-yl]methyl}-4-methoxy-2,6-dimethylbenzenesulfonamide trifluoroacetate N-Cyclopropyl-N-[(4-{[4-hydroxy-4-(morpholin-4-ylmethyl)piperidin-1-yl]carbonyl}-1,3-oxazol-2-yl)methyl]-4-methoxy-2,6-dimethylbenzenesulfonamide trifluoroacetate 2-({Cyclopropyl[(4-methoxy-2,6-dimethylphenyl)sulfonyl]amino}methyl)-N-methyl-N-[(2-methyl-2,3-dihydro-1H-isoindol-5-yl)methyl]-1,3-oxazole-4-carboxamide trifluoroacetate N-Cyclopropyl-4-methoxy-2,6-dimethyl-N-({4-[(4-pyridin-3-ylpiperazin-1-yl)carbonyl]-1,3-oxazol-2-yl}methyl)benzenesulfonamide N-Cyclopropyl-4-methoxy-2,6-dimethyl-N-[(4-{[4-(pyridin-2-ylmethyl)piperazin-1-yl]carbonyl}-1,3-oxazol-2-yl)methyl]benzenesulfonamide trifluoroacetate N-Cyclopropyl-4-methoxy-2,6-dimethyl-N-[(4-{[4-(2-pyridin-2-ylethyl)piperazin-1-yl]carbonyl}-1,3-oxazol-2-yl)methyl]benzenesulfonamide trifluoroacetate N-Cyclopropyl-4-methoxy-2,6-dimethyl-N-{[4-({4-[(4-methylpiperazin-1-yl)carbonyl]piperidin-1-yl}carbonyl)-1,3-oxazol-2-yl]methyl}benzenesulfonamide trifluoroacetate N-Cyclopropyl-4-methoxy-2,6-dimethyl-N-[(4-{[4-(piperidin-4-ylmethyl)piperazin-1-yl]carbonyl}-1,3-oxazol-2-yl)methyl]benzenesulfonamide trifluoroacetate N-Cyclopropyl-4-methoxy-2,6-dimethyl-N-({4-[(4-pyridin-4-ylpiperidin-1-yl)carbonyl]-1,3-oxazol-2-yl}methyl)benzenesulfonamide N-Cyclopropyl-N-{[4-({4-[(3-fluoropyridin-4-yl)methyl]piperazin-1-yl}carbonyl)-1,3-oxazol-2-yl]methyl}-4-methoxy-2,6-dimethylbenzenesulfonamide trifluoroacetate N-Cyclopropyl-N-{[4-({4-[(3,5-dichloropyridin-4-yl)methyl]piperazin-1-yl}carbonyl)-1,3-oxazol-2-yl]methyl}-4-methoxy-2,6-dimethylbenzenesulfonamide trifluoroacetate N-Cyclopropyl-N-{[4-({4-[(6-fluoropyridin-3-yl)methyl]piperazin-1-yl}carbonyl)-1,3-oxazol-2-yl]methyl}-4-methoxy-2,6-dimethylbenzenesulfonamide trifluoroacetate N-Cyclopropyl-4-methoxy-N-{[4-({4-[(6-methoxypyridin-3-yl)methyl]piperazin-1-yl}carbonyl)-1,3-oxazol-2-yl]methyl}-2,6-dimethylbenzenesulfonamide trifluoroacetate N-Cyclopropyl-4-methoxy-2,6-dimethyl-N-({4-[(4-{[6-(trifluoromethyl)pyridin-3-yl]methyl}piperazin-1-yl)carbonyl]-1,3-oxazol-2-yl}methyl)benzenesulfonamide trifluoroacetate N-Cyclopropyl-4-methoxy-2,6-dimethyl-N-{[4-({4-[(6-pyrrolidin-1-ylpyridin-3-yl)methyl]piperazin-1-yl}carbonyl)-1,3-oxazol-2-yl]methyl}benzenesulfonamide trifluoroacetate 2-({Cyclopropyl[(4-methoxy-2,6-dimethylphenyl)sulfonyl]amino}methyl)-N-(2-piperidin-3-ylethyl)-1,3-oxazole-4-carboxamide trifluoroacetate N-{[4-(4,4'-Bipiperidin-1-ylcarbonyl)-1,3-oxazol-2-yl]methyl}-N-cyclopropyl-4-methoxy-2,6-dimethylbenzenesulfonamide trifluoroacetate.

N-Cyclopropyl-N-{[4-({4-hydroxy-4-[(E)-2-pyridin-3-ylethenyl]piperidin-1-yl}carbonyl)-1,3-oxazol-2-yl]methyl}-4-methoxy-2,6-dimethylbenzenesulfonamide trifluoroacetate.

N-Cyclopropyl-N-{[4-({4-hydroxy-4-[(E)-2-pyridin-4-ylethenyl]piperidin-1-yl}carbonyl)-1,3-oxazol-2-yl]methyl}-4-methoxy-2,6-dimethylbenzenesulfonamide trifluoroacetate.

2-({Cyclopropyl[(4-methoxy-2,6-dimethylphenyl)sulfonyl]amino}methyl)-N-[3-(4-ethylpiperazin-1-yl)propyl]-1,3-oxazole-4-carboxamide trifluoroacetate.

2-({Cyclopropyl[(4-methoxy-2,6-dimethylphenyl)sulfonyl]amino}methyl)-N-methyl-N-[4-(4-methylpiperazin-1-yl)cyclohexyl]-1,3-oxazole-4-carboxamide trifluoroacetate 2-({Cyclopropyl[(4-methoxy-2,6-dimethylphenyl)sulfonyl]amino}methyl)-N-methyl-N-[3-(4-methylpiperazin-1-yl)cyclohexyl]-1,3-oxazole-4-carboxamide N-Cyclopropyl-4-methoxy-2,6-dimethyl-N-{[2-({4-[(1-methylpiperidin-4-yl)methyl]piperazin-1-yl}carbonyl)-1,3-oxazol-5-yl]methyl}benzenesulfonamide N-Cyclopropyl-N-({4-[(4-{[2-(dimethylamino)ethoxy]methyl}-4-hydroxypiperidin-1-yl)carbonyl]-1,3-oxazol-2-yl}methyl)-4-methoxy-2,6-dimethylbenzenesulfonamide trifluoroacetate N-Cyclopropyl-4-methoxy-2,6-dimethyl-N-{[4-({4-[(1-methylpyrrolidin-3-yl)oxy]piperidin-1-yl}carbonyl)-1,3-oxazol-2-yl]methyl}benzenesulfonamide N-Cyclopropyl-4-methoxy-2,6-dimethyl-N-{[4-({4-[(1-methylpiperidin-3-yl)oxy]piperidin-1-yl}carbonyl)-1,3-oxazol-2-yl]methyl}benzenesulfonamide trifluoroacetate N-Cyclopropyl-N-[(4-{[4-(1H-imidazol-4-ylmethyl)piperazin-1-yl]carbonyl}-1,3-oxazol-2-yl)methyl]-4-methoxy-2,6-dimethylbenzenesulfonamide N-Cyclopropyl-4-methoxy-2,6-dimethyl-N-{[4-({4-[(2-methyl-1H-imidazol-4-yl)methyl]piperazin-1-yl}carbonyl)-1,3-oxazol-2-yl]methyl}benzenesulfonamide N-Cyclopropyl-4-methoxy-2,6-dimethyl-N-{[4-({4-[(1-methyl-1H-imidazol-5-yl)methyl]piperazin-1-yl}carbonyl)-1,3-oxazol-2-yl]methyl}benzenesulfonamide N-Cyclopropyl-4-methoxy-2,6-dimethyl-N-{[4-({4-[(2-methylpyridin-4-yl)methyl]piperazin-1-yl}carbonyl)-1,3-oxazol-2-yl]methyl}benzenesulfonamide N-{[4-({4-[(2-Aminopyridin-3-yl)methyl]piperazin-1-yl}carbonyl)-1,3-oxazol-2-yl]methyl}-N-cyclopropyl-4-methoxy-2,6-dimethylbenzenesulfonamide N-Cyclopropyl-4-methoxy-2,6-dimethyl-N-[(4-{[4-(quinolin-3-ylmethyl)piperazin-1-yl]carbonyl}-1,3-oxazol-2-yl)methyl]benzenesulfonamide N-Cyclopropyl-4-methoxy-2,6-dimethyl-N-{[4-({4-[(3-methyl-1H-pyrazol-4-yl)methyl]piperazin-1-yl}carbonyl)-1,3-oxazol-2-yl]methyl}benzenesulfonamide N-Cyclopropyl-4-methoxy-2,6-dimethyl-N-{[4-({4-[(2-pyrrolidin-1-ylpyridin-4-yl)methyl]piperazin-1-yl}carbonyl)-1,3-oxazol-2-yl]methyl}benzenesulfonamide 2-({Cyclopropyl[(4-methoxy-2,6-dimethylphenyl)sulfonyl]amino}methyl)-N-methyl-N-[2-(pyridin-4-yloxy)ethyl]-1,3-oxazole-4-carboxamide 4-Methoxy-N,2,6-trimethyl-N-{[5-({4-[(1-methylpiperidin-4-yl)methyl]piperazin-1-yl}carbonyl)-1,3,4-oxadiazol-2-yl]methyl}benzenesulfonamide 4-Methoxy-N,2,6-trimethyl-N-[(5-{[4-(3-pyrrolidin-1-ylpropyl)piperazin-1-yl]carbonyl}-1,3,4-oxadiazol-2-yl)methyl]benzenesulfonamide 4-Methoxy-N-{[5-({4-[(6-methoxypyridin-3-yl)methyl]piperazin-1-yl}carbonyl)-1,3,4-oxadiazol-2-yl]methyl}-N,2,6-trimethylbenzenesulfonamide trifluoroacetate 4-Methoxy-N,2,6-trimethyl-N-{[5-({4-[(6-pyrrolidin-1-ylpyridin-3-yl)methyl]piperazin-1-yl}carbonyl)-1,3,4-oxadiazol-2-yl]methyl}benzenesulfonamide trifluoroacetate 4-Methoxy-N,2,6-trimethyl-N-({5-[(4-{[6-(trifluoromethyl)pyridin-3-yl]methyl}piperazin-1-yl)carbonyl]-1,3,4-oxadiazol-2-yl}methyl)benzenesulfonamide trifluoroacetate tert-Butyl 4-[(4-{[5-({[[(4-methoxy-2,6-dimethylphenyl)sulfonyl](methyl)amino}methyl)-1,3,4-oxadiazol-2-yl]carbonyl}piperazin-1-yl)methyl]piperidine-1-carboxylate 4-Methoxy-N,2,6-trimethyl-N-({5-[(4-{[1-(1-methylethyl)piperidin-4-yl]methyl}piperazin-1-yl)carbonyl]-1,3,4-oxadiazol-2-yl}methyl)benzenesulfonamide trifluoroacetate N-{[5-({4-[(1-Cyclobutylpiperidin-4-yl)methyl]piperazin-1-yl}carbonyl)-1,3,4-oxadiazol-2-yl]methyl}-4-methoxy-N,2,6-trimethylbenzenesulfonamide trifluoroacetate N-({5-[(4-{[1-(2-Hydroxy-2-methylpropyl)piperidin-4-yl]methyl}piperazin-1-yl)carbonyl]-1,3,4-oxadiazol-2-yl}methyl)-4-methoxy-N,2,6-trimethylbenzenesulfonamide N-{2-[4-(4,5-Dihydro-1H-imidazol-2-yl)phenyl]ethyl}-5-({[(4-methoxy-2,6-dimethylphenyl)sulfonyl](methyl)amino}methyl)-N-methyl-1,3,4-oxadiazole-2-carboxamide 5-({[(4-Methoxy-2,6-dimethylphenyl)sulfonyl](methyl)
amino}methyl)-N-methyl-N-[4-(pyrrolidin-1-ylmethyl)
benzyl]-1,3,4-oxadiazole-2-carboxamide trifluoroacetate N-{2-[4-(4,5-Dihydro-1H-imidazol-2-yl)phenyl]ethyl}-5-
({[(4-methoxy-2,6-dimethylphenyl)sulfonyl](methyl)
amino}methyl)-1,3,4-oxadiazole-2-carboxamide trifluoroacetate 4-Methoxy-N,2,6-trimethyl-N-[(5-{[4-(1-methylpiperidin-
4-yl)piperazin-1-yl]carbonyl}-1,3,4-oxadiazol-2-yl)methyl]benzenesulfonamide trifluoroacetamide N-Cyclopropyl-4-methoxy-2,6-dimethyl-N-[(5-{[4-(1-methylpiperidin-4-yl)piperazin-1-yl]carbonyl}-1,3,4-oxadiazol-2-yl)methyl]benzenesulfonamide N-Cyclopropyl-4-methoxy-2,6-dimethyl-N-{5-({4-[(1-methylpiperidin-4-yl)methyl]piperazin-1-yl}carbonyl)-1,3,4-oxadiazol-2-yl]methyl}benzenesulfonamide N-Cyclopropyl-4-methoxy-2,6-dimethyl-N-[(5-{[4-(3-pyrrolidin-1-ylpropyl)piperazin-1-yl]carbonyl}-1,3,4-oxadiazol-2-yl)methyl]benzenesulfonamide N-Cyclopropyl-4-methoxy-2,6-dimethyl-N-[(5-{[4-(2-pyrrolidin-1-ylethyl)piperidin-1-yl]carbonyl}-1,3,4-oxadiazol-2-yl)methyl]benzenesulfonamide N-Cyclopropyl-4-methoxy-2,6-dimethyl-N-{5-({4-[(1-methylpiperidin-3-yl)methyl]piperazin-1-yl}carbonyl)-1,3,4-oxadiazol-2-yl]methyl}benzenesulfonamide N-Cyclopropyl-N-{[5-({4-[3-(dimethylamino)propyl]piperazin-1-yl}carbonyl)-1,3,4-oxadiazol-2-yl]methyl}-4-methoxy-2,6-dimethylbenzenesulfonamide N-Cyclopropyl-4-methoxy-2,6-dimethyl-N-[(5-{[4-(2-pyrrolidin-1-ylethyl)piperazin-1-yl]carbonyl}-1,3,4-oxadiazol-2-yl)methyl]benzenesulfonamide 4-Methoxy-N,2,6-trimethyl-N-{[5-({4-[(1-methylpiperidin-3-yl)methyl]piperazin-1-yl}carbonyl)-1,3,4-oxadiazol-2-yl]methyl}benzenesulfonamide N-{[5-({4-[3-(Dimethylamino)propyl]piperazin-1-yl}carbonyl)-1,3,4-oxadiazol-2-yl]methyl}-4-methoxy-N,2,6-trimethylbenzenesulfonamide 4-Methoxy-N,2,6-trimethyl-N-[(5-{[4-(2-pyrrolidin-1-ylethyl)piperidin-1-yl]carbonyl}-1,3,4-oxadiazol-2-yl)methyl]benzenesulfonamide 5-({Cyclopropyl[(4-methoxy-2,6-dimethylphenyl)sulfonyl]
amino}methyl)-N-methyl-N-[4-(pyrrolidin-1-ylmethyl)
benzyl]-1,3,4-oxadiazole-2-carboxamide 5-({[(4-Methoxy-2,6-dimethylphenyl)sulfonyl](methyl)
amino}methyl)-N-{4-[(3-methoxypyrrolidin-1-yl)methyl]benzyl}-N-methyl-1,3,4-oxadiazole-2-carboxamide 5-({[(4-Methoxy-2,6-dimethylphenyl)sulfonyl](methyl)
amino}methyl)-N-{4-[(4-methoxypiperidin-1-yl)methyl]
benzyl}-N-methyl-1,3,4-oxadiazole-2-carboxamide 5-({[(4-Methoxy-2,6-dimethylphenyl)sulfonyl](methyl)
amino}methyl)-N-{4-[(3-methoxypiperidin-1-yl)methyl]
benzyl}-N-methyl-1,3,4-oxadiazole-2-carboxamide N-(4-{[3-(Dimethylamino)pyrrolidin-1-yl]methyl}benzyl)-
5-({[(4-methoxy-2,6-dimethylphenyl)sulfonyl](methyl)
amino}methyl)-N-methyl-1,3,4-oxadiazole-2-carboxamide 5-({[(4-Methoxy-2,6-dimethylphenyl)sulfonyl](methyl)
amino}methyl)-N-methyl-N-{[4-(pyrrolidin-1-ylmethyl)-
1,3-thiazol-2-yl]methyl}-1,3,4-oxadiazole-2-carboxamide N-{4-[(3-Methoxyazetidin-1-yl)methyl]benzyl}-5-({[(4-methoxy-2,6-dimethylphenyl)sulfonyl](methyl)
amino}methyl)-N-methyl-1,3,4-oxadiazole-2-carboxamide 5-({[(4-Methoxy-2,6-dimethylphenyl)sulfonyl](methyl)
amino}methyl)-N-methyl-N-[(2-methyl-2,3-dihydro-1H-isoindol-5-yl)methyl]-1,3,4-oxadiazole-2-carboxamide 5-({[(4-Methoxy-2,6-dimethylphenyl)sulfonyl](methyl)
amino}methyl)-N-methyl-N-[3-(pyrrolidin-1-ylmethyl)
benzyl]-1,3,4-oxadiazole-2-carboxamide 4-Methoxy-2,6-dimethyl-N-{5-[4-(1-methyl-piperidin-4-yl-methyl)-piperazine-1-carbonyl]-1,3,4-oxadiazol-2-ylmethyl}-benzenesulfonamide 4-Methoxy-2,6-dimethyl-N-($^2$H$_3$)methyl-N-{[5-({4-[(1-methylpiperidin-4-yl)methyl]piperazin-1-yl}carbonyl)-1,3,4-oxadiazol-2-yl]methyl}benzenesulfonamide trifluoroacetate 4-Methoxy-N,2,6-trimethyl-N-{[5-({4-[(2-methyl-1H-imidazol-4-yl)methyl]piperazin-1-yl}carbonyl)-1,3,4-oxadiazol-2-yl]methyl}benzenesulfonamide 4-Methoxy-N,2,6-trimethyl-N-{[5-({4-[(1-methyl-1H-imidazol-5-yl)methyl]piperazin-1-yl}carbonyl)-1,3,4-oxadiazol-2-yl]methyl}benzenesulfonamide 4-Methoxy-N,2,6-trimethyl-N-{[5-({4-[(2-methylpyridin-4-yl)methyl]piperazin-1-yl}carbonyl)-1,3,4-oxadiazol-2-yl]methyl}benzenesulfonamide N-{[5-({4-[(2-Aminopyridin-3-yl)methyl]piperazin-1-yl}carbonyl)-1,3,4-oxadiazol-2-yl]methyl}-4-methoxy-N,2,6-trimethylbenzenesulfonamide 4-Methoxy-N,2,6-trimethyl-N-[(5-{[4-(quinolin-3-ylmethyl)piperazin-1-yl]carbonyl}-1,3,4-oxadiazol-2-yl)methyl]benzenesulfonamide N-{[5-({4-[(6-Chloropyridin-3-yl)methyl]piperazin-1-yl}carbonyl)-1,3,4-oxadiazol-2-yl]methyl}-4-methoxy-N,2,6-trimethylbenzenesulfonamide 4-Methoxy-N,2,6-trimethyl-N-({5-[(4-{[1-(trifluoro acetyl)
piperidin-4-yl]methyl}piperazin-1-yl)carbonyl]-1,3,4-oxadiazol-2-yl}methyl)benzenesulfonamide trifluoroacetate N-{[5-({4-[4-(Dimethylamino)butyl]piperazin-1-yl}carbonyl)-1,3,4-oxadiazol-2-yl]methyl}-4-methoxy-N,2,6-trimethylbenzenesulfonamide trifluoroacetate 3-({[(4-Methoxy-2,6-dimethylphenyl)sulfonyl](methyl)
amino}methyl)-N-methyl-N-[4-(pyrrolidin-1-ylmethyl)
benzyl]-1,2,4-oxadiazole-5-carboxamide trifluoroacetamide N-{2-[4-(4,5-Dihydro-1H-imidazol-2-yl)phenyl]ethyl}-3-
({[(4-methoxy-2,6-dimethylphenyl)sulfonyl](methyl)
amino}methyl)-N-methyl-1,2,4-oxadiazole-5-carboxamide trifluoroacetamide 4-Methoxy-N,2,6-trimethyl-N-[(5-{[4-(1-methylpiperidin-4-yl)piperazin-1-yl]carbonyl}-1,2,4-oxadiazol-3-yl)methyl]benzenesulfonamide trifluoroacetate 4-Methoxy-N,2,6-trimethyl-N-{[5-({4-[(1-methylpiperidin-3-yl)methyl]piperazin-1-yl}carbonyl)-1,2,4-oxadiazol-3-yl]methyl}benzenesulfonamide trifluoroacetamide 4-Methoxy-N,2,6-trimethyl-N-[(5-{[4-(3-pyrrolidin-1-ylpropyl)piperazin-1-yl]carbonyl}-1,2,4-oxadiazol-3-yl)methyl]benzenesulfonamide trifluoroacetamide 4-Methoxy-N,2,6-trimethyl-N-{[5-({4-[(1-methylpiperidin-4-yl)methyl]piperazin-1-yl}carbonyl)-1,2,4-oxadiazol-3-yl]methyl}benzenesulfonamide trifluoroacetate 3-({Cyclopropyl[(4-methoxy-2,6-dimethylphenyl)sulfonyl]
amino}methyl)-N-methyl-N-[4-(pyrrolidin-1-ylmethyl)
benzyl]-1,2,4-oxadiazole-5-carboxamide trifluoroacetate 3-({Cyclopropyl[(4-methoxy-2,6-dimethylphenyl)sulfonyl]
amino}methyl)-N-methyl-N-{[4-(pyrrolidin-1-ylmethyl)-
1,3-thiazol-2-yl]methyl}-1,2,4-oxadiazole-5-carboxamide trifluoroacetate 4-Methoxy-N,2,6-trimethyl-N-[(5-{[4-(2-pyrrolidin-1-ylethyl)piperazin-1-yl]carbonyl}-1,2,4-oxadiazol-3-yl)methyl]benzenesulfonamide N-{[5-({4-[3-(Dimethylamino)propyl]piperazin-1-yl}carbonyl)-1,2,4-oxadiazol-3-yl]methyl}-4-methoxy-N,2,6-trimethylbenzenesulfonamide 4-Methoxy-N,2,6-trimethyl-N-[(5-{[4-(2-pyrrolidin-1-ylethyl)piperidin-1-yl]carbonyl}-1,2,4-oxadiazol-3-yl)methyl]benzenesulfonamide N-Cyclopropyl-4-methoxy-2,6-dimethyl-N-[(5-{[4-(1-methylpiperidin-4-yl)piperazin-1-yl]carbonyl}-1,2,4-oxadiazol-3-yl)methyl]benzenesulfonamide N-Cyclopropyl-4-methoxy-2,6-dimethyl-N-[(5-{[4-(2-pyrrolidin-1-ylethyl)piperidin-1-yl]carbonyl}-1,2,4-oxadiazol-3-yl)methyl]benzenesulfonamide 3-({Cyclopropyl[(4-methoxy-2,6-dimethylphenyl)sulfonyl]amino}methyl)-N-methyl-N-{[5-(pyrrolidin-1-ylmethyl)-1,3,4-thiadiazol-2-yl]methyl}-1,2,4-oxadiazole-5-carboxamide N-Cyclopropyl-4-methoxy-2,6-dimethyl-N-{[5-({4-[(1-methylpiperidin-4-yl)methyl]piperazin-1-yl}carbonyl)-1,2,4-oxadiazol-3-yl]methyl}benzenesulfonamide N-Cyclopropyl-4-methoxy-2,6-dimethyl-N-{[5-({4-[(1-methylpiperidin-3-yl)methyl]piperazin-1-yl}carbonyl)-1,2,4-oxadiazol-3-yl]methyl}benzenesulfonamide N-Cyclopropyl-N-{[5-({4-[3-(dimethylamino)propyl]piperazin-1-yl}carbonyl)-1,2,4-oxadiazol-3-yl]methyl}-4-methoxy-2,6-dimethylbenzenesulfonamide N-Cyclopropyl-4-methoxy-2,6-dimethyl-N-[(5-{[4-(3-pyrrolidin-1-ylpropyl)piperazin-1-yl]carbonyl}-1,2,4-oxadiazol-3-yl)methyl]benzenesulfonamide N-Cyclopropyl-4-methoxy-2,6-dimethyl-N-[(5-{[4-(2-pyrrolidin-1-ylethyl)piperazin-1-yl]carbonyl}-1,2,4-oxadiazol-3-yl)methyl]benzenesulfonamide N-{[5-({4-[4-(Dimethylamino)butyl]piperazin-1-yl}carbonyl)-1,2,4-oxadiazol-3-yl]methyl}-4-methoxy-N,2,6-trimethylbenzenesulfonamide trifluoroacetate N-Cyclopropyl-N-{[5-({4-[4-(dimethylamino)butyl]piperazin-1-yl}carbonyl)-1,2,4-oxadiazol-3-yl]methyl}-4-methoxy-2,6-dimethylbenzenesulfonamide trifluoroacetate 4-Methoxy-N,2,6-trimethyl-N-{[3-({4-[(1-methylpiperidin-4-yl)methyl]piperazin-1-yl}carbonyl)-1,2,4-oxadiazol-5-yl]methyl}benzenesulfonamide N-{[3-({4-[4-(Dimethylamino)butyl]piperazin-1-yl}carbonyl)-1,2,4-oxadiazol-5-yl]methyl}-4-methoxy-N,2,6-trimethylbenzenesulfonamide trifluoroacetate 4-Methoxy-N,2,6-trimethyl-N-[(3-{[4-(pyridin-3-ylmethyl)piperazin-1-yl]carbonyl}-1,2,4-oxadiazol-5-yl)methyl]benzenesulfonamide 5-({[(4-Methoxy-2,6-dimethylphenyl)sulfonyl](methyl)amino}methyl)-N-methyl-N-[3-(pyrrolidin-1-ylmethyl)benzyl]-1,2,4-oxadiazole-3-carboxamide trifluoroacetate 4-Methoxy-N,2,6-trimethyl-N-[(3-{[4-(3-pyrrolidin-1-ylpropyl)piperazin-1-yl]carbonyl}-1,2,4-oxadiazol-5-yl)methyl]benzenesulfonamide 4-Methoxy-N,2,6-trimethyl-N-[(5-{[4-(2-pyrrolidin-1-ylethyl)piperazin-1-yl]carbonyl}-1,3,4-thiadiazol-2-yl)methyl]benzenesulfonamide 4-Methoxy-N,2,6-trimethyl-N-[(5-{[4-(3-pyrrolidin-1-ylpropyl)piperazin-1-yl]carbonyl}-1,3,4-thiadiazol-2-yl)methyl]benzenesulfonamide N-{2-[4-(4,5-Dihydro-1H-imidazol-2-yl)phenyl]ethyl}-5-({[(4-methoxy-2,6-dimethylphenyl)sulfonyl](methyl)amino}methyl)-N-methyl-1,3,4-thiadiazole-2-carboxamide 5-({[(4-Methoxy-2,6-dimethylphenyl)sulfonyl](methyl)amino}methyl)-N-methyl-N-[4-(pyrrolidin-1-ylmethyl)benzyl]-1,3,4-thiadiazole-2-carboxamide N-{2-[4-(4,5-Dihydro-1H-imidazol-2-yl)phenyl]ethyl}-5-({[(4-methoxy-2,6-dimethylphenyl)sulfonyl](methyl)amino}methyl)-1,3,4-thiadiazole-2-carboxamide trifluoroacetamide 5-({[(4-Methoxy-2,6-dimethylphenyl)sulfonyl](methyl)amino}methyl)-N-methyl-N-[3-(pyrrolidin-1-ylmethyl)benzyl]-1,3,4-thiadiazole-2-carboxamide trifluoroacetate 4-Methoxy-N,2,6-trimethyl-N-[(5-{[4-(1-methylpiperidin-4-yl)piperazin-1-yl]carbonyl}-1,3,4-thiadiazol-2-yl)methyl]benzenesulfonamide trifluoroacetamide 4-Methoxy-N,2,6-trimethyl-N-{[5-({4-[(1-methylpiperidin-4-yl)methyl]piperazin-1-yl}carbonyl)-1,3,4-thiadiazol-2-yl]methyl}benzenesulfonamide N-Cyclopropyl-4-methoxy-2,6-dimethyl-N-[(5-{[4-(1-methylpiperidin-4-yl)piperazin-1-yl]carbonyl}-1,3,4-thiadiazol-2-yl)methyl]benzenesulfonamide N-Cyclopropyl-4-methoxy-2,6-dimethyl-N-{[5-({4-[(1-methylpiperidin-4-yl)methyl]piperazin-1-yl}carbonyl)-1,3,4-thiadiazol-2-yl]methyl}benzenesulfonamide N-Cyclopropyl-4-methoxy-2,6-dimethyl-N-[(5-{[4-(3-pyrrolidin-1-ylpropyl)piperazin-1-yl]carbonyl}-1,3,4-thiadiazol-2-yl)methyl]benzenesulfonamide N-Cyclopropyl-4-methoxy-2,6-dimethyl-N-[(5-{[4-(2-pyrrolidin-1-ylethyl)piperidin-1-yl]carbonyl}-1,3,4-thiadiazol-2-yl)methyl]benzenesulfonamide 4-Methoxy-N,2,6-trimethyl-N-{[5-({4-[(1-methylpiperidin-4-yl)methyl]piperazin-1-yl}carbonyl)-4H-1,2,4-triazol-3-yl]methyl}benzenesulfonamide.

Prodrugs of the compounds of the invention are also within the scope of the present invention. "Prodrug" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of a prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods.

Metabolites of compounds of formula (I) are also within the scope of the present invention.

Where tautomerism, like e.g. keto-enol tautomerism, of compounds of general formula (I) may occur, the individual forms, like e.g. the keto and enol form, are comprised separately and together as mixtures in any ratio. Same applies for stereoisomers, like e.g. enantiomers, cis/trans isomers, conformers and the like.

Isotopic labeled compounds of formula (I) are also within the scope of the present invention. Methods for isotope labeling are known in the art. Preferred isotopes are those of the elements H, C, N, O and S.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials.

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

The present invention provides compounds of general formula (I) as Bradykinin B1 antagonists. There utilities are described in detail in the utility section of WO-A 2006/132837, page 8, line 9 to page 12, line 2, which paragraph is herewith incorporated by reference.

Accordingly, compounds of the present inventions may be useful for the treatment or prophylaxis of pain and inflammation including visceral pain (like pancreatitis, interstitial cystitis, renal colic, prostatitis, chronic pelvic pain), neuropathic pain (including postherpetic neuralgia, acute zoster pain, nerve injury, the "dynias", including vulvodynia, phantom limb pain, root avulsions, radiculopathy, painful traumatic mononeuropathy, painful entrapment neuropathy, carpal tunnel syndrome, ulnar neuropathy, tarsal tunnel syndrome, painful diabetic neuropathy, painful polyneuropathy, trigeminal neuralgia), central pain syndromes (potentially caused by virtually any lesion at any level of the nervous system including but not limited to stroke, multiple sclerosis, spinal cord injury), and postsurgical pain syndromes (including postmastectomy syndrome, postthoracotomy syndrome, stump pain)), bone and joint pain (osteoarthritis), spine pain (including acute and chronic low back pain, neck pain, spinal stenosis), shoulder pain, repetitive motion pain, dental pain, sore throat, cancer pain, burn pain, myofascial pain (muscular injury, fibromyalgia), postoperative, perioperative pain and preemptive analgesia (including but not limited to general surgery, orthopedic, and gynecological), chronic pain, dysmenorrhea (primary and secondary), as well as pain associated with angina, and inflammatory pain of varied origins (including osteoarthritis, rheumatoid arthritis, rheumatic disease, teno-synovitis and gout, ankylosing spondylitis, bursitis); hyperreactive airways and to treat inflammatory events associated with airways disease like asthma including allergic asthma (atopic or non-atopic) as well as exercise-induced bronchoconstriction, occupational asthma, viral- or bacterial exacerbation of asthma, other non-allergic asthma and "wheezy-infant syndrome"; chronic obstructive pulmonary disease including emphysema, adult respiratory distress syndrome, bronchitis, pneumonia, allergic rhinitis (seasonal and perennial), and vasomotor rhinitis; pneumoconiosis, including aluminosis, anthracosis, asbestosis, chalicosis, ptilosis, siderosis, silicosis, tabacosis and byssinosis; inflammatory bowel disease including Crohn's disease and ulcerative colitis, irritable bowel syndrome, pancreatitis, nephritis, cystitis (interstitial cystitis), uveitis, inflammatory skin disorders including psoriasis and eczema, rheumatoid arthritis and edema resulting from trauma associated with burns, sprains or fracture, cerebral edema and angioedema (including hereditary angioedema and drug-induced angioedema including that caused by angiotensin converting enzyme (ACE) or ACE/neutral endopeptidase inhibitors like omepatrilat); diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion); spasm of the gastrointestinal tract or uterus; liver disease, multiple sclerosis, cardiovascular disease, including atherosclerosis, congestive heart failure, myocardial infarct; neurodegenerative diseases, including Parkinson's and Alzheimers disease, epilepsy, septic shock, headache including cluster headache, migraine including prophylactic and acute use, stroke, closed head trauma, cancer, sepsis, gingivitis, osteoporosis, benign prostatic hyperplasia and hyperactive bladder.

Furthermore, from recent research it can be expected that B1 is expressed in adipocytes under healthy condition, and the blockage of B1 receptor should show an anti-obesity role, due to reduction of insulin sensitivity in adipocytes and due to inhibition of insulin-mediated glucose transporter 4 (Glut4) translocation ($2^{nd}$ International Conference on "Exploring the Future of Vascular and Inflammatory Mediators"—Kinin 2007, 30 May-2 Jun., Max Delbrück Center (MDC) in Berlin; *Kinin B1 receptor: from gene cloning to a new function in adiposity*. By Pesquero, Brazil (T24, Award Lecture), *Kinin B1 receptor deficiency reduces insulin responsiveness and differentiation of adipocytes, and protects from high fat diet-induced obesity*. By Mori, Brazil/Germany (T17)).

Accordingly, compounds of the present invention may be useful for the treatment or prophylaxis of obesity.

Accordingly, the present invention provides compounds of formula (I) or pharmaceutically acceptable salts thereof for use as a medicament.

Furthermore, the compounds of the present invention can be used for the manufacture of a medicament for the treatment or prophylaxis of pain and inflammation including visceral pain (like pancreatitis, interstitial cystitis, renal colic, prostatitis, chronic pelvic pain), neuropathic pain (including postherpetic neuralgia, acute zoster pain, nerve injury, the "dynias", including vulvodynia, phantom limb pain, root avulsions, radiculopathy, painful traumatic mononeuropathy, painful entrapment neuropathy, carpal tunnel syndrome, ulnar neuropathy, tarsal tunnel syndrome, painful diabetic neuropathy, painful polyneuropathy, trigeminal neuralgia), central pain syndromes (potentially caused by virtually any lesion at any level of the nervous system including but not limited to stroke, multiple sclerosis, spinal cord injury), and postsurgical pain syndromes (including postmastectomy syndrome, postthoracotomy syndrome, stump pain), bone and joint pain (osteoarthritis), spine pain (including acute and chronic low back pain, neck pain, spinal stenosis), shoulder pain, repetitive motion pain, dental pain, sore throat, cancer pain, burn pain, myofascial pain (muscular injury, fibromyalgia), postoperative, perioperative pain and preemptive analgesia (including but not limited to general surgery, orthopedic, and gynecological), chronic pain, dysmenorrhea (primary and secondary), as well as pain associated with angina, and inflammatory pain of varied origins (including osteoarthritis, rheumatoid arthritis, rheumatic disease, teno-synovitis and gout, ankylosing spondylitis, bursitis); hyperreactive airways and to treat inflammatory events associated with airways disease like asthma including allergic asthma (atopic or non-atopic) as well as exercise-induced bronchoconstriction, occupational asthma, viral- or bacterial exacerbation of asthma, other non-allergic asthmas and "wheezy-infant syndrome"; chronic obstructive pulmonary disease including emphysema, adult respiratory distress syndrome, bronchitis, pneumonia, allergic rhinitis (seasonal and perennial), and vasomotor rhinitis; pneumoconiosis, including aluminosis, anthracosis, asbestosis, chalicosis, ptilosis, siderosis, silicosis, tabacosis and byssinosis; inflammatory bowel disease including Crohn's disease and ulcerative colitis, irritable bowel syndrome, pancreatitis, nephritis, cystitis (interstitial cystitis), uveitis, inflammatory skin disorders including psoriasis and eczema, rheumatoid arthritis and edema resulting from trauma associated with burns, sprains or fracture, cerebral edema and angioedema (including hereditary angioedema and drug-induced angioedema including that caused by angiotensin converting enzyme (ACE) or ACE/neutral endopeptidase inhibitors like omepatrilat); diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion); spasm of the gastrointestinal tract or uterus; liver disease, multiple sclerosis, cardiovascular disease, including atherosclerosis, congestive heart failure, myocardial infarct; neurodegenerative diseases, including Parkinson's and Alzheimers disease, epilepsy, septic shock, headache including cluster headache, migraine including prophylactic and acute use, stroke, closed head trauma, cancer, sepsis, gingivitis, osteoporosis, benign prostatic hyperplasia, hyperactive bladder; and obesity.

More preferred are the treatment or prophylaxis of pain and inflammation and the more specific diseases related to pain and inflammation.

The present invention also provides a method for treating, controlling, delaying or preventing in a mammalian patient in need of treatment one or more conditions selected from the group consisting of pain and inflammation including visceral pain (like pancreatitis, interstitial cystitis, renal colic, prostatitis, chronic pelvic pain), neuropathic pain (like postherpetic neuralgia, acute zoster pain, nerve injury, the "dynias", including vulvodynia, phantom limb pain, root avulsions, radiculopathy, painful traumatic mononeuropathy, painful entrapment neuropathy, carpal tunnel syndrome, ulnar neuropathy, tarsal tunnel syndrome, painful diabetic neuropathy, painful polyneuropathy, trigeminal neuralgia), central pain syndromes (potentially caused by virtually any lesion at any level of the nervous system including but not limited to stroke, multiple sclerosis, spinal cord injury), and postsurgical pain syndromes (including postmastectomy syndrome, postthoracotomy syndrome, stump pain)), bone and joint pain (osteoarthritis), spine pain (including acute and chronic low back pain, neck pain, spinal stenosis), shoulder pain, repetitive motion pain, dental pain, sore throat, cancer pain, burn pain, myofascial pain (muscular injury, fibromyalgia), postoperative, perioperative pain and preemptive analgesia (including but not limited to general surgery, orthopedic, and gynecological), chronic pain, dysmenorrhea (primary and secondary), as well as pain associated with angina, and inflammatory pain of varied origins (including osteoarthritis, rheumatoid arthritis, rheumatic disease, teno-synovitis and gout, ankylosing spondylitis, bursitis); hyperreactive airways and to treat inflammatory events associated with airways disease like asthma including allergic asthma (atopic or non-atopic) as well as exercise-induced bronchoconstriction, occupational asthma, viral- or bacterial exacerbation of asthma, other non-allergic asthmas and "wheezy-infant syndrome"; chronic obstructive pulmonary disease including emphysema, adult respiratory distress syndrome, bronchitis, pneumonia, allergic rhinitis (seasonal and perennial), and vasomotor rhinitis; pneumoconiosis, including aluminosis, anthracosis, asbestosis, chalicosis, ptilosis, siderosis, silicosis, tabacosis and byssinosis; inflammatory bowel disease including Crohn's disease and ulcerative colitis, irritable bowel syndrome, pancreatitis, nephritis, cystitis (interstitial cystitis), uveitis, inflammatory skin disorders including psoriasis and eczema, rheumatoid arthritis and edema resulting from trauma associated with burns, sprains or fracture, cerebral edema and angioedema (including hereditary angioedema and drug-induced angioedema including that caused by angiotensin converting enzyme (ACE) or ACE/neutral endopeptidase inhibitors like omepatrilat); diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion); spasm of the gastrointestinal tract or uterus; liver disease, multiple sclerosis, cardiovascular disease, including atherosclerosis, congestive heart failure, myocardial infarct; neurodegenerative diseases, including Parkinson's and Alzheimers disease, epilepsy, septic shock, headache including cluster headache, migraine including prophylactic and acute use, stroke, closed head trauma, cancer, sepsis, gingivitis, osteoporosis, benign prostatic hyperplasia, hyperactive bladder; and obesity.

The present invention provides pharmaceutical compositions comprising a compound of formula (I) or a pharmaceutically acceptable salt thereof as active ingredient together with a pharmaceutically acceptable carrier, optionally in combination with one or more other pharmaceutical compositions.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may comprise one or more additional compounds as active ingredients like one or more compounds of formula (I) not being the first compound in the composition or other Bradykinin B1 antagonists.

Other active ingredients are disclosed, e.g., in WO-A 2006/132837 under the paragraph "Combination Therapy" starting on page 12, which paragraph is herewith incorporated by reference.

The active ingredients may be comprised in one or more different pharmaceutical compositions (combination of pharmaceutical compositions).

The term "pharmaceutically acceptable salts" refers to salts prepared from pharmaceutically acceptable non-toxic bases or acids, including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

Available starting materials for the synthesis of preferred embodiments of the invention may be readily available by synthesis or they may be purchased from commercially available sources such as Array, Sigma Aldrich, Fluka, ABCR or be synthesized by one skilled in the art.

In general, compound of formula (I) may be prepared starting from compounds of formula (II).

Accordingly, a further aspect of the present invention is a method for the preparation of a compound of the present invention, comprising the step of
reacting a compound of formula (II)

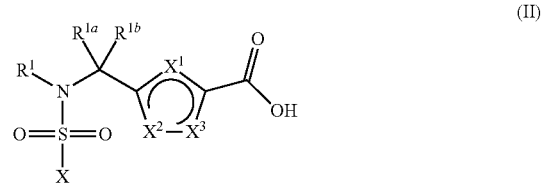

(II)

with a compound of formula $HN(R^2)R^3$ to yield a compound of formula (I).

More specific methods for the preparation of compounds of the present invention are described below, which are exemplary and may be combined.

EXAMPLES

Biological Evaluation

Calcium Flux Assay for Bradykinin B1 Antagonist

The potency to inhibit the Bradykinin B1 receptors was determined for the compounds of this invention in a cell-based fluorescent calcium-mobilization assay. The assay measures the ability of test compounds to inhibit Bradykinin B1 receptor agonist-induced increase of intracellular free $Ca^{2+}$ in cell lines expressing B1.

Specifically, calcium indicator-loaded cells are pre-incubated in the absence or presence of different concentrations of test compounds followed by the stimulation with a selective B1 receptor agonist peptide. The change of the intracellular $Ca^{2+}$ concentration is monitored with a specifically designed fluorescent plate reader (FlexStation, Molecular Devices).

CHO-K1 cell line expressing human B1 was purchased from Euroscreen (Gosselies, Belgium, with reference name hB1-D1). CHO-K1 cell lines expressing rat B1 or mouse B1 were established in the following way: the full-length receptor-coding cDNA clones were obtained by PCR performed on rat or mouse brain cDNAs. The respective cDNAs were cloned into an expression vector under the control of a CMV promotor. The resultant plasmids were introduced into CHO-K1 cells with liposome technology (FuGENE; Roche Diagnostics, Basel), according to the standard protocols described by the manufacturer. Cell lines expressing a Bradykinin receptor were selected in the culture medium containing 400 µg/ml G418 (Sigma). From selected cell populations, monoclonal cell lines were isolated by single cell cloning. The expression of Bradykinin receptors was confirmed by immunofluorescence staining of the cells, as well as by calcium flux assay.

Human B1-expressing cells were grown in Nutrient Mixture Ham's F12 (Sigma) containing 10% Foetal bovine serum (Sigma) and 400 µg/ml G418 (Sigma), 5 µg/ml puromycim (Sigma); Rat B1 and mouse B1-expressing cells were grown in DMEM/F12 medium (Sigma) containing 10% Foetal bovine serum (Sigma) and 400 µg/ml G418 (Sigma).

For the calcium flux assay, 80% confluent cells were detached from the culture vessels with Versene (Gibco; for human B1 cell-line) or with 1× trypsin-EDTA solution (Sigma; for rodent B1 cell-line), and seeded into 384-well plates (Cell binding Surface; Corning, N.Y.; #3683) at a density of 15,000 cells per well for human B1 or at a density of 20,000 cells per well for rodent B1. Cells were seeded in a volume of 50 µl in medium without antibiotics and incubated overnight in a humidified atmosphere with 5% $CO_2$ at 37° C. The following day, the medium was replaced with 20 µl of 5 µM Fluo-4AM dye (Molecular Probes) in assay buffer (2.5 mM probenicid, 1 mg/ml pluronic acid, 0.1% BSA, 135 mM NaCl, 5 mM KCl, 1.8 mM CaCl, 1 mM $MgCl_2$, 10 mM HEPES, 5.6 mM glucose, 0.05% gelatine, pH 7.4). The calcium indicator loaded cells were incubated at 37° C. for 2 hrs. Extracellular dye was then removed and each well was filled with 45 µl of assay buffer. Cell plates were kept in dark until used. Test compounds were assayed at 8 concentrations in triplicate. Serial 10-fold dilutions in 100% DMSO were made at a 100-times higher concentration than the final concentration, and then diluted 1:10 in assay buffer. 5 µl of each diluted compound was added to the well of cell plates (yielding final concentration with 1% DMSO), and incubated for 30 min at 25° C. before the addition of B1 agonist on the FlexStation.

Agonist plates contained the B1 agonist Lys-(Des-Arg)-Bradykinin (Bachem, Brackley) at $3.5 \times EC_{90}$ in assay buffer with 1% DMSO. The addition of agonist 20 µl per well to the assay plate was carried out on the FlexStation while continuously monitoring $Ca^{2+}$-dependent fluorescence at 538 nm. The integrated values, normalized with the background fluorescence, were plotted against the logarithm of the antagonist concentrations.

As observed, typical $EC_{50}$ values for the B1 agonist Lys-(Des-Arg)-Bradykinin were the following: 2 nM (human), 250 nM (rat) and 10 nM (mouse); typical $IC_{50}$ values for the B1 antagonist Lys-(Des-Arg-Leu)-Bradykinin (Bachem, Brackley) were 0.5 nM (human), 12 nM (rat) or 15 nM (mouse).

In the embodiment of the present invention, an active compound was selected from those that exhibited an $IC_{50}$ value against human B1 of <1 µM. Based on their levels of potency, the selected compounds are grouped in the present invention as below:
A=1000 nM-100 nM
B=100 nM-10 nM
C=<10 nM In addition, the Calcium flux Assay was carried out on part of the compounds utilizing IMR-90 human fetal lung fibroblasts (American Type Culture Collection, Rockville, Md.; and Coriell Institute, Camden, N.J.) as well as WI-38 fibroblasts (Coriell Institute, Camden, N.J.), that express native human B1 receptors after induction with human IL-1β.

The fibroblasts were cultured in complete growth media comprised of Dulbecco's modified Eagle's medium (DMEM; Sigma) containing 10%-20% fetal bovine serum, 4 mM L-glutamine, and 1% nonessential amino acids. The cells were maintained in a humidified atmosphere with 5% $CO_2$ at 37° C. and were sub-cultured at a ratio of 1:3, every other day.

For the assay, IMR-90 fibroblasts or WI-38 fibroblasts, respectively, were harvested using TrypLE Express (GIBCO/Invitrogen) and seeded into 384-well plates (Corning Cell-binding Surface, Cat. 3683) at a density of 15000 cells/well. The following day, cells were treated with 0.35 ng/ml human IL-1β in 10% FBS/MEM for four hours to up-regulate B1 receptors. Induced cells were loaded with fluorescent calcium indicator by incubation with 2.5 µM Fluo-4/AM (Invitrogen) at 37° C., 5% $CO_2$ for 1.5 h in the presence of 2.5 mM probenecid in 1% FBS/MEM. Extracellular dye was removed by washing with assay buffer (2.5 mM probenecid and 0.1% BSA in 20 mM HEPES/HBSS without bicarbonate or phenol red, pH 7.5). Test compounds were assayed at 8 concentrations in triplicate. After addition of test compounds to the cell plate and incubation for 5 min at 35° C., the addition of B1 agonist Lys-(Des-Arg)-Bradykinin (Bachem, Brackley) at a final concentration of 20 nM (EC90) was carried out on the FlexStation (Molecular Devices, Sunnyvale, Calif.) while continuously monitoring $Ca^{2+}$-dependent fluorescence at 538 nm. Peak height of agonist-induced fluorescence as a function of antagonist concentration was fitted sigmoidally (Prism; GraphPad Software Inc.) to determine IC50 values.

Bradykinin 1 Receptor Radioligand Binding Assay

The ability of the compounds to bind the B1 receptors was also demonstrated by radioligand binding assay.

The human fetal lung fibroblast cells IMR-90 American Type Culture Collection, Rockville, Md.; and Coriell Institute, Camden, N.J.) or WI-38 (Coriell Institute, Camden, N.J.), respectively, were cultured in complete growth media comprised of Dulbecco's modified Eagle's medium (DMEM; Sigma) containing 10% or 20% fetal bovine serum, 4 mM L-glutamine, and 1% nonessential amino acids. The cells were maintained in a humidified atmosphere with 5% $CO_2$ at 37° C., and were subcultured at a ratio of 1:3, at minimum twice weekly. To induce the expression of B1 receptors, the fibroblasts were treated with 0.35 ng/ml human IL-1β in 10% FBS/MEM for 4 hours and then washed with PBS before harvested.

For membrane preparation, the fibroblast cells were spun down at 160 g for 10 min at room temperature in $Ca^{2+}/Mg^{2+}$-free PBS (pH 7.4). The cell pellet was homogenised in 25 mM Tris-HCl (pH 7.4) containing 1 mM phenanthroline, 140 µg/ml Bacitracin and 2 µM Captopril, and the suspension was centrifuged at 50,000 g for 30 min at 4° C. (Beckman Coulter Ultracentrifuge, Rotor: TLS-55, 24000 rpm). The obtained pellet was resuspended in binding assay buffer (10 mM HEPES, pH7.4, 0.1% Pluronic F-127, 135 mM NaCl, 5 mM KCl, 1.8 mM CaCl $l_2$, 1 mM MgCl$_2$, 0.4 mM KH$_2$PO$_4$, 0.3 mM Na$_2$HPO$_4$, 1 mM Phenantroline; 2 µM Captopril, 140 µg/mL Bacitracin, and 0.1% BSA). Binding assays were performed at 25° C. in triplicate in a 96-well plate in a final volume of 0.1 ml. Membranes (40 µg/well) were incubated with [$^3$H]-desArg$^{10}$KD (ARC, Inc., St. Louis, USA) and various concentrations of test compound in the binding buffer for 1 h at room temperature. The incubations were terminated by filtration through GF/B filter plates (Ultima Gold, Packard Biosciences) pre-soaked in 0.3% polyethylenimine for 2 h at room temperature. The filter plate was dried at 37° C. for 30 min. Afterwards, the filter plate was washed three times with ice-cold binding buffer and three times with wash buffer (1M HEPES, pH 7.4 containing 4 M NaCl). The amount of bound radioactivity was determined by liquid scintillation counting in a Packard Topcount scintillation In addition, a radioligand binding assay was performed by using membranes prepared from CHO-K1 cells expressing the human B1 receptor (from Euroscreen, Gosselies, Belgium, with reference name hBl-D1).

For membrane preparation, the CHO-K1 cells were spun down at 340 g for 5 min at 4° C. in Ca$^{2+}$/Mg$^{2+}$-free PBS (pH 7.4). The cell pellet was homogenised in 25 mM Tris-HCl (pH 7.4) containing 1 mM phenanthroline, 140 µg/ml Bacitracin and 2 µM Captopril, and the suspension was centrifuged at 40,000 g for 20 min. The obtained membrane pellet was resuspended in binding assay buffer (10 mM HEPES, pH7.4, 0.1% Pluronic F-127, 135 mM NaCl, 5 mM KCl, 1.8 mM CaCl$_2$, 1 mM MgCl$_2$, 0.4 mM KH$_2$PO$_4$, 0.3 mM Na$_2$HPO$_4$, 1 mM Phenantroline, 2 µM Captopril, 140 µg/mL Bacitracin, and 0.1% BSA). Binding assays were performed as described above for the fibrobast cells, by using the membranes at 20 µg/well or 40 µg/well, respectively.

The K$_D$ of the radio-ligand used in the above radioligand binding assays was determined and displacement studies were carried out using a radioligand concentration of 1-1.5 times the determined K$_D$, e.g. in one case the K$_D$ of the radio-ligand used was determined to be 1.0 nM and displacement studies were carried out using a radioligand concentration of 1.5 nM. Nonspecific binding was determined using 5 µM desArg$^{10}$KD to block the radio-ligand binding.

For data analysis, IC$_{50}$ values were determined by a non-linear, least squares regression analysis using Data Analysis Toolbox (MDL Information Systems, San Leandro, Calif., USA), or using Prism (GraphPad Software Inc.).

REFERENCES

McEachern, A. E. et al. (1991) Expression cloning of a rat B2 bradykinin receptor. *Proc. Natl. Acad. Sci. USA* 88, 7724-28

Menke, J. G. et al. (1994) Expression cloning of a human B1 bradykinin receptor. *J. Biol. Chem.* 269, 21583-86

Leeb-Lundberg, L. M. et al. (2005) International Union of Pharmacology. XLV. Classification of the kinin receptor family: from molecular mechanisms to pathophysiological consequences. *Pharmacol. Rev.* 57, 27-77

Moreau, M. E et al. (2005) The kallikrein-kinin system: current and future pharmacological targets. *J Pharmacol Sci.* 99, 6-38

Campos, M. M. et al. (2006) Non-peptide antagonists for kinin B1 receptors: new insights into their therapeutic potential for the management of inflammation and pain. *Trends Pharmacol. Sci.* 27, 646-51

Chen, J. J. and Johnson, E. J. (2007) Targeting the bradykinin B1 receptor to reduce pain. *Expert Opin. Ther. Targets* 11, 21-35

Ferreira, J. et al. (2001) Evidence for the participation of kinins in freund's adjuvant-induced inflammatory and nociceptive responses in kinin B1 and B2 receptor knock-out mice. *Neuropharmacology* 41, 1006-12

Ferreira, J. et al. (2005) Reduced nerve injury-induced neuropathic pain in kinin B1 receptor knock-out mice. *J. Neurosci.* 25, 2405-2412

Fox, A. et al. (2005) Antihyperalgesic activity of a novel nonpeptide bradykinin B1 receptor antagonist in transgenic mice expressing the human B1 receptor. *Br. J. Pharmacol.* 144, 889-899

Gougat, J. et al. (2004) SSR240612 [(2R)-2-[((3R)-3-(1,3-benzodioxol-5-yl)-3-[[(6-methoxy-2-naphthyl)sulfonyl]amino]propanoyl)amino]-3-(4-[[(2R,6S)-2,6 dimethylpiperidinyl]methyl]phenyl)-N-isopropyl-Nmethylpropanamide hydrochloride], a new nonpeptide antagonist of the bradykinin B1 receptor: biochemical and pharmacological characterization. *J. Pharmacol. Exp. Ther.* 309, 661-669

Phagoo, S. B. (2001) Bradykinin B1 receptor up-regulation by interleukin-1beta and B1 agonist occurs through independent and synergistic intracellular signaling mechanisms in human lung fibroblasts. *J Pharmacol Exp Ther.* 298, 77-85.

Hawkinson, J. E. et al. (2007) Pharmacological, pharmacokinetic, and primate analgesic efficacy profile of the novel Bradykinin B1 receptor antagonist ELN441958. *J Pharmacol Exp Ther.* 322, 619-630.

Synthesis of Compounds

NMR Spectrometers Used:

Configuration of the Bruker DRX 500 MHz NMR (B114)

High performance digital NMR spectrometer, 2-channel microbay console and Windows XP host workstation running Topspin version 1.3.

Equipped with:

Oxford instruments magnet 11.74 Tesla (500 MHz proton resonance frequency)

B-VT 3000 temperature controller

GRASP II gradient spectroscopy accessory for fast acquisition of 2D pulse sequences Deuterium lock switch for gradient shimming 5 mm Broad Band Inverse geometry double resonance probe with automated tuning and matching (BBI ATMA). Allows $^1$H observation with pulsing/decoupling of nuclei in the frequency range $^{15}$N and $^{31}$P with $^2$H lock and shielded z-gradient coils.

Configuration of the Bruker DPX 250 MHz NMR (B114)

High performance one bay Bruker 250 MHz digital two channel NMR spectrometer console and Windows XP host workstation running XwinNMR version 3.5.

Equipped with:

Oxford instruments magnet 5.87 Tesla (250 MHz proton resonance frequency)

B-VT 3300 variable temperature controller unit

Four nucleus (QNP) switchable probe for observation of $^1$H, $^{13}$C, $^{19}$F and $^{31}$P with $^2$H lock Configuration of the Bruker AVANCE 400 MHz NMR (B111)

High performance one bay Bruker AVANCE 400 MHz digital two channel NMR spectrometer console Equipped with:

Bruker magnet 9.40 Tesla (400 MHz proton resonance frequency)

B-VT 3200 variable temperature controller unit

GRASP II gradient spectroscopy accessory for the generation of one field gradient of up to 50 Gauss cm$^{-1}$ Four nucleus (QNP) switchable probe for observation of $^1$H, $^{13}$C, $^{19}$F and $^{31}$P with $^2$H lock with z-gradient coils for gradient spectroscopy.

Configuration of the Bruker 300 MHz NMR

High performance digital NMR spectrophotometer, Avance 300 console and Windows XP host workstation running Topspin version 1.3.

Equipped with:

Bruker instruments magnet 7.0463 Tesla (300 MHz proton resonance frequency) Probe 5 mm, BBO BB-1 H/D with 1H, 13C, 15N and 31P nuclei.

LCMS Methods Used

LCMS Method a (2 Min Method)

|  | Generic 2 minute method | |
| --- | --- | --- |
| Column | Atlantis dC18 2.1 × 30 mm, 3 um | |
| Mobile phase | A - Formic acid (aq) 0.1% B - Formic acid (MeCN) 0.1% | |
| Flow rate | 1 mL/min | |
| Injection volume | 3 μl | |
| Detector | 215 nm (nominal) | |
|  | Time (min) | % Organic |
| Gradient | 0 | 5 |
|  | 1.50 | 100 |
|  | 1.60 | 100 |
|  | 1.61 | 5 |

LCMS Method B (3.5 Min Method)

|  | Standard 3.5 minute method | |
| --- | --- | --- |
| Column | Atlantis dC18 2.1 × 50 mm, 5 um | |
| Mobile phase | A - Formic acid (aq) 0.1% B - Formic acid (MeCN) 0.1% | |
| Flow rate | 1 mL/min | |
| Injection volume | 3 μl | |
| Detector | 215 nm (nominal) | |
|  | Time (min) | % Organic |
| Gradient | 0 | 5 |
|  | 2.5 | 100 |
|  | 2.7 | 100 |
|  | 2.71 | 5 |
|  | 3.0 | 5 |

LCMS Method C (7 Min Method)

|  | High resolution method' | |
| --- | --- | --- |
| Column | Waters Atlantis dC18 100 × 2.1 mm, 3 μm column 40° C. | |
| Mobile phase | A - 0.1% Formic acid (water) B - 0.1% Formic acid (MeCN) | |
| Flow rate | 0.6 mL/min | |
| Injection volume | 3 μl | |
| Detector | 215 nm (nominal) | |
|  | Time (min) | % Organic |
| Gradient | 0.00 | 5 |
|  | 5.00 | 100 |
|  | 5.40 | 100 |
|  | 5.42 | 5 |
|  | 7.00 | 5 |

LCMS Method D (10 Min Method)

|  |  | |
| --- | --- | --- |
| Column | Chromolith Speed Rod RP -18c 4.6 × 50 mm | |
| Mobile phase | A - Buffer + MeCN (95:5) Buffer: 0.01% ammonium acetate pH 5.00 (water) B - MeCN | |
| Flow rate | 1.5 mL/min | |
| Injection volume | 10 μl | |
| Detector | PDA detector Detection: Spectrum Max | |
|  | Time (min) | % Organic |
| Gradient | 0.00 | 5 |
|  | 0.60 | 5 |
|  | 5.00 | 95 |
|  | 8.00 | 95 |
|  | 8.50 | 5 |
|  | 10.0 | 5 |

LCMS Method E (15 Min Method)

|  |  | |
| --- | --- | --- |
| Column | Waters X-terra MS C-18 4.6 × 50 mm, 5 micron | |
| Mobile phase | A - Buffer + MeCN (95:5) Buffer: 0.01% ammonium acetate pH 5.00 (water) B - MeCN | |
| Flow rate | 1.0 mL/min | |
| Injection volume | 10 μl | |
| Detector | PDA detector Detection: Spectrum Max | |
|  | Time (min) | % Organic |
| Gradient | 0.00 | 5 |
|  | 1.00 | 5 |
|  | 7.00 | 95 |
|  | 12.0 | 95 |
|  | 13.0 | 5 |
|  | 15.0 | 5 |

Prep Methods Used:

Prep Method A

| Column | Waters SunFire Prep C18 OBD 5 um 19 × 100 mm |
| --- | --- |
| Mobile Phase | A - TFA (aq) 0.1% B - TFA (CH$_3$CN) 0.1% |

Prep Method B

| Column | Phenomenex Gemini C18 NX 5u 100 × 21.2 mm |
|---|---|
| Mobile Phase | A - 2 mM ammonium bicarbonate, buffered to pH10<br>B - MeCN:2 mM ammonium bicarbonate 95:5 |

Prep Method C

| Column | Waters SunFire Prep C18 OBD 5 um 19 × 100 mm |
|---|---|
| Mobile Phase | A - H$_2$O<br>B - CH$_3$CN |

Prep Method D

| Column | Waters SunFire Prep C18 OBD 5 um 19 × 100 mm |
|---|---|
| Mobile Phase | A - Water<br>B - Methanol |

Compound Naming

All compounds are named using ACD Labs 10.0 naming software which conforms to IUPAC naming protocols.

List of Abbreviations

AcOH acetic acid
AIBN azobisobutyronitrile
Boc$_2$O Di-tert-butyldicarbonate
br s broad singlet
cat catalytic
CC Column Chromatography (gravity)
CDI 1,1'-carbonyldiimidazole
DCC Dicyclohexylcarbodiimide
DCE 1,2-dichloroethane
DCM dichloromethane
DCU Dicyclohexylurea
DIAD Diisopropylazodicarboxylate
DIC N,N'-Diisopropylcarbodiimide
DIPEA N,N-diisopropylethylamine
DMAP N,N-dimethylpyridin-4-amine
DMSO Dimethylsulfoxide
EDCI N-(3-dimethylaminopropyl)-N'-ethylcarbodiimide hydrochloride
eq equivalent
Et$_2$O diethyl ether
EtOAc ethyl acetate
EtOH ethanol
FCC flash column chromatography
h hours
HOAt hydroxyazotriazole
HOBt hydroxybenzotriazole hydrate
IPA propan-2-ol
LCMS liquid chromatography and mass spectrometry
mCPBA m-chloroperbenzoic acid
MeCN acetonitrile
MeOH methanol
min minutes
mol/M mole/molar
MP-TsOH macroporous tosic acid
MW molecular weight
NBS N-Bromosuccinimide
NMM N-methylmorpholine
NMO N-methylmorpholine oxide
NMR nuclear magnetic resonance
PCC Pyridinium chlorochromate
PS-DIPEA polymer-supported N,N-diisopropylethylamine
PL-MIA polymer-supported methylisatoic anhydride
SCX strong cation exchange
STAB Sodium triacetoxyborohydride
TBAF tetra-n-butylammonium fluoride
TBAI tetra-n-butylammonium iodide
TBDMSCl tert-butyldimethylsilyl chloride
TEA triethylamine
TFA 2,2,2-trifluoroacetic acid
TFE 2,2,2-trifluoroethanol
THF tetrahydrofuran
TLC thin layer chromatography
Tosic p-toluene sulfonyl
TMS trimethylsilyl
TsCl p-toluenesulfonyl chloride General Procedures for the Syntheses of Amines General Procedure AP: Boc Protection of Long and Short Chain Amino Anilines To a stirred solution of amine (1.0 eq), TEA (2 eq) in DCM (25 vol) was added di-tert-butyl dicarbonate, (1.1 eq). The mixture was stirred overnight at ambient temperature. The mixture was concentrated in vacuo and purified by FCC eluting with EtOAc:Heptane, 1:3.

tert-butyl[2-(4-aminophenyl)ethyl]carbamate

Int 1

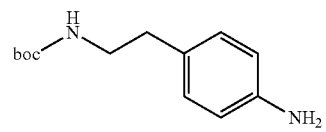

The title compound was prepared according to general procedure AP using 2-(4-aminophenyl)ethylamine (1.0 g, 7.3 mmol), TEA (2 mL, 14 mmol), DCM (25 mL), and di-tert-butyl dicarbonate (1.7 g, 7.7 mmol). The title product was obtained as a white solid.

No further purification was required.

Yield: 1.6 g, 92%.

tert-butyl (4-aminobenzyl)carbamate

Int2

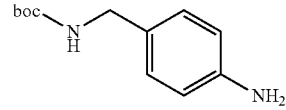

The title compound was prepared according to general procedure AP using 4-amino benzylamine (0.5 g, 4.1 mmol), TEA (1 mL, 8.2 mmol), DCM (12.5 mL), and di-tert-butyl dicarbonate (0.95 g, 0.38 mol). The title product was obtained as a white solid.

No further purification was required.

Yield: 0.850 g, 93%.

General Procedure AQ: Long and Short Chain Mukaiyamas

To a stirred solution of aniline (1.0 eq), TEA (2.2 eq) in DCM (25 vol) was added Mukaiyama's reagent, (1.2 eq). The mixture was stirred overnight at ambient temperature. The mixture was washed with water (50 vol) and extracted with DCM (2×30 vol). The combined organic extracts were dried over MgSO$_4$, and concentrated in vacuo. The residue was purified by FCC eluting with DCM:MeOH:NH$_3$, 92:7:1

2-[(4-{[(tert-butoxycarbonyl)amino]methyl}phenyl)amino]-1-methylpyridinium Iodide Int3

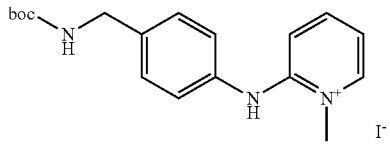

The title compound was prepared according to general procedure AQ using tert-butyl (4-aminobenzyl)carbamate (0.5 g, 2.2 mmol), TEA (0.7 mL, 4.9 mmol), DCM (12.5 mL), and Mukaiyama's reagent (0.7 g, 2.7 mmol). The title product was obtained as a yellow viscous oil. No further purification was required.
Yield: 0.93 g, 95%.
$^1$H NMR (250 MHz, CDCl$_3$) δ ppm 7.54 (1H, d, J=5.63 Hz), 7.27 (3H, m,), 7.12 (2H, d, J=8.07 Hz), 6.69 (1H, d, J=9.29 Hz), 6.30 (1H, t, J=6.40 Hz), 4.97 (1H, br. s.), 4.29 (2H, d, J=5.79 Hz), 3.93 (3H, s), 1.46 (9H, s)

2-[(4-{2-[(tert-butoxycarbonyl)amino]ethyl}phenyl)amino]-1-methylpyridinium Iodide Int 4

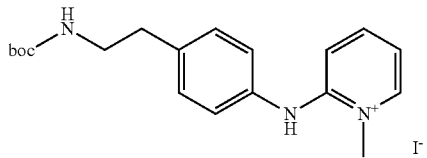

The title compound was prepared according to general procedure AQ using tert-butyl[2-(4-aminophenyl)ethyl]carbamate (0.20 g, 0.89 mmol), TEA (0.28 mL, 1.96 mmol), DCM (5 mL), and Mukaiyama's reagent (0.28 g, 1.07 mmol). The title product was obtained as a yellow viscous oil. No further purification was required.
Yield: 0.390 g, 95%.
$^1$H NMR (250 MHz, CDCl$_3$) δ ppm, 6.97-7.12 (3H, m), 6.70-6.91 (3H, m), 6.40 (1H, d, J=9.44 Hz), 5.75 (1H, t, J=6.55 Hz), 4.45 (1H, br. s.), 3.48 (3H, s), 3.29 (2H, q, J=6.45 Hz), 2.68 (2H, t, J=6.85 Hz), 2.00 (1H, br. s.), 1.37 (9H, s)

Aminochloropyrimidines

Int 5 & 6

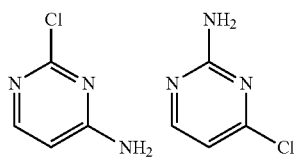

To 2,4-Dichloropyrimidine (1.0 g, 6.7 mmol) was added 28% w/v ammonium hydroxide solution (20 mL). The mixture was stirred overnight at ambient temperature then concentrated in vacuo. The residue was dry loaded and purified by FCC eluting with 2-10% EtOH in CHCl$_3$ to afford 2-amino-4-chloropyrimidine and 2-chloro-4-aminopyrimidine.
Yield: 2-amino-4-chloropyrimidine 200 mg, 23%; 2-chloro-4-aminopyrimidine 600 mg, 69%.

General Procedure AR: Pyrimidines

To a stirred solution of aniline (1.0 eq), in DMSO (10 vol) was added chloropyrimidine (1.2-1.8 eq). The mixture was stirred for 1.5 hours at 120° C. The mixture was cooled to ambient temperature, washed with saturated aqueous NaHCO$_3$ (50 vol) and extracted with EtOAc (2×30 vol). The combined organic extracts were washed with brine (50 vol), dried over MgSO$_4$, and concentrated in vacuo. The residue was purified by FCC eluting with DCM:MeOH:NH$_3$, 92:7:1.

tert-butyl (2-{4-[(4-aminopyrimidin-2-yl)amino]phenyl}ethyl)carbamate

Int 7

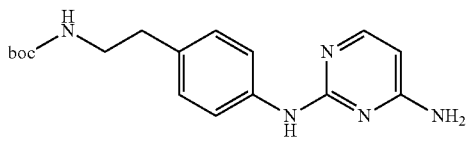

The title compound was prepared according to general procedure AR using tert-butyl[2-(4-aminophenyl)ethyl]carbamate (0.1 g, 0.42 mmol) DMSO (2 mL), and 2-chloro-4-aminopyrimidine (0.066 g, 0.51 mmol). The title product was obtained as a yellow oil.
Yield: 130 mg, 93%.
$^1$H NMR (250 MHz, CDCl$_3$) δ ppm 7.90 (1H, d, J=5.63 Hz), 7.79 (1H, br. s.), 7.46 (2H, d, J=8.38 Hz), 7.05 (2H, d, J=8.22 Hz), 5.88 (1H, d, J=5.63 Hz), 5.17 (2H, br. s.), 4.82 (1H, br. s.), 3.30 (2H, d, J=5.94 Hz), 2.69 (2H, t, J=7.01 Hz), 2.58 (2H, s), 1.41 (11H, s)

tert-butyl{4-[(4-aminopyrimidin-2-yl)amino]benzyl}carbamate

Int 8

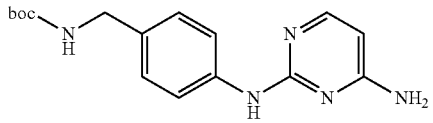

The title compound was prepared according to general procedure AR using tert-butyl (4-aminobenzyl)carbamate (0.1 g, 0.45 mmol) DMSO (2 mL), and 2-chloro-4-aminopyrimidine (1.8 eq. 0.1 g, 0.787 mmol). The title product was obtained as a yellow oil and was used in the next step without any further purification.
Yield: 100 mg, 70%.

tert-butyl (2-{4-[(2-aminopyrimidin-4-yl)amino]phenyl}ethyl)carbamate

Int 9

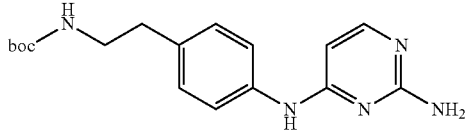

The title compound was prepared according to general procedure AR using tert-butyl[2-(4-aminophenyl)ethyl]carbamate (0.1 g, 0.45 mmol) DMSO (2 mL), and 2-chloro-4-aminopyrimidine (0.066 g, 0.51 mmol). The title product was obtained as a yellow oil.
Yield: 136 mg, 98%.

$^1$H NMR (500 MHz, CDCl$_3$) δ ppm 7.83 (1H, s), 7.76 (1H, d, J=5.87 Hz), 7.20 (2H, d, J=8.25 Hz), 7.06 (2H, d, J=8.07 Hz), 5.99 (1H, d, J=5.87 Hz), 5.32 (2H, br. s.), 5.03 (1H, br. s.), 3.28 (2H, d, J=6.05 Hz), 2.69 (2H, t, J=6.79 Hz), 1.38 (9H, br. s.)

4-[1-(tert-butoxycarbonyl)piperidin-3-yl]benzoic acid

Int 10

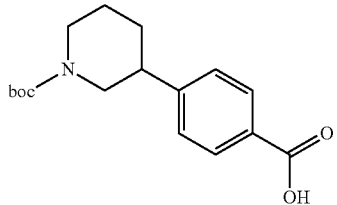

To a stirred solution of 4-piperidin-3-yl-benzoic acid (1.0 eq, 0.250 g, 1.18 mmol), TEA (2 eq, 0.335 mL, 2.36 mmol) in DCM (6.3 mL) was added di-tert-butyl dicarbonate, (0.273 g, 1.24 mmol). The mixture was stirred overnight at ambient temperature. The reaction was quenched by addition of N,N-dimethylethylenediamine (0.15 mL). The reaction mixture was washed with 10% w/v citric acid solution and extracted with DCM. The combined organic extracts were washed with saturated brine, dried over MgSO$_4$, and concentrated in vacuo to afford the product as a white solid. No further purification was required.

Yield: 348 mg, 96%.

tert-butyl 3-[4-(hydroxymethyl)phenyl]piperidine-1-carboxylate

Int 11

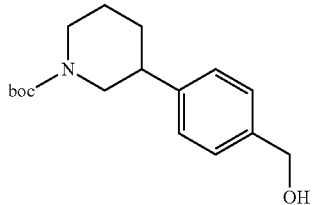

To a stirred solution of 4-[1-(tert-butoxycarbonyl)piperidin-3-yl]benzoic acid (0.866 g, 2.8 mmol), in THF (9 mL, 10 vol) at 0° C. under N$_2$ was added a solution of lithium aluminium hydride 1.0 M in THF (2.84 mL, 2.84 mmol). The mixture was stirred overnight at ambient temperature. The reaction was quenched by dropwise addition of an aqueous solution of 30% w/v Rochelle's salt until no further gas evolution could be observed. The mixture was filtered through celite and the filter cake washed with ethanol. The filtrate was concentrated in vacuo. The crude residue was purified by FCC eluting with DCM:MeOH:NH$_3$, 95:4.5:0.5. This afforded the title compound as a colourless oil.

Yield: 380 mg, 46% tert-butyl 3-(4-formylphenyl)piperidine-1-carboxylate

Int 12

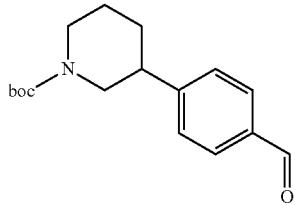

To a stirred solution of tert-butyl 3-[4-(hydroxymethyl)phenyl]piperidine-1-carboxylate (0.380 g, 1.30 mmol), in acetonitrile (8 mL) were added activated 4 Å molecular sieves (3-5 beads), TPAP (0.092 g, 0.261 mmol) and NMO (0.183 g, 1.57 mmol). The mixture was stirred under N$_2$ overnight at ambient temperature. The crude reaction mixture was purified by FCC eluting with Heptane:EtOAc, 4:1, to afford the product as a white solid.

Yield: 310 mg, 82%.

tert-Butyl 3-[4-(4,5-dihydro-1H-imidazol-2-yl)phenyl]piperidine-1-carboxylate

Int 13

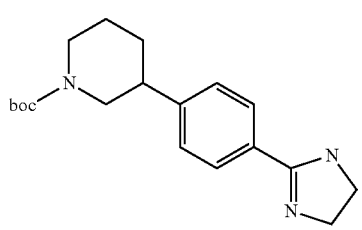

To a stirred solution of tert-butyl 3-(4-formylphenyl)piperidine-1-carboxylate (0.056 g, 0.194 mmol), in DCM (1 mL) was added 1,2-diamino ethane (0.012 g, 0.203 mmol). The mixture was stirred at ambient temperature for 30 min prior to addition of NBS (0.183 g, 1.57 mmol) and the mixture stirred overnight at ambient temperature. The reaction mixture was quenched by dropwise addition of saturated aqueous Na$_2$S$_2$O$_5$ until decolourisation of the solution is observed, then basified to pH 14 with 2N NaOH and extracted with DCM. The organic extract was dried over MgSO$_4$, and concentrated in vacuo to afford the product as a white solid. No further purification was required.

Yield: 52 mg, 81%

$^1$H NMR (250 MHz, CDCl$_3$) δ ppm 7.68 (2H, d, J=8.22 Hz), 7.18 (2H, d, J=8.38 Hz), 4.79 (2H, br. s.), 4.06 (2H, d, J=11.88 Hz), 3.69 (4H, s), 2.50-2.82 (3H, m) 1.95 (1H, d, J=0.30 Hz), 1.45-1.80 (2H, m), 1.42 (9H, s)

tert-Butyl[2-(4-{[(2-methylpropyl)amino]methyl}phenyl)ethyl]carbamate

Int 14

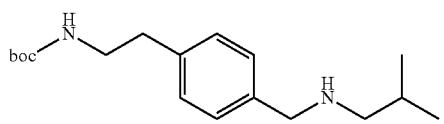

tert-butyl[2-(4-formylphenyl)ethyl]carbamate (0.060 g, 0.229 mmol) was dissolved in EtOH (3 mL) and isobutylamine (0.084 mg, 1.14 mmol) was added followed by Pd/C (10%, 12 mg, cat). The resultant suspension was purge-filled with nitrogen (3 cycles), then with hydrogen (3 cycles). The reaction was stirred for 3 hours maintaining constant pressure of hydrogen with a hydrogen balloon. The reaction mixture was filtered through Celite, the filter cake was washed with ethanol and the filtrate concentrated in vacuo. The residue was purified by FCC eluting with EtOAc/Heptane, 1:1.

Yield: 24 mg, 34%.

$^1$H NMR (250 MHz, CD$_3$OD) δ ppm 7.15 (2H, d, J=8.07 Hz), 7.07 (2H, d, J=8.07 Hz), 3.60 (2H, s), 3.14 (2H, t, J=7.39 Hz), 2.64 (2H, t, J=7.31 Hz), 2.26 (2H, d, J=7.01 Hz), 1.68 (1H, spt, J=6.7 Hz), 1.31 (9H, s), 0.80 (6H, d, J=6.70 Hz)

General Procedure AS for the De-Protection Boc-Amines

Thionyl chloride (3 eq) was added to stirred MeOH (5 vol) at 0° C. The resultant solution was added to the boc-amine (1 eq.) in MeOH (5 vol) and the mixture stirred at ambient temperature overnight. The reaction was concentrated in vacuo to afford the title amine as the HCl salt.

2-{[4-(Aminomethyl)phenyl]amino}-1-methylpyridinium iodide

Int 15

The title compound was prepared according to general procedure AS using 2-[(4-{[(tert-butoxycarbonyl)amino]methyl}phenyl)amino]-1-methylpyridinium iodide (0.3 g, 0.680 mmol) and thionyl chloride (0.098 mL, 1.361 mmol) in MeOH (3.0 mL).

Yield: 280 mg, quantitative.

2-{[4-(2-Aminoethyl)phenyl]amino}-1-methylpyridinium iodide

Int 16

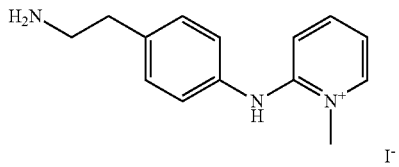 [SMILES: C[n+]1ccccc1Nc1ccc(CCN)cc1 ; [I-]]

The title compound was prepared according to general procedure AS using 2-[(4-{2-[(tert-butoxycarbonyl)amino]ethyl}phenyl)amino]-1-methylpyridinium iodide (0.2 g, 0.439 mmol) and thionyl chloride (0.063 mL, 0.878 mmol) in MeOH (2.0 mL)

Yield: 180 mg, quantitative.

$N^2$-[4-(2-Aminoethyl)phenyl]pyrimidine-2,4-diamine

Int 17

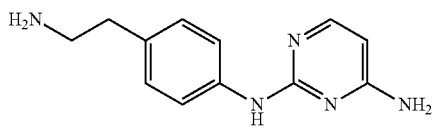 [SMILES: NCCc1ccc(Nc2nccc(N)n2)cc1]

The title compound was prepared according to general procedure AS using tert-butyl (2-{4-[(4-aminopyrimidin-2-yl)amino]phenyl}ethyl)carbamate (0.112 g, 0.357 mmol) and thionyl chloride (0.043 mL, 0.602 mmol) in MeOH (2.0 mL)

Yield: 103 mg, quantitative.

$N^2$-[4-(Aminomethyl)phenyl]pyrimidine-2,4-diamine

Int 18

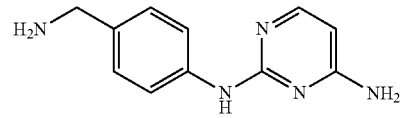 [SMILES: NCc1ccc(Nc2nccc(N)n2)cc1]

The title compound was prepared according to general procedure AS using tert-butyl {4-[(4-aminopyrimidin-2-yl)amino]benzyl}carbamate (0.100 g, 0.301 mmol) and thionyl chloride (0.043 mL, 0.602 mmol) in MeOH (2.0 mL)

Yield: 103 mg, quantitative.

$N^4$-[4-(2-Aminoethyl)phenyl]pyrimidine-2,4-diamine

Int 19

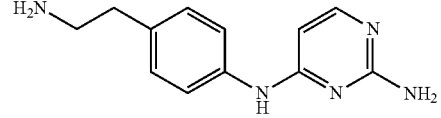 [SMILES: NCCc1ccc(Nc2ccnc(N)n2)cc1]

The title compound was prepared according to general procedure AS using tert-butyl (2-{4-[(2-aminopyrimidin-4-yl)amino]phenyl}ethyl)carbamate (0.136 g, 0.392 mmol) and thionyl chloride (0.043 mL, 0.602 mmol) in MeOH (2.0 mL)

Yield: 150 mg, quantitative.

3-[4-(4,5-Dihydro-1H-imidazol-2-yl)phenyl]piperidine

Int 20

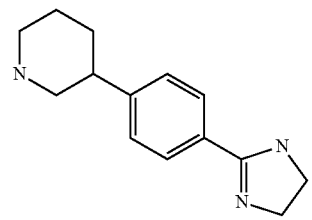 [SMILES: c1cc(C2CCCNC2)ccc1C1=NCCN1]

The title compound was prepared according to general procedure AS using tert-butyl 3-[4-(4,5-dihydro-1H-imidazol-2-yl)phenyl]piperidine-1-carboxylate (0.052 g, 0.158 mmol) and thionyl chloride (0.023 mL, 0.316 mmol) in MeOH (2.0 mL)

Yield: 48 mg, quantitative.

N-[4-(2-aminoethyl)benzyl]-2-methylpropan-1-amine

Int 21

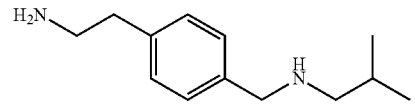

The title compound was prepared according to general procedure AS using tert-Butyl[2-(4-{[(2-methylpropyl)amino]methyl}phenyl)ethyl]carbamate (0.024 g, 0.098 mmol) and thionyl chloride (0.043 mL, 0.602 mmol) in MeOH (2.0 mL)

Yield: 27 mg, quantitative.

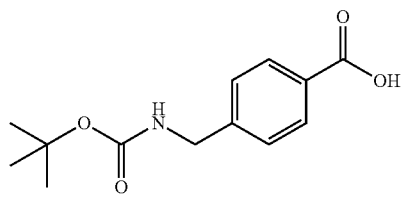 [SMILES: CC(C)(C)OC(=O)NCc1ccc(C(=O)O)cc1]

4-{[(tert-Butoxycarbonyl)amino]methyl}benzoic acid

Int 22
General Procedure BD 4-(aminomethyl)benzoic acid hydrochloride (8.0 g, 52 mmol) was dissolved in EtOH (200 mL) and the solution cooled to 10-15° C. and basified to pH 8 with 10% w/v NaOH solution. Boc$_2$O (12.7 g, 58 mmol) in EtOH (50 mL) was added dropwise at 15° C. and the reaction then stirred at ambient temperature for 11 h. The solvent was removed in vacuo and water (100 mL) added. The aqueous solution was extracted with EtOAc (100 mL) and the aqueous layer acidified to pH 1 with 5N HCl (aq). The aqueous layer was extracted with EtOAc (3×100 mL) and the combined organic extracts washed with saturated brine (100 mL). The solvent was removed in vacuo to afford the title compound as a white solid. No further purification was required.

Yield: 7.0 g, 52%.

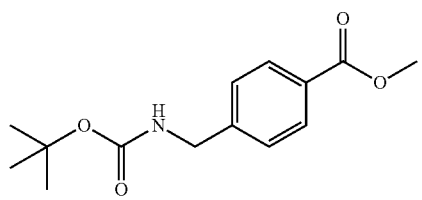 [SMILES: COC(=O)c1ccc(CNC(=O)OC(C)(C)C)cc1]

Methyl 4-{[(tert-butoxycarbonyl)amino]methyl}benzoate

Int 23
General Procedure BE

To a solution of 4-{[(tert-butoxycarbonyl)amino]methyl}benzoic acid (7.0 g, 27.8 mmol) in DCM (200 mL) was added HOBt (6.41 g, 41.8 mmol), MeOH (1.78 g, 55 mmol) and NMM (8.45 g, 83.6 mmol). This solution was cooled to 0° C. prior to addition of EDCI (10.69 g, 55 mmol) and the reaction stirred at ambient temperature overnight. The solvent was removed in vacuo, and the residue taken back up in DCM (200 mL). The organic solution was washed with 5% w/v KHSO$_4$ solution (100 mL), water (100 mL) and saturated brine (100 mL) then dried over Na$_2$SO$_4$. The solvent was removed in vacuo to afford the title compound, which required no further purification.

Yield: 5.0 g, 68%

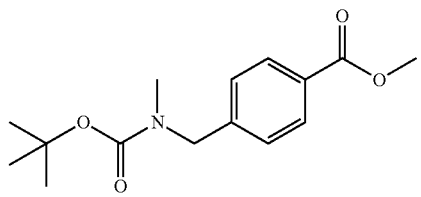 [SMILES: COC(=O)c1ccc(CN(C)C(=O)OC(C)(C)C)cc1]

Methyl 4-{[(tert-butoxycarbonyl)(methyl)amino]methyl}benzoate

Int 24

To a solution of NaH (60% dispersion in mineral oil, 0.9 g, 22 mmol) in DMF (10 mL) under a N$_2$ atmosphere was added methyl 4-{[(tert-butoxycarbonyl)amino]methyl}benzoate (5.0 g, 18.8 mmol) in DMF (40 mL) and MeI (3.21 g, 22 mmol) in DMF (10 mL). The reaction was stirred at room temperature for 3 h and cooled to 5-10° C. prior to addition of water (50 mL). The solution was extracted with EtOAc (3×50 mL) and the combined organic extracts washed with saturated brine solution (100 mL). The organic extracts were dried over Na$_2$SO$_4$ and the solvent removed in vacuo to afford the title compound as an oil. No further purification was required.

Yield: 4.0 g, 76%

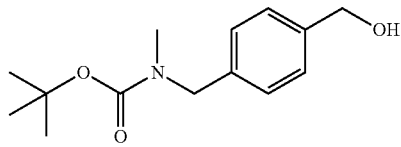 [SMILES: CN(Cc1ccc(CO)cc1)C(=O)OC(C)(C)C]

tert-Butyl[4-(hydroxymethyl)benzyl]methylcarbamate

Int 25
General Procedure BA

LiAlH$_4$ (6.5 g, 172 mmol) was dissolved in dry THF (120 mL) under a N$_2$ atmosphere. Methyl 4-{[(tert-butoxycarbonyl)(methyl)amino]methyl}benzoate (12.0 g, 43 mmol) in THF (30 mL) was added dropwise and the reaction stirred at ambient temperature for 5 min. The reaction was then cooled to 0° C. and a 1:1 mixture of THF/water added until no further effervescence could be observed. A solution of 10% w/v NaOH (20 mL) was added and the resulting slurry filtered. The residue was washed with EtOAc (100 mL) and the combined organic extracts dried with Na$_2$SO$_4$ to afford the title compound as an oil.

Yield: 9.9 g, 92%.

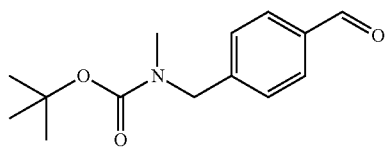 [SMILES: CN(Cc1ccc(C=O)cc1)C(=O)OC(C)(C)C]

tert-butyl (4-formylbenzyl)methylcarbamate

Int 26
General Procedure BB

To a solution of PCC (12.8 g, 59.5 mmol) in DCM (200 mL) was added a solution of tert-butyl [4-(hydroxymethyl)benzyl]methylcarbamate (10.0 g, 39.6 mmol) in DCM (100 mL). The reaction was stirred at ambient temperature for 5 min and then filtered through silica. The filtrate was washed with DCM and the solvent removed in vacuo to afford the title compound as an oil.

Yield: 8.0 g, 81%.

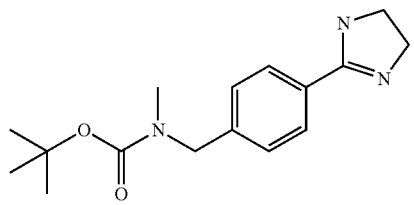 [SMILES: CN(Cc1ccc(C2=NCCN2)cc1)C(=O)OC(C)(C)C]

tert-Butyl[4-(4,5-dihydro-1H-imidazol-2-yl)benzyl]
methylcarbamate, oxalate salt Int 27
General Procedure BC To a solution of tert-butyl (4-formylbenzyl)methylcarbamate (8.0 g, 32.1 mmol) in DCM (75 mL) at 0° C. was added ethylene diamine (2.02 g, 33.7 mmol) in DCM (25 mL). The reaction was stirred at 0° C. for 20 min and NBS (5.97 g, 33.7 mmol) added in one portion. The reaction was stirred at ambient temperature for 11 h and then cooled to 0° C. prior to dropwise addition of 10% w/v NaOH solution (50 mL). The organic layer was separated and the aqueous layer washed with DCM (50 mL). The combined organic extracts were dried over Na$_2$SO$_4$ and concentrated in vacuo. The resulting crude oil was redissolved in EtOAc (100 mL) and oxalic acid (3.18 g, 35 mmol) added and the slurry stirred for 1 h. The resultant precipitate was filtered and washed with EtOAc (50 mL) and dried to afford title compound as the mono oxalate salt.

Yield: 3.5 g, 37%.

LCMS method D: r.t. 4.51/15 min, 98%, m/z 290.10 (M+H, 100%)

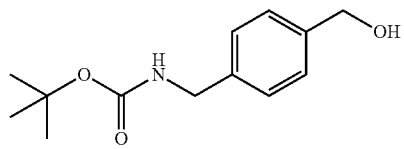 [SMILES: CC(C)(C)OC(=O)NCc1ccc(CO)cc1]

tert-Butyl[4-(hydroxymethyl)benzyl]carbamate

Int 28

The title compound was prepared according to general procedure BA using methyl 4-{[(tert-butoxycarbonyl)amino]methyl}benzoate (3.0 g, 11.3 mmol), LiAlH$_4$ (1.72 g, 0.045 mmol) and THF (50 mL). The resulting crude product was purified by CC eluting with 1:1 heptanes/EtOAc to afford the title compound as an oil.

Yield: 2.0 g, 71%.

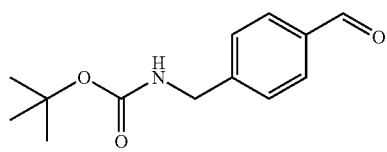 [SMILES: CC(C)(C)OC(=O)NCc1ccc(C=O)cc1]

tert-Butyl (4-formylbenzyl)carbamate

Int 29

The title compound was prepared according to general procedure BB using tert-butyl[4-(hydroxymethyl)benzyl]carbamate (1.0 g, 4.2 mmol), PCC (1.36 g, 6.3 mmol) and DCM (30 mL). No purification was required.

Yield: 600 mg, 57%.

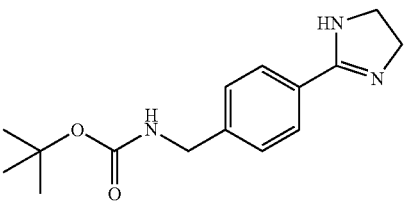 [SMILES: CC(C)(C)OC(=O)NCc1ccc(C2=NCCN2)cc1]

tert-butyl[4-(4,5-dihydro-1H-imidazol-2-yl)benzyl]
carbamate

Int 30

The title compound was prepared according to general procedure BC using tert-Butyl (4-formylbenzyl)carbamate (0.8 g, 3.4 mmol), ethylene diamine (0.22 mL, 3.4 mmol), NBS (0.6 g, 3.4 mmol) and DCM (25 mL). The resulting crude compound was used without any further purification.

Yield: 0.5 g, 53%

LCMS method D: r.t. 2.67/10 min, 94%, m/z 276.0 (M+H, 100%)

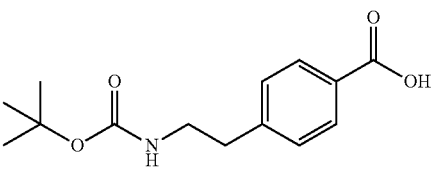 [SMILES: CC(C)(C)OC(=O)NCCc1ccc(C(=O)O)cc1]

4-{2-[(tert-butoxycarbonyl)amino]ethyl}benzoic
acid

Int 31

The title compound was prepared according to general procedure BD using 4-(2-aminoethyl)-benzoic acid (9.0 g, 54.5 mmol), Boc$_2$O (13.1 g, 60 mmol), 10% w/v aqueous NaOH and EtOH (150 mL). The title compound was obtained as an off-white solid, which required no further purification.

Yield: 12.5 g, 86%

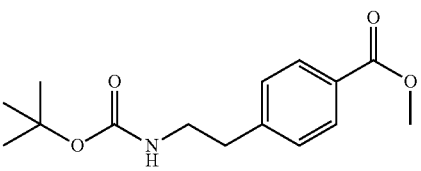 [SMILES: COC(=O)c1ccc(CCNC(=O)OC(C)(C)C)cc1]

Methyl 4-{2-[(tert-butoxycarbonyl)amino]
ethyl}benzoate

Int 32

The title compound was prepared according to general procedure BE using 4-{2-[(tert-butoxycarbonyl)amino]

ethyl}benzoic acid (10 g, 37.7 mmol), HOBt (8.66 g, 56.6 mmol), EDCI (14.57 g, 75.4 mmol), NMM (11.4 g, 113 mmol), MeOH (2.41 g, 75.4 mmol) and DCM (200 mL). The title compound was obtained as a yellow solid, which required no further purification.

Yield: 10.6 g, 92%

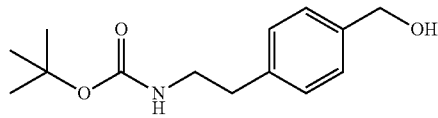 [SMILES: CC(C)(C)OC(=O)NCCc1ccc(CO)cc1]

tert-butyl {2-[4-(hydroxymethyl)phenyl]ethyl}carbamate

Int 33

The title compound was prepared according to general procedure BA using methyl 4-{2-[(tert-butoxycarbonyl)amino]ethyl}benzoate (5.0 g, 17.9 mmol), LiAlH$_4$ (2.72 g, 71.6 mmol) and THF (125 mL). The crude product was purified by CC eluting with 1:1 hexane/EtOAc.

Yield: 3.0 g, 66%.

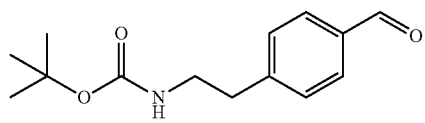 [SMILES: CC(C)(C)OC(=O)NCCc1ccc(C=O)cc1]

tert-butyl[2-(4-formylphenyl)ethyl]carbamate

Int 34

The title compound was prepared according to general procedure BB using tert-butyl {2-[4-(hydroxymethyl)phenyl]ethyl}carbamate (2.0 g, 7.9 mmol), PCC (2.57 g, 11.9 mmol) and DCM (50 mL). The crude product was purified by CC eluting with 2% MeOH in DCM.

Yield: 1.0 g, 50%.

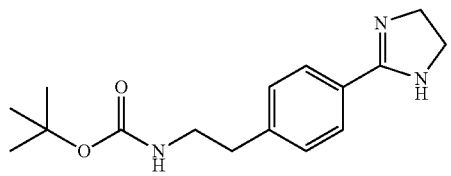 [SMILES: CC(C)(C)OC(=O)NCCc1ccc(C2=NCCN2)cc1]

tert-Butyl {2-[4-(4,5-dihydro-1H-imidazol-2-yl)phenyl]ethyl}carbamate

Int 35

The title compound was prepared according to general procedure BC using tert-butyl[2-(4-formylphenyl)ethyl]carbamate (0.8 g, 3.21 mmol), ethylene diamine (0.2 g, 3.37 mmol), NBS (0.6 g, 3.37 mmol) and DCM (20 mL). The crude product was purified by CC eluting with 1:4:95 NH$_3$/MeOH/DCM.

Yield: 0.81 g, 87%
LCMS method D: r.t. 2.89/10 min, 96%, m/z 290.08 (M+H, 100%)

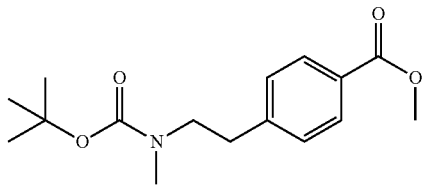 [SMILES: COC(=O)c1ccc(CCN(C)C(=O)OC(C)(C)C)cc1]

Methyl 4-{2-[(tert-butoxycarbonyl)(methyl)amino]ethyl}benzoate

Int 36

NaH (11.2 g, 377 mmol) was dissolved in dry DMF (175 mL) at 0° C. under a N$_2$ atmosphere. 4-{2-[(tert-Butoxycarbonyl)amino]ethyl}benzoic acid (25.0 g, 94.3 mmol) in DMF (100 mL) at 0° C. was added dropwise and the reaction stirred at 0° C. for 1 h. MeI (66.45 g, 377 mmol) was added dropwise at 0° C. and the reaction was stirred at ambient temperature overnight. The solvent was removed in vacuo and the residue diluted with water (100 mL). The aqueous solution was extracted with EtOAc (4×100 mL) and the combined organic extracts washed with water (100 mL) and saturated brine (100 mL) and dried over Na$_2$SO$_4$. The solvent was removed in vacuo to afford the title compound as a pale yellow oil. No further purification was required.

Yield: 24.0 g, 86%.

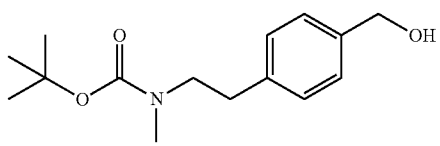 [SMILES: CN(CCc1ccc(CO)cc1)C(=O)OC(C)(C)C]

tert-Butyl {2-[4-(hydroxymethyl)phenyl]ethyl}methylcarbamate

Int 37

The title compound was prepared according to general procedure BA using methyl 4-{2-[(tert-butoxycarbonyl)(methyl)amino]ethyl}benzoate (16.0 g, 54.6 mmol), 2 M LiAlH$_4$ in THF (109 mL, 218 mmol) and THF (160 mL). The crude product was purified by CC eluting with 15% EtOAc in hexane to afford the title compound.

Yield: 7.0 g, 48%.

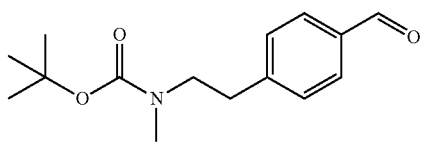 [SMILES: CN(CCc1ccc(C=O)cc1)C(=O)OC(C)(C)C]

tert-Butyl[2-(4-formylphenyl)ethyl]methylcarbamate

Int 38

The title compound was prepared according to general procedure BB using tert-butyl {2-[4-(hydroxymethyl)phenyl]ethyl}methylcarbamate (8.8 g, 33.2 mmol), PCC (10.7 g, 49.8 mmol) and DCM (220 mL). The crude product was purified by CC eluting with 1:1 EtOAc/hexane.

Yield: 8.0 g, 92%

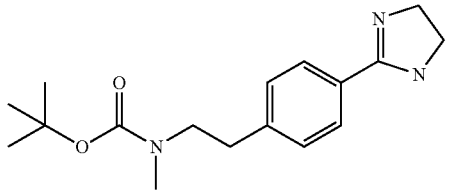 [SMILES: CN(CCc1ccc(C2=NCCN2)cc1)C(=O)OC(C)(C)C]

tert-Butyl[2-(4-formylphenyl)ethyl]methylcarbamate

Int 39

The title compound was prepared according to general procedure BC using tert-butyl[2-(4-formylphenyl)ethyl]methylcarbamate (8.0 g, 30.4 mmol), ethylene diamine (1.83 g, 30.4 mmol), NBS (5.4 g, 30.4 mmol) and DCM (150 mL). The crude product was purified by CC eluting with 2:5:93 $NH_3$/MeOH/DCM. The yellow oil thus obtained was triturated with $Et_2O$ to afford the title compound as a white solid.

Yield: 7.1 g, 77%.

LCMS method D: r.t. 3.06/10 min, 97%, m/z 304.1 (M+H, 100%)

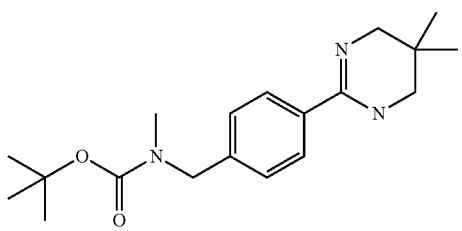 [SMILES: CN(Cc1ccc(C2=NCC(C)(C)CN2)cc1)C(=O)OC(C)(C)C]

tert-Butyl[4-(5,5-dimethyl-1,4,5,6-tetrahydropyrimidin-2-yl)benzyl]methylcarbamate Int 40 tert-Butyl[4-(4,5-dihydro-1H-imidazol-2-yl)benzyl]methylcarbamate (0.1 g, 0.35 mmol) was suspended in 2,2-dimethyl-1,3-diaminopropane (1 mL, excess). The slurry was heated to 155° C. for 1 h and cooled. Excess diamine was removed by distillation at 80° C. The resultant title product was used without any further purification.

Yield: 0.1 g, 98%.

LCMS method D: r.t. 3.36/10 min, 88%, m/z 332.12 (M+H, 100%)

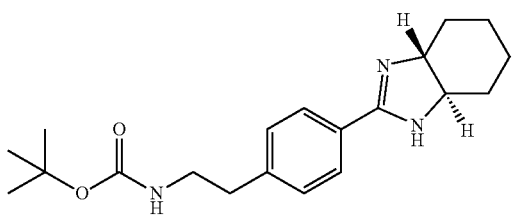 [SMILES: CC(C)(C)OC(=O)NCCc1ccc(C2=N[C@@H]3CCCC[C@H]3N2)cc1]

tert-butyl (2-{4-[(3aR,7aR)-3a,4,5,6,7,7a-hexahydro-1H-benzimidazol-2-yl]phenyl}ethyl)carbamate Int 41 tert-butyl[2-(4-formylphenyl)ethyl]carbamate (1.0 g, 3.58 mmol) and 1,2-diaminocyclohexane (0.4 g, 3.58 mmol) were dissolved in toluene (50 mL) and the solution refluxed for 15 h. The reaction was cooled and NBS (0.64 g, 3.58 mmol) was added in one portion and the reaction stirred at ambient temperature for 8 h. The pH of the reaction mixture was adjusted to 12 with 10% w/v NaOH and extracted with DCM (2×50 mL). The combined organic extracts were dried over $Na_2SO_4$ and the solvent removed in vacuo. The crude product was purified by CC eluting with MeOH/DCM.

Yield: 380 mg, 31%

LCMS method D: r.t. 3.51/10 min, 93%, m/z 344.10 (M+H, 100%)

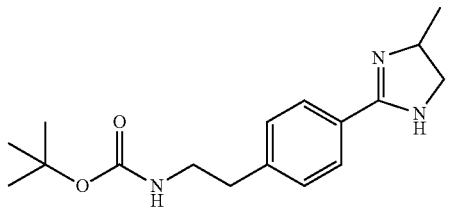 [SMILES: CC1CNC(c2ccc(CCNC(=O)OC(C)(C)C)cc2)=N1]

tert-Butyl {2-[4-(4-methyl-4,5-dihydro-1H-imidazol-2-yl)phenyl]ethyl}carbamate

Int 42

The title compound was prepared according to general procedure BC using tert-butyl[2-(4-formylphenyl)ethyl]carbamate (2.7 g, 10.8 mmol), 1,2-diaminopropane (1.0 mL, 10.8 mmol), NBS (1.91 g, 10.8 mmol) and DCM (75 mL). The title compound required no further purification.

Yield: 200 mg, 99%

LCMS method D: r.t. 3.07/10 min, 99%, m/z 304.05 (M+H, 100%)

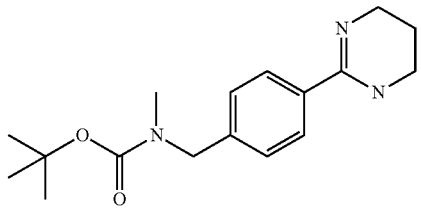 [SMILES: CN(Cc1ccc(C2=NCCCN2)cc1)C(=O)OC(C)(C)C]

tert-Butyl methyl[4-(1,4,5,6-tetrahydropyrimidin-2-yl)benzyl]carbamate

Int 43 tert-Butyl[4-(4,5-dihydro-1H-imidazol-2-yl)benzyl]methylcarbamate (0.2 g, 0.69 mmol) was suspended in 1,3-diaminopropane (2 mL, excess). The slurry was heated to 145° C. for 3 h and cooled. Excess diamine was removed by high vacuum distillation. The resultant title product was used without any further purification.

Yield: 0.2 g, 87%

LCMS method E: r.t. 4.59/15 min, 99%, m/z 304.0 (M+H, 100%)

Furan Synthesis

Scheme 1 describes the general synthesis of furan derivatives.

($R^1$=Me, Et, cyclopropyl, isopropyl, cyclopropylmethyl, cyclobutyl, phenyl; $R^{1a}$=$R^{1b}$=H; X=various sulfonamides; $X^1$=$X^3$=CH; $X^2$=O; $NR^2R^3$=various amines)

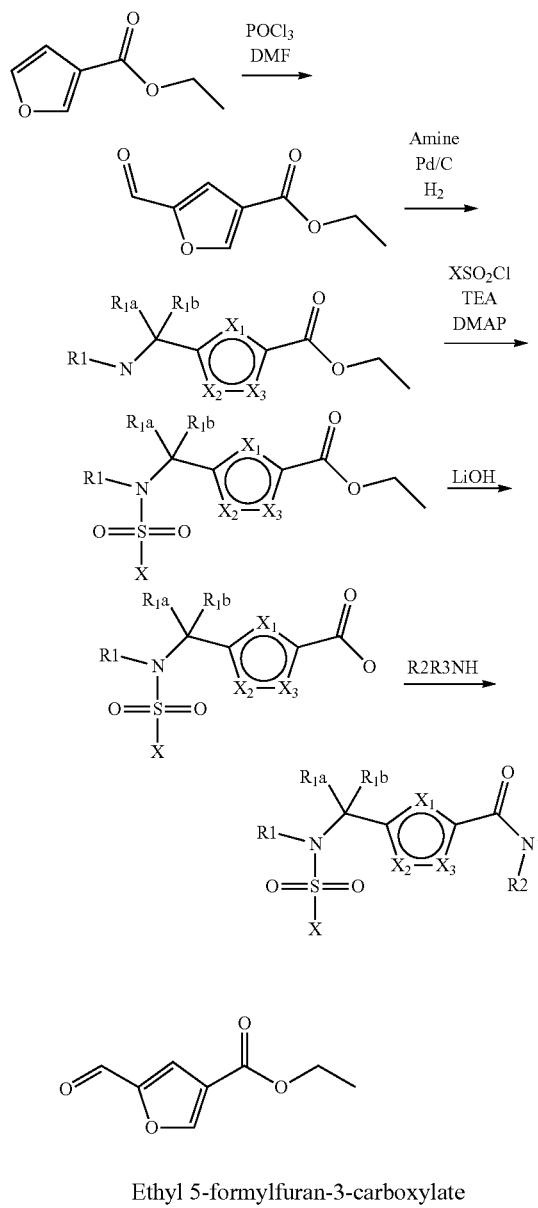

Ethyl 5-formylfuran-3-carboxylate

Int 44

To a vigorously stirred solution of 3-ethyl furoate (25 g, 0.162 mol) in dry DMF (21.4 mL, 0.275 mol) at 0° C. under $N_2$ was added $POCl_3$ (19.7 mL, 0.211 mol) dropwise such that the reaction temperature did not exceed 10° C. When addition was complete, the flask and its contents were transferred to a heating mantle and the reaction heated for 1 h at 120° C. under $N_2$. The reaction was cooled and poured into a 5 L conical flask containing a 1:1:1 mixture of 35% w/w NaOH (aq), sat aq $K_2CO_3$ and ice water (1 L) and DCM (1 L). The DCM layer was washed with water (2×500 mL) and dried over $MgSO_4$. DCM and DMF were removed in vacuo and the resulting oil purified by dry flash chromatography, eluting with 500 mL volumes of 10% EtOAc in heptanes. This afforded the title compound and its regioisomers as a yellow oil. Upon standing, the desired regioisomers was observed to crystallise. The crystals were filtered and washed with 20% $Et_2O$ in heptanes.

Yield: 2.04 g, 7%.

$^1$H NMR (500 MHz, $CDCl_3$) δ ppm 9.70 (1H, S), 8.21 (1H, s), 7.51 (1H, s), 4.38 (2H, q, J 7.18), 1.39 (3H, t, J 7.18)

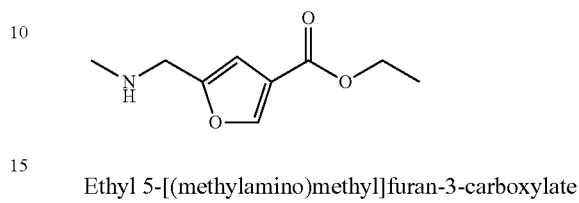

Ethyl 5-[(methylamino)methyl]furan-3-carboxylate

Int 45

Ethyl 5-formylfuran-3-carboxylate (3.2 g, 19.0 mmol) was dissolved in EtOH (60 mL) and 33% $MeNH_2$ in EtOH (5.2 mL, 57.1 mmol) and Pd/C added (500 mg, cat). The resultant suspension was purge-filled with nitrogen (3 cycles), then with hydrogen (3 cycles). Constant pressure of hydrogen was maintained with a hydrogen balloon. The mixture was stirred vigorously at ambient temperature. Upon complete consumption (as determined by LCMS) of the aldehyde starting material, the reaction mixture was filtered through Celite. The filter cake was washed with ethanol and the solvent was concentrated in vacuo.

No further purification was required.

Yield: 2.52 g, 72%

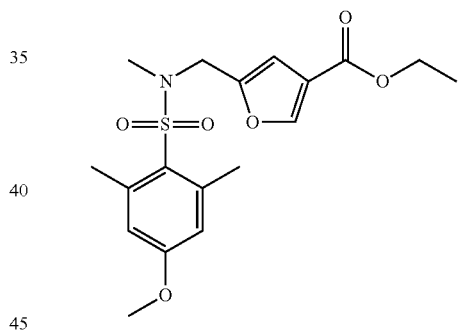

Ethyl 5-({[(4-methoxy-2,6-dimethylphenyl)sulfonyl](methyl)amino}methyl)furan-3-carboxylate

Int 46

Ethyl 5-[(methylamino)methyl]furan-3-carboxylate (2.0 g, 10.9 mmol) was dissolved in DCM (40 mL) and TEA (3.0 mL, 21.8 mmol) and DMAP (133 mg, 1.09 mmol) added. The resultant solution was cooled to 0° C. in an ice bath and a solution of 2,6-dimethyl-4-methoxybenzenesulfonamide (3.1 g, 13.1 mmol) in DCM (10 mL) added dropwise over 15 min. Upon complete addition of the sulfonyl chloride, the ice bath was removed and the reaction temperature increased to ambient temperature. After 1 h, the reaction was washed with an equal volume of 10% w/v citric acid and the organic layer dried over $MgSO_4$ and the DCM removed in vacuo.

The resulting oil was purified using FCC eluting with 10% EtOAc in heptanes to afford the title compound.

Yield: 1.03 g, 25%.

$^1$H NMR (250 MHz, $CDCl_3$) δ ppm 7.92 (1H, s), 6.64 (2H, s), 6.59 (1H, s), 4.30 (2H, s), 4.28 (2H, q, J=7.04 Hz), 3.82 (3H, s), 2.64 (3H, s), 2.63 (6H, s), 1.33 (3H, t, J=7.01 Hz)

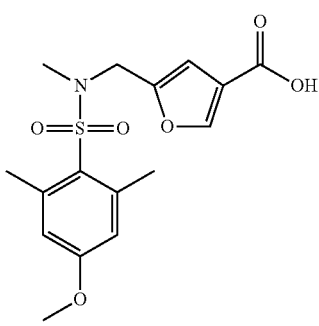 [SMILES: COc1cc(C)c(S(=O)(=O)N(C)Cc2cc(C(=O)O)co2)c(C)c1]

5-({[(4-Methoxy-2,6-dimethylphenyl)sulfonyl](methyl)amino}methyl)furan-3-carboxylic acid Int 47

Ethyl 5-({[(4-methoxy-2,6-dimethylphenyl)sulfonyl](methyl)amino}methyl)furan-3-carboxylate (1.3 g, 3.4 mmol) was dissolved in a 3:2 mixture of THF/water (25 mL). Lithium hydroxide (429 mg, 10.2 mmol) was added and the reaction heated with 60° C. for 2 h. The reaction was cooled and the THF removed in vacuo. The resulting aqueous solution was washed with EtOAc (15 mL) and then acidified to pH 1 using 6 N HCl. The acidic aqueous was extracted with EtOAc (3×15 mL) and the combined organic extracts dried over $Na_2SO_4$. The solvent was removed in vacuo to afford the title compound, which required no further purification.

Yield: 0.735 g, 62%.

$^1$H NMR (250 MHz, $CD_3OD$) δ ppm 8.04 (1H, s), 6.76 (2H, s), 6.58 (1H, s), 4.32 (2H, s), 3.83 (3H, s), 2.67 (3H, s), 2.60 (6H, s).

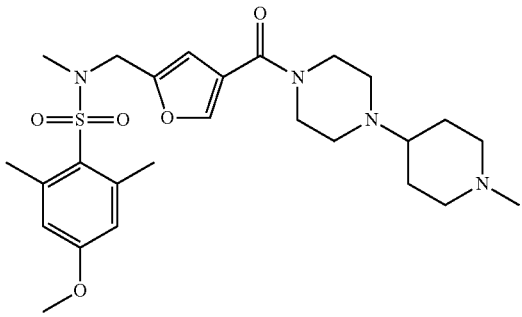

4-Methoxy-N,2,6-trimethyl-N-[(4-{[4-(1-methylpiperidin-4-yl)piperazin-1-yl]carbonyl}furan-2-yl)methyl]benzenesulfonamide Ex 1

5-({[(4-Methoxy-2,6-dimethylphenyl)sulfonyl](methyl)amino}methyl)furan-3-carboxylic acid (74 mg, 0.21 mmol) is dissolved in THF (4 mL) and CDI (68 mg, 0.42 mmol) added. The resulting solution was stirred for 90 min prior to the addition of 1-(1-methylpiperidin-4-yl)piperazine (77 mg, 0.42 mmol). The reaction was stirred at ambient temperature for 18 h, concentrated in vacuo and a portion of the resulting crude product purified using prep method B to afford the title compound.

LCMS Method C: rt 2.65 min, 96%; m/z 519.46.10 (MH$^+$, 100%).

Potency: A

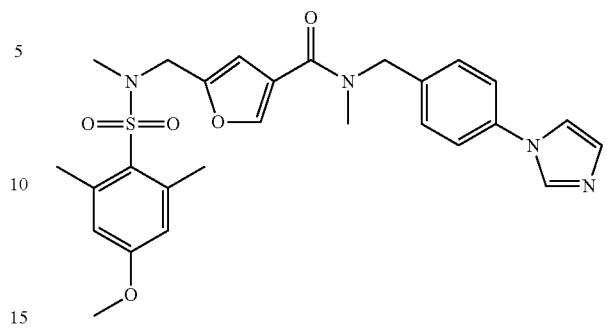

N-[4-(1H-imidazol-1-yl)benzyl]-5-({[(4-methoxy-2,6-dimethylphenyl)sulfonyl](methyl)amino}methyl)-N-methylfuran-3-carboxamide Ex 2

5-({[(4-Methoxy-2,6-dimethylphenyl)sulfonyl](methyl)amino}methyl)furan-3-carboxylic acid (53 mg, 0.15 mmol) was dissolved in THF (0.5 mL) and CDI (24 mg, 0.15 mmol) added. The reaction was stirred for 2 h prior to addition of 1-[4-(1H-imidazol-1-yl)phenyl]-N-methylmethanamine (25 mg, 0.135 mmol). The reaction was stirred at ambient temperature for 3 days, and diluted with DCM (1 mL) and washed with 2M aqueous $K_2CO_3$ (1 mL). The organic layer was dried over $MgSO_4$, the solvent removed in vacuo and a portion of the crude product purified using prep method A.

LCMS Method B: rt 1.58 min, 100%; m/z 523.10 (MH$^+$, 100%).

Potency: A

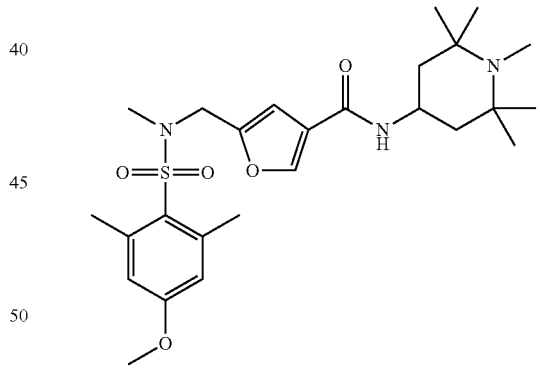

5-({[(4-methoxy-2,6-dimethylphenyl)sulfonyl](methyl)amino}methyl)-N-(1,2,2,6,6-pentamethylpiperidin-4-yl)furan-3-carboxamide Ex 3

5-({[(4-Methoxy-2,6-dimethylphenyl)sulfonyl](methyl)amino}methyl)furan-3-carboxylic acid (53 mg, 0.15 mmol) was dissolved in DMF (1 mL) and HOBt (23 mg, 0.15 mmol) and EDCI (29 mg, 0.15 mmol) were added. The reaction was stirred for 1 h prior to addition of 2,2,6,6-tetramethylpiperidin-4-amine (21 mg, 0.135 mmol). The reaction was stirred for 16 h and then absorbed directly on to Isolute SCX-2 cartridge, washed with MeOH (5 mL) and then eluted with 7

N NH₃ in MeOH (5 mL). The solvent was removed under a stream of N₂ and the resulting crude product purified using prep method A.

¹H NMR (250 MHz, CD₃OD) δ ppm 8.01 (1H, s), 6.76 (2H, s), 6.71 (1H, s), 4.44 (1H, m), 4.34 (2H, s), 3.83 (3H, s), 2.86 (3H, s), 2.66 (3H, s), 2.60 (6H, s), 2.19 (2H, dd, J=14.1 Hz & 3.65 Hz), 1.83 (2H, t, J=13.25 Hz), 1.52 (12H, 2 s).

Potency: A

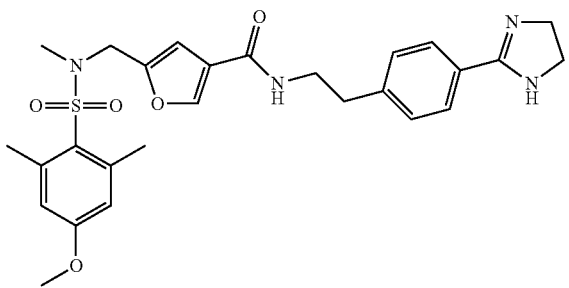 [SMILES: COc1cc(C)c(S(=O)(=O)N(C)Cc2cc(C(=O)NCCc3ccc(C4=NCCN4)cc3)co2)c(C)c1]

N-{2-[4-(4,5-dihydro-1H-imidazol-2-yl)phenyl]ethyl}-5-({[(4-methoxy-2,6-dimethylphenyl)sulfonyl](methyl)amino}methyl)furan-3-carboxamide Ex 4
General Procedure AA 5-({[(4-Methoxy-2,6-dimethylphenyl)sulfonyl](methyl)amino}methyl)furan-3-carboxylic acid (100 mg, 0.3 mmol) was dissolved in DCE (6 mL) and CDI (195 mg, 0.6 mmol) was added. The reaction was stirred at room temperature until complete as determined by LCMS. 2-[4-(4,5-dihydro-1H-imidazol-2-yl)phenyl]ethanamine (54 mg, 0.3 mmol) and DIPEA (0.63 mL, 1.8 mmol) was added and the reaction stirred for 4 days. The reaction was washed with saturated aqueous NH₄Cl (6 mL) and the aqueous wash extracted with DCE (3×6 mL). The combined organic extracts were dried over MgSO₄ and the solvent removed in vacuo. The resulting crude product was purified using prep method B to afford the title compound.

LCMS Method C: rt 3.17 min, 100%; m/z 525.32 (MH⁺, 100%).

Potency: C

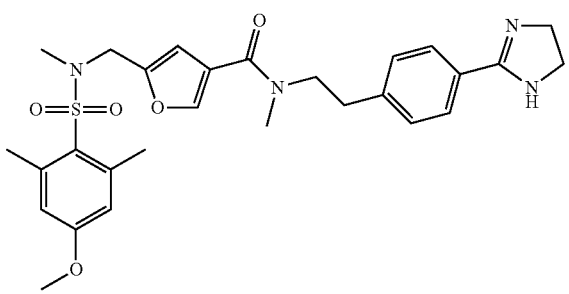 [SMILES: COc1cc(C)c(S(=O)(=O)N(C)Cc2cc(C(=O)N(C)CCc3ccc(C4=NCCN4)cc3)co2)c(C)c1]

N-{2-[4-(4,5-dihydro-1H-imidazol-2-yl)phenyl]ethyl}-5-({[(4-methoxy-2,6-dimethylphenyl)sulfonyl](methyl)amino}methyl)-N-methylfuran-3-carboxamide Ex 5
The title compound was prepared according to general procedure AA using 5-({[(4-Methoxy-2,6-dimethylphenyl)sulfonyl](methyl)amino}methyl)furan-3-carboxylic acid (150 mg, 0.42 mmol), CDI (276 mg, 0.84 mmol) and 2-[4-(4,5-dihydro-1H-imidazol-2-yl)phenyl]-N-methylethanamine (80 mg, 0.42 mmol) in DCE (8 mL).

The crude product was purified using prep method A.

LCMS Method C: rt 3.27 min, 100%; m/z 539.30 (MH⁺, 100%).

Potency: C

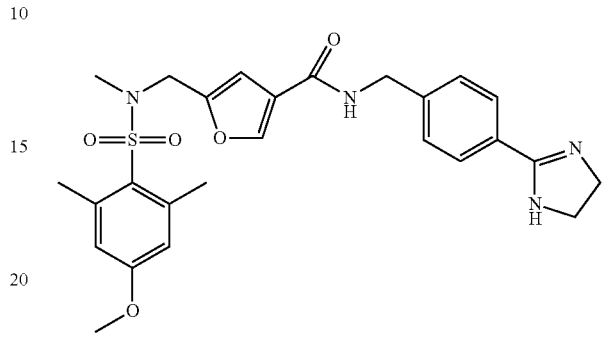

N-[4-(4,5-dihydro-1H-imidazol-2-yl)benzyl]-5-({[(4-methoxy-2,6-dimethylphenyl)sulfonyl](methyl)amino}methyl)furan-3-carboxamide Ex 6
The title compound was prepared according to general procedure AA using 5-({[(4-Methoxy-2,6-dimethylphenyl)sulfonyl](methyl)amino}methyl)furan-3-carboxylic acid (100 mg, 0.3 mmol), CDI (195 mg, 0.6 mmol) and 1-[4-(4,5-dihydro-1H-imidazol-2-yl)phenyl]methanamine (52 mg, 0.3 mmol) in DCE (6 mL).

The crude product was purified using prep method B.

LCMS Method C: rt 3.16 min, 100%; m/z 511.22 (MH⁺, 100%).

Potency: B

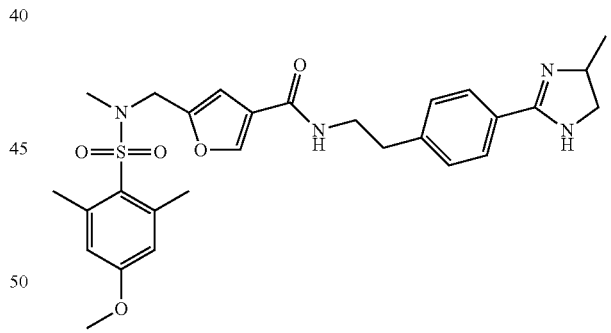

5-({[(4-methoxy-2,6-dimethylphenyl)sulfonyl](methyl)amino}methyl)-N-{2-[4-(4-methyl-4,5-dihydro-1H-imidazol-2-yl)phenyl]ethyl}furan-3-carboxamide Ex 7
General Procedure AD 5-({[(4-Methoxy-2,6-dimethylphenyl)sulfonyl](methyl)amino}methyl)furan-3-carboxylic acid (50 mg, 0.13 mmol) was dissolved in DCE (1 mL) and the solution cooled in an ice bath. CDI (33 mg, 0.20 mmol) was added and the reaction stirred for 20 min. This solution was added to a solution of 2-[4-(4-methyl-4,5-dihydro-1H-imidazol-2-yl)phenyl]ethanamine dihydrochloride (44 mg, 0.14 mmol) and DIPEA (0.14 mL, 0.81 mmol) in DCE (1 mL) and DMF (several drops). The reaction was stirred at ambient temperature for 16 h, concentrated in vacuo and a portion purified using prep method A.

LCMS Method C: rt 3.27 min, 100%; m/z 539.23 (MH+, 100%).

$^1$H NMR (250 MHz, CDCl$_3$) δ ppm 10.37 (1H, br. s) 7.94 (1H, s) 7.73 (2H, d, J=8.07 Hz) 7.55-7.66 (1H, m) 7.11 (2H, d, J=7.92 Hz) 6.59-6.73 (3H, m) 4.38-4.54 (1H, m) 4.34 (2H, s) 4.01-4.20 (1H, m) 3.83 (3H, s) 3.52-3.64 (1H, m) 3.38-3.52 (2H, m) 2.75-2.92 (2H, m) 2.64 (3H, s) 2.60 (6H, s) 1.43 (3H, d, J=6.24 Hz)

Potency: C

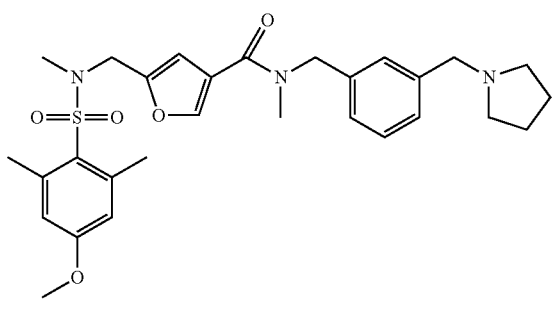 [SMILES: COc1cc(C)c(S(=O)(=O)N(C)Cc2cc(C(=O)N(C)Cc3cccc(CN4CCCC4)c3)co2)c(C)c1]

5-({[(4-methoxy-2,6-dimethylphenyl)sulfonyl](methyl)amino}methyl)-N-methyl-N-[3-(pyrrolidin-1-ylmethyl)benzyl]furan-3-carboxamide Ex 8

The title compound was prepared according to general procedure AD using 5-({[(4-Methoxy-2,6-dimethylphenyl)sulfonyl](methyl)amino}methyl)furan-3-carboxylic acid (60 mg, 0.16 mmol), CDI (48 mg, 0.29 mmol), DIPEA (0.17 mL, 0.97 mmol) and N-methyl-1-[3-(pyrrolidin-1-ylmethyl)phenyl]methanamine (31 mg, 0.14 mmol) in DCE (1.2 mL).

The crude product was purified using prep method B.

LCMS Method C: rt 3.40 min, 100%; m/z 540.27 (MH+, 100%).

Potency: B

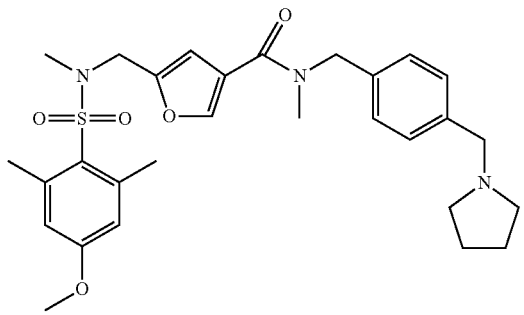 [SMILES: COc1cc(C)c(S(=O)(=O)N(C)Cc2cc(C(=O)N(C)Cc3ccc(CN4CCCC4)cc3)co2)c(C)c1]

5-({[(4-methoxy-2,6-dimethylphenyl)sulfonyl](methyl)amino}methyl)-N-methyl-N-[4-(pyrrolidin-1-ylmethyl)benzyl]furan-3-carboxamide Ex 9

General Procedure AE 5-({[(4-Methoxy-2,6-dimethylphenyl)sulfonyl](methyl)amino}methyl)furan-3-carboxylic acid (60 mg, 0.16 mmol) was dissolved in DCE (1 mL) and the solution cooled in an ice bath. CDI (33 mg, 0.20 mmol) was added and the reaction stirred for 20 min. This solution was added to a solution of N-methyl-[4-(pyrrolidin-1-ylmethyl)phenyl]methanamine (44 mg, 0.14 mmol) and DIPEA (0.17 mL, 0.97 mmol) in DCE (1 mL). The reaction was stirred at 60° C. for 16 h, washed with saturated aqueous NH$_4$Cl (1 mL), saturated aqueous NaHCO$_3$ (1 mL) and 1:1 brine/water (1 mL). The organic phase was dried over MgSO$_4$ and the solvent removed in vacuo.

A portion of the resulting crude product was purified using prep method A.

LCMS Method C: rt 3.31 min, 100%; m/z 540.31 (MH+, 100%).

Potency: B

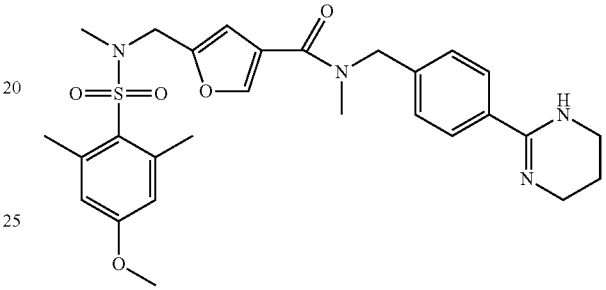

5-({[(4-methoxy-2,6-dimethylphenyl)sulfonyl](methyl)amino}methyl)-N-methyl-N-[4-(1,4,5,6-tetrahydropyrimidin-2-yl)benzyl]furan-3-carboxamide Ex 10

The title compound was prepared according to general procedure AE using 5-({[(4-Methoxy-2,6-dimethylphenyl)sulfonyl](methyl)amino}methyl)furan-3-carboxylic acid (60 mg, 0.16 mmol), CDI (48 mg, 0.29 mmol), N-methyl-1-[4-(1,4,5,6-tetrahydropyrimidin-2-yl)phenyl]methanamine dihydrochloride (42 mg, 0.15 mmol) and DIPEA (0.17 mL, 0.97 mmol) in DCE (2 mL).

A portion of the crude product was purified using prep method B.

LCMS Method C: rt 3.29 min, 100%; m/z 539.22 (MH+, 100%).

Potency: B

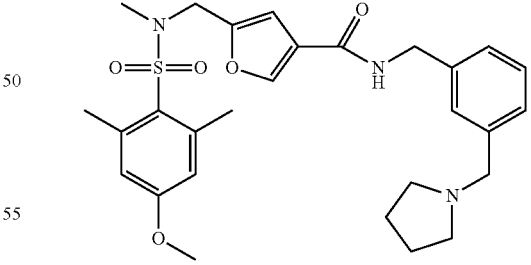

5-({[(4-methoxy-2,6-dimethylphenyl)sulfonyl](methyl)amino}methyl)-N-[3-(pyrrolidin-1-ylmethyl)benzyl]furan-3-carboxamide Ex 11

The title compound was prepared according to general procedure AE using 5-({[(4-Methoxy-2,6-dimethylphenyl)sulfonyl](methyl)amino}methyl)furan-3-carboxylic acid (60 mg, 0.16 mmol), CDI (48 mg, 0.29 mmol), 1-[3-(pyrrolidin- 1-ylmethyl)phenyl]methanamine (28 mg, 0.15 mmol) and DIPEA (0.17 mL, 0.97 mmol) in DCE (2 mL).

A portion of the crude product was purified using prep method B.

LCMS Method C: rt 3.32 min, 97%; m/z 526.22 (MH+, 100%).

Potency: A

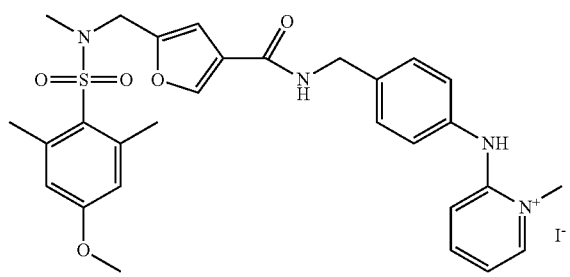

2-({4-[({[5-({[(4-methoxy-2,6-dimethylphenyl)sulfonyl](methyl)amino}methyl)furan-3-yl]carbonyl}amino)methyl]phenyl}amino)-1-methylpyridinium iodide Ex 12

The title compound was prepared according to general procedure AD using 5-({[(4-Methoxy-2,6-dimethylphenyl)sulfonyl](methyl)amino}methyl)furan-3-carboxylic acid (50 mg, 0.13 mmol), CDI (33 mg, 0.2 mmol), DIPEA (0.14 mL, 0.81 mmol) and 2-{[4-(aminomethyl)phenyl]amino}-1-methylpyridinium iodide hydrochloride (53 mg, 0.14 mmol) in DCE (1.0 mL).

A portion of the crude product was purified using prep method A.

LCMS Method C: rt 3.27 min, 100%; m/z 549.23 (M+, 100%).

¹H NMR (250 MHz, CDCl₃) δ ppm 10.81 (1H, br. s) 7.98 (1H, s) 7.83 (1H, br. d, J=5.94 Hz) 7.71 (1H, br. t, J=8.15 Hz) 7.49 (1H, br. s.) 7.35 (2H, d, J=7.16 Hz) 7.19 (2H, d, J=7.92 Hz) 7.01 (1H, br. d, J=8.98 Hz) 6.86 (1H, br. t, J 6.62) 6.67 (1H, s) 6.65 (2H, s) 4.52 (2H, d, J=5.18 Hz) 4.28 (2H, s) 4.02 (3H, br. s) 3.82 (3H, s) 2.61 (9H, s)

Potency: A

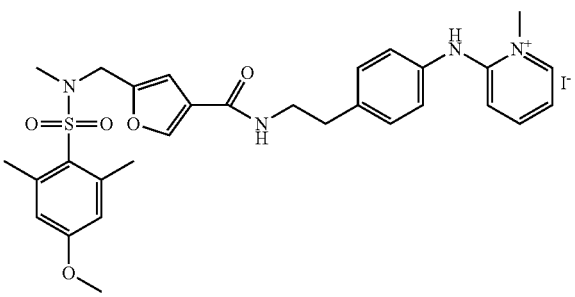 [SMILES: COc1cc(C)c(S(=O)(=O)N(C)Cc2cc(C(=O)NCCc3ccc(Nc4cccc[n+]4C)cc3)co2)c(C)c1 ; [I-]]

2-({4-[2-({[5-({[(4-methoxy-2,6-dimethylphenyl)sulfonyl](methyl)amino}methyl)furan-3-yl]carbonyl}amino)ethyl]phenyl}amino)-1-methylpyridinium iodide Ex 13

The title compound was prepared according to general procedure AD using 5-({[(4-Methoxy-2,6-dimethylphenyl)sulfonyl](methyl)amino}methyl)furan-3-carboxylic acid (50 mg, 0.13 mmol), CDI (33 mg, 0.2 mmol), DIPEA (0.14 mL, 0.81 mmol) and 2-{[4-(2-aminoethyl)phenyl]amino}-1-methylpyridinium iodide hydrochloride (55 mg, 0.14 mmol) in DCE (1.0 mL).

A portion of the crude product was purified using prep method A.

LCMS Method C: rt 3.36 min, 100%; m/z 563.21 (M+, 100%).

¹H NMR (250 MHz, CDCl₃) δ ppm 10.83 (1H, br. s) 7.89 (1H, s) 7.66-7.84 (2H, m) 7.16-7.26 (4H, m) 7.06 (1H, d, J=8.83 Hz) 6.88 (1H, t, J=6.62 Hz) 6.69-6.79 (1H, m) 6.65 (2H, s) 6.56 (1H, s) 4.29 (2H, s) 4.15 (3H, s) 3.83 (3H, s) 3.50-3.62 (2H, m) 2.88 (2H, t, J=6.78 Hz) 2.62 (3H, s) 2.61 (6H, s)

Potency: C

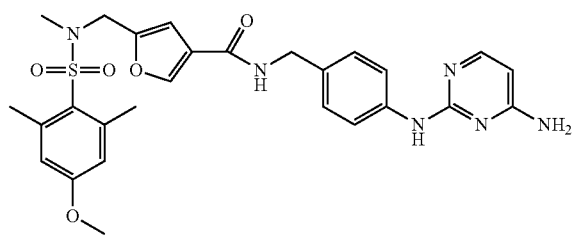 [SMILES: COc1cc(C)c(S(=O)(=O)N(C)Cc2cc(C(=O)NCc3ccc(Nc4nccc(N)n4)cc3)co2)c(C)c1]

N-{4-[(4-aminopyrimidin-2-yl)amino]benzyl}-5-({[(4-methoxy-2,6-dimethylphenyl)sulfonyl](methyl)amino}methyl)furan-3-carboxamide Ex 14

The title compound was prepared according to general procedure AE using 5-({[(4-Methoxy-2,6-dimethylphenyl)sulfonyl](methyl)amino}methyl)furan-3-carboxylic acid (60 mg, 0.16 mmol), CDI (48 mg, 0.29 mmol), N²-[4-(aminomethyl)phenyl]pyrimidine-2,4-diamine dihydrochloride (46 mg, 0.15 mmol) and DIPEA (0.17 mL, 0.97 mmol) in DCE (2 mL).

A portion of the crude product was purified using prep method C.

LCMS Method C: rt 3.27 min, 100%; m/z 551.27 (MH+, 100%).

¹H NMR (500 MHz, CD₃OD) δ ppm 8.00 (1H, s) 7.65 (1H, d, J=7.15 Hz) 7.49 (2H, d, J=8.25 Hz) 7.39 (2H, d, J=8.44 Hz) 6.76 (2H, s) 6.69 (1H, s) 6.19 (1H, d, J=7.15 Hz) 4.51 (2H, br. s) 4.33 (2H, s) 3.82 (3H, s) 2.67 (3H, s) 2.60 (6H, s)

Potency: A

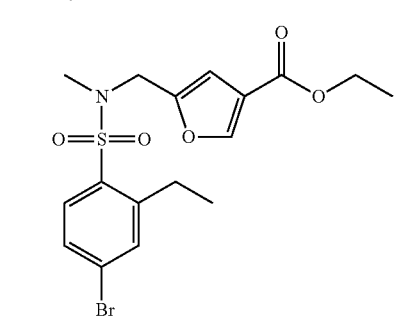 [SMILES: CCOC(=O)c1coc(CN(C)S(=O)(=O)c2ccc(Br)cc2CC)c1]

Ethyl 5-({[(4-bromo-2-ethylphenyl)sulfonyl](methyl)amino}methyl)furan-3-carboxylate Int 48

To s stirred solution of ethyl 5-[(methylamino)methyl]furan-3-carboxylate (567 mg, 3.03 mmol) in pyridine (6 mL) was added 4-bromo-2-ethylbenzenesulfonyl chloride (1 g, 3.52 mmol) and the reaction was stirred at ambient temperature. After 18 h, the reaction was concentrated and purified by FCC, eluting with 20% EtOAc in heptane, to afford the title compound.

Yield: 812 mg, 61%.

$^1$H NMR (400 MHz, CDCl$_3$) δ ppm 7.93 (1H, s), 7.76 (1H, d, J=8.6 Hz), 7.54 (1H, d, J=2.0 Hz) 7.47 (1H, dd, J 8.4, 2.1 Hz), 6.62 (1H, s), 4.37 (2H, s), 4.30 (2H, q, J=7.2 Hz), 2.99 (2H, q, J=7.6 Hz), 2.76 (3H, s), 1.35 (3H, t, J=7.1 Hz), 1.28 (3H, t, J=7.5 Hz)

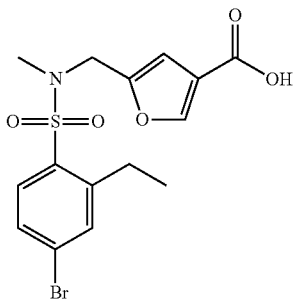 [SMILES: CCc1cc(Br)ccc1S(=O)(=O)N(C)Cc1cc(C(=O)O)co1]

5-({[(4-bromo-2-ethylphenyl)sulfonyl](methyl)amino}methyl)furan-3-carboxylic acid Int 49

Ethyl 5-({[(4-bromo-2-ethylphenyl)sulfonyl](methyl)amino}methyl)furan-3-carboxylate (530 mg, 1.23 mmol) and LiOH.H$_2$O (150 mg, 3.75 mmol) were dissolved in a 1:1 mixture of THF/H$_2$O (10 mL). The reaction was stirred at ambient temperature for 18 h, then acidified to pH 1 with 1M aqueous HCl. The mixture was extracted with EtOAc and the organic phase was dried over MgSO$_4$. The solvent was removed in vacuo to afford the title compound, which required no further purification.

Yield: 465 mg, 94%.

$^1$H NMR (400 MHz, CD$_3$OD) δ ppm 8.04 (1H, s) 7.76 (1H, d, J=8.6 Hz) 7.65 (1H, d, J=2.0 Hz) 7.6 (1H, dd, J 8.6, 2.2 Hz) 6.62 (1H, s) 4.43 (2H, s) 3.00 (2H, q, J=7.6 Hz) 2.79 (3H, s) 1.25 (3H, t, J=7.5 Hz)

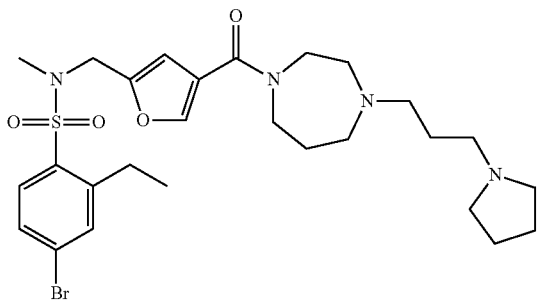 [SMILES: CCc1cc(Br)ccc1S(=O)(=O)N(C)Cc1cc(C(=O)N2CCCN(CCCN3CCCC3)CC2)co1]

4-bromo-2-ethyl-N-methyl-N-[(4-{[4-(3-pyrrolidin-1-ylpropyl)-1,4-diazepan-1-yl]carbonyl}furan-2-yl)methyl]benzenesulfonamide Ex 15

The title compound was prepared according to general procedure AA using 5-({[(4-bromo-2-ethylphenyl)sulfonyl](methyl)amino}methyl)furan-3-carboxylic acid (50 mg, 0.12 mmol), CDI (41 mg, 0.25 mmol) and 1-[3-(pyrrolidin-1-yl)propyl]-1,4-diazepane (53 mg, 0.25 mmol) in DCE (2 mL). The crude product was purified using prep method A.

LCMS Method C: rt 2.95 min, 98%; m/z 299.10 (MH$_2^{2+}$, 100%) 597.21 (MH$^+$, 32%).

Potency: B

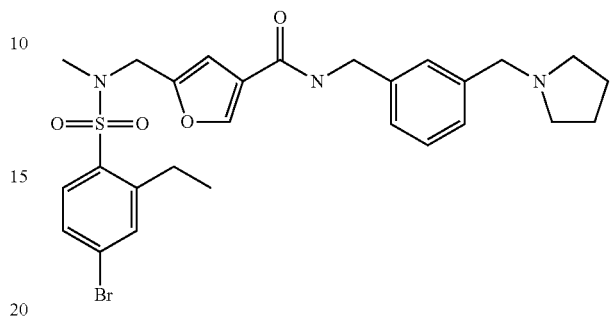

5-({[(4-bromo-2-ethylphenyl)sulfonyl](methyl)amino}methyl)-N-[3-(pyrrolidin-1-ylmethyl)benzyl]furan-3-carboxamide Ex 16

The title compound was prepared according to general procedure AA using 5-({[(4-bromo-2-ethylphenyl)sulfonyl](methyl)amino}methyl)furan-3-carboxylic acid (40 mg, 0.10 mmol), CDI (32 mg, 0.2 mmol) and 1-[3-(pyrrolidin-1-ylmethyl)phenyl]methanamine (57 mg, 0.3 mmol) in DCE (2 mL). The crude product was purified using prep method A.

LCMS Method C: rt 3.53 min, 98%; m/z 576.25 (MH$^+$, 100%).

Potency: A

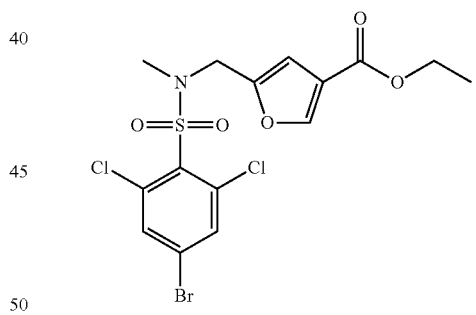

Ethyl 5-({[(4-bromo-2,6-dichlorophenyl)sulfonyl](methyl)amino}methyl)furan-3-carboxylate Int 50
General Procedure AK To a stirred solution of ethyl 5-[(methylamino)methyl]furan-3-carboxylate (358 mg, 1.95 mmol), Et$_3$N (0.27 mL, 1.95 mmol) and DMAP (24 mg, 0.195 mmol) in DCM (5 mL) at 0° C. was added 4-bromo-2,6-dichlorobenzenesulfonyl chloride (634 mg, 1.95 mmol) slowly as a solution in DCM (5 mL). The reaction was allowed to warm to ambient temperature and stirred overnight. The mixture was diluted with DCM (30 mL) and washed with 1M aqueous HCl (3×10 mL), saturated aqueous NaHCO$_3$ (2×10 mL) and saturated brine (10 mL), then dried over MgSO$_4$. Solvents were removed in vacuo and the product was purified using FCC, eluting with 20% EtOAc in heptane, to afford the title compound.

Yield: 331 mg, 41%.

¹H NMR (400 MHz, CDCl₃) δ ppm 7.92 (1H, s) 7.64 (2H, s) 6.64 (1H, s) 4.48 (2H, s) 4.30 (2H, q, J=7.07 Hz) 2.92 (3H, s) 1.35 (4H, t, J 7.17)

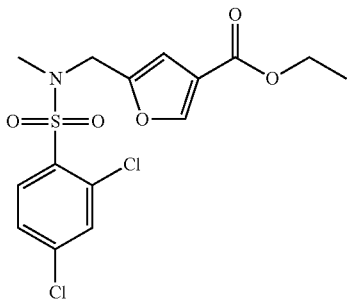 [SMILES: CCOC(=O)c1coc(CN(C)S(=O)(=O)c2ccc(Cl)cc2Cl)c1]

Ethyl 5-({[(2,4-dichlorophenyl)sulfonyl](methyl)amino}methyl)furan-3-carboxylate Int 51

The title compound was prepared according to general procedure AK using ethyl 5-[(methylamino)methyl]furan-3-carboxylate (358 mg, 1.95 mmol), Et₃N (0.27 mL, 1.95 mmol), DMAP (24 mg, 0.195 mmol) and 2,4-dichlorobenzenesulfonyl chloride (479 mg, 1.95 mmol) in DCM (5 mL).

The product was purified using FCC, eluting with 20% EtOAc in heptane, to afford the title compound.

Yield: 343 mg, 45%.

¹H NMR (400 MHz, CDCl₃) δ ppm 8.05 (1H, d, J=8.56 Hz) 7.91 (1H, s) 7.54 (1H, d, J=2.20 Hz) 7.39 (1H, dd, J 8.56, 2.20 Hz) 6.60 (1H, s) 4.45 (2H, s) 4.30 (2H, q, J=7.17 Hz) 2.86 (3H, s) 1.35 (3H, t, J=7.21 Hz)

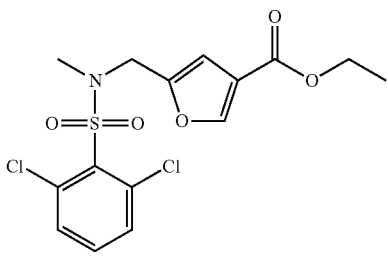 [SMILES: CCOC(=O)c1coc(CN(C)S(=O)(=O)c2c(Cl)cccc2Cl)c1]

Ethyl 5-({[(2,6-dichlorophenyl)sulfonyl](methyl)amino}methyl)furan-3-carboxylate Int 52

The title compound was prepared according to general procedure AK using ethyl 5-[(methylamino)methyl]furan-3-carboxylate (358 mg, 1.95 mmol), Et₃N (0.27 mL, 1.95 mmol), DMAP (24 mg, 0.195 mmol) and 2,6-dichlorobenzenesulfonyl chloride (479 mg, 1.95 mmol) in DCM (5 mL).

The product was purified using FCC, eluting with 20% EtOAc in heptane, to afford the title compound.

Yield: 284 mg, 37%.

¹H NMR (400 MHz, CDCl₃) δ ppm 7.92 (1H, s) 7.43-7.52 (2H, m) 7.30-7.38 (1H, m) 6.64 (1H, s) 4.50 (2H, s) 4.30 (2H, q, J=7.17 Hz) 2.92 (3H, s) 1.35 (4H, t, J=7.09 Hz)

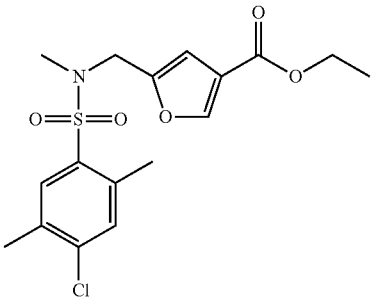 [SMILES: CCOC(=O)c1coc(CN(C)S(=O)(=O)c2cc(C)c(Cl)cc2C)c1]

Ethyl 5-({[(4-chloro-2,5-dimethylphenyl)sulfonyl](methyl)amino}methyl)furan-3-carboxylate Int 53

The title compound was prepared according to general procedure AK using ethyl 5-[(methylamino)methyl]furan-3-carboxylate (358 mg, 1.95 mmol), Et₃N (0.27 mL, 1.95 mmol), DMAP (24 mg, 0.195 mmol) and 4-chloro-2,5-dimethylbenzenesulfonyl chloride (466 mg, 1.95 mmol) in DCM (5 mL).

The product was purified using FCC, eluting with 20% EtOAc in heptane, to afford the title compound.

Yield: 348 mg, 46%.

¹H NMR (250 MHz, CDCl₃) δ ppm 7.92 (1H, d, J=0.76 Hz) 7.78 (1H, s) 7.31 (1H, s) 6.61 (1H, s) 4.36 (2H, s) 4.30 (2H, q, J=7.16 Hz) 2.76 (3H, s) 2.54 (3H, s) 2.39 (3H, s) 1.35 (3H, t, J=7.16 Hz)

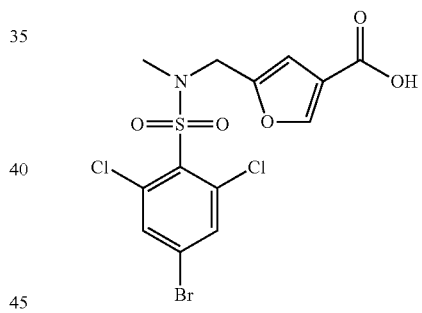

5-({[(4-bromo-2,6-dichlorophenyl)sulfonyl](methyl)amino}methyl)furan-3-carboxylic acid Int 54

General Procedure AL

To a stirred solution of ethyl 5-({[(4-bromo-2,6-dichlorophenyl)sulfonyl](methyl)amino}methyl)furan-3-carboxylate (331 mg, 0.70 mmol) in a 1:1 mixture of THF/H₂O (4 mL) was added 2 M aqueous LiOH (1.35 mL, 2.7 mmol) and the reaction was monitored by TLC. Further portions of LiOH were added as necessary to drive the reaction to completion. The reaction was stirred at ambient temperature for 3 days, then acidified to pH 1 with 1 M aqueous HCl. The mixture was extracted with DCM (2×30 mL) and the organic phase was dried over MgSO₄. The solvent was removed in vacuo to afford the title compound, which required no further purification.

Yield: 302 mg, 97%.

¹H NMR (400 MHz, CDCl₃) δ ppm 8.02 (1H, s) 7.65 (2H, s) 6.68 (1H, s) 4.51 (2H, s) 2.93 (3H, s)

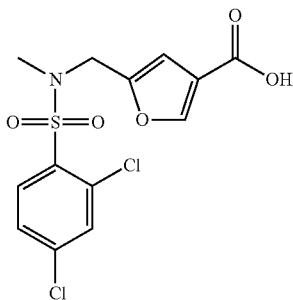 [SMILES: CN(Cc1cc(C(=O)O)co1)S(=O)(=O)c1ccc(Cl)cc1Cl]

5-({[(2,4-dichlorophenyl)sulfonyl](methyl)
amino}methyl)furan-3-carboxylic acid

Int 55

The title compound was prepared according to general procedure AL using ethyl 5-({[(2,4-dichlorophenyl)sulfonyl](methyl)amino}methyl)furan-3-carboxylate (343 mg, 0.87 mmol) and 2 M aqueous LiOH (1.35 mL, 2.7 mmol) in a 1:1 mixture of THF/H$_2$O (4 mL). The crude product required no further purification.

Yield: 304 mg, 96%.

$^1$H NMR (400 MHz, CDCl$_3$) δ ppm 8.06 (1H, d, J=8.56 Hz) 8.02 (1H, s) 7.55 (1H, d, J=1.96 Hz) 7.40 (1H, dd, J 8.44, 2.08 Hz) 6.63 (1H, s) 4.48 (2H, s) 2.87 (3H, s)

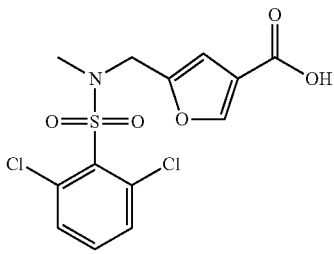 [SMILES: CN(Cc1cc(C(=O)O)co1)S(=O)(=O)c1c(Cl)cccc1Cl]

5-({[(2,6-dichlorophenyl)sulfonyl](methyl)
amino}methyl)furan-3-carboxylic acid

Int 56

The title compound was prepared according to general procedure AL using ethyl 5-({[(2,6-dichlorophenyl)sulfonyl](methyl)amino}methyl)furan-3-carboxylate (284 mg, 0.72 mmol) and 2 M aqueous LiOH (1.35 mL, 2.7 mmol) in a 1:1 mixture of THF/H$_2$O (4 mL). The crude product required no further purification.

Yield: 277 mg, >100%.

$^1$H NMR (400 MHz, CDCl$_3$) δ ppm 8.01 (1H, s) 7.46-7.50 (2H, m) 7.31-7.38 (1H, m) 6.66 (1H, s) 4.52 (2H, s) 2.95 (3H, s)

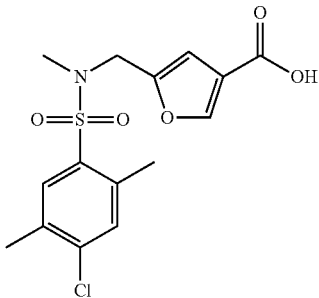 [SMILES: Cc1cc(S(=O)(=O)N(C)Cc2cc(C(=O)O)co2)c(C)cc1Cl]

5-({[(4-chloro-2,5-dimethylphenyl)sulfonyl](methyl)
amino}methyl)furan-3-carboxylic acid Int 57

The title compound was prepared according to general procedure AL using ethyl 5-({[(4-chloro-2,5-dimethylphenyl)sulfonyl](methyl)amino}methyl)furan-3-carboxylate (348 mg, 0.90 mmol) and 2 M aqueous LiOH (1.35 mL, 2.7 mmol) in a 1:1 mixture of THF/H$_2$O (4 mL). The crude product required no further purification.

Yield: 317 mg, 98%.

$^1$H NMR (400 MHz, CDCl$_3$) δ ppm 8.02 (1H, s) 7.79 (1H, s) 7.31 (1H, s) 6.64 (1H, s) 4.38 (2H, s) 2.77 (3H, s) 2.55 (3H, s) 2.39 (3H, s)

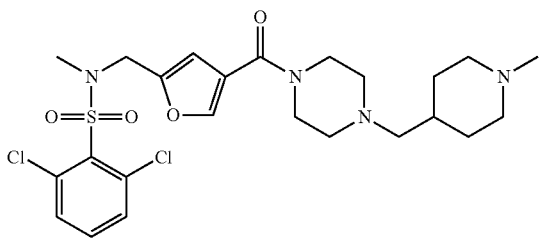 [SMILES: CN1CCC(CN2CCN(C(=O)c3coc(CN(C)S(=O)(=O)c4c(Cl)cccc4Cl)c3)CC2)CC1]

2,6-dichloro-N-methyl-N-{[4-({4-[(1-methylpiperidin-4-yl)methyl]piperazin-1-yl}carbonyl)furan-2-yl]methyl}benzenesulfonamide Ex 17

5-({[(2,6-dichlorophenyl)sulfonyl](methyl)
amino}methyl)furan-3-carboxylic acid (465 mg, 1.3 mmol) was dissolved in DCE (40 mL) and CDI (422 mg, 2.6 mmol) was added. The reaction was stirred for 1 h. 4 mL of activated acid solution in DCE was added to a vial containing 1-[(1-methylpiperidin-4-yl)methyl]piperazine (51 mg, 0.258 mmol). The reaction was stirred at ambient temperature for 3 days, then washed with saturated aqueous NaHCO$_3$. The organic layer was dried over MgSO$_4$ and shaken with PL-MIA and Ambersep resins, then filtered. The solvent was removed in vacuo and a portion of the crude product purified using prep method B.

LCMS Method C: rt 2.61 min, 100%; m/z 272.17 (MH$_2^{2+}$, 100%) 543.26 (MH$^+$, 8%).

Potency: A

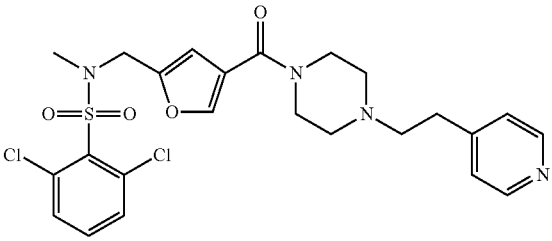 [SMILES: CN(Cc1cc(C(=O)N2CCN(CCc3ccncc3)CC2)co1)S(=O)(=O)c1c(Cl)cccc1Cl]

2,6-dichloro-N-methyl-N-[(4-{[4-(2-pyridin-4-yl-ethyl)piperazin-1-yl]carbonyl}furan-2-yl)methyl]
benzenesulfonamide Ex 18

5-({[(2,6-dichlorophenyl)sulfonyl](methyl)
amino}methyl)furan-3-carboxylic acid (465 mg, 1.3 mmol) was dissolved in DCE (40 mL) and CDI (422 mg, 2.6 mmol) was added. The reaction was stirred for 1 h. 4 mL of activated acid solution in DCE was added to a vial containing 1-[2-

(pyridin-4-yl)ethyl]piperazine (50 mg, 0.261 mmol). The reaction was stirred at ambient temperature for 3 days, then washed with saturated aqueous NaHCO$_3$. The organic layer was dried over MgSO$_4$ and shaken with PL-MIA and Ambersep resins, then filtered. The solvent was removed in vacuo and a portion of the crude product purified using prep method B.

LCMS method C: rt 2.68 min, 100%; m/z 269.15 (MH$_2^{2+}$, 100%) 537.21 (MH$^+$, 13%).
Potency: A

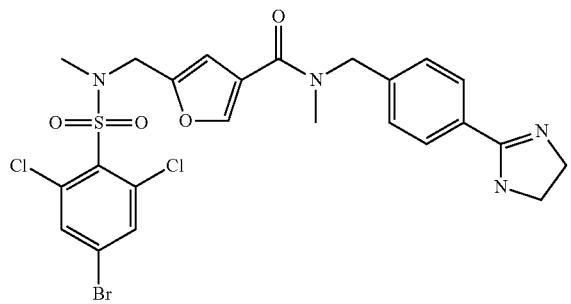 [SMILES: CN(Cc1ccc(C2=NCCN2)cc1)C(=O)c1coc(CN(C)S(=O)(=O)c2c(Cl)cc(Br)cc2Cl)c1]

5-({[(4-bromo-2,6-dichlorophenyl)sulfonyl](methyl)amino}methyl)-N-[4-(4,5-dihydro-1H-imidazol-2-yl)benzyl]-N-methylfuran-3-carboxamide Ex 19

To a stirred solution of 5-({[(4-bromo-2,6-dichlorophenyl)sulfonyl](methyl)amino}methyl)furan-3-carboxylic acid (60 mg, 0.14 mmol), EDCI (33 mg, 0.17 mmol) and HOAt (23 mg, 0.17 mmol) in DMF (0.5 mL) was added a solution of 1-[4-(4,5-dihydro-1H-imidazol-2-yl)phenyl]-N-methylmethanamine.HCl (28 mg, 0.13 mmol) and DIPEA (0.025 mL, 0.14 mmol) in DMF (0.5 mL). The reaction was heated to 60° C. for 5 h, then concentrated and diluted with DCM. The solution was washed with saturated aqueous NH$_4$Cl(2×2 mL) and saturated brine (2 mL), and dried over MgSO$_4$. The filtrate was shaken with Ambersep resin for 48 h, then filtered. The solvent was removed in vacuo and a portion of the crude product purified using prep method C.

LCMS Method C: rt 3.44 min, 100%; m/z 615.04 (MH$^+$, 100%).
Potency: C

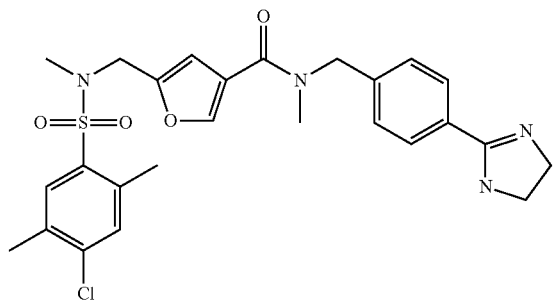 [SMILES: Cc1cc(S(=O)(=O)N(C)Cc2cc(C(=O)N(C)Cc3ccc(C4=NCCN4)cc3)co2)c(C)cc1Cl]

5-({[(4-chloro-2,5-dimethylphenyl)sulfonyl](methyl)amino}methyl)-N-[4-(4,5-dihydro-1H-imidazol-2-yl)benzyl]-N-methylfuran-3-carboxamide Ex 20

5-({[(4-chloro-2,5-dimethylphenyl)sulfonyl](methyl)amino}methyl)furan-3-carboxylic acid (28 mg, 0.08 mmol) was dissolved in DCE (1 mL) and CDI (26 mg, 0.16 mmol) was added. The reaction was stirred for 2 h. The activated acid solution in DCE was added to a vial containing 1-[4-(4,5-dihydro-1H-imidazol-2-yl)phenyl]-N-methylmethanamine-.HCl (41 mg, 0.16 mmol) and TEA (0.022 mL, 0.16 mmol). The reaction was stirred at ambient temperature for 18 h, then partitioned between saturated aqueous NaHCO$_3$ (1 mL) and DCE (3×1 mL). The organic layer was dried over MgSO$_4$ and solvents were removed in vacuo. A portion of the crude product was purified using prep method A.

LCMS Method C: rt 3.47 min, 98%; m/z 529.16 (MH$^+$, 100%).
Potency: C

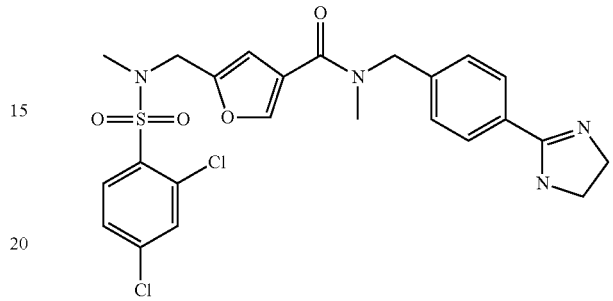

5-({[(2,4-dichlorophenyl)sulfonyl](methyl)amino}methyl)-N-[4-(4,5-dihydro-1H-imidazol-2-yl)benzyl]-N-methylfuran-3-carboxamide Ex 21

5-({[(2,4-dichlorophenyl)sulfonyl](methyl)amino}methyl)furan-3-carboxylic acid (34 mg, 0.08 mmol) was dissolved in DCE (1 mL) and CDI (26 mg, 0.16 mmol) was added. The reaction was stirred for 2 h. The activated acid solution in DCE was added to a vial containing 1-[4-(4,5-dihydro-1H-imidazol-2-yl)phenyl]-N-methylmethanamine-.HCl (41 mg, 0.16 mmol) and TEA (0.022 mL, 0.16 mmol). The reaction was stirred at ambient temperature for 18 h, then partitioned between saturated aqueous NaHCO$_3$ (1 mL) and DCE (3×1 mL)). The organic layer was dried over MgSO$_4$ and solvents were removed in vacuo. A portion of the crude was product purified using prep method A.

LCMS Method C: rt 3.32 min, 99%; m/z 535.11 (MH$^+$, 100%).
Potency: C

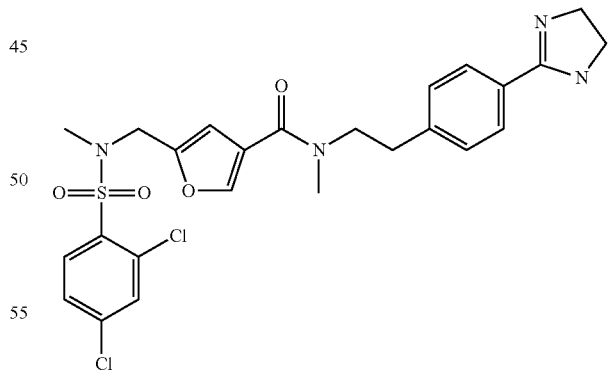

5-({[(2,4-dichlorophenyl)sulfonyl](methyl)amino}methyl)-N-{2-[4-(4,5-dihydro-1H-imidazol-2-yl)phenyl]ethyl}-N-methylfuran-3-carboxamide Ex 22

5-({[(2,4-dichlorophenyl)sulfonyl](methyl)amino}methyl)furan-3-carboxylic acid (34 mg, 0.08 mmol) was dissolved in DCE (1 mL) and CDI (26 mg, 0.16 mmol) was added. The reaction was stirred for 2 h. The activated acid solution in DCE was added to a vial containing 2-[4-(4,5-dihydro-1H-imidazol-2-yl)phenyl]-N-methylethanamine-.HCl (43 mg, 0.16 mmol) and TEA (0.022 mL, 0.16 mmol). The reaction was stirred at ambient temperature for 18 h, then partitioned between saturated aqueous NaHCO₃ (1 mL) and DCE (3×1 mL)). The organic layer was dried over MgSO₄ and solvents were removed in vacuo. A portion of the crude product was purified by prep method A.

LCMS Method C: rt 3.21 min, 99%; m/z 549.08 (MH⁺, 100%).
Potency: A

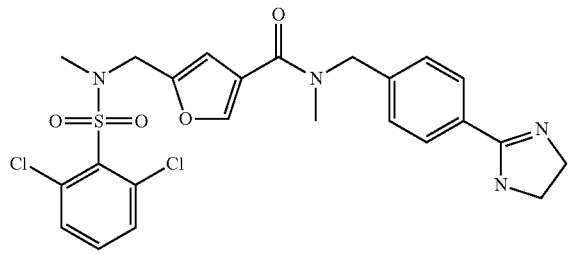 [SMILES: CN(Cc1ccc(C2=NCCN2)cc1)C(=O)c1coc(CN(C)S(=O)(=O)c2c(Cl)cccc2Cl)c1]

5-({[(2,6-dichlorophenyl)sulfonyl](methyl)amino}methyl)-N-[4-(4,5-dihydro-1H-imidazol-2-yl)benzyl]-N-methylfuran-3-carboxamide Ex 23

5-({[(2,6-dichlorophenyl)sulfonyl](methyl)amino}methyl)furan-3-carboxylic acid (51 mg, 0.14 mmol) was dissolved in DMF (1 mL) and CDI (34 mg, 0.21 mmol) was added. The mixture was stirred until acid activation was complete. 1-[4-(4,5-dihydro-1H-imidazol-2-yl)phenyl]-N-methylmethanamine.HCl (32 mg, 0.14 mmol) and DIPEA (0.074 mL, 0.42 mmol) were sonicated in DMF (0.5 mL) for 15 min. 0.5 mL of activated acid solution was added to 0.25 mL of amine solution and the reaction was stirred at ambient temperature for 18 h, then microwaved (120° C., 200 W) for 2×20 min. The reaction was concentrated, dissolved in DCM and washed with water (3×1.5 mL) and saturated brine (1 mL)). The organic layer was dried over MgSO₄ and solvents were removed in vacuo. A portion of the crude product was purified using prep method A.

LCMS Method C: rt 3.21 min, 99%; m/z 535.08 (MH⁺, 100%).
Potency: C

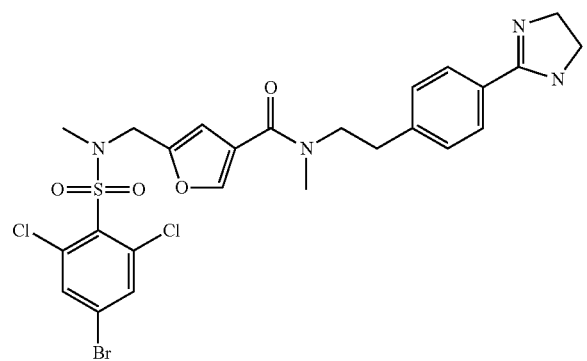 [SMILES: CN(CCc1ccc(C2=NCCN2)cc1)C(=O)c1coc(CN(C)S(=O)(=O)c2c(Cl)cc(Br)cc2Cl)c1]

5-({[(4-bromo-2,6-dichlorophenyl)sulfonyl](methyl)amino}methyl)-N-{2-[4-(4,5-dihydro-1H-imidazol-2-yl)phenyl]ethyl}-N-methylfuran-3-carboxamide Ex 24

To a stirred solution of 5-({[(4-bromo-2,6-dichlorophenyl)sulfonyl](methyl)amino}methyl)furan-3-carboxylic acid (54 mg, 0.12 mmol), EDCI (29 mg, 0.15 mmol) and HOBt (20 mg, 0.15 mmol) in DMF (3 mL) was added a solution of 2-[4-(4,5-dihydro-1H-imidazol-2-yl)phenyl]-N-methylethanamine.HCl (29 mg, 0.11 mmol) and DIPEA (0.084 mL, 0.48 mmol) in DMF (2 mL). The reaction was stirred at ambient temperature for 18 h, then diluted with EtOAc. The solution was washed with water, saturated aqueous NaHCO₃ and 1:1 saturated brine:water. The organic extracts were dried over MgSO₄, and solvent was removed in vacuo. A portion of the crude product was purified using prep method C.

LCMS Method C: rt 3.46 min, 98%; m/z 629.09 (MH⁺, 100%).
Potency: C

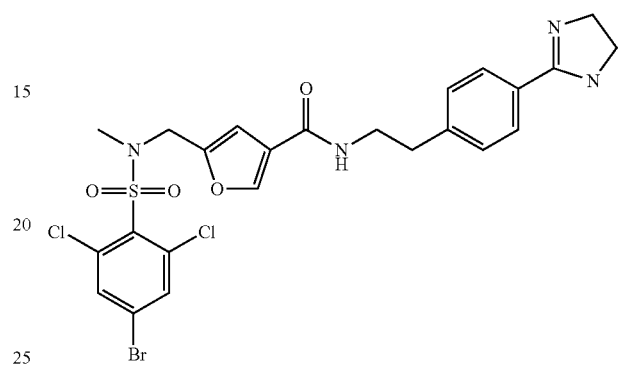

5-({[(4-bromo-2,6-dichlorophenyl)sulfonyl](methyl)amino}methyl)-N-{2-[4-(4,5-dihydro-1H-imidazol-2-yl)phenyl]ethyl}furan-3-carboxamide Ex 25

5-({[(4-bromo-2,6-dichlorophenyl)sulfonyl](methyl)amino}methyl)furan-3-carboxylic acid (60 mg, 0.14 mmol)), EDCI (40 mg, 0.21 mmol) and HOAt (28 mg, 0.21 mmol) were dissolved in DMF (1 mL) and the mixture was stirred until acid activation was complete. 2-[4-(4,5-Dihydro-1H-imidazol-2-yl)phenyl]ethanamine.HCl (114 mg, 0.50 mmol) and DIPEA (0.174 mL, 1.00 mmol) were sonicated in 1 mL DMF for 5 min. The activated acid solution was added to 0.25 mL of amine solution and the reaction was stirred at ambient temperature for 3 h. The reaction was diluted with DCM (15 mL) and washed with saturated aqueous NH₄Cl (2×3 mL). The organic layer was dried over MgSO₄ and solvents were removed in vacuo. A portion of the crude product was purified using prep method C.

LCMS Method C: rt 3.44 min, 100%; m/z 614.98 (MH⁺, 100%).
¹H NMR (250 MHz, CD₃OD) δ ppm 7.90 (1H, d, J=0.91 Hz) 7.82 (2H, s) 7.76-7.81 (2H, m) 7.53 (2H, d, J=8.38 Hz) 6.65 (1H, d, J=0.76 Hz) 4.51 (2H, s) 4.09 (4H, s) 3.60 (2H, t, J=7.16 Hz) 3.01 (2H, t, J=7.16 Hz) 2.92 (3H, s)
Potency: A

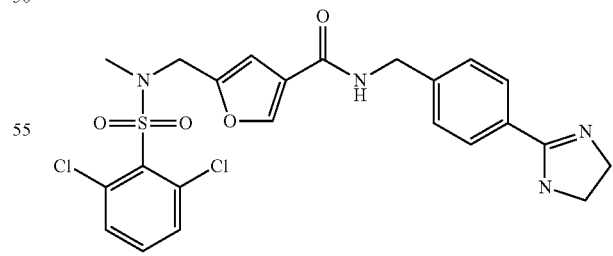

5-({[(2,6-dichlorophenyl)sulfonyl](methyl)amino}methyl)-N-[4-(4,5-dihydro-1H-imidazol-2-yl)benzyl]furan-3-carboxamide Ex 26

5-({[(2,6-dichlorophenyl)sulfonyl](methyl)amino}methyl)furan-3-carboxylic acid (51 mg, 0.14 mmol) was dissolved in DCE (0.5 mL) and CDI (34 mg, 0.21 mmol) was added. The mixture was stirred until acid activation was complete. 1-[4-(4,5-dihydro-1H-imidazol-2-yl)phenyl]methanamine.HCl (180 mg, 0.42 mmol) and DIPEA (0.22 mL, 1.26 mmol) were sonicated in DMF (3 mL) for 15 min, 0.25 mL of activated acid solution was added to 0.5 mL of amine solution and the reaction was diluted with DMF (1.5 mL) and stirred at ambient temperature for 18 h. The reaction was concentrated, dissolved in DCM and washed with water (3×1.5 mL) and saturated brine (1 mL)). The organic layer was dried over MgSO$_4$, shaken with Ambersep and PL-MIA resins, and solvents were removed in vacuo. A portion of the crude product was purified using prep method C.

LCMS Method C: rt 3.17 min, 96%; m/z 521.10 (MH$^+$, 100%).
Potency: A

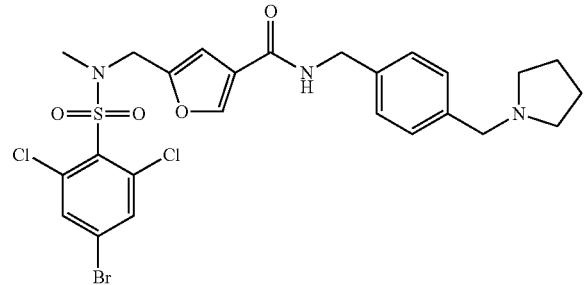 [SMILES: CN(Cc1cc(C(=O)NCc2ccc(CN3CCCC3)cc2)co1)S(=O)(=O)c1c(Cl)cc(Br)cc1Cl]

5-({[(4-bromo-2,6-dichlorophenyl)sulfonyl](methyl)
amino}methyl)-N-[4-(pyrrolidin-1-ylmethyl)benzyl]
furan-3-carboxamide Ex 27

To a stirred solution of 5-({[(4-bromo-2,6-dichlorophenyl) sulfonyl](methyl)amino}methyl)furan-3-carboxylic acid (40 mg, 0.09 mmol), EDCI (23 mg, 0.12 mmol) and HOBt (15 mg, 0.11 mmol) in DMF (3 mL) was added 1-[4-(pyrrolidin-1-ylmethyl)phenyl]methanamine (17 mg, 0.09 mmol). The reaction was stirred at ambient temperature for 3 days, then absorbed on to an Isolute SCX-2 cartridge, washing with MeOH and eluting the product with 7M NH$_3$ in MeOH. The filtrate was concentrated in vacuo and a portion of the crude product purified using prep method C.

LCMS Method C: rt 3.48 min, 100%; m/z 616.08 (MH$^+$, 100%).
Potency: A

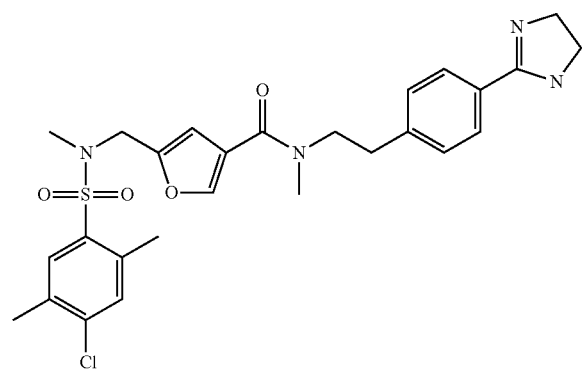 [SMILES: Cc1cc(S(=O)(=O)N(C)Cc2cc(C(=O)N(C)CCc3ccc(C4=NCCN4)cc3)co2)c(C)cc1Cl]

5-({[(4-chloro-2,5-dimethylphenyl)sulfonyl](methyl)
amino}methyl)-N-{2-[4-(4,5-dihydro-1H-imidazol-
2-yl)phenyl]ethyl}-N-methylfuran-3-carboxamide Ex 28

5-({[(4-chloro-2,5-dimethylphenyl)sulfonyl](methyl) amino}methyl)furan-3-carboxylic acid (30 mg, 0.08 mmol) was dissolved in DMF (1 mL) and CDI (20 mg, 0.12 mmol) was added. The mixture was stirred until acid activation was complete. 2-[4-(4,5-dihydro-1H-imidazol-2-yl)phenyl]-N-methylethanamine.HCl (19 mg, 0.08 mmol) and DIPEA (0.042 mL, 0.24 mmol) were sonicated in DMF (1 mL) for 15 min, 0.5 mL of activated acid solution was added to 0.25 mL of amine solution and the reaction was microwaved (120° C., 200 W) for 20 min, then 2×60 min. A portion of the reaction was concentrated and purified using prep method A.

LCMS Method C: rt 3.39 min, 97%; m/z 543.33 (MH$^+$, 100%).
Potency: A

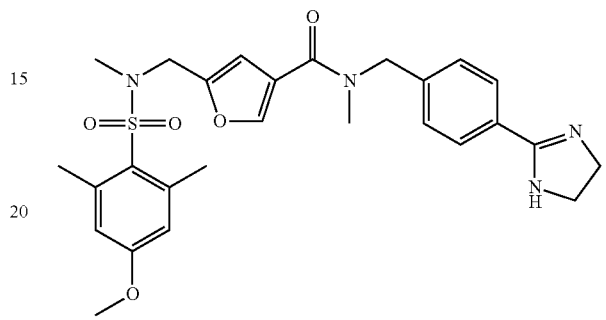

N-[4-(4,5-dihydro-1H-imidazol-2-yl)benzyl]-5-({
[(4-methoxy-2,6-dimethylphenyl)sulfonyl](methyl)
amino}methyl)-N-methylfuran-3-carboxamide Ex 29

5-({[(4-Methoxy-2,6-dimethylphenyl)sulfonyl](methyl) amino}methyl)furan-3-carboxylic acid (30 mg, 0.09 mmol) was dissolved in DCE (2 mL) and CDI (30 mg, 0.18 mmol) added. The reaction was stirred at room temperature until complete as determined by LCMS. 1-[4-(4,5-dihydro-1H-imidazol-2-yl)phenyl]-N-methylmethanamine (32 mg, 0.17 mmol) and DIPEA (0.032 mL, 0.18 mmol) was added and the reaction stirred for 3 days at ambient temperature. A further 32 mg 1-[4-(4,5-dihydro-1H-imidazol-2-yl)phenyl]-N-methylmethanamine was added, followed by DMF (0.5 mL) and the reaction was stirred for 18 h. The reaction was washed with saturated aqueous NH$_4$Cl (3×5 mL) and the organic layer dried over MgSO$_4$, shaken with PL-MIA and Ambersep resins, and concentrated. A portion of the crude product was purified using prep method C.

LCMS Method C: rt 3.22 min, 100%; m/z 525.25 (MH$^+$, 100%).
Potency: C

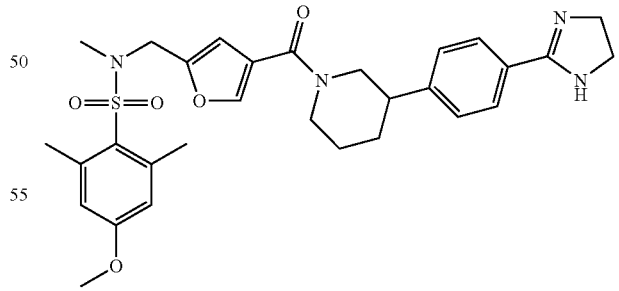

N-{[4-({3-[4-(4,5-dihydro-1H-imidazol-2-yl)phenyl]
piperidin-1-yl}carbonyl)furan-2-yl]methyl}-4-methoxy-N,2,6-trimethylbenzenesulfonamide Ex 30

The title compound was prepared according to general procedure AA using 5-({[(4-Methoxy-2,6-dimethylphenyl)

sulfonyl](methyl)amino}methyl)furan-3-carboxylic acid (60 mg, 0.15 mmol), CDI (51 mg, 0.31 mmol), 3-[4-(4,5-dihydro-1H-imidazol-2-yl)phenyl]piperidine (49 mg, 0.15 mmol) and DIPEA (0.134 mL, 0.76 mmol) in DCE (1.2 mL).

A portion of the crude product was purified using prep method A.

LCMS Method C: rt 3.35 min, 100%; m/z 565.29 (MH+, 100%).
Potency: C

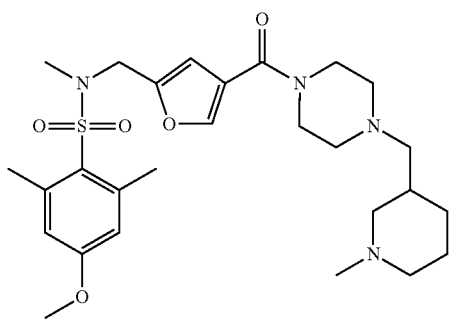 [SMILES: COc1cc(C)c(S(=O)(=O)N(C)Cc2cc(C(=O)N3CCN(CC4CCCN(C)C4)CC3)co2)c(C)c1]

4-methoxy-N,2,6-trimethyl-N-{[4-({4-[(1-methylpi-peridin-3-yl)methyl]piperazin-1-yl}carbonyl)furan-2-yl]methyl}benzenesulfonamide Ex 31

The title compound was prepared according to general procedure AA using 5-({[(4-Methoxy-2,6-dimethylphenyl)sulfonyl](methyl)amino}methyl)furan-3-carboxylic acid (63 mg, 0.18 mmol), CDI (58 mg, 0.36 mmol) and 1-[(1-methylpiperidin-3-yl)methyl]piperazine (59 mg, 0.30 mmol) in DCE (4.5 mL).

A portion of the crude product was purified using Ambersep and PL-MIA resins.

LCMS Method C: rt 2.68 min, 100%; m/z 198.01 (fragment, 100%), 336.14 (fragment, 92%), 533.34 (MH+, 66%).
Potency: B

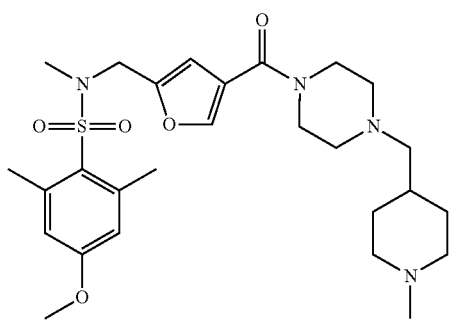 [SMILES: COc1cc(C)c(S(=O)(=O)N(C)Cc2cc(C(=O)N3CCN(CC4CCN(C)CC4)CC3)co2)c(C)c1]

4-methoxy-N,2,6-trimethyl-N-{[4-({4-[(1-methylpi-peridin-4-yl)methyl]piperazin-1-yl}carbonyl)furan-2-yl]methyl}benzenesulfonamide Ex 32

The title compound was prepared according to general procedure AA using 5-({[(4-Methoxy-2,6-dimethylphenyl)sulfonyl](methyl)amino}methyl)furan-3-carboxylic acid (63 mg, 0.18 mmol), CDI (58 mg, 0.36 mmol) and 1-[(1-methylpiperidin-4-yl)methyl]piperazine (59 mg, 0.30 mmol) in DCE (4.5 mL). The crude product was purified using Ambersep and PL-MIA resins to afford the title compound.

LCMS Method C: rt 2.60 min, 95%; m/z 336.14 (fragment, 100%), 198.21 (fragment, 92%), 533.35 (MH+, 84%).
Potency: A

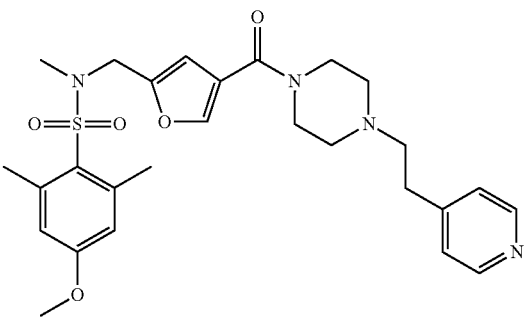 [SMILES: COc1cc(C)c(S(=O)(=O)N(C)Cc2cc(C(=O)N3CCN(CCc4ccncc4)CC3)co2)c(C)c1]

4-methoxy-N,2,6-trimethyl-N-[(4-{[4-(2-pyridin-4-ylethyl)piperazin-1-yl]carbonyl}furan-2-yl)methyl]benzenesulfonamide Ex 33

The title compound was prepared according to general procedure AA using 5-({[(4-Methoxy-2,6-dimethylphenyl)sulfonyl](methyl)amino}methyl)furan-3-carboxylic acid (63 mg, 0.18 mmol), CDI (58 mg, 0.36 mmol) and 1-[2-(pyridin-4-yl)ethyl]piperazine (57 mg, 0.30 mmol) in DCE (4.5 mL). The crude product was purified using Ambersep and PL-MIA resins, then using prep method A.

LCMS Method C: rt 2.69 min, 100%; m/z 527.33 (MH+, 93%).
Potency: A

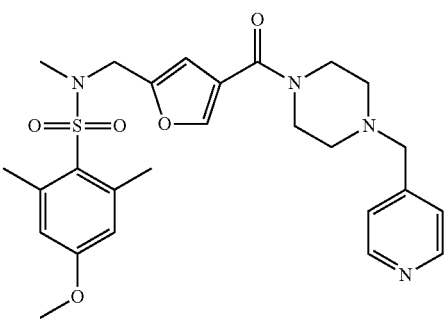 [SMILES: COc1cc(C)c(S(=O)(=O)N(C)Cc2cc(C(=O)N3CCN(Cc4ccncc4)CC3)co2)c(C)c1]

4-methoxy-N,2,6-trimethyl-N-[(4-{[4-(pyridin-4-ylmethyl)piperazin-1-yl]carbonyl}furan-2-yl)methyl]benzenesulfonamide Ex 34

The title compound was prepared according to general procedure AA using 5-({[(4-Methoxy-2,6-dimethylphenyl)sulfonyl](methyl)amino}methyl)furan-3-carboxylic acid (63 mg, 0.18 mmol), CDI (58 mg, 0.36 mmol) and 1-(pyridin-4-ylmethyl)piperazine (53 mg, 0.30 mmol) in DCE (4.5 mL).

The crude product was purified using Ambersep and PL-MIA resins, then using prep method A.

LCMS Method C: rt 3.07 min, 98%; m/z 513.31 (MH+, 100%)

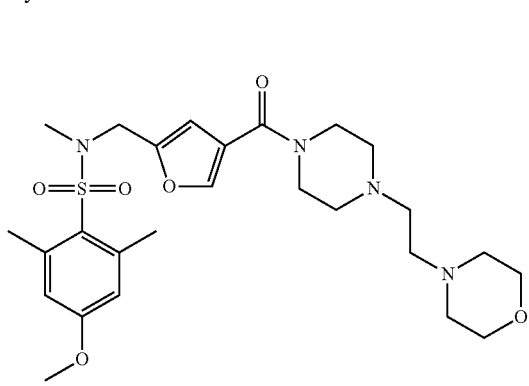

4-methoxy-N,2,6-trimethyl-N-[(4-{[4-(2-morpholin-4-ylethyl)piperazin-1-yl]carbonyl}furan-2-yl)methyl]benzenesulfonamide Ex 35

The title compound was prepared according to general procedure AA using 5-({[(4-Methoxy-2,6-dimethylphenyl)sulfonyl](methyl)amino}methyl)furan-3-carboxylic acid (63 mg, 0.18 mmol), CDI (58 mg, 0.36 mmol) and 4-[2-(piperazin-1-yl)ethyl]morpholine (60 mg, 0.30 mmol) in DCE (4.5 mL).

The crude product was purified using Ambersep and PL-MIA resins, then using prep method A.

LCMS Method C: rt 3.01 min, 94%; m/z 535.36 (MH+, 100%)

Potency: A

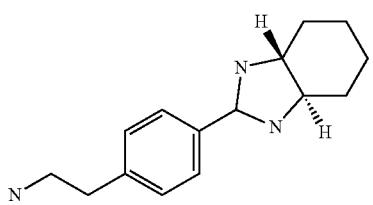 [SMILES: NCCc1ccc(C2N[C@@H]3CCCC[C@H]3N2)cc1]

2-{4-[(3aR,7aR)-octahydro-1H-benzimidazol-2-yl]phenyl}ethanamine

General Procedure AN

Int 58 tert-butyl (2-{4-[(3aR,7aR)-octahydro-1H-benzimidazol-2-yl]phenyl}ethyl)carbamate (50 mg, 0.15 mmol) was stirred in a 4:1 mixture of DCM:TFA (1 mL) at ambient temperature for 18 h. The reaction was concentrated in vacuo and the crude product used without further purification.

Yield: 82 mg, 93%

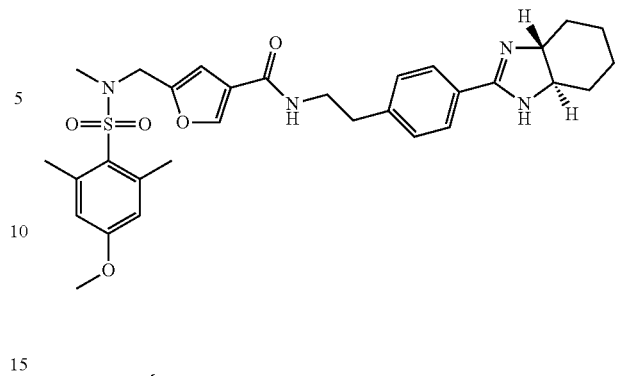

N-(2-{4-[(3aR,7aR)-3a,4,5,6,7,7a-hexahydro-1H-benzimidazol-2-yl]phenyl}ethyl)-5-({[(4-methoxy-2,6-dimethylphenyl)sulfonyl](methyl)amino}methyl)furan-3-carboxamide Ex 36

The title compound was prepared according to general procedure AG using 5-({[(4-Methoxy-2,6-dimethylphenyl)sulfonyl](methyl)amino}methyl)furan-3-carboxylic acid (56 mg, 0.16 mmol), EDCI (36 mg, 0.19 mmol), HOAt (26 mg, 0.19 mmol), DIPEA (0.084 mL, 0.48 mmol) and 2-{4-[(3aR,7aR)-3a,4,5,6,7,7a-hexahydro-1H-benzimidazol-2-yl]phenyl}ethanamine (82 mg, 0.14 mmol) in DMF (1 mL). The crude product was purified using Ambersep resin, then using prep method C.

LCMS Method C: rt 3.46 min, 100%; m/z 579.26 (MH+, 100%)

Potency: B

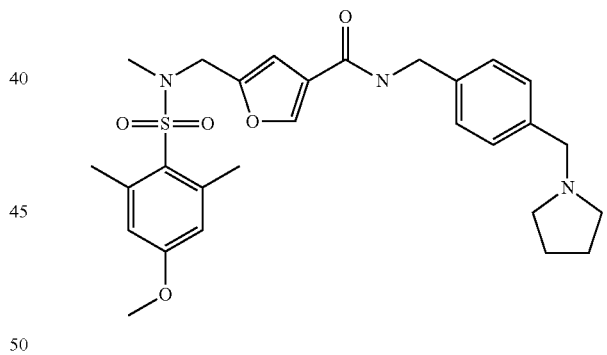

5-({[(4-methoxy-2,6-dimethylphenyl)sulfonyl](methyl)amino}methyl)-N-[4-(pyrrolidin-1-ylmethyl)benzyl]furan-3-carboxamide Ex 37

The title compound was prepared according to general procedure AA using 5-({[(4-Methoxy-2,6-dimethylphenyl)sulfonyl](methyl)amino}methyl)furan-3-carboxylic acid (75 mg, 0.21 mmol), CDI (41 mg, 0.25 mmol) and 1-[4-(pyrrolidin-1-ylmethyl)phenyl]methanamine (37 mg, 0.21 mmol) in THF (4.5 mL) and DMF (0.6 mL). A portion of the crude product was purified using prep method A.

LCMS Method C: rt 3.25 min, 100%; m/z 526.20 (MH+, 100%)

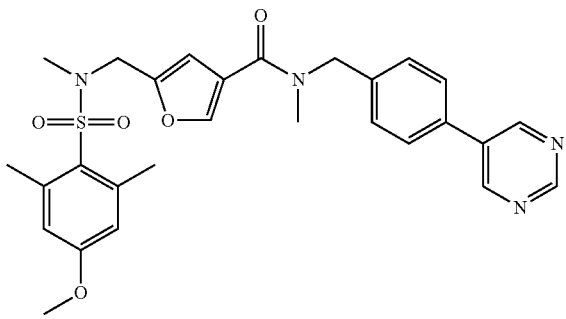 [SMILES: COc1cc(C)c(S(=O)(=O)N(C)Cc2cc(C(=O)N(C)Cc3ccc(-c4cncnc4)cc3)co2)c(C)c1]

5-({[(4-methoxy-2,6-dimethylphenyl)sulfonyl](methyl)amino}methyl)-N-methyl-N-(4-pyrimidin-5-ylbenzyl)furan-3-carboxamide Ex 38

The title compound was prepared according to general procedure AA using 5-({[(4-Methoxy-2,6-dimethylphenyl)sulfonyl](methyl)amino}methyl)furan-3-carboxylic acid (75 mg, 0.21 mmol), CDI (41 mg, 0.25 mmol) and N-methyl-1-[4-(pyrimidin-5-yl)phenyl]methanamine (42 mg, 0.21 mmol) in THF (4.5 mL) and DMF (0.6 mL). The crude product was purified using prep method A.

LCMS Method C: rt 4.21 min, 98%; m/z 535.19 (MH+, 100%)

Potency: A

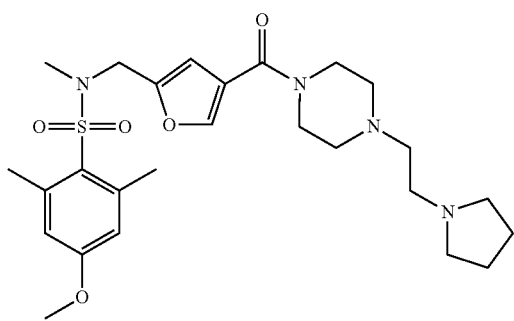 [SMILES: COc1cc(C)c(S(=O)(=O)N(C)Cc2cc(C(=O)N3CCN(CCN4CCCC4)CC3)co2)c(C)c1]

4-methoxy-N,2,6-trimethyl-N-[(4-{[4-(2-pyrrolidin-1-ylethyl)piperazin-1-yl]carbonyl}furan-2-yl)methyl]benzenesulfonamide Ex 39

The title compound was prepared according to general procedure AA using 5-({[(4-Methoxy-2,6-dimethylphenyl)sulfonyl](methyl)amino}methyl)furan-3-carboxylic acid (69 mg, 0.20 mmol), CDI (63 mg, 0.39 mmol) and 1-[2-(pyrrolidin-1-yl)ethyl]piperazine (72 mg, 0.39 mmol) in THF (4 mL). The crude product was purified using prep method A.

LCMS Method C: rt 3.04 min, 100%; m/z 519.31 (MH+, 100%)

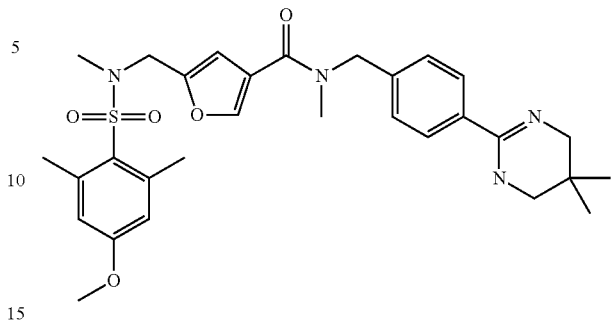

N-[4-(5,5-dimethyl-1,4,5,6-tetrahydropyrimidin-2-yl)benzyl]-5-({[(4-methoxy-2,6-dimethylphenyl)sulfonyl](methyl)amino}methyl)-N-methylfuran-3-carboxamide Ex 40

The title compound was prepared according to general procedure AG using 5-({[(4-Methoxy-2,6-dimethylphenyl)sulfonyl](methyl)amino}methyl)furan-3-carboxylic acid (55 mg, 0.15 mmol), EDCI (35 mg, 0.18 mmol), HOAt (25 mg, 0.18 mmol), DIPEA (0.156 mL, 0.89 mmol) and 1-[4-(5,5-dimethyl-1,4,5,6-tetrahydropyrimidin-2-yl)phenyl]-N-methylmethanamine (43 mg, 0.13 mmol) in DCE (1 mL). The crude product was purified using prep method C.

LCMS Method C: rt 3.40 min, 97%; m/z 567.26 (MH+, 100%)

Potency: A

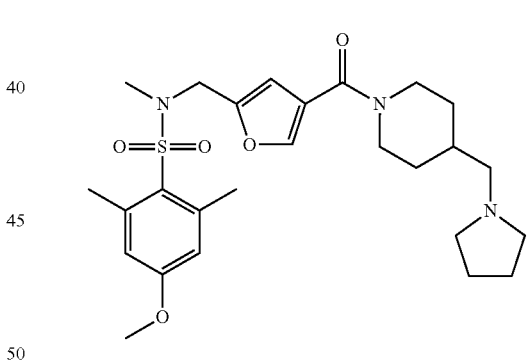

4-methoxy-N,2,6-trimethyl-N-[(4-{[4-(pyrrolidin-1-ylmethyl)piperidin-1-yl]carbonyl}furan-2-yl)methyl]benzenesulfonamide Ex 41

The title compound was prepared according to general procedure AG using 5-({[(4-Methoxy-2,6-dimethylphenyl)sulfonyl](methyl)amino}methyl)furan-3-carboxylic acid (60 mg, 0.17 mmol), EDCI (33 mg, 0.17 mmol), HOAt (24 mg, 0.17 mmol and 4-(pyrrolidin-1-ylmethyl)piperidine (28 mg, 0.17 mmol) in DMF (1 mL). The crude product was purified by FCC and then using prep method C.

LCMS Method C: rt 3.16 min, 100%; m/z 504.24 (MH+, 100%)

Potency: A

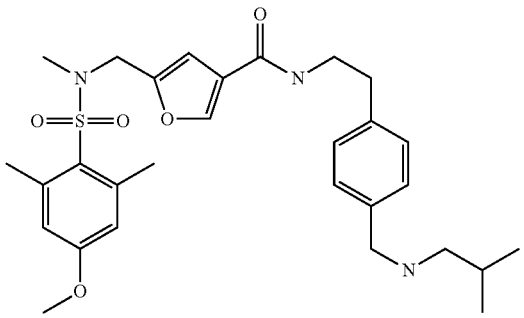 [SMILES: COc1cc(C)c(S(=O)(=O)N(C)Cc2cc(C(=O)NCCc3ccc(CNCC(C)C)cc3)co2)c(C)c1]

5-({[(4-methoxy-2,6-dimethylphenyl)sulfonyl](methyl)amino}methyl)-N-[2-(4-{[(2-methylpropyl)amino]methyl}phenyl)ethyl]furan-3-carboxamide Ex 42

The title compound was prepared according to general procedure AA using 5-({[(4-Methoxy-2,6-dimethylphenyl)sulfonyl](methyl)amino}methyl)furan-3-carboxylic acid (60 mg, 0.15 mmol), CDI (46 mg, 0.27 mmol), DIPEA (0.134 mL, 0.76 mmol) and N-[4-(2-aminoethyl)benzyl]-2-methylpropan-1-amine (40 mg, 0.14 mmol) in DCE (1 mL). A portion of the crude product was purified using prep method A.

LCMS Method C: rt 3.39 min, 96%; m/z 542.34 (MH+, 100%)

Potency: A

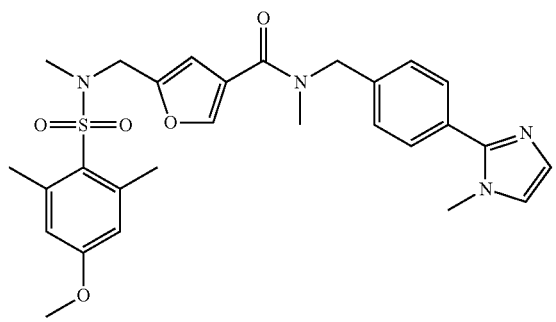 [SMILES: COc1cc(C)c(S(=O)(=O)N(C)Cc2cc(C(=O)N(C)Cc3ccc(-c4nccn4C)cc3)co2)c(C)c1]

5-({[(4-methoxy-2,6-dimethylphenyl)sulfonyl](methyl)amino}methyl)-N-methyl-N-[4-(1-methyl-1H-imidazol-2-yl)benzyl]furan-3-carboxamide Ex 43
General Procedure AC 5-({[(4-Methoxy-2,6-dimethylphenyl)sulfonyl](methyl)amino}methyl)furan-3-carboxylic acid (50 mg, 0.14 mmol) was dissolved in DMF (3 mL) and EDCI (32 mg, 0.17 mmol) and HOBt (23 mg, 0.17 mmol) were added. The resulting solution was stirred for 60 min prior to the addition of N-methyl-1-[4-(1-methyl-1H-imidazol-2-yl)phenyl]methanamine (31 mg, 0.17 mmol) dissolved in DMF (2 mL) and stirred at ambient temperature for 18 h. The reaction was diluted with EtOAc (20 mL) and washed with water, saturated aqueous NaHCO3, saturated brine, dried over Na2SO4 and concentrated in vacuo. The resulting oil was purified using prep method C.

LCMS Method C: rt 3.29 min, 100%; m/z 537.24 (MH+, 100%)

Potency: A

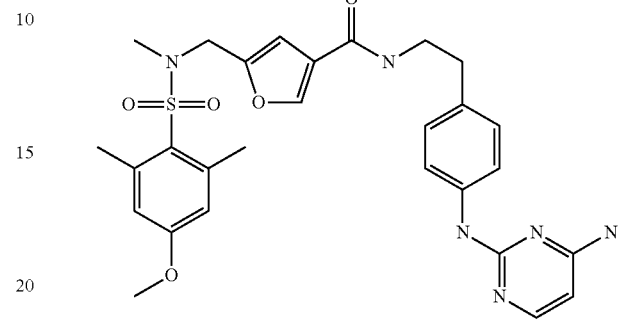

N-(2-{4-[(4-aminopyrimidin-2-yl)amino]phenyl}ethyl)-5-({[(4-methoxy-2,6-dimethylphenyl)sulfonyl](methyl)amino}methyl)furan-3-carboxamide Ex 44

The title compound was prepared according to general procedure AE using 5-({[(4-Methoxy-2,6-dimethylphenyl)sulfonyl](methyl)amino}methyl)furan-3-carboxylic acid (60 mg, 0.15 mmol), CDI (51 mg, 0.31 mmol), DIPEA (0.134 mL, 0.76 mmol) and N²-[4-(2-aminoethyl)phenyl]pyrimidine-2,4-diamine (49 mg, 0.15 mmol) in DCE (1 mL). A portion of the crude product was purified using prep method A.

LCMS Method C: rt 3.29 min, 95%; m/z 565.31 (MH+, 100%)

Potency: A

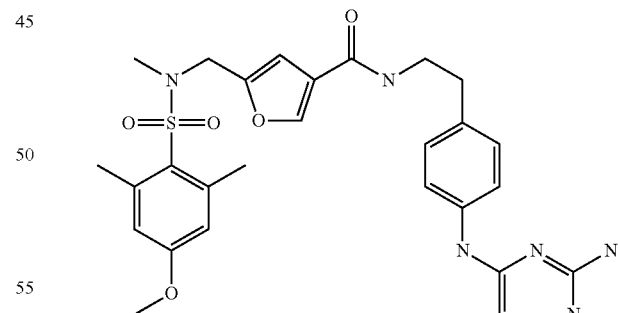

N-(2-{4-[(2-aminopyrimidin-4-yl)amino]phenyl}ethyl)-5-({[(4-methoxy-2,6-dimethylphenyl)sulfonyl](methyl)amino}methyl)furan-3-carboxamide Ex 45

The title compound was prepared according to general procedure AE using 5-({[(4-Methoxy-2,6-dimethylphenyl)

sulfonyl](methyl)amino}methyl)furan-3-carboxylic acid (60 mg, 0.15 mmol), CDI (51 mg, 0.31 mmol), DIPEA (0.134 mL, 0.76 mmol) and $N^4$-[4-(2-aminoethyl)phenyl]pyrimidine-2,4-diamine (49 mg, 0.15 mmol) in DCE (1 mL). A portion of the crude product was purified using prep method A.

LCMS Method C: rt 3.31 min, 96%; m/z 565.30 (MH$^+$, 100%)

Potency: A

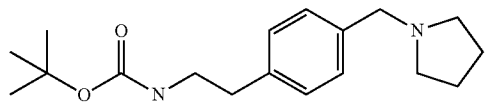 [SMILES: CC(C)(C)OC(=O)NCCc1ccc(CN2CCCC2)cc1]

tert-butyl {2-[4-(pyrrolidin-1-ylmethyl)phenyl]ethyl}carbamate

Int 59

General Procedure AO

To a stirred solution of tert-butyl[2-(4-formylphenyl)ethyl] carbamate (50 mg, 0.2 mmol) and pyrrolidine (0.050 mL, 0.61 mmol) in EtOH (3 mL) was added Pd (10% on activated C, 10 mg) and the reaction vessel was purge-filled three times with $N_2$ and then purge-filled three times with $H_2$ and the reaction was stirred at ambient temperature for 3 h maintaining constant pressure of $H_2$ using a balloon. The mixture was then filtered through a plug of Celite and solvents were removed in vacuo to afford 82 mg orange oil. The oil was dissolved in DCM (5 mL) and shaken with PL-MIA resin (400 mg, 2.46 mmol/g) for 1 h, then filtered. Solvents were removed and the crude product was used without further purification.

Yield: 66 mg, 71% purity, 77%.

LCMS Method A: rt 1.10 min, 71%; m/z 305.15 (MH$^+$, 100%)

$^1$H NMR (500 MHz, CDCl$_3$) δ ppm 7.27 (2H, d, J=7.70 Hz) 7.15 (2H, d, J=7.70 Hz) 4.54 (1H, br. s.) 3.63 (2H, s) 3.38 (2H, d, J=6.05 Hz) 2.78 (2H, t, J=6.88 Hz) 2.55 (4H, br. s.) 1.76-1.85 (4H, m) 1.44 (9H, s)

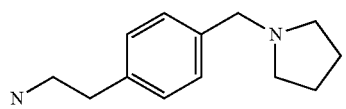 [SMILES: NCCc1ccc(CN2CCCC2)cc1]

2-[4-(pyrrolidin-1-ylmethyl)phenyl]ethanamine

Int 60

The title compound was prepared as the bis-HCl salt according to General Procedure AS, using tert-butyl {2-[4-(pyrrolidin-1-ylmethyl)phenyl]ethyl}carbamate (47 mg, 0.15 mmol), thionyl chloride (0.058 mL, 0.79 mmol) and MeOH (3 mL).

Yield: 40 mg, 97%.

$^1$H NMR (500 MHz, CD$_3$OD) δ ppm 7.58 (2H, d, J=8.07 Hz) 7.42 (2H, d, J=7.89 Hz) 4.39 (2H, s) 3.43-3.54 (2H, m) 3.14-3.25 (4H, m) 3.00-3.07 (2H, m) 2.18 (2H, t, J=7.06 Hz) 1.96-2.08 (2H, m)

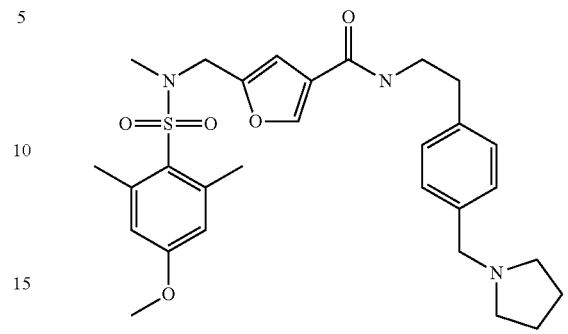

5-({[(4-methoxy-2,6-dimethylphenyl)sulfonyl](methyl)amino}methyl)-N-{2-[4-(pyrrolidin-1-ylmethyl)phenyl]ethyl}furan-3-carboxamide Ex 46

The title compound was prepared according to general procedure AC using 5-({[(4-Methoxy-2,6-dimethylphenyl)sulfonyl](methyl)amino}methyl)furan-3-carboxylic acid (76 mg, 0.22 mmol), EDCI (50 mg, 0.26 mmol), HOBt (35 mg, 0.26 mmol), TEA (0.030 mL, 0.22 mmol) and 2-[4-(pyrrolidin-1-ylmethyl)phenyl]ethanamine (40 mg, 0.20 mmol) in DMF (5 mL). A portion of the crude product was purified using prep method A.

LCMS Method C: rt 3.35 min, 100%; m/z 540.13 (MH$^+$, 100%)

Potency: A

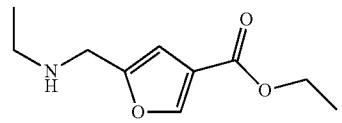

Ethyl 5-[(ethylamino)methyl]furan-3-carboxylate

Int 61

General Procedure AJ

Ethyl 5-formylfuran-3-carboxylate (250 mg, 1.49 mmol) was dissolved in EtOH (3 mL) and 2 M ethylamine in MeOH (7.5 mL, 15 mmol) was added followed by 10% Pd/C (20 mg, cat). The reaction vessel was purge-filled with nitrogen (3 cycles), then with hydrogen (3 cycles). 5 atmospheres pressure of hydrogen was maintained for 3 h with stirring. The reaction mixture was filtered through Celite. The filter cake was washed with MeOH and the combined organic extracts were concentrated in vacuo.

No further purification was required.

Yield: 293 mg, 100%.

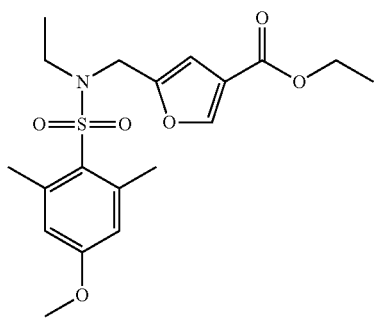

Ethyl 5-({ethyl[(4-methoxy-2,6-dimethylphenyl)
sulfonyl]amino}methyl)furan-3-carboxylate Int 62

General Procedure AU

To a stirred solution of 4-methoxy-2,6-dimethylbenzenesulfonyl chloride (400 mg, 1.64 mmol) and TEA (0.42 mL, 3 mmol) in DCM (5 mL) at 0° C. was added a solution of ethyl 5-[(ethylamino)methyl]furan-3-carboxylate (295 mg, 1.49 mmol) in DCM (5 mL). The reaction was allowed to warm to ambient temperature and stirred overnight. The mixture was diluted with DCM and washed with water, then dried over $Na_2SO_4$. Solvents were removed in vacuo and the crude product was purified using FCC eluting with EtOAc to afford the title compound.

Yield: 510 mg, 87%.

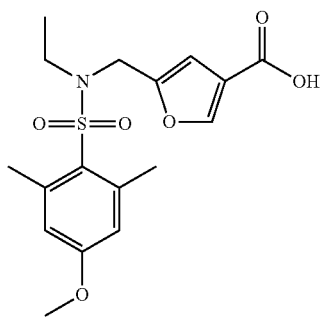 [SMILES: CCN(Cc1cc(C(=O)O)co1)S(=O)(=O)c1c(C)cc(OC)cc1C]

5-({Ethyl[(4-methoxy-2,6-dimethylphenyl)sulfonyl]
amino}methyl)furan-3-carboxylic acid Int 63

The title compound was prepared according to general procedure AF using ethyl 5-({ethyl[(4-methoxy-2,6-dimethylphenyl)sulfonyl]amino}methyl)furan-3-carboxylate (530 mg, 1.3 mmol) and LiOH (164 mg, 3.9 mmol) in 1:1 THF/water (10 mL) to afford the title compound, which required no further purification.

Yield: 380 mg, 79%.

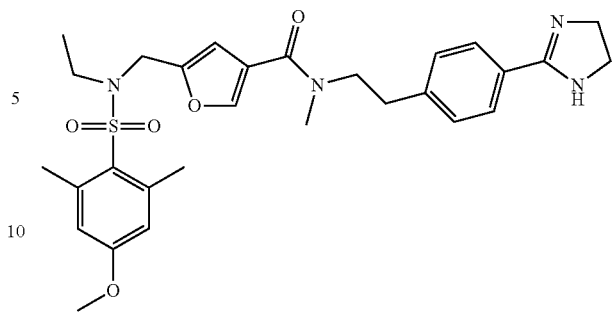

N-{2-[4-(4,5-dihydro-1H-imidazol-2-yl)phenyl]
ethyl}-5-({ethyl[(4-methoxy-2,6-dimethylphenyl)
sulfonyl]amino}methyl)-N-methylfuran-3-carboxamide Ex 47

The title compound was prepared according to general procedure AH using 5-({ethyl[(4-methoxy-2,6-dimethylphenyl)sulfonyl]amino}methyl)furan-3-carboxylic acid (150 mg, 0.41 mmol), the bis HCl salt of 2-[4-(4,5-dihydro-1H-imidazol-2-yl)phenyl]-N-methylethanamine (102 mg, 0.37 mmol), EDCI (94 mg, 0.49 mmol), HOBt (66 mg, 0.49 mmol) and DIPEA (0.42 mL, 2.46 mmol) in DMF (10 mL). The resulting crude product was purified using prep method B to afford the title compound as a TFA salt.

Yield: 12 mg, 5%.

LCMS method C: rt 3.30 min, 100%; m/z 552.70 ($MH^+$, 100%).

Potency: C

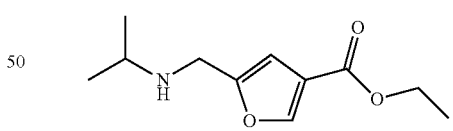

Ethyl
5-[(propan-2-ylamino)methyl]furan-3-carboxylate

Int 64

The title compound was prepared according to general procedure AJ using ethyl 5-formylfuran-3-carboxylate (200 mg, 1.19 mmol) and isopropylamine (702 mg, 11.9 mmol). The crude product required no further purification.

Yield: 293 mg, 100%.

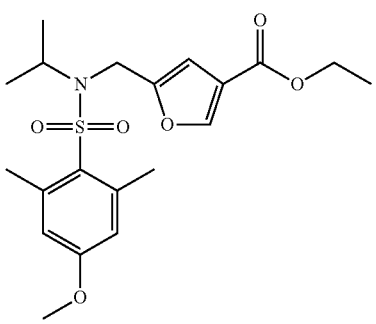 [SMILES: CCOC(=O)c1coc(CN(C(C)C)S(=O)(=O)c2c(C)cc(OC)cc2C)c1]

Ethyl 5-({[(4-methoxy-2,6-dimethylphenyl)sulfonyl](1-methylethyl)amino}methyl)furan-3-carboxylate Int 65

The title compound was prepared according to general procedure AU using ethyl 5-[(propan-2-ylamino)methyl]furan-3-carboxylate (250 mg, 1.13 mmol), 4-methoxy-2,6-dimethylbenzenesulfonyl chloride (290 mg, 1.24 mmol) and TEA (0.3 mL, 2.26 mmol) in DCM (10 mL). The crude product was purified using FCC eluting with 10% EtOAc in heptane to afford the title compound.

Yield: 463 mg, 100%.

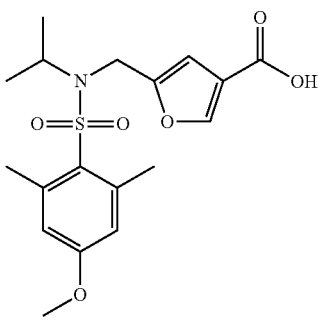 [SMILES: COc1cc(C)c(S(=O)(=O)N(Cc2cc(C(=O)O)co2)C(C)C)c(C)c1]

5-({[(4-methoxy-2,6-dimethylphenyl)sulfonyl](propan-2-yl)amino}methyl)furan-3-carboxylic acid Int 66

The title compound was prepared according to general procedure AF using ethyl 5-({[(4-methoxy-2,6-dimethylphenyl)sulfonyl](1-methylethyl)amino}methyl)furan-3-carboxylate (463 mg, 1.13 mmol) and LiOH (200 mg, 4.8 mmol) in 1:1 THF/water (20 mL) to afford the title compound, which required no further purification.

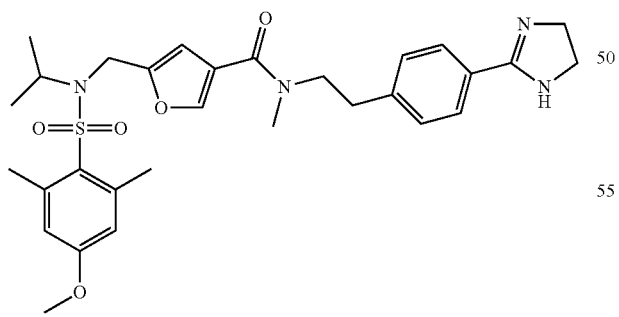

N-{2-[4-(4,5-dihydro-1H-imidazol-2-yl)phenyl]ethyl}-5-({[(4-methoxy-2,6-dimethylphenyl)sulfonyl](1-methylethyl)amino}methyl)-N-methylfuran-3-carboxamide Ex 48

The title compound was prepared according to general procedure AH using 5-({[(4-methoxy-2,6-dimethylphenyl)sulfonyl](propan-2-yl)amino}methyl)furan-3-carboxylic acid (50 mg, 0.13 mmol), the bis HCl salt of 2-[4-(4,5-dihydro-1H-imidazol-2-yl)phenyl]-N-methylethanamine (32 mg, 0.12 mmol), EDCI (27 mg, 0.14 mmol), HOBt (20 mg, 0.14 mmol) and DIPEA (0.1 mL, 0.52 mmol) in DMF (5 mL). The resulting crude product was purified using prep method B to afford the title compound as a TFA salt.

Yield: 6 mg, 8%.

LCMS method C: rt 3.34 min, 100%; m/z 566.73 (MH$^+$, 100%).

$^1$H NMR (500 MHz, CD$_3$OD) δ ppm 7.80 (2H, br. s.), 7.55-7.71 (2H, m), 7.43 (1H, br. s.), 6.72 (2H, br. s.), 6.10-6.32 (1H, m), 4.41 (2H, s), 4.06-4.13 (4H, m), 3.97-4.05 (1H, m), 3.81-3.84 (3H, m), 3.78 (2H, t, J=7.17 Hz), 3.03-3.10 (5H, m), 2.59 (6H, s), 1.08-1.21 (6H, m).

Potency: B

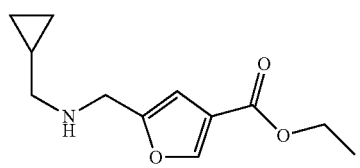 [SMILES: CCOC(=O)c1coc(CNCC2CC2)c1]

Ethyl 5-{[(cyclopropylmethyl)amino]methyl}furan-3-carboxylate

Int 67

The title compound was prepared according to general procedure AJ using ethyl 5-formylfuran-3-carboxylate (200 mg, 1.19 mmol) and cyclopropyl methyl amine (846 mg, 11.9 mmol). The crude product required no further purification.

Yield: 265 mg, 100%.

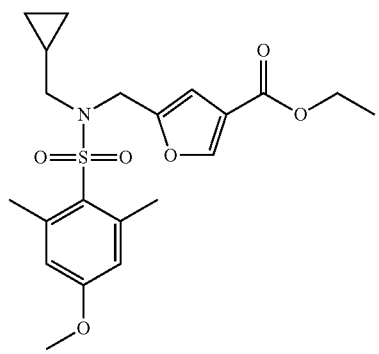 [SMILES: CCOC(=O)c1coc(CN(CC2CC2)S(=O)(=O)c2c(C)cc(OC)cc2C)c1]

Ethyl 5-({(cyclopropylmethyl)[(4-methoxy-2,6-dimethylphenyl)sulfonyl]amino}methyl)furan-3-carboxylate Int 68

The title compound was prepared according to general procedure AU using ethyl 5-{[(cyclopropylmethyl)amino]methyl}furan-3-carboxylate (250 mg, 1.13 mmol), 4-methoxy-2,6-dimethylbenzenesulfonyl chloride (287 mg, 1.23 mmol) and TEA (0.31 mL, 2.24 mmol) in DCM (10 mL). The crude product was purified using FCC eluting with 10% EtOAc in heptane to afford the title compound.

Yield: 290 mg, 58%.

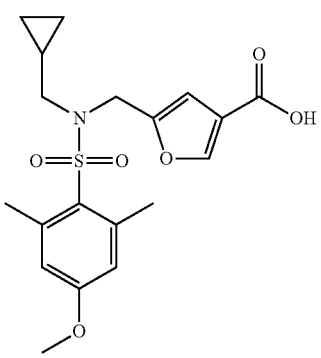 [SMILES: COc1cc(C)c(S(=O)(=O)N(Cc2cc(C(=O)O)co2)CC2CC2)c(C)c1]

5-({(Cyclopropylmethyl)[(4-methoxy-2,6-dimethylphenyl)sulfonyl]amino}methyl)furan-3-carboxylic acid Int 69

The title compound was prepared according to general procedure AF using ethyl 5-({(cyclopropylmethyl)[(4-methoxy-2,6-dimethylphenyl)sulfonyl]amino}methyl)furan-3-carboxylate (290 mg, 0.69 mmol) and LiOH (100 mg, 2.37 mmol) in 1:1 THF/water (20 mL). The resultant crude product required no further purification.

Yield: 273 mg, 100%.

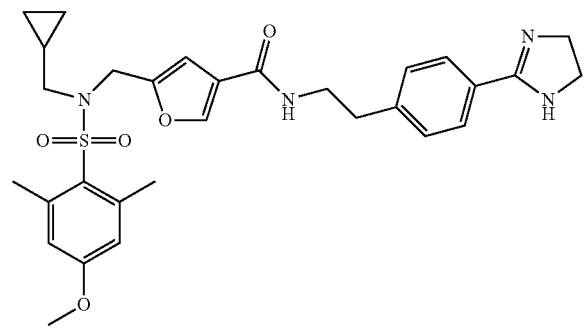 [SMILES: COc1cc(C)c(S(=O)(=O)N(Cc2cc(C(=O)NCCc3ccc(C4=NCCN4)cc3)co2)CC2CC2)c(C)c1]

5-({(Cyclopropylmethyl)[(4-methoxy-2,6-dimethylphenyl)sulfonyl]amino}methyl)-N-{2-[4-(4,5-dihydro-1H-imidazol-2-yl)phenyl]ethyl}furan-3-carboxamide Ex 49

The title compound was prepared according to general procedure AH using 5-({(cyclopropylmethyl)[(4-methoxy-2,6-dimethylphenyl)sulfonyl]amino}methyl)furan-3-carboxylic acid (100 mg, 0.25 mmol), the bis HCl salt of 2-[4-(4,5-dihydro-1H-imidazol-2-yl)phenyl]ethanamine (60 mg, 0.22 mmol), EDCI (55 mg, 0.29 mmol), HOBt (40 mg, 0.29 mmol) and DIPEA (0.2 mL, 1 mmol) in DMF (5 mL). The resulting crude product was purified using prep method A to afford the title compound as a TFA salt.

Yield: 2 mg, 1.4%.

LCMS method C: rt 3.44 min, 95%; m/z 564.71 (MH$^+$, 100%).

$^1$H NMR (500 MHz, CD$_3$OD) δ ppm 8.27 (1H, s), 7.87 (1H, s), 7.77 (1H, d, J=8.07 Hz), 7.52 (2H, d, J=8.25 Hz), 6.73 (2H, s), 6.56 (1H, s), 4.51 (2H, s), 4.07 (4H, s), 3.80 (2H, m), 3.58 (2H, s), 2.97 (4H, m), 2.64 (3H, s), 2.58 (5H, m), 1.28 (1H, s), 0.86 (1H, br. s.), 0.43 (2H, m), −0.01 (2H, d, J=5.69 Hz).

Potency: B

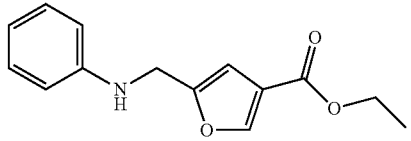 [SMILES: CCOC(=O)c1coc(CNc2ccccc2)c1]

Ethyl 5-[(phenylamino)methyl]furan-3-carboxylate

Int 70

The title compound was prepared according to general procedure AJ using ethyl 5-formylfuran-3-carboxylate (200 mg, 1.2 mmol) and aniline (1.1 g, 12 mmol). The crude product required no further purification.

Yield: 294 mg, 100%.

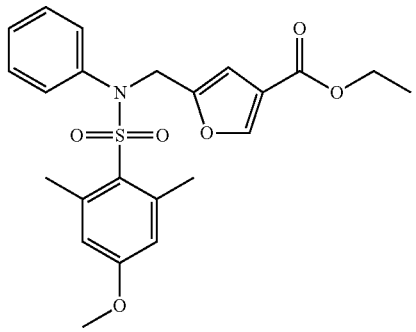 [SMILES: CCOC(=O)c1coc(CN(c2ccccc2)S(=O)(=O)c2c(C)cc(OC)cc2C)c1]

Ethyl 5-({[(4-methoxy-2,6-dimethylphenyl)sulfonyl](phenyl)amino}methyl)furan-3-carboxylate Int 71

A solution of 4-methoxy-2,6-dimethylbenzenesulfonyl chloride (313 mg, 1.34 mmol) and ethyl 5-[(phenylamino)methyl]furan-3-carboxylate (294 mg, 1.2 mmol) in pyridine (10 mL) was stirred at ambient temperature over 16 h. The mixture was concentrated in vacuo, diluted with DCM, washed with water, then dried over Na$_2$SO$_4$. Solvents were removed in vacuo. The crude product required no further purification.

Yield: 532 mg, 100%.

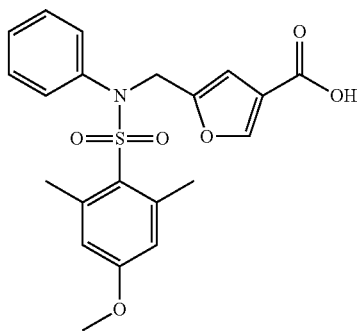 [SMILES: COc1cc(C)c(S(=O)(=O)N(Cc2cc(C(=O)O)co2)c2ccccc2)c(C)c1]

5-({[(4-Methoxy-2,6-dimethylphenyl)sulfonyl](phenyl)amino}methyl)furan-3-carboxylic acid Int 72

The title compound was prepared according to general procedure AF using ethyl 5-({[(4-methoxy-2,6-dimethylphenyl)sulfonyl](phenyl)amino}methyl)furan-3-carboxylate (532 mg, 1.2 mmol) and LiOH (227 mg, 5.42 mmol) in 1:1

THF/water (20 mL) to afford the title compound, which required no further purification.

Yield: 500 mg, 100%.

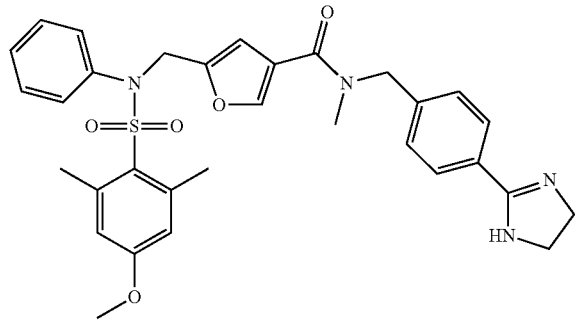 [SMILES: COc1cc(C)c(S(=O)(=O)N(Cc2cc(C(=O)N(C)Cc3ccc(C4=NCCN4)cc3)co2)c2ccccc2)c(C)c1]

N-[4-(4,5-dihydro-1H-imidazol-2-yl)benzyl]-5-({[(4-methoxy-2,6-dimethylphenyl)sulfonyl] (phenyl)amino}methyl)-N-methylfuran-3-carboxamide Ex 50

The title compound was prepared according to general procedure AH using 5-({[(4-methoxy-2,6-dimethylphenyl)sulfonyl](phenyl)amino}methyl)furan-3-carboxylic acid (100 mg, 0.24 mmol), the bis HCl salt of 1-[4-(4,5-dihydro-1H-imidazol-2-yl)phenyl]-N-methylmethanamine (58 mg, 0.22 mmol), EDCI (55 mg, 0.29 mmol), HOBt (40 mg, 0.29 mmol) and DIPEA (0.17 mL, 0.96 mmol) in DMF (5 mL). The resulting crude product was purified using prep method B to afford the title compound as a TFA salt.

Yield: 1 mg, 0.7%.

LCMS method C: rt 3.42 min, 100%; m/z 586.72 (MH+, 100%).

Potency: A

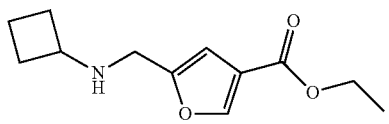 [SMILES: CCOC(=O)c1coc(CNC2CCC2)c1]

Ethyl 5-[(cyclobutylamino)methyl]furan-3-carboxylate

Int 73

The title compound was prepared according to general procedure AJ using ethyl 5-formylfuran-3-carboxylate (200 mg, 1.19 mmol) and cyclobutylamine (846 mg, 11.9 mmol). The crude product required no further purification.

Yield: 265 mg, 100%.

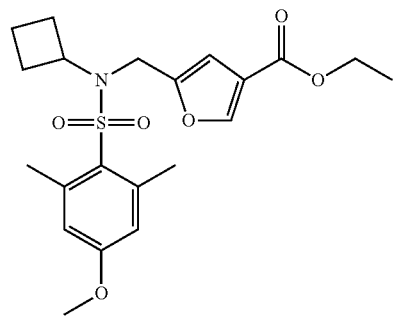 [SMILES: CCOC(=O)c1coc(CN(C2CCC2)S(=O)(=O)c2c(C)cc(OC)cc2C)c1]

Ethyl 5-({cyclobutyl[(4-methoxy-2,6-dimethylphenyl)sulfonyl]amino}methyl)furan-3-carboxylate Int 74

The title compound was prepared according to general procedure AU using ethyl 5-{[(cyclopropylmethyl)amino]methyl}furan-3-carboxylate (265 mg, 1.19 mmol), 4-methoxy-2,6-dimethylbenzenesulfonyl chloride (335 mg, 1.43 mmol) and TEA (0.4 mL, 2.86 mmol) in DCM (10 mL). The crude product required no further purification.

Yield: 548 mg, 100%.

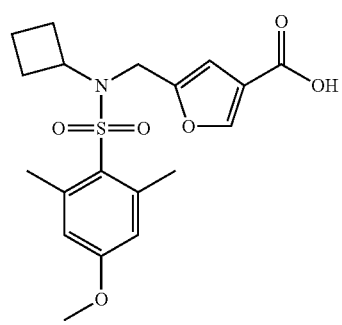 [SMILES: COc1cc(C)c(S(=O)(=O)N(Cc2cc(C(=O)O)co2)C2CCC2)c(C)c1]

5-({Cyclobutyl[(4-methoxy-2,6-dimethylphenyl)sulfonyl]amino}methyl)furan-3-carboxylic acid Int 75

The title compound was prepared according to general procedure AF using ethyl 5-({cyclobutyl[(4-methoxy-2,6-dimethylphenyl)sulfonyl]amino}methyl)furan-3-carboxylate (548 mg, 1.3 mmol) and LiOH (227 mg, 5.42 mmol) in 1:1 THF/water (20 mL). A portion of the crude product was purified using prep method A to afford the title compound.

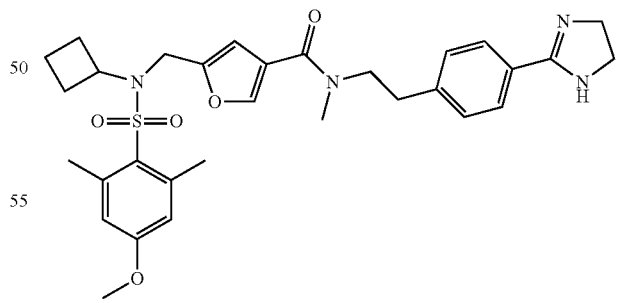

5-({Cyclobutyl[(4-methoxy-2,6-dimethylphenyl)sulfonyl]amino}methyl)-N-{2-[4-(4,5-dihydro-1H-imidazol-2-yl)phenyl]ethyl}-N-methylfuran-3-carboxamide Ex 51

The title compound was prepared according to general procedure AH using 5-({cyclobutyl[(4-methoxy-2,6-dimethylphenyl)sulfonyl]amino}methyl)furan-3-carboxylic acid (82 mg, 0.21 mmol), the bis HCl salt of 2-[4-(4,5-dihydro-1H-imidazol-2-yl)phenyl]-N-methylethanamine (52 mg, 0.2 mmol), EDCI (48 mg, 0.25 mmol), HOBt (34 mg, 0.25 mmol) and DIPEA (0.15 mL, 0.84 mmol) in DMF (7 mL). The resulting crude product was purified using prep method B to afford the title compound as a TFA salt.

Yield: 17 mg, 14%.

LCMS method C: rt 3.43 min, 100%; m/z 578.74 (MH+, 100%).

$^1$H NMR (500 MHz, CD$_3$OD) δ ppm 7.81 (2H, br. s.), 7.65 (2H, m), 7.44 (1H, br. s.), 6.74 (2H, m), 6.30 (1H, m), 4.52 (2H, m), 4.10 (4H, s), 3.81 (5H, m), 3.08 (5H, m), 2.59 (6H, m), 1.98 (5H, m), 1.58 (2H, br. s.).

Potency: C

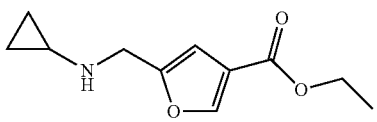

Ethyl 5-[(cyclopropylamino)methyl]furan-3-carboxylate

Int 76

Ethyl 5-formylfuran-3-carboxylate (840 mg, 5.0 mmol) was dissolved in EtOH (17 mL) and cooled to 0° C. prior to the addition of cyclopropylamine (1.04 mL, 15 mmol). 10% Pd/C (84 mg, cat) was added after warming the reaction to ambient temperature over 10 min. The resultant suspension was purge-filled with nitrogen (3 cycles), then with hydrogen (3 cycles). Constant pressure of hydrogen was maintained with a hydrogen balloon. The mixture was stirred vigorously at ambient temperature for 4 h. The reaction mixture was filtered through Celite. The filter cake was washed with methanol. The combined organic layers were concentrated in vacuo. No further purification was required.

Yield: 1.05 g, 100%.

LCMS method B: rt 0.78 min, 87%; m/z 210.05 (MH+, 100%).

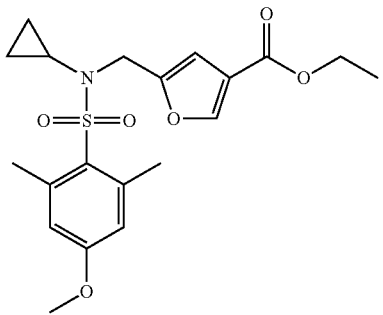 [SMILES: CCOC(=O)c1coc(CN(C2CC2)S(=O)(=O)c2c(C)cc(OC)cc2C)c1]

Ethyl 5-({cyclopropyl[(4-methoxy-2,6-dimethylphenyl)sulfonyl]amino}methyl)furan-3-carboxylate Int 77

The title compound was prepared according to general procedure AU using ethyl 5-[(cyclopropylamino)methyl]furan-3-carboxylate (1.04 g, 5.0 mmol), 4-methoxy-2,6-dimethylbenzenesulfonyl chloride (1.17 g, 5.0 mmol) and TEA (1.4 mL, 10 mmol) in DCM (50 mL). The crude product was purified using FCC eluting with DCM to afford the title compound.

Yield: 1.27 g, 62%.

$^1$H NMR (250 MHz, CD$_3$OD) δ ppm 7.98 (1H, s), 6.73 (1H, s), 6.63 (2H, s), 4.52 (2H, s), 4.29 (2H, q, J=7.16 Hz), 3.83 (3H, s), 2.58 (6H, s), 2.46 (1H, m), 1.35 (3H, t, J=7.01 Hz), 0.51 (2H, m), 0.13 (2H, m).

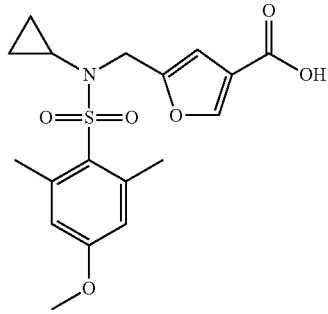 [SMILES: COc1cc(C)c(S(=O)(=O)N(Cc2cc(C(=O)O)co2)C2CC2)c(C)c1]

5-({Cyclopropyl[(4-methoxy-2,6-dimethylphenyl)sulfonyl]amino}methyl)furan-3-carboxylic acid Int 78

The title compound was prepared according to general procedure AF using ethyl 5-({cyclopropyl[(4-methoxy-2,6-dimethylphenyl)sulfonyl]amino}methyl)furan-3-carboxylate (1.27 g, 3.1 mmol) and LiOH (521 mg, 12.4 mmol) in 1:1 THF/water (20 mL) to afford the title compound, which required no further purification.

Yield: 735 mg, 62%.

$^1$H NMR (250 MHz, CD$_3$OD) δ ppm 7.92 (1H, s), 6.59 (2H, s), 6.53 (1H, s), 4.38 (2H, s), 3.68 (3H, s), 2.28 (1H, m), 1.83 (6H, s), 0.37 (2H, m), 0.00 (2H, m).

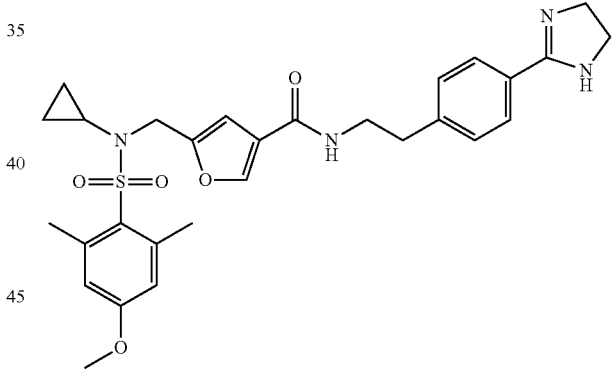

5-({Cyclopropyl[(4-methoxy-2,6-dimethylphenyl)sulfonyl]amino}methyl)-N-{2-[4-(4,5-dihydro-1H-imidazol-2-yl)phenyl]ethyl}furan-3-carboxamide Ex 52

General Procedure AM

To a suspension of 5-({cyclopropyl[(4-methoxy-2,6dimethylphenyl)sulfonyl]amino}methyl)furan-3-carboxylic acid (47 mg, 0.12 mmol) in DCM (3 mL) were added DIC (0.3 mL, 1.87 mmol) and HOBt (29 mg, 0.19 mmol). The resulting solution was stirred for 15 min prior to the addition of the bis TFA salt of 2-[4-(4,5-dihydro-1H-imidazol-2-yl)phenyl]ethanamine (47 mg, 0.11 mmol) and stirred at ambient temperature for 2 h. TEA (0.07 mL, 0.48 mmol) was added and the reaction mixture was stirred for an additional 2 h. The reaction was diluted with DCM (1 mL) and washed with 2 M K$_2$CO$_3$ (2 mL) followed by 6 M HCl (2 mL). The acidic aqueous layer was adjusted to pH ~11 with solid K$_2$CO$_3$ and extracted with DCM (2×2 mL), dried over MgSO$_4$ and concentrated in vacuo to afford 86 mg of crude product. A portion of the crude product was purified using prep method A to afford the title compound as the mono TFA salt.

Yield: 2.3 mg, 11%.

$^1$H NMR (500 MHz, CD$_3$OD) δ ppm 7.80 (1H, d, J=0.91 Hz), 7.64 (2H, m), 7.39 (2H, m), 6.60 (3H, m), 4.37 (2H, s), 3.93 (4H, s), 3.69 (3H, s), 3.45 (2H, m), 2.87 (2H, m), 2.41 (6H, s), 2.27 (1H, m), 0.37 (2H, m), 0.01 (2H, m).

Potency: C

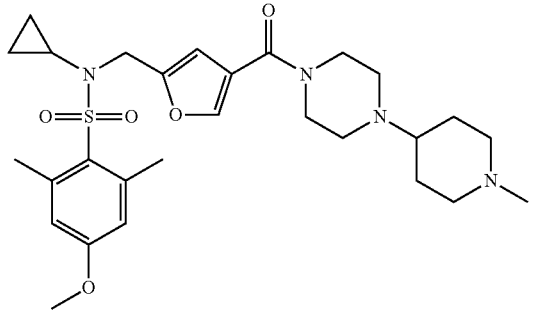 [SMILES: COc1cc(C)c(S(=O)(=O)N(Cc2cc(C(=O)N3CCN(C4CCN(C)CC4)CC3)co2)C2CC2)c(C)c1]

N-cyclopropyl-4-methoxy-2,6-dimethyl-N-[(4-{[4-(1-methylpiperidin-4-yl)piperazin-1-yl]carbonyl}furan-2-yl)methyl]benzenesulfonamide Ex 53

The title compound was prepared according to general procedure AM using 5-({cyclopropyl[(4-methoxy-2,6 dimethylphenyl)sulfonyl]amino}methyl)furan-3-carboxylic acid (47 mg, 0.12 mmol), 1-(1-methylpiperidin-4-yl)piperazine (21 mg, 0.11 mmol), DIC (0.3 mL, 1.87 mmol), HOBt (29 mg, 0.19 mmol) and TEA (0.07 mL, 0.48 mmol) in DCM (5 mL). The crude product was purified using Isolute SCX-2 cartridge, washing with MeOH (3 mL) and eluting with 7N NH$_3$ in MeOH (3 mL) to afford the title compound.

Yield: 19 mg, 28%.

LCMS method C: rt 2.70 min, 99%; m/z 545.10 (MH$^+$, 100%).

Potency: A

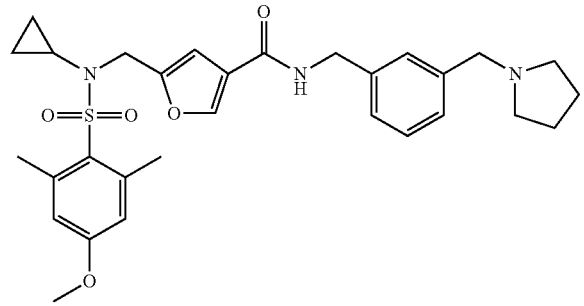 [SMILES: COc1cc(C)c(S(=O)(=O)N(Cc2cc(C(=O)NCc3cccc(CN4CCCC4)c3)co2)C2CC2)c(C)c1]

5-({Cyclopropyl[(4-methoxy-2,6-dimethylphenyl)sulfonyl]amino}methyl)-N-[3-(pyrrolidin-1-ylmethyl)benzyl]furan-3-carboxamide Ex 54

The title compound was prepared according to general procedure AI using 5-({cyclopropyl[(4-methoxy-2,6 dimethylphenyl)sulfonyl]amino}methyl)furan-3-carboxylic acid (47 mg, 0.12 mmol), 1-[3-(pyrrolidin-1-ylmethyl)phenyl]methanamine (26 mg, 0.23 mmol), EDCI (27 mg, 0.14 mmol), HOBt (19 mg, 0.14 mmol) and DIPEA (0.08 mL, 0.47 mmol) in DMF (7 mL). The reaction mixture was absorbed onto 1.5 mL of free flow SCX sorbent, washed with MeOH (5 mL), eluted with 7 N NH$_3$ in MeOH (5 mL) and concentrated in vacuo. The crude product was purified using prep method A to afford the title compound as the mono TFA salt.

Yield: 9 mg, 9%.

$^1$H NMR (500 MHz, CD$_3$OD) δ ppm 7.89 (1H, s), 7.31 (3H, m), 7.24 (1H, m), 6.64 (1H, s), 6.58 (2H, s), 4.39 (4H, 2s), 4.20 (2H, s), 3.67 (3H, s), 3.32 (2H, m), 3.02 (2H, m), 2.40 (6H, s), 2.29 (1H, dt, J 6.88, 3.35 Hz), 2.01 (2H, m), 1.84 (2H, m), 0.37 (2H, m), 0.02 (2H, m).

Potency: B

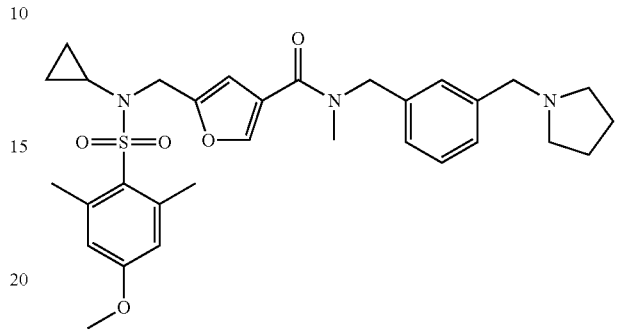

5-({Cyclopropyl[(4-methoxy-2,6-dimethylphenyl)sulfonyl]amino}methyl)-N-methyl-N-[3-(pyrrolidin-1-ylmethyl)benzyl]furan-3-carboxamide Ex 55

The title compound was prepared according to general procedure AI using 5-({cyclopropyl[(4-methoxy-2,6 dimethylphenyl)sulfonyl]amino}methyl)furan-3-carboxylic acid (47 mg, 0.12 mmol), N-methyl-1-[3-(pyrrolidin-1-ylmethyl)phenyl]methanamine (28 mg, 0.23 mmol), EDCI (27 mg, 0.14 mmol), HOBt (19 mg, 0.14 mmol) and DIPEA (0.08 mL, 0.47 mmol) in DMF (7 mL). The reaction mixture was absorbed onto 1.5 mL of free flow SCX sorbent, washed with MeOH (5 mL), eluted with 7 N NH$_3$ in MeOH (5 mL) and concentrated in vacuo. The crude product was purified using prep method A to afford the title compound as the mono TFA salt.

Yield: 8 mg, 8%.

$^1$H NMR (500 MHz, CD$_3$OD) δ ppm 7.72 (1H, m), 7.29 (4H, m), 6.58 (2H, s), 6.39 (1H, br. s.), 4.64 (2H, m), 4.38 (2H, m), 4.23 (2H, s), 3.70 (3H, s) 3.33 (2H, m), 3.04 (3H, br. s.), 2.90 (1H, br. s.), 2.33 (7H, m), 2.02 (2H, m), 1.85 (2H, m), 0.36 (2H, br. s.), 0.00 (2H, br. s.).

Potency: B

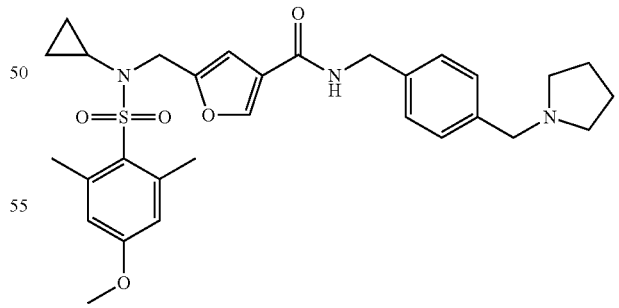

5-({Cyclopropyl[(4-methoxy-2,6-dimethylphenyl)sulfonyl]amino}methyl)-N-[4-(pyrrolidin-1-ylmethyl)benzyl]furan-3-carboxamide Ex 56

The title compound was prepared according to general procedure AI using 5-({cyclopropyl[(4-methoxy-2,6 dimethylphenyl)sulfonyl]amino}methyl)furan-3-carboxylic acid (47 mg, 0.12 mmol), 1-[4-(pyrrolidin-1-ylmethyl)phenyl] methanamine (26 mg, 0.23 mmol), EDCI (27 mg, 0.14 mmol), HOBt (19 mg, 0.14 mmol) and DIPEA (0.08 mL, 0.47 mmol) in DMF (7 mL). The reaction mixture was absorbed onto 1.5 mL of free flow SCX sorbent, washed with MeOH (5 mL), eluted with 7 N $NH_3$ in MeOH (5 mL) and concentrated in vacuo. The crude product was purified using prep method A to afford the title compound as the mono TFA salt.

Yield: 19 mg, 19%.

$^1$H NMR (500 MHz, $CD_3OD$) δ ppm 7.88 (1H, s), 7.30 (4H, m), 6.60 (3H, m), 4.38 (4H, 2s), 4.19 (2H, s), 3.67 (3H, s), 3.31 (2H, m), 3.01 (2H, m), 2.40 (6H, s), 2.29 (1H, m), 2.01 (2H, m), 1.81 (2H, m), 0.38 (2H, m), 0.01 (2H, m).

Potency: B

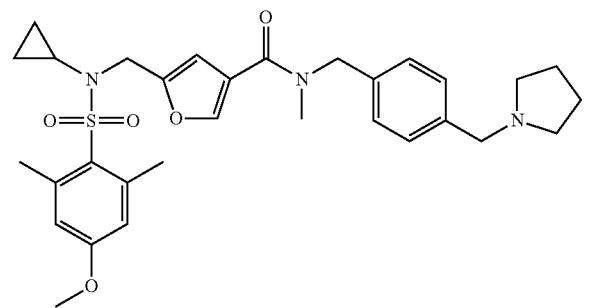 [SMILES: COc1cc(C)c(S(=O)(=O)N(Cc2cc(C(=O)N(C)Cc3ccc(CN4CCCC4)cc3)co2)C2CC2)c(C)c1]

5-({Cyclopropyl[(4-methoxy-2,6-dimethylphenyl) sulfonyl]amino}methyl)-N-methyl-N-[4-(pyrrolidin-1-ylmethyl)benzyl]furan-3-carboxamide Ex 57

The title compound was prepared according to general procedure AI using 5-({cyclopropyl[(4-methoxy-2,6 dimethylphenyl)sulfonyl]amino}methyl)furan-3-carboxylic acid (47 mg, 0.12 mmol), N-methyl-1[4(pyrrolidinylmethyl)phenyl]methanamine (28 mg, 0.23 mmol), EDCI (27 mg, 0.14 mmol), HOBt (19 mg, 0.14 mmol) and DIPEA (0.08 mL, 0.47 mmol) in DMF (7 mL). The reaction mixture was absorbed onto free flow SCX sorbent (1.5 mL), washed with MeOH (5 mL), eluted with 7 N $NH_3$ in MeOH (5 mL) and concentrated in vacuo. The crude product was purified using prep method A to afford the title compound as the mono TFA salt.

Yield: 7 mg, 7%.

LCMS method C: rt 3.43 min, 100%; m/z 566.51 ($MH^+$, 100%).

Potency: B

Substituted Furans Synthesis

Scheme 2 describes the general synthesis of furan derivatives.

($R^1$=Me; $R^{1a}$=$R^{1b}$=H; X=various sulfonamides; $X^1$=CH; $X^3$=C-Me; $X^2$=O; $NR^2R^3$=various amines)

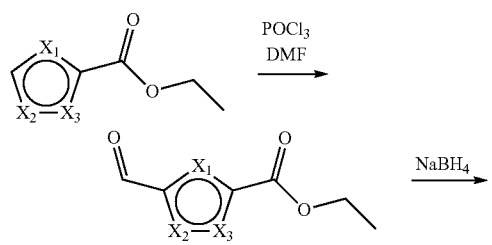

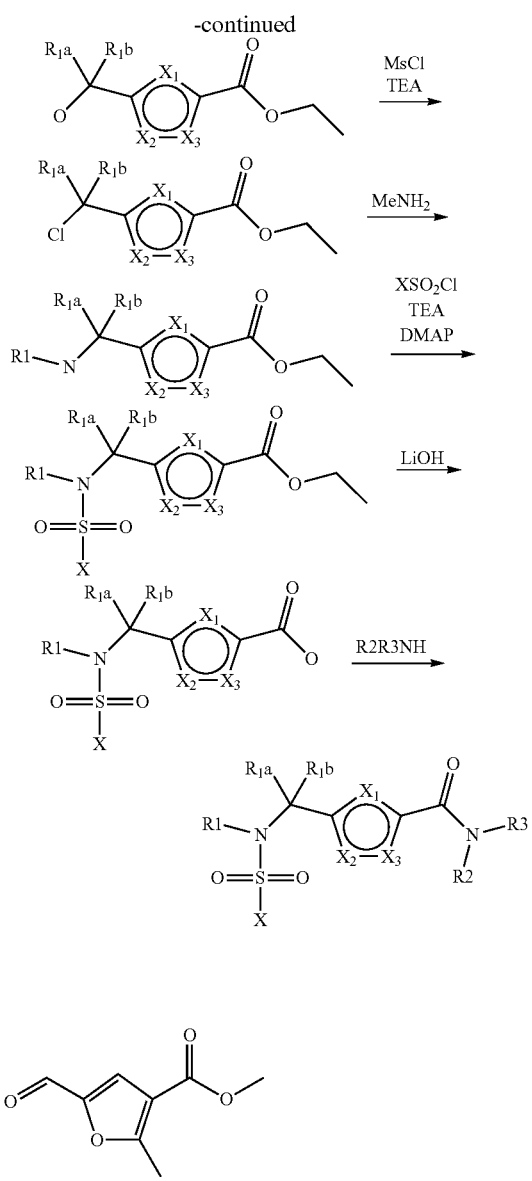

methyl 5-formyl-2-methylfuran-3-carboxylate

Int 79

To a vigorously stirred solution of ethyl 2-methylfuran-3-carboxylate (5 g, 32.4 mmol) in dry DMF (4.28 mL, 0.55.1 mmol) at 0° C. under $N_2$ was added $POCl_3$ (3.82 mL, 42.1 mmol) dropwise such that the reaction temperature did not exceed 10° C. When the addition was complete, the flask and its contents were allowed to warm to ambient temperature and the reaction stirred for 7 h under $N_2$, and then allowed to stand overnight. The reaction was slurried with toluene (7 mL) and poured into a flask containing 10% NaOH (aq) (100 mL) and ice water (30 mL). The mixture was extracted with ether (3×80 mL) and the combined organic extracts were washed with 5% aqueous HCl (2×30 mL), water (2×30 mL) and saturated brine (30 mL), and dried over $MgSO_4$. Solvents were removed in vacuo and the resulting oil was purified by FCC, eluting with 5-20% EtOAc in heptanes. This afforded the title compound as a yellow oil.

Yield: 2.82 g, 47%.

¹H NMR (250 MHz, CDCl₃) δ ppm 9.57 (1H, s), 7.48 (1H, s), 3.88 (3H, s), 2.71 (3H, s)

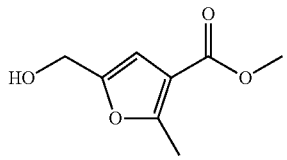

methyl 5-(hydroxymethyl)-2-methylfuran-3-carboxylate

Int 80

To a stirred solution of methyl 5-formyl-2-methylfuran-3-carboxylate (2.81 g, 16.7 mmol) in MeOH/DCM (30 mL/15 mL) at 0° C. was added NaBH₄ (1.39 g, 36.8 mmol) portionwise over 5 min. The reaction was stirred at 0° C. for 45 min, then quenched with saturated aqueous NaHCO₃ (40 mL) and extracted with DCM (3×40 mL). The combined organic extracts were washed with sat. brine (30 mL), dried over MgSO₄ and concentrated in vacuo to afford an orange oil containing the title compound and DCM.

Yield: 2.88 g, >100%.
¹H NMR (250 MHz, CDCl₃) δ ppm 6.52 (1H, s), 4.54 (2H, br d, J=5.5 Hz) 3.81 (3H, s), 2.56 (3H, s), 2.02 (1H, br t, J=5.6 Hz)

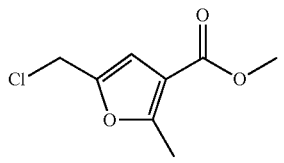

methyl 5-(chloromethyl)-2-methylfuran-3-carboxylate

Int 81

To a stirred solution of methyl 5-(hydroxymethyl)-2-methylfuran-3-carboxylate (16.7 mmol) and MsCl (2.58 mL, 33.4 mmol) in DCM (28 mL) at 0° C. was added TEA (4.63 mL, 33.4 mmol) and the reaction was stirred and allowed to warm to ambient temperature overnight. The reaction mixture was filtered through a plug of silica and concentrated in vacuo to afford the title compound. No further purification was required.

Yield: 1.92 g, 61%.
¹H NMR (250 MHz, CDCl₃) δ ppm 6.62 (1H, s), 4.53 (2H, s) 3.83 (3H, s), 2.60 (3H, s)

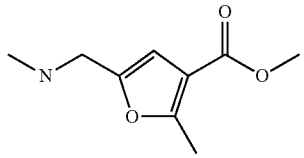

methyl 2-methyl-5-[(methylamino)methyl]furan-3-carboxylate

Int 82

To a stirred ~8 M solution of MeNH₂ in EtOH (70 mL) at 5-10° C. was added methyl 5-(chloromethyl)-2-methylfuran-3-carboxylate (1.916 g, 10.2 mmol) as a solution in EtOH (5 mL). The reaction was allowed to warm to ambient temperature with stirring over 2.5 h, then acidified to pH 1 with 1 M aqueous HCl, saturated with solid NaCl and extracted with EtOAc (3×200 mL). The aqueous layer was basified with saturated aqueous NaHCO₃ and extracted with EtOAc (3×100 mL). These combined organic extracts were dried over MgSO₄ and concentrated in vacuo to afford the title compound as a light brown oil, which was used without further purification Yield: 920 mg, 49%.
¹H NMR (400 MHz, CDCl₃) δ ppm 6.42 (1H, s), 3.80 (3H, s) 3.67 (2H, s) 2.55 (3H, s), 2.42 (3H, s)

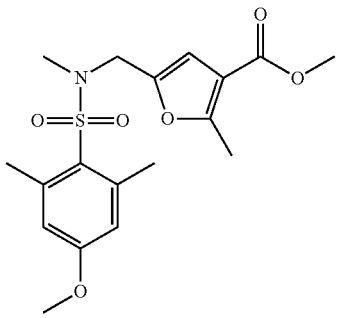

methyl 5-({[(4-methoxy-2,6-dimethylphenyl)sulfonyl](methyl)amino}methyl)-2-methylfuran-3-carboxylate Int 83

To a stirred solution of methyl 2-methyl-5-[(methylamino)methyl]furan-3-carboxylate (920 mg, 5.02 mmol), DMAP (61 mg, 0.50 mmol) and TEA (0.696 mL, 5.02 mmol) in DCM (10 mL) at 0° C. was added slowly a solution of 4-methoxy-2,6-dimethylbenzenesulfonyl chloride (1178 mg, 5.02 mmol) in DCM (10 mL). The reaction was allowed to warm to ambient temperature and stirred overnight, then diluted with DCM (20 mL) and washed with 1 M aqueous HCl (3×10 mL), saturated aqueous NaHCO₃ (2×10 mL), and saturated brine (10 mL). The combined organic extracts were dried over MgSO₄ and concentrated in vacuo to afford the title compound as a light brown oil.

Yield: 1.603 g, 84%.
¹H NMR (400 MHz, CDCl₃) δ ppm 6.65 (2H, s), 6.48 (1H, s), 4.24 (2H, s), 3.83 (3H, s), 3.81 (3H, s), 2.67 (3H, s), 2.64 (6H, s), 2.52 (3H, s);
LCMS Method B: rt 2.16 min, 95%; m/z 403.95 (MNa⁺, 100%).

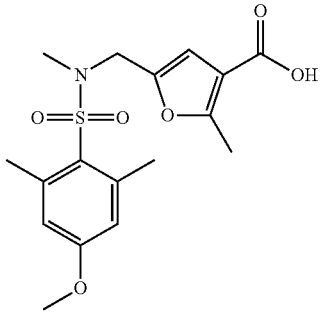 [SMILES: COc1cc(C)c(S(=O)(=O)N(C)Cc2cc(C(=O)O)c(C)o2)c(C)c1]

5-({[(4-methoxy-2,6-dimethylphenyl)sulfonyl](methyl)amino}methyl)-2-methylfuran-3-carboxylic acid Int 84

Methyl 5-({[(4-methoxy-2,6-dimethylphenyl)sulfonyl](methyl)amino}methyl)-2-methylfuran-3-carboxylate (150 mg, 0.41 mmol) was dissolved in a 3:2 mixture of THF/2 M aqueous LiOH (1.67 mL). The reaction was heated to 60° C. for 6 h, then allowed to cool, diluted with DCM (30 mL) and acidified to pH 1 with 1 M aqueous HCl. The layers were separated and the organic phase was washed with saturated brine (5 mL) and dried over MgSO$_4$. The solvent was removed in vacuo to afford the title compound, which required no further purification.

Yield: 137 mg, 91%.

$^1$H NMR (400 MHz, CDCl$_3$) δ ppm 6.65 (2H, s), 6.51 (1H, s), 4.25 (2H, s), 3.83 (3H, s), 2.68 (3H, s), 2.65 (6H, s), 2.55 (3H, s);

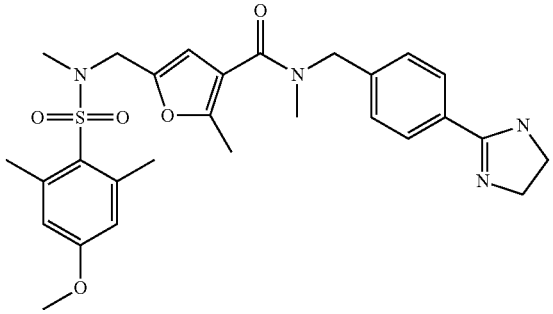 [SMILES: COc1cc(C)c(S(=O)(=O)N(C)Cc2cc(C(=O)N(C)Cc3ccc(C4=NCCN4)cc3)c(C)o2)c(C)c1]

N-[4-(4,5-dihydro-1H-imidazol-2-yl)benzyl]-5-({[(4-methoxy-2,6-dimethylphenyl)sulfonyl](methyl)amino}methyl)-N,2-dimethylfuran-3-carboxamide Ex 58

5-({[(4-methoxy-2,6-dimethylphenyl)sulfonyl](methyl)amino}methyl)-2-methylfuran-3-carboxylic acid (82 mg, 0.22 mmol) was dissolved in DCE (1 mL) and CDI (72 mg, 0.33 mmol) was added. The reaction was stirred at ambient temperature for 2 h and 0.5 mL of this solution was added to a flask containing 1-[4-(4,5-dihydro-1H-imidazol-2-yl)phenyl]-N-methylmethanamine.3 HCl (31 mg, 0.11 mmol) and DIPEA (0.076 mL, 0.44 mmol) in DMF (2 mL). The reaction was stirred at ambient temperature for 3 days, then heated in a microwave at 120° C., 250 psi, 200 W for 2×20 min. The reaction was concentrated and diluted with DCM, then washed with water and saturated brine, and dried over MgSO$_4$. The filtrate was shaken with Ambersep and PL-MIA resins, then filtered. The solvent was removed in vacuo and a portion of the crude product purified using prep method C.

LCMS Method C: rt 3.23 min, 100%; m/z 539.23 (MH$^+$, 100%).

Potency: B

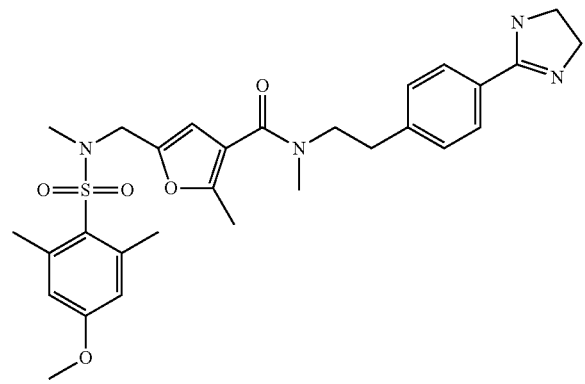 [SMILES: COc1cc(C)c(S(=O)(=O)N(C)Cc2cc(C(=O)N(C)CCc3ccc(C4=NCCN4)cc3)c(C)o2)c(C)c1]

N-{2-[4-(4,5-dihydro-1H-imidazol-2-yl)phenyl]ethyl}-5-({[(4-methoxy-2,6-dimethylphenyl)sulfonyl](methyl)amino}methyl)-N,2-dimethylfuran-3-carboxamide Ex 59

5-({[(4-methoxy-2,6-dimethylphenyl)sulfonyl](methyl)amino}methyl)-2-methylfuran-3-carboxylic acid (82 mg, 0.22 mmol) was dissolved in DCE (1 mL) and CDI (72 mg, 0.33 mmol) was added. The reaction was stirred at ambient temperature for 2 h and 0.5 mL of this solution was added to a flask containing 2-[4-(4,5-dihydro-1H-imidazol-2-yl)phenyl]-N-methylethanamine 0.3 HCl (34 mg, 0.11 mmol) and DIPEA (0.076 mL, 0.44 mmol) in DMF (2 mL). The reaction was stirred at ambient temperature for 3 days, then heated in a microwave at 120° C., 250 psi, 200 W for 2×20 min. The reaction was concentrated and diluted with DCM, then washed with water and saturated brine, and dried over MgSO$_4$. The filtrate was shaken with Ambersep and PL-MIA resins, then filtered. The solvent was removed in vacuo and a portion of the crude product purified using prep method C.

LCMS Method C: rt 3.23 min, 99%; m/z 553.32 (MH$^+$, 100%).

Potency: A

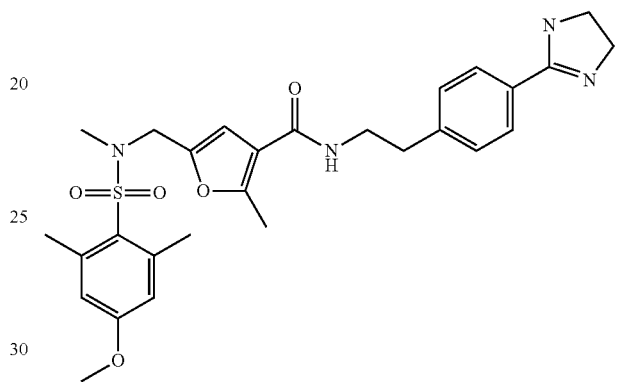

N-{2-[4-(4,5-dihydro-1H-imidazol-2-yl)phenyl]ethyl}-5-({[(4-methoxy-2,6-dimethylphenyl)sulfonyl](methyl)amino}methyl)-2-methylfuran-3-carboxamide Ex 61

5-({[(4-methoxy-2,6-dimethylphenyl)sulfonyl](methyl)amino}methyl)-2-methylfuran-3-carboxylic acid (100 mg, 0.28 mmol) was dissolved in DMF (2 mL) and EDCI (65 mg, 0.34 mmol) and HOAt (46 mg, 0.34 mmol) were added. 1 mL of this solution was added to a flask containing 1-[4-(4,5-dihydro-1H-imidazol-2-yl)phenyl]ethanamine.HCl (27 mg, 0.13 mmol) and DIPEA (0.024 mL, 0.14 mmol) in DMF (2 mL). The reaction was concentrated and diluted with DCM, then washed with saturated aqueous NH$_4$Cl (2×2 mL) and saturated brine (2 mL), and dried over MgSO$_4$. The filtrate was shaken with Ambersep and PL-MIA resins for 48 h, then filtered. The solvent was removed in vacuo and a portion of the crude product purified using prep method C.

LCMS Method C: rt 3.33 min, 100%; m/z 539.26 (MH$^+$, 100%).

Potency: B

Furans Synthesis

Scheme 3 describes the general synthesis of furan derivatives.

($R^1$=Me; $R^{1a}$=$R^{1b}$=H; X=various sulfonamides; $X^2$=$X^3$=CH; $X^1$=O; NR$^2$R$^3$=substituted piperazine)

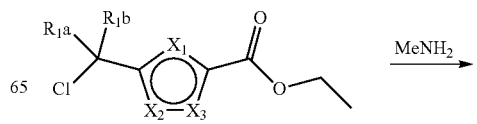

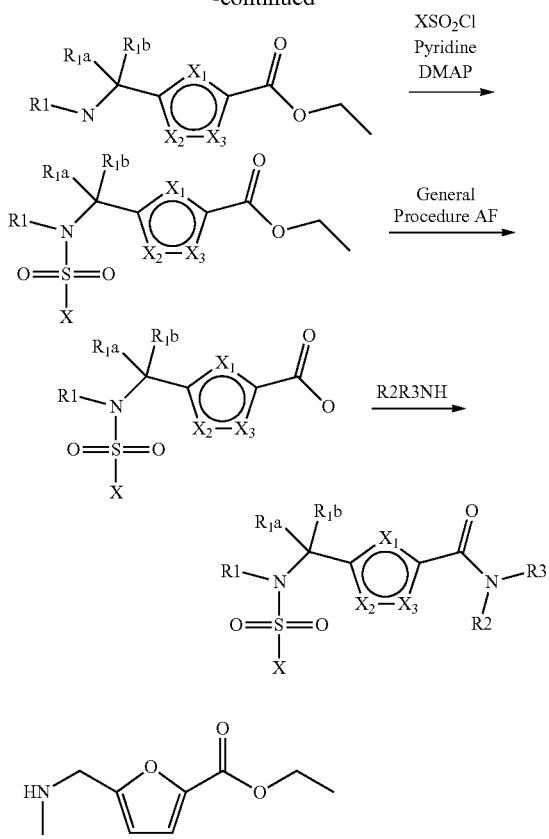

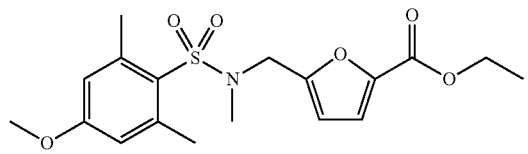 [SMILES: CCOC(=O)c1ccc(CN(C)S(=O)(=O)c2c(C)cc(OC)cc2C)o1]

Ethyl 5-[(methylamino)methyl]furan-2-carboxylate

Int 85

Ethyl 5-(chloromethyl)furan-2-carboxylate (1.0 g, 5.3 mmol) was dissolved in a 33% solution of methylamine in EtOH (20 mL) and allowed to stir at ambient temperature for 1 h. The reaction was filtered over a sinter under reduced pressure and the filtrate was absorbed onto polymer-supported tosic acid resin (3.3 mmol/g, 5 g), washed with MeOH (50 mL) and eluted with 10% aqueous ammonia in MeOH (50 mL). The resultant solution was concentrated in vacuo to afford the title compound, which required no further purification.

Yield: 730 mg, 75%.

Ethyl 5-({[(4-methoxy-2,6-dimethylphenyl)sulfonyl](methyl)amino}methyl)furan-2-carboxylate Int 86

To a solution of Ethyl 5-[(methylamino)methyl]furan-2-carboxylate (700 mg, 3.8 mmol) in THF (15 mL), was added pyridine (0.6 mL, 7.6 mmol), 4-methoxy-N,2,6-trimethyl-benzenesulfonamide (893 mg, 3.8 mmol) and DMAP (46 mg, 0.38 mmol) before stirring at ambient temperature for 18 h. The reaction was concentrated in vacuo., dissolved in DCM (50 mL), washed with 10% aqueous solution of citric acid (2×50 mL), dried over MgSO$_4$ and concentrated in vacuo. The crude product was purified using FCC eluting with 5% MeOH in DCM to afford the title compound.

Yield: 459 mg, 32%.

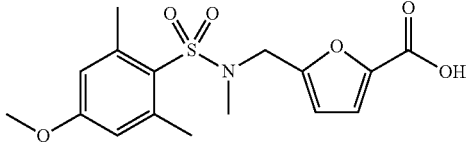 [SMILES: COc1cc(C)c(S(=O)(=O)N(C)Cc2ccc(C(=O)O)o2)c(C)c1]

5-({[(4-Methoxy-2,6-dimethylphenyl)sulfonyl](methyl)amino}methyl)furan-2-carboxylic acid Int 87

The title compound was prepared according to general procedure AF using ethyl 5-({[(4-methoxy-2,6-dimethylphenyl)sulfonyl](methyl)amino}methyl)furan-2-carboxylate (450 mg, 1.18 mmol) and LiOH (1.37 g, 32.5 mmol) in 1:1 THF/water (20 mL), which required no further purification.

Yield: 417 mg, 100%.

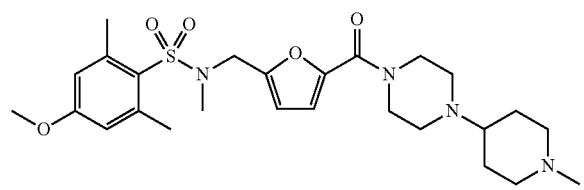

4-Methoxy-N,2,6-trimethyl-N-[(5-{[4-(1-methylpiperidin-4-yl)piperazin-1-yl]carbonyl}furan-2-yl)methyl]benzenesulfonamide Ex 62

To a solution of 5-({[(4-methoxy-2,6-dimethylphenyl)sulfonyl](methyl)amino}methyl)furan-2-carboxylic acid (177 mg, 0.5 mmol) in THF (10 mL) was added CDI (81 mg, 0.5 mmol) before the addition of 1-(1-methylpiperidin-4-yl)piperazine (82 mg, 0.45 mmol) and DIPEA (0.17 mL, 1.0 mmol). The reaction was stirred at ambient temperature for 2 h. The crude product was purified using prep method A to afford the title compound as the mono TFA salt.

LCMS method C: 99%; m/z 518.68 (MH$^+$, 100%).

Potency: A

Procedure for the preparation of 3-({[(4-methoxy-2,6-dimethylphenyl)sulfonyl](methyl)amino}methyl)-N-{2-[4-(4,5-dihydro-1H-imidazol-2-yl)phenyl]ethyl}-1,2,4-thiadiazole-5-carboxamide Thiadiazole Synthesis Scheme 4 describes the general synthesis of thiadiazole derivative.

(R$^1$=Me; R$^{1a}$=R$^{1b}$=H; X=2,6-dimethyl-4-methoxybenzenesulfonyl; X$^1$=X$^2$=N; X$^3$=S; NR$^2$R$^3$=2-[4-(4,5-dihydro-1H-imidazol-2-yl)phenyl]ethanamine)

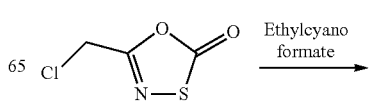

-continued

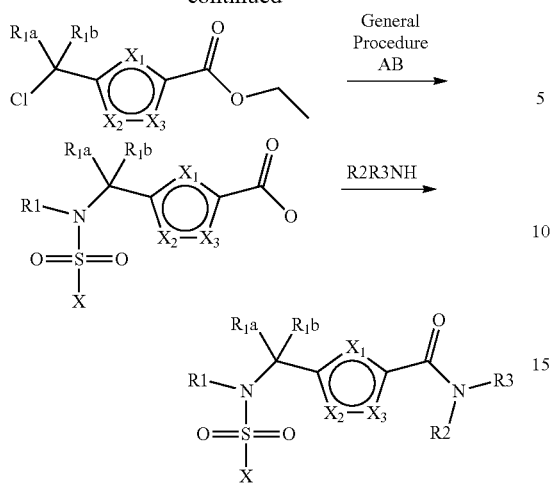

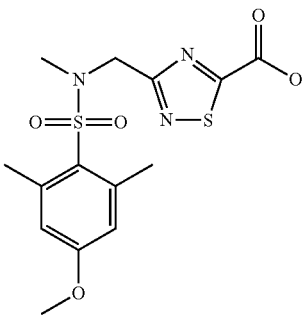

3-({[(4-methoxy-2,6-dimethylphenyl)sulfonyl](methyl)amino}methyl)-1,2,4-thiadiazole-5-carboxylic acid Int 90

The title compound was prepared according to general procedure AB using 4-methoxy-N,2,6-trimethylbenzenesulfonamide (95 mg, 0.56 mmol), NaH (60% wt in mineral oil, 20 mg, 0.5 mmol) and ethyl 3-(chloromethyl)-1,2,4-thiadiazole-5-carboxylate (125 mg, 0.61 mmol). After stirring at ambient temperature overnight LCMS analysis (Method B) revealed alkylation with concomitant ester hydrolysis (rt 1.7 min—ve ion 369.9, M–H). The mixture was partitioned between EtOAc and water and the aqueous layer was concentrated to afford the product, which was used in the next step without any further purification.

Yield: 120 mg, 53%

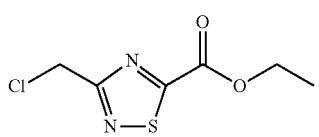

5-(chloromethyl)-1,3,4-oxathiazol-2-one (J. Org. Chem. Vol. 3, No. 19, 1978, 3736-3742—compound 5s)

Int 88

To a stirred solution of chloroacetamide (1.0 eq, 1.6 mmol) in toluene at 20° C. was added ClCOSCl (5 eq, 8 mmol) dropwise over 5 min. The mixture was heated to 60° C. for 18 h after which time crystals had formed. The reaction mixture was allowed to cool to ambient temperature and concentrated in vacuo to afford the title compound as colourless oil/crystals Yield: 170 mg, 70%.

$^1$H NMR (500 MHz, CDCl$_3$) δ ppm 4.37 (2H, s, Lit. value 4.47 ppm).

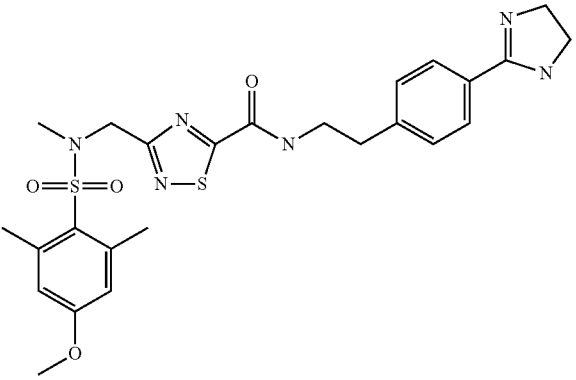 [SMILES: COc1cc(C)c(S(=O)(=O)N(C)Cc2nsc(C(=O)NCCc3ccc(C4=NCCN4)cc3)n2)c(C)c1]

N-{2-[4-(4,5-dihydro-1H-imidazol-2-yl)phenyl]ethyl}-3-({[(4-methoxy-2,6-dimethylphenyl)sulfonyl](methyl)amino}methyl)-1,2,4-thiadiazole-5-carboxamide Ex 63

The title compound was prepared according to General Procedure AC using 3-({[(4-methoxy-2,6-dimethylphenyl)sulfonyl](methyl)amino}methyl)-1,2,4-thiadiazole-5-carboxylic acid (120 mg, 0.32 mmol), 2-[4-(4,5-dihydro-1H-imidazol-2-yl)phenyl]ethanamine bis-trifluoroacetate (133 mg, 0.32 mmol), EDCI, (76.8 mg, 0.4 mmol), HOBt (54.4 mg, 0.4 mmol) and DIPEA (0.097 mL, 0.96 mmol) in DMF (5 mL). After stirring at ambient temperature for 42 h the reaction was concentrated and the crude product was purified using prep method C, affording the title compound.

LCMS Method C: rt 3.29 min, 98%; m/z 543.23 (MH$^+$, 100%).

Ethyl 3-(chloromethyl)-1,2,4-thiadiazole-5-carboxylate

Int 89

To a stirred solution of 5-(chloromethyl)-1,3,4-oxathiazol-2-one (1.0 eq, 2.3 mmol) in chlorobenzene (35 mL) at ambient temperature was added ethyl cyanoformate (5.0 eq, 11.5 mmol) and the reaction was heated to 135° C. for 42 h, then concentrated in vacuo. Purification by FCC, eluting with 20% EtOAc in heptanes, afforded the title compound as a colourless oil.

Yield: 125 mg, 26%.

$^1$H NMR (500 MHz, CDCl$_3$) δ ppm 4.81 (2H, s), 4.47 (2H, q, J=7.2 Hz), 1.40 (3H, t, J=7.2 Hz)

Potency: C

Oxadiazole Synthesis

Scheme 5 describes the general synthesis of oxadiazole derivative.

(R¹=Me; R¹ᵃ=R¹ᵇ=H; X=2,6-dimethyl-4-methoxybenzenesulfonyl; X¹=X²=N; X³=O; NR²R³=2-[4-(4,5-dihydro-1H-imidazol-2-yl)phenyl]ethanamine)

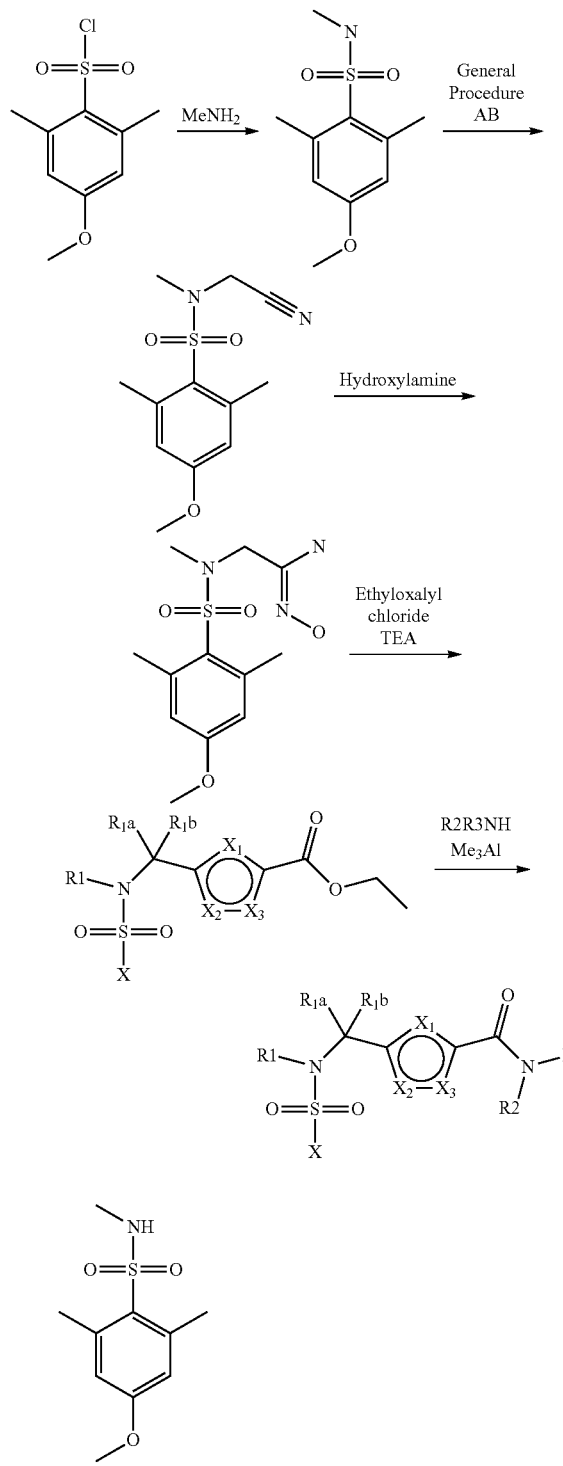

4-methoxy-N,2,6-trimethylbenzenesulfonamide

Int 91

To a stirred solution of 4-methoxy-2,6-dimethylbenzenesulfonyl chloride (2 g, 8.5 mmol) in EtOH (5 mL) under $N_2$ was added an 8 M solution of $MeNH_2$ in EtOH (15 mL, 120 mmol) dropwise. The reaction was stirred at ambient temperature for 18 h, then concentrated and partitioned between water (40 mL) and DCM (3×30 mL). The combined organic extracts were dried over $MgSO_4$ and solvents were removed in vacuo to afford the title compound as a white solid, which was used without further purification.

Yield: 1.66 g, 85%.

¹H NMR (500 MHz, $CDCl_3$) δ ppm 6.67 (2H, s) 4.32 (1H, d, J=5.19 Hz) 3.84 (3H, s) 2.66 (6H, s) 2.61 (3H, d, J=5.49 Hz)

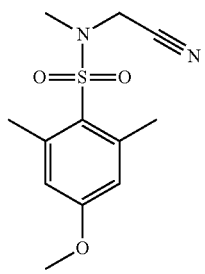 [SMILES: COc1cc(C)c(S(=O)(=O)N(C)CC#N)c(C)c1]

N-(cyanomethyl)-4-methoxy-N,2,6-trimethylbenzenesulfonamide

Int 92

The title compound was prepared according to general procedure AB using 4-methoxy-N,2,6-trimethylbenzenesulfonamide (500 mg, 2.18 mmol), NaH (60% wt in mineral oil, 105 mg, 2.65 mmol), chloroacetonitrile (0.165 mL, 2.60 mmol) and NaI (cat.) in dry THF (10 mL). The reaction mixture was partitioned between 1:1 saturated brine:water (20 mL) and EtOAc (3×15 mL) and the combined organics were dried over $MgSO_4$. Solvents were removed in vacuo to afford a 3:1 mixture of the title compound and 4-methoxy-N,2,6-trimethylbenzenesulfonamide (as assigned using ¹H-NMR), which was used without further purification.

Yield: 500 mg, 75% purity, 64%.

¹H NMR (500 MHz, $CDCl_3$) δ ppm 6.68 (2H, s) 4.13 (2H, s) 3.85 (3H, s) 2.84 (3H, s) 2.63 (6H, s)

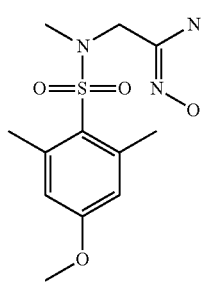 [SMILES: COc1cc(C)c(S(=O)(=O)N(C)C/C(N)=N/O)c(C)c1]

(1Z)—N'-hydroxy-2-{[(4-methoxy-2,6-dimethylphenyl)sulfonyl](methyl)amino}ethanimidamide Int 93

To a solution of N-(cyanomethyl)-4-methoxy-N,2,6-trimethylbenzenesulfonamide (0.436 mmol) in EtOH (1 mL) was added hydroxylamine solution (50% in water, 0.08 mL, 2.61 mmol) and the reaction was heated to 60° C. for 18 h. The reaction was concentrated and the product used without further purification.

LCMS Method A: rt 0.94 min, 76%; m/z 302.10 (MH+, 100%)

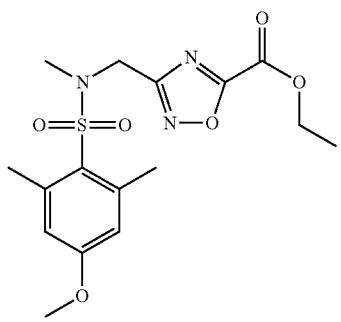 [SMILES: CCOC(=O)c1nc(CN(C)S(=O)(=O)c2c(C)cc(OC)cc2C)no1]

Ethyl 3-({[(4-methoxy-2,6-dimethylphenyl)sulfonyl](methyl)amino}methyl)-1,2,4-oxadiazole-5-carboxylate Int 94

To a stirred solution of (1Z)—N'-hydroxy-2-{[(4-methoxy-2,6-dimethylphenyl)sulfonyl](methyl)amino}ethanimidamide (258 mg, 0.86 mmol) in DCE (5 mL) was added ethyl oxalyl chloride (0.105 mL, 0.94 mmol) followed by TEA (0.262 mL, 1.88 mmol) and the reaction was heated at 60° C. for 18 h. The mixture was concentrated and partitioned between saturated brine (15 mL) and EtOAc (4×15 mL). The combined organics were dried over MgSO$_4$ and solvents were removed in vacuo. The crude product was purified using FCC, eluting with 20% EtOAc in heptanes, to afford the title compound as a colourless oil.

Yield: 228 mg, 60%.

LCMS Method A: rt 1.37 min, 91%; m/z 406.10 (MNa+, 100%), 384.05 (MH+, 80%)

$^1$H NMR (500 MHz, CDCl$_3$) δ ppm 6.64 (2H, s) 4.56 (2H, s) 4.53 (2H, t J 7.17 Hz) 3.83 (3H, s) 2.87 (3H, s) 2.65 (6H, s) 1.47 (3H, t, J=7.17 Hz)

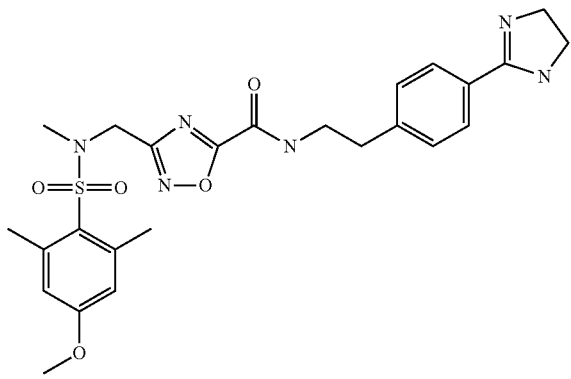 [SMILES: COc1cc(C)c(S(=O)(=O)N(C)Cc2noc(C(=O)NCCc3ccc(C4=NCCN4)cc3)n2)c(C)c1]

N-{2-[4-(4,5-dihydro-1H-imidazol-2-yl)phenyl]ethyl}-3-({[(4-methoxy-2,6-dimethylphenyl)sulfonyl](methyl)amino}methyl)-1,2,4-oxadiazole-5-carboxamide Ex 64

General Procedure AT

To a stirred solution of 2-[4-(4,5-dihydro-1H-imidazol-2-yl)phenyl]ethanamine (bis TFA salt, 108 mg, 0.26 mmol) in DCM (3 mL) at 0° C. was added trimethyl aluminium (2 M in toluene, 0.13 mL, 0.26 mmol) and the mixture was stirred at 0° C. for 15 min. Ethyl 3-({[(4-methoxy-2,6-dimethylphenyl)sulfonyl](methyl)amino}methyl)-1,2,4-oxadiazole-5-carboxylate (50 mg, 0.13 mmol) was added dropwise as a solution in DCM (2 mL), followed by TEA (0.045 mL, 0.32 mmol). The reaction was stirred at ambient temperature for 18 h, after which time TEA (0.110 mL, 0.79 mmol) and DCE (4 mL) were added. The reaction was heated to 60° C. for 18 h, then partitioned between saturated aqueous NH$_4$Cl (20 mL) and EtOAc (2×20 mL). The aqueous layer was extracted with DCM (2×10 mL) and these extracts were dried over MgSO$_4$ and solvents were removed in vacuo. A portion of the product was purified using prep method A.

LCMS Method C: rt 3.12 min, 100%; m/z 527.46 (MH+, 100%)

$^1$H NMR (500 MHz, CDCl$_3$) δ ppm 7.80 (2H, d, J=8.20 Hz) 7.56 (2H, d, J=8.35 Hz) 6.75 (2H, s) 4.57 (2H, s) 4.09 (4H, s) 3.83 (3H, s) 3.70 (2H, t J 7.17 Hz) 3.07 (2H, t, J=7.17 Hz) 2.82 (3H, s) 2.60 (6H, s)

Potency: C

Isoxazole Synthesis

Scheme 6 describes the general synthesis of isoxazole derivative.

(R$^1$=Me; R$^{1a}$=R$^{1b}$=H; X=2,6-dimethyl-4-methoxybenzenesulfonyl; X$^1$=CH; X$^2$=O; X$^3$=N; NR$^2$R$^3$=substituted piperazine)

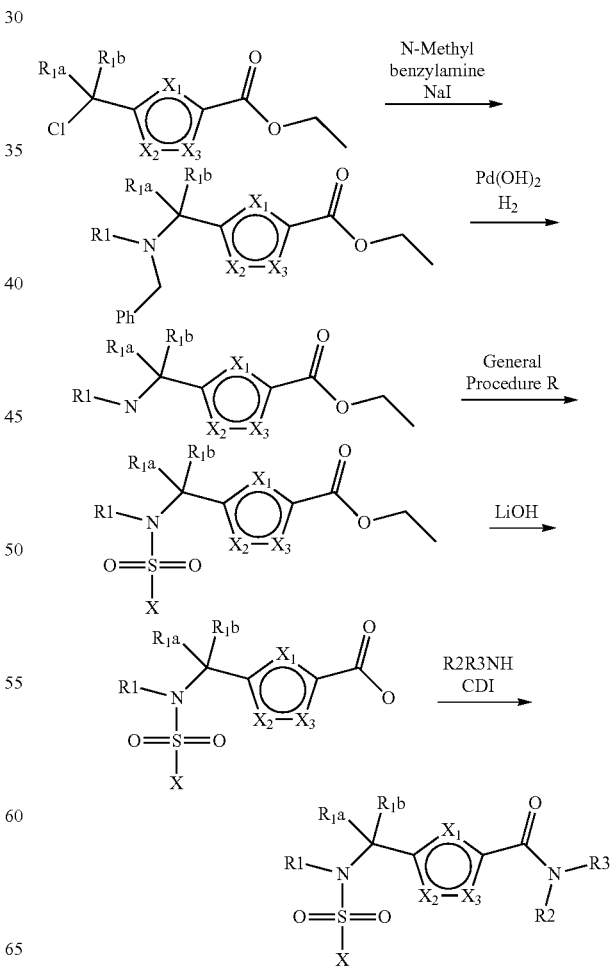

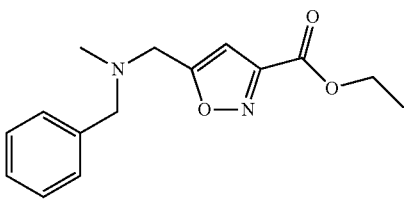 [SMILES: CCOC(=O)c1cc(CN(C)Cc2ccccc2)on1]

Ethyl 5-{[benzylmethyl)amino]methyl}isoxazole-3-carboxylate

Int 95

Ethyl 5-(chloromethyl)isoxazole-3-carboxylate (100 mg, 0.53 mmol) was dissolved in THF (5 mL) followed by the addition of NaI (10 mg, cat.) and N-methyl benzylamine (71 mg, 0.58 mmol). The reaction was stirred at ambient temperature for 18 h. The reaction was diluted with EtOAc (20 mL) and washed with water (5 mL), dried over $Na_2SO_4$ and concentrated in vacuo. The resulting oil was purified using FCC eluting with 10% MeOH in DCM to afford the title compound.

Yield: 145 mg, 100%.

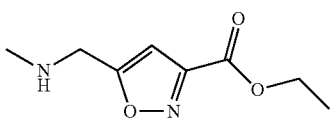

Ethyl 5-[(methylamino)methyl]isoxazole-3-carboxylate

Int 96

Ethyl 5-{[benzyl(methyl)amino]methyl}isoxazole-3-carboxylate (140 mg, 0.74 mmol) was dissolved in EtOH (5 mL) and $Pd(OH)_2$ added (20 mg, cat). The reaction vessel was purge-filled with nitrogen (3 cycles), then with hydrogen (3 cycles). Constant pressure of hydrogen was maintained with a hydrogen balloon. The mixture was stirred vigorously at ambient temperature for 18 h. The reaction mixture was filtered through Celite. The filter cake was washed with methanol. The combined organic layers were concentrated in vacuo to afford the title compound. No further purification was required.

Yield: 82 mg, 60%.

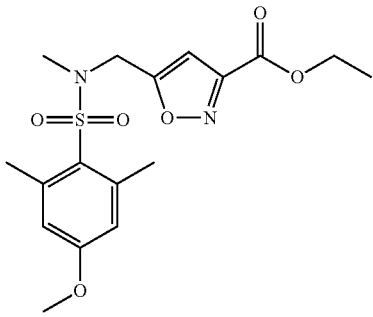

Ethyl 5-({[(4-methoxy-2,6-dimethylphenyl)sulfonyl](methyl)amino}methyl)isoxazole-3-carboxylate Int 97

The title compound was prepared according to general procedure AU using ethyl 5-[(methylamino)methyl]isoxazole-3-carboxylate (82 mg, 0.45 mmol), 4-methoxy-2,6-dimethylbenzenesulfonyl chloride (127 mg, 0.54 mmol) and TEA (0.15 mL, 1.08 mmol) in DCM. The crude product was purified using FCC eluting with 50% EtOAc in heptanes to afford the title compound.

Yield: 50 mg, 29%.

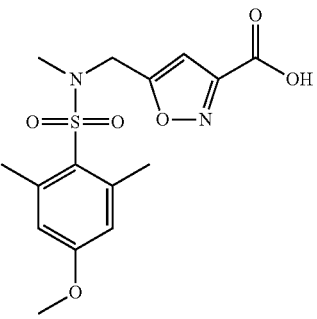

5-({[(4-Methoxy-2,6-dimethylphenyl)sulfonyl](methyl)amino}methyl)isoxazole-3-carboxylic acid Int 98

General Procedure AF

Ethyl 5-({[(4-methoxy-2,6-dimethylphenyl)sulfonyl](methyl)amino}methyl)isoxazole-3-carboxylate (50 mg, 0.13 mmol) was dissolved in a 1:1 mixture of THF/water (5 mL). Lithium hydroxide (16 mg, 0.39 mmol) was added and the reaction heated at 60° C. for 2 h. The reaction mixture was cooled and diluted with EtOAc (20 mL) and then acidified to pH1 using 1:1 mixture of 1 N HCl/saturated brine. The acidic aqueous layer was extracted with EtOAc (2×10 mL) and the combined organic extracts dried over $Na_2SO_4$. The solvent was removed in vacuo to afford the title compound, which required no further purification.

Yield: 46 mg, 100%.

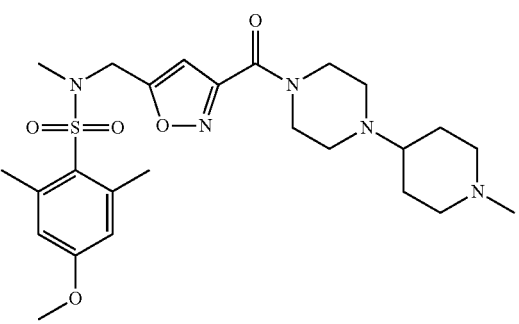

4-Methoxy-N,2,6-trimethyl-N-[(3-{[4-(1-methylpiperidin-4-yl)piperazin-1-yl]carbonyl}isoxazol-5-yl)methyl]benzenesulfonamide Ex 65

5-({[(4-Methoxy-2,6-dimethylphenyl)sulfonyl](methyl)amino}methyl)isoxazole-3-carboxylic acid (50 mg, 0.14 mmol) was dissolved in DCM (3 mL) and CDI (34 mg, 0.21 mmol) added. The resulting solution was stirred at ambient temperature for 60 min prior to the addition of a solution of 1-(1-methylpiperidin-4-yl)piperazine (26 mg, 0.14 mmol) in DCM (2 mL). The reaction was stirred at ambient temperature for 18 h. The reaction was diluted with DCM and washed with saturated aqueous $NH_4Cl$, saturated aqueous $NaHCO_3$, dried over Na₂SO₄ and concentrated in vacuo. The resulting crude product was purified using prep method A to afford the title compound as TFA salts.

Yield: 4.4 mg, 6%.

LCMS method C: rt 2.72 min, 97%; m/z 519.67 (MH⁺, 100%).

Potency: A

Oxazole Synthesis

Scheme 7 describes the general synthesis of oxazole derivatives.

($R^1$=Me, cyclopropyl; $R^{1a}$=$R^{1b}$=H; X=2,6-dimethyl-4-methoxybenzenesulfonyl; $X^1$=N; $X^2$=O; $X^3$=CH; $NR^2R^3$=various amines)

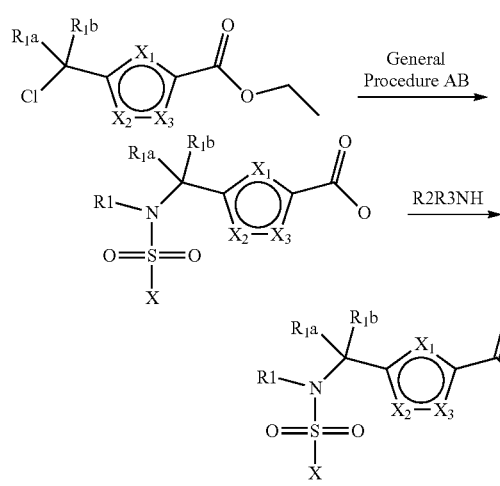

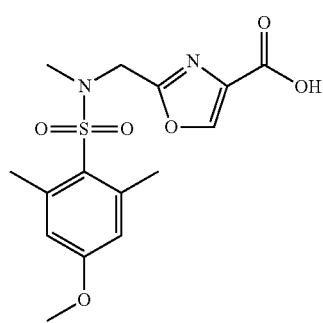 [SMILES: COc1cc(C)c(S(=O)(=O)N(C)Cc2nc(C(=O)O)co2)c(C)c1]

2-({[(4-Methoxy-2,6-dimethylphenyl)sulfonyl](methyl)amino}methyl)-1,3-oxazole-4-carboxylic acid Int 99

The title compound was prepared according to general procedure AB using methyl 2-(chloromethyl)-1,3-oxazole-4-carboxylate (1.76 g, 10 mmol), 4-4-methoxy-N,2,6-trimethylbenzenesulfonamide (2.09 g, 9.1 mmol) and NaH (436 mg, 18 mmol) in THF (40 mL). The reaction was diluted with EtOAc and washed with water, dried over Na₂SO₄ and concentrated in vacuo. The crude product (2.2 g, 5.97 mmol) was saponified according to General Procedure AF using LiOH (752 mg, 18 mmol) in 1:1 THF/water (30 mL) to afford the title compound, which required no further purification.

Yield: 800 mg, 31% over 2 steps.

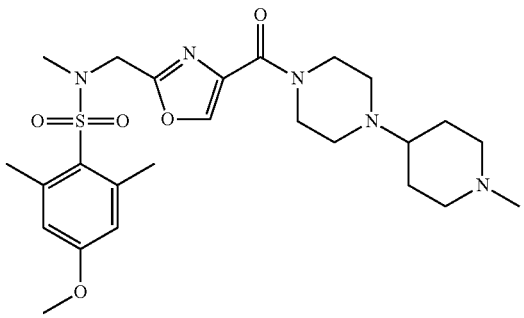

4-Methoxy-N,2,6-trimethyl-N-[(4-{[4-(1-methylpiperidin-4-yl)piperazin-1-yl]carbonyl}-1,3-oxazol-2-yl)methyl]benzenesulfonamide Ex 66
General Procedure AG 2-({[(4-Methoxy-2,6-dimethylphenyl)sulfonyl](methyl)amino}methyl)-1,3-oxazole-4-carboxylic acid (50 mg, 0.14 mmol) was dissolved in DMF (3 mL) and EDCI (32 mg, 0.17 mmol) and HOAt (23 mg, 0.17 mmol) were added. The resulting solution was stirred for 60 min at ambient temperature prior to the addition of a solution of 1-(1-methylpiperidin-4-yl)piperazine (31 mg, 0.17 mmol) in DMF (2 mL) and the reaction stirred at ambient temperature for 18 h. The reaction was diluted with EtOAc (20 mL) and washed with water (2×5 mL), saturated brine (5 mL), dried over Na₂SO₄ and concentrated in vacuo. The resulting oil was purified using FCC, eluting with 10% MeOH in DCM, to afford the title compound.

Yield: 8 mg, 11%.

LCMS method C: rt 2.64 min, 99%; m/z 519.67 (MH⁺, 100%).

Potency: B

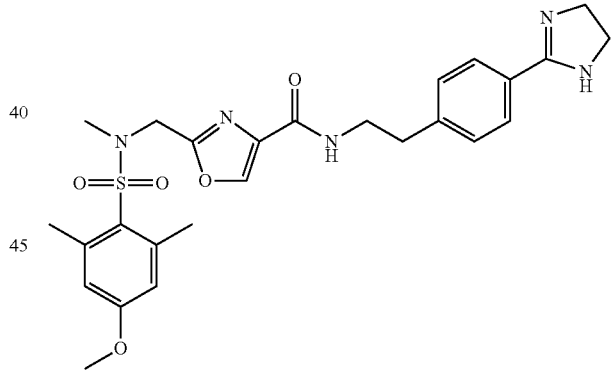

N-{2-[4-(4,5-dihydro-1H-imidazol-2-yl)phenyl]ethyl}-2-({[(4-methoxy-2,6-dimethylphenyl)sulfonyl](methyl)amino}methyl)-1,3-oxazole-4-carboxamide Ex 67

The title compound was prepared according to general procedure AI using 2-({[(4-methoxy-2,6-dimethylphenyl)sulfonyl](methyl)amino}methyl)-1,3-oxazole-4-carboxylic acid (200 mg, 0.56 mmol), the bis HCl salt of 2-[4-(4,5-dihydro-1H-imidazol-2-yl)phenyl]ethanamine (210 mg, 0.50 mmol), DIPEA (0.4 mL, 2.24 mmol), HOBt (91 mg, 0.67 mmol) and EDCI (129 mg, 0.67 mmol) in DMF (8 mL). The resulting crude product was purified using prep method B to afford the title compound as a TFA salt.

Yield: 40 mg, 14%.

LCMS method C: rt 3.20 min, 100%; m/z 525.63 (MH⁺, 100%).

$^1$H NMR (250 MHz, CD$_3$OD) δ ppm 8.27 (1H, s), 7.79 (2H, d, J=8.53 Hz), 7.54 (2H, d, J=8.38 Hz), 6.75 (2H, s), 4.51 (2H, s), 4.08 (4H, s), 3.83 (3H, s), 3.64 (2H, t, J=7.16 Hz), 3.03 (2H, t, J=7.16 Hz), 2.80 (3H, s), 2.62 (6H, m).
Potency: C

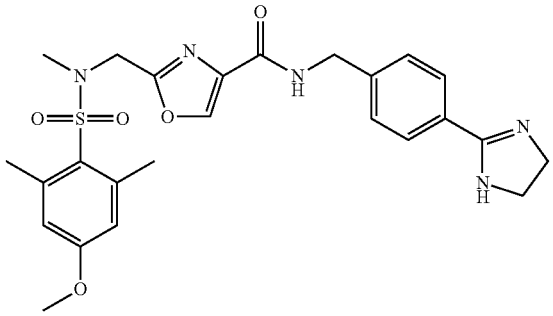 [SMILES: COc1cc(C)c(S(=O)(=O)N(C)Cc2nc(C(=O)NCc3ccc(C4=NCCN4)cc3)co2)c(C)c1]

N-[4-(4,5-dihydro-1H-imidazol-2-yl)benzyl]-2-({[(4-methoxy-2,6-dimethylphenyl)sulfonyl](methyl)amino}methyl)-1,3-oxazole-4-carboxamide Ex 68

The title compound was prepared according to general procedure AI using 2-({[(4-methoxy-2,6-dimethylphenyl)sulfonyl](methyl)amino}methyl)-1,3-oxazole-4-carboxylic acid (200 mg, 0.56 mmol), the bis HCl salt of 1-[4-(4,5-dihydro-1H-imidazol-2-yl)phenyl]methanamine (200 mg, 0.50 mmol), DIPEA (0.4 mL, 2.24 mmol), HOBt (91 mg, 0.67 mmol) and EDCI (129 mg, 0.67 mmol) in DMF (8 mL). The resulting crude product was purified using prep method B to afford the title compound as a TFA salt.
Yield: 28 mg, 10%.
LCMS method C: rt 3.13 min, 100%; m/z 511.60 (MH$^+$, 100%).
$^1$H NMR (250 MHz, CD$_3$OD) δ ppm 8.34 (1H, s), 7.83 (2H, d, J=8.38 Hz), 7.61 (2H, d, J=8.53 Hz), 6.74 (2H, s), 4.64 (2H, s), 4.54 (2H, s), 4.10 (4H, s), 3.81 (3H, s), 2.82 (3H, s), 2.62 (6H, m).
Potency: A

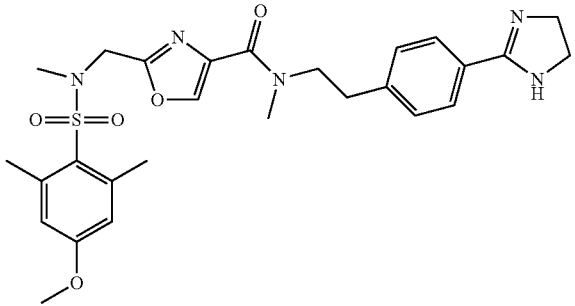

N-{2-[4-(4,5-dihydro-1H-imidazol-2-yl)phenyl]ethyl}-2-({[(4-methoxy-2,6-dimethylphenyl)sulfonyl](methyl)amino}methyl)-N-methyl-1,3-oxazole-4-carboxamide Ex 69
General Procedure AH A suspension of bis HCl salt of 2-[4-(4,5-dihydro-1H-imidazol-2-yl)phenyl]-N-methylethanamine (90 mg, 0.38 mmol) in DIPEA (0.29 mL, 1.68 mmol) and DMF (5 mL) was heated at 70° C. for 30 min. The suspension was added to a solution of 2-({[(4-methoxy-2,6-dimethylphenyl)sulfonyl](methyl)amino}methyl)-1,3-oxazole-4-carboxylic acid (150 mg, 0.42 mmol), EDCI (97 mg, 0.50 mmol) and HOBt (68 mg, 0.5 mmol) in DMF (5 mL). The reaction was stirred at 70° C. for 18 h. The reaction mixture was allowed to cool to ambient temperature and diluted with EtOAc, washed sequentially with water, saturated brine, saturated aqueous NaHCO$_3$, dried over Na$_2$SO$_4$ and concentrated in vacuo. The resulting crude product was purified using prep method B to afford the title compound as a TFA salt.
Yield: 27 mg, 12%.
LCMS method C: rt 3.23 min, 100%; m/z 539.66 (MH$^+$, 100%).
Potency: C

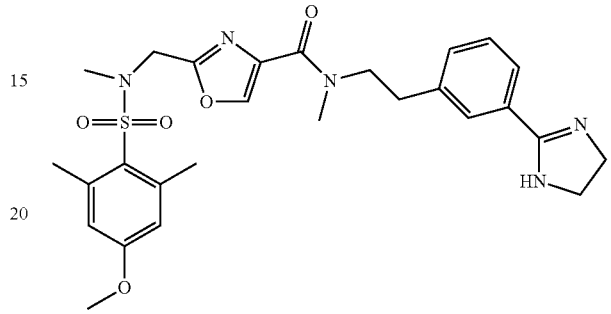

N-[4-(4,5-dihydro-1H-imidazol-2-yl)benzyl]-2-({[(4-methoxy-2,6-dimethylphenyl)sulfonyl](methyl)amino}methyl)-N-methyl-1,3-oxazole-4-carboxamide Ex 70

The title compound was prepared according to general procedure AI using 2-({[(4-methoxy-2,6-dimethylphenyl)sulfonyl](methyl)amino}methyl)-1,3-oxazole-4-carboxylic acid (200 mg, 0.56 mmol), the bis HCl salt of 1-[4-(4,5-dihydro-1H-imidazol-2-yl)phenyl]-N-methylmethanamine (86 mg, 0.38 mmol), DIPEA (0.29 mL, 1.68 mmol), HOBt (91 mg, 0.67 mmol) and EDCI (129 mg, 0.67 mmol) in DMF (6 mL). The resulting crude product was purified using prep method B to afford the title compound as a TFA salt.
Yield: 63 mg, 29%.
LCMS method C: rt 3.15 min, 100%; m/z 525.63 (MH$^+$, 100%).
Potency: C

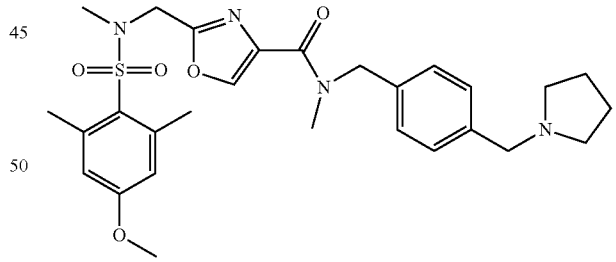

2({[(4-Methoxy-2,6dimethylphenyl)sulfonyl](methyl)amino}methyl)-N-methyl-N-[4-(pyrrolidin-1-ylmethyl)benzyl]-1,3-oxazole-4-carboxamide Ex 71
General Procedure AI 2-({[(4-Methoxy-2,6-dimethylphenyl)sulfonyl](methyl)amino}methyl)-1,3-oxazole-4-carboxylic acid (100 mg, 0.28 mmol) was dissolved in DMF (4 mL) and EDCI (65 mg, 0.34 mmol), HOBt (45 mg, 0.34 mmol) and DIPEA (0.2 mL, 1.12 mmol) were added. The resulting solution was stirred for 60 min prior to the addition of a solution of N-methyl-1[4(pyrrolidinylmethyl)phenyl]methanamine (51 mg, 0.25 mmol) in DMF (1 mL) and the reaction stirred at ambient temperature for 18 h. The reaction was diluted with EtOAc and washed with water, saturated brine, dried over $Na_2SO_4$ and concentrated in vacuo. The resulting crude product was purified using prep method B to afford the title compound as a TFA salt.

Yield: 37 mg, 12%.
LCMS method C: rt 3.20 min, 100%; m/z 540.69 ($MH^+$, 100%).
Potency: C

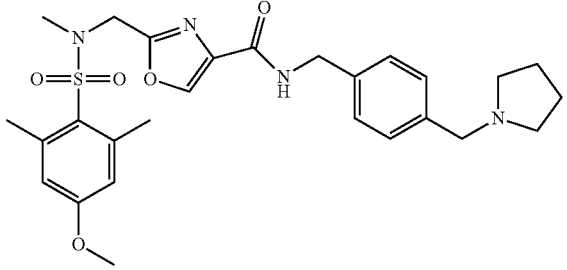 [SMILES: COc1cc(C)c(S(=O)(=O)N(C)Cc2nc(C(=O)NCc3ccc(CN4CCCC4)cc3)co2)c(C)c1]

2-({[(4-Methoxy-2,6dimethylphenyl)sulfonyl](methyl)amino}methyl)-N-[4-(pyrrolidin-1-ylmethyl)benzyl]-1,3-oxazole-4-carboxamide Ex 72

The title compound was prepared according to general procedure AI using 2-({[(4-methoxy-2,6-dimethylphenyl)sulfonyl](methyl)amino}methyl)-1,3-oxazole-4-carboxylic acid (100 mg, 0.28 mmol), 1-[4-(pyrrolidin-1-ylmethyl)phenyl]methanamine (48 mg, 0.25 mmol), EDCI (65 mg, 0.34 mmol), HOBt (45 mg, 0.34 mmol) and DIPEA (0.2 mL, 1.12 mmol) in DMF (5 mL). The resulting crude product was purified using prep method B to afford the title compound as a TFA salt.

Yield: 37 mg, 12%.
LCMS method C: rt 3.19 min, 100%; m/z 526.66 ($MH^+$, 100%).
$^1$H NMR (500 MHz, $CD_3OD$) δ ppm 8.93 (1H, br. s.), 8.34 (1H, s), 7.48 (4H, m), 6.75 (2H, s), 4.59 (2H, m), 4.55 (2H, s), 4.37 (2H, s), 3.83 (3H, s), 3.49 (2H, br. s.), 3.20 (2H, br. s.), 2.84 (3H, s), 2.61 (6H, s), 2.19 (2H, br. s.), 2.01 (2H, m).
Potency: B

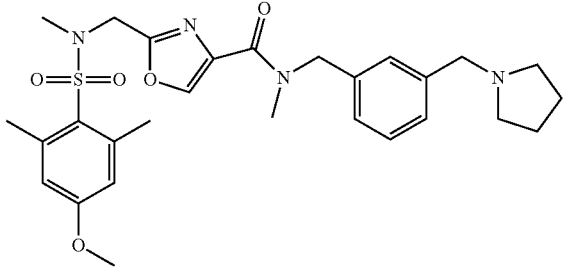 [SMILES: COc1cc(C)c(S(=O)(=O)N(C)Cc2nc(C(=O)N(C)Cc3cccc(CN4CCCC4)c3)co2)c(C)c1]

2-({[(4-Methoxy-2,6-dimethylphenyl)sulfonyl](methyl)amino}methyl)-N-methyl-N-[3-(pyrrolidin-1-ylmethyl)benzyl]-1,3-oxazole-4-carboxamide Ex 73

The title compound was prepared according to general procedure AI using 2-({[(4-methoxy-2,6-dimethylphenyl)sulfonyl](methyl)amino}methyl)-1,3-oxazole-4-carboxylic acid (66 mg, 0.12 mmol), N-methyl-1-[3-(pyrrolidin-1-ylmethyl)phenyl]methanamine (34 mg, 0.17 mmol), EDCI (28 mg, 0.15 mmol), HOBt (20 mg, 0.15 mmol) and DIPEA (0.2 mL, 1.12 mmol). The resulting crude product was purified using prep method B to afford the title compound as a TFA salt.

Yield: 31 mg, 31%.
LCMS method C: rt 3.23 min, 100%; m/z 540.69 ($MH^+$, 100%).
Potency: C

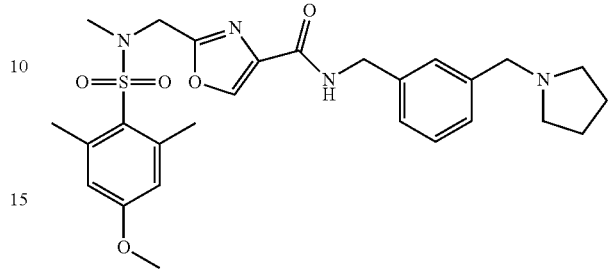

2-({[(4-Methoxy-2,6-dimethylphenyl)sulfonyl](methyl)amino}methyl)-N-[3-(pyrrolidin-1-ylmethyl)benzyl]-1,3-oxazole-4-carboxamide Ex 74

The title compound was prepared according to general procedure AI using 2-({[(4-methoxy-2,6-dimethylphenyl)sulfonyl](methyl)amino}methyl)-1,3-oxazole-4-carboxylic acid (100 mg, 0.28 mmol), 1-[3-(pyrrolidin-1-ylmethyl)phenyl]methanamine (48 mg, 0.25 mmol), EDCI (65 mg, 0.34 mmol), HOBt (45 mg, 0.34 mmol) and DIPEA (0.2 mL, 1.12 mmol) in DMF (5 mL). The resulting crude product was purified using prep method B to afford the title compound as a TFA salt.

Yield: 23 mg, 18%.
LCMS method C: rt 3.24 min, 100%; m/z 526.66 ($MH^+$, 100%).
$^1$H NMR (500 MHz, $CD_3OD$) δ ppm 8.92 (1H, m), 8.35 (1H, s), 7.47 (4H, m), 6.76 (2H, s), 4.60 (2H, s), 4.55 (2H, s), 4.38 (2H, s), 3.83 (3H, s), 3.50 (2H, br. s.), 3.20 (2H, br. s.), 2.83 (3H, s), 2.61 (6H, s), 2.18 (2H, br. s.), 2.01 (2H, m).
Potency: C

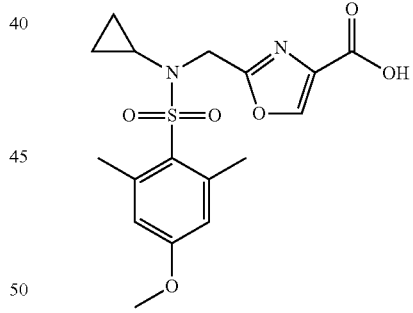

2-({Cyclopropyl[(4-methoxy-2,6-dimethylphenyl)sulfonyl]amino}methyl)-1,3-oxazole-4-carboxylic acid Int 100

The title compound was prepared according to general procedure AB using methyl 2-(chloromethyl)-1,3-oxazole-4-carboxylate (430 mg, 2.45 mmol), N-cyclopropyl-4-methoxy-2,6-dimethylbenzenesulfonamide (570 mg, 2.23 mmol) and NaH (118 mg, 4.9 mmol) in THF (10 mL). The reaction was diluted with EtOAc and washed with water, dried over $Na_2SO_4$ and concentrated in vacuo. The crude product (950 mg, 2.41 mmol) was saponified according to General Procedure AF using LiOH (405 mg, 9.64 mmol) in 1:1 THF/water (40 mL) to afford the title compound, which required no further purification.

Yield: 915 mg, 100% over 2 steps.

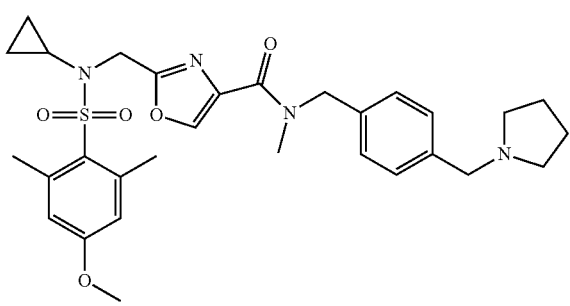 [SMILES: COc1cc(C)c(S(=O)(=O)N(Cc2nc(C(=O)N(C)Cc3ccc(CN4CCCC4)cc3)co2)C2CC2)c(C)c1]

2-({Cyclopropyl[(4-methoxy-2,6-dimethylphenyl)
sulfonyl]amino}methyl)-N-methyl-N-[4-(pyrrolidin-
1-ylmethyl)benzyl]-1,3-oxazole-4-carboxamide Ex 75

The title compound was prepared according to general procedure AI using 2-({cyclopropyl[(4-methoxy-2,6-dimethylphenyl)sulfonyl]amino}methyl)-1,3-oxazole-4-carboxylic acid (100 mg, 0.26 mmol), N-methyl-1[4(pyrrolidinylmethyl)phenyl]methanamine (47 mg, 0.23 mmol), EDCI (60 mg, 0.31 mmol), HOBt (42 mg, 0.31 mmol) and DIPEA (0.2 mL, 1.04 mmol) in DMF (8 mL). The resulting crude product was purified using prep method B to afford the title compound as a TFA salt.

Yield: 40 mg, 27%.

LCMS method C: rt 3.28 min, 100%; m/z 566.73 (MH$^+$, 100%).

$^1$H NMR (500 MHz, CD$_3$OD) δ ppm 8.22 (1H, m), 7.31 (4H, m), 6.59 (2H, m), 5.03 (1H, m), 4.62 (1H, m), 4.50 (2H, m), 4.22 (2H, m), 3.68 (3H, s), 3.33 (2H, m), 2.99 (5H, m), 2.42 (7H, m), 2.02 (2H, m), 1.84 (2H, m), 0.41 (1H, m), 0.27 (1H, m), 0.09 (1H, m), 0.02 (1H, m).

Potency: C

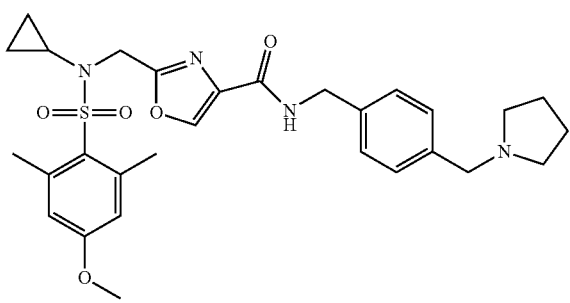 [SMILES: COc1cc(C)c(S(=O)(=O)N(Cc2nc(C(=O)NCc3ccc(CN4CCCC4)cc3)co2)C2CC2)c(C)c1]

2-({Cyclopropyl[(4-methoxy-2,6-dimethylphenyl)
sulfonyl]amino}methyl)-N-[4-(pyrrolidin-1-ylm-
ethyl)benzyl]-1,3-oxazole-4-carboxamide Ex 76

The title compound was prepared according to general procedure AI using 2-({cyclopropyl[(4-methoxy-2,6-dimethylphenyl)sulfonyl]amino}methyl)-1,3-oxazole-4-carboxylic acid (100 mg, 0.26 mmol), 1-[4-(pyrrolidin-1-ylmethyl)phenyl]methanamine (43 mg, 0.23 mmol), EDCI (60 mg, 0.31 mmol), HOBt (42 mg, 0.31 mmol) and DIPEA (0.2 mL, 1.04 mmol) in DMF (8 mL). The resulting crude product was purified using prep method B to afford the title compound as a TFA salt.

Yield: 35 mg, 24%.

LCMS method C: rt 3.27 min, 99%; m/z 552.70 (MH$^+$, 100%).

$^1$H NMR (500 MHz, CD$_3$OD) δ ppm 8.14 (2H, s), 7.25 (4H, s), 6.52 (2H, s), 4.47 (2H, s), 4.31-4.38 (2H, m), 4.13 (2H, s), 3.60 (3H, s), 3.20-3.30 (2H, m), 2.87-3.01 (2H, m), 2.43 (1H, dt, J 6.83, 3.28 Hz), 2.35 (6H, s), 1.88-1.98 (2H, m), 1.72-1.80 (2H, m), 0.26-0.39 (2H, m), 0.02 (2H, m).

Potency: C

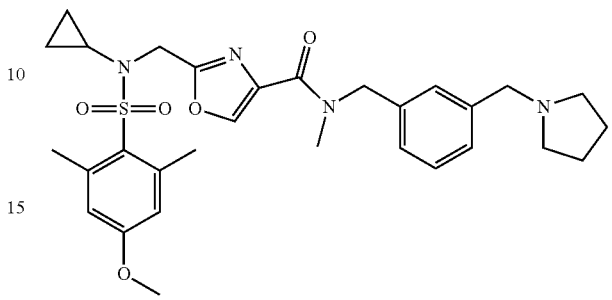

2-({Cyclopropyl[(4-methoxy-2,6-dimethylphenyl)
sulfonyl]amino}methyl)-N-methyl-N-[3-(pyrrolidin-
1-ylmethyl)benzyl]-1,3-oxazole-4-carboxamide Ex 77

The title compound was prepared according to general procedure AI using 2-({cyclopropyl[(4-methoxy-2,6-dimethylphenyl)sulfonyl]amino}methyl)-1,3-oxazole-4-carboxylic acid (100 mg, 0.26 mmol), N-methyl-1-[3-(pyrrolidin-1-ylmethyl)phenyl]methanamine (47 mg, 0.23 mmol), EDCI (60 mg, 0.31 mmol), HOBt (42 mg, 0.31 mmol) and DIPEA (0.2 mL, 1.04 mmol) in DMF (8 mL). The resulting crude product was purified using prep method B to afford the title compound as a TFA salt.

Yield: 31 mg, 21%.

LCMS method C: rt 3.32 min, 100%; m/z 566.73 (MH$^+$, 100%).

$^1$H NMR (500 MHz, CD$_3$OD) δ ppm 8.22 (1H, s), 7.31 (4H, m), 6.58 (2H, d, J=7.34 Hz), 5.00 (1H, s), 4.54 (3H, m), 4.22 (2H, s), 3.67 (3H, s), 3.24-3.37 (2H, m), 3.18 (1H, s), 2.77 (5H, m), 2.36 (6H, m), 1.99 (2H, m), 1.80 (2H, m), 0.40 (1H, d, J=5.69 Hz), 0.29 (1H, d, J=5.87 Hz), 0.06 (1H, br. s.), 0.00 (1H, br. s.).

Potency: C

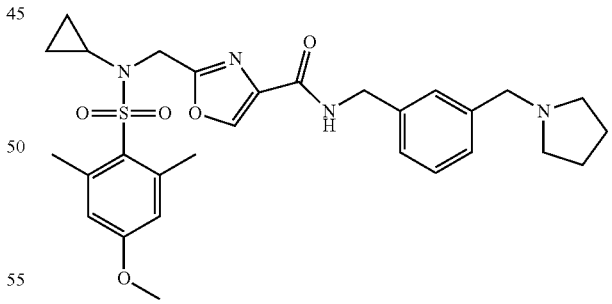

2-({Cyclopropyl[(4-methoxy-2,6-dimethylphenyl)
sulfonyl]amino}methyl)-N-[3-(pyrrolidin-1-ylm-
ethyl)benzyl]-1,3-oxazole-4-carboxamide Ex 78

The title compound was prepared according to general procedure AI using 2-({cyclopropyl[(4-methoxy-2,6-dimethylphenyl)sulfonyl]amino}methyl)-1,3-oxazole-4-carboxylic acid (100 mg, 0.26 mmol), 1-[3-(pyrrolidin-1-ylmethyl)phenyl]methanamine (44 mg, 0.23 mmol), EDCI (60 mg, 0.31 mmol), HOBt (42 mg, 0.31 mmol) and DIPEA (0.2 mL, 1.04 mmol) in DMF (8 mL). The resulting crude product was purified using prep method B to afford the title compound as a TFA salt.

Yield: 35 mg, 24%.

LCMS method C: rt 3.32 min, 100%; m/z 552.70 (MH+, 100%).

$^1$H NMR (500 MHz, CD$_3$OD) δ ppm 8.16 (1H, s), 7.23 (4H, m), 6.53 (2H, s), 4.48 (2H, s), 4.37 (2H, s), 4.14 (2H, s), 3.61 (3H, s), 3.21-3.33 (2H, m), 2.95 (2H, m), 2.46 (1H, m), 2.38 (6H, s), 1.96 (2H, m), 1.75 (2H, m), 0.34 (2H, m), 0.04 (2H, m).

Potency: C

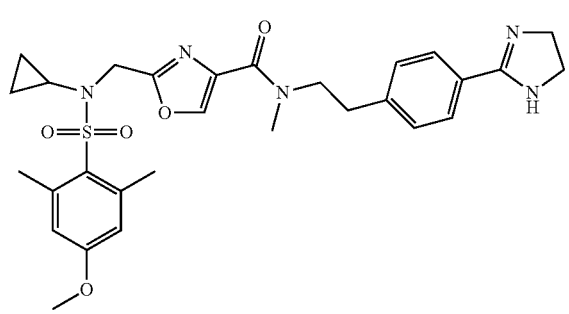 [SMILES: COc1cc(C)c(S(=O)(=O)N(Cc2nc(C(=O)N(C)CCc3ccc(C4=NCCN4)cc3)co2)C2CC2)c(C)c1]

2-({Cyclopropyl[(4-methoxy-2,6-dimethylphenyl)sulfonyl]amino}methyl)-N-{2-[4-(4,5-dihydro-1H-imidazol-2-yl)phenyl]ethyl}-N-methyl-1,3-oxazole-4-carboxamide Ex 79

The title compound was prepared according to general procedure AH using 2-({cyclopropyl[(4-methoxy-2,6-dimethylphenyl)sulfonyl]amino}methyl)-1,3-oxazole-4-carboxylic acid (100 mg, 0.26 mmol), the bis HCl salt of 2-[4-(4,5-dihydro-1H-imidazol-2-yl)phenyl]-N-methylethanamine (65 mg, 0.23 mmol), EDCI (60 mg, 0.31 mmol), HOBt (42 mg, 0.31 mmol) and DIPEA (0.2 mL, 1.04 mmol) in DMF (8 mL).

The resulting crude product was purified using prep method B to afford the title compound as a TFA salt.

Yield: 5 mg, 3%.

LCMS method C: rt 3.29 min, 97%; m/z 565.70 (MH+, 100%).

$^1$H NMR (500 MHz, CD$_3$OD) δ ppm 7.95 (1H, m), 7.56 (2H, m), 7.33 (2H, m), 6.54 (2H, s), 4.47 (2H, m), 4.00 (1H, t, J=7.15 Hz), 3.86 (4H, s), 3.62 (3H, s), 3.56 (1H, m), 2.90 (4H, m), 2.46 (2H, m), 2.36 (6H, s), 0.33 (2H, m), 0.03 (2H, m).

Potency: C

Thiazole Synthesis

Scheme 8 describes the general synthesis of thiazole derivatives.

(R$^1$=Me; R$^{1a}$=R$^{1b}$=H; X=2,6-dimethyl-4-methoxybenzenesulfonyl; X$^1$=N; X$^2$=S; X$^3$=CH; NR$^2$R$^3$=various amines)

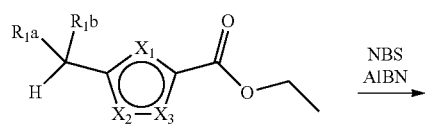

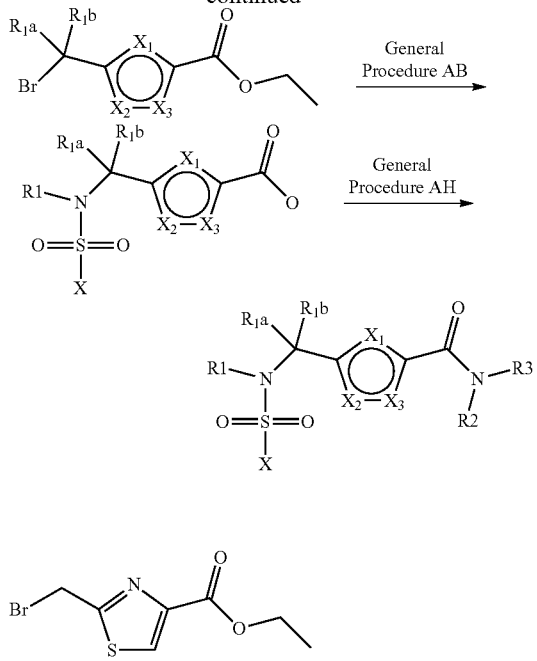

Ethyl 2-(bromomethyl)-1,3-thiazole-4-carboxylate

Int 101

Ethyl 2-methyl-1,3-thiazole-4-carboxylate (500 mg, 2.92 mmol) was dissolved in CCl$_4$ (10 mL) and NBS (624 mg, 3.50 mmol) was added and the reaction heated at 76° C. for 60 min. AIBN (36 mg, 0.21 mmol) was added and heating continued at 76° C. for 4 h. The reaction mixture was allowed to cool to ambient temperature and filtered through Celite. The filter cake was washed with DCM. The combined organic layers were concentrated in vacuo with silica and purified using FCC, eluting with 50% EtOAc in heptanes, to afford the title compound.

Yield: 274 mg, 38%.

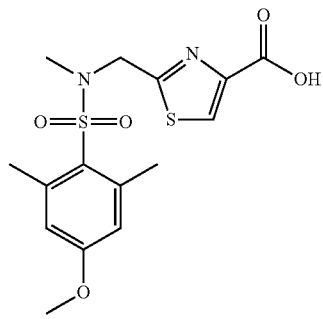

2-({[(4-Methoxy-2,6-dimethylphenyl)sulfonyl](methyl)amino}methyl)-1,3-thiazole-4-carboxylic acid Int 102

The title compound was prepared according to general procedure AB using ethyl 2-(bromomethyl)-1,3-thiazole-4-carboxylate (250 mg, 1 mmol), 4-4-methoxy-N,2,6-trimethylbenzenesulfonamide (230 mg, 1 mmol) and NaH (48 mg, 2 mmol) in THF (10 mL). The reaction was diluted with EtOAc and washed with water, dried over Na$_2$SO$_4$ and concentrated in vacuo. The crude product (355 mg, 0.89 mmol) was saponified according to General Procedure AF using LiOH (112 mg, 2.67 mmol) in 1:1 THF/water (20 mL) to afford the title compound, which required no further purification.

Yield: 334 mg, 95% over 2 steps.

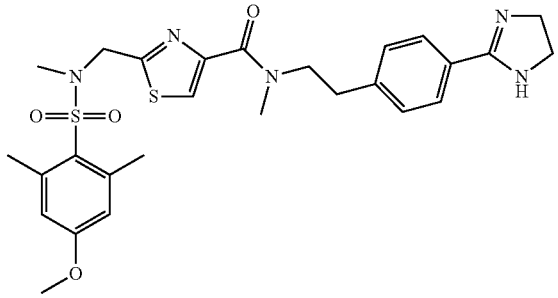 [SMILES: COc1cc(C)c(S(=O)(=O)N(C)Cc2nc(C(=O)N(C)CCc3ccc(C4=NCCN4)cc3)cs2)c(C)c1]

N-{2-[4-(4,5-dihydro-1H-imidazol-2-yl)phenyl]ethyl}-2-({[(4-methoxy-2,6-dimethylphenyl)sulfonyl](methyl)amino}methyl)-N-methyl-1,3-thiazole-4-carboxamide Ex 80

The title compound was prepared according to general procedure AH using 2-({[(4-methoxy-2,6-dimethylphenyl)sulfonyl](methyl)amino}methyl)-1,3-thiazole-4-carboxylic acid (150 mg, 0.41 mmol), the bis HCl salt of 2-[4-(4,5-dihydro-1H-imidazol-2-yl)phenyl]-N-methylethanamine (100 mg, 0.36 mmol), EDCI (94 mg, 0.49 mmol), HOBt (66 mg, 0.49 mmol) and DIPEA (0.3 mL, 1.62 mmol) in DMF (10 mL). The resulting crude product was purified using prep method B to afford the title compound as a TFA salt.

Yield: 28 mg, 12%.

LCMS method C: rt 3.21 min, 98%; m/z 555.72 (MH$^+$, 100%).

$^1$H NMR (250 MHz, CD$_3$OD) δ ppm 8.00 (1H, m), 7.67 (3H, m), 7.40 (1H, d, J=8.22 Hz), 6.81 (2H, s), 4.68 (2H, s), 4.11 (4H, m), 3.84 (3H, m), 3.07 (5H, m), 2.81 (3H, m), 2.65 (6H, m), 2.08 (3H, s).

Potency: A

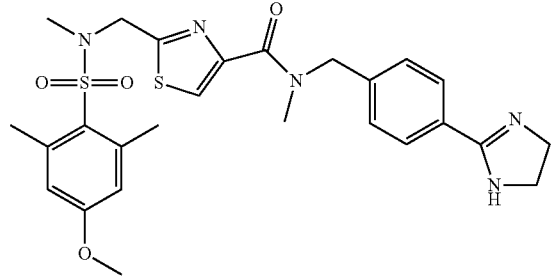 [SMILES: COc1cc(C)c(S(=O)(=O)N(C)Cc2nc(C(=O)N(C)Cc3ccc(C4=NCCN4)cc3)cs2)c(C)c1]

N-[4-(4,5-dihydro-1H-imidazol-2-yl)benzyl]-2-({[(4-methoxy-2,6-dimethylphenyl)sulfonyl](methyl)amino}methyl)-N-methyl-1,3-thiazole-4-carboxamide Ex 81

The title compound was prepared according to general procedure AH using 2-({[(4-methoxy-2,6-dimethylphenyl)sulfonyl](methyl)amino}methyl)-1,3-thiazole-4-carboxylic acid (150 mg, 0.41 mmol), the bis HCl salt of 1-[4-(4,5-dihydro-1H-imidazol-2-yl)phenyl]-N-methylmethanamine (94 mg, 0.36 mmol), EDCI (94 mg, 0.49 mmol), HOBt (66 mg, 0.49 mmol) and DIPEA (0.3 mL, 1.62 mmol) in DMF (10 mL). The resulting crude product was purified using prep method B to afford the title compound as a TFA salt.

Yield: 19 mg, 9%.

LCMS method C: rt 3.20 min, 100%; m/z 541.70 (MH$^+$, 100%).

Potency: A

Furans


5-({cyclopropyl[(4-methoxy-2,6-dimethylphenyl)sulfonyl]amino}methyl)-N-[4-(4,5-dihydro-1H-imidazol-2-yl)benzyl]furan-3-carboxamide trifluoroacetate Ex 82

The title compound was prepared according to general procedure AH using 1-[4-(4,5-dihydro-1H-imidazol-2-yl)phenyl]methanamine, bis trifluoroacetate (54 mg, 0.14 mmol), TEA (0.06 mL, 0.45 mmol), DMF (1.5 mL), 5-({cyclopropyl[(4-methoxy-2,6-dimethylphenyl)sulfonyl]amino}methyl)furan-3-carboxylic acid (150 mg, 0.42 mmol), EDCI (35 mg, 0.18 mmol) and HOBt monohydrate (28 mg, 0.18 mmol). The crude product was purified using MP-TsOH resin, washing with MeOH (5 mL) and eluting with 7N NH$_3$ in MeOH (7 mL). A portion of the resulting partially purified product was purified using prep method A to afford the title compound as a TFA salt.

LCMS method C: rt 3.29 min, 99%; m/z 537.24 (MH$^+$, 100%).

Potency: A

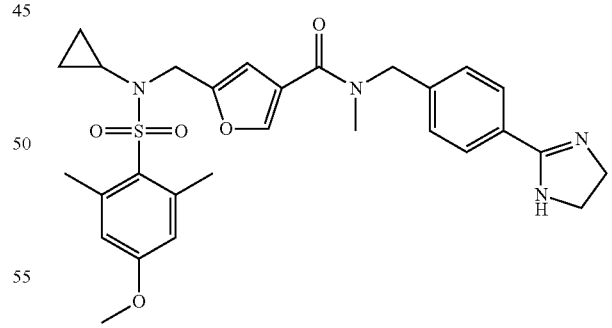

5-({cyclopropyl[(4-methoxy-2,6-dimethylphenyl)sulfonyl]amino}methyl)-N-[4-(4,5-dihydro-1H-imidazol-2-yl)benzyl]-N-methylfuran-3-carboxamide trifluoroacetate Ex 83

The title compound was prepared according to general procedure AH using 1-[4-(4,5-dihydro-1H-imidazol-2-yl)phenyl]-N-methylmethanamine dihydrochloride (35 mg, 0.14 mmol), TEA (0.06 mL, 0.45 mmol), DMF (1.5 mL), 5-({cyclopropyl[(4-methoxy-2,6-dimethylphenyl)sulfonyl]amino}methyl)furan-3-carboxylic acid (150 mg, 0.42 mmol), EDCI (35 mg, 0.18 mmol) and HOBt monohydrate (28 mg, 0.18 mmol). The crude product was purified using MP-TsOH resin, washing with MeOH (5 mL) and eluting with 7N NH$_3$ in MeOH (7 mL). A portion of the resulting partially purified product was purified using prep method A to afford the title compound as a TFA salt.

LCMS method C: rt 3.32 min, 100%; m/z 551.19 (MH$^+$, 100%).

Potency: B

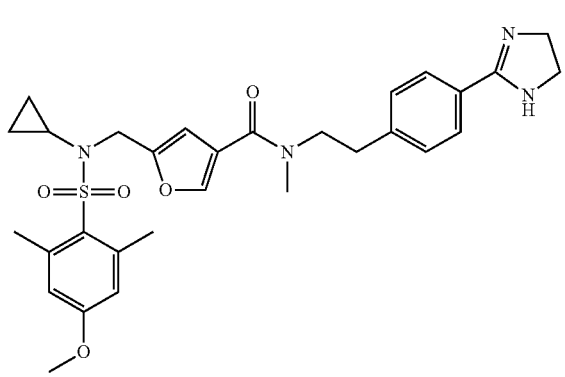 [SMILES: COc1cc(C)c(S(=O)(=O)N(Cc2cc(C(=O)N(C)CCc3ccc(C4=NCCN4)cc3)co2)C2CC2)c(C)c1]

5-({cyclopropyl[(4-methoxy-2,6-dimethylphenyl)sulfonyl]amino}methyl)-N-{2-[4-(4,5-dihydro-1H-imidazol-2-yl)phenyl]ethyl}-N-methylfuran-3-carboxamide trifluoroacetate Ex 84

The title compound was prepared according to general procedure AH using bis HCl 2-[4-(4,5-dihydro-1H-imidazol-2-yl)phenyl]-N-methylethanamine, (37 mg, 0.14 mmol), TEA (0.06 mL, 0.45 mmol), DMF (1.5 mL), 5-({cyclopropyl[(4-methoxy-2,6-dimethylphenyl)sulfonyl]amino}methyl)furan-3-carboxylic acid (150 mg, 0.42 mmol), EDCI (35 mg, 0.18 mmol) and HOBt monohydrate (28 mg, 0.18 mmol). The crude product was purified using MP-TsOH resin, washing with MeOH (5 mL) and eluting with 7N NH$_3$ in MeOH (7 mL). A portion of the resulting partially purified product was purified using prep method A to afford the title compound as a TFA salt.

LCMS method C: rt 3.32 min, 100%; m/z 565.24 (MH$^+$, 100%).

Potency: C

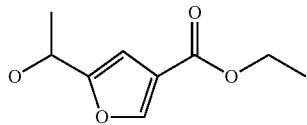

Ethyl 5-(1-hydroxyethyl)furan-3-carboxylate

Int 103

Ethyl 5-formylfuran-3-carboxylate (0.5 g, 3.0 mmol) was dissolved in toluene (3 mL) under a N$_2$ atmosphere and cooled to −78° C. using an acetone/dry ice bath. To this cooled solution was added dropwise methylmagnesium bromide (1.4 M in toluene, 2.1 mL). The resulting solution was stirred at −78° C. for 10 min and then warmed to ambient temperature for 160 min. The reaction was quenched by addition of 2 M ammonium chloride (3 mL) and extracted with EtOAc (3×3 mL). The combined organic extracts were dried over MgSO$_4$ and concentrated in vacuo. The crude product was purified by FCC eluting with 33% EtOAc in heptane to afford the title compound.

Yield: 436 mg, 79%.

$^1$H NMR (500 MHz, CDCl$_3$) δ ppm 7.93 (1H, s), 6.57 (1H, s), 4.74-4.95 (1H, m), 4.29 (2H, q, J=7.2 Hz), 2.27 (1H, d, J=4.7 Hz), 1.54 (3H, d, J=6.6 Hz), 1.33 (3H, t)

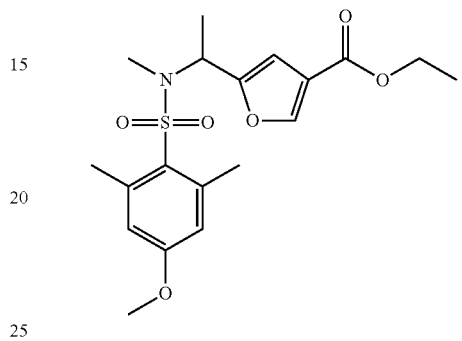

Ethyl 5-(1-{[(4-methoxy-2,6-dimethylphenyl)sulfonyl](methyl)amino}ethyl)furan-3-carboxylate Int 104

A solution of ethyl 5-(1-hydroxyethyl)furan-3-carboxylate (92 mg, 0.5 mmol), 4-methoxy-N,2,6-trimethylbenzenesulfonamide (115 mg, 0.5 mmol) and triphenylphosphine (197 mg, 0.75 mmol) in anhydrous THF (2 mL) was cooled to 0-5° C. with an ice bath prior to addition of DIAD (152 mg, 0.75 mmol) in one portion. The reaction was stirred at ambient temperature for 4 h and diluted with water (10 mL). The mixture was extracted with DCM (3×10 mL), dried (MgSO$_4$) and concentrated in vacuo. The resulting crude product was purified by FCC eluting with 5-20% EtOAc in heptane to afford the title compound.

Yield: 57 mg, 28%.

Potency:

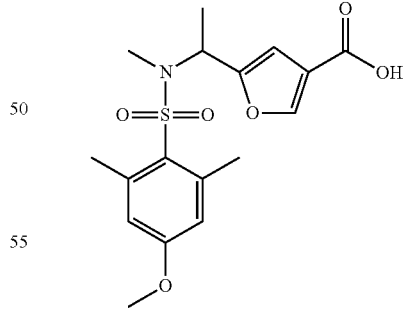

5-(1-{[(4-Methoxy-2,6-dimethylphenyl)sulfonyl](methyl)amino}ethyl)furan-3-carboxylic acid Int 105

The title compound was prepared according to general procedure AF using ethyl 5-(1-{[(4-methoxy-2,6-dimethylphenyl)sulfonyl](methyl)amino}ethyl)furan-3-carboxylate (55 mg, 0.14 mmol), LiOH monohydrate (18 mg, 0.42 mmol), THF (3 mL) and water (2 mL). The crude product required no further purification.

Yield: 39 mg, 76%.

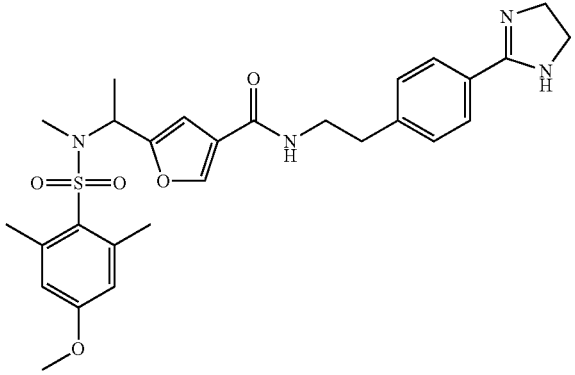 [SMILES: COc1cc(C)c(S(=O)(=O)N(C)C(C)c2cc(C(=O)NCCc3ccc(C4=NCCN4)cc3)co2)c(C)c1]

N-{2-[4-(4,5-dihydro-1H-imidazol-2-yl)phenyl]ethyl}-5-(1-{[(4-methoxy-2,6-dimethylphenyl)sulfonyl](methyl)amino}ethyl)furan-3-carboxamide trifluoroacetamide Ex 85

The title compound was prepared according to general procedure AH using the bis TFA salt of 2-[4-(4,5-dihydro-1H-imidazol-2-yl)phenyl]ethanamine, (40 mg, 0.1 mmol), TEA (0.05 mL, 0.32 mmol), DMF (1 mL), 5-(1-{[(4-methoxy-2,6-dimethylphenyl)sulfonyl](methyl)amino}ethyl)furan-3-carboxylic acid (39 mg, 0.11 mmol), EDCI (24 mg, 0.13 mmol) and HOBt monohydrate (17 mg, 0.13 mmol). The crude product was purified using MP-TsOH resin, washing with MeOH (5 mL) and eluting with 7N $NH_3$ in MeOH (7 mL). A portion of the resulting partially purified product was purified using prep method C to afford the title compound.

LCMS method C: rt 3.31 min, 85%; m/z 539.10 ($MH^+$, 100%).

Potency: A

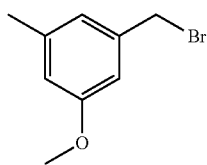

1-(Bromomethyl)-3-methoxy-5-methylbenzene

Int 106

To a solution of 3,5-dimethylanisol (5.0 g, 36.70 mmol) in $CCl_4$ (100 mL) were added NBS (6.2 g, 34.80 mmol) and benzoyl peroxide (100 mg, 0.041 mmol) and the resultant solution was refluxed for 1 h. The reaction mixture was filtered through Celite. The organic layer was washed with water (100 mL), dried over $Na_2SO_4$ and concentrated in vacuo. The resulting residue was purified by FCC eluting with 100% hexane to afford the title compound as a colourless liquid.

Yield: 3.2 g, 41%.

$^1$H NMR (300 MHz, $CDCl_3$) δ ppm 6.80 (1H, s), 6.73 (1H, s), 6.65 (1H, s), 4.43 (2H, s), 3.78 (3H, s), 2.31 (3H, s).

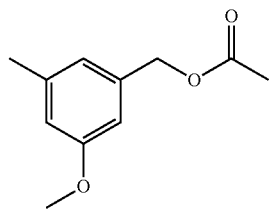

3-Methoxy-5-methylbenzyl acetate

Int 107

1-(Bromomethyl)-3-methoxy-5-methylbenzene (4.7 g, 14.88 mmol) was dissolved in EtOH (50 mL) and potassium acetate (3.2 g, 22.32 mmol) added. The resultant solution was refluxed for 12 h. The reaction was cooled to ambient temperature and the solvent was removed in vacuo. The residue was purified by FCC eluting with 0-1% EtOAc in hexane to afford the title compound as a colourless liquid.

Yield: 3.1 g, 74%.

$^1$H NMR (300 MHz, $CDCl_3$) δ ppm 6.76 (1H, s), 6.70-6.69 (2H, m), 5.04 (2H, s), 3.80 (3H, s), 2.33 (3H, s), 2.12 (3H, s).

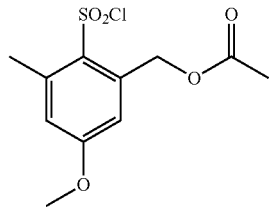 [SMILES: COc1cc(C)c(S(=O)(=O)Cl)c(COC(C)=O)c1]

2-(Chlorosulfonyl)-5-methoxy-3-methylbenzyl acetate

Int 108

3-Methoxy-5-methylbenzyl acetate (3.1 g, 16.0 mmol) was dissolved in $CHCl_3$ (50 mL) and the resulting solution was cooled to 0° C. prior to the dropwise addition of chlorosulfonic acid (1.2 g, 10 mmol). The reaction was stirred at ambient temperature for 2 h and quenched with ice water (100 mL). The organic layer was separated, dried over $Na_2SO_4$ and concentrated in vacuo to afford the title compound, which was used without further purification.

Yield: 580 mg, 39%.

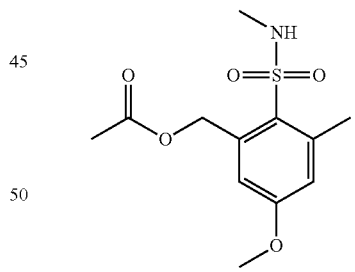

5-methoxy-3-methyl-2-(methylsulfamoyl)benzyl acetate

Int 109

To a stirred solution of 2-(chlorosulfonyl)-5-methoxy-3-methylbenzyl acetate (580 mg, 1.97 mmol) in THF (2 mL) at 0° C. was added methylamine (4 mL, 2M in THF). The reaction was stirred at ambient temperature 4 h and the solvent was removed in vacuo. The residue was purified by FCC eluting with 0-8% EtOAc in hexane to afford the title compound as a colourless oil.

Yield: 220 mg, 39%.

$^1$H NMR (300 MHz, $CDCl_3$): δ ppm 6.94-6.93 (1H, m), 6.77-6.76 (1H, m), 5.54 (2H, s), 4.92-4.90 (1H, m), 3.86 (3H, s), 2.69 (3H, s), 2.66-2.64 (3H, s), 2.15 (3H, s).

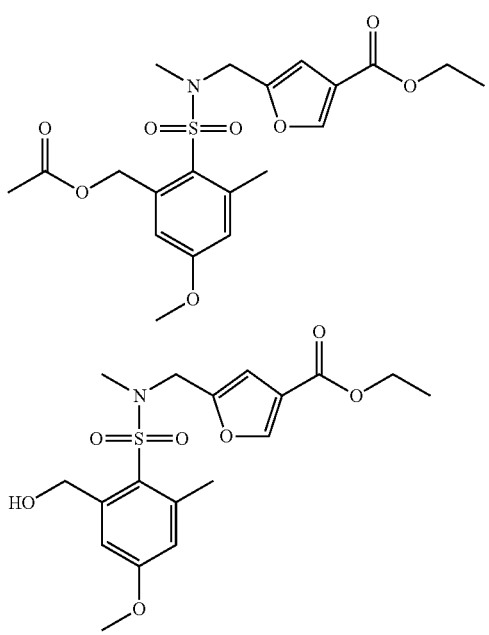

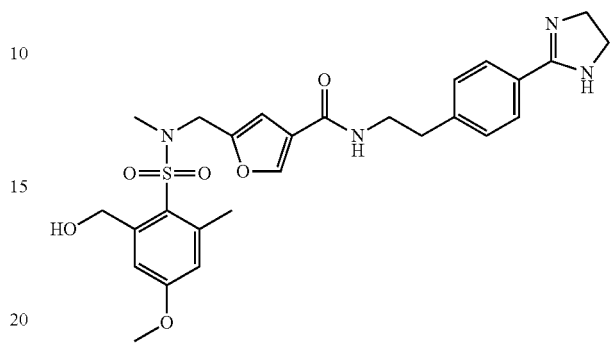

ethyl 5-{[({2-[(acetyloxy)methyl]-4-methoxy-6-methylphenyl}sulfonyl)(methyl)amino]methyl}furan-3-carboxylate and ethyl 5-{[{[2-(hydroxymethyl)-4-methoxy-6-methylphenyl]sulfonyl}(methyl)amino]methyl}furan-3-carboxylate Int 110 & 111

To an ice-cold solution of 5-methoxy-3-methyl-2-(methylsulfamoyl)benzyl acetate (365 mg, 1.27 mmol) and sodium iodide (15 mg, cat) in anhydrous DMF (12 mL) was added sodium hydride (60%, 76 mg, 1.9 mmol) followed 5 min later by ethyl 5-(chloromethyl)furan-3-carboxylate (240 mg, 1.27 mmol). The reaction was stirred at ambient temperature for 90 min and then diluted with water (20 mL) and extracted with DCM (3×20 mL). The combined organic extracts were dried (MgSO₄) and concentrated in vacuo to afford a mixture of the title compounds as a brown oil.

The crude products were carried through to the next step without further purification.

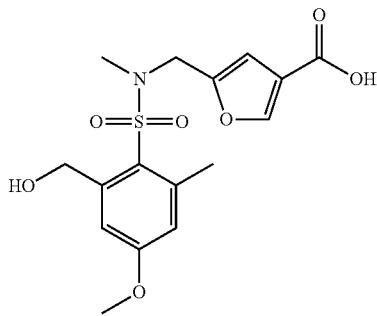 [SMILES: COc1cc(C)c(S(=O)(=O)N(C)Cc2cc(C(=O)O)co2)c(CO)c1]

5-{[{[2-(Hydroxymethyl)-4-methoxy-6-methylphenyl]sulfonyl}(methyl)amino]methyl}furan-3-carboxylic acid Int 111

The title compound was prepared according to general procedure AF using a mixture of ethyl 5-{[({2-[(acetyloxy)methyl]-4-methoxy-6-methylphenyl}sulfonyl)(methyl)amino]methyl}furan-3-carboxylate and ethyl 5-{[{[2-(hydroxymethyl)-4-methoxy-6-methylphenyl]sulfonyl}(methyl)amino]methyl}furan-3-carboxylate (440 mg), LiOH monohydrate (210 mg, 5 mmol), THF (3.5 mL) and water (2 mL). The crude product was purified by FCC eluting with 40% EtOAc in heptane to afford the title compound.

Yield: 138 mg, 37%.

N-{2-[4-(4,5-Dihydro-1H-imidazol-2-yl)phenyl]ethyl}-5-{[{[2-(hydroxymethyl)-4-methoxy-6-methylphenyl]sulfonyl}(methyl)amino]methyl}furan-3-carboxamide trifluoroacetate Ex 86

5-{[{[2-(hydroxymethyl)-4-methoxy-6-methylphenyl]sulfonyl}(methyl)amino]methyl}furan-3-carboxylic acid (37 mg, 100 µmol), 2-[4-(4,5-dihydro-1H-imidazol-2-yl)phenyl]ethanamine (19 mg, 0.1 mmol) and HOBt monohydrate (23 mg, 0.15 mmol) were suspended in DCM (0.5 mL) and stirred prior to addition of a solution of DCC (31 mg, 0.15 mmol) in DCM (0.5 mL). The reaction was stirred for 16 h at ambient temperature and blown dry under a stream of N₂. A portion of the crude product was purified using prep method A to afford the title compound.

¹H NMR (500 MHz, CD₃OD) δ ppm 7.90 (1H, br s), 7.77 (2H, d, J=8.39 Hz), 7.50 (2H, d, J=8.39 Hz), 7.24-7.29 (1H, m), 6.78-6.82 (1H, m), 6.60 (1H, s), 4.94 (2H, s), 4.30 (2H, s), 4.06 (3H, s), 3.85 (2H, s), 3.57 (2H, t, J=7.17 Hz), 3.23-3.34 (4H, m), 2.99 (2H, t, J=7.17 Hz), 2.64 (3H, s), 2.58 (3H, s).

Potency: A

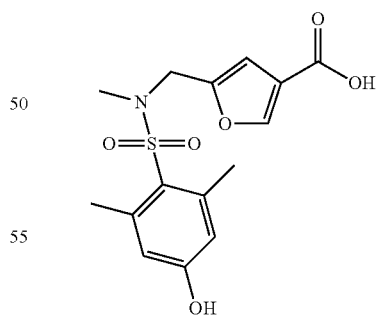

5-({[(4-Hydroxy-2,6-dimethylphenyl)sulfonyl](methyl)amino}methyl)furan-3-carboxylic acid Int 112

A solution of 5-({[(4-hydroxy-2,6 dimethylphenyl)sulfonyl](methyl)amino}methyl)furan-3-carboxylic acid (250 mg, 0.71 mmol) in DCM (25 mL), under a N₂ atmosphere was treated dropwise with boron tribromide (0.2 mL, 2.2 mmol). Once the addition was complete the mixture was stirred at ambient temperature for 2 h. The reaction mixture was quenched with water and the phases separated. The organics were dried (Na₂SO₄) and concentrated in vacuo to an orange oil. The crude material was used without further purification.

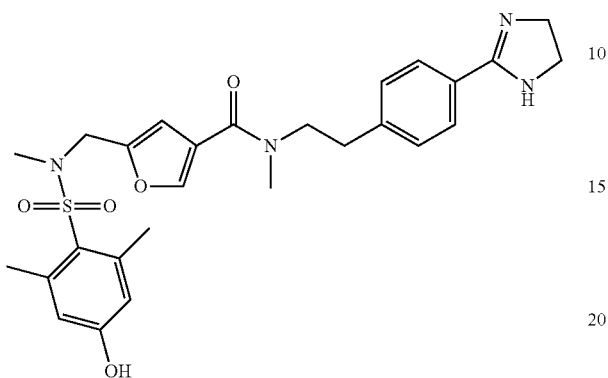

N-{2-[4-(4,5-Dihydro-1H-imidazol-2-yl)phenyl]ethyl}-5-({[(4-hydroxy-2,6-dimethylphenyl)sulfonyl](methyl)amino}methyl)-N-methylfuran-3-carboxamide, trifluoroacetate Ex 87

The title compound was prepared according to general procedure AI using 5-({[(4-hydroxy-2,6-dimethylphenyl)sulfonyl](methyl)amino}methyl)furan-3-carboxylic acid (100 mg, 0.29 mmol), DIPEA (0.2 mL, 1.2 mmol), DMF (8 mL) and EDCI (61 mg, 0.32 mmol), HOBt (43 mg, 0.32 mmol) and 2-[4-(4,5-dihydro-1H-imidazol-2-yl)phenyl]-N-methylethanamine (73 mg, 0.27 mmol). The resulting crude product was purified using prep method C to afford the title compound as a TFA salt.

Yield: 6 mg, 4%.

LCMS Method C: rt 3.26 min, 93%; m/z 525.31 (M+H⁺, 100%).

Potency: B

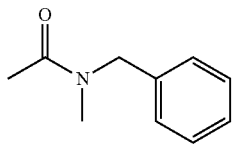

N-Benzyl-N-methylacetamide

Int 113

A solution of N-methyl benzylamine (5.0 g, 40 mmol) and TEA (6.3 mL, 45 mmol), under a N₂ atmosphere, in DCM (20 mL) was cooled to 0° C. before dropwise addition of acetyl chloride (3.2 mL, 45 mmol). The reaction mixture was allowed to warm to ambient temperature overnight. The mixture was diluted with DCM and washed with water (50 mL). The organics were dried (Na₂SO₄) and concentrated in vacuo. The crude material was used without further purification.

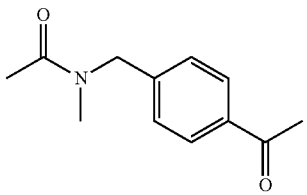

N-(4-Acetylbenzyl)-N-methylacetamide

Int 114

A solution of N-benzyl-N-methylacetamide (1.0 g, 6.13 mmol) and acetyl chloride (0.5 mL, 6.74 mmol), in DCM (10 mL), under a N₂ atmosphere, was cooled to 0° C. before AlCl₃ (900 mg, 6.74 mmol) was added. Once the addition was complete the mixture was stirred at ambient temperature for 18 h. More AlCl₃ (900 mg, 6.74 mmol) was added portionwise over 30 min and the mixture was stirred at ambient temperature for 18 h. The mixture was quenched onto ice and diluted with DCM. The phases were separated and the organics were dried (Na₂SO₄) and concentrated in vacuo to give a red oil, which was purified by prep method A to afford the title compound as a red oil.

Yield: 1.03 g, 80%.

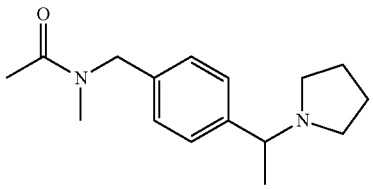 [SMILES: CC(=O)N(C)Cc1ccc(C(C)N2CCCC2)cc1]

N-Methyl-N-{4-[1-(pyrrolidin-1-yl)ethyl]benzyl}acetamide trifluoroacetate

Int 115

N-(4-acetylbenzyl)-N-methylacetamide (0.5 g, 2.44 mmol) in MeOH (10 mL), under a N₂ atmosphere, was treated with pyrrolidine (2 mL, 24.4 mmol) and hydrochloric acid (1 M, 1 drop). This mixture was stirred at ambient temperature for 1 h before addition of sodium cyanoborohydride (230 mg, 3.66 mmol). The mixture was stirred at ambient temperature for 16 h. The reaction was quenched by the addition of water and evaporated under vacuum. The residue was diluted with DCM dried (Na₂SO₄) and evaporated under vacuum to give a deep red oil. The oil was purified using prep method A to afford the title compound as a red oil.

Yield: 100 mg, 16%.

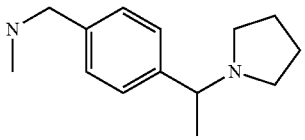 [SMILES: CNCc1ccc(C(C)N2CCCC2)cc1]

N-Methyl-1-{4-[1-(pyrrolidin-1-yl)ethyl]phenyl}methanamine

Int 116

Thionyl chloride (0.03 mL, 0.76 mmol) was added dropwise to methanol (1 mL) at 0° C. and the mixture was allowed to warm to ambient temperature before N-methyl-N-{4-[1-(pyrrolidin-1-yl)ethyl]benzyl}acetamide (100 mg, 0.38 mmol) was added. This mixture was stirred at ambient temperature for 2 h and at 60° C. for 16 h. More thionyl chloride (0.03 mL, 0.76 mmol) was added and the mixture was stirred at 60° C. for 3 h. Hydrochloric acid (6 M, 2 mL) was added and the heating was continued. During the heating the reaction boiled dry, analysis indicated the reaction was complete. The crude hydrochloride salt was used without purification.

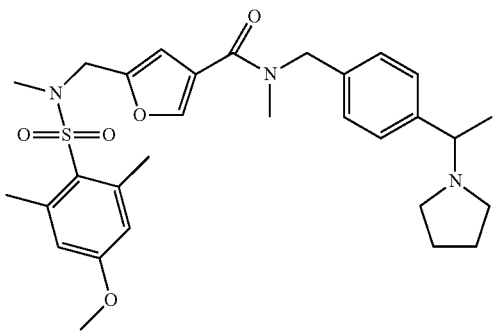 [SMILES: COc1cc(C)c(S(=O)(=O)N(C)Cc2cc(C(=O)N(C)Cc3ccc(C(C)N4CCCC4)cc3)co2)c(C)c1]

5-({[(4-Methoxy-2,6-dimethylphenyl)sulfonyl](methyl)amino}methyl)-N-methyl-N-[4-(1-pyrrolidin-1-ylethyl)benzyl]furan-3-carboxamide trifluoroacetate Ex 88

The title compound was prepared according to general procedure AI using 5-({[(4-methoxy-2,6-dimethylphenyl)sulfonyl](methyl)amino}methyl)furan-3-carboxylic acid (133 mg, 0.37 mmol), DIPEA (0.4 mL, 2.4 mmol), DMF (8 mL) and EDCI (85 mg, 0.44 mmol), HOBt (60 mg, 0.44 mmol) and N-methyl-1-{4-[1-(pyrrolidin-1-yl)ethyl]phenyl}methanamine hydrochloride (100 mg, 0.34 mmol). The resulting crude product was purified by prep method C to afford the title compound as a TFA salt.

Yield: 46 mg, 20%.
LCMS Method C: rt 3.22 min, 100%; m/z 554.50 (M+H$^+$, 100%).
Potency: A

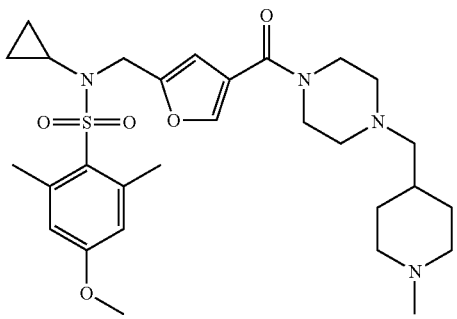 [SMILES: COc1cc(C)c(S(=O)(=O)N(Cc2cc(C(=O)N3CCN(CC4CCN(C)CC4)CC3)co2)C2CC2)c(C)c1]

N-Cyclopropyl-4-methoxy-2,6-dimethyl-N-{[4-({4-[(1-methylpiperidin-4-yl)methyl]piperazin-1-yl}carbonyl)furan-2-yl]methyl}benzenesulfonamide Ex 89

The title compound was prepared according to general procedure AM using 5-({cyclopropyl[(4-methoxy-2,6 dim-ethylphenyl)sulfonyl]amino}methyl)furan-3-carboxylic acid (126 mg, 0.33 mmol), 1-[(1-methylpiperidin-4-yl)methyl]piperazine (59 mg, 0.30 mmol), DIC (79 µL, 0.5 mmol) and HOBt monohydrate (76 mg, 0.5 mmol) in DCM (2.5 mL). The crude product was purified by FCC eluting with 95:5 DCM:7N NH$_3$ in MeOH.

Yield: 138 mg, 74%.
LCMS method C: rt 2.89 min, 100%; m/z 559.55 (MH$^+$, 100%).
Potency: C

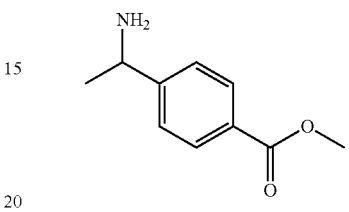

Methyl 4-(1-aminoethyl)benzoate

Int 117

Methyl 4-acetylbenzoate (1.07 g, 6 mmol), methylamine (33% in EtOH, 4.5 mL), methylamine hydrochloride (1.62 g, 24.0 mmol) and sodium cyanoborohydride (0.56 g, 9.0 mmol) were dissolved in a mixture of THF (12 mL) and Methanol (7 mL) and the reaction stirred at 65° C. for 16 h. The reaction was concentrated in vacuo and the residue redissolved in DCM (20 mL) and washed with water (20 mL). The organic phase was dried over Na$_2$SO$_4$ and concentrated in vacuo to afford the title compound, which was used without further purification.

Yield: 0.86 g, 75%
LCMS method B: rt 0.98 min, 89%; m/z 194.05 (MH$^+$, 100%).

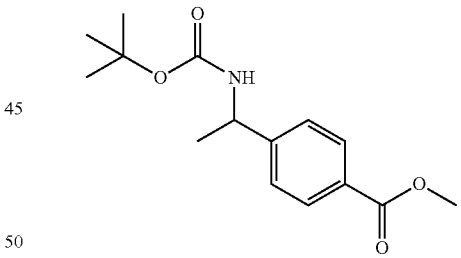

Methyl 4-{1-[(tert-butoxycarbonyl)amino]ethyl}benzoate

Int 118

Methyl 4-(1-aminoethyl)benzoate (0.86 g, 4.5 mmol), di-tert-butyl-dicarbonate (1.07 g, 4.91 mmol) and DIPEA were dissolved in DCM (8 mL) prior to addition of DMAP (60 mg, 0.45 mmol). The reaction was stirred at ambient temperature for 16 h, diluted with DCM (10 mL) and washed with aqueous citric acid solution (10% w/v, 20 mL) and saturated aqueous NaHCO$_3$ solution (20 mL). The organic phase was dried over Na$_2$SO$_4$ and concentrated in vacuo to afford the title compound, which was used without further purification.

Yield: 1.14 g, 86%

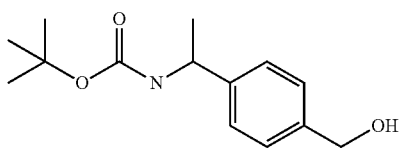 [SMILES: CC(NC(=O)OC(C)(C)C)c1ccc(CO)cc1]

tert-Butyl {1-[4-(hydroxymethyl)phenyl]ethyl}carbamate

Int 119

Methyl 4-{1-[(tert-butoxycarbonyl)amino]ethyl}benzoate (1.14 g, 3.9 mmol) was dissolved in THF (8 mL) and the solution cooled to <−5° C. in an ice/salt bath. LiAlH₄ (1M in THF, 2.1 mL) was added dropwise over 15 min. Upon completion of addition, the reaction was stirred at 0° C. for 75 min. Water (0.16 mL) was added dropwise followed by 2 M aqueous NaOH solution (0.16 mL) and then water (0.16 mL). The suspension was stirred for 15 min and then diluted with EtOAc (15 mL). The mixture was dried over Na₂SO₄ and filtered and the resulting filtrated concentrated in vacuo to afford the title compound, which was used without further purification.

Yield: 0.92 g, 89%.

LCMS method B: rt 1.87 min, 71%; m/z 210.05 ([M-tBu+H]⁺, 100%).

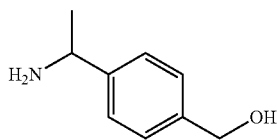

[4-(1-Aminoethyl)phenyl]methanol

Int 120

Tert-butyl {1-[4-(hydroxymethyl)phenyl]ethyl}carbamate (0.45 g, 1.7 mmol), TFA (1.7 mL) and DCM (5 mL) were stirred at ambient temperature for 1 h. The reaction was diluted with DCM (10 mL), washed with saturated aqueous NaHCO₃ solution (2×10 mL) and dried over Na₂SO₄. The solvent was removed in vacuo to afford the title compound.

Yield: 0.30 g, 100%.

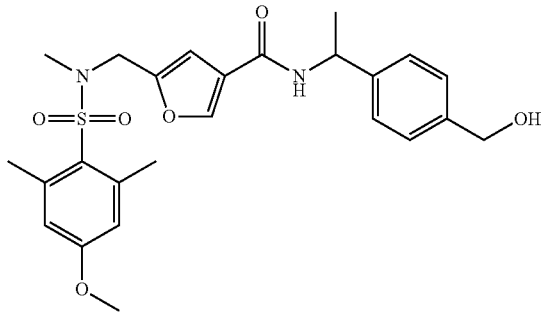 [SMILES: COc1cc(C)c(S(=O)(=O)N(C)Cc2cc(C(=O)NC(C)c3ccc(CO)cc3)co2)c(C)c1]

N-{1-[4-(Hydroxymethyl)phenyl]ethyl}-5-({[(4-methoxy-2,6-dimethylphenyl)sulfonyl](methyl)amino}methyl)furan-3-carboxamide Int 121

The title compound was prepared according to general procedure AI using 5-({[(4-methoxy-2,6-dimethylphenyl)sulfonyl](methyl)amino}methyl)furan-3-carboxylic acid (110 mg, 0.32 mmol), EDCI (78 mg, 0.40 mmol), HOBt monohydrate (61 mg, 0.4 mmol), DIPEA (70 μL, 0.4 mmol), [4-(1-aminoethyl)phenyl]methanol (77 mg, 0.50 mmol) and DMF (2 mL). Following work-up, the title compound was used directly in the next step without any further purification.

Yield: 0.14 g, 90%.

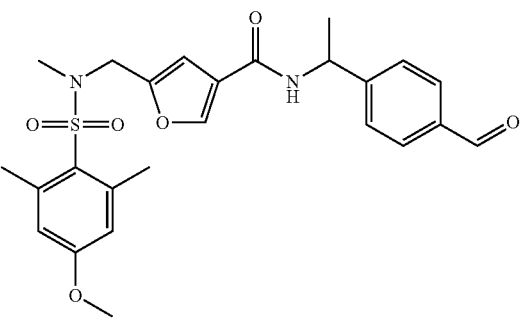 [SMILES: COc1cc(C)c(S(=O)(=O)N(C)Cc2cc(C(=O)NC(C)c3ccc(C=O)cc3)co2)c(C)c1]

N-[1-(4-Formylphenyl)ethyl]-5-({[(4-methoxy-2,6-dimethylphenyl)sulfonyl](methyl)amino}methyl)furan-3-carboxamide Int 122

N-{1-[4-(hydroxymethyl)phenyl]ethyl}-5-({[(4-methoxy-2,6-dimethylphenyl)sulfonyl](methyl)amino}methyl)furan-3-carboxamide (0.14 g, 0.29 mmol) was dissolved in DCM (1.5 mL) and Dess-Martin periodinane (0.14 g, 0.33 mmol) was added in one portion. The reaction was stirred at ambient temperature for 3 d and diluted with DCM (3 mL) and washed with saturated aqueous NaHCO₃ solution (5 mL). The organic phase was dried over Na₂SO₄ and the solvent removed in vacuo to afford the title compound.

Yield: 0.14 g, 100%

LCMS method B: rt 2.09 min, 91%; m/z 507.40 (M+Na⁺, 100%).

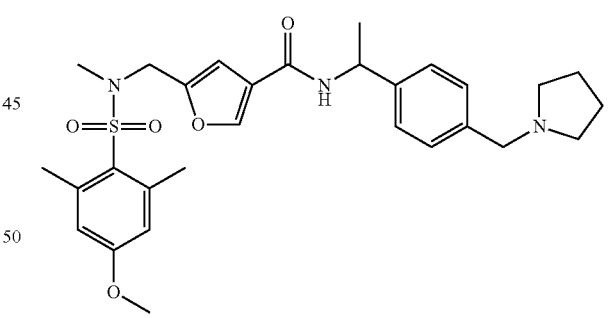

5-({[(4-Methoxy-2,6-dimethylphenyl)sulfonyl](methyl)amino}methyl)-N-{1-[4-(pyrrolidin-1-ylmethyl)phenyl]ethyl}furan-3-carboxamide Ex 90

The title compound was prepared according to general procedure BF using N-[1-(4-formylphenyl)ethyl]-5-({[(4-methoxy-2,6-dimethylphenyl)sulfonyl](methyl)amino}methyl)furan-3-carboxamide (39 mg, 0.08 mmol), pyrrolidine (6.8 mg, 0.1 mmol), AcOH (7 mg, 0.12 mmol), STAB (34 mg, 0.16 mmol) and DCE (1 mL). The reaction was diluted with DCM (1 mL) and washed with saturated aqueous NaHCO₃ solution (5 mL). The organic phase was dried over Na₂SO₄ and the solvent removed in vacuo. The crude product was purified by FCC eluting with 2-10% MeOH in DCM to afford the title compound.
Yield: 14.3 mg, 33%
LCMS method C: rt 3.29 min, 100%; m/z 540.55 (M+H⁺, 100%).
Potency: A

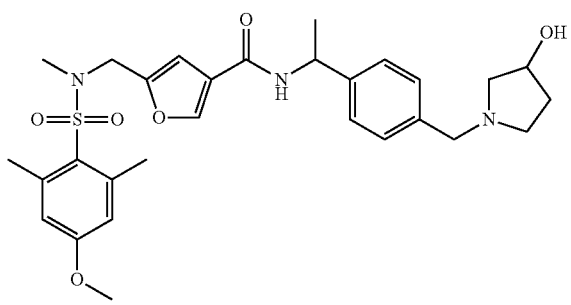 [SMILES: COc1cc(C)c(S(=O)(=O)N(C)Cc2cc(C(=O)NC(C)c3ccc(CN4CCC(O)C4)cc3)co2)c(C)c1]

N-(1-{4-[(3-Hydroxypyrrolidin-1-yl)methyl] phenyl}ethyl)-5-({[(4-methoxy-2,6-dimethylphenyl) sulfonyl](methyl)amino}methyl)furan-3-carboxamide Ex 91

The title compound was prepared according to general procedure BF using N-[1-(4-formylphenyl)ethyl]-5-({[(4-methoxy-2,6-dimethylphenyl)sulfonyl](methyl) amino}methyl)furan-3-carboxamide (39 mg, 0.08 mmol), 3-hydroxypyrrolidine (8.7 mg, 0.1 mmol), AcOH (7 mg, 0.12 mmol), STAB (34 mg, 0.16 mmol) and DCE (1 mL). The reaction was diluted with DCM (1 mL) and washed with saturated aqueous NaHCO₃ solution (5 mL). The organic phase was dried over Na₂SO₄ and the solvent removed in vacuo. The crude product was purified by FCC eluting with 2-10% MeOH in DCM to afford the title compound.
Yield: 19.5 mg, 43%
LCMS method C: rt 3.26 min, 98%; m/z 556.50 (M+H⁺, 100%).
Potency: A

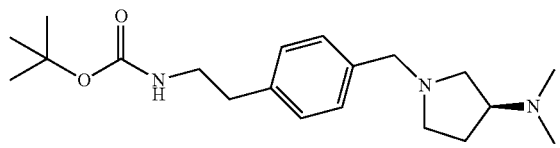 [SMILES: CN(C)[C@H]1CCN(Cc2ccc(CCNC(=O)OC(C)(C)C)cc2)C1]

tert-Butyl[2-(4-{[(3S)-3-(dimethylamino)pyrrolidin-1-yl]methyl}phenyl)ethyl]carbamate Int 123

The title compound was prepared according to general procedure AO using tert-butyl[2-(4-formylphenyl)ethyl]carbamate (60 mg, 0.229 mmol) and (3S)-(−)-3-(dimethylamino)pyrrolidine (0.053 mg, 0.457 mmol), Pd/C (10 mg, cat) and EtOH (2 mL) under a H₂ atmosphere. The crude residue was purified by FCC eluting with 95:4.5:0.5 DCM/MeOH/NH₃
Yield: 52 mg, 66%.

¹H NMR (250 MHz, CD₃OD) δ ppm 7.08-7.28 (4H, m), 3.45-3.64 (2H, m), 3.25-3.29 (1H, m), 3.14-3.25 (2H, m), 2.63-2.91 (5H, m), 2.39-2.55 (1H, m), 2.20-2.33 (1H, m), 2.16 (6H, s), 1.88-2.05 (1H, m), 1.59-1.77 (1H, m), 1.38 (9H, s)

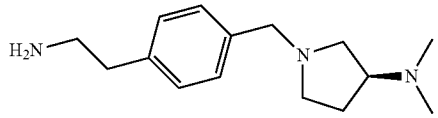 [SMILES: CN(C)[C@H]1CCN(Cc2ccc(CCN)cc2)C1]

(3S)-1-[4-(2-Aminoethyl)benzyl]-N,N-dimethylpyrrolidin-3-amine, trihydrochloride Int 124

The title compound was prepared according to general procedure AS, using tert-butyl[2-(4-{[(3S)-3-(dimethylamino)pyrrolidin-1-yl]methyl}phenyl)ethyl]carbamate (52 mg, 0.15 mmol), thionyl chloride (0.05 mL, 0.75 mmol) and MeOH (2 mL).
Yield: 57 mg, 100%

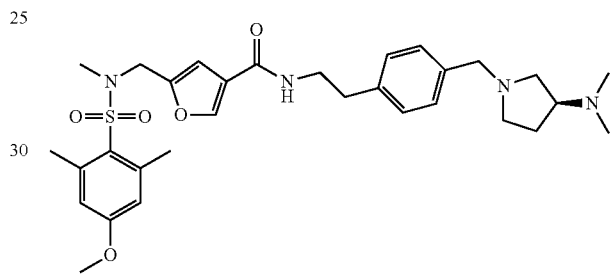

N-[2-(4-{[(3S)-3-(Dimethylamino)pyrrolidin-1-yl] methyl}phenyl)ethyl]-5-({[(4-methoxy-2,6-dimethylphenyl)sulfonyl](methyl)amino}methyl)furan-3-carboxamide, trifluoroacetate Ex 92

The title compound was prepared according to general procedure AA using 5-({[(4-Methoxy-2,6-dimethylphenyl)sulfonyl](methyl)amino}methyl)furan-3-carboxylic acid (60 mg, 0.15 mmol), CDI (46 mg, 0.275 mmol), (3S)-1-[4-(2-aminoethyl)benzyl]-N,N-dimethylpyrrolidin-3-amine trihydrochloride (57 mg, 0.15 mmol) and DCE (1.5 mL). A portion of the crude product was purified using prep method C
LCMS Method C: rt 2.89 min, 100%; m/z 199.15 (ArSO₂⁺, 100%), 342.30 ([M-ArSO₂N(CH3)CH2+2H]⁺, 76%), 583.43 (MH⁺, 71%)
Potency: A

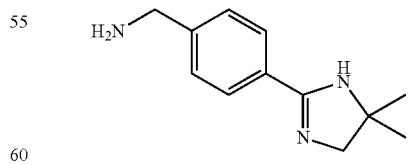

1-[4-(5,5-Dimethyl-4,5-dihydro-1H-imidazol-2-yl) phenyl]methanamine, dihydrochloride Int 125

The title compound was prepared according to general procedure AS using tert-butyl[4-(5,5-dimethyl-4,5-dihydro- 1H-imidazol-2-yl)benzyl]carbamate (200 mg, 0.659 mmol), thionyl chloride (0.23 mL, 3.15 mmol) and MeOH (2.0 mL).

Yield: 44 mg, 100%.

¹H NMR (500 MHz, CD₃OD) δ ppm 7.95 (2H, d, J=8.3 Hz), 7.73 (2H, d, J=8.3 Hz), 4.24 (2H, s), 3.85 (2H, s), 1.53 (6H, s)

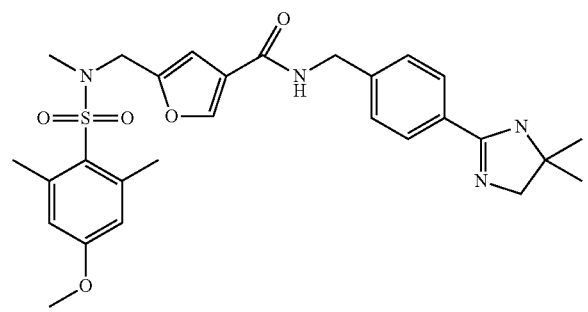

N-[4-(5,5-Dimethyl-4,5-dihydro-1H-imidazol-2-yl)benzyl]-5-({[(4-methoxy-2,6-dimethylphenyl)sulfonyl](methyl)amino}methyl)furan-3-carboxamide trifluoroacetate Ex 93

The title compound was prepared according to general procedure AA using 5-({[(4-Methoxy-2,6-dimethylphenyl)sulfonyl](methyl)amino}methyl)furan-3-carboxylic acid (60 mg, 0.15 mmol), CDI (51 mg, 0.31 mmol), 1-[4-(5,5-dimethyl-4,5-dihydro-1H-imidazol-2-yl)phenyl]methanamine dihydrochloride (44 mg, 0.15 mmol) and DCE (1.5 mL). A portion of the crude product was purified using prep method A LCMS Method C: rt 3.39 min, 97%; m/z 539.41 (MH⁺, 100%)

Potency: B

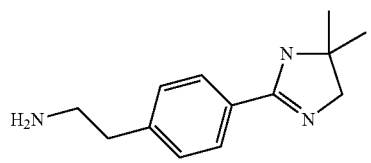 [SMILES: CC1(C)CN=C(c2ccc(CCN)cc2)N1]

2-[4-(5,5-Dimethyl-4,5-dihydro-1H-imidazol-2-yl)phenyl]ethanamine, dihydrochloride Int 126

The title compound was prepared according to general procedure AS using tert-butyl {2-[4-(5,5-dimethyl-4,5-dihydro-1H-imidazol-2-yl)phenyl]ethyl}carbamate (200 mg, 0.63 mmol), thionyl chloride (0.23 mL, 3.15 mmol) and MeOH (2.0 mL).

Yield: 47 mg, 100%.

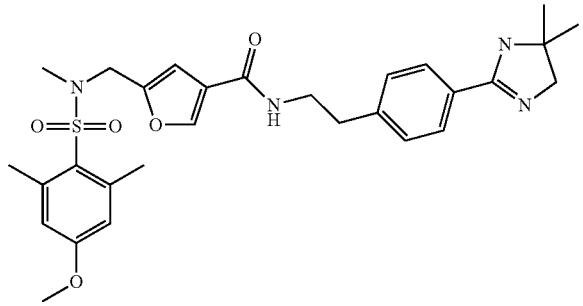

N-{2-[4-(5,5-Dimethyl-4,5-dihydro-1H-imidazol-2-yl)phenyl]ethyl}-5-({[(4-methoxy-2,6-dimethylphenyl)sulfonyl](methyl)amino}methyl)furan-3-carboxamide trifluoroacetate Ex 94

The title compound was prepared according to general procedure AA using 5-({[(4-Methoxy-2,6-dimethylphenyl)sulfonyl](methyl)amino}methyl)furan-3-carboxylic acid (60 mg, 0.15 mmol), CDI (51 mg, 0.31 mmol) and 2-[4-(5,5-dimethyl-4,5-dihydro-1H-imidazol-2-yl)phenyl]ethanamine dihydrochloride (47 mg, 0.15 mmol) in DCE (1.5 mL). A portion of the crude product was purified using prep method A.

LCMS Method C: rt 3.40 min, 98%; m/z 553.43 (MH⁺, 100%)

Potency: C

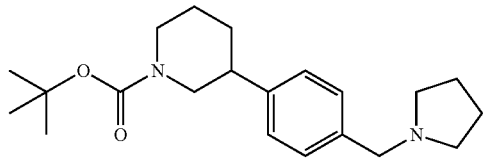 [SMILES: CC(C)(C)OC(=O)N1CCCC(c2ccc(CN3CCCC3)cc2)C1]

tert-Butyl 3-[4-(pyrrolidin-1-ylmethyl)phenyl]piperidine-1-carboxylate

Int 127

The title compound was prepared according to general procedure AO using tert-butyl 3-(4-formylphenyl)piperidine-1-carboxylate (75 mg, 0.25 mmol) and Pyrrolidine (0.06 mL, 0.74 mmol) in EtOH (2 mL). The crude residue was purified by FCC eluting with 10-30% EtOAc in heptane.

Yield: 38 mg, 44%.

LCMS Method A: rt 1.09 min, 99%; m/z 345.50 (MH⁺, 100%)

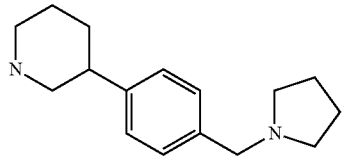 [SMILES: c1cc(C2CCCNC2)ccc1CN1CCCC1]

3-[4-(Pyrrolidin-1-ylmethyl)phenyl]piperidine, dihydrochloride

Int 128

The title compound was prepared according to general procedure AS using tert-butyl 3-[4-(pyrrolidin-1-ylmethyl)

phenyl]piperidine-1-carboxylate (38 mg, 0.11 mmol) and thionyl chloride (0.06 mL, 0.55 mmol) in MeOH (2.0 mL).

Yield: 35 mg, 100%.

$^1$H NMR (500 MHz, CD$_3$OD) δ ppm 7.55 (2H, d, J=7.7 Hz), 7.40 (2H, d, J=7.7 Hz), 4.36 (2

H, s), 3.34-3.50 (4H, m), 3.27 (1H, s), 2.98-3.21 (5H, m), 2.07-2.21 (2H, m), 1.74-2.07 (6H, m)

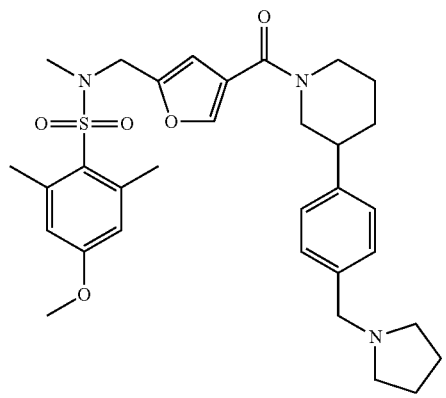 [SMILES: COc1cc(C)c(S(=O)(=O)N(C)Cc2cc(C(=O)N3CCCC(c4ccc(CN5CCCC5)cc4)C3)co2)c(C)c1]

4-Methoxy-N,2,6-trimethyl-N-{[4-({3-[4-(pyrrolidin-1-ylmethyl)phenyl]piperidin-1-yl}carbonyl)furan-2-yl]methyl}benzenesulfonamide trifluoroacetamide Ex 95

The title compound was prepared according to general procedure AA using 5-({[(4-Methoxy-2,6-dimethylphenyl)sulfonyl](methyl)amino}methyl)furan-3-carboxylic acid (60 mg, 0.15 mmol), CDI (51 mg, 0.31 mmol) and bis HCl 3-[4-(pyrrolidin-1-ylmethyl)phenyl]piperidine (46 mg, 0.14 mmol) in DCE (1.5 mL). A portion of the crude product was purified using prep method C LCMS Method C: rt 3.43 min, 93%; m/z 580.47 (MH$^+$, 100%)

Potency: A

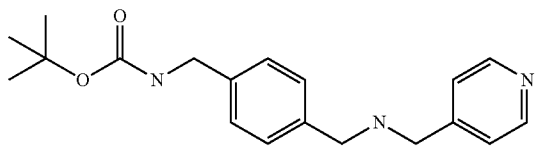 [SMILES: CC(C)(C)OC(=O)NCc1ccc(CNCc2ccncc2)cc1]

tert-Butyl (4-{[(pyridin-4-ylmethyl)amino]methyl}benzyl)carbamate

Int 129

The title compound was prepared according to general procedure AO using tert-butyl[2-(4-formylphenyl)ethyl]carbamate (65 mg, 0.26 mmol) and N-(4-pyridinylmethyl)amine (0.14 mg, 1.31 mmol), Pd/C (10 mg, cat) and EtOH (2 mL) under a H$_2$ atmosphere. A portion of the crude residue was purified by FCC eluting with 10-30% EtOAc in heptane.

Yield: 58 mg, 68%.

LCMS Method A: rt 0.84 min, 98%; m/z 342.30 (MH$^+$, 100%)

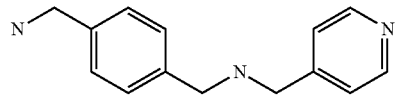 [SMILES: NCc1ccc(CNCc2ccncc2)cc1]

1-[4-(Aminomethyl)phenyl]-N-(pyridin-4-ylmethyl)methanamine, trihydrochloride

Int 130

The title compound was prepared according to General Procedure AS, using tert-butyl (4-{[(pyridin-4-ylmethyl)amino]methyl}benzyl)carbamate (60 mg, 0.18 mmol), thionyl chloride (0.64 mL, 0.89 mmol) and MeOH (2 mL).

Yield: 60 mg, 100%

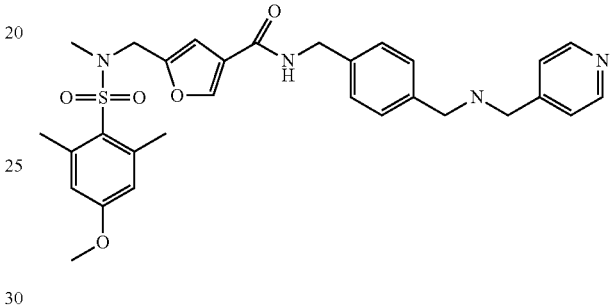

5-({[(4-Methoxy-2,6-dimethylphenyl)sulfonyl](methyl)amino}methyl)-N-(4-{[(pyridin-4-ylmethyl)amino]methyl}benzyl)furan-3-carboxamide trifluoroacetate Ex 96

The title compound was prepared according to general procedure AA using 5-({[(4-methoxy-2,6-dimethylphenyl)sulfonyl](methyl)amino}methyl)furan-3-carboxylic acid (60 mg, 0.15 mmol), CDI (51 mg, 0.306 mmol) and tris HCl 1-[4-(aminomethyl)phenyl]-N-(pyridin-4-ylmethyl)methanamine (49 mg, 0.14 mmol) in DCE (1.5 mL). A portion of the crude product was purified using prep method A LCMS Method C: rt 3.06 min, 98%; m/z 563.24 (MH$^+$, 100%)

$^1$H NMR (500 MHz, CD$_3$OD) δ ppm 8.74 (2H, d, J=6.2 Hz), 7.99 (1H, d, J=0.7 Hz), 7.73 (2H, d, J=6.2 Hz), 7.48 (2H, d, J=8.3 Hz), 7.44 (2H, d, J=8.3 Hz), 6.75 (2H, s), 6.69 (1H, s), 4.53 (2H, s), 4.42 (2H, s), 4.30-4.35 (4H, m), 3.82 (3H, s), 2.66 (3H, s), 2.60 (6H, s)

Potency: A

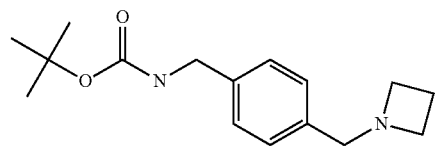 [SMILES: CC(C)(C)OC(=O)NCc1ccc(CN2CCC2)cc1]

tert-Butyl[4-(azetidin-1-ylmethyl)benzyl]carbamate

Int 131

The title compound was prepared according to general procedure AO using tert-butyl[2-(4-formylphenyl)ethyl]carbamate (65 mg, 0.26 mmol), azetidine hydrochloride (0.13 mg, 1.31 mmol), TEA (0.37 mL, 2.62 mmol), Pd/C (10 mg, cat) and EtOH (2 mL) under a $H_2$ atmosphere. The crude residue was purified by FCC eluting with 10-30% EtOAc in heptane.

Yield: 71 mg, 98%.

LCMS Method A: rt 0.92 min, 100%; m/z 277.05 (MH+, 100%)

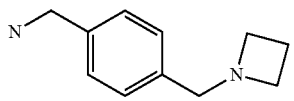 [SMILES: NCc1ccc(CN2CCC2)cc1]

1-[4-(Azetidin-1-ylmethyl)phenyl]methanamine, dihydrochloride

Int 132

The title compound was prepared according to general procedure AS using tert-butyl[4-(azetidin-1-ylmethyl)benzyl]carbamate (71 mg, 0.26 mmol), thionyl chloride (0.64 mL, 0.89 mmol) and MeOH (2 mL).

Yield: 64 mg, 100%.

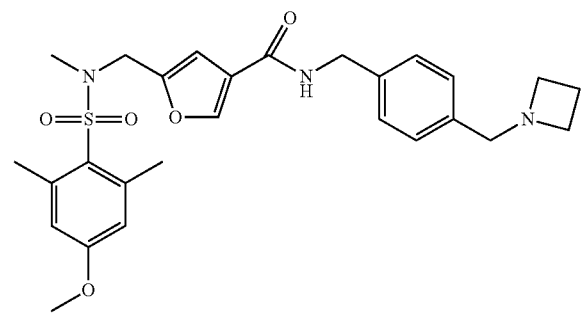 [SMILES: COc1cc(C)c(S(=O)(=O)N(C)Cc2cc(C(=O)NCc3ccc(CN4CCC4)cc3)co2)c(C)c1]

N-[4-(Azetidin-1-ylmethyl)benzyl]-5-({[(4-methoxy-2,6-dimethylphenyl)sulfonyl](methyl)amino}methyl)furan-3-carboxamide trifluoroacetate Ex 97

The title compound was prepared according to general procedure AA using 5-({[(4-methoxy-2,6-dimethylphenyl)sulfonyl](methyl)amino}methyl)furan-3-carboxylic acid (60 mg, 0.15 mmol), CDI (51 mg, 0.31 mmol) and 1-[4-(azetidin-1-ylmethyl)phenyl]methanamine dihydrochloride (36 mg, 0.14 mmol) in DCE (1.5 mL). A portion of the crude product was purified using prep method A LCMS Method C: rt 3.22 min, 98%; m/z 512.25 (MH+, 100%)

$^1$H NMR (500 MHz, $CD_3OD$) δ ppm 7.99 (1H, s), 7.39-7.47 (4H, m), 6.76 (2H, s), 6.69 (1H, s), 4.52 (2H, s), 4.33 (4H, d, J=3.1 Hz), 4.13-4.21 (2H, m), 4.03-4.11 (2H, m), 3.83 (3H, s), 2.67 (3H, s), 2.60 (6H, s), 2.49-2.59 (1H, m), 2.38-2.49 (1H, m)

Potency: B

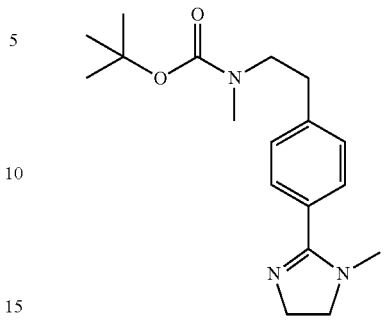

tert-Butyl methyl{2-[4-(1-methyl-4,5-dihydro-1H-imidazol-2-yl)phenyl]ethyl}carbamate trifluoroacetamide Int 133

To a stirred solution of tert-butyl {2-[4-(4,5-dihydro-1H-imidazol-2-yl)phenyl]ethyl}methylcarbamate (200 mg, 0.66 mmol) in anhydrous THF (2.0 mL) was added NaH (60%, 29 mg, 0.72 mmol). After 30 min methyl iodide (0.041 mL, 0.659 mmol) was added and the reaction stirred at ambient temperature for 3 days. The crude product was purified using prep method C Yield: 21 mg, 10%

LCMS Method C: rt 2.81 min, 100%; m/z 318.15 (MH+, 100%)

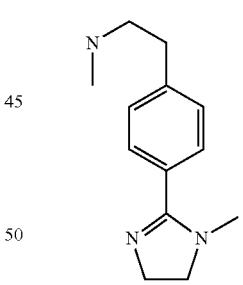

N-Methyl-2-[4-(1-methyl-4,5-dihydro-1H-imidazol-2-yl)phenyl]ethanamine, dihydrochloride Int 134

The title compound was prepared according to general procedure AS using tert-butyl methyl{2-[4-(1-methyl-4,5-dihydro-1H-imidazol-2-yl)phenyl]ethyl}carbamate (21 mg, 0.07 mmol) and thionyl chloride (0.03 mL, 0.46 mmol) in MeOH (2.0 mL).

Yield: 20 mg, 98%

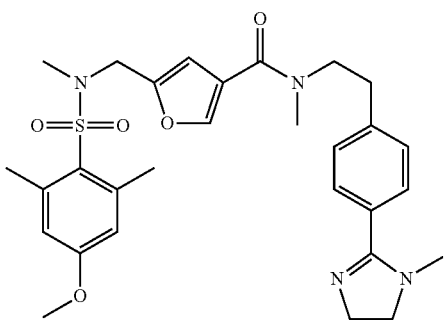

5-({[(4-Methoxy-2,6-dimethylphenyl)sulfonyl](methyl)amino}methyl)-N-methyl-N-{2-[4-(1-methyl-4,5-dihydro-1H-imidazol-2-yl)phenyl]ethyl}furan-3-carboxamide trifluoroacetamide Ex 98

The title compound was prepared according to general procedure AA using 5-({methyl[(4-methoxy-2,6-dimethylphenyl)sulfonyl]amino}methyl)furan-3-carboxylic acid (50 mg, 0.13 mmol), CDI (42 mg, 0.26 mmol), N-methyl-2-[4-(1-methyl-4,5-dihydro-1H-imidazol-2-yl)phenyl]ethanamine dihydrochloride (20 mg, 0.06 mmol), DIPEA (0.11 mL, 0.64 mmol) and DCE (1.5 mL). A portion of the crude product was purified using prep method C LCMS Method C: rt 3.20 min, 100%; m/z 553.60 (MH+, 100%)

Potency: A

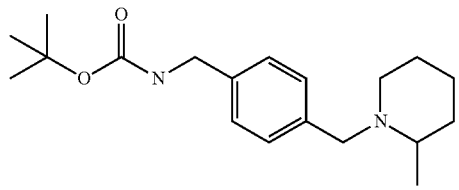 [SMILES: CC1CCCCN1Cc1ccc(CNC(=O)OC(C)(C)C)cc1]

tert-Butyl {4-[(2-methylpiperidin-1-yl)methyl]benzyl}carbamate

Int 135

The title compound was prepared according to general procedure AO using tert-butyl[2-(4-formylphenyl)ethyl]carbamate (65 mg, 0.26 mmol) and 2-methylpiperidine (0.16 mL, 1.31 mmol), Pd/C (10 mg, cat) and EtOH (2 mL) under a H$_2$ atmosphere. The crude residue was purified by FCC eluting with 20-40% EtOAc in Heptane.

Yield: 48 mg, 58%.

LCMS Method A: rt 1.00 min, 88%; m/z 319.15 (MH+, 100%)

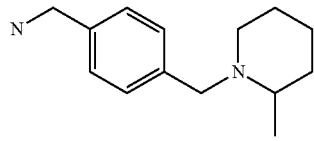 [SMILES: CC1CCCCN1Cc1ccc(CN)cc1]

1-{4-[(2-Methylpiperidin-1-yl)methyl]phenyl}methanamine, dihydrochloride

Int 136

The title compound was prepared according to general procedure AS using tert-butyl {4-[(2-methylpiperidin-1-yl) methyl]benzyl}carbamate (48 mg, 0.15 mmol), thionyl chloride (0.03 mL, 0.46 mmol) and MeOH (2.0 mL).

Yield: 41.2 mg, 88%

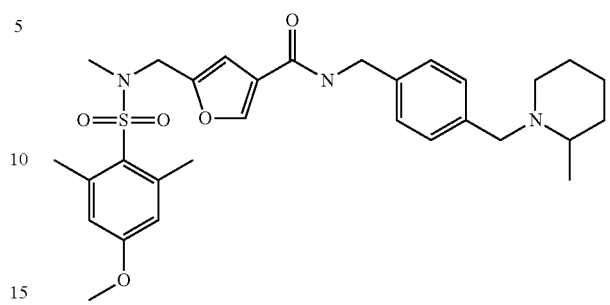

5-({[(4-Methoxy-2,6-dimethylphenyl)sulfonyl](methyl)amino}methyl)-N-{4-[(2-methylpiperidin-1-yl)methyl]benzyl}furan-3-carboxamide trifluoroacetate Ex 99

The title compound was prepared according to general procedure AA using 5-({methyl[(4-methoxy-2,6-dimethylphenyl)sulfonyl]amino}methyl)furan-3-carboxylic acid (50 mg, 0.13 mmol), CDI (42 mg, 0.26 mmol), 1-{4-[(2-methylpiperidin-1-yl)methyl]phenyl}methanamine dihydrochloride (41 mg, 0.13 mmol), DIPEA (0.11 mL, 0.64 mmol) and DCE (1.5 mL). A portion of the crude product was purified using prep method A LCMS Method C: rt 3.25 min, 100%; m/z 554.56 (MH+, 100%)

Potency: A

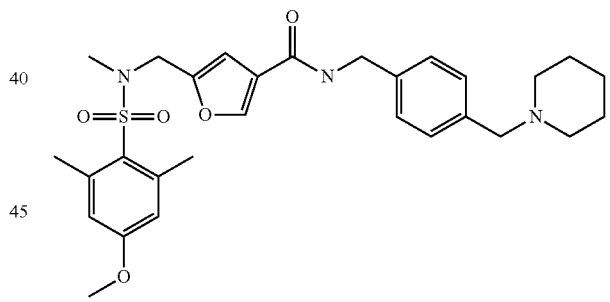

5-({[(4-Methoxy-2,6-dimethylphenyl)sulfonyl](methyl)amino}methyl)-N-[4-(piperidin-1-ylmethyl)benzyl]furan-3-carboxamide trifluoroacetate Ex 100

The title compound was prepared according to general procedure AA using 5-({methyl[(4-methoxy-2,6-dimethylphenyl)sulfonyl]amino}methyl)furan-3-carboxylic acid (60 mg, 0.15 mmol), CDI (51 mg, 0.31 mmol), 1-[4-(piperidin-1-ylmethyl)phenyl]methanamine (32 mg, 0.15 mmol) and DCE (1.5 mL). The crude product was purified using prep method A Yield: 28 mg, 35%.

LCMS Method C: rt 3.20 min, 100%; m/z 540.51 (MH+, 100%)

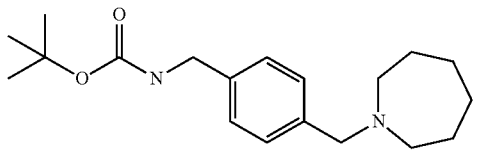 [SMILES: CC(C)(C)OC(=O)NCc1ccc(CN2CCCCCC2)cc1]

tert-Butyl[4-(azepan-1-ylmethyl)benzyl]carbamate

Int 137

The title compound was prepared according to general procedure AO using tert-butyl[2-(4-formylphenyl)ethyl]carbamate (65 mg, 0.26 mmol) and hexamethyleneimine (13 mg, 1.31 mmol), Pd/C (10 mg, cat) and EtOH (2 mL) under a $H_2$ atmosphere. The crude residue was purified by FCC eluting with 10-33% EtOAc in heptane.

Yield: 67 mg, 80%.

LCMS Method A: rt 1.00 min, 94%; m/z 319.15 (MH$^+$, 100%)

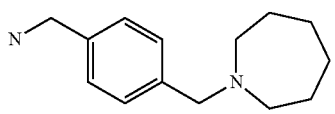 [SMILES: NCc1ccc(CN2CCCCCC2)cc1]

1-[4-(Azepan-1-ylmethyl)phenyl]methanamine, dihydrochloride

Int 138

The title compound was prepared according to general procedure AS using tert-butyl[4-(azepan-1-ylmethyl)benzyl]carbamate (67 mg, 0.20 mmol), thionyl chloride (0.06 mL, 0.89 mmol) and MeOH (2.0 mL).

Yield: 58 mg, 100%

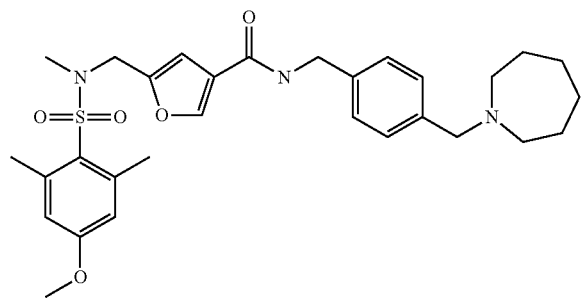 [SMILES: COc1cc(C)c(S(=O)(=O)N(C)Cc2cc(C(=O)NCc3ccc(CN4CCCCCC4)cc3)co2)c(C)c1]

N-[4-(Azepan-1-ylmethyl)benzyl]-5-({[(4-methoxy-2,6-dimethylphenyl)sulfonyl](methyl)amino}methyl)furan-3-carboxamide trifluoroacetate Ex 101

The title compound was prepared according to general procedure AA using 5-({methyl[(4-methoxy-2,6-dimethylphenyl)sulfonyl]amino}methyl)furan-3-carboxylic acid (60 mg, 0.15 mmol), CDI (51 mg, 0.31 mmol), 1-[4-(azepan-1-ylmethyl)phenyl]methanamine dihydrochloride (47 mg, 0.15 mmol), DIPEA (0.13 mL, 0.76 mmol) and DCE (1.5 mL).

The crude product was purified using prep method A

Yield: 22 mg, 26%.

LCMS Method C: rt 3.27 min, 100%; m/z 554.56 (MH$^+$, 100%)

Potency: A

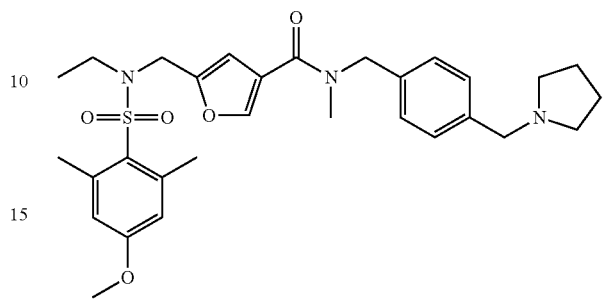

5-({Ethyl[(4-methoxy-2,6-dimethylphenyl)sulfonyl]amino}methyl)-N-methyl-N-[4-(pyrrolidin-1-ylmethyl)benzyl]furan-3-carboxamide trifluoroacetate Ex 102

The title compound was prepared according to general procedure AA using 5-({Ethyl[(4-methoxy-2,6-dimethylphenyl)sulfonyl]amino}methyl)furan-3-carboxylic acid (53 mg, 0.13 mmol), CDI (43 mg, 0.26 mmol), N-methyl-1-[4-(pyrrolidin-1-ylmethyl)phenyl]methanamine (28 mg, 0.13 mmol), DIPEA (0.12 mL, 0.65 mmol) and DCE (1.5 mL). A portion of the crude product was purified using prep method A LCMS Method C: rt 3.36 min, 100%; m/z 554.40 (MH$^+$, 100%)

Potency: A

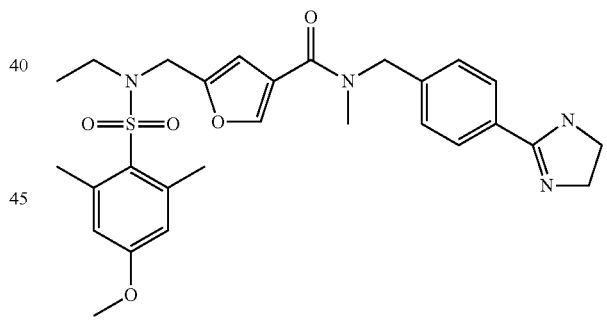

N-[4-(4,5-Dihydro-1H-imidazol-2-yl)benzyl]-5-({ethyl[(4-methoxy-2,6-dimethylphenyl)sulfonyl]amino}methyl)-N-methylfuran-3-carboxamide trifluoroacetate Ex 103

The title compound was prepared according to general procedure AA using 5-({ethyl[(4-methoxy-2,6-dimethylphenyl)sulfonyl]amino}methyl)furan-3-carboxylic acid (53 mg, 0.131 mmol), CDI (43 mg, 0.26 mmol), 1-[4-(4,5-dihydro-1H-imidazol-2-yl)phenyl]-N-methylmethanamine dihydrochloride (36 mg, 0.13 mmol), DIPEA (0.12 mL, 0.65 mmol) and DCE (1.5 mL). A portion of the crude product was purified using prep method A LCMS Method C: rt 3.28 min, 100%; m/z 539.36 (MH$^+$, 100%)

Potency: B

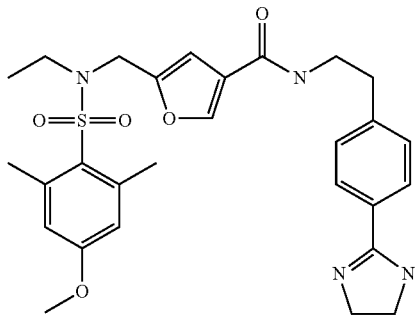 [SMILES: CCN(Cc1cc(C(=O)NCCc2ccc(C3=NCCN3)cc2)co1)S(=O)(=O)c1c(C)cc(OC)cc1C]

N-{2-[4-(4,5-Dihydro-1H-imidazol-2-yl)phenyl]ethyl}-5-({ethyl[(4-methoxy-2,6-dimethylphenyl)sulfonyl]amino}methyl)furan-3-carboxamide trifluoroacetate Ex 104

The title compound was prepared according to general procedure AA using 5-({ethyl[(4-methoxy-2,6-dimethylphenyl)sulfonyl]amino}methyl)furan-3-carboxylic acid (53 mg, 0.13 mmol), CDI (43 mg, 0.26 mmol), 2-[4-(4,5-dihydro-1H-imidazol-2-yl)phenyl]ethanamine dihydrochloride (57 mg, 0.13 mmol), DIPEA (0.12 mL, 0.65 mmol) and DCE (1.5 mL). A portion of the crude product was purified using prep method A LCMS Method C: rt 3.31 min, 97%; m/z 539.36 (MH+, 100%)

Potency: B

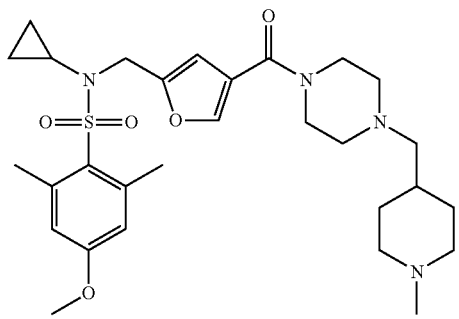 [SMILES: COc1cc(C)c(S(=O)(=O)N(Cc2cc(C(=O)N3CCN(CC4CCN(C)CC4)CC3)co2)C2CC2)c(C)c1]

N-Cyclopropyl-4-methoxy-2,6-dimethyl-N-{[4-({4-[(1-methylpiperidin-4-yl)methyl]piperazin-1-yl}carbonyl)furan-2-yl]methyl}benzenesulfonamide trifluoroacetate Ex 105

The title compound was prepared according to general procedure AA using 5-({cyclopropyl[(4-methoxy-2,6-dimethylphenyl)sulfonyl]amino}methyl)furan-3-carboxylic acid (60 mg, 0.16 mmol), CDI (52 mg, 0.32 mmol), 1-[(1-methylpiperidin-4-yl)methyl]piperazine (33 mg, 0.16 mmol) and DCE (1.5 mL). A portion of the crude product was purified using prep method A LCMS Method C: rt 2.75 min, 100%; m/z 280.32 (M+2H)$^{2+}$, 100%) 559.36 (MH+, 13%)

Potency: B

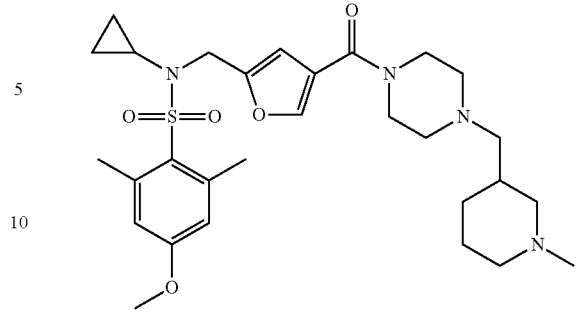

N-Cyclopropyl-4-methoxy-2,6-dimethyl-N-{[4-({4-[(1-methylpiperidin-3-yl)methyl]piperazin-1-yl}carbonyl)furan-2-yl]methyl}benzenesulfonamide trifluoroacetate Ex 106

The title compound was prepared according to general procedure AA using 5-({cyclopropyl[(4-methoxy-2,6-dimethylphenyl)sulfonyl]amino}methyl)furan-3-carboxylic acid (60 mg, 0.16 mmol), CDI (52 mg, 0.32 mmol), 1-[(1-methylpiperidin-3-yl)methyl]piperazine (33 mg, 0.16 mmol) and DCE (1.5 mL). A portion of the crude product was purified using prep method A LCMS Method C: rt 2.79 min, 100%; m/z 280.31 (M+2H)$^{2+}$, 100%) 559.35 (MH+, 12%)

Potency: B

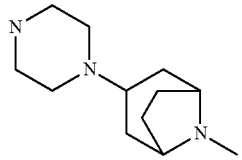

8-Methyl-3-(piperazin-1-yl)-8-azabicyclo[3.2.1]octane, dihydrochloride

Int 139

The title compound was prepared according to general procedure AS using tert-butyl 4-(8-methyl-8-azabicyclo[3.2.1]oct-3-yl)piperazine-1-carboxylate (100 mg, 0.32 mmol), thionyl chloride (0.05 mL, 0.08 mmol) and MeOH (2.0 mL).

Yield: 90 mg, 100%.

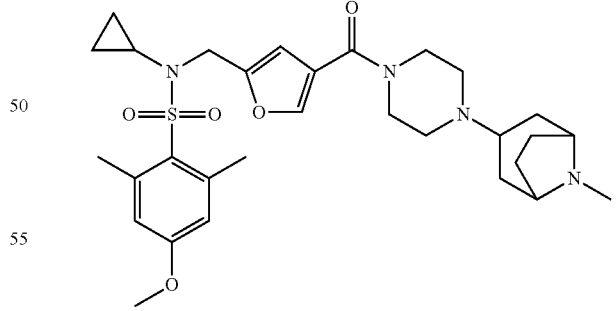

N-Cyclopropyl-4-methoxy-2,6-dimethyl-N-[(4-{[4-(8-methyl-8-azabicyclo[3.2.1]oct-3-yl)piperazin-1-yl]carbonyl}furan-2-yl)methyl]benzenesulfonamide trifluoroacetate Ex 107

The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol) and HOBt monohydrate (22 mg, 0.16 mmol) in DCE (1 mL). and 8-methyl-3-(piperazin-1-yl)-8-azabicyclo[3.2.1]octane dihydrochloride (23 mg, 0.08 mmol) in DMF (0.5 mL). A portion of the crude product was purified using prep method A.

LCMS Method C: rt 2.81 min, 100%; m/z 571.14 (MH+, 100%)

Potency: B

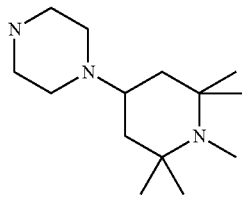 [SMILES: CN1C(C)(C)CC(N2CCNCC2)CC1(C)C]

1-(1,2,2,6,6-Pentamethylpiperidin-4-yl)piperazine, dihydrochloride

Int 140

The title compound was prepared according to general procedure AS using tert-butyl 4-(1,2,2,6,6-pentamethylpiperidin-4-yl)piperazine-1-carboxylate (100 mg, 0.30 mmol), thionyl chloride (0.05 mL, 0.08 mmol) and MeOH (2.0 mL).

Yield: 93 mg, 100%

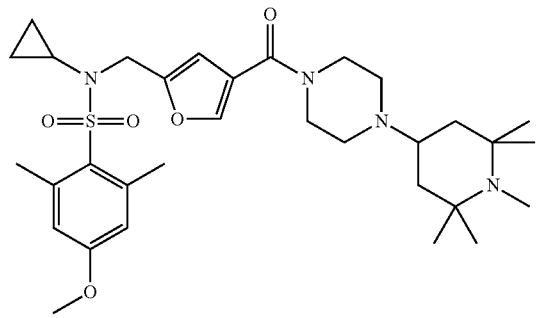 [SMILES: COc1cc(C)c(S(=O)(=O)N(Cc2cc(C(=O)N3CCN(C4CC(C)(C)N(C)C(C)(C)C4)CC3)co2)C2CC2)c(C)c1]

N-Cyclopropyl-4-methoxy-2,6-dimethyl-N-[(4-{[4-(1,2,2,6,6-pentamethylpiperidin-4-yl)piperazin-1-yl] carbonyl}furan-2-yl)methyl]benzenesulfonamide trifluoroacetate Ex 108

The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol) and HOBt monohydrate (22 mg, 0.16 mmol) in DCE (1 mL). and 1-(1,2,2,6,6-pentamethylpiperidin-4-yl)piperazine dihydrochloride (26 mg, 0.08 mmol) in DMF (0.5 mL). A portion of the crude product was purified using prep method A.

LCMS Method C: rt 2.87 min, 100%; m/z 601.20 (MH+, 100%)

Potency: A

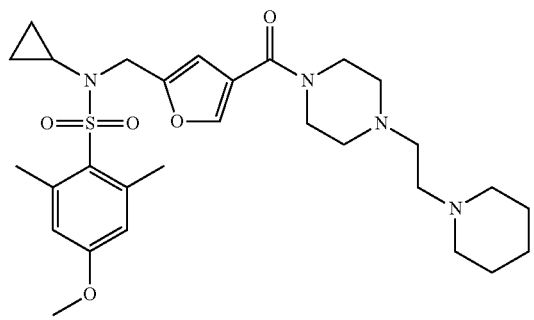 [SMILES: COc1cc(C)c(S(=O)(=O)N(Cc2cc(C(=O)N3CCN(CCN4CCCCC4)CC3)co2)C2CC2)c(C)c1]

N-Cyclopropyl-4-methoxy-2,6-dimethyl-N-[(4-{[4-(2-piperidin-1-ylethyl)piperazin-1-yl] carbonyl}furan-2-yl)methyl]benzenesulfonamide trifluoroacetate Ex 109

The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol) and HOBt monohydrate (22 mg, 0.16 mmol), 1-[2-(piperidin-1-yl)ethyl]piperazine (16 mg, 0.08 mmol) and DCE (1.5 mL). A portion of the crude product was purified using prep method A LCMS Method C: rt 3.16 min, 100%; m/z 559.13 (MH+, 100%)

Potency: A

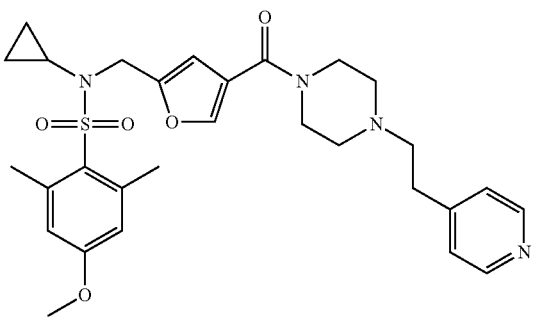 [SMILES: COc1cc(C)c(S(=O)(=O)N(Cc2cc(C(=O)N3CCN(CCc4ccncc4)CC3)co2)C2CC2)c(C)c1]

N-Cyclopropyl-4-methoxy-2,6-dimethyl-N-[(4-{[4-(2-pyridin-4-ylethyl)piperazin-1-yl]carbonyl}furan-2-yl)methyl]benzenesulfonamide trifluoroacetate Ex 110

The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol) and HOBt monohydrate (22 mg, 0.16 mmol), 1-[2-(pyridin-4-yl)ethyl]piperazine (16 mg, 0.08 mmol) and DCE (1.5 mL). A portion of the crude product was purified using prep method A.

LCMS Method C: rt 2.84 min, 95%; m/z 553.11 (MH+, 100%)

Potency: A

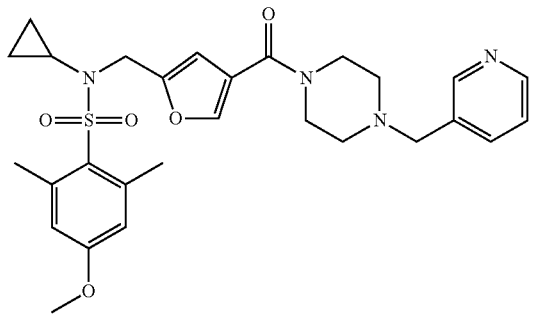 [SMILES: COc1cc(C)c(S(=O)(=O)N(Cc2cc(C(=O)N3CCN(Cc4cccnc4)CC3)co2)C2CC2)c(C)c1]

N-Cyclopropyl-4-methoxy-2,6-dimethyl-N-[(4-{[4-(pyridin-3-ylmethyl)piperazin-1-yl]carbonyl}furan-2-yl)methyl]benzenesulfonamide trifluoroacetate Ex 111

The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol) and HOBt monohydrate (22 mg, 0.16 mmol), 1-(pyridin-3-ylmethyl)piperazine (14 mg, 0.08 mmol) and DCE (1.5 mL). A portion of the crude product was purified using prep method A LCMS Method C: rt 3.17 min, 100%; m/z 539.08 (MH$^+$, 100%)

$^1$H NMR (500 MHz, CDCl$_3$) δ ppm 8.99 (1H, br. s.), 8.78 (1H, d, J=4.1 Hz), 8.48 (1H, d, J=7.5 Hz), 7.82 (1H, t, J=6.3 Hz), 7.69 (1H, s), 6.61 (2H, s), 6.53 (1H, s), 4.35-4.57 (4H, m), 3.92 (4H, br. s.), 3.81 (3H, s), 3.22 (4H, br. s.), 2.51 (6H, s), 2.41-2.49 (1H, m), 0.44-0.58 (2H, m), 0.05-0.18 (2H, m)

Potency: A

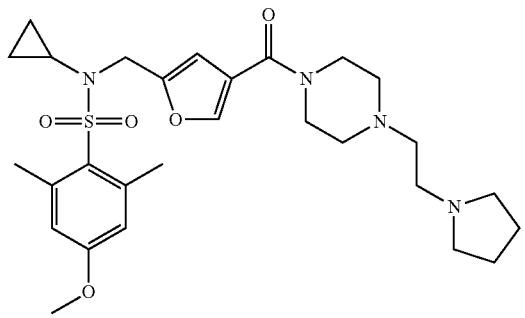 [SMILES: COc1cc(C)c(S(=O)(=O)N(Cc2cc(C(=O)N3CCN(CCN4CCCC4)CC3)co2)C2CC2)c(C)c1]

N-Cyclopropyl-4-methoxy-2,6-dimethyl-N-[(4-{[4-(2-pyrrolidin-1-ylethyl)piperazin-1-yl]carbonyl}furan-2-yl)methyl]benzenesulfonamide trifluoroacetate Ex 112

The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol) and HOBt monohydrate (22 mg, 0.16 mmol), 1-[2-(pyrrolidinoethyl]piperazine (15 mg, 0.08 mmol) and DCE (1.5 mL). A portion of the crude product was purified using prep method A LCMS Method C: rt 3.10 min, 100%; m/z 545.11 (MH$^+$, 100%)

Potency: B

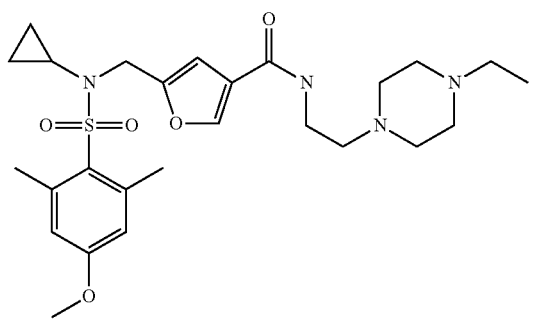 [SMILES: CCN1CCN(CCNC(=O)c2coc(CN(C3CC3)S(=O)(=O)c3c(C)cc(OC)cc3C)c2)CC1]

5-({Cyclopropyl[(4-methoxy-2,6-dimethylphenyl)sulfonyl]amino}methyl)-N-[2-(4-ethylpiperazin-1-yl)ethyl]furan-3-carboxamide trifluoroacetate Ex 113

The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol) and HOBt monohydrate (22 mg, 0.16 mmol), 2-(4-ethylpiperazin-1-yl)ethanamine (13 mg, 0.08 mmol) and DCE (1.5 mL). A portion of the crude product was purified using prep method A LCMS Method C: rt 3.03 min, 100%; m/z 519.10 (MH$^+$, 100%)

Potency: A

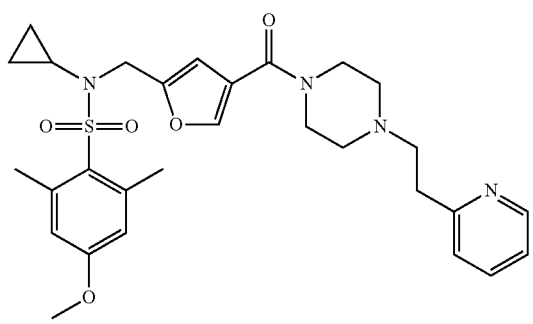 [SMILES: COc1cc(C)c(S(=O)(=O)N(Cc2cc(C(=O)N3CCN(CCc4ccccn4)CC3)co2)C2CC2)c(C)c1]

N-Cyclopropyl-4-methoxy-2,6-dimethyl-N-[(4-{[4-(2-pyridin-2-ylethyl)piperazin-1-yl]carbonyl}furan-2-yl)methyl]benzenesulfonamide trifluoroacetate Ex 114

The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol) and HOBt monohydrate (22 mg, 0.16 mmol), 1-[2-(pyridin-2-yl)ethyl]piperazine (16 mg, 0.08 mmol) and DCE (1.5 mL). A portion of the crude product was purified using prep method A LCMS Method C: rt 3.15 min, 100%; m/z 553.08 (MH$^+$, 100%)

Potency: A

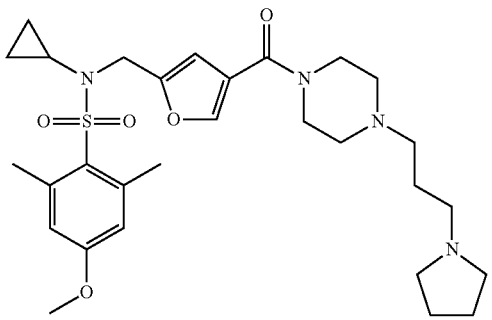 [SMILES: COc1cc(C)c(S(=O)(=O)N(Cc2cc(C(=O)N3CCN(CCCN4CCCC4)CC3)co2)C2CC2)c(C)c1]

N-Cyclopropyl-4-methoxy-2,6-dimethyl-N-[(4-{[4-(3-pyrrolidin-1-ylpropyl)piperazin-1-yl]carbonyl}furan-2-yl)methyl]benzenesulfonamide trifluoroacetate Ex 115
The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol), HOBt monohydrate (22 mg, 0.16 mmol), 1-[3-(pyrrolidin-1-yl)propyl]piperazine (16 mg, 0.08 mmol) and DCE (1.5 mL). A portion of the crude product was purified using prep method A LCMS Method C: rt 2.70 min, 100%; m/z 559.14 (MH+, 100%)
Potency: B Potency: B

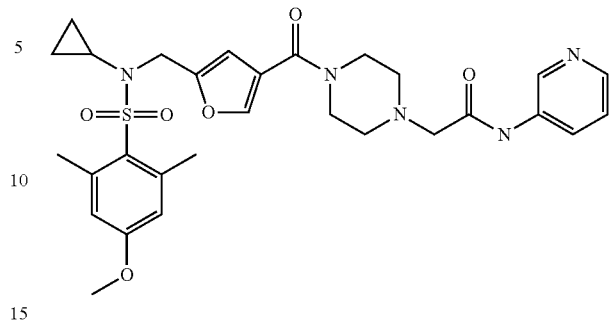

2-(4-{[5-({Cyclopropyl[(4-methoxy-2,6-dimethylphenyl)sulfonyl]amino}methyl)furan-3-yl]carbonyl}piperazin-1-yl)-N-pyridin-3-ylacetamide trifluoroacetate Ex 117
The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol) and HOBt monohydrate (22 mg, 0.16 mmol), 2-(piperazin-1-yl)-N-(pyridin-3-yl)acetamide (18 mg, 0.08 mmol) and DCE (1.5 mL). A portion of the crude product was purified using prep method A.

LCMS Method C: rt 3.20 min, 99%; m/z 582.07 (MH+, 100%)
Potency: A

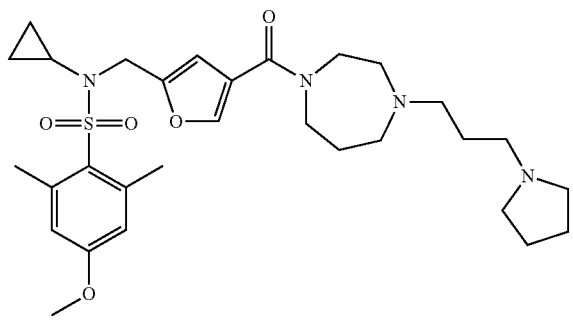 [SMILES: COc1cc(C)c(S(=O)(=O)N(Cc2cc(C(=O)N3CCCN(CCCN4CCCC4)CC3)co2)C2CC2)c(C)c1]

N-Cyclopropyl-4-methoxy-2,6-dimethyl-N-[(4-{[4-(3-pyrrolidin-1-ylpropyl)-1,4-diazepan-1-yl]carbonyl}furan-2-yl)methyl]benzenesulfonamide trifluoroacetate Ex 116
The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol), HOBt monohydrate (22 mg, 0.16 mmol), 1-[3-(pyrrolidin-1-yl)propyl]-1,4-diazepane (17 mg, 0.08 mmol) and DCE (1.5 mL). A portion of the crude product was purified using prep method A LCMS Method C: rt 2.75 min, 100%; m/z 573.13 (MH+, 100%)

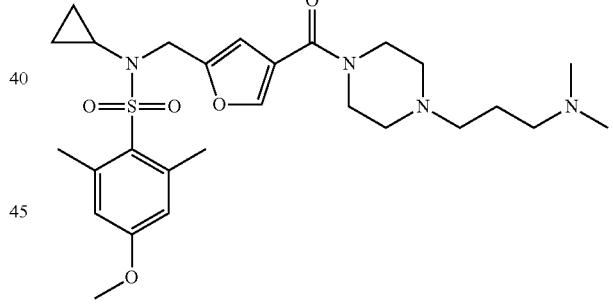

N-Cyclopropyl-N-{[4-({4-[3-(dimethylamino)propyl]piperazin-1-yl}carbonyl)furan-2-yl]methyl}-4-methoxy-2,6-dimethylbenzenesulfonamide trifluoroacetate Ex 118
The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol), HOBt monohydrate (22 mg, 0.16 mmol), 2-(piperazin-1-yl)-N-(pyridin-3-yl)acetamide (14 mg, 0.08 mmol) and DCE (1.5 mL). A portion of the crude product was purified using prep method A LCMS Method C: rt 2.73 min, 99%; m/z 533.12 (MH+, 100%)

Potency: B

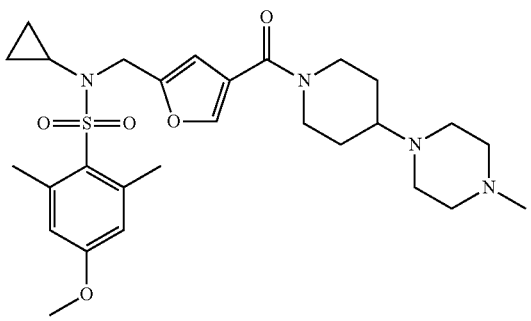 [SMILES: COc1cc(C)c(S(=O)(=O)N(Cc2cc(C(=O)N3CCC(N4CCN(C)CC4)CC3)co2)C2CC2)c(C)c1]

N-Cyclopropyl-4-methoxy-2,6-dimethyl-N-[(4-{[4-(4-methylpiperazin-1-yl)piperidin-1-yl]carbonyl}furan-2-yl)methyl]benzenesulfonamide trifluoroacetate Ex 119

The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol), HOBt monohydrate (22 mg, 0.16 mmol), 1-methyl-4-(piperidin-4-yl)piperazine (15 mg, 0.08 mmol) and DCE (1.5 mL). A portion of the crude product was purified using prep method A LCMS Method C: rt 3.04 min, 100%; m/z 545.13 (MH+, 100%)

Potency: A

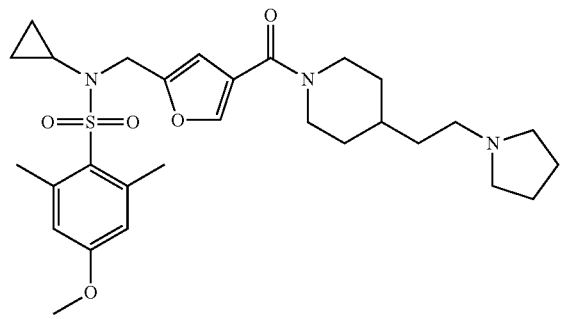 [SMILES: COc1cc(C)c(S(=O)(=O)N(Cc2cc(C(=O)N3CCC(CCN4CCCC4)CC3)co2)C2CC2)c(C)c1]

N-Cyclopropyl-4-methoxy-2,6-dimethyl-N-[(4-{[4-(2-pyrrolidin-1-ylethyl)piperidin-1-yl]carbonyl}furan-2-yl)methyl]benzenesulfonamide trifluoroacetate Ex 120

The title compound was prepared according to general procedure AC using 5-({cyclopropyl[(4-methoxy-2,6-dimethylphenyl)sulfonyl]amino}methyl)furan-3-carboxylic acid (30 mg, 0.08 mmol), EDCI (31 mg, 0.16 mmol), HOBt monohydrate (22 mg, 0.16 mmol), 4-[2-(pyrrolidin-1-yl)ethyl]piperidine (23 mg, 0.13 mmol) and DCE (1.5 mL). A portion of the crude product was purified using prep method A LCMS Method C: rt 3.31 min, 100%; m/z 544.25 (MH+, 100%)

Potency: C

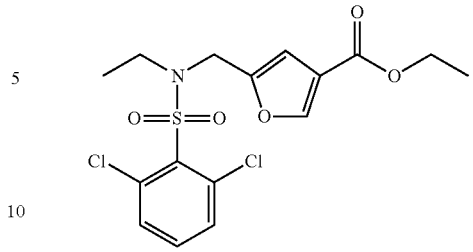

Ethyl 5-({[(2,6-dichlorophenyl)sulfonyl](ethyl)amino}methyl)furan-3-carboxylate trifluoroacetate Int 141

The title compound was prepared according to general procedure CC using ethyl 5-[(methylamino)methyl]furan-3-carboxylate (140 mg, 0.71 mmol), DIPEA (0.37 mL, 2.12 mmol), DMAP (9 mg, 0.07 mmol) and 2,6-dichlorobenzenesulfonyl chloride (208 mg, 0.85 mmol) in DCM (3 mL). The product was purified using FCC, eluting with 10% EtOAc in heptane, followed by purification by prep method A.

Yield: 117 mg, 40%

LCMS Method B: rt 2.26 min, 100%; m/z 427.85 (MNa+, 100%).

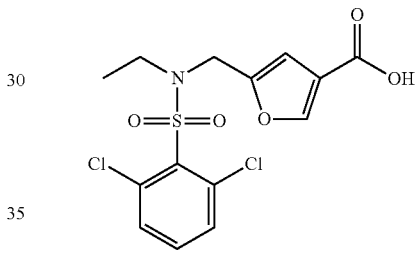

5-({[(2,6-Dichlorophenyl)sulfonyl](ethyl)amino}methyl)furan-3-carboxylic acid

Int 142

The title compound was prepared according to general procedure AL using ethyl 5-({[(2,6-dichlorophenyl)sulfonyl](ethyl)amino}methyl)furan-3-carboxylate (117 mg, 0.29 mmol) and 2 M aqueous LiOH (0.85 mL, 1.71 mmol) in THF (3 mL). The crude product required no further purification.

Yield: 104 mg, 95%.

LCMS Method A: rt 1.32 min, 90%; m/z 399.80 (MH+, 100%).

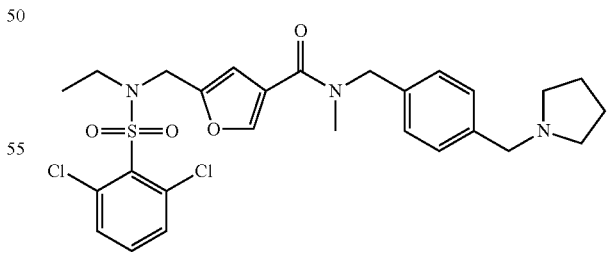

5-({[(2,6-Dichlorophenyl)sulfonyl](ethyl)amino}methyl)-N-methyl-N-[4-(pyrrolidin-1-ylmethyl)benzyl]furan-3-carboxamide trifluoroacetate Ex 121

The title compound was prepared according to general procedure AA using 5-({[(2,6-dichlorophenyl)sulfonyl]

(ethyl)amino}methyl)furan-3-carboxylic acid (52 mg, 0.12 mmol), CDI (41 mg, 0.25 mmol), N-methyl-1-[4-(pyrrolidin-1-ylmethyl)phenyl]methanamine (26 mg, 0.12 mmol) in DCE (1.5 mL). A portion of the crude product was purified using prep method A LCMS Method C: rt 3.31 min, 100%; m/z 564.24 (MH+, 100%)

Potency: A

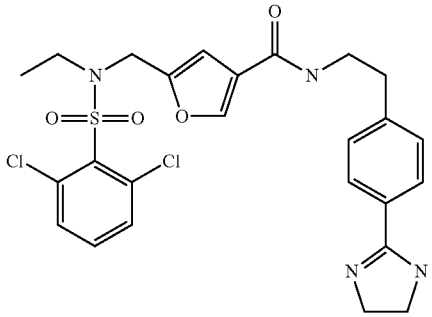 [SMILES: CCN(Cc1cc(C(=O)NCCc2ccc(C3=NCCN3)cc2)co1)S(=O)(=O)c1c(Cl)cccc1Cl]

5-({[(2,6-Dichlorophenyl)sulfonyl](ethyl)amino}methyl)-N-{2-[4-(4,5-dihydro-1H-imidazol-2-yl)phenyl]ethyl}furan-3-carboxamide trifluoroacetate Ex 122

The title compound was prepared according to general procedure AA using 5-({[(2,6-dichlorophenyl)sulfonyl](ethyl)amino}methyl)furan-3-carboxylic acid (52 mg, 0.12 mmol), CDI (41 mg, 0.25 mmol), 2-[4-(4,5-dihydro-1H-imidazol-2-yl)phenyl]ethanamine dihydrochloride (54 mg, 0.12 mmol), DIPEA (0.11 mL, 0.64 mmol) and DCE (1.5 mL). A portion of the crude product was purified using prep method A LCMS Method C: rt 3.26 min, 100%; m/z 549.23 (MH+, 100%)

$^1$H NMR (500 MHz, CDCl$_3$) δ ppm 10.48 (2H, br. s.), 7.92 (1H, s), 7.71 (2H, d, J=8.1 Hz), 7.57 (1H, t, J=5.6 Hz), 7.49 (2H, d, J=7.9 Hz), 7.34-7.40 (1H, m), 7.10 (2H, d, J=8.1 Hz), 6.70 (1H, s), 4.59 (2H, s), 4.02 (4H, s), 3.48 (2H, q, J=6.5 Hz), 3.36 (2H, q, J=7.0 Hz), 2.87 (2H, t, J=6.8 Hz), 1.04 (3H, t, J=7.2 Hz)

Potency: A

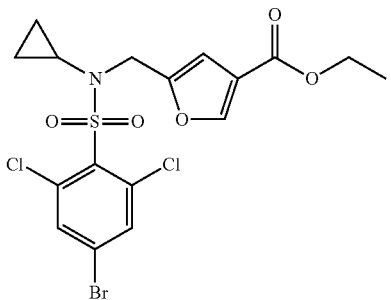 [SMILES: CCOC(=O)c1coc(CN(C2CC2)S(=O)(=O)c2c(Cl)cc(Br)cc2Cl)c1]

Ethyl 5-({[(4-bromo-2,6-dichlorophenyl)sulfonyl](cyclopropyl)amino}methyl)furan-3-carboxylate Int 143

General Procedure CC—(Sulfonamide Formation with DMEDA Quench)

To a stirred solution of ethyl 5-[(cyclopropylamino)methyl]furan-3-carboxylate (370 mg, 1.42 mmol), DIPEA (0.75 mL, 4.24 mmol), DMAP (17 mg, 0.14 mmol) in DCM (5 mL) was added 4-bromo-2,6-dichlorobenzenesulfonyl chloride (505 mg, 1.95 mmol) slowly as a solution in DCM (5 mL). The reaction was stirred overnight at ambient temperature. The mixture was quenched with N,N-dimethylethylenediamine (0.08 mL 0.71 mmol) and stirred for a further 30 min, diluted with DCM (30 mL) and washed with 10% aqueous citric acid solution (2×30 mL), then dried over MgSO$_4$. Solvents were removed in vacuo and the product was purified using FCC eluting with 10% EtOAc in heptane to afford the title compound.

Yield: 459 mg, 65%.

LCMS Method A: rt 1.65 min, 99%; m/z 519.80 (MNa+, 100%).

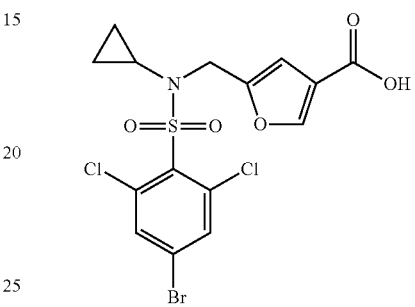

5-({[(4-Bromo-2,5-dichlorophenyl)sulfonyl](cyclopropyl)amino}methyl)furan-3-carboxylic acid Int 144

The title compound was prepared according to general procedure AL using ethyl 5-({[(4-bromo-2,6-dichlorophenyl)sulfonyl](cyclopropyl)amino}methyl)furan-3-carboxylate (460 mg, 0.92 mmol) and 2 M aqueous LiOH (0.33 mL, 1.85 mmol) in THF (5 mL). The crude product required no further purification.

Yield: 399 mg, 92%.

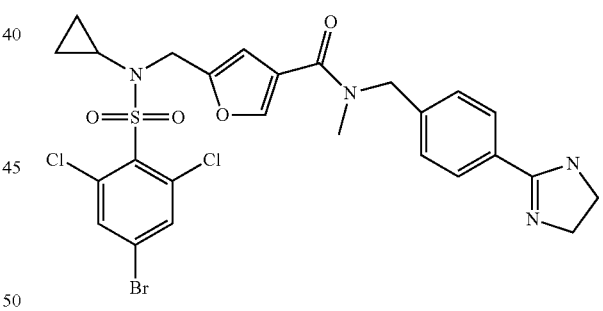

5-({[(4-Bromo-2,6-dichlorophenyl)sulfonyl](cyclopropyl)amino}methyl)-N-[4-(4,5-dihydro-1H-imidazol-2-yl)benzyl]-N-methylfuran-3-carboxamide trifluoroacetate Ex 123

The title compound was prepared according to general procedure AA using 5-({[(4-bromo-2,6-dichlorophenyl)sulfonyl](cyclopropyl)amino}methyl)furan-3-carboxylic acid (60 mg, 0.12 mmol), CDI (38 mg, 0.23 mmol), 1-[4-(4,5-dihydro-1H-imidazol-2-yl)phenyl]-N-methylmethanamine dihydrochloride (29 mg, 0.10 mmol), DIPEA (0.11 mL, 0.64 mmol) and DCE (1.5 mL). A portion of the crude product was purified using prep method A.

LCMS Method C: rt 3.54 min, 99%; m/z 640.99 (MH+, 100%)

Potency: C

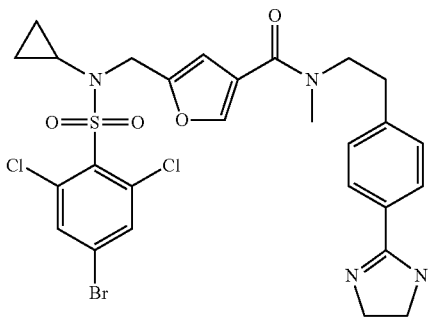 [SMILES: CN(CCc1ccc(C2=NCCN2)cc1)C(=O)c1coc(CN(C2CC2)S(=O)(=O)c2c(Cl)cc(Br)cc2Cl)c1]

5-({[(4-Bromo-2,6-dichlorophenyl)sulfonyl](cyclopropyl)amino}methyl)-N-{2-[4-(4,5-dihydro-1H-imidazol-2-yl)phenyl]ethyl}-N-methylfuran-3-carboxamide trifluoroacetate Ex 124

The title compound was prepared according to general procedure AA using 5-({[(4-bromo-2,6-dichlorophenyl)sulfonyl](cyclopropyl)amino}methyl)furan-3-carboxylic acid (60 mg, 0.12 mmol), CDI (38 mg, 0.23 mmol), 2-[4-(4,5-dihydro-1H-imidazol-2-yl)phenyl]-N-methylethanamine dihydrochloride (30 mg, 0.10 mmol), DIPEA (0.11 mL, 0.64 mmol) and DCE (1.5 mL). A portion of the crude product was purified using prep method A.

LCMS Method C: rt 3.56 min, 99%; m/z 655.03 (MH+, 100%)
Potency: C

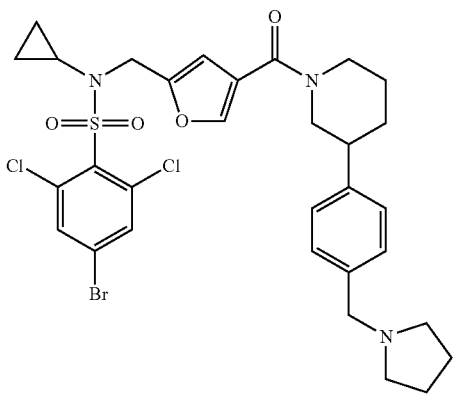 [SMILES: O=C(c1coc(CN(C2CC2)S(=O)(=O)c2c(Cl)cc(Br)cc2Cl)c1)N1CCCC(c2ccc(CN3CCCC3)cc2)C1]

4-Bromo-2,6-dichloro-N-cyclopropyl-N-{[4-({3-[4-(pyrrolidin-1-ylmethyl)phenyl]piperidin-1-yl}carbonyl)furan-2-yl]methyl}benzenesulfonamide trifluoroacetate Ex 125

The title compound was prepared according to general procedure AA using 5-({[(4-bromo-2,6-dichlorophenyl)sulfonyl](cyclopropyl)amino}methyl)furan-3-carboxylic acid (60 mg, 0.12 mmol), CDI (38 mg, 0.23 mmol), 3-[4-(pyrrolidin-1-ylmethyl)phenyl]piperidine dihydrochloride (33 mg, 0.10 mmol), DIPEA (0.11 mL, 0.64 mmol) and DCE (1.5 mL). A portion of the crude product was purified using prep method A.

LCMS Method C: rt 3.67 min, 99%; m/z 681.23 (MH+, 100%)
Potency: A

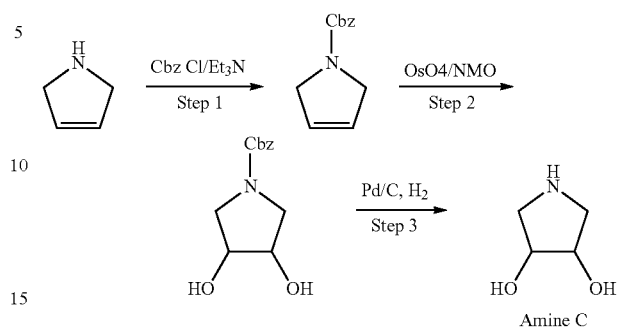

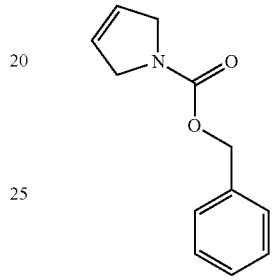

Benzyl 2,5-dihydro-1H-pyrrole-1-carboxylate

Int 145

3-Pyrroline (0.4 g, 5.79 mmol) was dissolved in toluene (10 mL) and NaHCO$_3$ (0.57 g, 6.96 mmol) was added. The resulting suspension was cooled to 0° C. prior to the slow addition of benzylchloroformate (0.92 mL, 6.38 mmol) and the reaction was stirred for 18 h at ambient temperature. The reaction was quenched by addition of water (5 mL) and extracted with DCM (2×25 mL). The combined organic extracts were washed with water (10 mL), brine (10 mL), dried over Na$_2$SO$_4$ and concentrated in vacuo. The resulting residue was purified by FCC eluting with 3% EtOAc in hexane.

Yield: 800 mg, 67%
$^1$H NMR (300 MHz, CDCl$_3$) δ ppm 7.35 (5H, m), 5.82 (2H, m), 5.26 (2H, s), 4.20 (4H, m).

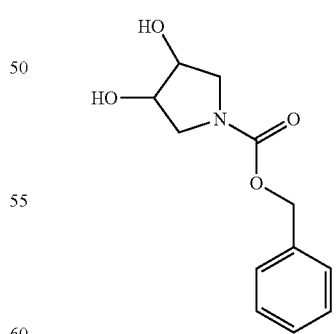

Benzyl 3,4-dihydroxypyrrolidine-1-carboxylate

Int 146

Benzyl 2,5-dihydro-1H-pyrrole-1-carboxylate (0.88 g, 4.33 mmol) was dissolved in a mixture of THF (20 mL) and water (5 mL) and the resulting solution was cooled to 0° C. NMO (0.558 g, 4.76 mmol) and OsO$_4$ (13 mg, cat) were added and the reaction was stirred for 18 h at ambient temperature. The reaction was washed with water (15 mL) and extracted with EtOAc (3×20 mL). The combined organic extracts were washed with brine (10 mL), dried over Na$_2$SO$_4$ and concentrated in vacuo. The resulting residue was purified by FCC eluting with 30% EtOAc in hexane to afford the title compound.

Yield: 0.85 g, 83%.

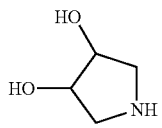

Pyrrolidine-3,4-diol

Int 147

To a stirred solution of benzyl 3,4-dihydroxypyrrolidine-1-carboxylate (0.05 g, 0.21 mmol) in MeOH (20 mL) in a Parr reaction vessel was added 10% Pd/C (5 mg, cat). The vessel was purge-filled with N$_2$ (3 cycles), then with hydrogen (3 cycles) and 20 psi pressure of hydrogen was maintained for 1 h. The reaction mixture was filtered through Celite. The filter cake was washed with MeOH and the combined filtrates were concentrated in vacuo to afford the title compound as a brown oil.

The resulting crude product was used without further purification.

Yield: 20 mg, 95%.

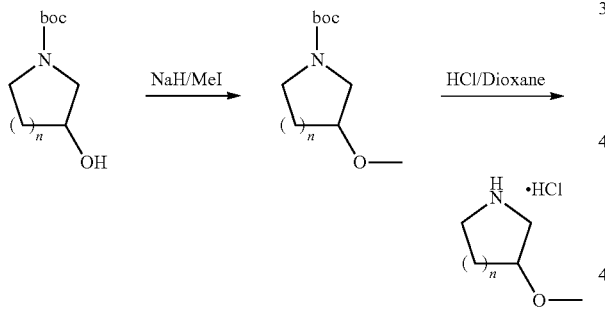

n = 1, Amine E
n = 2, Amine H
(OH group is at 4th position of N)
n = 2, Amine L
n = 0, Amine J

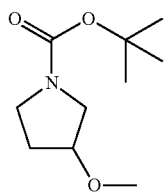

tert-Butyl 3-methoxypyrrolidine-1-carboxylate

General Procedure BJ—Methylation

Int 148

To a stirred solution of tert-butyl 3-hydroxypyrrolidine-1-carboxylate (0.5 g, 2.67 mmol) in THF (20 mL) at 0° C. was added NaH (60%, 0.077 g, 3.2 mmol) and the mixture was stirred for 15 min. Methyl iodide (0.2 mL, 3.2 mmol) was slowly added and the reaction was stirred for 18 h at ambient temperature. The reaction was quenched with water (5 mL) and extracted with DCM (3×10 mL). The combined organic extracts were washed with water (6 mL), brine (8 mL), dried over Na$_2$SO$_4$ and concentrated in vacuo. The resulting residue was purified by FCC eluting with DCM to afford the title compound.

Yield: 0.53 g, 99%.

$^1$H NMR (300 MHz, CDCl$_3$) δ ppm 3.92 (1H, br s), 3.43 (4H, m), 3.32 (3H, s), 1.98 (2H, m), 1.46 (9H, s).

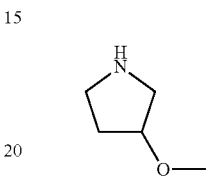

3-Methoxypyrrolidine

General Procedure BI—Boc Deprotection

Int 149

Tert-butyl 3-methoxypyrrolidine-1-carboxylate (0.8 g, 3.98 mmol) was stirred in a 4 M HCl solution in dioxane (30 mL) for 18 h at ambient temperature. The solvent was removed in vacuo and the resulting HCl salt was dissolved in MeOH (20 mL). Amberjet 4000 ion-exchange resin (1 g) was added and the mixture was stirred for 2 h at ambient temperature. After filtration the solvent was removed in vacuo to afford the title compound, which was used without further purification.

Yield: 0.35, 87%.

$^1$H NMR (300 MHz, CDCl$_3$) δ ppm 4.15 (1H, br s), 3.30 (3H, s), 3.02 (2H, m), 2.83 (2H, m), 1.90 (2H, m).

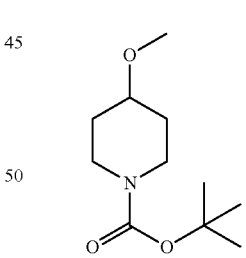

tert-Butyl 4-methoxypiperidine-1-carboxylate

Int 150

The title compound was prepared according to general procedure BJ using tert-butyl 4-hydroxypiperidine-1-carboxylate (1.0 g, 4.9 mmol), NaH (60%, 0.14 g, 5.9 mmol), methyl iodide (0.36 mL, 5.9 mmol) and THF (30 mL). The crude product was purified by FCC eluting with 2% EtOAc in hexane.

Yield: 0.71 g, 67%.

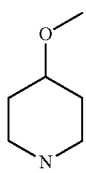

4-Methoxypiperidine

Int 151

The title compound was prepared according to general procedure BI using tert-butyl 4-methoxypiperidine-1-carboxylate (1.2 g, 5.58 mmol), a solution of 4 M HCl in dioxane (30 mL), MeOH (20 mL) and Amberjet 4000 ion-exchange resin (1 g).

Yield: 0.2 g, 31%.

$^1$H NMR (300 MHz, CDCl$_3$) δ ppm 3.36 (3H, s), 3.29 (1H, m), 3.09 (2H, s), 2.66 (2H, m), 1.93 (2H, m), 1.41 (2H, m).

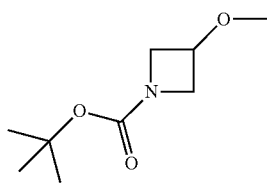

tert-Butyl 3-methoxyazetidine-1-carboxylate

Int 152

The title compound was prepared according to general procedure BJ using tert-butyl 3-hydroxyazetidine-1-carboxylate (1.2 g, 6.9 mmol), NaH (60%, 0.322 g, 8.3 mmol) and methyl iodide (0.6 mL, 9.0 mmol) in THF (10 mL). The crude product was purified by FCC eluting with 2% EtOAc in hexane.

Yield: 0.75 g, 58%.

$^1$H NMR (300 MHz, CDCl$_3$) δ ppm 4.14 (3H, m), 4.06 (2H, m), 3.28 (3H, s), 1.43 (9H, s).

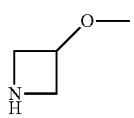

3-Methoxyazetidine

Int 153

The title compound was prepared according to general procedure BI using tert-butyl 3-methoxyazetidine-1-carboxylate (1.2 g, 5.58 mmol) and a solution of 4 M HCl in dioxane (30 mL). The solvent was removed in vacuo and the HCl salt of the title compound was used in the next step without further purification.

Yield: 0.6 g, 87%.

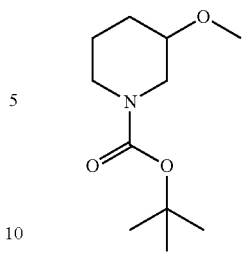

tert-Butyl 3-methoxypiperidine-1-carboxylate

Int 154

The title compound was prepared according to general procedure BJ using tert-butyl 3-hydroxypiperidine-1-carboxylate (0.39 g, 1.43 mmol), NaH (60%, 0.055 g, 2.3 mmol) and methyl iodide (0.14 mL, 2.3 mmol) in THF (20 mL). The crude product was purified by FCC eluting with 2% EtOAc in hexane.

Yield: 0.415 g, 65%.

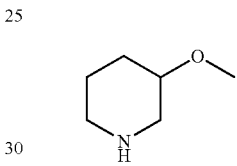

3-Methoxypiperidine

Int 155

The title compound was prepared according to general procedure BI using tert-butyl 3-methoxypiperidine-1-carboxylate (0.7 g, 3.2 mmol), a solution of 4 M HCl in dioxane (20 mL), MeOH (20 mL) and Amberjet 4000 ion exchange resin (1.0 g).

Yield: 0.37 g, 100%.

$^1$H NMR (300 MHz, CDCl$_3$) δ ppm 3.50 (3H, s), 3.19 (1H, s), 3.06 (1H, s), 2.66 (1H, m), 2.63 (2H, m), 1.97 (1H, m), 1.66 (1H, m), 1.47 (2H, br s).

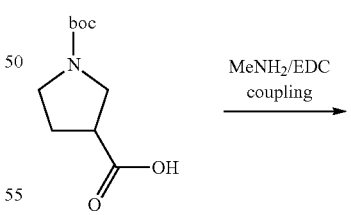

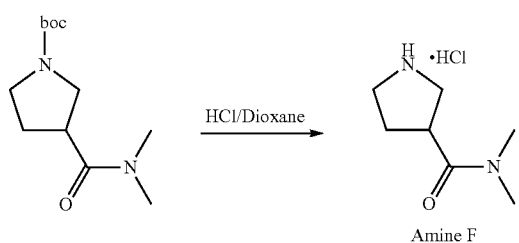

171

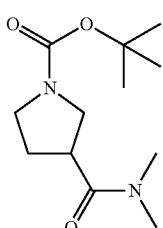

tert-Butyl 3-(dimethylcarbamoyl)pyrrolidine-1-carboxylate

Int 156

1-(Tert-butoxycarbonyl)pyrrolidine-3-carboxylic acid (0.25 g, 1.16 mmol) was dissolved in DCM (20 mL) and EDCI (0.312 g, 1.62 mmol), HOBt (0.23 g, 1.75 mmol) and DIPEA (0.4 mL, 2.32 mmol) were added. The resulting solution was stirred for 10 min prior to the addition of N,N-dimethylamine (2.0 M solution in THF, 0.7 mL) and the reaction stirred at ambient temperature for 16 h. The reaction was quenched with water (4 mL) and the product extracted with DCM (50 mL). The combined organic extracts were washed with water (2×5 mL) and saturated brine (10 mL), dried over $Na_2SO_4$, and concentrated in vacuo. The crude product was purified by FCC eluting with 2% MeOH in DCM.

Yield: 0.15 g, 53%.

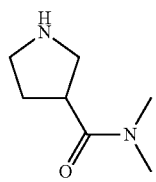

N,N-Dimethylpyrrolidine-3-carboxamide

Int 157

Tert-butyl 3-(dimethylcarbamoyl)pyrrolidine-1-carboxylate (0.14 g, 0.57 mmol) was treated with 4 M HCl in dioxane (10 mL) and stirred for 18 h at 0° C. The solvent was removed in vacuo and the resulting salt was dissolved in MeOH (20 mL). Amberjet 4000 ion-exchange resin (1.0 g) was added and the mixture stirred for 15 min. After filtration, the solvent was removed in vacuo and the crude product was used in the next step without further purification.

Yield: 70 mg, 87%.

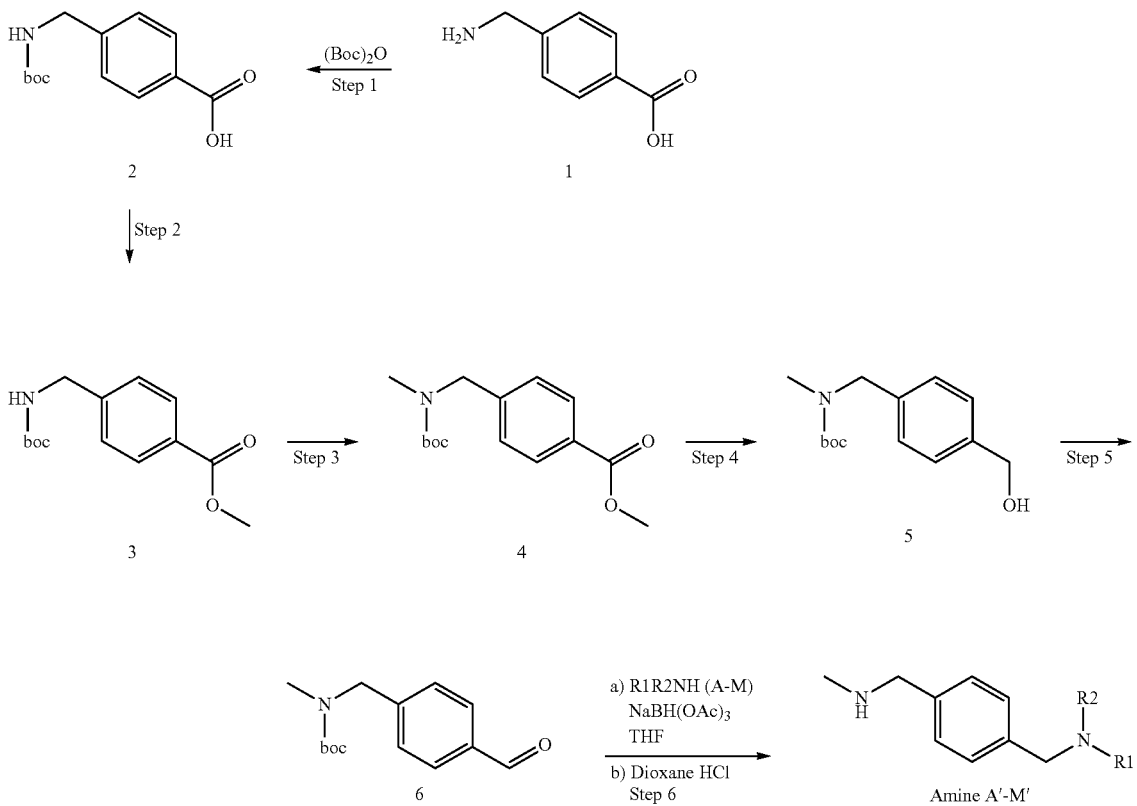

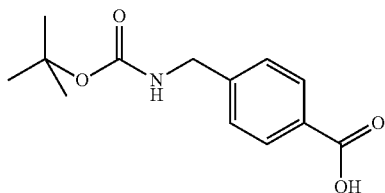 [SMILES: CC(C)(C)OC(=O)NCc1ccc(C(=O)O)cc1]

4-{[(tert-Butoxycarbonyl)amino]methyl}benzoic acid

Int 158

4-Aminomethylbenzoic acid (10.0 g, 66 mmol) was dissolved in a mixture of 10% aqueous NaOH (90 mL) and EtOH (250 mL). The solution was cooled to 0° C. and di-tert-butyl-dicarbonate (15.2 g, 73.0 mmol) was added slowly. The reaction mixture was stirred for 18 h at ambient temperature and TLC showed the consumption of amino acid. The ethanol was removed in vacuo and water (500 mL) was added. The aqueous layer was acidified slowly with a saturated solution of citric acid (20 mL) and the precipitate formed was filtered under suction, and dried in vacuo to afford the title compound as a white solid. No further purification was required.

Yield: 16.0 g, 96%.

$^1$H NMR (300 MHz, CDCl$_3$) δ ppm 7.88 (2H, d, J=8.1 Hz), 7.45 (1H, br s), 7.33 (2H, d, J=8.1 Hz), 4.18 (2H, d), 1.30 (9H, s)

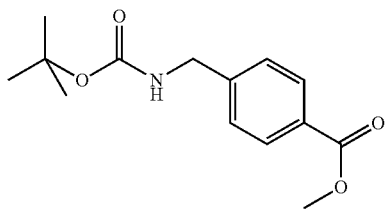 [SMILES: COC(=O)c1ccc(CNC(=O)OC(C)(C)C)cc1]

Methyl 4-{[(tert-butoxycarbonyl)amino]methyl}benzoate

Int 159

4-{[(tert-butoxycarbonyl)amino]methyl}benzoic acid (16.0 g, 63.7 mmol) was dissolved in DCM (150 mL) and EDCI (17.1 g, 89.2 mmol), HOBt (12.8 g, 95.6 mmol) and DIPEA (22 mL, 127 mmol) were added. The resulting solution was stirred for 5 min prior to the addition of methanol (5 mL), then stirred at ambient temperature for 18 h. The reaction was diluted with DCM (200 mL) and washed with water (2×30 mL) and brine (25 mL), dried over Na$_2$SO$_4$, and concentrated in vacuo. The resulting residue was purified by FCC eluting with DCM to afford the title compound.

Yield: 16 g, 95%.

$^1$H NMR (300 MHz, CDCl$_3$) δ ppm 7.01 (2H, d), 7.33 (2H, d), 4.91 (1H, br s), 4.37 (2H, d), 3.91 (3H, s), 1.46 (9H, s).

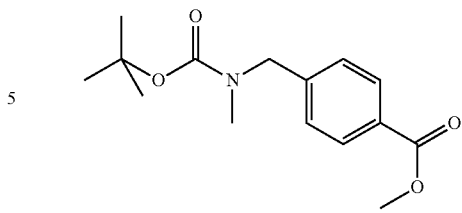

Methyl 4-{[(tert-butoxycarbonyl)(methyl)amino]methyl}benzoate

Int 160

To a stirred solution of methyl 4-{[(tert-butoxycarbonyl)amino]methyl}benzoate (16.0 g, 60.33 mmol) in DMF (150 mL) at 0° C. was added NaH (60%, 6.0 g, 150.83 mmol) and the resulting mixture was stirred for 20 min at 0° C. Methyl iodide (9.4 mL, 150.8 mmol) was added dropwise and the reaction was stirred at 0° C. for 30 min. The reaction was quenched with water and extracted with EtOAc (200 mL). The organic layer was washed with water (2×30 mL) and brine (25 mL), dried over Na$_2$SO$_4$, and concentrated in vacuo. The resulting residue was purified by FCC eluting with 1% EtOAc in hexane to afford the title compound.

Yield: 10.0 g, 59%.

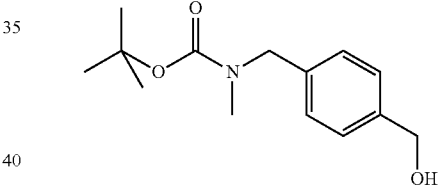

tert-Butyl[4-(hydroxymethyl)benzyl]methylcarbamate

Int 161

To the suspension of LiAlH$_4$ (5.17 g, 136.2 mmol) in THF (130 mL) at 0° C. under N$_2$ was added a solution of methyl 4-{[(tert-butoxycarbonyl)(methyl)amino]methyl}benzoate (9.5 g, 34.0 mmol) in THF (20 mL). The resulting reaction was stirred at 0° C. for 10 min, quenched with EtOAc (5 mL) and with a 10% w/v solution of aqueous NaOH (10 mL). EtOAc (200 mL) was added and the solid formed was removed by filtration through Celite (25 g). The solid cake was washed with EtOAc (4×20 mL). The combined organic extracts were washed with water (2×25 mL) and brine (25 mL), dried over Na$_2$SO$_4$, and concentrated in vacuo. The resulting residue was purified by FCC eluting with 50% EtOAc in hexane.

Yield: 7.0 g, 82%.

$^1$H NMR (300 MHz, CDCl$_3$) δ ppm 7.32 (2H, d), 7.20 (2H, d), 4.66 (2H, s), 4.40 (2H, s), 2.80 (3H, s), 1.47 (9H, s).

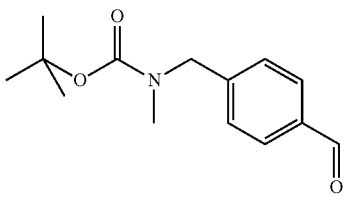 [SMILES: CN(Cc1ccc(C=O)cc1)C(=O)OC(C)(C)C]

tert-Butyl (4-formylbenzyl)methylcarbamate

Int 162

To a stirred suspension of PCC (1.4 g, 6.6 mmol) in DCM (20 mL) was added a solution of (4-tert-butyl[4-(hydroxymethyl)benzyl]methylcarbamate (1.1 g, 4.40 mmol) in DCM (20 mL) and the resulting reaction was stirred for 30 min at ambient temperature. The mixture was diluted with DCM (30 mL) and filtered through a pad of silica (20 g). The silica pad was washed with DCM (20 mL) and the filtrate was concentrated in vacuo to afford the title compound. No further purification was required.

Yield: 0.9 g, 83%.

$^1$H NMR (300 MHz, CDCl$_3$) δ ppm 10.6 (1H, s), 7.86 (2H, d), 7.38 (2H, d), 4.50 (2H, s), 2.85 (3H, s), 1.47 (9H, s).

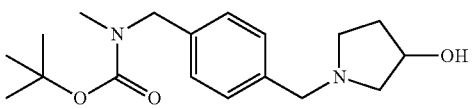 [SMILES: CN(Cc1ccc(CN2CCC(O)C2)cc1)C(=O)OC(C)(C)C]

tert-Butyl {4-[(3-hydroxypyrrolidin-1-yl)methyl]benzyl}methylcarbamate

Int 163
General Procedure BF—Reductive Amination

To a stirred solution of tert-butyl (4-formylbenzyl)methylcarbamate (0.5 g, 2.0 mmol) in DCE (20 mL) were added 3-pyrrolidinol (0.2 g, 2.4 mmol) and AcOH (0.125 mL, 2.0 mmol) and the reaction mixture was stirred for 5 h at ambient temperature. STAB (1.7 g, 8.0 mmol) was added and the reaction was stirred for 18 h. The reaction mixture was basified with aqueous NH$_3$ and extracted with DCM (50 mL). The organic layer was washed with water (10 mL) and brine (10 mL), dried over Na$_2$SO$_4$, and concentrated in vacuo. The crude product was purified by FCC eluting with 7% MeOH in DCM.

Yield: 0.31 g, 46%.

LCMS method D: rt 3.40 min, 100%; m/z 321.30 (MH$^+$, 100%).

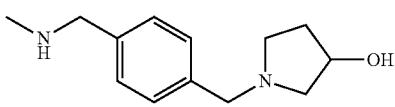 [SMILES: CNCc1ccc(CN2CCC(O)C2)cc1]

1-{4-[(Methylamino)methyl]benzyl}pyrrolidin-3-ol dihydrochloride

Int 164
General Procedure BG tert-butyl {4-[(3-hydroxypyrrolidin-1-yl)methyl]benzyl}methylcarbamate (0.176 g, 0.55 mmol) was stirred with 4 M HCl in dioxane or Et$_2$O (10 mL) for 4 h at ambient temperature. The reaction was concentrated in vacuo and the solid obtained was washed with Et$_2$O to afford the title compound as a dihydrochloride salt. This material was used without further purification.

Yield: 136 mg, 84%

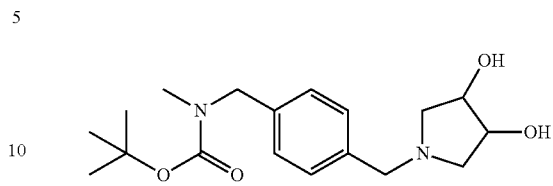

tert-Butyl {4-[(3,4-dihydroxypyrrolidin-1-yl)methyl]benzyl}methylcarbamate

Int 165

The title compound was prepared according to general procedure BF using tert-butyl (4-formylbenzyl)methylcarbamate (0.2 g, 0.8 mmol), pyrrolidine-3,4-diol (0.099 g, 0.96 mmol), AcOH (0.48 mL, 8.0 mmol) and STAB (0.679 g, 3.2 mmol) and the reaction mixture was stirred for 5 days at ambient temperature in DCE (30 mL). The crude product was purified by FCC eluting with MeOH:DCM:aqueous NH$_3$ (4:95:1).

Yield: 0.055 g, 20%.

$^1$H NMR (300 MHz, CDCl$_3$) δ ppm 7.26-7.16 (4H, m), 4.39 (2H, s), 4.15 (2H, s), 3.57 (3H, s), 2.80 (2H, br s), 2.64 (4H, m), 1.48 (9H, s).

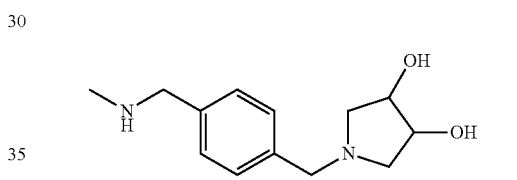

1-{4-[(Methylamino)methyl]benzyl}pyrrolidine-3,4-diol dihydrochloride

Int 166

The title compound was prepared according to general procedure BG using tert-butyl {4-[(3,4-dihydroxypyrrolidin-1-yl)methyl]benzyl}methylcarbamate (0.2 g, 0.59 mmol) and 4 M HCl in dioxane (8 mL).

Yield: 0.14 g, 76%.

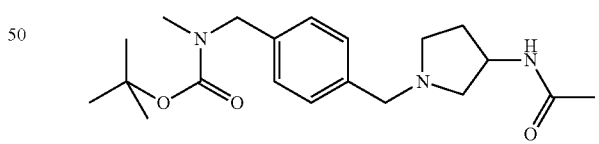

tert-Butyl (4-{[3-(acetylamino)pyrrolidin-1-yl]methyl}benzyl)methylcarbamate

Int 167

The title compound was prepared according to general procedure BF using tert-butyl (4-formylbenzyl)methylcarbamate (0.1 g, 0.40 mmol), N-pyrrolidin-3-yl-acetamide (0.062 g, 0.48 mmol), AcOH (0.24 mL, 0.4 mmol), STAB (0.34 g, 1.6 mmol) and DCE (10 mL). The crude product was purified by FCC eluting with 7% MeOH in DCM.

Yield: 60 mg, 43%.

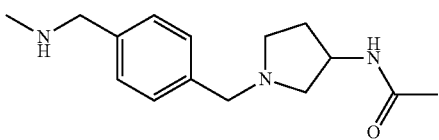 [SMILES: CNCc1ccc(CN2CCC(NC(C)=O)C2)cc1]

N-(1-{4-[(Methylamino)methyl]benzyl}pyrrolidin-3-yl)acetamide dihydrochloride

Int 168

The title compound was prepared according to general procedure BG using tert-butyl (4-{[3-(acetylamino)pyrrolidin-1-yl]methyl}benzyl)methylcarbamate (0.25 g, 0.69 mmol) and 4 M HCl in dioxane (10 mL).

Yield: 0.204 g, 88%.

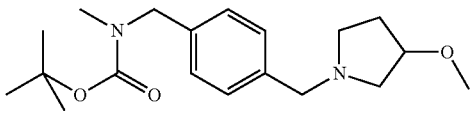 [SMILES: COC1CCN(Cc2ccc(CN(C)C(=O)OC(C)(C)C)cc2)C1]

tert-Butyl {4-[(3-methoxypyrrolidin-1-yl)methyl]benzyl}methylcarbamate

Int 169

The title compound was prepared according to general procedure BF using tert-butyl (4-formylbenzyl)methylcarbamate (0.5 g, 2.0 mmol), 3-methoxypyrrolidine (0.22 g, 2.14 mmol), AcOH (0.12 mL, 2 mmol), STAB (1.7 g, 8.0 mmol) and DCE (10 mL). The crude product was purified by FCC eluting with 8% MeOH in DCM.

Yield: 0.45 g, 67%.

$^1$H NMR (300 MHz, CDCl$_3$) δ ppm 7.32-7.18 (4H, m), 4.40 (2H, s), 3.97 (1H, m), 3.77 (2H, s), 3.27 (3H, s), 3.02 (1H, m), 2.80 (5H, m), 2.65 (1H, m), 2.06 (1H, m), 1.67 (1H, m), 1.48 (9H, s).

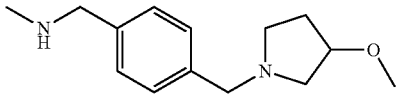

1-{4-[(3-Methoxypyrrolidin-1-yl)methyl]phenyl}-N-methylmethanamine dihydrochloride Int 170

The title compound was prepared according to general procedure BG using tert-butyl {4-[(3-methoxypyrrolidin-1-yl)methyl]benzyl}methylcarbamate (0.35 g, 1.05 mmol) and 4 M HCl in dioxane (8 mL).

Yield: 0.24 g, 75%.

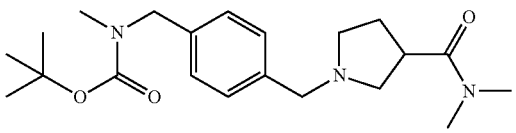 [SMILES: CN(C)C(=O)C1CCN(Cc2ccc(CN(C)C(=O)OC(C)(C)C)cc2)C1]

tert-Butyl (4-{[3-(dimethylcarbamoyl)pyrrolidin-1-yl]methyl}benzyl)methylcarbamate Int 171

The title compound was prepared according to general procedure BF using tert-butyl (4-formylbenzyl)methylcarbamate (0.3 g, 1.2 mmol), N,N-dimethylpyrrolidine-3-carboxamide (0.2 g, 1.4 mmol), AcOH (0.07 mL, 1.2 mmol), STAB (1.01 g, 4.8 mmol) and DCE (20 mL). The crude product was purified by FCC eluting with MeOH:DCM:aq. NH$_3$ (4:95:1).

Yield: 0.27 g, 60%.

LCMS Method D: rt 3.77 min, 100%; m/z 376.40 MH$^+$, 100%).

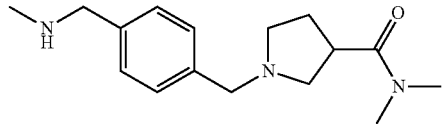

N,N-Dimethyl-1-{4-[(methylamino)methyl]benzyl}pyrrolidine-3-carboxamide dihydrochloride Int 172

The title compound was prepared according to general procedure BG using tert-butyl (4-{[3-(dimethylcarbamoyl)pyrrolidin-1-yl]methyl}benzyl)methylcarbamate (0.16 g, 0.42 mmol) and 4 M HCl in Et$_2$O (10 mL).

Yield: 0.09 g, 62%.

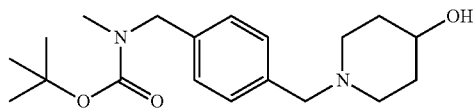 [SMILES: CN(Cc1ccc(CN2CCC(O)CC2)cc1)C(=O)OC(C)(C)C]

tert-Butyl {4-[(4-hydroxypiperidin-1-yl)methyl]benzyl}methylcarbamate

Int 173

The title compound was prepared according to general procedure BF using tert-butyl (4-formylbenzyl)methylcarbamate (0.2 g, 0.802 mmol), piperidin-4-ol (0.097 g, 0.963 mmol), AcOH (0.05 mL, 0.8 mmol), STAB (0.68 g, 3.2 mmol) and DCE (10 mL). The crude product was purified by FCC eluting with 5% MeOH in DCM.

Yield: 0.08 g, 30%.

LCMS Method D: rt 3.92 min, 100%; m/z 336.30 (MH$^+$, 100%).

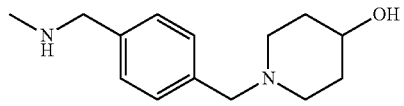 [SMILES: CNCc1ccc(CN2CCC(O)CC2)cc1]

1-{4-[(Methylamino)methyl]benzyl}piperidin-4-ol dihydrochloride

Int 174

The title compound was prepared according to general procedure BG using tert-butyl {4-[(4-hydroxypiperidin-1-yl)methyl]benzyl}methylcarbamate (0.2 g, 0.59 mmol) and 4 M HCl in dioxane (10 mL).

Yield: 0.15 g, 83%.

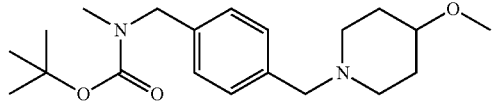 [SMILES: COC1CCN(Cc2ccc(CN(C)C(=O)OC(C)(C)C)cc2)CC1]

tert-Butyl {4-[(4-methoxypiperidin-1-yl)methyl]benzyl}methylcarbamate

Int 175

The title compound was prepared according to general procedure BF using tert-butyl (4-formylbenzyl)methylcarbamate (0.2 g, 0.802 mmol), piperidin-4-ol (0.3 g, 1.2 mmol), AcOH (0.06 mL, 1.07 mmol), STAB (0.91 g, 4.29 mmol) and DCE (20 mL). The crude product was purified by FCC eluting with 7% MeOH in DCM.

Yield: 0.23 g, 56%.

$^1$H NMR (300 MHz, CDCl$_3$) δ ppm 7.30-7.19 (4H, m), 4.40 (2H, s), 3.61 (2H, s), 3.32 (3H, s), 3.28 (1H, m), 2.81 (5H, m), 2.36 (2H, m), 1.94 (2H, m), 1.70 (2H, m), 1.48 (9H, s).

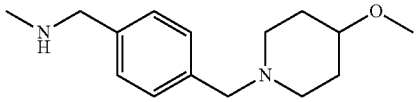

1-{4-[(4-Methoxypiperidin-1-yl)methyl]phenyl}-N-methylmethanamine dihydrochloride Int 176

The title compound was prepared according to general procedure BG using tert-butyl {4-[(4-methoxypiperidin-1-yl)methyl]benzyl}methylcarbamate (0.14 g, 0.4 mmol) and 4 M HCl in dioxane (10 mL).

Yield: 102 mg, 79%.

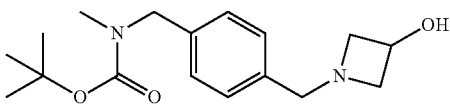 [SMILES: CN(Cc1ccc(CN2CC(O)C2)cc1)C(=O)OC(C)(C)C]

tert-Butyl {4-[(3-hydroxyazetidin-1-yl)methyl]benzyl}methylcarbamate

Int 177

3-Hydroxyazetidine hydrochloride (0.171 g, 1.5 mmol) was dissolved in DCM (5 mL) and TEA (0.17 mL, 1.2 mmol). The resulting solution was stirred for 30 min at ambient temperature and concentrated in vacuo and the residue redissolved in DCE (2 mL) and added to a stirred solution of tert-butyl (4-formylbenzyl)methylcarbamate (0.3 g, 1.2 mmol) in DCE (15 mL) AcOH (0.15 mL, 2.4 mmol). The reaction mixture was stirred for 16 h at ambient temperature prior to the addition of STAB (1.01 g, 4.8 mmol), and stirred for 1 d at ambient temperature. The reaction mixture was basified with aqueous NH$_3$ and extracted with DCM (50 mL). The organic layer was washed with water (5 mL) and brine (10 mL), dried over Na$_2$SO$_4$, and concentrated in vacuo. The resulting residue was purified by FCC eluting with MeOH:DCM:aq. NH$_3$ (4:95:1).

Yield: 140 mg, 39%.

LCMS Method D: rt 3.53 min, 100%; m/z 307.30 (MH$^+$, 100%).

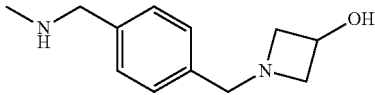

1-{4-[(Methylamino)methyl]benzyl}azetidin-3-ol dihydrochloride

Int 178

The title compound was prepared according to general procedure BG using tert-butyl {4-[(3-hydroxyazetidin-1-yl)methyl]benzyl}methylcarbamate (0.14 g, 0.46 mmol) and 4 M HCl in dioxane (10 mL).

Yield: 105 mg, 82%.

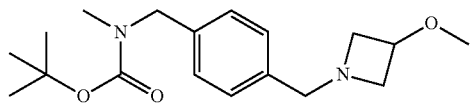 [SMILES: COC1CN(Cc2ccc(CN(C)C(=O)OC(C)(C)C)cc2)C1]

tert-Butyl {4-[(3-methoxyazetidin-1-yl)methyl]benzyl}methylcarbamate

Int 179

3-Methoxyazetidine hydrochloride (0.41 g, 3.3 mmol) was dissolved in DCM (20 mL) and TEA (0.5 mL, 3.82 mmol). The resulting solution was stirred for 30 min at ambient temperature and concentrated in vacuo. The residue was redissolved in DCE (5 mL) and added to a stirred solution of tert-butyl (4-formylbenzyl)methylcarbamate (0.636 g, 2.55 mmol) in DCE (15 mL) and AcOH (0.15 mL, 0.25 mmol). The reaction mixture was stirred for 5 h at ambient temperature prior to the addition of STAB (2.16 g, 1.02 mmol) and then stirred for 16 h. The reaction mixture was basified with aqueous NH$_3$ and extracted with DCM (60 mL). The organic layer was washed with water (5 mL) and brine (10 mL), dried over Na$_2$SO$_4$, and concentrated in vacuo. The resulting residue was purified by FCC eluting with MeOH:DCM:aq. NH$_3$ (4:95:1).

Yield: 145 mg, 18%.

$^1$H NMR (300 MHz, CDCl$_3$) δ ppm 7.26-7.16 (4H, m), 4.39 (2H, s), 4.04 (1H, m), 3.62 (4H, m), 3.25 (3H, s), 2.97 (2H, m), 2.80 (3H, s), 1.47 (9H, s).

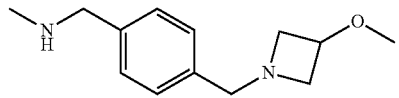

1-{4-[(3-Methoxyazetidin-1-yl)methyl]phenyl}-N-methylmethanamine dihydrochloride Int 180

The title compound was prepared according to general procedure BG using tert-butyl {4-[(3-methoxyazetidin-1-yl)methyl]benzyl}methylcarbamate (0.12 g, 0.375 mmol) and 4 M HCl in dioxane (10 mL).

Yield: 85 mg, 78%

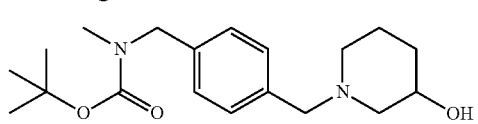

tert-Butyl {4-[(3-hydroxypiperidin-1-yl)methyl]benzyl}methylcarbamate

Int 181

The title compound was prepared according to general procedure BF using tert-butyl (4-formylbenzyl)methylcarbamate (0.2 g, 0.802 mmol), piperidin-3-ol (0.097 g, 0.963 mmol), AcOH (0.05 mL, 0.8 mmol), STAB (0.68 g, 3.2 mmol) and DCE (10 mL). The crude product was purified by FCC eluting with 5% MeOH in DCM.

Yield: 0.2 g, 75%

LCMS Method D: rt 3.95 min, 100%; m/z 335.30 (MH$^+$, 100%).

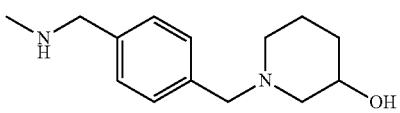 [SMILES: CNCc1ccc(CN2CCCC(O)C2)cc1]

1-{4-[(Methylamino)methyl]benzyl}piperidin-3-ol
dihydrochloride

Int 182

The title compound was prepared according to general procedure BG using tert-butyl {4-[(3-hydroxypiperidin-1-yl)methyl]benzyl}methylcarbamate (0.2 g, 0.6 mmol) and 4 M HCl in dioxane (10 mL).

Yield: 130 mg, 71%

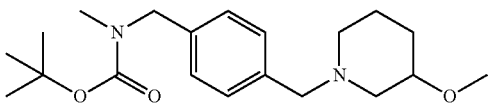 [SMILES: COC1CCCN(Cc2ccc(CN(C)C(=O)OC(C)(C)C)cc2)C1]

tert-Butyl {4-[(3-methoxypiperidin-1-yl)methyl]benzyl}methylcarbamate

Int 183

The title compound was prepared according to general procedure BF using tert-butyl (4-formylbenzyl)methylcarbamate (0.5 g, 2.0 mmol), 3-methoxypiperidine (0.249 g, 2.15 mmol), AcOH (0.1 mL, 1.79 mmol), STAB (1.51 g, 7.16 mmol) and DCE (20 mL). The crude product was purified by FCC eluting with 7% MeOH in DCM.

Yield: 0.35 g, 56%.

LCMS Method D: rt 3.77 min, 95%; m/z 349.30 (MH$^+$, 100%).

$^1$H NMR (300 MHz, CDCl$_3$) δ ppm 7.27-7.16 (4H, m), 4.40 (2H, s), 3.56 (2H, s), 3.31 (4H, m), 2.94-2.67 (5H, m), 2.01 (3H, m), 1.71 (1H, m), 1.50 (1H, m), 1.48 (9H, s), 1.20 (1H, m).

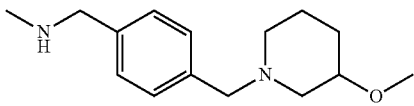

1-{4-[(3-Methoxypiperidin-1-yl)methyl]phenyl}-N-methylmethanamine dihydrochloride Int 184

The title compound was prepared according to general procedure BG using tert-butyl {4-[(3-methoxypiperidin-1-yl)methyl]benzyl}methylcarbamate (0.25 g, 0.71 mmol) and 4 M HCl in dioxane (10 mL).

Yield: 200 mg, 88%.

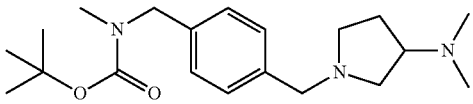 [SMILES: CN(Cc1ccc(CN2CCC(N(C)C)C2)cc1)C(=O)OC(C)(C)C]

tert-Butyl (4-{[3-(dimethylamino)pyrrolidin-1-yl]methyl}benzyl)methylcarbamate

Int 185

The title compound was prepared according to general procedure BF using tert-butyl (4-formylbenzyl)methylcarbamate (0.4 g, 1.6 mmol), dimethyl-pyrrolidin-3-yl-amine (0.22 g, 1.9 mmol), AcOH (0.1 mL, 1.6 mmol), STAB (1.35 g, 6.4 mmol) and DCE (15 mL). The crude was purified by FCC eluting with 10% MeOH in DCM.

Yield: 0.11 g, 40%.

LCMS Method D: rt 5.13 min, 100%; m/z 348.30 (MH$^+$, 100%).

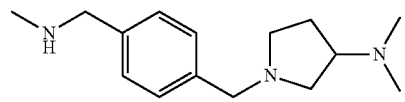

N,N-Dimethyl-1-{4-[(methylamino)methyl]benzyl}pyrrolidin-3-amine trihydrochloride Int 186

The title compound was prepared according to general procedure BG using [tert-butyl (4-{[3-(dimethylamino)pyrrolidin-1-yl]methyl}benzyl)methylcarbamate (0.23 g, 0.66 mmol) and 4 M HCl in Et$_2$O (10 mL).

Yield: 0.2 g, 87%.

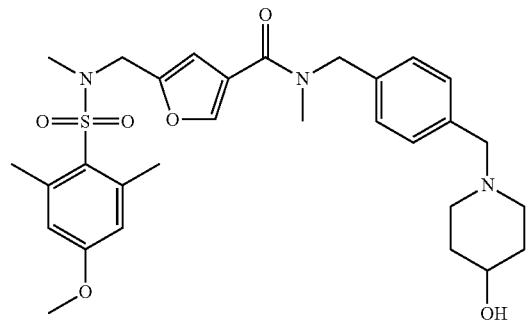 [SMILES: COc1cc(C)c(S(=O)(=O)N(C)Cc2cc(C(=O)N(C)Cc3ccc(CN4CCC(O)CC4)cc3)co2)c(C)c1]

N-{4-[(4-Hydroxypiperidin-1-yl)methyl]benzyl}-5-({[(4-methoxy-2,6-dimethylphenyl)sulfonyl](methyl)amino}methyl)-N-methylfuran-3-carboxamide Ex 126

General Procedure BH 5-({[(4-methoxy-2,6-dimethylphenyl)sulfonyl](methyl)amino}methyl)furan-3-carboxylic acid (30 mg, 0.085 mmol) was dissolved in DCM (10 mL) and EDCI (27 mg, 0.11 mmol), HOBt (17 mg, 0.127 mmol) and DIPEA (0.03 mL, 0.17 mmol) were added. The resulting solution was stirred for 5 min prior to the addition of 1-{4-[(methylamino)methyl]benzyl}piperidin-4-ol dihydrochloride (28 mg, 0.102 mmol) and stirred at ambient temperature for 16 h. The reaction was diluted with water (5 mL) and extracted with EtOAc (2×15 mL). The combined organic extracts were washed with water (2×5 mL) and brine (5 mL), dried over Na$_2$SO$_4$, and concentrated in vacuo. The resulting residue was purified by FCC eluting with 5% MeOH in DCM to afford the title compound.

Yield: 23 mg, 50%.

LCMS method C: rt 3.12 min, 100%; m/z 570.20 (MH$^+$, 100%).

Potency: B

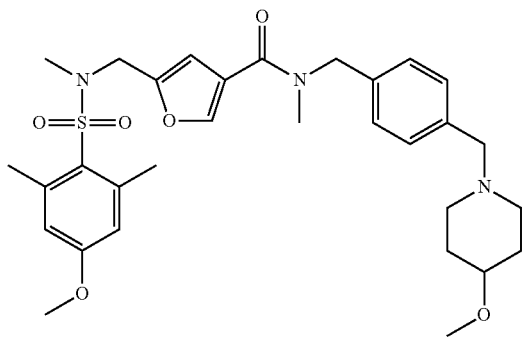

5-({[(4-Methoxy-2,6-dimethylphenyl)sulfonyl](methyl)amino}methyl)-N-{4-[(4-methoxypiperidin-1-yl)methyl]benzyl}-N-methylfuran-3-carboxamide Ex 127

The title compound was prepared according to general procedure BH using 5-{[(4-methoxy-2,6-dimethyl-benzenesulfonyl)-methyl-amino]-methyl}-furan-3-carboxylic acid (35 mg, 0.10 mmol), EDCI (26 mg, 0.13 mmol), HOBt (20 mg, 0.15 mmol), DIPEA (0.04 mL, 0.20 mmol), [4-(4-methoxy-piperidin-1-ylmethyl)-benzyl]-methyl-amine hydrochloride (32 mg, 0.10 mmol) and DCM (10 mL).

Yield: 28 mg, 48%.

LCMS method C: rt 3.26 min, 98%; m/z 584.22 (MH+, 100%).

Potency: B

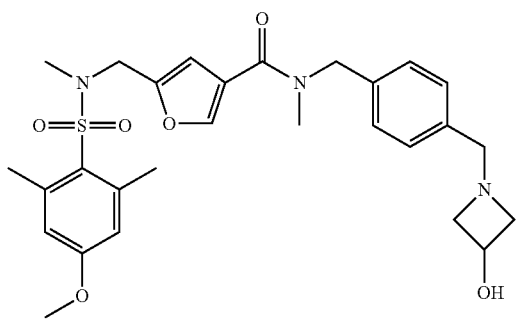 [SMILES: COc1cc(C)c(S(=O)(=O)N(C)Cc2cc(C(=O)N(C)Cc3ccc(CN4CC(O)C4)cc3)co2)c(C)c1]

N-{4-[(3-Hydroxyazetidin-1-yl)methyl]benzyl}-5-({[(4-methoxy-2,6-dimethylphenyl)sulfonyl](methyl)amino}methyl)-N-methylfuran-3-carboxamide Ex 128

The title compound was prepared according to general procedure BH using 5-{[(4-methoxy-2,6-dimethyl-benzenesulfonyl)-methyl-amino]-methyl}-furan-3-carboxylic acid (35 mg, 0.10 mmol), EDCI (27 mg, 0.14 mmol), HOBt (20 mg, 0.15 mmol), DIPEA (0.04 mL, 0.20 mmol), 1-(4-methylaminomethyl-benzyl)-azetidin-3-ol hydrochloride (29 mg, 0.11 mmol) and DCM (10 mL).

Yield: 27 mg, 50%.

LCMS method C: rt 3.15 min, 97%; m/z 542.17 (MH+, 100%).

Potency: A

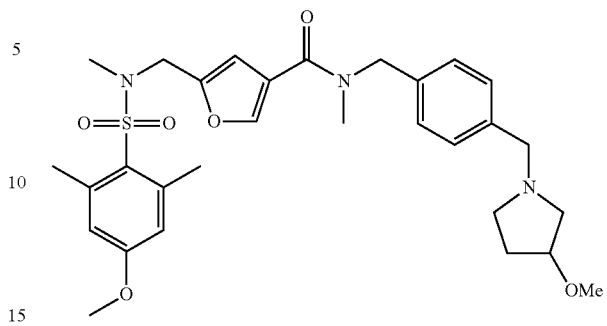

5-({[(4-Methoxy-2,6-dimethylphenyl)sulfonyl](methyl)amino}methyl)-N-{4-[(3-methoxypyrrolidin-1-yl)methyl]benzyl}-N-methylfuran-3-carboxamide Ex 129

The title compound was prepared according to general procedure BH using 5-({[(4-methoxy-2,6-dimethylphenyl)sulfonyl](methyl)amino}methyl)furan-3-carboxylic acid (40 mg, 0.11 mmol), EDCI (30 mg, 0.15 mmol), HOBt (23 mg, 0.17 mmol), DIPEA (0.04 mL, 0.23 mmol) and 1-{4-[(3-methoxypyrrolidin-1-yl)methyl]phenyl}-N-methylmethanamine dihydrochloride (37 mg, 0.13 mmol) in DCM (10 mL).

Yield: 17 mg, 27%.

LCMS method C: rt 3.29 min, 95%; m/z 570.20 (MH+, 100%).

Potency: A

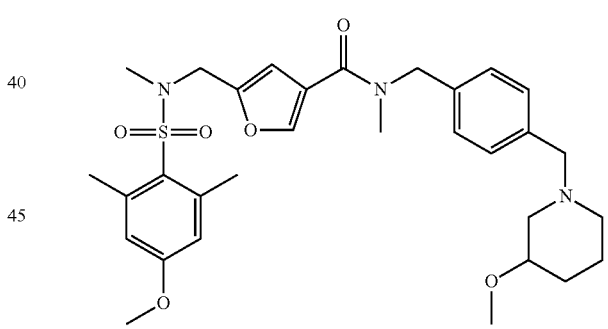

5-({[(4-Methoxy-2,6-dimethylphenyl)sulfonyl](methyl)amino}methyl)-N-{4-[(3-methoxypiperidin-1-yl)methyl]benzyl}-N-methylfuran-3-carboxamide Ex 130

The title compound was prepared according to general procedure BH using 5-({[(4-methoxy-2,6-dimethylphenyl)sulfonyl](methyl)amino}methyl)furan-3-carboxylic acid (40 mg, 0.11 mmol), EDCI (30 mg, 0.16 mmol), HOBt (23 mg, 0.17 mmol), DIPEA (0.04 mL, 0.22 mmol), 1-{4-[(3-methoxypiperidin-1-yl)methyl]phenyl}-N-methylmethanamine dihydrochloride (39 mg, 0.13 mmol) and DCM (10 mL).

Yield: 22 mg, 33%.

LCMS method C: rt 3.28 min, 98%; m/z 584.25 (MH+, 100%).

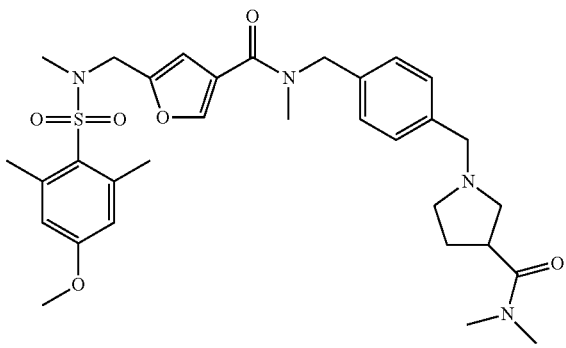 [SMILES: COc1cc(C)c(S(=O)(=O)N(C)Cc2cc(C(=O)N(C)Cc3ccc(CN4CCC(C(=O)N(C)C)C4)cc3)co2)c(C)c1]

1-(4-{[{[5-({[(4-Methoxy-2,6-dimethylphenyl)sulfonyl](methyl)amino}methyl)furan-3-yl]carbonyl}(methyl)amino]methyl}benzyl)-N,N-dimethylpyrrolidine-3-carboxamide Ex 131

The title compound was prepared according to general procedure BH using 5-({[(4-methoxy-2,6-dimethylphenyl)sulfonyl](methyl)amino}methyl)furan-3-carboxylic acid (40 mg, 0.11 mmol), EDCI (29 mg, 0.15 mmol), HOBt (22 mg, 0.16 mmol), DIPEA (0.04 mL, 0.22 mmol), N,N-dimethyl-1-{4-[(methylamino)methyl]benzyl}pyrrolidine-3-carboxamide dihydrochloride (42 mg, 0.13 mmol) and DCM (5 mL).

Yield: 18 mg, 26%.

LCMS method C: rt 3.23 min, 97%; m/z 584.25 (MH$^+$, 100%).

Potency: A

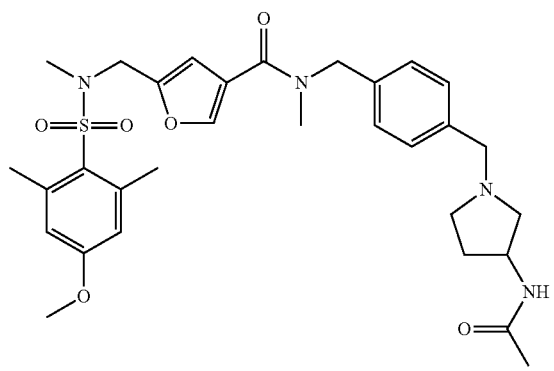 [SMILES: COc1cc(C)c(S(=O)(=O)N(C)Cc2cc(C(=O)N(C)Cc3ccc(CN4CCC(NC(C)=O)C4)cc3)co2)c(C)c1]

N-(4-{[3-(Acetylamino)pyrrolidin-1-yl]methyl}benzyl)-5-({[(4-methoxy-2,6-dimethylphenyl)sulfonyl](methyl)amino}methyl)-N-methylfuran-3-carboxamide Ex 132

The title compound was prepared according to general procedure BH using 5-({[(4-methoxy-2,6-dimethylphenyl)sulfonyl](methyl)amino}methyl)furan-3-carboxylic acid (80 mg, 0.22 mmol), EDCI (61 mg, 0.32 mmol), HOBt (45 mg, 0.34 mmol), DIPEA (0.08 mL, 0.45 mmol), N-(1-{4-[(methylamino)methyl]benzyl}pyrrolidin-3-yl)acetamide dihydrochloride (36 mg, 0.13 mmol) and DCM (20 mL).

Yield: 27 mg, 20%.

LCMS method C: rt 3.44 min, 90%; m/z 597.04 (MH$^+$, 100%).

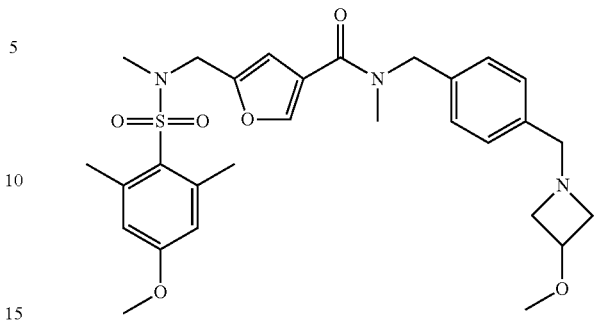

N-{4-[(3-Methoxyazetidin-1-yl)methyl]benzyl}-5-({[(4-methoxy-2,6-dimethylphenyl)sulfonyl](methyl)amino}methyl)-N-methylfuran-3-carboxamide Ex 133

The title compound was prepared according to general procedure BH using 5-({[(4-methoxy-2,6-dimethylphenyl)sulfonyl](methyl)amino}methyl)furan-3-carboxylic acid (40 mg, 0.11 mmol), EDCI (29 mg, 0.15 mmol), HOBt (22 mg, 0.16 mmol), DIPEA (0.04 mL, 0.22 mmol), 1-{4-[(3-methoxyazetidin-1-yl)methyl]phenyl}-N-methylmethanamine dihydro chloride (35 mg, 0.13 mmol) and DCM (5 mL).

Yield: 35 mg, 55%.

LCMS method C: rt 3.28 min, 96%; m/z 556.31 (MH$^+$, 100%).

Potency: A

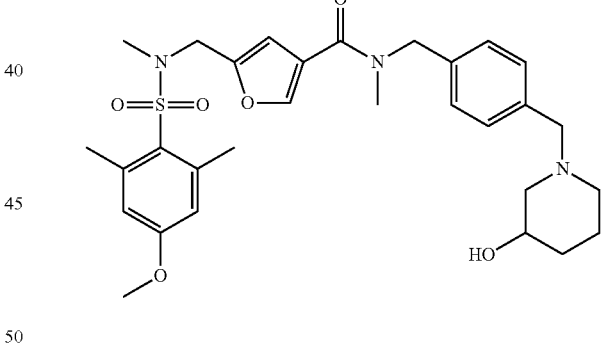

N-{4-[(3-Hydroxypiperidin-1-yl)methyl]benzyl}-5-({[(4-methoxy-2,6-dimethylphenyl)sulfonyl](methyl)amino}methyl)-N-methylfuran-3-carboxamide Ex 134

The title compound was prepared according to general procedure BH using 5-{[(4-methoxy-2,6-dimethyl-benzenesulfonyl)-methyl-amino]-methyl}-furan-3-carboxylic acid (30 mg, 0.08 mmol), EDCI (23 mg, 0.12 mmol), HOBt (17 mg, 0.13 mmol) DIPEA (0.03 mL, 0.17 mmol), [4-(3-1-(4-methylaminomethyl-benzyl)-piperidin-3-ol hydrochloride (29 mg, 0.10 mmol) and DCM (10 mL).

Yield: 40 mg, 83%.

LCMS method C: rt 3.16 min, 99%; m/z 570.25 (MH$^+$, 100%).

Potency: C

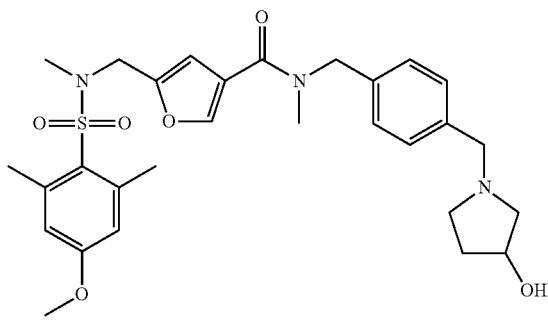 [SMILES: COc1cc(C)c(S(=O)(=O)N(C)Cc2cc(C(=O)N(C)Cc3ccc(CN4CCC(O)C4)cc3)co2)c(C)c1]

N-{4-[(3-Hydroxypyrrolidin-1-yl)methyl]benzyl}-5-({[(4-methoxy-2,6-dimethylphenyl)sulfonyl](methyl)amino}methyl)-N-methylfuran-3-carboxamide Ex 135

The title compound was prepared according to general procedure BH using 5-{[(4-methoxy-2,6-dimethyl-benzenesulfonyl)-methyl-amino]-methyl}-furan-3-carboxylic acid (35 mg, 0.10 mmol), EDCI (27 mg, 0.14 mmol), HOBt (20 mg, 0.15 mmol), DIPEA (0.03 mL, 0.20 mmol), 1-(4-methylaminomethyl-benzyl)-pyrrolidin-3-ol hydrochloride (30 mg, 0.10 mmol) and DCM (10 mL).

Yield: 45 mg, 82%.

LCMS method C: rt 3.14 min, 96%; m/z 556.22 (MH+, 100%).

Potency: B

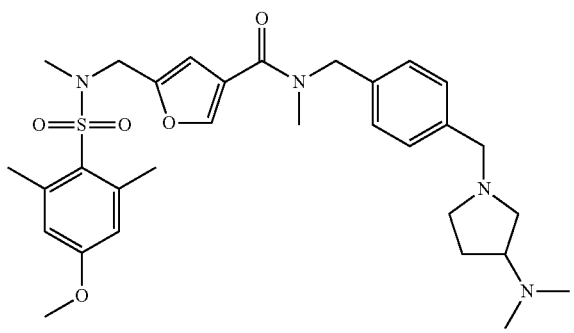

N-(4-{[3-(Dimethylamino)pyrrolidin-1-yl]methyl}benzyl)-5-({[(4-methoxy-2,6-dimethylphenyl)sulfonyl](methyl)amino}methyl)-N-methylfuran-3-carboxamide Ex 136

The title compound was prepared according to general procedure BH using 5-{[(4-methoxy-2,6-dimethyl-benzenesulfonyl)-methyl-amino]-methyl}-furan-3-carboxylic acid (35 mg, 0.10 mmol), EDCI (27 mg, 0.14 mmol), HOBt (20 mg, 0.15 mmol), DIPEA (0.03 mL, 0.20 mmol), dimethyl-[1-(4-methylaminomethyl-benzyl)-pyrrolidin-3-yl]-amine hydrochloride (30 mg, 0.09 mmol) and DCM (10 mL).

Yield: 40 mg, 69%.

LCMS method C: rt 2.81 min, 98%; m/z 292.22 ([M+2H]$^{2+}$, 100%), 583.26 (MH+, 49%).

Potency: B

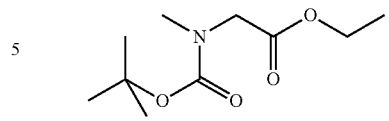

Ethyl[(tert-butoxycarbonyl)(methyl)amino]acetate

Int 187

Methylamino-acetic acid ethyl ester hydrochloride (5.0 g, 32.5 mmol) was dissolved in DMF (55 mL) and TEA (4.87 mL, 35.7 mmol) was added. The resulting solution was cooled to 0° C. and di-tert-butyl-dicarbonate (8.5 g, 39.1 mmol) was added portionwise over 5 min. The reaction was stirred at 0° C. for 30 min and at ambient temperature for 12 h. After completion of the reaction, water (50 mL) was added, followed by Et$_2$O (125 mL). The organic layer was separated, dried over Na$_2$SO$_4$ and concentrated in vacuo. The residue was purified by FCC eluting with 20-30% EtOAc in hexane to afford the title compound.

Yield: 6.46 g, 91%.

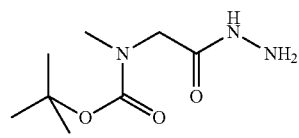

tert-Butyl (2-hydrazinyl-2-oxoethyl)methylcarbamate

Int 188

Ethyl[(tert-butoxycarbonyl)(methyl)amino]acetate (6.4 g, 29.5 mmol) was dissolved in EtOH (150 mL) and hydrazine hydrate (12.9 mL, 0.265 mol) added. The resulting solution was refluxed for 5 h. The reaction was cooled to ambient temperature and EtOH was removed in vacuo to afford the title compound, which was used without further purification.

Yield: 5.7 g, 95%.

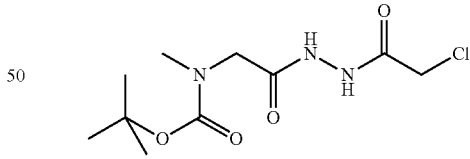

tert-Butyl {2-[2-(chloroacetyl)hydrazinyl]-2-oxoethyl}methylcarbamate

Int 189 tert-Butyl (2-hydrazinyl-2-oxoethyl)methylcarbamate (2.5 g, 12.3 mmol) was dissolved in MeCN (125 mL) and K$_2$CO$_3$ (3.37 g, 24.4 mmol) was added. The resulting solution was cooled to 0° C. and a solution of chloroacetyl chloride (1.5 g, 13.3 mmol) in MeCN (10 mL) was added. The reaction was stirred at 0° C. for 4.5 h. The mixture was quenched with water (125 mL) and extracted with EtOAc (2×250 mL). The combined organic extracts were dried over MgSO$_4$ and concentrated in vacuo. The residue was purified by FCC eluting with DCM:MeOH, 98:2 to afford the title compound.

Yield: 1.7 g, 49%.

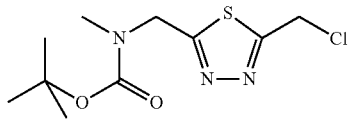 [SMILES: CN(Cc1nnc(CCl)s1)C(=O)OC(C)(C)C]

tert-Butyl {[5-(chloromethyl)-1,3,4-thiadiazol-2-yl]methyl}methylcarbamate

Int 190 tert-Butyl {2-[2-(chloroacetyl)hydrazinyl]-2-oxoethyl}methylcarbamate (2.0 g, 7.15 mmol) was dissolved in THF (50 mL) and the resulting solution cooled to 0° C. Lawesson's reagent (3.2 g, 7.9 mmol) was added and the reaction temperature increased to ambient temperature. After stirring for 16 h, the reaction was quenched with water (40 mL) and extracted with EtOAc (2×40 mL). The combined organic extracts were dried over $Na_2SO_4$ and concentrated in vacuo. The residue was purified by FCC eluting with 10% DCM in hexane to afford the title compound.

Yield: 1.4 g, 71%

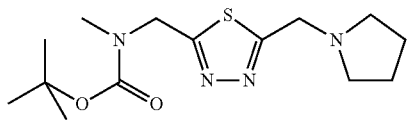 [SMILES: CN(Cc1nnc(CN2CCCC2)s1)C(=O)OC(C)(C)C]

tert-Butyl methyl{[5-(pyrrolidin-1-ylmethyl)-1,3,4-thiadiazol-2-yl]methyl}carbamate Int 191 tert-Butyl {[5-(chloromethyl)-1,3,4-thiadiazol-2-yl]methyl}methylcarbamate (1.4 g, 5.04 mmol) was dissolved in DCM (100 mL) and DIPEA (1.76 mL, 10.08 mmol) was added. The resulting solution was cooled to 0° C. and a solution of pyrrolidine (0.5 mL, 6.05 mmol) in DCM (5 mL) was slowly added. Upon complete addition of the amine the reaction was stirred at ambient temperature for 16 h. Water (125 mL) was added and the mixture was extracted with DCM (2×200 mL). The combined organic extracts were dried over $Na_2SO_4$ and concentrated in vacuo. The residue was purified by FCC eluting with 1% MeOH in DCM to afford the title compound.

Yield: 550 mg, 35%

$^1$H NMR (300 MHz, $CDCl_3$) δ ppm 4.76 (2H, br s), 4.05 (2H, s), 2.92 (3H, br s), 2.64 (4H, m), 1.81 (4H, m), 1.49 (9H, s).

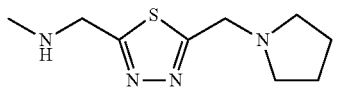

N-Methyl-1-[5-(pyrrolidin-1-ylmethyl)-1,3,4-thiadiazol-2-yl]methanamine dihydrochloride Int 192 tert-Butyl methyl{[5-(pyrrolidin-1-ylmethyl)-1,3,4-thiadiazol-2-yl]methyl}carbamate (100 mg, 0.32 mmol) was dissolved in a 4 M solution of HCl in 1,4-dioxane (5 mL). The reaction was stirred at ambient temperature for 16 h. Dioxane was removed in vacuo and the residue was dissolved in DCM with a drop of DMF. By addition of n-pentane a solid formed, which was filtered off to afford the title compound. No further purification was required.

Yield: 60 mg, 66%.

$^1$H NMR (300 MHz, DMSO) δ ppm 11.97 (1H, br s), 9.94 (2H, br s), 4.97 (2H, s), 4.70 (2H, s), 3.37 (4H, m), 2.63 (3H, s), 1.96 (4H, m).

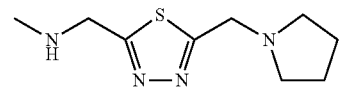

N-Methyl-1-[5-(pyrrolidin-1-ylmethyl)-1,3,4-thiadiazol-2-yl]methanamine bis trifluoroacetate Int 193 tert-Butyl methyl{[5-(pyrrolidin-1-ylmethyl)-1,3,4-thiadiazol-2-yl]methyl}carbamate (100 mg, 0.32 mmol) was dissolved in a 1:3 mixture of TFA:DCM (2 mL). The reaction was stirred at ambient temperature for 1 h and concentrated in vacuo to afford the title compound.

No further purification was required.

Yield: 145 mg, 100%

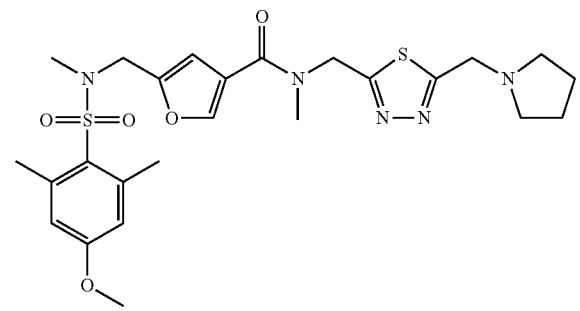 [SMILES: COc1cc(C)c(S(=O)(=O)N(C)Cc2cc(C(=O)N(C)Cc3nnc(CN4CCCC4)s3)co2)c(C)c1]

5-({[(4-Methoxy-2,6-dimethylphenyl)sulfonyl](methyl)amino}methyl)-N-methyl-N-{[5-(pyrrolidin-1-ylmethyl)-1,3,4-thiadiazol-2-yl]methyl}furan-3-carboxamide Ex 137

N-methyl-1-[5-(pyrrolidin-1-ylmethyl)-1,3,4-thiadiazol-2-yl]methanamine dihydrochloride (25 mg, 0.087 mmol) was dissolved in DCM (5 mL), on addition of DIPEA (0.03 mL, 0.17 mmol). 5-({[(4-methoxy-2,6-dimethylphenyl)sulfonyl](methyl)amino}methyl)furan-3-carboxylic acid (30 mg, 0.09 mmol) and HOBt (17 mg, 0.12 mmol) were added and the resulting solution was cooled to 0° C. prior to the addition of EDCI (24 mg, 0.13 mmol). The mixture was stirred at ambient temperature for 7 h, quenched with saturated aqueous $NaHCO_3$ (3 mL) and extracted with DCM (2×10 mL). The combined organic extracts were dried over $Na_2SO_4$ and concentrated in vacuo. The residue was purified by FCC eluting with 2% MeOH in DCM to afford the title compound.

Yield: 25 mg, 54%.

LCMS method C: rt 3.09 min, 97%; m/z 548.30 ($MH^+$, 100%).

Potency: A

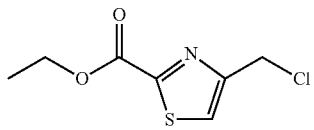

Ethyl 4-(chloromethyl)-1,3-thiazole-2-carboxylate

Int 194

Ethyl thiooxamate (2.5 g, 18.8 mmol) was dissolved in EtOH (50 mL) and 1,3-dichloroacetone (2.62 g, 20.6 mmol) was added. The resulting solution was refluxed for 15 h. The reaction was cooled and EtOH was removed in vacuo. The residue was diluted with water (100 mL) and extracted with DCM (2×100 mL). The combined organic extracts were dried over $Na_2SO_4$ and concentrated in vacuo. The residue was purified by FCC eluting with 4% EtOAc in hexane to afford the title compound.
Yield: 1.5 g, 39%.
$^1$H NMR (300 MHz, $CDCl_3$) δ ppm 7.64 (1H, s), 4.78 (2H, s), 4.49 (2H, q, J=6 Hz), 1.45 (3H, t, J=6 Hz).

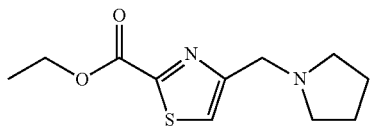 [SMILES: CCOC(=O)c1nc(CN2CCCC2)cs1]

Ethyl 4-(pyrrolidin-1-ylmethyl)-1,3-thiazole-2-carboxylate

Int 195

Pyrrolidine (0.44 mL, 5.35 mmol) was dissolved in DCM (50 mL) and DIPEA (1.6 mL, 9.71 mmol) was added. The resulting solution was stirred at ambient temperature for 20 min and cooled to 0° C. prior to the addition of ethyl 4-(chloromethyl)-1,3-thiazole-2-carboxylate (1.0 g, 4.86 mmol). The temperature was increased to ambient temperature and the reaction was stirred for 3 days. The DCM was removed in vacuo and the residue was diluted with water (25 mL) and extracted with EtOAc (2×50 mL). The combined organic extracts were dried over $Na_2SO_4$ and concentrated in vacuo. The resulting oil was purified by FCC eluting with 3% MeOH in DCM to afford the title compound as a brown oil.
Yield: 1.0 g, 85%.
$^1$H NMR (300 MHz, $CDCl_3$) δ ppm 7.49 (1H, s), 4.49 (2H, q, J=7.2 Hz), 3.90 (2H, s), 2.61 (4H, m), 1.79 (4H, m), 1.45 (3H, t, J=7.2 Hz).

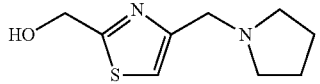 [SMILES: OCc1nc(CN2CCCC2)cs1]

[4-(Pyrrolidin-1-ylmethyl)-1,3-thiazol-2-yl]methanol

Int 196

Ethyl 4-(pyrrolidin-1-ylmethyl)-1,3-thiazole-2-carboxylate (0.1 g, 0.42 mmol) was dissolved in EtOH (10 mL) and $NaBH_4$ (47 mg, 1.23 mmol) was added. The reaction was heated at 70° C. for 2 h, cooled to ambient temperature and concentrated in vacuo. The residue was purified by FCC eluting with 7% MeOH in DCM to afford the title compound.
Yield: 60 mg, 72%.

$^1$H NMR (300 MHz, $CDCl_3$) δ ppm 7.26 (1H, s), 4.90 (2H, s), 3.82 (2H, s), 3.40 (1H, br s), 2.68 (4H, m), 1.85 (4H, m).

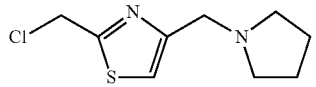 [SMILES: ClCc1nc(CN2CCCC2)cs1]

2-(Chloromethyl)-4-(pyrrolidin-1-ylmethyl)-1,3-thiazole

Int 197

[4-(pyrrolidin-1-ylmethyl)-1,3-thiazol-2-yl]methanol (0.5 g, 2.52 mmol) was dissolved in DCM (50 mL) and the resulting solution was cooled to 0° C. Thionyl chloride (0.9 g, 7.56 mmol) was added slowly and the reaction was stirred at 0° C. for 30 min. The reaction temperature was increased slowly to ambient temperature. After 2 h the DCM was removed in vacuo. The resulting residue was diluted with saturated aqueous $NaHCO_3$ (50 mL) and extracted with DCM (2×100 mL). The combined organic extracts were dried over $Na_2SO_4$ and concentrated in vacuo to afford the title compound which was used without further purification.
Yield: 500 mg, 91%.
$^1$H NMR (300 MHz, $CDCl_3$) δ ppm 7.18 (1H, s), 4.84 (2H, s), 3.76 (2H, s), 2.58 (4H, m), 1.81 (4H, m).

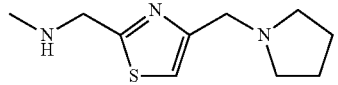

N-Methyl-1-[4-(pyrrolidin-1-ylmethyl)-1,3-thiazol-2-yl]methanamine

Int 198

2-(chloromethyl)-4-(pyrrolidin-1-ylmethyl)-1,3-thiazole (50 mg, 0.23 mmol) was dissolved in EtOH (10 mL) and a solution of methyl amine (8 M in EtOH, 0.29 mL) was added. The reaction was stirred at ambient temperature for 2 days. EtOH was removed in vacuo and the residue was purified by FCC eluting with $DCM:MeOH:NH_3$, 95:4:1 to afford the title compound as a pale yellow oil.
Yield: 23 mg, 47%.
$^1$H NMR (300 MHz, $CDCl_3$) δ ppm 7.05 (1H, s), 4.06 (2H, s), 3.74 (2H, s), 2.58 (4H, m), 2.52 (3H, s), 1.81 (4H, m)

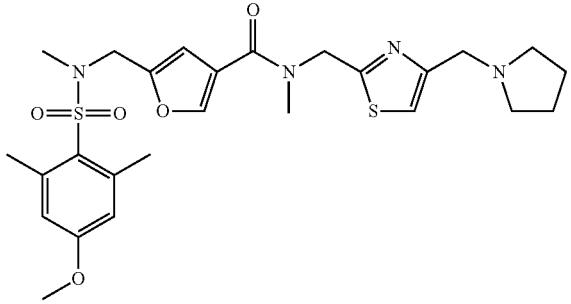 [SMILES: COc1cc(C)c(S(=O)(=O)N(C)Cc2cc(C(=O)N(C)Cc3nc(CN4CCCC4)cs3)co2)c(C)c1]

5-({[(4-Methoxy-2,6-dimethylphenyl)sulfonyl](methyl)amino}methyl)-N-methyl-N-{[4-(pyrrolidin-1-ylmethyl)-1,3-thiazol-2-yl]methyl}furan-3-carboxamide Ex 138

5-({[(4-methoxy-2,6-dimethylphenyl)sulfonyl](methyl)amino}methyl)furan-3-carboxylic acid (30 mg, 0.085 mmol) was dissolved in DCM (10 mL) and EDCI (30 mg, 0.15 mmol) and HOBt (21 mg, 0.15 mmol) were added. The resulting solution was stirred for 45 min prior to the addition of a solution of N-methyl-1-[4-(pyrrolidin-1-ylmethyl)-1,3-thiazol-2-yl]methanamine (26 mg, 0.12 mmol) in DCM (2 mL). The reaction was stirred at ambient temperature for 5 h, saturated aqueous NaHCO₃ (15 mL) was added and the mixture was extracted with DCM (3×15 mL). The combined organic extracts were dried over Na₂SO₄ and concentrated in vacuo. The residue was purified by FCC eluting with 3% MeOH in DCM. A portion of the resulting product was purified by prep method B to afford the title compound.

Yield: 10 mg, 21%.
LCMS method C: rt 3.16 min, 83%; m/z 547.14 (MH⁺, 100%).
Potency: C

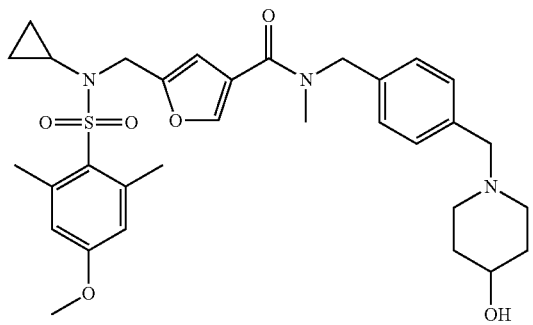 [SMILES: COc1cc(C)c(S(=O)(=O)N(Cc2cc(C(=O)N(C)Cc3ccc(CN4CCC(O)CC4)cc3)co2)C2CC2)c(C)c1]

5-({Cyclopropyl[(4-methoxy-2,6-dimethylphenyl) sulfonyl]amino}methyl)-N-{4-[(4-hydroxypiperidin-1-yl)methyl]benzyl}-N-methylfuran-3-carboxamide Ex 139

The title compound was prepared according to general procedure BH using 5-({cyclopropyl[(4-methoxy-2,6-dimethylphenyl)sulfonyl]amino}methyl)furan-3-carboxylic acid (40 mg, 0.105 mmol), EDCI (29 mg, 0.15 mmol), HOBt (22 mg, 0.16 mmol), DIPEA (0.04 mL, 0.22 mmol), 1-{4-[(methylamino)methyl]benzyl}piperidin-4-ol dihydrochloride (34 mg, 0.13 mmol) and DCM (10 mL).

Yield: 40 mg, 63%.
LCMS method C: rt 3.32 min, 99%; m/z 596.22 (MH⁺, 100%).
Potency: B

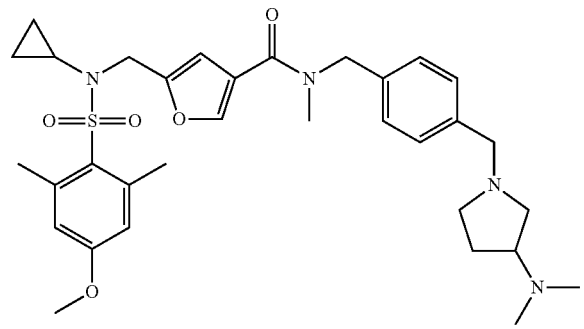

5-({Cyclopropyl[(4-methoxy-2,6-dimethylphenyl) sulfonyl]amino}methyl)-N-(4-{[3-(dimethylamino) pyrrolidin-1-yl]methyl}benzyl)-N-methylfuran-3-carboxamide Ex 140

The title compound was prepared according to general procedure BH using 5-({cyclopropyl[(4-methoxy-2,6-dimethylphenyl)sulfonyl]amino}methyl)furan-3-carboxylic acid (40 mg, 0.105 mmol), EDCI (29 mg, 0.15 mmol), HOBt (22 mg, 0.16 mmol), DIPEA (0.04 mL, 0.22 mmol), N,N-dimethyl-1-{4-[(methylamino)methyl]benzyl}pyrrolidin-3-amine trihydrochloride (34 mg, 0.13 mmol) and DCM (10 mL).

Yield: 35 mg, 55%.
LCMS method C: rt 2.94 min, 99%; m/z 609.26 (MH⁺, 49%), 305.30 ([M+2H]²⁺, 100%).
Potency: B

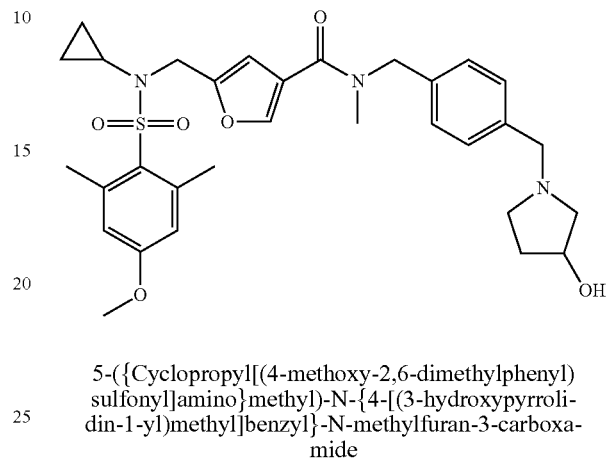

5-({Cyclopropyl[(4-methoxy-2,6-dimethylphenyl) sulfonyl]amino}methyl)-N-{4-[(3-hydroxypyrrolidin-1-yl)methyl]benzyl}-N-methylfuran-3-carboxamide Ex 141

The title compound was prepared according to general procedure BH using 5-({cyclopropyl[(4-methoxy-2,6-dimethylphenyl)sulfonyl]amino}methyl)furan-3-carboxylic acid (40 mg, 0.105 mmol), EDCI (28 mg, 0.158 mmol), HOBt (21 mg, 0.16 mmol), DIPEA (0.036 mL, 0.21 mmol), 1-{4-[(methylamino)methyl]benzyl}pyrrolidin-3-ol dihydrochloride (34 mg, 0.13 mmol) and DCM (10 mL).

Yield: 35 mg, 56%.
LCMS method C: rt 3.28 min, 96%; m/z 582.23 (MH⁺, 100%).
Potency: B

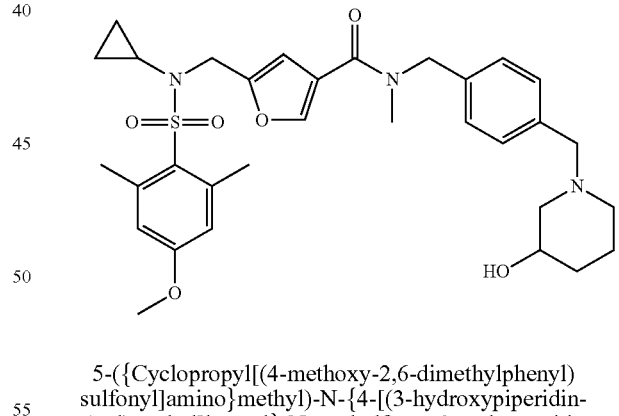

5-({Cyclopropyl[(4-methoxy-2,6-dimethylphenyl) sulfonyl]amino}methyl)-N-{4-[(3-hydroxypiperidin-1-yl)methyl]benzyl}-N-methylfuran-3-carboxamide Ex 142

The title compound was prepared according to general procedure BH using 5-({cyclopropyl[(4-methoxy-2,6-dimethylphenyl)sulfonyl]amino}methyl)furan-3-carboxylic acid (40 mg, 0.105 mmol), EDCI (28 mg, 0.158 mmol), HOBt (21 mg, 0.16 mmol), DIPEA (0.036 mL, 0.21 mmol), 1-{4-[(methylamino)methyl]benzyl}piperidin-3-ol dihydrochloride (34 mg, 0.13 mmol) and DCM (10 mL).

Yield: 35 mg, 56%.
LCMS method C: rt 3.30 min, 97%; m/z 596.22 (MH⁺, 100%).

Potency: C

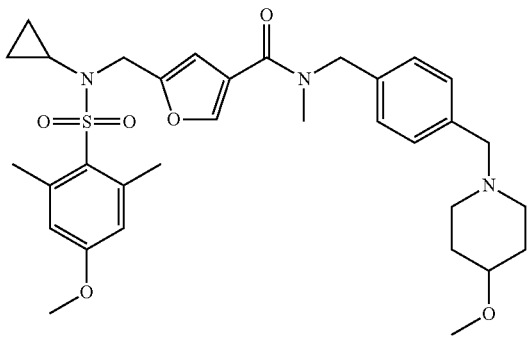 [SMILES: COc1cc(C)c(S(=O)(=O)N(Cc2cc(C(=O)N(C)Cc3ccc(CN4CCC(OC)CC4)cc3)co2)C2CC2)c(C)c1]

5-({Cyclopropyl[(4-methoxy-2,6-dimethylphenyl)sulfonyl]amino}methyl)-N-{4-[(4-methoxypiperidin-1-yl)methyl]benzyl}-N-methylfuran-3-carboxamide Ex 143

The title compound was prepared according to general procedure BH using 5-({cyclopropyl[(4-methoxy-2,6-dimethylphenyl)sulfonyl]amino}methyl)furan-3-carboxylic acid (40 mg, 0.105 mmol), EDCI (28 mg, 0.158 mmol), HOBt (21 mg, 0.16 mmol), DIPEA (0.04 mL, 0.21 mmol), 1-{4-[(4-methoxypiperidin-1-yl)methyl]phenyl}-N-methyl-methanamine dihydrochloride (36 mg, 0.13 mmol) and DCM (10 mL).

Yield: 22 mg, 34%.

LCMS method C: rt 3.40 min, 97%; m/z 610.26 (MH$^+$, 100%).

Potency: B

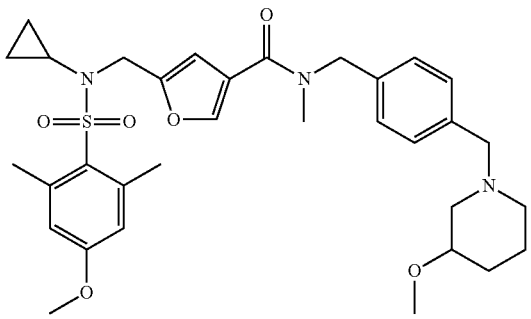 [SMILES: COc1cc(C)c(S(=O)(=O)N(Cc2cc(C(=O)N(C)Cc3ccc(CN4CCCC(OC)C4)cc3)co2)C2CC2)c(C)c1]

5-({Cyclopropyl[(4-methoxy-2,6-dimethylphenyl)sulfonyl]amino}methyl)-N-{4-[(3-methoxypiperidin-1-yl)methyl]benzyl}-N-methylfuran-3-carboxamide Ex 144

The title compound was prepared according to general procedure BH using 5-({cyclopropyl[(4-methoxy-2,6-dimethylphenyl)sulfonyl]amino}methyl)furan-3-carboxylic acid (40 mg, 0.105 mmol), EDCI (28 mg, 0.158 mmol), HOBt (21 mg, 0.16 mmol), DIPEA (0.04 mL, 0.21 mmol), 1-{4-[(3-methoxypiperidin-1-yl)methyl]phenyl}-N-methyl-methanamine dihydrochloride (36 mg, 0.13 mmol) and DCM (10 mL).

Yield: 20 mg, 31%.

LCMS method C: rt 3.55 min, 97%; m/z 610.26 (MH$^+$, 100%).

Potency: A

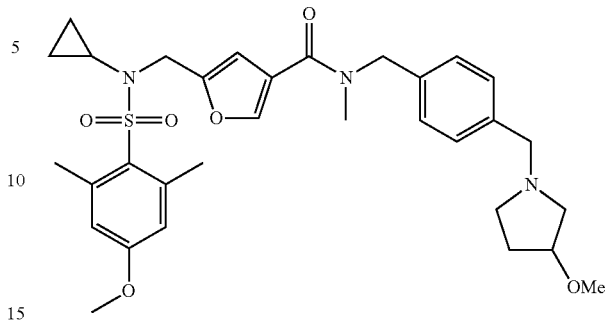

5-({Cyclopropyl[(4-methoxy-2,6-dimethylphenyl)sulfonyl]amino}methyl)-N-{4-[(3-methoxypyrrolidin-1-yl)methyl]benzyl}-N-methylfuran-3-carboxamide Ex 145

The title compound was prepared according to general procedure BH using 5-({cyclopropyl[(4-methoxy-2,6-dimethylphenyl)sulfonyl]amino}methyl)furan-3-carboxylic acid (40 mg, 0.105 mmol), EDCI (28 mg, 0.158 mmol), HOBt (21 mg, 0.16 mmol), DIPEA (0.04 mL, 0.21 mmol), 1-{4-[(3-methoxypyrrolidin-1-yl)methyl]phenyl}-N-methyl-methanamine dihydrochloride (36 mg, 0.13 mmol) and DCM (10 mL).

Yield: 35 mg, 55%.

LCMS method C: rt 3.28 min, 98%; m/z 584.25 (MH$^+$, 100%).

Potency: B

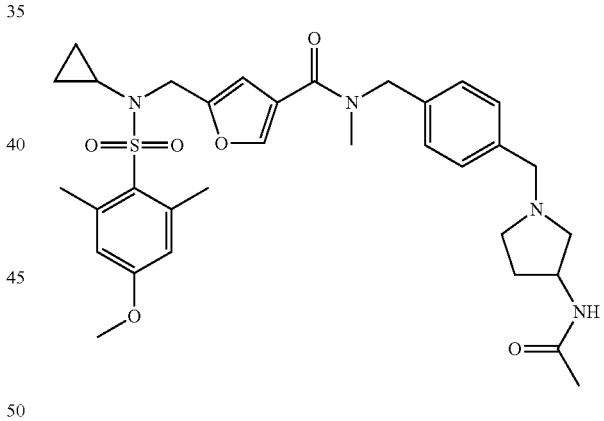

N-(4-{[3-(Acetylamino)pyrrolidin-1-yl]methyl}benzyl)-5-({cyclopropyl[(4-methoxy-2,6-dimethylphenyl)sulfonyl]amino}methyl)-N-methyl-furan-3-carboxamide Ex 146

The title compound was prepared according to general procedure BH using 5-({cyclopropyl[(4-methoxy-2,6-dimethylphenyl)sulfonyl]amino}methyl)furan-3-carboxylic acid (40 mg, 0.105 mmol), EDCI (28 mg, 0.158 mmol), HOBt (21 mg, 0.16 mmol), DIPEA (0.04 mL, 0.21 mmol), 1-(4-methylaminomethyl-benzyl)-pyrrolidine-3-carboxylic acid dimethylamide-amine hydrochloride (36 mg, 0.13 mmol) and DCM (10 mL).

Yield: 30 mg, 46%.

LCMS method C: rt 3.26 min, 92%; m/z 623.30 (MH$^+$, 100%).

Potency: A

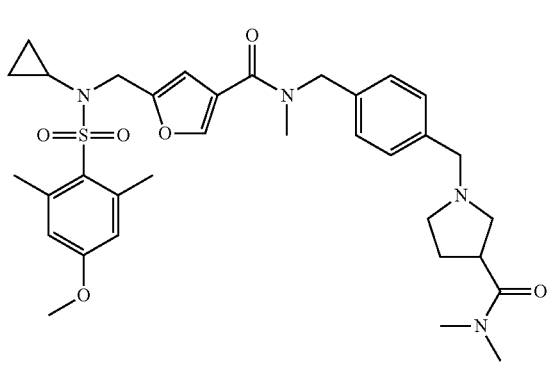 [SMILES: COc1cc(C)c(S(=O)(=O)N(Cc2cc(C(=O)N(C)Cc3ccc(CN4CCC(C(=O)N(C)C)C4)cc3)co2)C2CC2)c(C)c1]

1-(4-{[{[5-({Cyclopropyl[(4-methoxy-2,6-dimethylphenyl)sulfonyl]amino}methyl)furan-3-yl]carbonyl}(methyl)amino]methyl}benzyl)-N,N-dimethylpyrrolidine-3-carboxamide Ex 147

The title compound was prepared according to general procedure BH using 5-({cyclopropyl[(4-methoxy-2,6-dimethylphenyl)sulfonyl]amino}methyl)furan-3-carboxylic acid (40 mg, 0.105 mmol), EDCI (28 mg, 0.158 mmol), HOBt (21 mg, 0.16 mmol), DIPEA (0.04 mL, 0.21 mmol), N,N-dimethyl-1-{4-[(methylamino)methyl]benzyl}pyrrolidine-3-carboxamide dihydrochloride (40 mg, 0.12 mmol) and DCM (5 mL).

Yield: 30 mg, 45%.

LCMS method C: rt 3.31 min, 97%; m/z 637.34 (MH+, 100%).

Potency: B

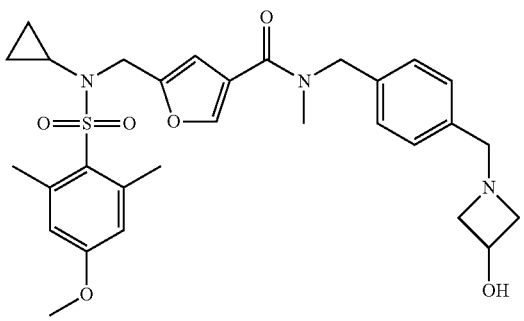 [SMILES: COc1cc(C)c(S(=O)(=O)N(Cc2cc(C(=O)N(C)Cc3ccc(CN4CC(O)C4)cc3)co2)C2CC2)c(C)c1]

5-({Cyclopropyl[(4-methoxy-2,6-dimethylphenyl)sulfonyl]amino}methyl)-N-{4-[(3-hydroxyazetidin-1-yl)methyl]benzyl}-N-methylfuran-3-carboxamide Ex 148

The title compound was prepared according to general procedure BH using 5-({cyclopropyl[(4-methoxy-2,6-dimethylphenyl)sulfonyl]amino}methyl)furan-3-carboxylic acid (40 mg, 0.105 mmol), EDCI (28 mg, 0.158 mmol), HOBt (21 mg, 0.16 mmol), DIPEA (0.04 mL, 0.21 mmol), 1-{4-[(methylamino)methyl]benzyl}azetidin-3-ol dihydrochloride (40 mg, 0.12 mmol) and DCM (10 mL).

Yield: 20 mg, 32%.

LCMS method C: rt 3.27 min, 95%; m/z 568.25 (MH+, 100%).

Potency: B

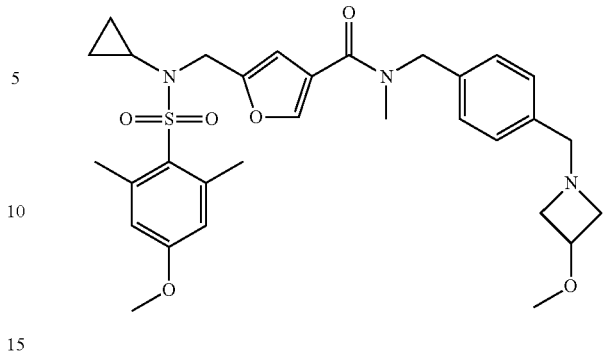

5-({Cyclopropyl[(4-methoxy-2,6-dimethylphenyl)sulfonyl]amino}methyl)-N-{4-[(3-methoxyazetidin-1-yl)methyl]benzyl}-N-methylfuran-3-carboxamide Ex 149

The title compound was prepared according to general procedure BH using 5-({cyclopropyl[(4-methoxy-2,6-dimethylphenyl)sulfonyl]amino}methyl)furan-3-carboxylic acid (45 mg, 0.12 mmol), EDCI (32 mg, 0.168 mmol), HOBt (24 mg, 0.18 mmol), DIPEA (0.04 mL, 0.24 mmol), 1-{4-[(3-methoxyazetidin-1-yl)methyl]phenyl}-N-methylmethanamine dihydrochloride (37 mg, 0.14 mmol) and DCM (10 mL).

Yield: 34 mg, 55%.

LCMS method C: rt 3.40 min, 100%; m/z 582.38 (MH+, 100%).

Potency: A

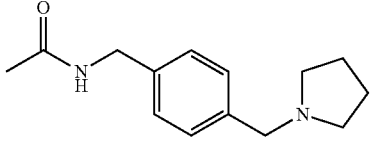 [SMILES: CC(=O)NCc1ccc(CN2CCCC2)cc1]

N-[4-(Pyrrolidin-1-ylmethyl)benzyl]acetamide

Int 199

1-[4-(pyrrolidin-1-ylmethyl)phenyl]methanamine (100 mg, 0.526 mmol), Ac$_2$O (0.1 mL, 1.06 mmol) and TEA (0.146 mL, 1.05 mmol) were stirred at ambient temperature in DCM (3 mL) for 18 h. The mixture was partitioned between saturated brine (50 mL) and EtOAc (3×50 mL) and the combined organic extracts were washed with brine (100 mL), then dried over MgSO$_4$. The solvent was removed in vacuo to afford the title compound as a colourless oil.

No further purification was performed.

$^1$H NMR (250 MHz, CD$_3$OD): δ ppm 7.23-7.35 (4H, m), 4.34 (2H, s), 3.65 (2H, s), 2.53-2.63 (4H, m), 1.98 (3H, s), 1.78-1.85 (4H, m)

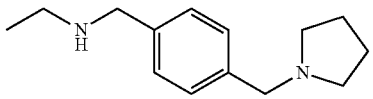 [SMILES: CCNCc1ccc(CN2CCCC2)cc1]

N-[4-(Pyrrolidin-1-ylmethyl)benzyl]ethanamine trifluoroacetate

Int 200

N-[4-(pyrrolidin-1-ylmethyl)benzyl]acetamide (100 mg, 0.43 mmol) was dissolved in anhydrous THF (4 mL) and the solution was cooled to 0° C. Borane (2 M in THF, 0.86 mL) was added dropwise and the reaction was stirred and allowed to warm to ambient temperature over 18 h. The reaction was then heated to 60° C. for 4 h. The reaction was quenched with 5 mL MeOH and concentrated, then partitioned between saturated aqueous NaHCO₃ (20 mL) and EtOAc (3×20 mL). The combined organic extracts were dried over MgSO₄ and concentrated in vacuo. The crude product was purified using prep method A to afford the title compound.

Yield: 16 mg, 17%

LCMS Method A: rt 0.91 min, 100%; m/z 219.05 (MH⁺, 100%)

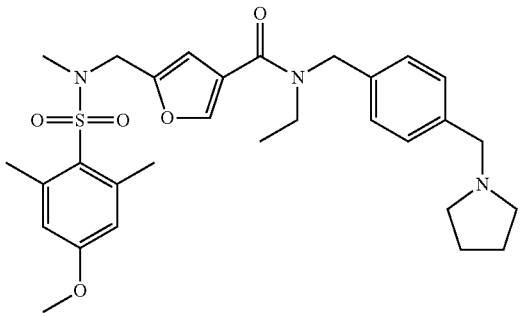 [SMILES: CCN(Cc1ccc(CN2CCCC2)cc1)C(=O)c1coc(CN(C)S(=O)(=O)c2c(C)cc(OC)cc2C)c1]

N-Ethyl-5-({[(4-methoxy-2,6-dimethylphenyl)sulfonyl](methyl)amino}methyl)-N-[4-(pyrrolidin-1-ylmethyl)benzyl]furan-3-carboxamide trifluoroacetate Ex 150

The title compound was prepared according to general procedure AC using 5-({[(4-Methoxy-2,6-dimethylphenyl)sulfonyl](methyl)amino}methyl)furan-3-carboxylic acid (25 mg, 0.07 mmol), EDCI (16 mg, 0.08 mmol), HOBt monohydrate (12 mg, 0.09 mmol), DIPEA (0.013 mL, 0.07 mmol) and N-[4-(pyrrolidin-1-ylmethyl)benzyl]ethanamine (16 mg, 0.07 mmol) in DMF (3 mL). A portion of the crude product was purified using prep method A.

LCMS Method C: rt 3.34 min, 100%; m/z 554.15 (MH⁺, 100%)

Potency: B

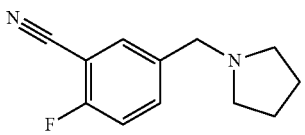 [SMILES: N#Cc1cc(CN2CCCC2)ccc1F]

2-Fluoro-5-(pyrrolidin-1-ylmethyl)benzonitrile

Int 201

2-Fluoro-5-formylbenzonitrile (200 mg, 1.34 mmol), pyrrolidine (0.109 mL, 1.33 mmol), STAB (284 mg, 1.34 mmol) and acetic acid (0.01 mL, 0.017 mmol) were stirred at ambient temperature in DCE (10 mL) for 2 h. The mixture was partitioned between saturated aqueous NaHCO₃ (10 mL) and DCM (3×15 mL) and the combined organic extracts were dried over MgSO₄. The solvent was removed in vacuo and the crude product was purified using FCC eluting with 20% EtOAc in heptane to afford the title compound.

Yield: 175 mg, 64%

¹H NMR (500 MHz, CDCl₃): δ ppm 7.63 (1H, dd, J 6.1, 1.7 Hz), 7.59 (1H, br s), 7.17 (1H, t, J=8.6 Hz), 3.62 (2H, s), 2.51 (4H, t, J=6.0 Hz), 1.77-1.87 (4H, m)

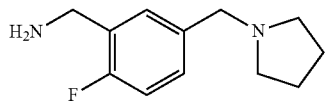 [SMILES: NCc1cc(CN2CCCC2)ccc1F]

1-[2-Fluoro-5-(pyrrolidin-1-ylmethyl)phenyl]methanamine

Int 202

2-Fluoro-5-(pyrrolidin-1-ylmethyl)benzonitrile (175 mg, 0.86 mmol) was dissolved in anhydrous THF (3 mL) under N₂ and the solution was cooled to 0° C. LiAlH₄ solution (1 M in THF, 0.95 mL) was added and the reaction was stirred and allowed to warm to ambient temperature over 3 h. MeOH (1 mL) was added and the reaction was concentrated in vacuo and partitioned between 1:1 saturated aqueous NaHCO₃:30% aqueous Rochelle's salt (30 mL) and DCM (3×30 mL) and the combined organic extracts were dried over MgSO₄ and concentrated in vacuo to afford the title compound. No further purification was required.

Yield: 83 mg, 46%

¹H NMR (500 MHz, CD₃OD): δ ppm 7.39 (1H, dd, J 7.3, 1.8 Hz), 7.28 (1H, ddd, J 8.0, 5.3, 2.2 Hz), 7.05 (1H, dd, J 9.9, 8.5 Hz), 3.85 (2H, s), 3.64 (2H, s), 2.52-2.61 (4H, m), 1.79-1.86 (4H, m)

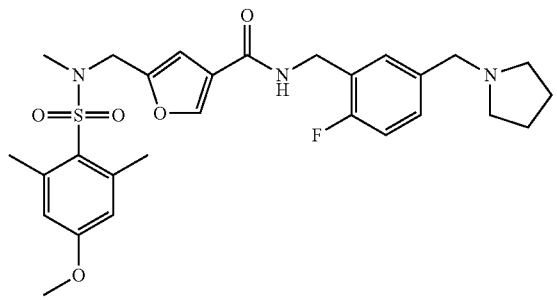

N-[2-Fluoro-5-(pyrrolidin-1-ylmethyl)benzyl]-5-({[(4-methoxy-2,6-dimethylphenyl)sulfonyl](methyl)amino}methyl)furan-3-carboxamide trifluoroacetate Ex 151

The title compound was prepared according to general procedure AC using 5-({[(4-methoxy-2,6-dimethylphenyl)sulfonyl](methyl)amino}methyl)furan-3-carboxylic acid (25 mg, 0.07 mmol), EDCI (16 mg, 0.08 mmol), HOBt monohydrate (12 mg, 0.09 mmol), TEA (0.011 mL, 0.08 mmol) and 1-[2-fluoro-5-(pyrrolidin-1-ylmethyl)phenyl]methanamine (22 mg, 0.11 mmol) in DMF (3 mL). The crude product was purified using prep method A.

Yield: 26.2 mg, 69%.

LCMS Method C: rt 3.27 min, 100%; m/z 544.06 (MH⁺, 100%)

¹H NMR (500 MHz, CD₃OD): δ ppm 8.82 (1H, br s), 8.04 (1H, s), 7.56 (1H, dd, J 6.9, 2.1 Hz), 7.45-7.50 (1H, m), 7.21-7.27 (1H, m), 6.78 (2H, s), 6.73 (1H, s), 4.58 (2H, s), 4.36 (2H, s), 4.35 (2H, s), 3.84 (3H, s), 3.49 (2H, br s), 3.18 (2H, br s), 2.68 (3H, s), 2.62 (6H, s), 2.18 (2H, br s), 2.01 (2H, br s)

Potency: A

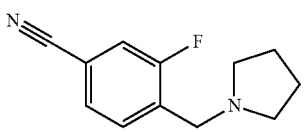 [SMILES: N#Cc1ccc(CN2CCCC2)c(F)c1]

3-Fluoro-4-(pyrrolidin-1-ylmethyl)benzonitrile

Int 203

4-Cyano-2-fluorobenzyl bromide (200 mg, 0.934 mmol), pyrrolidine (0.084 mL, 1.03 mmol), and TEA (0.144 mL, 1.03 mmol) were stirred at ambient temperature in DCM (5 mL) for 3 h. The mixture was partitioned between saturated aqueous NaHCO$_3$ (20 mL) and DCM (3×20 mL) and the combined organic extracts were dried over MgSO$_4$. The solvent was removed in vacuo and the crude product was used without further purification.

$^1$H NMR (500 MHz, CDCl$_3$): δ ppm 7.60 (1H, t, J=7.6 Hz), 7.45 (1H, d, J=7.8 Hz), 7.35 (1H, d, J=9.2 Hz), 3.74 (2H, s), 2.53-2.61 (4H, m), 1.77-1.89 (4H, m)

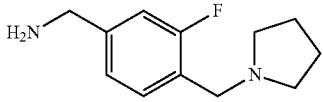 [SMILES: NCc1ccc(CN2CCCC2)c(F)c1]

1-[3-Fluoro-4-(pyrrolidin-1-ylmethyl)phenyl]methanamine

Int 204

3-Fluoro-4-(pyrrolidin-1-ylmethyl)benzonitrile (0.934 mmol) was dissolved in anhydrous THF (3 mL) under N$_2$ and the solution was cooled to 0° C. LiAlH$_4$ solution (1 M in THF, 0.95 mL) was added and the reaction was stirred and allowed to warm to ambient temperature over 4 h. MeOH (1 mL) was added and the reaction was concentrated in vacuo and partitioned between 1:1 saturated aqueous NaHCO$_3$: 30% aqueous Rochelle's salt (30 mL) and DCM (3×20 mL) and the combined organic extracts were dried over MgSO$_4$ and concentrated in vacuo to afford the title compound. No further purification was required.

Yield: 172 mg, 89%

$^1$H NMR (500 MHz, CD$_3$OD): δ ppm 7.37 (1H, t, J=7.7 Hz), 7.09-7.17 (2H, m), 3.80 (2H, s), 3.70 (2H, s), 2.52-2.65 (4H, m), 1.74-1.86 (4H, m)

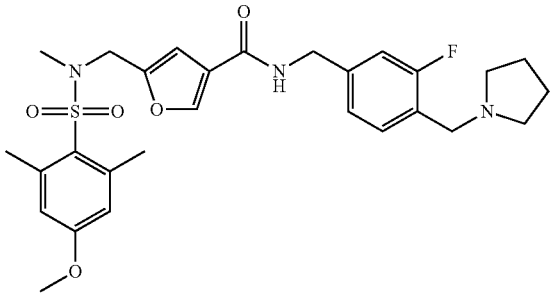 [SMILES: COc1cc(C)c(S(=O)(=O)N(C)Cc2cc(C(=O)NCc3ccc(CN4CCCC4)c(F)c3)co2)c(C)c1]

N-[3-Fluoro-4-(pyrrolidin-1-ylmethyl)benzyl]-5-({[(4-methoxy-2,6-dimethylphenyl)sulfonyl](methyl)amino}methyl)furan-3-carboxamide trifluoroacetate Ex 152

The title compound was prepared according to general procedure AC using 5-({[(4-methoxy-2,6-dimethylphenyl)sulfonyl](methyl)amino}methyl)furan-3-carboxylic acid (25 mg, 0.07 mmol), EDCI (16 mg, 0.08 mmol), HOBt monohydrate (12 mg, 0.09 mmol), TEA (0.011 mL, 0.08 mmol) and 1-[3-fluoro-4-(pyrrolidin-1-ylmethyl)phenyl]methanamine (22 mg, 0.11 mmol) in DMF (3 mL). The crude product was purified using prep method A.

Yield: 34.0 mg, 89%.

LCMS Method C: rt 3.22 min, 100%; m/z 544.06 (MH$^+$, 100%)

$^1$H NMR (500 MHz, CD$_3$OD): δ ppm 8.03 (1H, s), 7.54 (1H, t, J=7.7 Hz), 7.21-7.33 (2H, m), 6.77 (2H, s), 6.72 (1H, s), 4.56 (2H, s), 4.46 (2H, s), 4.35 (2H, s), 3.84 (3H, s), 3.55 (2H, br s), 3.23 (2H, br s), 2.69 (3H, s), 2.62 (6H, s), 2.20 (2H, br s), 2.03 (2H, br s)

Potency: A

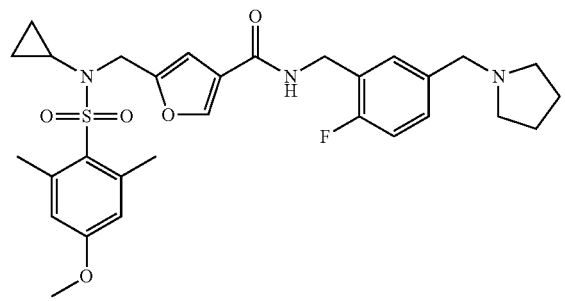 [SMILES: COc1cc(C)c(S(=O)(=O)N(Cc2cc(C(=O)NCc3cc(CN4CCCC4)ccc3F)co2)C2CC2)c(C)c1]

5-({Cyclopropyl[(4-methoxy-2,6-dimethylphenyl)sulfonyl]amino}methyl)-N-[2-fluoro-5-(pyrrolidin-1-ylmethyl)benzyl]furan-3-carboxamide trifluoroacetate Ex 153

The title compound was prepared according to general procedure AC using 5-({cyclopropyl[(4-methoxy-2,6-dimethylphenyl)sulfonyl]amino}methyl)furan-3 carboxylic acid (25 mg, 0.07 mmol), EDCI (15 mg, 0.08 mmol), HOBt monohydrate (11 mg, 0.08 mmol), TEA (0.01 mL, 0.07 mmol) and 1-[2-fluoro-5-(pyrrolidin-1-ylmethyl)phenyl]methanamine (20 mg, 0.1 mmol) in DMF (3 mL). A portion of the crude product was purified using prep method A.

LCMS Method C: rt 3.42 min, 100%; m/z 570.07 (MH$^+$, 100%)

Potency: A

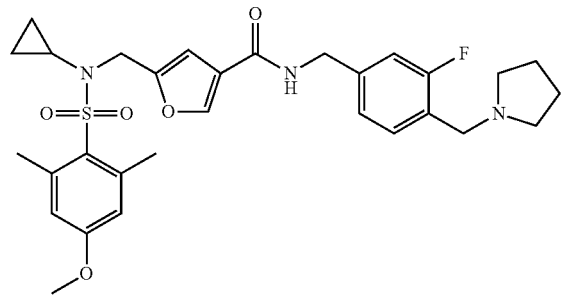 [SMILES: COc1cc(C)c(S(=O)(=O)N(Cc2cc(C(=O)NCc3ccc(CN4CCCC4)c(F)c3)co2)C2CC2)c(C)c1]

5-({Cyclopropyl[(4-methoxy-2,6-dimethylphenyl)sulfonyl]amino}methyl)-N-[3-fluoro-4-(pyrrolidin-1-ylmethyl)benzyl]furan-3-carboxamide trifluoroacetate Ex 154

The title compound was prepared according to general procedure AC using 5-({cyclopropyl[(4-methoxy-2,6-dimethylphenyl)sulfonyl]amino}methyl)furan-3 carboxylic acid (25 mg, 0.07 mmol), EDCI (15 mg, 0.08 mmol), HOBt monohydrate (11 mg, 0.08 mmol), TEA (0.01 mL, 0.07 mmol) and 1-[3-fluoro-4-(pyrrolidin-1-ylmethyl)phenyl]methanamine (20 mg, 0.1 mmol) in DMF (3 mL). A portion of the crude product was purified using prep method A.

LCMS Method C: rt 3.38 min, 100%; m/z 570.08 (MH+, 100%)

$^1$H NMR (500 MHz, CD$_3$OD): δ ppm 8.03 (1H, s), 7.51 (1H, t, J=7.6 Hz), 7.19-7.30 (2H, m), 6.78 (1H, s), 6.72 (2H, s), 4.52 (4H, s), 4.42 (2H, s), 3.81 (3H, s), 3.52 (2H, br s), 3.18 (2H, br s), 2.54 (6H, s), 2.29-2.46 (1H, m), 2.16 (2H, br s), 1.99 (2H, br s), 0.47-0.55 (2H, m), 0.11-0.17 (2H, m)

Potency: A

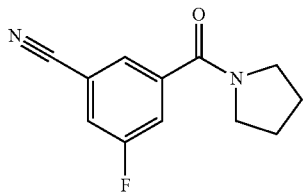 [SMILES: N#Cc1cc(F)cc(C(=O)N2CCCC2)c1]

3-Fluoro-5-(pyrrolidin-1-ylcarbonyl)benzonitrile

Int 205

3-Cyano-5-fluorobenzoic acid (200 mg, 1.21 mmol), EDCI (280 mg, 1.46 mmol) and HOBt monohydrate (196 mg, 1.45 mmol) were stirred at ambient temperature in DMF (10 mL) for 30 mins. Pyrrolidine (0.118 mL, 1.44 mmol), and TEA (0.2 mL, 1.43 mmol) were added. After stirring at ambient temperature for 16 h the mixture was partitioned between 1:1 brine:H$_2$O (4×20 mL) and EtOAc (20 mL) and the organic extracts were dried over MgSO$_4$. The solvent was removed in vacuo and the crude product was purified using FCC, eluting with 20% EtOAc in heptane to afford the title compound as a white solid.

Yield: 249 mg, 94%

$^1$H NMR (250 MHz, CDCl$_3$): δ ppm 7.59-7.66 (1H, m), 7.50 (1H, ddd, J 8.5, 2.6, 1.4 Hz), 7.42 (1H, ddd, J 7.8, 2.6, 1.4 Hz), 3.65 (2H, t, J=6.8 Hz), 3.42 (2H, t, J=6.3 Hz), 1.85-2.09 (4H, m)

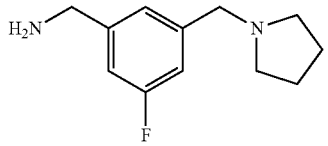 [SMILES: NCc1cc(F)cc(CN2CCCC2)c1]

1-[3-Fluoro-5-(pyrrolidin-1-ylmethyl)phenyl]methanamine

Int 206

3-Fluoro-5-(pyrrolidin-1-ylcarbonyl)benzonitrile (249 mg, 1.14 mmol) was dissolved in anhydrous THF (5 mL) under N$_2$ and the solution was cooled to 0° C. LiAlH$_4$ solution (1 M in THF, 4.56 mL) was added and the reaction was stirred and allowed to warm to ambient temperature over 4 h. MeOH (2 mL) was added dropwise and the reaction was partitioned between 1:1 saturated aqueous NaHCO$_3$:30% aqueous Rochelle's salt (20 mL) and DCM (3×20 mL) and the combined organic extracts were dried over MgSO$_4$ and concentrated in vacuo to afford the title compound as a light yellow oil. No further purification was required.

Yield: 172 mg, 78%

$^1$H NMR (500 MHz, CDCl$_3$): δ ppm 7.07 (1H, s), 6.89-6.97 (2H, m), 3.86 (2H, s), 3.60 (2H, s), 2.48-2.56 (4H, m), 1.77-1.84 (4H, m)

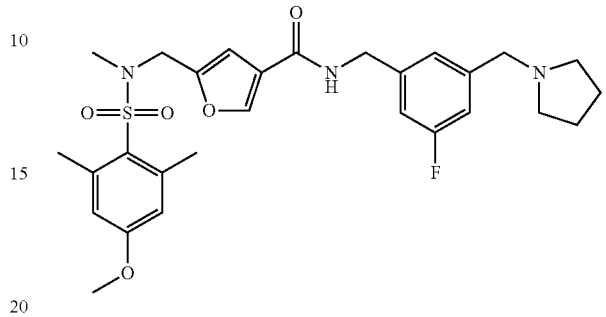

N-[3-Fluoro-5-(pyrrolidin-1-ylmethyl)benzyl]-5-({[(4-methoxy-2,6-dimethylphenyl)sulfonyl](methyl)amino}methyl)furan-3-carboxamide trifluoroacetate Ex 155

The title compound was prepared according to general procedure AC using 5-({[(4-methoxy-2,6-dimethylphenyl)sulfonyl](methyl)amino}methyl)furan-3-carboxylic acid (25 mg, 0.07 mmol), EDCI (16 mg, 0.08 mmol), HOBt monohydrate (12 mg, 0.09 mmol), TEA (0.011 mL, 0.08 mmol) and 1-[3-fluoro-5-(pyrrolidin-1-ylmethyl)phenyl]methanamine (25 mg, 0.12 mmol) in DMF (3 mL). The crude product was purified using prep method A.

Yield: 16.5 mg, 43%.

LCMS Method C: rt 3.31 min, 100%; m/z 544.18 (MH+, 100%)

$^1$H NMR (500 MHz, CD$_3$OD): δ ppm 8.04 (1H, s), 7.32 (1H, s), 7.23 (1H, s), 7.21 (1H, s), 6.78 (2H, s), 6.73 (1H, s), 4.56 (2H, s), 4.39 (2H, s), 4.36 (2H, s), 3.84 (3H, s), 3.52 (2H, br s), 3.14-3.24 (2H, m), 2.69 (3H, s), 2.62 (6H, s), 2.20 (2H, br s), 1.97-2.08 (2H, m)

Potency: B

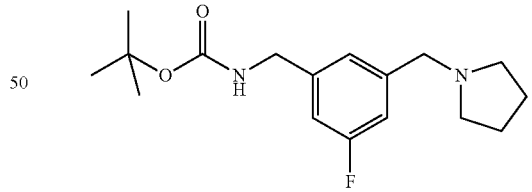

tert-Butyl[3-fluoro-5-(pyrrolidin-1-ylmethyl)benzyl]carbamate

General Procedure CA—Boc protection

Int 207

1-[3-fluoro-5-(pyrrolidin-1-ylmethyl)phenyl]methanamine (150 mg, 0.72 mmol), di-tert-butyl dicarbonate (236 mg, 1.08 mmol) and TEA (0.15 mL, 1.08 mmol) were stirred in DCM (5 mL) at ambient temperature for 18 h. The reaction was partitioned between saturated aqueous NaHCO$_3$ (10 mL) and DCM (3×10 mL) and the combined organic extracts were dried over MgSO₄ and concentrated in vacuo to afford the title compound as a light yellow oil. No further purification was required.

¹H NMR (250 MHz, CDCl₃): δ ppm 6.82-7.09 (3H, m), 4.24-4.36 (2H, m), 3.58 (2H, s), 2.41-2.57 (4H, m), 1.74-1.86 (4H, m), 1.46 (9H, s)

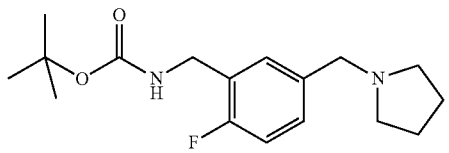 [SMILES: CC(C)(C)OC(=O)NCc1cc(CN2CCCC2)ccc1F]

tert-Butyl[2-fluoro-5-(pyrrolidin-1-ylmethyl)benzyl]carbamate

Int 208

The title compound was prepared according to general procedure CA using 1-[2-fluoro-5-(pyrrolidin-1-ylmethyl)phenyl]methanamine (40 mg, 0.19 mmol), di-tert-butyl dicarbonate (63 mg, 0.29 mmol) and TEA (0.04 mL, 0.29 mmol) in DCM (3 mL).

Yield: 59 mg, 97%
LCMS Method A: rt 1.07 min, 100%; m/z 309.00 (MH⁺, 100%)

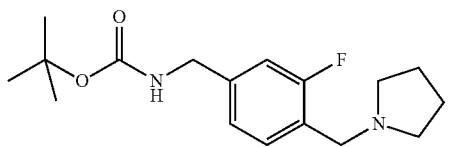 [SMILES: CC(C)(C)OC(=O)NCc1ccc(CN2CCCC2)c(F)c1]

tert-Butyl[3-fluoro-4-(pyrrolidin-1-yl)benzyl]carbamate

Int 209

The title compound was prepared according to general procedure CA using 1-[3-fluoro-4-(pyrrolidin-1-ylmethyl)phenyl]methanamine (130 mg, 0.625 mmol), di-tert-butyl dicarbonate (200 mg, 0.916 mmol) and TEA (0.13 mL, 0.933 mmol) in DCM (10 mL).

Yield: 144 mg, 75%
LCMS Method A: rt 1.04 min, 100%; m/z 309.45 (MH⁺, 100%)

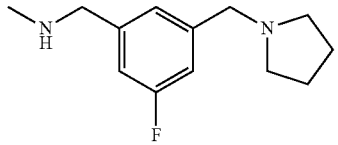 [SMILES: CNCc1cc(F)cc(CN2CCCC2)c1]

1-[3-Fluoro-5-(pyrrolidin-1-ylmethyl)phenyl]-N-methylmethanamine

General Procedure CB—Boc Reduction

Int 210 tert-butyl[3-fluoro-5-(pyrrolidin-1-ylmethyl)benzyl]carbamate (0.72 mmol) was dissolved in anhydrous THF (2 mL) under N₂ and the solution was cooled to 0° C. LiAlH₄ (1 M in THF, 1.62 mL) was added and the reaction was stirred at between 0° C. and 40° C. for 40 h. The reaction was partitioned between 1:1 saturated aqueous NaHCO₃: 30% aqueous Rochelle's salt (20 mL) and DCM (3×15 mL) and the combined organic extracts were dried over MgSO₄ and concentrated in vacuo to afford the title compound as a yellow oil. No further purification was required.

Yield: 149 mg, 94%.

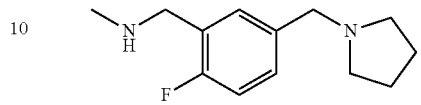

1-[2-Fluoro-5-(pyrrolidin-1-ylmethyl)phenyl]-N-methylmethanamine

Int 211

The title compound was prepared according to general procedure CB using tert-butyl[2-fluoro-5-(pyrrolidin-1-ylmethyl)benzyl]carbamate (57 mg, 0.19 mmol) and LiAlH₄ (1 M in THF, 0.74 mL) in anhydrous THF (3 mL), heating at 70° C. for 4 h.

Yield: 22 mg, 54%

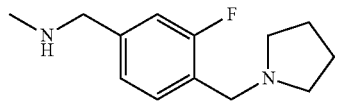 [SMILES: CNCc1ccc(CN2CCCC2)c(F)c1]

1-[3-Fluoro-4-(pyrrolidin-1-ylmethyl)phenyl]-N-methylmethanamine

Int 212

The title compound was prepared according to general procedure CB using tert-butyl[3-fluoro-4-(pyrrolidin-1-yl)benzyl]carbamate (144 mg, 0.47 mmol) and LiAlH₄ (1 M in THF, 1.87 mL) in anhydrous THF (10 mL), heating at 70° C. for 4 h.

Yield: 77 mg, 74%

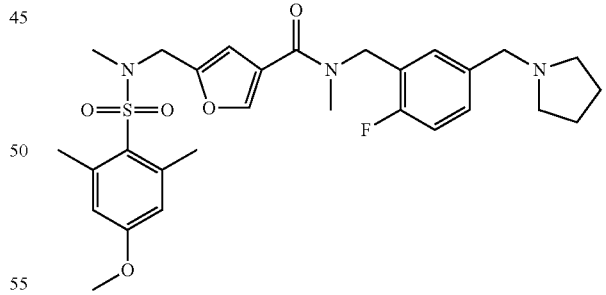

N-[2-Fluoro-5-(pyrrolidin-1-ylmethyl)benzyl]-5-({[(4-methoxy-2,6-dimethylphenyl)sulfonyl](methyl)amino}methyl)-N-methylfuran-3-carboxamide trifluoroacetate Ex 156

The title compound was prepared according to general procedure AC using 5-({[(4-methoxy-2,6-dimethylphenyl)sulfonyl](methyl)amino}methyl)furan-3-carboxylic acid (25 mg, 0.07 mmol), EDCI (16 mg, 0.08 mmol), HOBt monohydrate (12 mg, 0.09 mmol), TEA (0.011 mL, 0.08 mmol) and 1-[2-fluoro-5-(pyrrolidin-1-ylmethyl)phenyl]-N-methyl-methanamine (22 mg, 0.11 mmol) in DMF (3 mL). The crude product was purified using prep method A.

Yield: 12.1 mg, 31%.
LCMS Method C: rt 3.37 min, 90%; m/z 558.22 (MH+, 100%)
Potency: B

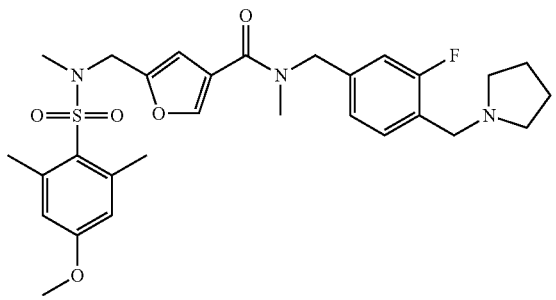 [SMILES: COc1cc(C)c(S(=O)(=O)N(C)Cc2cc(C(=O)N(C)Cc3ccc(CN4CCCC4)c(F)c3)co2)c(C)c1]

N-[3-Fluoro-4-(pyrrolidin-1-ylmethyl)benzyl]-5-({[(4-methoxy-2,6-dimethylphenyl)sulfonyl](methyl)amino}methyl)-N-methylfuran-3-carboxamide trifluoroacetate Ex 157
The title compound was prepared according to general procedure AC using 5-({[(4-methoxy-2,6-dimethylphenyl)sulfonyl](methyl)amino}methyl)furan-3-carboxylic acid (25 mg, 0.07 mmol), EDCI (16 mg, 0.08 mmol), HOBt monohydrate (12 mg, 0.09 mmol), TEA (0.011 mL, 0.08 mmol) and 1-[3-fluoro-4-(pyrrolidin-1-ylmethyl)phenyl]-N-methyl-methanamine (25 mg, 0.11 mmol) in DMF (3 mL). The crude product was purified using prep method A.

Yield: 10.9 mg, 28%.
LCMS Method C: rt 3.30 min, 99%; m/z 558.19 (MH+, 100%)
Potency: B

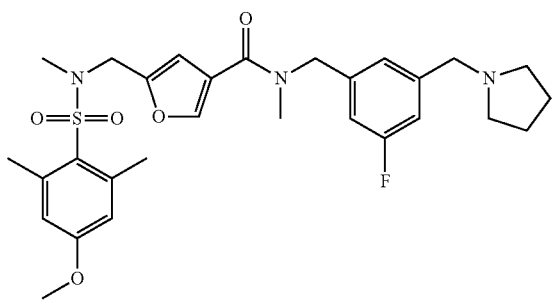 [SMILES: COc1cc(C)c(S(=O)(=O)N(C)Cc2cc(C(=O)N(C)Cc3cc(F)cc(CN4CCCC4)c3)co2)c(C)c1]

N-[3-Fluoro-5-(pyrrolidin-1-ylmethyl)benzyl]-5-({[(4-methoxy-2,6-dimethylphenyl)sulfonyl](methyl)amino}methyl)-N-methylfuran-3-carboxamide trifluoroacetate Ex 158
The title compound was prepared according to general procedure AC using 5-({[(4-methoxy-2,6-dimethylphenyl)sulfonyl](methyl)amino}methyl)furan-3-carboxylic acid (25 mg, 0.07 mmol), EDCI (16 mg, 0.08 mmol), HOBt monohydrate (12 mg, 0.09 mmol), TEA (0.011 mL, 0.08 mmol) and 1-[3-fluoro-5-(pyrrolidin-1-ylmethyl)phenyl]-N-methyl-methanamine (25 mg, 0.12 mmol) in DMF (3 mL). The crude product was purified using prep method A.

Yield: 19.8 mg, 50%.
LCMS Method C: rt 3.34 min, 100%; m/z 558.23 (MH+, 100%)
Potency: B Oxazoles (all Substitution Patterns)

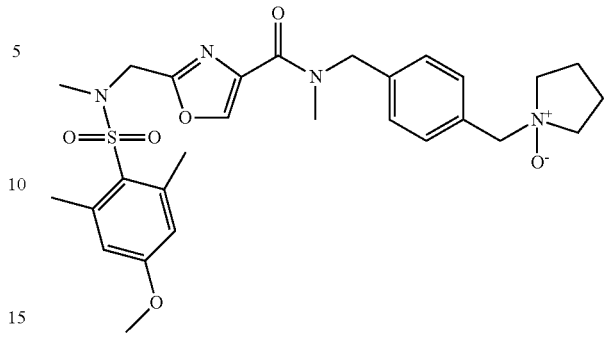

2-({[(4-Methoxy-2,6-dimethylphenyl)sulfonyl](methyl)amino}methyl)-N-methyl-N-{4-[(1-oxidopyrrolidin-1-yl)methyl]benzyl}-1,3-oxazole-4-carboxamide trifluoroacetate Ex 159
2-({[(4-methoxy-2,6-dimethylphenyl)sulfonyl](methyl)amino}methyl)-1,3-oxazole-4-carboxylic acid (50 mg, 0.07 mmol) was dissolved in DCM and the solution was cooled to 0° C. before mCPBA (18 mg, 0.1 mmol) was added. The reaction mixture was stirred for one hour at ambient temperature before the mixture was concentrated in vacuo. The residue was dissolved in methanol and purified by Prep HPLC method A to provide the desired product as a colourless solid.

Yield: 2 mg, 4%.
LCMS Method C: rt 3.19 min, 95%; m/z 583.30 (MH+, 100%).
Potency: A

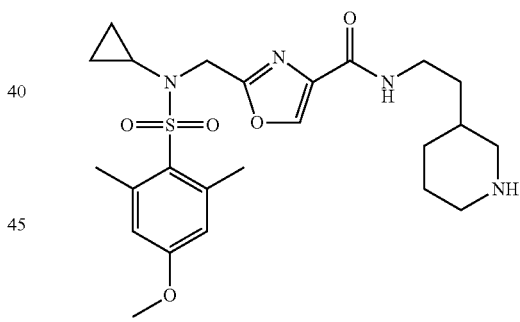

2-({Cyclopropyl[(4-methoxy-2,6-dimethylphenyl)sulfonyl]amino}methyl)-N-(2-piperidin-3-ylethyl)-1,3-oxazole-4-carboxamide Ex 159a
The title compound was prepared according to general procedure AH using 2-({cyclopropyl[(4-methoxy-2,6-dimethylphenyl)sulfonyl]amino}methyl)-1,3-oxazole-4-carboxylic acid (38 mg, 100 mop, EDCI (23 mg, 120 mop, HOBt monohydrate (18 mg, 120 μmol), DIPEA (69 μL, 400 mol), tert-butyl 3-(2-aminoethyl)piperidine-1-carboxylate (23 mg, 100 μmol) and DMF (750 L). The resulting crude compound was purified by FCC eluting with 100% EtOAc to afford tert-butyl 3-[2-({[2-({cyclopropyl[(4-methoxy-2,6-dimethylphenyl)sulfonyl]amino}methyl)-1,3-oxazol-4-yl]carbonyl}amino)ethyl]piperidine-1-carboxylate. Yield: 38 mg, 64%.

This material was dissolved in a 1:3 mixture of TFA/DCM (800 µL) and the resulting solution stirred at ambient temperature for 18 h. The solvent was removed in vacuo and the resulting oil redissolved in MeOH (1 mL) and absorbed on to MP-TsOH resin (1.5 mL). The resin was washed with MeOH (5 mL) and the product eluted with 7N NH$_3$ in MeOH (5 mL) and the solvent removed in vacuo.

Yield: 16 mg, 32%
LCMS method A: rt 1.06 min, 98%; m/z 491.45 (MH$^+$, 100%).
Potency: A

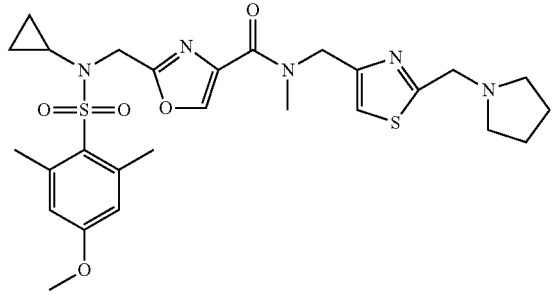 [SMILES: COc1cc(C)c(S(=O)(=O)N(Cc2nc(C(=O)N(C)Cc3csc(CN4CCCC4)n3)co2)C2CC2)c(C)c1]

2-({Cyclopropyl[(4-methoxy-2,6-dimethylphenyl)sulfonyl]amino}methyl)-N-methyl-N-{[2-(pyrrolidin-1-ylmethyl)-1,3-thiazol-4-yl]methyl}-1,3-oxazole-4-carboxamide Ex 160

The title compound was prepared according to general procedure AH using N-methyl-1-[2-(pyrrolidin-1-ylmethyl)-1,3-thiazol-4-yl]methanamine (40 mg, 189 µmol), 2-({cyclopropyl[(4-methoxy-2,6-dimethylphenyl)sulfonyl]amino}methyl)-1,3-oxazole-4-carboxylic acid (72 mg, 189 µmol), DIPEA (0.1 mL, 575 µmol), EDCI (72 mg, 378 µmol), HOBt monohydrate (58 mg, 378 µmol) and DMF (1.5 mL). The resulting crude compound was purified by FCC eluting with 99:1 DCM:7N NH$_3$ in MeOH.

Yield: 34 mg, 31%
LCMS method C: rt 3.34 min, 99%; m/z 574.17 (MH$^+$, 100%).
Potency: B

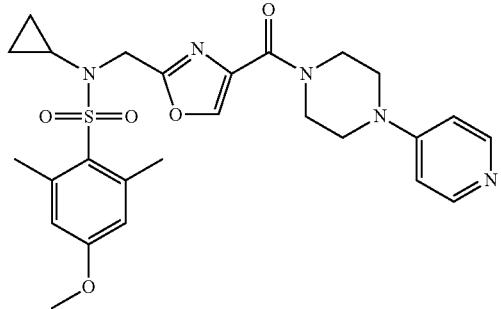

N-Cyclopropyl-4-methoxy-2,6-dimethyl-N-({4-[(4-pyridin-4-ylpiperazin-1-yl)carbonyl]-1,3-oxazol-2-yl}methyl)benzenesulfonamide trifluoroacetate Ex 161

The title compound was prepared according to general procedure AH using 1-pyridin-4-ylpiperazine (43 mg, 263 µmol), 2-({cyclopropyl[(4-methoxy-2,6-dimethylphenyl)sulfonyl]amino}methyl)-1,3-oxazole-4-carboxylic acid (100 mg, 263 µmol), DIPEA (180 µL, 1.05 mmol), DCC (108 mg, 526 µmol), HOBt monohydrate (80 mg, 526 µmol) and DMF (2.0 mL). A portion of the resulting crude compound was purified using prep method D to afford the title compound.

LCMS method C: rt 3.21 min, 97%; m/z 526.17 (MH$^+$, 100%).
Potency: A

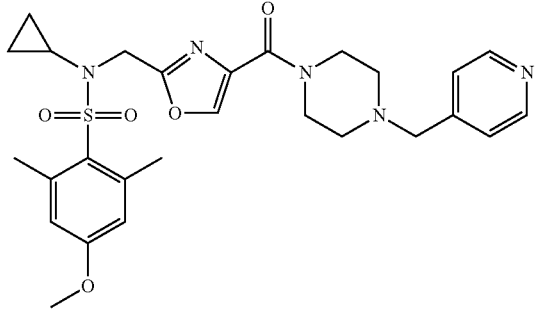 [SMILES: COc1cc(C)c(S(=O)(=O)N(Cc2nc(C(=O)N3CCN(Cc4ccncc4)CC3)co2)C2CC2)c(C)c1]

N-Cyclopropyl-4-methoxy-2,6-dimethyl-N-[(4-{[4-(pyridin-4-ylmethyl)piperazin-1-yl]carbonyl}-1,3-oxazol-2-yl)methyl]benzenesulfonamide trifluoroacetate Ex 162

The title compound was prepared according to general procedure AH using 1-(pyridin-4-ylmethyl)piperazine (47 mg, 263 µmol), 2-({cyclopropyl[(4-methoxy-2,6-dimethylphenyl)sulfonyl]amino}methyl)-1,3-oxazole-4-carboxylic acid (100 mg, 263 µmol), DIPEA (180 µL, 1.05 mmol), DCC (108 mg, 526 µmol), HOBt monohydrate (80 mg, 526 µmol) and DMF (2.0 mL). A portion of the resulting crude compound was purified using prep method D to afford the title compound.

LCMS method C: rt 3.15 min, 99%; m/z 540.22 (MH$^+$, 100%).
Potency: C

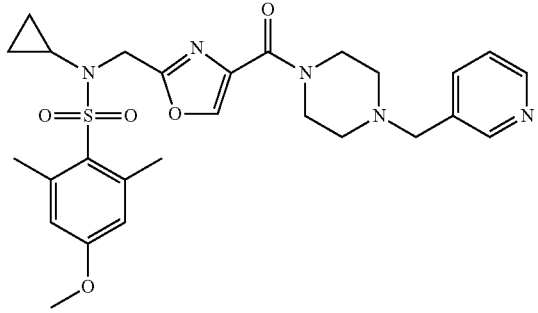 [SMILES: COc1cc(C)c(S(=O)(=O)N(Cc2nc(C(=O)N3CCN(Cc4cccnc4)CC3)co2)C2CC2)c(C)c1]

N-Cyclopropyl-4-methoxy-2,6-dimethyl-N-[(4-{[4-(pyridin-3-ylmethyl)piperazin-1-yl]carbonyl}-1,3-oxazol-2-yl)methyl]benzenesulfonamide trifluoroacetate Ex 163

The title compound was prepared according to general procedure AH using 1-(pyridin-3-ylmethyl)piperazine (47 mg, 263 µmol), 2-({cyclopropyl[(4-methoxy-2,6-dimethylphenyl)sulfonyl]amino}methyl)-1,3-oxazole-4-carboxylic acid (100 mg, 263 µmol), DIPEA (180 µL, 1.05 mmol), DCC (108 mg, 526 µmol), HOBt monohydrate (80 mg, 526 µmol) and DMF (2.0 mL). A portion of the resulting crude compound was purified using prep method D to afford the title compound.

LCMS method C: rt 3.13 min, 98%; m/z 540.22 (MH$^+$, 100%).

Potency: C

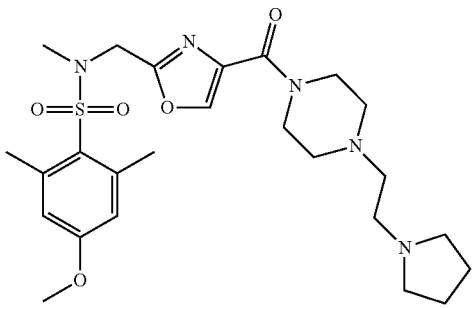 [SMILES: COc1cc(C)c(S(=O)(=O)N(C)Cc2nc(C(=O)N3CCN(CCN4CCCC4)CC3)co2)c(C)c1]

4-Methoxy-N,2,6-trimethyl-N-[(4-{[4-(2-pyrrolidin-1-ylethyl)piperazin-1-yl]carbonyl}-1,3-oxazol-2-yl)methyl]benzenesulfonamide Ex 164

2-({[(4-Methoxy-2,6-dimethylphenyl)sulfonyl](methyl)amino}methyl)-1,3-oxazole-4-carboxylic acid (100 mg, 0.28 mmol) was dissolved in DCM (15 mL) and EDCI (75 mg, 0.39 mmol), HOBt (56 mg, 0.42 mmol) and DIPEA (0.058 mL, 0.33 mmol) were added. The resulting solution was stirred for 15 min prior to the addition of 1-(2-pyrrolidin-1-ylethyl)piperazine (61 mg, 0.33 mmol) dissolved in DCM (2 mL) and stirred at ambient temperature for 12 h. The reaction was diluted with DCM (20 mL) and washed with water (10 mL), saturated aqueous NaHCO$_3$ (10 mL), saturated brine (5 mL), dried over Na$_2$SO$_4$ and concentrated in vacuo. The resulting residue was purified by FCC with 0-2% MeOH in DCM to afford the title compound as pale yellow oil.

Yield: 40 mg, 29%.

LCMS method C: rt 2.93 min, 91%; m/z 520.18 (MH$^+$, 100%).

Potency: A

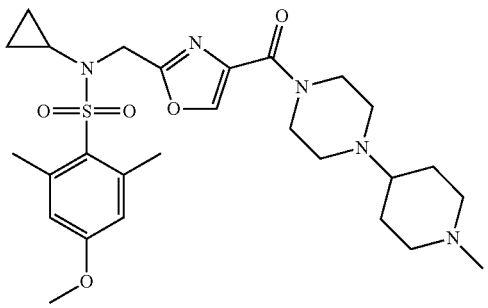 [SMILES: COc1cc(C)c(S(=O)(=O)N(Cc2nc(C(=O)N3CCN(C4CCN(C)CC4)CC3)co2)C2CC2)c(C)c1]

N-Cyclopropyl-4-methoxy-2,6-dimethyl-N-[(4-{[4-(1-methylpiperidin-4-yl)piperazin-1-yl]carbonyl}-1,3-oxazol-2-yl)methyl]benzenesulfonamide Ex 165

2-({Cyclopropyl[(4-methoxy-2,6-dimethylphenyl)sulfonyl]amino}methyl)-1,3-oxazole-4-carboxylic acid (100 mg, 0.26 mmol) was dissolved in DCM (15 mL) and EDCI (70 mg, 0.36 mmol), HOBt (53 mg, 0.39 mmol) and DIPEA (0.057 mL, 0.33 mmol) were added. The resulting solution was stirred for 15 min prior to the addition of 1-(1-methylpiperidin-4-yl)piperazine (57 mg, 0.31 mmol) dissolved in DCM (2 mL) and stirred at ambient temperature for 12 h. The reaction was diluted with DCM (20 mL) and washed with water (10 mL), saturated aqueous NaHCO$_3$ (10 mL), saturated brine (5 mL), dried over Na$_2$SO$_4$ and concentrated in vacuo. The resulting residue was purified by FCC with 0-2% MeOH in DCM to afford the title compound as pale yellow oil.

Yield: 30 mg, 21%.

LCMS method C: rt 2.70 min, 99%; m/z 546.20 (MH$^+$, 35%), 273.71 ([M+2H]$^{2+}$], 100%).

Potency: C

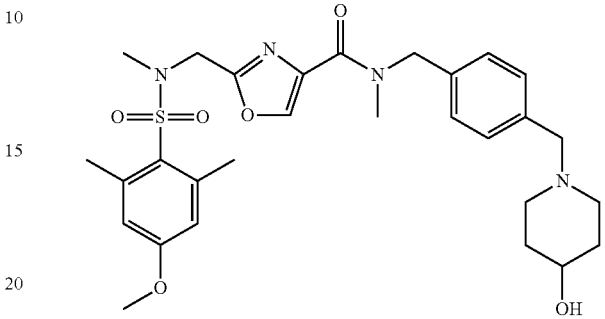

N-{4-[(4-Hydroxypiperidin-1-yl)methyl]benzyl}-2-({[(4-methoxy-2,6-dimethylphenyl)sulfonyl](methyl)amino}methyl)-N-methyl-1,3-oxazole-4-carboxamide Ex 166

The title compound was prepared according to general procedure BH using 2-({[(4-methoxy-2,6-dimethylphenyl)sulfonyl](methyl)amino}methyl)-1,3-oxazole-4-carboxylic acid (35 mg, 0.12 mmol), EDCI (26 mg, 0.14 mmol), HOBt (20 mg, 0.15 mmol) DIPEA (0.035 mL, 0.2 mmol), 1-{4-[(methylamino)methyl]benzyl}piperidin-4-ol dihydrochloride (32 mg, 0.14 mmol) and DCM (10 mL).

Yield: 35 mg, 62%.

LCMS method C: rt 3.10 min, 97%; m/z 571.20 (MH$^+$, 100%).

Potency: C

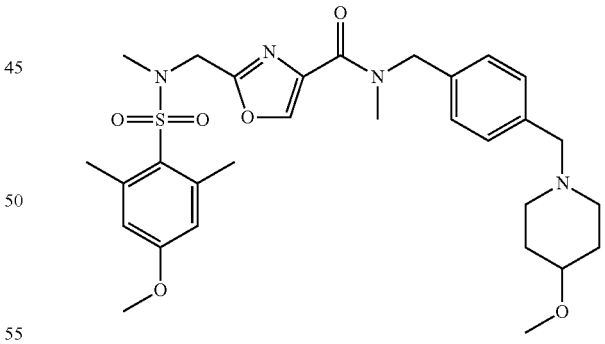

2-({[(4-Methoxy-2,6-dimethylphenyl)sulfonyl](methyl)amino}methyl)-N-{4-[(4-methoxypiperidin-1-yl)methyl]benzyl}-N-methyl-1,3-oxazole-4-carboxamide Ex 167

The title compound was prepared according to general procedure BH using 2-({[(4-methoxy-2,6-dimethylphenyl)sulfonyl](methyl)amino}methyl)-1,3-oxazole-4-carboxylic acid (40 mg, 0.11 mmol), EDCI (30 mg, 0.15 mmol), HOBt (23 mg, 0.17 mmol) DIPEA (0.04 mL, 0.22 mmol), 1-{4-[(4-methoxypiperidin-1-yl)methyl]phenyl}-N-methylmethanamine dihydrochloride (39 mg, 0.13 mmol) and DCM (5 mL).

Yield: 22 mg, 33%.
LCMS method C: rt 3.18 min, 99%; m/z 585.19 (MH+, 100%).
Potency: C

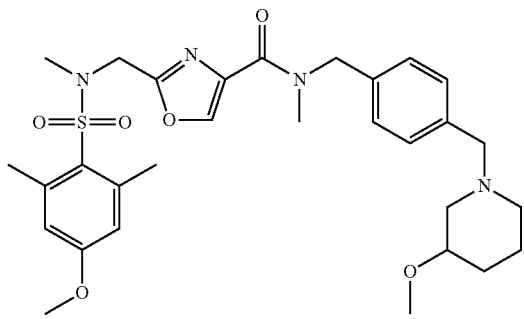 [SMILES: COc1cc(C)c(S(=O)(=O)N(C)Cc2nc(C(=O)N(C)Cc3ccc(CN4CCCC(OC)C4)cc3)co2)c(C)c1]

2-({[(4-Methoxy-2,6-dimethylphenyl)sulfonyl](methyl)amino}methyl)-N-{4-[(3-methoxypiperidin-1-yl)methyl]benzyl}-N-methyl-1,3-oxazole-4-carboxamide Ex 168
The title compound was prepared according to general procedure BH using 2-({[(4-methoxy-2,6-dimethylphenyl)sulfonyl](methyl)amino}methyl)-1,3-oxazole-4-carboxylic acid (40 mg, 0.11 mmol), EDCI (29 mg, 0.15 mmol), HOBt (22 mg, 0.16 mmol) DIPEA (0.04 mL, 0.21 mmol), 1-{4-[(3-methoxypiperidin-1-yl)methyl]phenyl}-N-methylmethanamine dihydrochloride (38 mg, 0.13 mmol) and DCM (5 mL).

Yield: 30 mg, 44%.
LCMS method C: rt 3.45 min, 100%; m/z 611.27 (MH+, 100%).
Potency: B

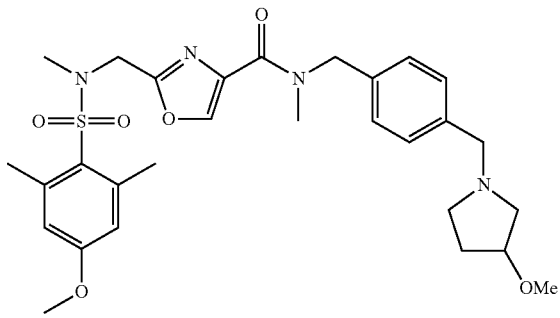 [SMILES: COc1cc(C)c(S(=O)(=O)N(C)Cc2nc(C(=O)N(C)Cc3ccc(CN4CCC(OC)C4)cc3)co2)c(C)c1]

2-({[(4-Methoxy-2,6-dimethylphenyl)sulfonyl](methyl)amino}methyl)-N-{4-[(3-methoxypyrrolidin-1-yl)methyl]benzyl}-N-methyl-1,3-oxazole-4-carboxamide Ex 169
The title compound was prepared according to general procedure BH using 2-({[(4-methoxy-2,6-dimethylphenyl)sulfonyl](methyl)amino}methyl)-1,3-oxazole-4-carboxylic acid (40 mg, 0.11 mmol), EDCI (29 mg, 0.15 mmol), HOBt (22 mg, 0.16 mmol) DIPEA (0.04 mL, 0.21 mmol), [4-(3-methoxy-pyrrolidin-1-ylmethyl)-benzyl]-methyl-amine hydrochloride (37 mg, 0.13 mmol) and DCM (5 mL).

Yield: 40 mg, 62%.
LCMS method C: rt 3.21 min, 94%; m/z 571.21 (MH+, 100%).
Potency: C

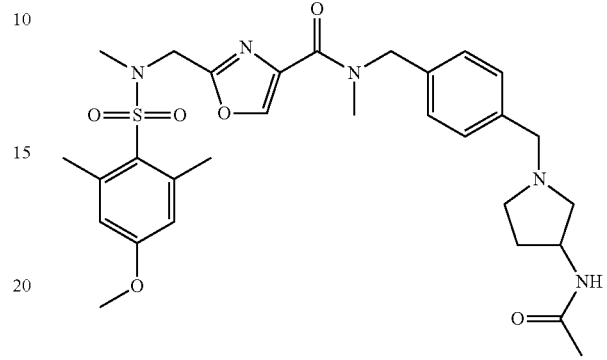

N-(4-{[3-(Acetylamino)pyrrolidin-1-yl]methyl}benzyl)-2-({[(4-methoxy-2,6-dimethylphenyl)sulfonyl](methyl)amino}methyl)-N-methyl-1,3-oxazole-4-carboxamide Ex 170
The title compound was prepared according to general procedure BH using 2-({[(4-methoxy-2,6-dimethylphenyl)sulfonyl](methyl)amino}methyl)-1,3-oxazole-4-carboxylic acid (40 mg, 0.11 mmol), EDCI (29 mg, 0.15 mmol), HOBt (22 mg, 0.16 mmol) DIPEA (0.04 mL, 0.21 mmol), 1-(4-methylaminomethyl-benzyl)-pyrrolidine-3-carboxylic acid dimethylamide-amine hydrochloride (37 mg, 0.13 mmol) and DCM (5 mL).

Yield: 27 mg, 40%.
LCMS method C: rt 3.03 min, 97%; m/z 598.29 (MH+, 100%).
Potency: B

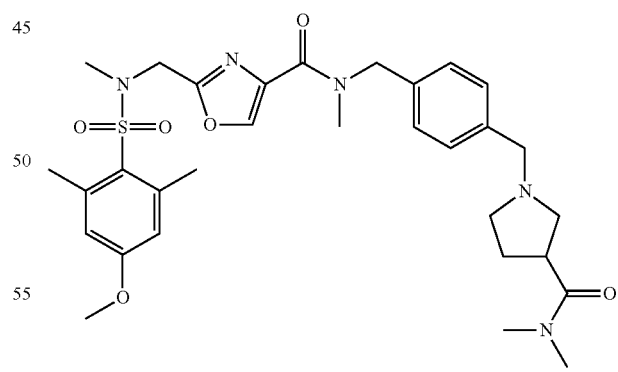

N-(4-{[3-(Dimethylcarbamoyl)pyrrolidin-1-yl]methyl}benzyl)-2-({[(4-methoxy-2,6-dimethylphenyl)sulfonyl](methyl)amino}methyl)-N-methyl-1,3-oxazole-4-carboxamide Ex 171
The title compound was prepared according to general procedure BH using 2-({[(4-methoxy-2,6-dimethylphenyl)

sulfonyl](methyl)amino}methyl)-1,3-oxazole-4-carboxylic acid (40 mg, 0.11 mmol), EDCI (29 mg, 0.15 mmol), HOBt (22 mg, 0.16 mmol) DIPEA (0.04 mL, 0.21 mmol), N,N-dimethyl-1-{4-[(methylamino)methyl]benzyl}pyrrolidine-3-carboxamide dihydrochloride (42 mg, 0.13 mmol) and DCM (5 mL).

Yield: 28 mg, 40%.

LCMS method C: rt 3.14 min, 98%; m/z 612.28 (MH$^+$, 100%).

Potency: C

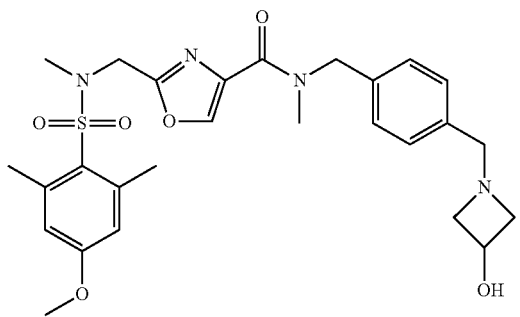 [SMILES: COc1cc(C)c(S(=O)(=O)N(C)Cc2nc(C(=O)N(C)Cc3ccc(CN4CC(O)C4)cc3)co2)c(C)c1]

N-{4-[(3-Hydroxyazetidin-1-yl)methyl]benzyl}-2-({[(4-methoxy-2,6-dimethylphenyl)sulfonyl](methyl)amino}methyl)-N-methyl-1,3-oxazole-4-carboxamide Ex 172

The title compound was prepared according to general procedure BH using 2-({[(4-methoxy-2,6-dimethylphenyl)sulfonyl](methyl)amino}methyl)-1,3-oxazole-4-carboxylic acid (40 mg, 0.11 mmol), EDCI (29 mg, 0.15 mmol), HOBt (22 mg, 0.16 mmol) DIPEA (0.04 mL, 0.21 mmol), 1-{4-[(methylamino)methyl]benzyl}azetidin-3-ol dihydrochloride (35 mg, 0.13 mmol) and DCM (5 mL).

Yield: 34 mg, 55%.

LCMS method C: rt 3.05 min, 97%; m/z 543.33 (MH$^+$, 100%).

Potency: B

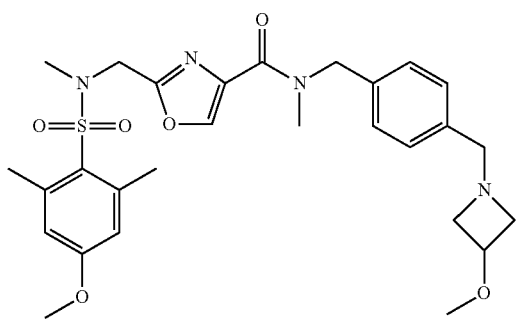 [SMILES: COc1cc(C)c(S(=O)(=O)N(C)Cc2nc(C(=O)N(C)Cc3ccc(CN4CC(OC)C4)cc3)co2)c(C)c1]

N-{4-[(3-Methoxyazetidin-1-yl)methyl]benzyl}-2-({[(4-methoxy-2,6-dimethylphenyl)sulfonyl](methyl)amino}methyl)-N-methyl-1,3-oxazole-4-carboxamide Ex 173

The title compound was prepared according to general procedure BH using 2-({[(4-methoxy-2,6-dimethylphenyl)sulfonyl](methyl)amino}methyl)-1,3-oxazole-4-carboxylic acid (40 mg, 0.11 mmol), EDCI (29 mg, 0.15 mmol), HOBt (22 mg, 0.16 mmol) DIPEA (0.04 mL, 0.21 mmol), 1-{4-[(3-methoxyazetidin-1-yl)methyl]phenyl}-N-methylmethanamine dihydrochloride (34 mg, 0.13 mmol) and DCM (5 mL).

Yield: 30 mg, 48%.

LCMS method C: rt 3.18 min, 95%; m/z 557.32 (MH$^+$, 100%).

Potency: B

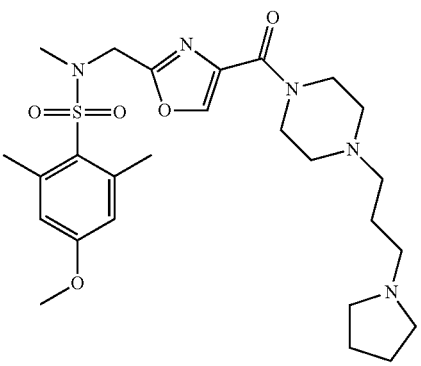 [SMILES: COc1cc(C)c(S(=O)(=O)N(C)Cc2nc(C(=O)N3CCN(CCCN4CCCC4)CC3)co2)c(C)c1]

4-Methoxy-N,2,6-trimethyl-N-[(4-{[4-(3-pyrrolidin-1-ylpropyl)piperazin-1-yl]carbonyl}-1,3-oxazol-2-yl)methyl]benzenesulfonamide Ex 174

The title compound was prepared according to general procedure BH using 2-{[(4-methoxy-2,6-dimethyl-benzenesulfonyl)-methyl-amino]-methyl}-oxazole-4-carboxylic acid (100 mg, 0.28 mmol), EDCI (75 mg, 0.39 mmol), HOBt (57 mg, 0.42 mmol) DIPEA (0.06 mL, 0.33 mmol), 1-(3-pyrrolidin-1-yl-propyl)-piperazine (66 mg, 0.33 mmol) and DCM (10 mL).

Yield: 90 mg, 60%

LCMS method C: rt 2.43 min, 99%; m/z 267.75 ([M+2H]$^{2+}$, 100%), 534.23 (MH$^+$, 67%).

Potency: C

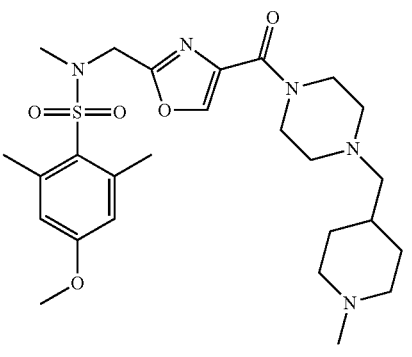 [SMILES: COc1cc(C)c(S(=O)(=O)N(C)Cc2nc(C(=O)N3CCN(CC4CCN(C)CC4)CC3)co2)c(C)c1]

4-Methoxy-N,2,6-trimethyl-N-{[4-({4-[(1-methylpiperidin-4-yl)methyl]piperazin-1-yl}carbonyl)-1,3-oxazol-2-yl]methyl}benzenesulfonamide Ex 175

The title compound was prepared according to general procedure BH using 2-{[(4-methoxy-2,6-dimethyl-benzenesulfonyl)-methyl-amino]-methyl}-oxazole-4-carboxylic acid (100 mg, 0.28 mmol), EDCI (75 mg, 0.39 mmol), HOBt (57 mg, 0.42 mmol) DIPEA (0.06 mL, 0.33 mmol), 1-(1-methyl-piperidin-4-ylmethyl)-piperazine (66 mg, 0.33 mmol) and DCM (10 mL).

Yield: 65 mg, 43%

LCMS method C: rt 2.41 min, 98%; m/z 267.86 ([M+2H]$^{2+}$, 100%), 534.23 (MH$^+$, 38%).

Potency: C

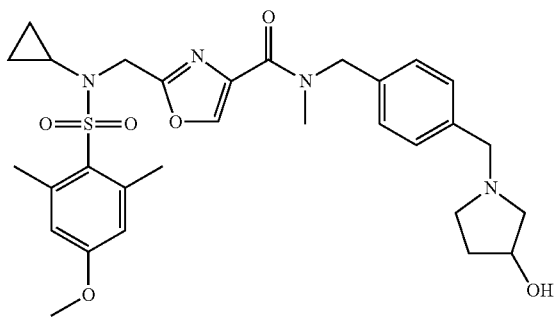 [SMILES: COc1cc(C)c(S(=O)(=O)N(Cc2nc(C(=O)N(C)Cc3ccc(CN4CCC(O)C4)cc3)co2)C2CC2)c(C)c1]

2-({Cyclopropyl[(4-methoxy-2,6-dimethylphenyl)sulfonyl]amino}methyl)-N-{4-[(3-hydroxypyrrolidin-1-yl)methyl]benzyl}-N-methyl-1,3-oxazole-4-carboxamide Ex 176

The title compound was prepared according to general procedure BH using 2-{[cyclopropyl-(4-methoxy-2,6-dimethyl-benzenesulfonyl)-amino]-methyl}-oxazole-4-carboxylic acid (35 mg, 0.09 mmol), EDCI (25 mg, 0.13 mmol), HOBt (19 mg, 0.14 mmol), DIPEA (0.03 mL, 0.19 mmol), 1-(4-methylaminomethyl-benzyl)-pyrrolidin-3-ol hydrochloride (30 mg, 0.11 mmol) and DCM (10 mL).

Yield: 35 mg, 65%.

LCMS method C: rt 2.80 min, 92%; m/z 305.84 ([M+2H]$^{2+}$, 100%), 610.26 (MH$^+$, 44%).

Potency: C

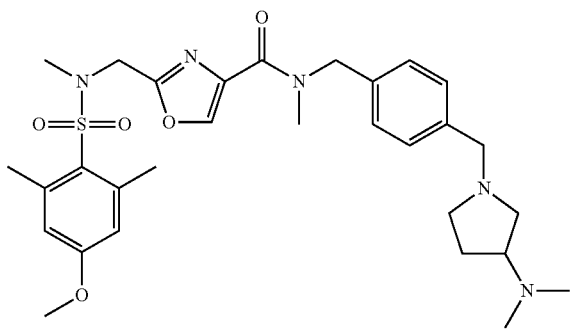

N-(4-{[3-(Dimethylamino)pyrrolidin-1-yl]methyl}benzyl)-2-({[(4-methoxy-2,6-dimethylphenyl)sulfonyl](methyl)amino}methyl)-N-methyl-1,3-oxazole-4-carboxamide Ex 177

The title compound was prepared according to general procedure BH using 2-{[(4-methoxy-2,6-dimethyl-benzene-sulfonyl)-methyl-amino]-methyl}-oxazole-4-carboxylic acid (35 mg, 0.10 mmol), EDCI (26 mg, 0.14 mmol), HOBt (19 mg, 0.15 mmol), DIPEA (0.03 mL, 0.19 mmol), dimethyl-[1-(4-methylaminomethyl-benzyl-pyrrolidin-3-yl]-amine hydrochloride (34 mg, 0.11 mmol) and DCM (10 mL).

Yield: 40 mg, 69%.

LCMS method C: rt 2.74 min, 88%; m/z 292.72 ([M+2H]$^{2+}$, 100%), 584.22 (MH$^+$, 29%).

Potency: B

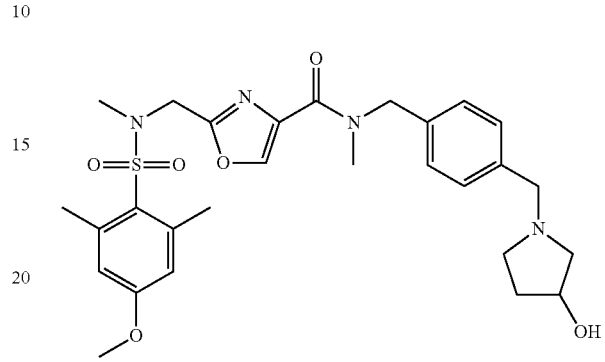

N-{4-[(3-Hydroxypyrrolidin-1-yl)methyl]benzyl}-2-({[(4-methoxy-2,6-dimethylphenyl)sulfonyl](methyl)amino}methyl)-N-methyl-1,3-oxazole-4-carboxamide Ex 178

The title compound was prepared according to general procedure BH using 2-{[(4-methoxy-2,6-dimethyl-benzene-sulfonyl)-methyl-amino]-methyl}-oxazole-4-carboxylic acid (35 mg, 0.10 mmol), EDCI (26 mg, 0.14 mmol), HOBt (19 mg, 0.15 mmol), DIPEA (0.03 mL, 0.19 mmol), 1-(4-methylaminomethyl-benzyl)-pyrrolidin-3-ol hydrochloride (30 mg, 0.11 mmol) and DCM (10 mL).

Yield: 36 mg, 65%.

LCMS method C: rt 3.08 min, 90%; m/z 557.16 (MH$^+$, 100%).

Potency: C

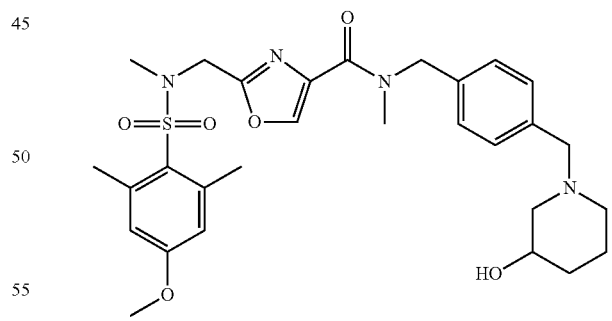

N-{4-[(3-Hydroxypiperidin-1-yl)methyl]benzyl}-2-({[(4-methoxy-2,6-dimethylphenyl)sulfonyl](methyl)amino}methyl)-N-methyl-1,3-oxazole-4-carboxamide Ex 179

The title compound was prepared according to general procedure BH using 2-{[(4-methoxy-2,6-dimethyl-benzene-sulfonyl)-methyl-amino]-methyl}-oxazole-4-carboxylic acid (30 mg, 0.08 mmol), EDCI (23 mg, 0.12 mmol), HOBt (17 mg, 0.13 mmol), DIPEA (0.035 mL, 0.20 mmol), [4-(3-1-(4-methylaminomethyl-benzyl)-piperidin-3-ol hydrochloride (28 mg, 0.10 mmol) and DCM (10 mL).

Yield: 27 mg, 56%.

LCMS method C: rt 3.11 min, 95%; m/z 571.21 (MH+, 100%).

Potency: C

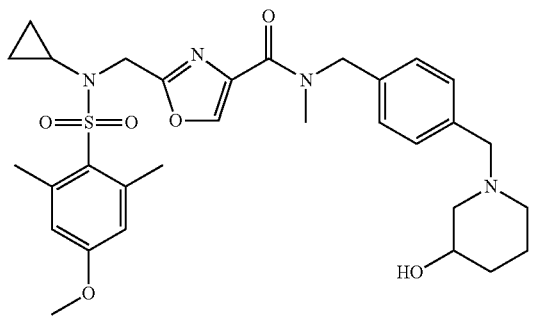 [SMILES: COc1cc(C)c(S(=O)(=O)N(Cc2nc(C(=O)N(C)Cc3ccc(CN4CCCC(O)C4)cc3)co2)C2CC2)c(C)c1]

2-({Cyclopropyl[(4-methoxy-2,6-dimethylphenyl)sulfonyl]amino}methyl)-N-{4-[(3-hydroxypiperidin-1-yl)methyl]benzyl}-N-methyl-1,3-oxazole-4-carboxamide Ex 180

The title compound was prepared according to general procedure BH using 2-{[cyclopropyl-(4-methoxy-2,6-dimethyl-benzenesulfonyl)-amino]-methyl}-oxazole-4-carboxylic acid (40 mg, 0.10 mmol), EDCI (27 mg, 0.14 mmol), HOBt (20 mg, 0.15 mmol), DIPEA (0.04 mL, 0.2 mmol), [4-(3-1-(4-methylaminomethyl-benzyl)-piperidin-3-ol hydrochloride (33 mg, 0.12 mmol) and DCM (5 mL).

Yield: 42 mg, 70%

LCMS method C: rt 3.20 min, 99%; m/z 597.22 (MH+, 100%).

Potency: C

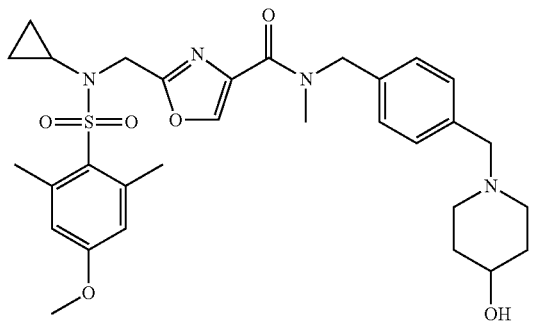 [SMILES: COc1cc(C)c(S(=O)(=O)N(Cc2nc(C(=O)N(C)Cc3ccc(CN4CCC(O)CC4)cc3)co2)C2CC2)c(C)c1]

2-({Cyclopropyl[(4-methoxy-2,6-dimethylphenyl)sulfonyl]amino}methyl)-N-{4-[(4-hydroxypiperidin-1-yl)methyl]benzyl}-N-methyl-1,3-oxazole-4-carboxamide Ex 181

The title compound was prepared according to general procedure BH using 2-{[cyclopropyl-(4-methoxy-2,6-dimethyl-benzenesulfonyl)-amino]-methyl}-oxazole-4-carboxylic acid (35 mg, 0.09 mmol), EDCI (25 mg, 0.13 mmol), HOBt (19 mg, 0.14 mmol), DIPEA (0.03 mL, 0.18 mmol), [4-(3-1-(4-methylaminomethyl-benzyl)-piperidin-4-ol hydrochloride (30 mg, 0.10 mmol) and DCM (10 mL).

Yield: 32 mg, 58%.

LCMS method C: rt 3.18 min, 95%; m/z 597.22 (MH+, 100%).

Potency: C

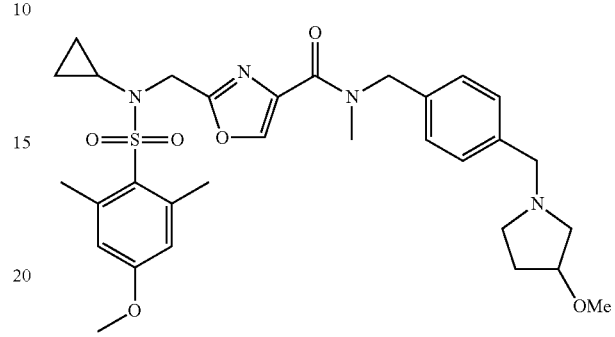

2-({Cyclopropyl[(4-methoxy-2,6-dimethylphenyl)sulfonyl]amino}methyl)-N-{4-[(3-methoxypyrrolidin-1-yl)methyl]benzyl}-N-methyl-1,3-oxazole-4-carboxamide Ex 182

The title compound was prepared according to general procedure BH using 2-({cyclopropyl[(4-methoxy-2,6-dimethylphenyl)sulfonyl]amino}methyl)-1,3-oxazole-4-carboxylic acid (40 mg, 0.11 mmol), EDCI (28 mg, 0.15 mmol), HOBt (21 mg, 0.16 mmol) DIPEA (0.04 mL, 0.21 mmol), 1-{4-[(3-methoxypyrrolidin-1-yl)methyl]phenyl}-N-methylmethanamine dihydrochloride (34 mg, 0.13 mmol) and DCM (10 mL).

Yield: 40 mg, 63%.

LCMS method C: rt 3.18 min, 99%; m/z 585.19 (MH+, 100%).

Potency: C

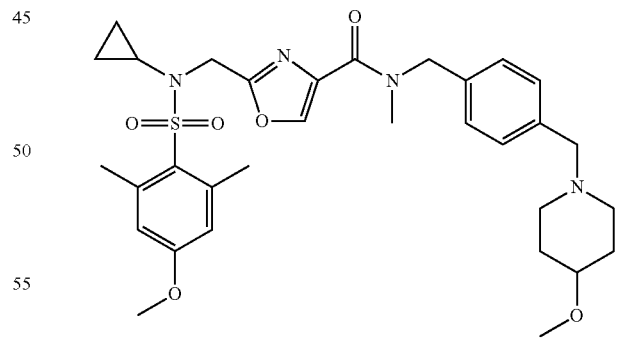

2-({Cyclopropyl[(4-methoxy-2,6-dimethylphenyl)sulfonyl]amino}methyl)-N-{4-[(4-methoxypiperidin-1-yl)methyl]benzyl}-N-methyl-1,3-oxazole-4-carboxamide Ex 183

The title compound was prepared according to general procedure BH using 2-({cyclopropyl[(4-methoxy-2,6-dimethylphenyl)sulfonyl]amino}methyl)-1,3-oxazole-4-carboxylic acid (40 mg, 0.105 mmol), EDCI (28 mg, 0.15 mmol), HOBt (21 mg, 0.16 mmol) DIPEA (0.04 mL, 0.21 mmol), 1-{4-[(4-methoxypiperidin-1-yl)methyl]phenyl}-N-methylmethanamine dihydrochloride (36 mg, 0.13 mmol) and DCM (10 mL).

Yield: 40 mg, 61%.

LCMS method C: rt 3.30 min, 98%; m/z 611.25 (MH$^+$, 100%).

Potency: C

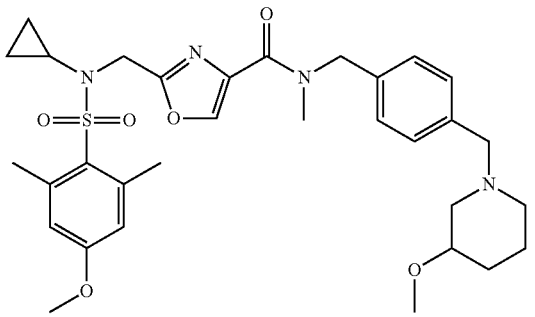 [SMILES: COc1cc(C)c(S(=O)(=O)N(Cc2nc(C(=O)N(C)Cc3ccc(CN4CCCC(OC)C4)cc3)co2)C2CC2)c(C)c1]

2-({Cyclopropyl[(4-methoxy-2,6-dimethylphenyl)sulfonyl]amino}methyl)-N-{4-[(3-methoxypiperidin-1-yl)methyl]benzyl}-N-methyl-1,3-oxazole-4-carboxamide Ex 184

The title compound was prepared according to general procedure BH using 2-({cyclopropyl[(4-methoxy-2,6-dimethylphenyl)sulfonyl]amino}methyl)-1,3-oxazole-4-carboxylic acid (40 mg, 0.11 mmol), EDCI (28 mg, 0.16 mmol), HOBt (21 mg, 0.16 mmol) DIPEA (0.04 mL, 0.21 mmol), 1-{4-[(3-methoxypiperidin-1-yl)methyl]phenyl}-N-methylmethanamine dihydrochloride (36 mg, 0.13 mmol) and DCM (10 mL).

Yield: 26 mg, 42%.

LCMS method C: rt 3.29 min, 92%; m/z 611.27 (MH$^+$, 100%).

Potency: C

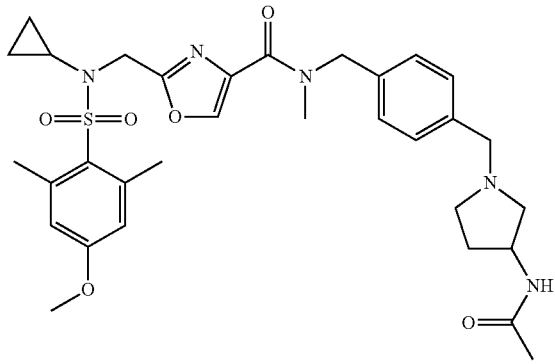 [SMILES: COc1cc(C)c(S(=O)(=O)N(Cc2nc(C(=O)N(C)Cc3ccc(CN4CCC(NC(C)=O)C4)cc3)co2)C2CC2)c(C)c1]

N-(4-{[3-(Acetylamino)pyrrolidin-1-yl]methyl}benzyl)-2-({cyclopropyl[(4-methoxy-2,6-dimethylphenyl)sulfonyl]amino}methyl)-N-methyl-1,3-oxazole-4-carboxamide Ex 185

The title compound was prepared according to general procedure BH using 2-({cyclopropyl[(4-methoxy-2,6-dimethylphenyl)sulfonyl]amino}methyl)-1,3-oxazole-4-carboxylic acid (40 mg, 0.11 mmol), EDCI (28 mg, 0.15 mmol), HOBt (21 mg, 0.16 mmol) DIPEA (0.04 mL, 0.21 mmol), 1-(4-methylaminomethyl-benzyl)-pyrrolidine-3-carboxylic acid dimethylamide-amine hydrochloride (36 mg, 0.13 mmol) and DCM (10 mL).

Yield: 32 mg, 49%.

LCMS method C: rt 3.26 min, 90%; m/z 624.25 (MH$^+$, 100%).

Potency: C

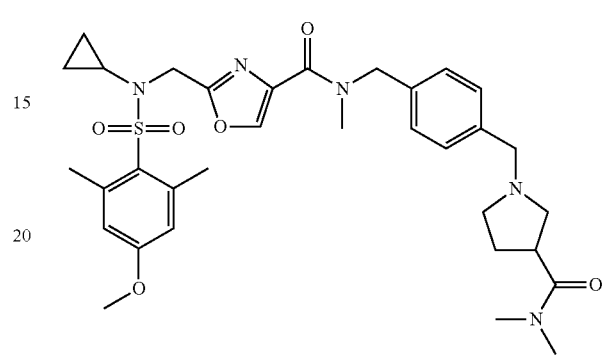

2-({Cyclopropyl[(4-methoxy-2,6-dimethylphenyl)sulfonyl]amino}methyl)-N-(4-{[3-(dimethylcarbamoyl)pyrrolidin-1-yl]methyl}benzyl)-N-methyl-1,3-oxazole-4-carboxamide Ex 186

The title compound was prepared according to general procedure BH using 2-({cyclopropyl[(4-methoxy-2,6-dimethylphenyl)sulfonyl]amino}methyl)-1,3-oxazole-4-carboxylic acid (40 mg, 0.1 mmol), EDCI (26 mg, 0.14 mmol), HOBt (20 mg, 0.15 mmol) DIPEA (0.035 mL, 0.20 mmol), N,N-dimethyl-1-{4-[(methylamino)methyl]benzyl}pyrrolidine-3-carboxamide dihydrochloride (40 mg, 0.11 mmol) and DCM (10 mL).

Yield: 35 mg, 52%.

LCMS method C: rt 3.24 min, 96%; m/z 638.30 (MH$^+$, 100%).

Potency: C

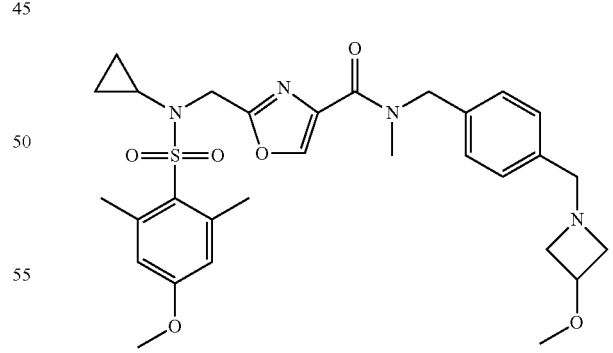

2-({Cyclopropyl[(4-methoxy-2,6-dimethylphenyl)sulfonyl]amino}methyl)-N-{4-[(3-methoxyazetidin-1-yl)methyl]benzyl}-N-methyl-1,3-oxazole-4-carboxamide Ex 187

The title compound was prepared according to general procedure BH using 2-({cyclopropyl[(4-methoxy-2,6-dimethylphenyl)sulfonyl]amino}methyl)-1,3-oxazole-4-carboxylic acid (37 mg, 0.1 mmol), EDCI (26 mg, 0.13 mmol), HOBt (19 mg, 0.15 mmol) DIPEA (0.04 mL, 0.21 mmol), 1-{4-[(3-methoxyazetidin-1-yl)methyl]phenyl}-N-methyl-methanamine dihydrochloride (30 mg, 0.12 mmol) and DCM (10 mL).

Yield: 23 mg, 39%.
LCMS method C: rt 3.56 min, 98%; m/z 583.02 (MH+, 100%).
Potency: C

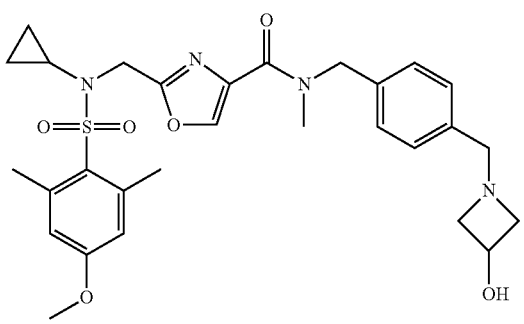 [SMILES: COc1cc(C)c(S(=O)(=O)N(Cc2nc(C(=O)N(C)Cc3ccc(CN4CC(O)C4)cc3)co2)C2CC2)c(C)c1]

2-({Cyclopropyl[(4-methoxy-2,6-dimethylphenyl)sulfonyl]amino}methyl)-N-{4-[(3-hydroxyazetidin-1-yl)methyl]benzyl}-N-methyl-1,3-oxazole-4-carboxamide Ex 188
The title compound was prepared according to general procedure BH using 2-({cyclopropyl[(4-methoxy-2,6-dimethylphenyl)sulfonyl]amino}methyl)-1,3-oxazole-4-carboxylic acid (40 mg, 0.11 mmol), EDCI (29 mg, 0.15 mmol), HOBt (22 mg, 0.16 mmol) DIPEA (0.04 mL, 0.21 mmol), 1-{4-[(methylamino)methyl]benzyl}azetidin-3-ol dihydrochloride (35 mg, 0.13 mmol) and DCM (10 mL).

Yield: 20 mg, 55%.
LCMS method C: rt 3.22 min, 94%; m/z 569.34 (MH+, 100%).
Potency: B

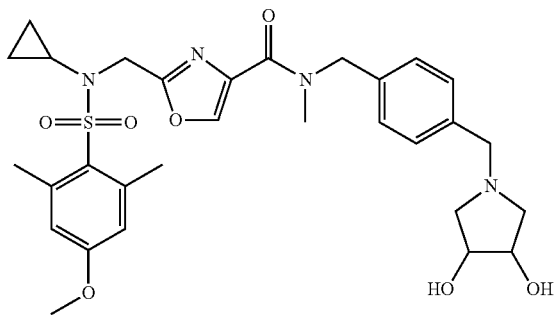 [SMILES: COc1cc(C)c(S(=O)(=O)N(Cc2nc(C(=O)N(C)Cc3ccc(CN4CC(O)C(O)C4)cc3)co2)C2CC2)c(C)c1]

2-({Cyclopropyl[(4-methoxy-2,6-dimethylphenyl)sulfonyl]amino}methyl)-N-{4-[(3,4-dihydroxypyrrolidin-1-yl)methyl]benzyl}-N-methyl-1,3-oxazole-4-carboxamide Ex 189
The title compound was prepared according to general procedure BH using 2-({cyclopropyl[(4-methoxy-2,6-dimethylphenyl)sulfonyl]amino}methyl)-1,3-oxazole-4-carboxylic acid (35 mg, 0.09 mmol), EDCI (25 mg, 0.13 mmol), HOBt (19 mg, 0.19 mmol) DIPEA (0.03 mL, 0.21 mmol), 1-{4-[(methylamino)methyl]benzyl}pyrrolidine-3,4-diol dihydrochloride (30 mg, 0.11 mmol) and DCM (10 mL).

Yield: 26 mg, 47%.
LCMS method C: rt 3.11 min, 99%; m/z 599.32 (MH+, 100%).
Potency: C

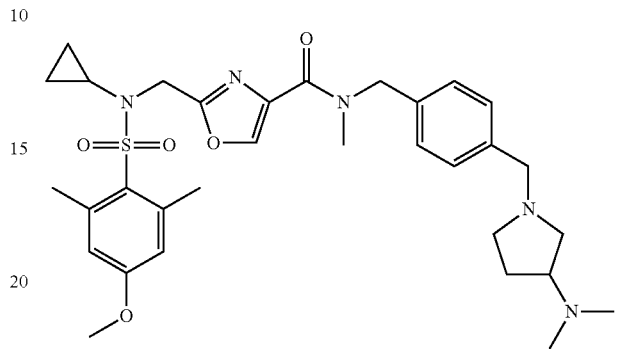

2-({Cyclopropyl[(4-methoxy-2,6-dimethylphenyl)sulfonyl]amino}methyl)-N-(4-{[3-(dimethylamino)pyrrolidin-1-yl]methyl}benzyl)-N-methyl-1,3-oxazole-4-carboxamide Ex 190
The title compound was prepared according to general procedure BH using 2-{[cyclopropyl-(4-methoxy-2,6-dimethyl-benzenesulfonyl)-amino]-methyl}-oxazole-4-carboxylic acid (35 mg, 0.09 mmol), EDCI (25 mg, 0.13 mmol), HOBt (19 mg, 0.14 mmol), DIPEA (0.03 mL, 0.19 mmol), dimethyl-[1-(4-methylaminomethyl-benzyl)-pyrrolidin-3-yl]-amine hydrochloride (31 mg, 0.11 mmol) and DCM (10 mL).

Yield: 37 mg, 66%.
LCMS method C: rt 2.80 min, 92%; m/z 305.84 ([M+2H]$^{2+}$, 100%), 610.26 (MH+, 44%).
Potency: C

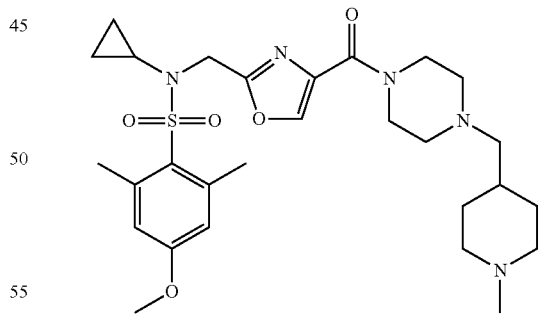

N-Cyclopropyl-4-methoxy-2,6-dimethyl-N-{[4-({4-[(1-methylpiperidin-4-yl)methyl]piperazin-1-yl}carbonyl)-1,3-oxazol-2-yl]methyl}benzenesulfonamide trifluoroacetate trifluoroacetate Ex 191
The title compound was prepared according to general procedure AC using 2-({cyclopropyl[(4-methoxy-2,6-dimethylphenyl)sulfonyl]amino}methyl)-1,3-oxazole-4-carboxylic acid (40 mg, 0.11 mmol), EDCI (41 mg, 0.21 mmol) and HOBt monohydrate (29 mg, 0.21 mmol) and 1-[(1-methylpiperidin-4-yl)methyl]piperazine (26 mg, 0.13 mmol) and DIPEA (0.093 mL, 0.53 mmol) in DCE (1.5 mL). A portion of the crude product was purified using prep method A LCMS Method C: rt 2.68 min, 100%; m/z 280.75 ([M+2H]$^{2+}$, 100%) 560.25 (MH$^+$, 14%)
Potency: C

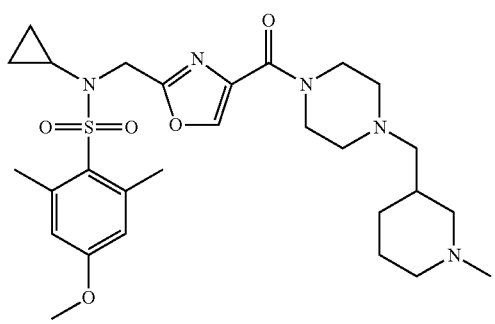 [SMILES: COc1cc(C)c(S(=O)(=O)N(Cc2nc(C(=O)N3CCN(CC4CCCN(C)C4)CC3)co2)C2CC2)c(C)c1]

N-Cyclopropyl-4-methoxy-2,6-dimethyl-N-{[4-({4-[(1-methylpiperidin-3-yl)methyl]piperazin-1-yl}carbonyl)-1,3-oxazol-2-yl]methyl}benzenesulfonamide trifluoroacetate Ex 192

The title compound was prepared according to general procedure AC using 2-({cyclopropyl[(4-methoxy-2,6-dimethylphenyl)sulfonyl]amino}methyl)-1,3-oxazole-4-carboxylic acid carboxylic acid (40 mg, 0.11 mmol), EDCI (41 mg, 0.21 mmol) and HOBt monohydrate (29 mg, 0.21 mmol) and 1-[(1-methylpiperidin-3-yl)methyl]piperazine (26 mg, 0.13 mmol) in DCE (1.5 mL). A portion of the crude product was purified using prep method A LCMS Method C: rt 2.71 min, 100%; m/z 280.75 ([M+2H]$^{2+}$, 100%), 560.25 (MH$^+$, 19%)
Potency: C

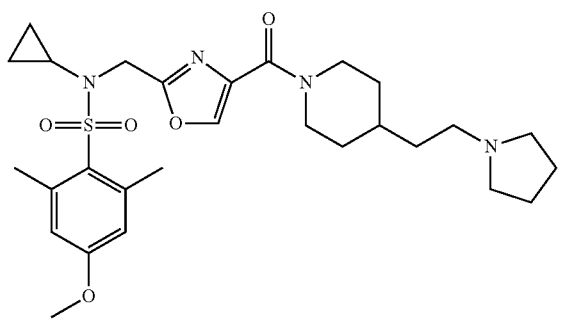 [SMILES: COc1cc(C)c(S(=O)(=O)N(Cc2nc(C(=O)N3CCC(CCN4CCCC4)CC3)co2)C2CC2)c(C)c1]

N-Cyclopropyl-4-methoxy-2,6-dimethyl-N-[(4-{[4-(2-pyrrolidin-1-ylethyl)piperidin-1-yl]carbonyl}-1,3-oxazol-2-yl)methyl]benzenesulfonamide trifluoroacetate Ex 193

The title compound was prepared according to general procedure AC using 2-({cyclopropyl[(4-methoxy-2,6-dimethylphenyl)sulfonyl]amino}methyl)-1,3-oxazole-4-carboxylic acid (40 mg, 0.11 mmol), EDCI (41 mg, 0.21 mmol) and HOBt monohydrate (29 mg, 0.21 mmol) and 4-[2-(pyrrolidin-1-yl)ethyl]piperidine (23 mg, 0.13 mmol) in DCE (1.5 mL). A portion of the crude product was purified using prep method A LCMS Method C: rt 3.20 min, 100%; m/z 545.25 (MH$^+$, 100%)
Potency: C

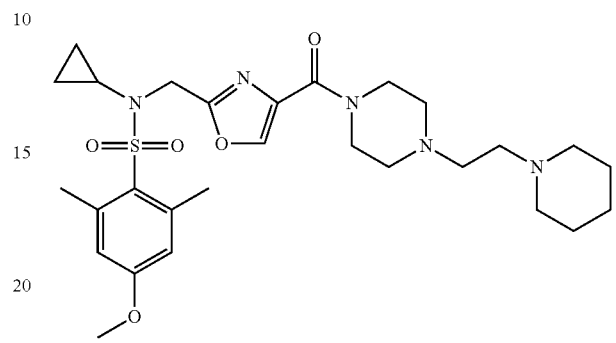

N-Cyclopropyl-4-methoxy-2,6-dimethyl-N-[(4-{[4-(2-piperidin-1-ylethyl)piperazin-1-yl]carbonyl}-1,3-oxazol-2-yl)methyl]benzenesulfonamide trifluoroacetate Ex 194

The title compound was prepared according to general procedure AC using 2-({cyclopropyl[(4-methoxy-2,6-dimethylphenyl)sulfonyl]amino}methyl)-1,3-oxazole-4-carboxylic acid (30 mg, 0.08 mmol), EDCI (31 mg, 0.16 mmol) and HOBt monohydrate (22 mg, 0.16 mmol) and 1-[2-(piperidin-1-yl)ethyl]piperazine (19 mg, 0.10 mmol) and DIPEA (0.07 mL, 0.39 mmol) in DCE (1.5 mL). A portion of the crude product was purified using prep method A LCMS Method C: rt 3.08 min, 100%; m/z 560.25 (MH$^+$, 100%)
Potency: C

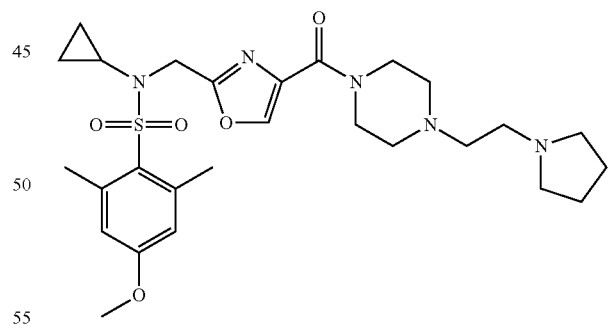

N-Cyclopropyl-4-methoxy-2,6-dimethyl-N-[(4-{[4-(2-pyrrolidin-1-ylethyl)piperazin-1-yl]carbonyl}-1,3-oxazol-2-yl)methyl]benzenesulfonamide trifluoroacetate Ex 195

The title compound was prepared according to general procedure AC using 2-({cyclopropyl[(4-methoxy-2,6-dimethylphenyl)sulfonyl]amino}methyl)-1,3-oxazole-4-carboxylic acid (30 mg, 0.08 mmol), EDCI (31 mg, 0.16 mmol)

and HOBt monohydrate (22 mg, 0.16 mmol) and 1-[2-(pyrrolidin-1-yl)ethyl]piperazine (18 mg, 0.10 mmol) and DIPEA (0.07 mL, 0.39 mmol) in DCE (1.5 mL). A portion of the crude product was purified using prep method A LCMS Method C: rt 3.06 min, 100%; m/z 546.26 (MH$^+$, 100%)

Potency: C

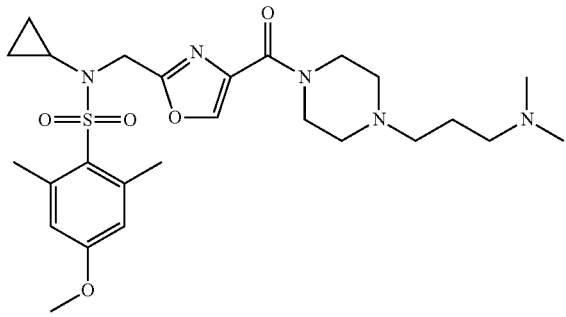 [SMILES: COc1cc(C)c(S(=O)(=O)N(Cc2nc(C(=O)N3CCN(CCCN(C)C)CC3)co2)C2CC2)c(C)c1]

N-Cyclopropyl-N-{[4-({4-[3-(dimethylamino)propyl]piperazin-1-yl}carbonyl)-1,3-oxazol-2-yl]methyl}-4-methoxy-2,6-dimethylbenzenesulfonamide trifluoroacetate Ex 196

The title compound was prepared according to general procedure AC using 2-({cyclopropyl[(4-methoxy-2,6-dimethylphenyl)sulfonyl]amino}methyl)-1,3-oxazole-4-carboxylic acid (30 mg, 0.08 mmol), EDCI (31 mg, 0.16 mmol) and HOBt monohydrate (22 mg, 0.16 mmol) and N,N-dimethyl-3-(piperazin-1-yl)propan-1-amine (17 mg, 0.10 mmol) and DIPEA (0.069 mL, 0.39 mmol) in DCE (1.5 mL). A portion of the crude product was purified using prep method A LCMS Method C: rt 2.66 min, 100%; m/z 267.73 ([M+2H]$^{2+}$, 100%), 534.23 (MH$^+$, 59%)

Potency: C

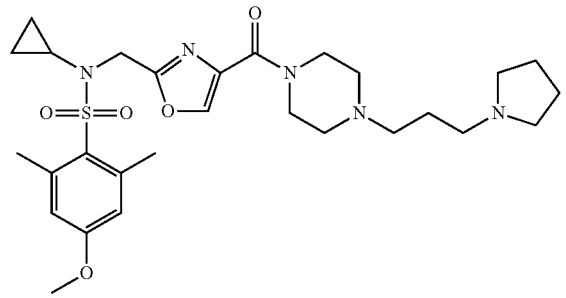 [SMILES: COc1cc(C)c(S(=O)(=O)N(Cc2nc(C(=O)N3CCN(CCCN4CCCC4)CC3)co2)C2CC2)c(C)c1]

N-Cyclopropyl-4-methoxy-2,6-dimethyl-N-[(4-{[4-(3-pyrrolidin-1-ylpropyl)piperazin-1-yl]carbonyl}-1,3-oxazol-2-yl)methyl]benzenesulfonamide trifluoroacetate Ex 197

The title compound was prepared according to general procedure AC using 2-({cyclopropyl[(4-methoxy-2,6-dimethylphenyl)sulfonyl]amino}methyl)-1,3-oxazole-4-carboxylic acid (30 mg, 0.08 mmol), EDCI (31 mg, 0.16 mmol) and HOBt monohydrate (22 mg, 0.16 mmol) and 1-[3-(pyrrolidin-1-yl)propyl]piperazine (19 mg, 0.10 mmol) and DIPEA (0.07 mL, 0.39 mmol) in DCE (1.5 mL). A portion of the crude product was purified using prep method A LCMS Method C: rt 2.70 min, 100%; m/z 280.75 ([M+2H]$^{2+}$, 100%), 560.25 (MH$^+$, 28%)

Potency: C

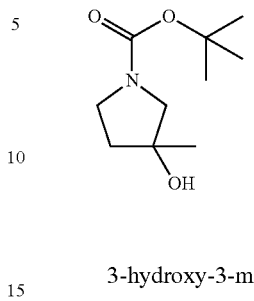

tert-Butyl 3-hydroxy-3-methylpyrrolidine-1-carboxylate

Int 213

To a stirred solution of N-boc-pyrrolidin-3-one (0.6 g, 3.2 mmol) in THF (10 mL) at −78° C. was slowly added a 3M solution of MeMgBr in THF (2.1 mL, 6.4 mmol). The resulting reaction mixture was stirred at −78° C. for 2 h. The reaction was quenched with a saturated solution of NH$_4$Cl (1 mL) and extracted with DCM (2×60 mL). The combined organic extracts were washed with water (25 mL), brine (25 mL) and dried over anhydrous Na$_2$SO$_4$. The solvent was removed in vacuo and the residue was purified by FCC eluting with 50% EtOAc in hexane to afford the title compound.

Yield: 0.29 g, 45%.

$^1$H NMR (300 MHz, CDCl$_3$) δ ppm: 3.51-3.19 (4H, m), 2.0-1.78 (3H, m), 1.50 (9H, s), 1.37 (3H, s).

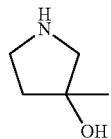

3-Methylpyrrolidin-3-ol hydrochloride

Int 214

The title compound was prepared according to general procedure BG using tert-butyl 3-hydroxy-3-methylpyrrolidine-1-carboxylate (0.29 g, 1.44 mmol) and 4M HCl in dioxane (10 mL).

Yield: 200 mg, 100%

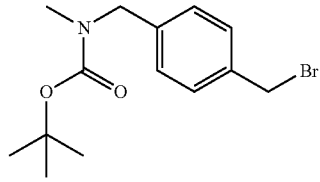 [SMILES: CN(Cc1ccc(CBr)cc1)C(=O)OC(C)(C)C]

tert-Butyl[4-(bromomethyl)benzyl]methylcarbamate

Int 215

To a solution of tert-butyl[4-(hydroxymethyl)benzyl]methylcarbamate (1.0 g, 3.97 mmol) in DCM (20 mL) at 0° C. under argon atmosphere were added PPh$_3$ (1.56 g, 5.95 mmol) and CBr$_4$ (1.98 g, 5.9 mmol). The reaction was stirred for 4 days at ambient temperature. The solvent was removed in vacuo and the residue was purified by FCC eluting with 20% EtOAc in hexane to afford the title compound.

Yield: 0.7 g, 56%.

$^1$H NMR (300 MHz, CDCl$_3$) δ ppm: 7.35 (2H, m), 7.20 (2H, m), 4.49 (2H, s), 4.41 (2H, s), 2.81 (3H, s), 1.47 (9H, s).

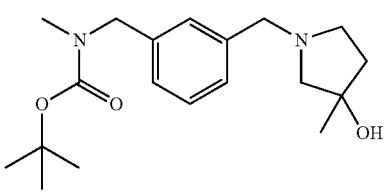 [SMILES: CN(Cc1cccc(CN2CCC(C)(O)C2)c1)C(=O)OC(C)(C)C]

tert-Butyl {3-[(3-hydroxy-3-methylpyrrolidin-1-yl)methyl]benzyl}methylcarbamate

Int 216

To a suspension of K$_2$CO$_3$ (0.82 g, 6.0 mmol) in MeCN (20 mL) was added 3-methyl-pyrrolidin-3-ol hydrochloride (0.23 g, 1.6 mmol) and the mixture stirred for 15 min at ambient temperature. Tert-butyl[4-(bromomethyl)benzyl]methylcarbamate (0.4 g, 1.27 mmol) was added and the resulting reaction mixture was stirred overnight. The reaction was filtered and the residue washed with EtOAc (50 mL). The combined organic extracts were concentrated in vacuo and the resulting residue was purified by FCC eluting with 5% MeOH in DCM to afford the title compound.
Yield: 140 mg, 35%.
$^1$H NMR (300 MHz, CDCl$_3$) δ ppm: 7.28 (2H, m), 7.16 (2H, m), 4.40 (2H, s), 3.61 (2H, s), 2.96 (1H, m), 2.81 (3H, s), 2.69 (1H, d), 2.33 (1H, m), 2.19 (1H, d), 1.88 (2H, t), 1.48 (9H, s), 1.33 (3H, s).

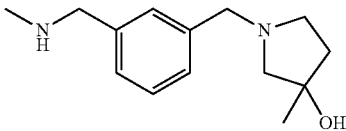 [SMILES: CNCc1cccc(CN2CCC(C)(O)C2)c1]

3-Methyl-1-{3-[(methylamino)methyl]benzyl}pyrrolidin-3-ol dihydrochloride

Int 217

The title compound was prepared according to general procedure BG using tert-butyl {3-[(3-hydroxy-3-methylpyrrolidin-1-yl)methyl]benzyl}methylcarbamate (140 mg, 0.41 mmol) and 4M HCl in Et$_2$O (5 mL) to afford the title compound as a dihydrochloride salt.
Yield: 85 mg, 68%

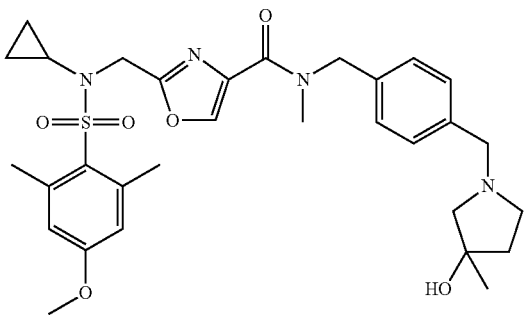 [SMILES: COc1cc(C)c(S(=O)(=O)N(Cc2nc(C(=O)N(C)Cc3ccc(CN4CCC(C)(O)C4)cc3)co2)C2CC2)c(C)c1]

2-({Cyclopropyl[(4-methoxy-2,6-dimethylphenyl)sulfonyl]amino}methyl)-N-{4-[(3-hydroxy-3-methylpyrrolidin-1-yl)methyl]benzyl}-N-methyl-1,3-oxazole-4-carboxamide Ex 198

The title compound was prepared according to general procedure BH using 2-({cyclopropyl[(4-methoxy-2,6-dimethylphenyl)sulfonyl]amino}methyl)-1,3-oxazole-4-carboxylic acid (35 mg, 0.09 mmol), EDCI (24 mg, 0.12 mmol), HOBt (18 mg, 0.14 mmol) DIPEA (0.032 mL, 0.18 mmol) and 3-methyl-1-{3-[(methylamino)methyl]benzyl}pyrrolidin-3-ol dihydrochloride (30 mg, 0.10 mmol) in DCM (5 mL). The resulting residue was purified by FCC eluting with 5% MeOH in DCM to afford the title compound.
Yield: 30 mg, 55%.
LCMS method C: rt 3.24 min, 93%; m/z 597.36 (MH$^+$, 100%).
Potency: C

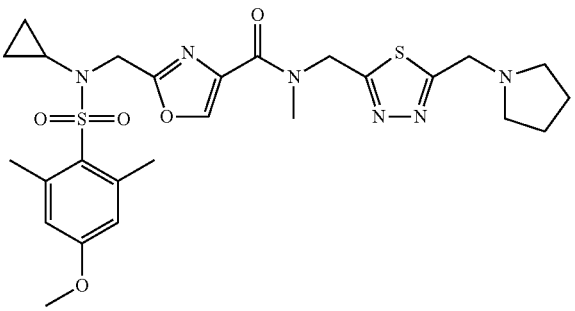 [SMILES: COc1cc(C)c(S(=O)(=O)N(Cc2nc(C(=O)N(C)Cc3nnc(CN4CCCC4)s3)co2)C2CC2)c(C)c1]

2-({Cyclopropyl[(4-methoxy-2,6-dimethylphenyl)sulfonyl]amino}methyl)-N-methyl-N-{[5-(pyrrolidin-1-ylmethyl)-1,3,4-thiadiazol-2-yl]methyl}-1,3-oxazole-4-carboxamide trifluoroacetate Ex 199

The title compound was prepared according to general procedure AI using 2-({cyclopropyl[(4-methoxy-2,6-dimethylphenyl)sulfonyl]amino}methyl)-1,3-oxazole-4-carboxylic acid (38 mg, 0.1 mmol), EDCI (29 mg, 0.15 mmol), HOBt monohydrate (23 mg, 0.15 mmol), DIPEA (70 mL, 0.4 mmol), N-methyl-1-[5-(pyrrolidin-1-ylmethyl)-1,3,4-thiadiazol-2-yl]methanamine bis trifluoroacetate (42 mg, 0.1 mmol) and DMF (0.8 mL). The crude products were absorbed directly on to MP-TsOH resin (1 mL) and washed with MeOH (7 mL) and the product eluted with 7N NH$_3$ in MeOH (7 mL). A portion of the resulting products was purified using prep method C to afford the title compound as the TFA salt.
LCMS method C: rt 3.12 min, 100%; m/z 575.18 (MH$^+$, 100%).
Potency: C

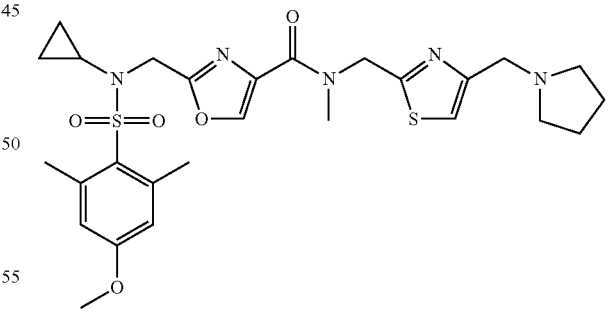

2-({Cyclopropyl[(4-methoxy-2,6-dimethylphenyl)sulfonyl]amino}methyl)-N-methyl-N-{[4-(pyrrolidin-1-ylmethyl)-1,3-thiazol-2-yl]methyl}-1,3-oxazole-4-carboxamide trifluoroacetate Ex 200

The title compound was prepared according to general procedure AI using 2-({cyclopropyl[(4-methoxy-2,6-dimethylphenyl)sulfonyl]amino}methyl)-1,3-oxazole-4-carboxylic acid (38 mg, 0.1 mmol), EDCI (29 mg, 0.15 mmol), HOBt monohydrate (23 mg, 0.15 mmol), DIPEA (70 mL, 0.4 mmol), N-methyl-1-[4-(pyrrolidin-1-ylmethyl)-1,3-thiazol-2-yl]methanamine (21 mg, 0.1 mmol) and DMF (0.8 mL). The crude products were absorbed directly on to MP-TsOH resin (1 mL) and washed with MeOH (7 mL) and the product eluted with 7N NH$_3$ in MeOH (7 mL). A portion of the resulting products was purified using prep method C to afford the title compound as the TFA salt.

LCMS method C: rt 3.19 min, 98%; m/z 574.17 (MH$^+$, 100%).
Potency: C

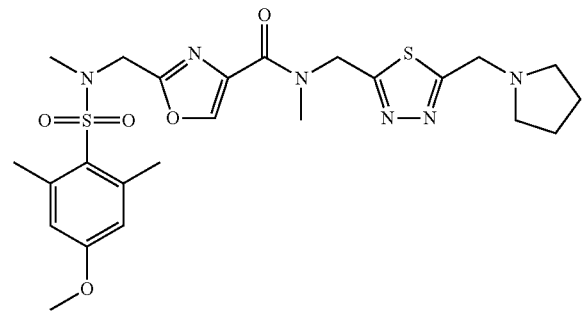 [SMILES: COc1cc(C)c(S(=O)(=O)N(C)Cc2nc(C(=O)N(C)Cc3nnc(CN4CCCC4)s3)co2)c(C)c1]

2-({[(4-Methoxy-2,6-dimethylphenyl)sulfonyl](methyl)amino}methyl)-N-methyl-N-{[5-(pyrrolidin-1-ylmethyl)-1,3,4-thiadiazol-2-yl]methyl}-1,3-oxazole-4-carboxamide trifluoroacetate Ex 201

The title compound was prepared according to general procedure AI using 2-({[(4-methoxy-2,6-dimethylphenyl)sulfonyl](methyl)amino}methyl)-1,3-oxazole-4-carboxylic acid (35 mg, 0.1 mmol), EDCI (29 mg, 0.15 mmol), HOBt monohydrate (23 mg, 0.15 mmol), DIPEA (70 mL, 0.4 mmol), N-methyl-1-[5-(pyrrolidin-1-ylmethyl)-1,3,4-thiadiazol-2-yl]methanamine bis trifluoroacetate (42 mg, 0.1 mmol) and DMF (0.8 mL). The crude products were absorbed directly on to MP-TsOH resin (1 mL) and washed with MeOH (7 mL) and the product eluted with 7N NH$_3$ in MeOH (7 mL). A portion of the resulting products was purified using prep method C to afford the title compound as the TFA salt.

LCMS method C: rt 3.01 min, 100%; m/z 549.11 (MH$^+$, 100%).
Potency: A

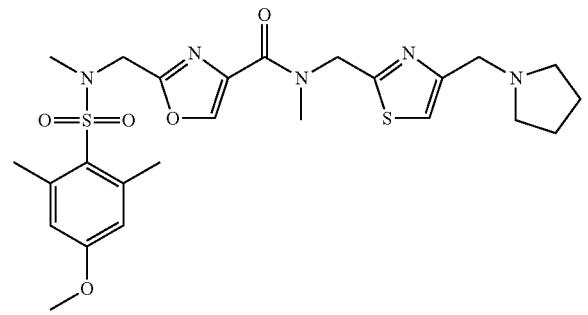 [SMILES: COc1cc(C)c(S(=O)(=O)N(C)Cc2nc(C(=O)N(C)Cc3nc(CN4CCCC4)cs3)co2)c(C)c1]

2-({[(4-Methoxy-2,6-dimethylphenyl)sulfonyl](methyl)amino}methyl)-N-methyl-N-{[4-(pyrrolidin-1-ylmethyl)-1,3-thiazol-2-yl]methyl}-1,3-oxazole-4-carboxamide trifluoroacetate Ex 202

The title compound was prepared according to general procedure AI using 2-({[(4-methoxy-2,6-dimethylphenyl)sulfonyl](methyl)amino}methyl)-1,3-oxazole-4-carboxylic acid (35 mg, 0.1 mmol), EDCI (29 mg, 0.15 mmol), HOBt monohydrate (23 mg, 0.15 mmol), DIPEA (70 mL, 0.4 mmol), N-methyl-1-[4-(pyrrolidin-1-ylmethyl)-1,3-thiazol-2-yl]methanamine (21 mg, 0.1 mmol) and DMF (0.8 mL). The crude products were absorbed directly on to MP-TsOH resin (1 mL) and washed with MeOH (7 mL) and the product eluted with 7N NH$_3$ in MeOH (7 mL). A portion of the resulting products was purified using prep method C to afford the title compound as the TFA salt.

LCMS method C: rt 3.09 min, 100%; m/z 548.15 (MH$^+$, 100%).
Potency: B

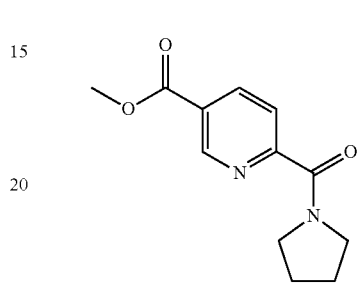

Methyl 6-(pyrrolidin-1-ylcarbonyl)pyridine-3-carboxylate

Int 218

Dimethylpyridine-2,5-dicarboxylate (5.0 g, 25.6 mmol) was dissolved in THF (125 mL) and the resulting solution was cooled to −40° C. prior to the addition of trimethylaluminium (2 M in toluene, 28.20 mL). The reaction was stirred at −40° C. for 10 min and pyrrolidine (1.82 g, 2.1 mL, 25.62 mmol) was added dropwise. The reaction was stirred at ambient temperature for 18 h before quenching with MeOH (25 mL). The solvents were removed in vacuo and the resulting residue was purified by FCC eluting with 0-20% EtOAc in hexane to afford the title compound as a white solid.

Yield: 3.30 g, 55%.
$^1$H NMR (300 MHz, CDCl$_3$): δ ppm 9.18 (1H, s), 8.40-8.37 (1H, m), 7.93-7.90 (1H, m), 3.97 (3H, s), 3.75-3.67 (4H, m), 1.97-1.91 (4H, m).

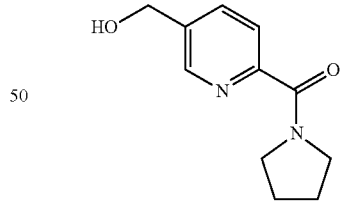

[5-(hydroxymethyl)pyridin-2-yl](pyrrolidin-1-yl)methanone

Int 219

A solution of methyl 6-(pyrrolidin-1-ylcarbonyl)pyridine-3-carboxylate (1.0 g, 4.29 mmol) in MeOH (15 mL) was cooled to 0° C. and NaBH$_4$ (808 mg, 21.36 mmol) was added portionwise. The reaction mixture was stirred at ambient temperature for 24 h. Aqueous HCl (2 M, 15 mL) was added and the MeOH removed in vacuo. The remaining aqueous layer was extracted with DCM (4×25 mL) and the combined organic extracts were washed with brine (10 mL), dried over Na₂SO₄ and concentrated in vacuo. The residue was purified by FCC eluting with 0-1% MeOH in DCM to afford the title compound as a pale yellow viscous liquid.

Yield: 550 mg, 62%.

¹H NMR (300 MHz, CDCl₃): δ ppm 8.45 (1H, s), 7.69-7.61 (2H, m), 4.69 (2H, s), 3.94 (1H, s), 3.68-3.63 (4H, m), 1.95-1.86 (4H, m).

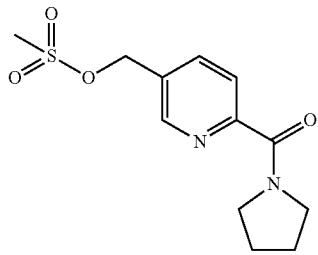 [SMILES: CS(=O)(=O)OCc1ccc(C(=O)N2CCCC2)nc1]

[6-(Pyrrolidin-1-ylcarbonyl)pyridin-3-yl]methyl methanesulfonate

Int 220

To a solution of [5-(hydroxymethyl)pyridin-2-yl](pyrrolidin-1-yl)methanone (550 mg, 2.66 mmol) and TEA (0.940 mL, 6.67 mmol) in DCM (10 mL) at 0° C., was added methanesulfonyl chloride (0.24 mL, 3.20 mmol) and the reaction stirred for 1 h at 0° C. The reaction mixture was diluted with DCM (10 mL), washed with aqueous NaHCO₃ (10% w/v, 3×5 mL) and brine (5 mL). The organic layer was dried over Na₂SO₄ and concentrated in vacuo to afford the title compound, which was used without further purification.

Crude Yield: 650 mg, 85%.

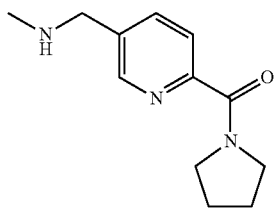 [SMILES: CNCc1ccc(C(=O)N2CCCC2)nc1]

{5-[(Methylamino)methyl]pyridin-2-yl}(pyrrolidin-1-yl)methanone

Int 221

To a stirred solution of [6-(pyrrolidin-1-ylcarbonyl)pyridin-3-yl]methyl methanesulfonate (650 mg, 2.28 mmol) in MeCN (10 mL) was added methylamine (2M in THF, 5.70 mL) and the reaction was heated at 60° C. for 14 h. The mixture was cooled to ambient temperature and concentrated in vacuo. The resulting residue was purified by FCC eluting with 0-5% MeOH in DCM to afford the title compound as a light brown viscous liquid.

Yield: 170 mg, 34%.

¹H NMR (300 MHz, CDCl₃): δ ppm 8.53 (1H, s), 7.79-7.78 (2H, m), 3.81 (2H, s), 3.76-3.66 (4H, m), 2.47 (3H, s), 1.95-1.89 (4H, m).

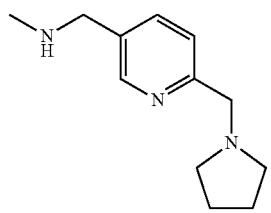

N-Methyl-1-[6-(pyrrolidin-1-ylmethyl)pyridin-3-yl]methanamine

Int 222

To a stirred solution of {5-[(methylamino)methyl]pyridin-2-yl}(pyrrolidin-1-yl)methanone (350 mg, 1.59 mmol) in anhydrous THF (10 mL) at 0° C. was added sodium bis(2-methoxyethoxy)aluminium hydride (70% in toluene, 6.90 mL, 23.93 mmol). The reaction mixture was stirred at 0° C. for 1 h then at ambient temperature for 1 h. The reaction was cooled to 0° C. and quenched with MeOH (10 mL) and aqueous NaOH (4% w/v, 10 mL). The mixture was concentrated in vacuo and the remaining aqueous layer was extracted with EtOAc (3×5 mL). The combined organic extracts were dried over Na₂SO₄ and concentrated in vacuo. The residue was purified by FCC eluting with 0-10% MeOH in DCM to afford the title compound as a yellow viscous liquid.

Yield: 80 mg, 24%.

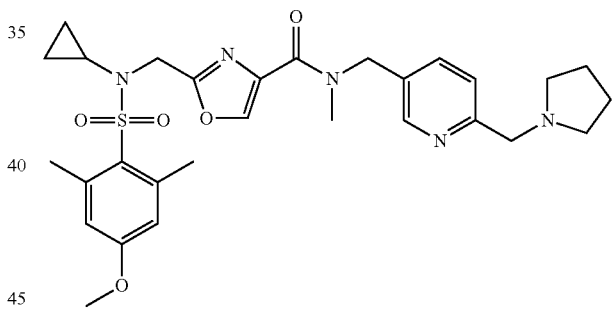

2-({Cyclopropyl[(4-methoxy-2,6-dimethylphenyl)sulfonyl]amino}methyl)-N-methyl-N-{[6-(pyrrolidin-1-ylmethyl)pyridin-3-yl]methyl}-1,3-oxazole-4-carboxamide Ex 203

The title compound was prepared according to general procedure AC using N-methyl-1-[6-(pyrrolidin-1-ylmethyl)pyridin-3-yl]methanamine (33 mg, 0.16 mmol), 2-({cyclopropyl[(4-methoxy-2,6-dimethylphenyl)sulfonyl]amino}methyl)-1,3-oxazole-4-carboxylic acid (30 mg, 0.08 mmol), EDCI (18 mg, 0.1 mmol), HOBt monohydrate (13 mg, 0.1 mmol), TEA (0.04 mL, 0.32 mmol) and DMF (1 mL). The crude product was purified using prep method D.

Yield: 14.6 mg, 32%.

LCMS method C: rt 3.23 min, 100%; m/z 568.33 (MH⁺, 100%)

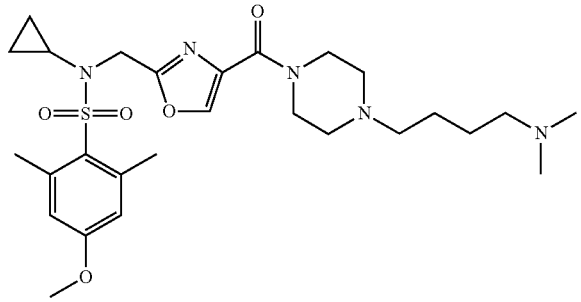 [SMILES: COc1cc(C)c(S(=O)(=O)N(Cc2nc(C(=O)N3CCN(CCCCN(C)C)CC3)co2)C2CC2)c(C)c1]

N-Cyclopropyl-N-{[4-({4-[4-(dimethylamino)butyl]
piperazin-1-yl}carbonyl)-1,3-oxazol-2-yl]methyl}-4-
methoxy-2,6-dimethylbenzenesulfonamide trifluoro-
acetate Ex 204

The title compound was prepared according to general procedure AI using N,N-dimethyl-4-piperazin-1-ylbutan-1-amine (13 mg, 0.07 mmol), 2-({cyclopropyl[(4-methoxy-2,6-dimethylphenyl)sulfonyl]amino}methyl)-1,3-oxazole-4-carboxylic acid (27 mg, 0.07 mmol), EDCI (27 mg, 0.14 mmol), HOBt monohydrate (21 mg, 0.14 mmol), DIPEA (0.05 mL, 0.28 mmol) and DMF (0.5 mL). A portion of the crude product was purified using prep method A.

LCMS method C: rt 2.68 min, 100%; m/z 274.73 ([M+2H]$^{2+}$], 100%), 548.37 (MH$^+$, 21%)

Potency: C

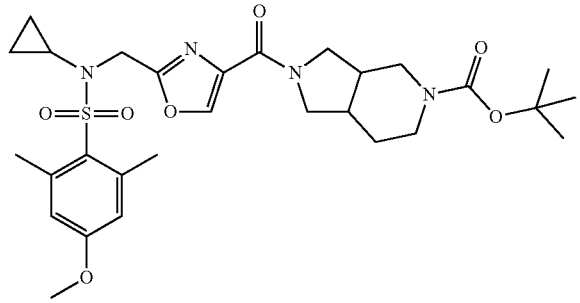 [SMILES: COc1cc(C)c(S(=O)(=O)N(Cc2nc(C(=O)N3CC4CCN(C(=O)OC(C)(C)C)CC4C3)co2)C2CC2)c(C)c1]

tert-Butyl 2-{[2-({cyclopropyl[(4-methoxy-2,6-dim-
ethylphenyl)sulfonyl]amino}methyl)-1,3-oxazol-4-
yl]carbonyl}octahydro-5H-pyrrolo[3,4-c]pyridine-5-
carboxylate Int 223

The title compound was prepared according to general procedure AH using 2-({cyclopropyl[(4-methoxy-2,6-dimethylphenyl)sulfonyl]amino}methyl)-1,3-oxazole-4-carboxylic acid (190 mg, 0.5 mmol), tert-butyl octahydro-5H-pyrrolo[3,4-c]pyridine-5-carboxylate (113 mg, 0.5 mmol), EDCI (192 mg, 1.0 mmol), HOBt monohydrate (153 mg, 1.0 mmol), DIPEA (0.35 mL, 2.0 mmol) and DMF (4 mL). The crude product was purified by FCC eluting with 2% MeOH in DCM.

Yield: 255 mg, 86%

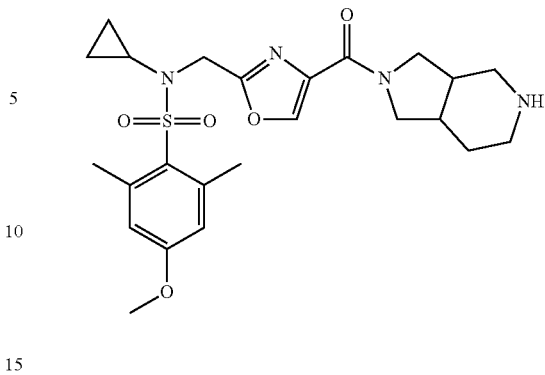

N-Cyclopropyl-4-methoxy-2,6-dimethyl-N-{[4-(oc-
tahydro-2H-pyrrolo[3,4-c]pyridin-2-ylcarbonyl)-1,3-
oxazol-2-yl]methyl}benzenesulfonamide Ex 205

The title compound was prepared according to general procedure AN using tert-butyl 2-{[2-({cyclopropyl[(4-methoxy-2,6-dimethylphenyl)sulfonyl]amino}methyl)-1,3-oxazol-4-yl]carbonyl}octahydro-5H-pyrrolo[3,4-c]pyridine-5-carboxylate (245 mg, 0.42 mmol), TFA (1 mL) and DCM (3 mL). Following the completion of the reaction the solvent was removed in vacuo, the residue redissolved in DCM (2 mL), absorbed on to 2 g SCX cartridge and washed with DCM (5 mL) and MeOH (5 mL). The title compound was eluted with 7 N NH$_3$ in MeOH (10 mL) and concentrated in vacuo.

Yield: 130 mg, 64%.

LCMS method C: rt 3.00 min, 97%; m/z 489.35 (MH$^+$, 100%)

Potency: A

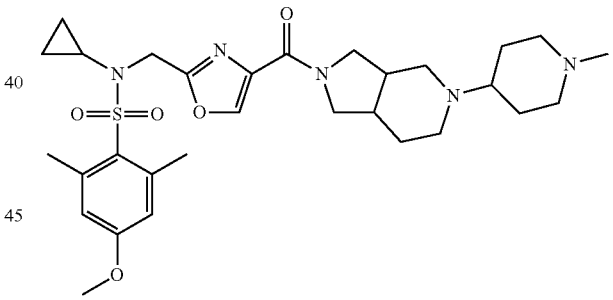

General Procedure CD

N-Cyclopropyl-4-methoxy-2,6-dimethyl-N-[(4-{[5-
(1-methylpiperidin-4-yl)octahydro-2H-pyrrolo[3,4-c]
pyridin-2-yl]carbonyl}-1,3-oxazol-2-yl)methyl]ben-
zenesulfonamide trifluoroacetate Ex 206

N-Cyclopropyl-4-methoxy-2,6-dimethyl-N-{[4-(octahydro-2H-pyrrolo[3,4-c]pyridin-2-ylcarbonyl)-1,3-oxazol-2-yl]methyl}benzenesulfonamide (24 mg, 0.05 mmol) was dissolved in THF (1 mL) and 1-methyl-4-piperidinone (7 mg, 0.06 mmol) and a few 4 Å molecular sieves added. The reaction was stirred for 30 min at ambient temperature prior to addition of STAB (21 mg, 0.1 mmol). The reaction was stirred for 3 h at ambient temperature and diluted with MeOH (0.1 mL). The solution was absorbed on to a 1 g SCX cartridge and the sorbent washed with MeOH (5 mL) and the crude product eluted off with 7 N NH₃ in MeOH (5 mL). The solvent was removed in vacuo and a portion of the resulting product was purified using prep method A to afford the title compound.

LCMS method C: rt 2.70 min, 97%; m/z 293.76 ([M+2H]²⁺], 100%), 586.34 (MH⁺, 15%)

Potency: A

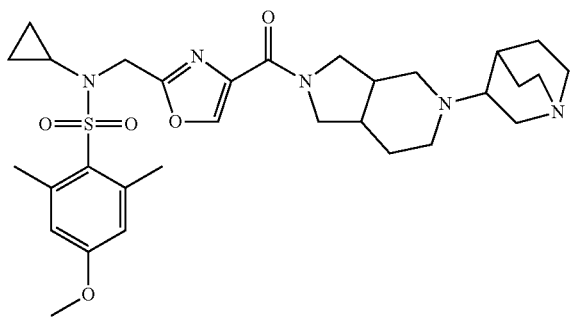 [SMILES: COc1cc(C)c(S(=O)(=O)N(Cc2nc(C(=O)N3CC4CCN(C5CN6CCC5CC6)CC4C3)co2)C2CC2)c(C)c1]

N-[(4-{[5-(1-Azabicyclo[2.2.2]oct-3-yl)octahydro-2H-pyrrolo[3,4-c]pyridin-2-yl]carbonyl}-1,3-oxazol-2-yl)methyl]-N-cyclopropyl-4-methoxy-2,6-dimethylbenzenesulfonamide trifluoroacetate Ex 207

The title compound was prepared according to general procedure CD using N-cyclopropyl-4-methoxy-2,6-dimethyl-N-{[4-(octahydro-2H-pyrrolo[3,4-c]pyridin-2-ylcarbonyl)-1,3-oxazol-2-yl]methyl}benzenesulfonamide (24 mg, 0.05 mmol), THF (1 mL), 1-azabicyclo[2.2.2]octan-3-one (7 mg, 0.06 mmol), 4 Å molecular sieves and STAB (21 mg, 0.1 mmol). The reaction was stirred for 3 h at ambient temperature and diluted with MeOH (0.1 mL). The solution was absorbed on to a 1 g SCX cartridge and the sorbent washed with MeOH (5 mL) and the crude product eluted off with 7 N NH₃ in MeOH (5 mL). The solvent was removed in vacuo and a portion of the resulting product was purified using prep method A.

LCMS method C: rt 2.72 min, 95%; m/z 299.74 ([M+2H]²⁺], 100%), 598.37 (MH⁺, 24%)

Potency: C

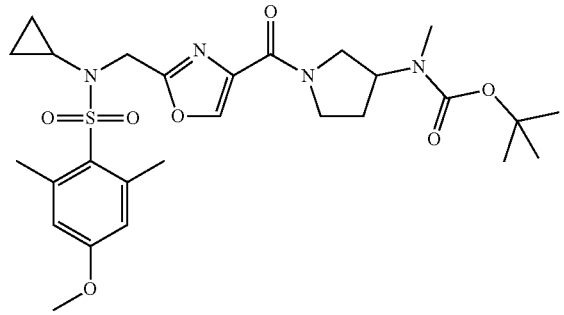 [SMILES: COc1cc(C)c(S(=O)(=O)N(Cc2nc(C(=O)N3CCC(N(C)C(=O)OC(C)(C)C)C3)co2)C2CC2)c(C)c1]

tert-Butyl (1-{[2-({cyclopropyl[(4-methoxy-2,6-dimethylphenyl)sulfonyl]amino}methyl)-1,3-oxazol-4-yl]carbonyl}pyrrolidin-3-yl)methylcarbamate Int 224

The title compound was prepared according to general procedure AH using 2-({cyclopropyl[(4-methoxy-2,6-dimethylphenyl)sulfonyl]amino}methyl)-1,3-oxazole-4-carboxylic acid (190 mg, 0.5 mmol), tert-butyl methyl(pyrrolidin-3-yl)carbamate (100 mg, 0.5 mmol), EDCI (192 mg, 1.0 mmol), HOBt monohydrate (153 mg, 1.0 mmol), DIPEA (0.35 mL, 2.0 mmol) and DMF (4 mL). The crude product was purified by FCC eluting with 2% MeOH in DCM.

Yield: 104 mg, 37%

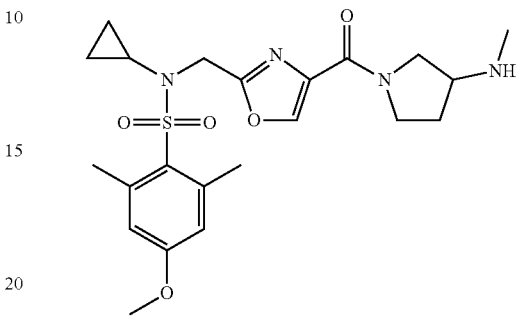

N-Cyclopropyl-4-methoxy-2,6-dimethyl-N-[(4-{[3-(methylamino)pyrrolidin-1-yl]carbonyl}-1,3-oxazol-2-yl)methyl]benzenesulfonamide Int 225

The title compound was prepared according to general procedure AN using tert-butyl (1-{[2-({cyclopropyl[(4-methoxy-2,6-dimethylphenyl)sulfonyl]amino}methyl)-1,3-oxazol-4-yl]carbonyl}pyrrolidin-3-yl)methylcarbamate (245 mg, 0.42 mmol), TFA (1 mL) and DCM (3 mL). Following the completion of the reaction the solvent was removed in vacuo, the residue redissolved in DCM (2 mL), absorbed on to 2 g SCX cartridge and washed with DCM (5 mL) and MeOH (5 mL). The title compound was eluted with 7 N NH₃ in MeOH (10 mL) and concentrated in vacuo.

Yield: 47 mg, 60%.

LCMS method C: rt 2.98 min, 88%; m/z 463.28 (MH⁺, 100%)

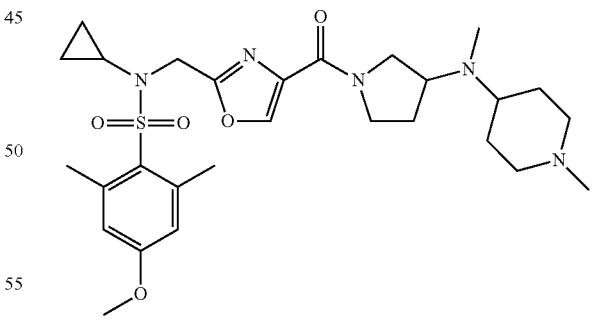

N-Cyclopropyl-4-methoxy-2,6-dimethyl-N-{[4-({3-[methyl(1-methylpiperidin-4-yl)amino]pyrrolidin-1-yl}carbonyl)-1,3-oxazol-2-yl]methyl}benzenesulfonamide trifluoroacetate Ex 208

The title compound was prepared according to general procedure CD using N-cyclopropyl-4-methoxy-2,6-dimethyl-N-[(4-{[3-(methylamino)pyrrolidin-1-yl]carbonyl}-1,3-oxazol-2-yl)methyl]benzenesulfonamide (23 mg, 0.05 mmol), THF (1 mL), 1-methyl-4-piperidinone (7 mg, 0.06 mmol), 4 Å molecular sieves and STAB (21 mg, 0.1 mmol). The reaction was stirred for 3 h at ambient temperature and diluted with MeOH (0.1 mL). The solution was absorbed on to a 1 g SCX cartridge and the sorbent washed with MeOH (5 mL) and the crude product eluted off with 7 N NH₃ in MeOH (5 mL). The solvent was removed in vacuo and a portion of the resulting product was purified using prep method A to afford the title compound.

LCMS method C: rt 2.72 min, 95%; m/z 280.73 ([M+2H]$^{2+}$], 100%), 560.34 (MH$^+$, 46%)

Potency: A

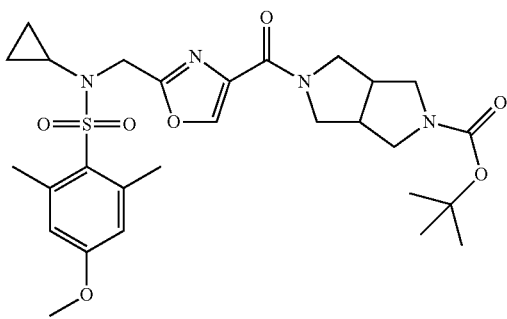 [SMILES: COc1cc(C)c(S(=O)(=O)N(Cc2nc(C(=O)N3CC4CN(C(=O)OC(C)(C)C)CC4C3)co2)C2CC2)c(C)c1]

tert-Butyl 5-{[2-({cyclopropyl[(4-methoxy-2,6-dimethylphenyl)sulfonyl]amino}methyl)-1,3-oxazol-4-yl]carbonyl}hexahydropyrrolo[3,4-c]pyrrole-2(1H)-carboxylate Int 226

The title compound was prepared according to general procedure AH using 2-({cyclopropyl[(4-methoxy-2,6-dimethylphenyl)sulfonyl]amino}methyl)-1,3-oxazole-4-carboxylic acid (190 mg, 0.5 mmol), tert-butyl hexahydropyrrolo[3,4-c]pyrrole-2(1H)-carboxylate (106 mg, 0.5 mmol), EDCI (192 mg, 1.0 mmol), HOBt monohydrate (153 mg, 1.0 mmol), DIPEA (0.35 mL, 2.0 mmol) and DMF (4 mL). The crude product was purified by FCC eluting with 2% MeOH in DCM to afford the title compound.

Yield: 280 mg, 97%

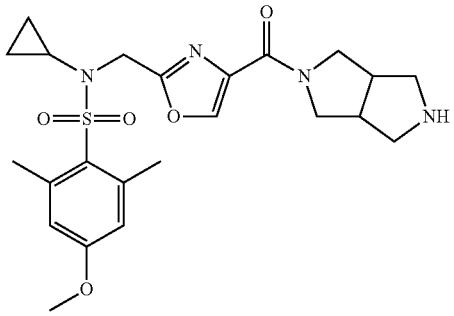 [SMILES: COc1cc(C)c(S(=O)(=O)N(Cc2nc(C(=O)N3CC4CNCC4C3)co2)C2CC2)c(C)c1]

N-Cyclopropyl-N-{[4-(hexahydropyrrolo[3,4-c]pyrrol-2(1H)-ylcarbonyl)-1,3-oxazol-2-yl]methyl}-4-methoxy-2,6-dimethylbenzenesulfonamide Int 227

The title compound was prepared according to general procedure AN using tert-butyl 5-{[2-({cyclopropyl[(4-methoxy-2,6-dimethylphenyl)sulfonyl]amino}methyl)-1,3-oxazol-4-yl]carbonyl}hexahydropyrrolo[3,4-c]pyrrole-2(1H)-carboxylate (245 mg, 0.42 mmol), TFA (1 mL) and DCM (3 mL). Following the completion of the reaction the solvent was removed in vacuo, the residue redissolved in DCM (2 mL), absorbed on to 2 g SCX cartridge and washed with DCM (5 mL) and MeOH (5 mL). The title compound was eluted with 7 N NH₃ in MeOH (10 mL) and concentrated in vacuo.

Yield: 142 mg, 66%

LCMS method C: rt 2.97 min, 99%; m/z 475.25 (MH$^+$, 100%)

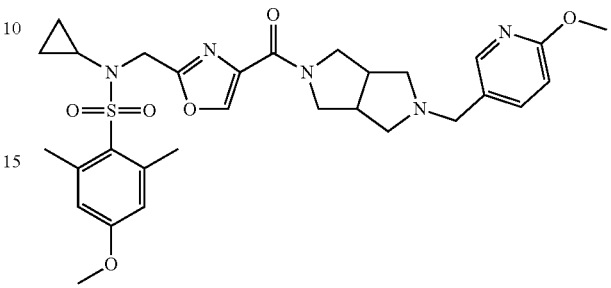

N-Cyclopropyl-4-methoxy-N-{[4-({5-[(6-methoxypyridin-3-yl)methyl]hexahydropyrrolo[3,4-c]pyrrol-2(1H)-yl}carbonyl)-1,3-oxazol-2-yl]methyl}-2,6-dimethylbenzenesulfonamide trifluoroacetate Ex 209

The title compound was prepared according to general procedure CD using N-cyclopropyl-N-{[4-(hexahydropyrrolo[3,4-c]pyrrol-2(1H)-ylcarbonyl)-1,3-oxazol-2-yl]methyl}-4-methoxy-2,6-dimethylbenzenesulfonamide (19 mg, 0.04 mmol), 6-methoxypyridine-3-carbaldehyde (6.5 mg, 0.05 mmol), STAB (17 mg, 0.08 mmol), DCE (1 mL) and a few 4 Å molecular sieves. The crude products were absorbed on to MP-TsOH resin (1 mL), washed with MeOH (2 mL) and the crude product eluted with 7 N NH₃ in MeOH (3 mL). The solvent was removed in vacuo and the crude product purified using prep method A to afford the title compound.

LCMS method C: rt 3.25 min, 88%; m/z 596.37 (MH$^+$, 100%)

Potency: A

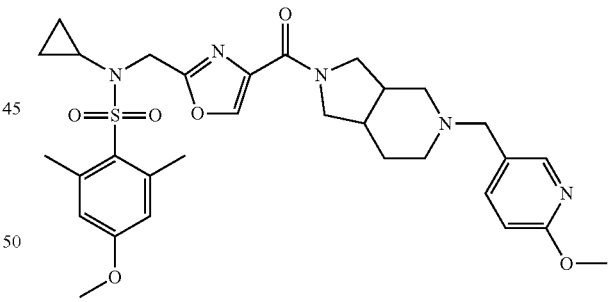

N-Cyclopropyl-4-methoxy-N-{[4-({5-[(6-methoxypyridin-3-yl)methyl]octahydro-2H-pyrrolo[3,4-c]pyridin-2-yl}carbonyl)-1,3-oxazol-2-yl]methyl}-2,6-dimethylbenzenesulfonamide trifluoroacetate Ex 210

The title compound was prepared according to general procedure CD using N-cyclopropyl-4-methoxy-2,6-dimethyl-N-{[4-(octahydro-2H-pyrrolo[3,4-c]pyridin-2-ylcarbonyl)-1,3-oxazol-2-yl]methyl}benzenesulfonamide (19 mg, 0.04 mmol), 6-methoxypyridine-3-carbaldehyde (6.5 mg, 0.05 mmol), STAB (17 mg, 0.08 mmol), DCE (1 mL) and a few 4 Å molecular sieves. The crude products were absorbed on to MP-TsOH resin (1 mL), washed with MeOH (2 mL) and the crude product eluted with 7 N NH$_3$ in MeOH (3 mL). The solvent was removed in vacuo and a portion of the crude product purified using prep method A.

LCMS method C: rt 3.25 min, 97%; m/z 610.40 (MH$^+$, 100%)

Potency: B

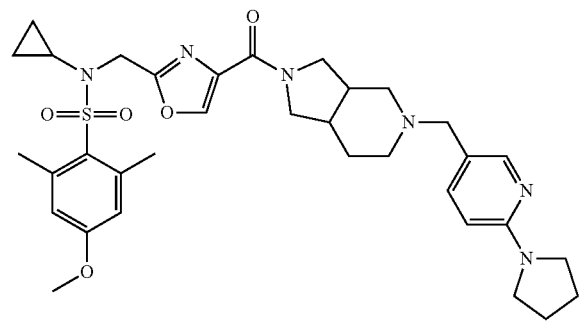 [SMILES: COc1cc(C)c(S(=O)(=O)N(Cc2nc(C(=O)N3CC4CCN(Cc5ccc(N6CCCC6)nc5)CC4C3)co2)C2CC2)c(C)c1]

N-Cyclopropyl-4-methoxy-2,6-dimethyl-N-{[4-({5-[(6-pyrrolidin-1-ylpyridin-3-yl)methyl]octahydro-2H-pyrrolo[3,4-c]pyridin-2-yl}carbonyl)-1,3-oxazol-2-yl]methyl}benzenesulfonamide trifluoroacetate Ex 211

The title compound was prepared according to general procedure CD using N-cyclopropyl-4-methoxy-2,6-dimethyl-N-{[4-(octahydro-2H-pyrrolo[3,4-c]pyridin-2-ylcarbonyl)-1,3-oxazol-2-yl]methyl}benzenesulfonamide (19 mg, 0.04 mmol), 6-pyrrolidin-1-ylpyridine-3-carbaldehyde (8.4 mg, 0.05 mmol), STAB (17 mg, 0.08 mmol), DCE (1 mL) and a few 4 Å molecular sieves. The crude products were absorbed on to MP-TsOH resin (1 mL), washed with MeOH (2 mL) and the crude product eluted with 7 N NH$_3$ in MeOH (3 mL). The solvent was removed in vacuo and a portion of the crude product purified using prep method A to afford the title compound.

LCMS method C: rt 2.85 min, 100%; m/z 325.32 (MH$^+$, 100%), 649.44 ([M+2H]$^{2+}$, 15%).

Potency: C

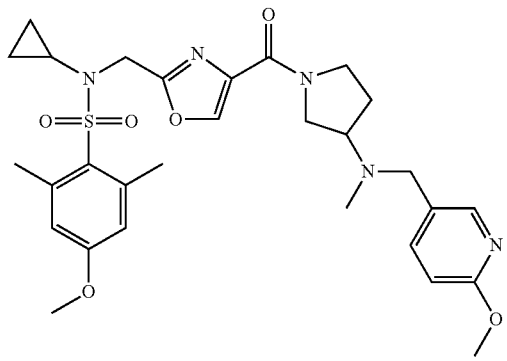 [SMILES: COc1cc(C)c(S(=O)(=O)N(Cc2nc(C(=O)N3CCC(N(C)Cc4ccc(OC)nc4)C3)co2)C2CC2)c(C)c1]

N-Cyclopropyl-4-methoxy-N-({4-[(3-{[(6-methoxy-pyridin-3-yl)methyl](methyl)amino}pyrrolidin-1-yl)carbonyl]-1,3-oxazol-2-yl}methyl)-2,6-dimethylbenzenesulfonamide trifluoroacetate Ex 212

The title compound was prepared according to general procedure CD using N-cyclopropyl-4-methoxy-2,6-dimethyl-N-[(4-{[3-(methylamino)pyrrolidin-1-yl]carbonyl}-1,3-oxazol-2-yl)methyl]benzenesulfonamide (19 mg, 0.04 mmol), 6-methoxypyridine-3-carbaldehyde (6.5 mg, 0.05 mmol), STAB (17 mg, 0.08 mmol), DCE (1 mL) and a few 4 Å molecular sieves. The crude products were absorbed on to MP-TsOH resin (1 mL), washed with MeOH (2 mL) and the crude product eluted with 7 N NH$_3$ in MeOH (3 mL). The solvent was removed in vacuo and a portion of the crude product purified using prep method A to afford the title compound.

LCMS method C: rt 3.26 min, 99%; m/z 584.39 (MH$^+$, 100%)

Potency: A

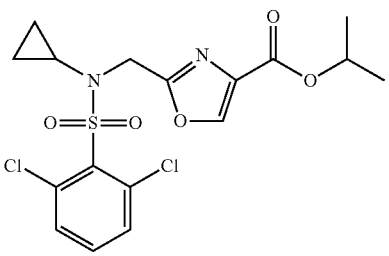 [SMILES: CC(C)OC(=O)c1coc(CN(C2CC2)S(=O)(=O)c2c(Cl)cccc2Cl)n1]

Isopropyl 2-({[(2,6-dichlorophenyl)sulfonyl](cyclopropyl)amino}methyl)oxazole-4-carboxylate Int 228

The title compound was prepared according to general procedure CC using isopropyl 2-[(cyclopropylamino)methyl]oxazole-4-carboxylate (100 mg, 0.45 mmol), DIPEA (0.24 mL, 1.34 mmol), DMAP (6 mg, 0.05 mmol) and 2,6-dichlorobenzenesulfonyl chloride (137 mg, 0.56 mmol) in DCM (3 mL).

The product was purified using FCC, eluting with 10% EtOAc in heptane.

Yield: 70 mg, 35%

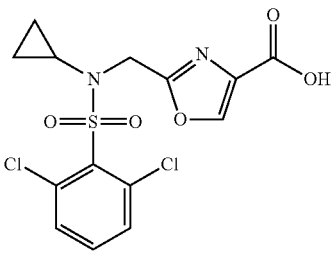 [SMILES: O=C(O)c1coc(CN(C2CC2)S(=O)(=O)c2c(Cl)cccc2Cl)n1]

2-({[(2,6-Dichlorophenyl)sulfonyl](cyclopropyl)amino}methyl)oxazole-4-carboxylic acid Int 229

The title compound was prepared according to general procedure AL using Isopropyl 2-({[(2,6-dichlorophenyl)sulfonyl](cyclopropyl)amino}methyl)oxazole-4-carboxylate (70 mg, 0.16 mmol) and 2 M aqueous LiOH (0.56 mL, 1.12 mmol) in THF (3 mL). The crude product required no further purification.

Yield: 47.6 mg, 75%.

LCMS Method A: rt 1.24 min, 85%; m/z 391.00 (MH$^+$, 100%)

$^1$H NMR (250 MHz, CDCl$_3$) δ ppm 8.37 (1H, s), 7.44-7.58 (2H, m), 7.31-7.44 (1H, m), 4.88 (2H, s), 2.56-2.70 (1H, m), 0.63-0.75 (2H, m), 0.43-0.54 (2H, m)

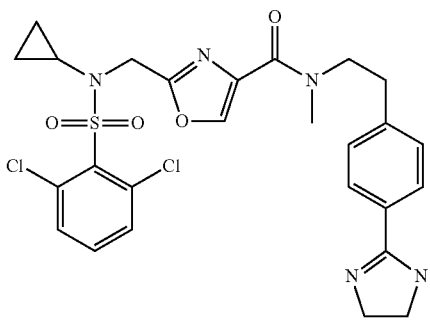 [SMILES: CN(CCc1ccc(C2=NCCN2)cc1)C(=O)c1coc(CN(C2CC2)S(=O)(=O)c2c(Cl)cccc2Cl)n1]

2-({Cyclopropyl[(2,6-dichlorophenyl)sulfonyl]amino}methyl)-N-{2-[4-(4,5-dihydro-1H-imidazol-2-yl)phenyl]ethyl}-N-methyl-1,3-oxazole-4-carboxamide trifluoroacetate Ex 213

The title compound was prepared according to general procedure AA using 2-({[(2,6-dichlorophenyl)sulfonyl](cyclopropyl)amino}methyl)oxazole-4-carboxylic acid (47 mg, 0.12 mmol), CDI (40 mg, 0.24 mmol) and bis HCl 2-[4-(4,5-dihydro-1H-imidazol-2-yl)phenyl]-N-methylethanamine (33 mg, 0.12 mmol) and DIPEA (0.11 mL, 0.60 mmol) in DCE (1.5 mL). A portion of the crude product was purified using prep method C LCMS Method C: rt 3.19 min, 94%; m/z 576.12 (MH+, 100%)

Potency: A

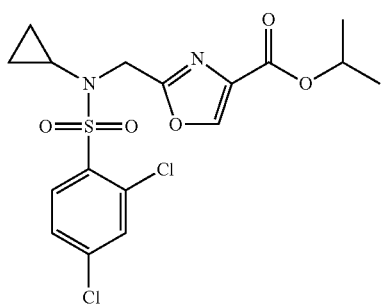 [SMILES: CC(C)OC(=O)c1coc(CN(C2CC2)S(=O)(=O)c2ccc(Cl)cc2Cl)n1]

Isopropyl 2-({[(2,4-dichlorophenyl)sulfonyl](cyclopropyl)amino}methyl)oxazole-4-carboxylate Int 230

The title compound was prepared according to general procedure CC using isopropyl 2-[(cyclopropylamino)methyl]oxazole-4-carboxylate (100 mg, 0.45 mmol), DIPEA (0.24 mL, 1.34 mmol), DMAP (6 mg, 0.05 mmol) and 2,4-dichlorobenzenesulfonyl chloride (223 mg, 0.89 mmol) in DCM (3 mL).

The product was purified using FCC, eluting with 10% EtOAc in heptane.

Yield: 96 mg, 50%

$^1$H NMR (500 MHz, CDCl$_3$) δ ppm 8.22 (1H, s), 8.11 (1H, d, J=8.5 Hz), 7.54 (1H, d, J=2.0 Hz), 7.42 (1H, dd, J 8.6, 2.1 Hz), 5.29 (1H, spt, J=6.3 Hz), 4.82 (2H, s), 2.50 (1H, spt), 1.38 (6H, d, J=6.3 Hz), 0.60-0.67 (2H, m), 0.48-0.54 (2H, m)

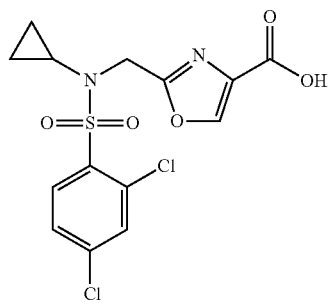 [SMILES: O=C(O)c1coc(CN(C2CC2)S(=O)(=O)c2ccc(Cl)cc2Cl)n1]

2-({[(2,4-Dichlorophenyl)sulfonyl](cyclopropyl)amino}methyl)oxazole-4-carboxylic acid Int 231

The title compound was prepared according to general procedure AL using isopropyl 2-({[(2,4-dichlorophenyl)sulfonyl](cyclopropyl)amino}methyl)oxazole-4-carboxylate (96 mg, 0.22 mmol) and 2 M aqueous LiOH (0.33 mL, 0.67 mmol) in THF (2 mL). The crude product required no further purification.

Yield: 79 mg, 91%.

LCMS Method A: rt 1.31 min, 87%; m/z 390.90 (MH+, 100%) 412.85 (MNa+, 80%)

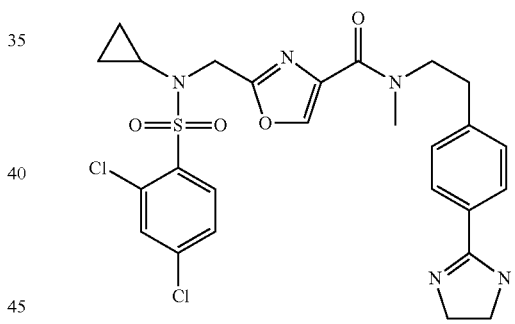

2-({Cyclopropyl[(2,4-dichlorophenyl)sulfonyl]amino}methyl)-N-{2-[4-(4,5-dihydro-1H-imidazol-2-yl)phenyl]ethyl}-N-methyl-1,3-oxazole-4-carboxamide trifluoroacetate Ex 214

The title compound was prepared according to general procedure AA using 2-({[(2,4-dichlorophenyl)sulfonyl](cyclopropyl)amino}methyl)oxazole-4-carboxylic acid (40 mg, 0.10 mmol), CDI (34 mg, 0.20 mmol) and bis HCl 2-[4-(4,5-dihydro-1H-imidazol-2-yl)phenyl]-N-methylethanamine (35 mg, 0.12 mmol) and DIPEA (0.10 mL, 0.60 mmol) in DCE (1.5 mL). A portion of the crude product was purified using prep method C LCMS Method C: rt 3.27 min, 99%; m/z 576.12 (MH+, 100%)

Potency: A

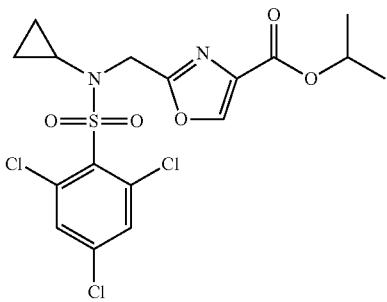 [SMILES: CC(C)OC(=O)c1coc(CN(C2CC2)S(=O)(=O)c2c(Cl)cc(Cl)cc2Cl)n1]

Isopropyl 2-({[(2,4,6-trichlorophenyl)sulfonyl](cyclopropyl)amino}methyl)oxazole-4-carboxylate Int 232

The title compound was prepared according to general procedure CC using isopropyl 2-[(cyclopropylamino)methyl]oxazole-4-carboxylate (150 mg, 0.67 mmol), DIPEA (0.35 mL, 2.01 mmol), DMAP (8 mg, 0.07 mmol) and 2,4,6-trichlorobenzenesulfonyl chloride (386 mg, 1.34 mmol) in DCM (3 mL).

The product was purified using FCC, eluting with 10-30% EtOAc in heptane, to afford the title compound.

Yield: 110 mg, 35%

$^1$H NMR (500 MHz, CDCl$_3$) δ ppm 8.24 (1H, s), 7.39 (1H, d), 7.34 (1H, t), 7.24 (1H, d, J=7.5 Hz), 4.85 (2H, s), 2.54 (1H, spt), 1.38 (6H, d, J=6.3 Hz), 0.56-0.62 (2H, m), 0.33-0.38 (2H, m)

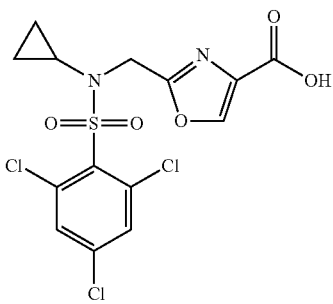 [SMILES: O=C(O)c1coc(CN(C2CC2)S(=O)(=O)c2c(Cl)cc(Cl)cc2Cl)n1]

2-({[(2,4,5-Trichlorophenyl)sulfonyl](cyclopropyl)amino}methyl)oxazole-4-carboxylic acid Int 234

The title compound was prepared according to general procedure AL using Isopropyl 2-({[(2,4,6-trichlorophenyl)sulfonyl](cyclopropyl)amino}methyl)oxazole-4-carboxylate (110 mg, 0.24 mmol) and 2 M aqueous LiOH (0.64 mL, 1.29 mmol) in THF (3 mL). The crude product required no further purification.

Yield: 88 mg, 88%.

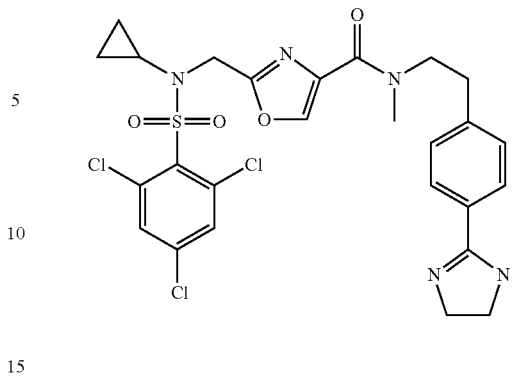

2-({Cyclopropyl[(2,4,6-trichlorophenyl)sulfonyl]amino}methyl)-N-{2-[4-(4,5-dihydro-1H-imidazol-2-yl)phenyl]ethyl}-N-methyl-1,3-oxazole-4-carboxamide trifluoroacetate Ex 215

The title compound was prepared according to general procedure AA using 2-({[(2,4,6-trichlorophenyl)sulfonyl](cyclopropyl)amino}methyl)oxazole-4-carboxylic acid (44 mg, 0.10 mmol), CDI (34 mg, 0.20 mmol) and bis HCl 2-[4-(4,5-dihydro-1H-imidazol-2-yl)phenyl]-N-methylethanamine (29 mg, 0.10 mmol) and DIPEA (0.28 mL, 1.59 mmol) in DCE (1.5 mL). A portion of the crude product was purified using prep method C LCMS Method C: rt 3.34 min, 97%; m/z 610.07 (MH$^+$, 94%), 612.09 (MH$^+$, 100%)

Potency: B

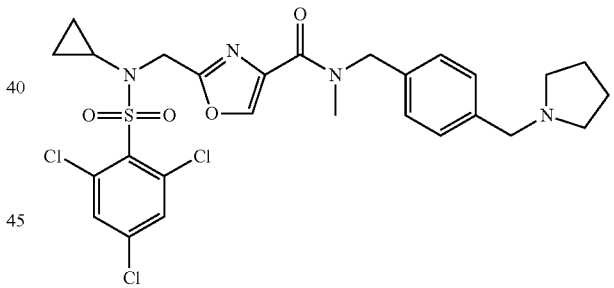

2-({Cyclopropyl[(2,4,6-trichlorophenyl)sulfonyl]amino}methyl)-N-methyl-N-[4-(pyrrolidin-1-ylmethyl)benzyl]-1,3-oxazole-4-carboxamide trifluoroacetate Ex 216

The title compound was prepared according to general procedure AA using 2-({[(2,4,6-trichlorophenyl)sulfonyl](cyclopropyl)amino}methyl)oxazole-4-carboxylic acid (44 mg, 0.10 mmol), CDI (34 mg, 0.20 mmol) and N-methyl-1-[4-(pyrrolidin-1-ylmethyl)phenyl]methanamine (22 mg, 0.10 mmol) and DIPEA (0.28 mL, 1.59 mmol) in DCE (1.5 mL). A portion of the crude product was purified using prep method A LCMS Method C: rt 3.45 min, 100%; m/z 611.15 (MH$^+$, 91%) 613.16 (MH$^+$, 100%)

Potency: A

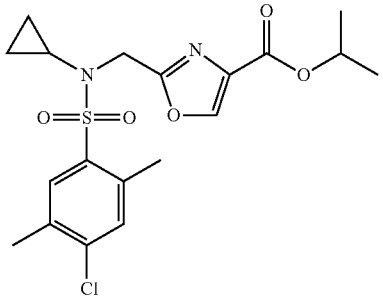 [SMILES: Cc1cc(S(=O)(=O)N(Cc2nc(C(=O)OC(C)C)co2)C2CC2)c(C)cc1Cl]

Isopropyl 2-({[(4-chloro-2,5-dimethylphenyl)sulfonyl](cyclopropyl)amino}methyl)oxazole-4-carboxylate Int 235

The title compound was prepared according to general procedure CC using isopropyl 2-[(cyclopropylamino)methyl]oxazole-4-carboxylate (150 mg, 0.67 mmol), DIPEA (0.35 mL, 2.01 mmol), DMAP (8 mg, 0.07 mmol) and 4-chloro-2,5-dimethylbenzenesulfonyl chloride (326 mg, 1.34 mmol) in DCM (3 mL).

The product was purified using FCC, eluting with 10-30% EtOAc in heptane, to afford the title compound.

Yield: 183 mg, 61%

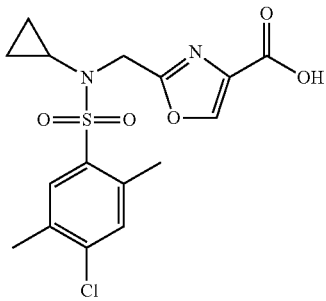 [SMILES: Cc1cc(S(=O)(=O)N(Cc2nc(C(=O)O)co2)C2CC2)c(C)cc1Cl]

2-({[(4-Chloro-2,5-dimethylphenyl)sulfonyl](cyclopropyl)amino}methyl)oxazole-4-carboxylic acid Int 236

The title compound was prepared according to general procedure AL using Isopropyl 2-({[(4-chloro-2,5-dimethylphenyl)sulfonyl](cyclopropyl)amino}methyl)oxazole-4-carboxylate (183 mg, 0.43 mmol) and 2 M aqueous LiOH (0.64 mL, 1.29 mmol) in THF (3 mL). The crude product required no further purification.

Yield: 122 mg, 74%.

LCMS Method A: rt 1.36 min, 98%; m/z 385.00 (MH$^+$, 100%), 407.05 (MNa$^+$, 100%)

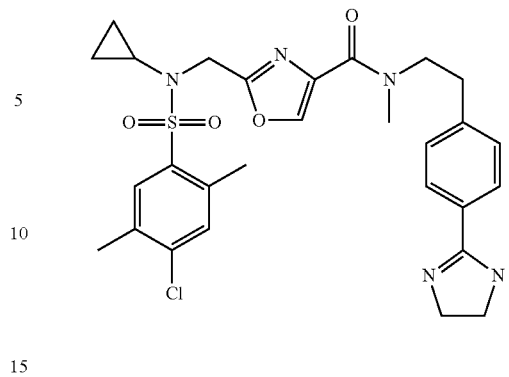

2-({[(4-Chloro-2,5-dimethylphenyl)sulfonyl](cyclopropyl)amino}methyl)-N-{2-[4-(4,5-dihydro-1H-imidazol-2-yl)phenyl]ethyl}-N-methyl-1,3-oxazole-4-carboxamide trifluoroacetate Ex 217

The title compound was prepared according to general procedure AA using 2-({[(4-chloro-2,5-dimethylphenyl)sulfonyl](cyclopropyl)amino}methyl)oxazole-4-carboxylic acid (67 mg, 0.16 mmol), CDI (53 mg, 0.32 mmol) and bis HCl 2-[4-(4,5-dihydro-1H-imidazol-2-yl)phenyl]-N-methylethanamine (44 mg, 0.16 mmol) and DIPEA (0.28 mL, 1.59 mmol) in DCE (1.5 mL). A portion of the crude product was purified using prep method C LCMS Method C: rt 3.42 min, 100%; m/z 570.20 (MH$^+$, 100%)

Potency: A

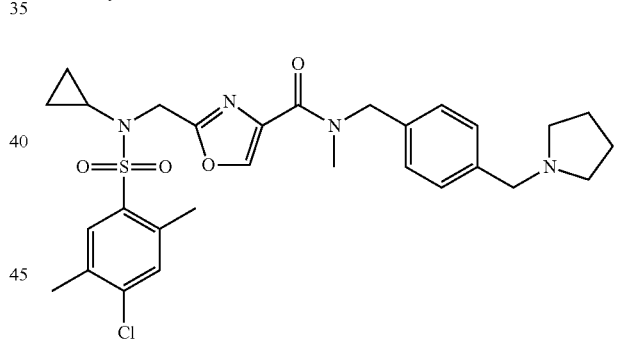

2-({[(4-Chloro-2,5-dimethylphenyl)sulfonyl](cyclopropyl)amino}methyl)-N-methyl-N-[4-(pyrrolidin-1-ylmethyl)benzyl]-1,3-oxazole-4-carboxamide trifluoroacetate Ex 218

The title compound was prepared according to general procedure AA using 2-({[(4-chloro-2,5-dimethylphenyl)sulfonyl](cyclopropyl)amino}methyl)oxazole-4-carboxylic acid (67 mg, 0.16 mmol), CDI (53 mg, 0.32 mmol) and N-methyl-1-[4-(pyrrolidin-1-ylmethyl)phenyl]methanamine (33 mg, 0.16 mmol) and DIPEA (0.28 mL, 1.59 mmol) in DCE (1.5 mL). A portion of the crude product was purified using prep method C LCMS Method C: rt 3.47 min, 99%; m/z 571.21 (MH$^+$, 100%)

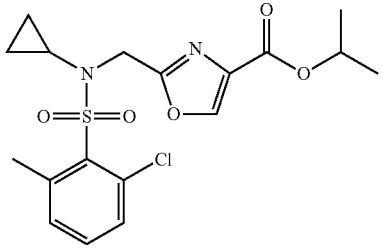 [SMILES: Cc1cccc(Cl)c1S(=O)(=O)N(Cc1nc(C(=O)OC(C)C)co1)C1CC1]

Isopropyl 2-({[(2-chloro-6-methyl phenyl)sulfonyl](cyclopropyl)amino}methyl)oxazole-4-carboxylate Int 237

The title compound was prepared according to general procedure CC using isopropyl 2-[(cyclopropylamino)methyl]oxazole-4-carboxylate (150 mg, 0.67 mmol), DIPEA (0.35 mL, 2.01 mmol), DMAP (8 mg, 0.07 mmol) and 2-chloro-6-methylbenzenesulfonyl chloride (307 mg, 1.34 mmol) in DCM (3 mL).

The product was purified using FCC, eluting with 10-30% EtOAc in heptane.

Yield: 160 mg, 58%

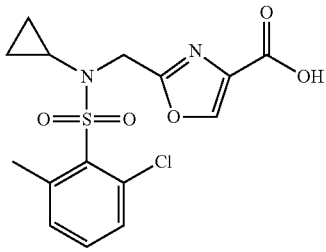 [SMILES: Cc1cccc(Cl)c1S(=O)(=O)N(Cc1nc(C(=O)O)co1)C1CC1]

2-({[(2-Chloro-6-methylphenyl)sulfonyl](cyclopropyl)amino}methyl)oxazole-4-carboxylic acid Int 238

The title compound was prepared according to general procedure AL using Isopropyl 2-({[(2-chloro-6-methylphenyl)sulfonyl](cyclopropyl)amino}methyl)oxazole-4-carboxylate (160 mg, 0.39 mmol) and 2 M aqueous LiOH (0.64 mL, 1.29 mmol) in THF (3 mL). The crude product required no further purification.

Yield: 118 mg, 82%.

LCMS Method A: rt 1.26 min, 97%; m/z 371.05 (MH$^+$, 100%), 392.95 (MNa$^+$, 85%)

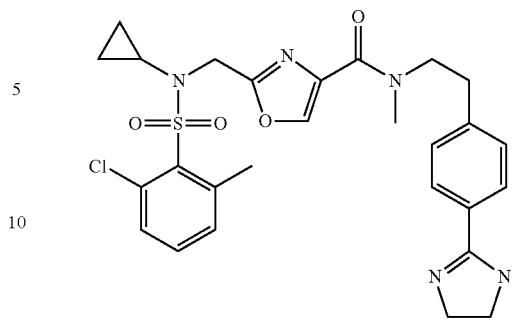

2-({[(2-Chloro-6-methylphenyl)sulfonyl](cyclopropyl)amino}methyl)-N-{2-[4-(4,5-dihydro-1H-imidazol-2-yl)phenyl]ethyl}-N-methyl-1,3-oxazole-4-carboxamide trifluoroacetate Ex 219

The title compound was prepared according to general procedure AA using 2-({[(2-chloro-6-methylphenyl)sulfonyl](cyclopropyl)amino}methyl)oxazole-4-carboxylic acid (59 mg, 0.16 mmol), CDI (53 mg, 0.32 mmol) and bis HCl 2-[4-(4,5-dihydro-1H-imidazol-2-yl)phenyl]-N-methylethanamine (44 mg, 0.16 mmol) and DIPEA (0.28 mL, 1.59 mmol) in DCE (1.5 mL). A portion of the crude product was purified using prep method C LCMS Method C: rt 3.21 min, 91%; m/z 556.15 (MH$^+$, 100%)

Potency: B

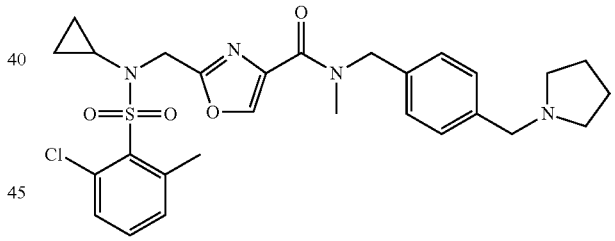

2-({[(2-Chloro-6-methylphenyl)sulfonyl](cyclopropyl)amino}methyl)-N-methyl-N-[4-(pyrrolidin-1-ylmethyl)benzyl]-1,3-oxazole-4-carboxamide trifluoroacetate Ex 220

The title compound was prepared according to general procedure AA using 2-({[(2-chloro-6-methylphenyl)sulfonyl](cyclopropyl)amino}methyl)oxazole-4-carboxylic acid (59 mg, 0.16 mmol), CDI (53 mg, 0.32 mmol) and N-methyl-1-[4-(pyrrolidin-1-ylmethyl)phenyl]methanamine (34 mg, 0.16 mmol) and DIPEA (0.28 mL, 1.59 mmol) in DCE (1.5 mL). A portion of the crude product was purified using prep method A LCMS Method C: rt 3.27 min, 100%; m/z 557.22 (MH$^+$, 100%)

Potency: A

Potency: A

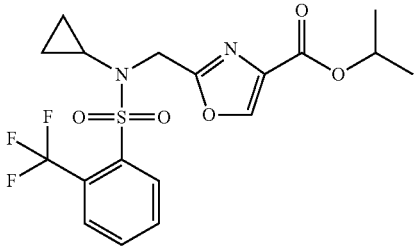 [SMILES: CC(C)OC(=O)c1coc(CN(C2CC2)S(=O)(=O)c2ccccc2C(F)(F)F)n1]

1-Methylethyl 2-[(cyclopropyl{[2-(trifluoromethyl)phenyl]sulfonyl}amino)methyl]-1,3-oxazole-4-carboxylate Int 239

The title compound was prepared according to general procedure CC using isopropyl 2-[(cyclopropylamino)methyl]oxazole-4-carboxylate (150 mg, 0.67 mmol), DIPEA (0.35 mL, 2.01 mmol), DMAP (8 mg, 0.07 mmol) and 2-(trifluoromethyl)benzenesulfonyl chloride (334 mg, 1.34 mmol) in DCM (3 mL).

The product was purified using FCC, eluting with 10-30% EtOAc in heptane.

Yield: 122 mg, 42%

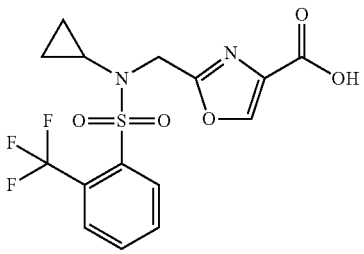 [SMILES: O=C(O)c1coc(CN(C2CC2)S(=O)(=O)c2ccccc2C(F)(F)F)n1]

2-[(Cyclopropyl{[2-(trifluoromethyl)phenyl]sulfonyl}amino)methyl]-1,3-oxazole-4-carboxylic acid Int 240

The title compound was prepared according to general procedure AL using 1-methylethyl 2-[(cyclopropyl{[2-(trifluoromethyl)phenyl]sulfonyl}amino)methyl]-1,3-oxazole-4-carboxylate (122 mg, 0.30 mmol) and 2 M aqueous LiOH (0.44 mL, 0.89 mmol) in THF (2 mL). The crude product required no further purification.

Yield: 107 mg, 93%.

LCMS Method A: rt 1.24 min, 94%; m/z 391.30 (MH$^+$, 100%), 413.00 (MNa$^+$, 85%)

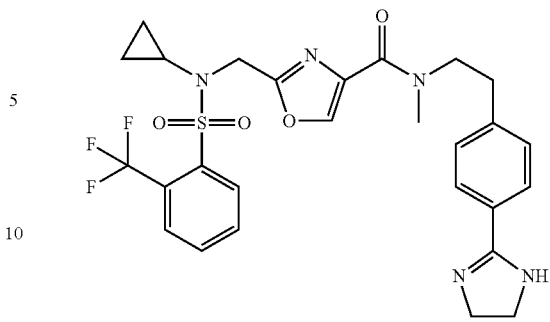

2-[(Cyclopropyl{[2-(trifluoromethyl)phenyl]sulfonyl}amino)methyl]-N-{2-[4-(4,5-dihydro-1H-imidazol-2-yl)phenyl]ethyl}-N-methyl-1,3-oxazole-4-carboxamide trifluoroacetate Ex 221

The title compound was prepared according to general procedure AA using 2-[(cyclopropyl{[2-(trifluoromethyl)phenyl]sulfonyl}amino)methyl]-1,3-oxazole-4-carboxylic acid (54 mg, 0.14 mmol), CDI (45 mg, 0.27 mmol) and bis HCl 2-[4-(4,5-dihydro-1H-imidazol-2-yl)phenyl]-N-methylethanamine (45 mg, 0.16 mmol) and DIPEA (0.24 mL, 1.37 mmol) in DCE (2 mL). A portion of the crude product was purified using prep method C LCMS Method C: rt 3.22 min, 99%; m/z 576.18 (MH$^+$, 100%)

Potency: A

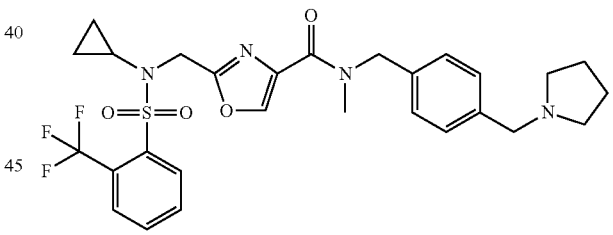

2-[(Cyclopropyl{[2-(trifluoromethyl)phenyl]sulfonyl}amino)methyl]-N-methyl-N-[4-(pyrrolidin-1-ylmethyl)benzyl]-1,3-oxazole-4-carboxamide trifluoroacetate Ex 222

The title compound was prepared according to general procedure AA using 2-[(cyclopropyl{[2-(trifluoromethyl)phenyl]sulfonyl}amino)methyl]-1,3-oxazole-4-carboxylic acid (54 mg, 0.14 mmol), CDI (45 mg, 0.27 mmol) and N-methyl-1-[4-(pyrrolidin-1-ylmethyl)phenyl]methanamine (41 mg, 0.20 mmol) and DIPEA (0.24 mL, 1.37 mmol) in DCE (2 mL). A portion of the crude product was purified using prep method A LCMS Method C: rt 3.25 min, 98%; m/z 577.25 (MH$^+$, 100%)

Potency: A

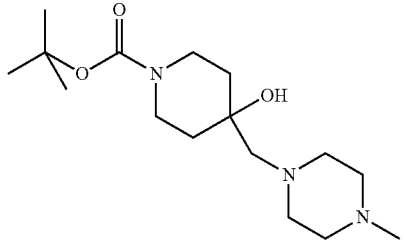 [SMILES: CN1CCN(CC2(O)CCN(C(=O)OC(C)(C)C)CC2)CC1]

tert-Butyl 4-hydroxy-4-[(4-methylpiperazin-1-yl)methyl]piperidine-1-carboxylate

Int 241 tert-Butyl 1-oxa-6-azaspiro[2.5]octane-6-carboxylate (250 mg, 1.17 mmol) and 1-methylpiperazine (0.39 mL, 3.52 mmol) were stirred in DCM (10 mL) at ambient temperature for 18 h. The mixture was concentrated in vacuo and the residue purified using FCC, eluting with 95:4.5:0.5 DCM:MeOH:NH$_3$, to afford the title compound as a colourless oil.

Yield: 186 mg, 51%

LCMS Method A: rt 0.80 min, 100%; m/z 314.15 (MH$^+$, 100%)

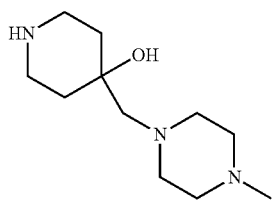

4-[(4-Methylpiperazin-1-yl)methyl]piperidin-4-ol

Int 242 tert-butyl 4-hydroxy-4-[(4-methylpiperazin-1-yl)methyl]piperidine-1-carboxylate (85 mg, 0.27 mmol) was stirred in DCM (5 mL) and trifluoroacetic acid (0.06 mL, 0.82 mmol) was added. The reaction was stirred at ambient temperature for 1 h, then concentrated in vacuo. The residue was dissolved in MeOH (10 mL) and MP-TsOH (4.44 mmol/g, 180 mg) was added. The mixture was shaken at ambient temperature for 1 h, then filtered and the beads washed with MeOH (10 mL). The beads were then washed with 7 M NH$_3$ in MeOH and this filtrate was concentrated in vacuo.

Yield: 40 mg, 70%.

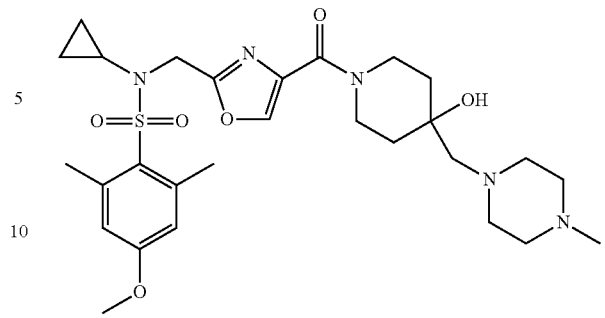

N-Cyclopropyl-N-{[4-({4-hydroxy-4-[(4-methylpiperazin-1-yl)methyl]piperidin-1-yl}carbonyl)-1,3-oxazol-2-yl]methyl}-4-methoxy-2,6-dimethylbenzenesulfonamide trifluoroacetate Ex 223

The title compound was prepared according to general procedure AC using 2-({cyclopropyl[(4-methoxy-2,6-dimethylphenyl)sulfonyl]amino}methyl)-1,3-oxazole-4-carboxylic acid (30 mg, 0.08 mmol), EDCI (18 mg, 0.09 mmol), HOBt monohydrate (13 mg, 0.10 mmol), TEA (0.012 mL, 0.08 mmol) and 4-[(4-methylpiperazin-1-yl)methyl]piperidin-4-ol (25 mg, 0.12 mmol) in DMF (2 mL). The crude product was purified using prep method D.

Yield: 6.1 mg, 13%.

LCMS Method C: rt 3.05 min, 100%; m/z 288.78 ([M+2H]$^{2+}$, 100%), 576.40 (MH$^+$, 32%)

$^1$H NMR (500 MHz, CD$_3$OD): δ ppm 8.28 (1H, s), 6.76 (2H, s), 4.68 (2H, s), 4.42-4.50 (1H, m), 4.26-4.34 (1H, m), 3.84 (3H, s), 3.51-3.60 (1H, m), 3.20-3.29 (1H, m), 2.60-2.75 (5H, m), 2.59 (6H, s), 2.42-2.57 (4H, m), 2.38 (2H, s), 2.27 (3H, s), 1.60-1.77 (4H, m), 0.53-0.59 (2H, m), 0.21-0.26 (2H, m)

Potency: C

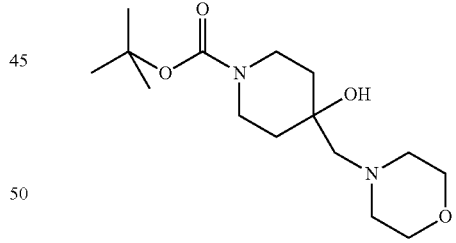

tert-Butyl 4-hydroxy-4-(morpholin-4-ylmethyl)piperidine-1-carboxylate

Int 243 tert-butyl 1-oxa-6-azaspiro[2.5]octane-6-carboxylate (200 mg, 0.94 mmol) and morpholine (0.24 mL, 2.82 mmol) were stirred in DCM (10 mL) at ambient temperature for 18 h. The mixture was concentrated in vacuo and the residue purified using FCC, eluting with 95:5:1 DCM:MeOH:NH$_3$, to afford the title compound as colourless crystals.

Yield: 151 mg, 53%.

LCMS Method A: rt 0.84 min, 100%; m/z 301.05 (MH$^+$, 100%)

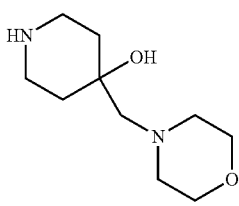

4-(Morpholin-4-ylmethyl)piperidin-4-ol trifluoroacetate

Int 244 tert-butyl 4-hydroxy-4-(morpholin-4-ylmethyl)piperidine-1-carboxylate (150 mg, 0.50 mmol) was stirred in DCM (5 mL) and trifluoroacetic acid (0.39 mL, 5.00 mmol) was added. The reaction was stirred at ambient temperature for 1 h, then concentrated in vacuo to afford the title compound as a TFA salt, which was used without further purification.

Yield: 214 mg, 100%.

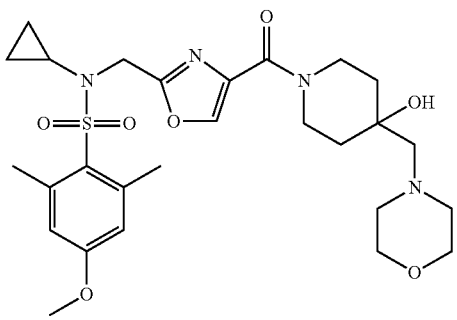 [SMILES: COc1cc(C)c(S(=O)(=O)N(Cc2nc(C(=O)N3CCC(O)(CN4CCOCC4)CC3)co2)C2CC2)c(C)c1]

N-Cyclopropyl-N-[(4-{[4-hydroxy-4-(morpholin-4-ylmethyl)piperidin-1-yl]carbonyl}-1,3-oxazol-2-yl)methyl]-4-methoxy-2,6-dimethylbenzenesulfonamide trifluoroacetate Ex 224

The title compound was prepared according to general procedure AC using 2-({cyclopropyl[(4-methoxy-2,6-dimethylphenyl)sulfonyl]amino}methyl)-1,3-oxazole-4-carboxylic acid (30 mg, 0.08 mmol), EDCI (18 mg, 0.09 mmol), HOBt monohydrate (13 mg, 0.10 mmol), TEA (0.05 mL, 0.32 mmol) and 4-(morpholin-4-ylmethyl)piperidin-4-ol Bis trifluoroacetate (69 mg, 0.16 mmol) in DMF (1 mL). A portion of the crude product was purified using prep method D, followed by prep method C.

LCMS Method C: rt 3.10 min, 97%; 563.36 (MH+, 100%)

$^1$H NMR (500 MHz, CD$_3$OD): δ ppm 8.29 (1H, s), 6.77 (2H, s), 4.69 (2H, s), 4.46 (1H, br. s), 4.31 (1H, d, J=1.4 Hz,), 3.86 (3H, s), 3.67-3.72 (4H, m), 3.57 (1H, br. s), 3.22-3.30 (1H, m), 2.67 (1H, dt, J 6.9, 3.3 Hz,), 2.58-2.64 (10H, m), 2.38 (2H, s), 1.69 (4H, br. s), 0.55-0.61 (m, 2H, m), 0.23-0.28 (2H, m).

Potency: B

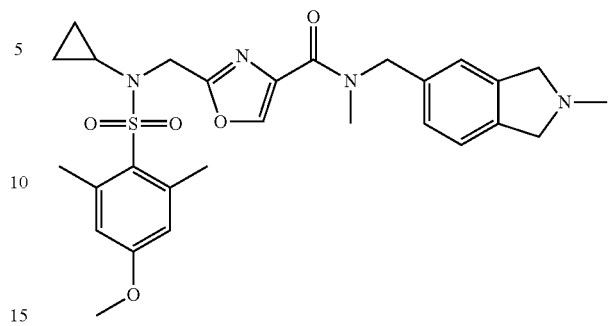

2-({Cyclopropyl[(4-methoxy-2,6-dimethylphenyl)sulfonyl]amino}methyl)-N-methyl-N-[(2-methyl-2,3-dihydro-1H-isoindol-5-yl)methyl]-1,3-oxazole-4-carboxamide trifluoroacetate Ex 225

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 µL, 0.52 mmol), N-methyl-1-(2-methyl-2,3-dihydro-1H-isoindol-5-yl)methanamine (23 mg, 0.13 mmol) and DMF (1 mL). The resulting crude compound was purified by FCC eluting with 99:1 DCM:7 N NH$_3$ in MeOH followed by purification using prep method D.

Yield: 8.9 mg, 13%.

LCMS method C: rt 3.23 min, 95%; m/z 539.37 (MH+, 100%)

Potency: B

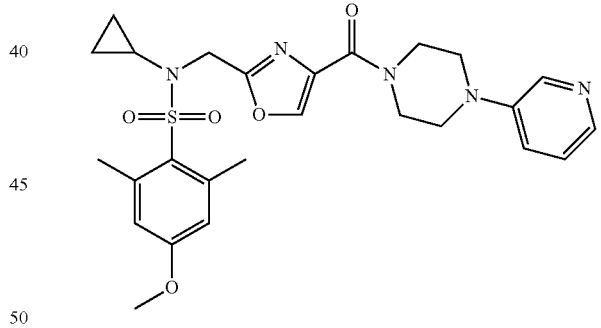

N-Cyclopropyl-4-methoxy-2,6-dimethyl-N-({4-[(4-pyridin-3-ylpiperazin-1-yl)carbonyl]-1,3-oxazol-2-yl}methyl)benzenesulfonamide Ex 226

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 µL, 0.52 mmol), 1-pyridin-3-ylpiperazine (21 mg, 0.13 mmol) and DMF (1 mL). The resulting crude compound was purified by FCC eluting with 99:1 DCM:7N NH$_3$ in MeOH.

Yield: 29.8 mg, 44%.

LCMS method C: rt 3.19 min, 96%; m/z 526.33 (MH+, 100%).

Potency: A

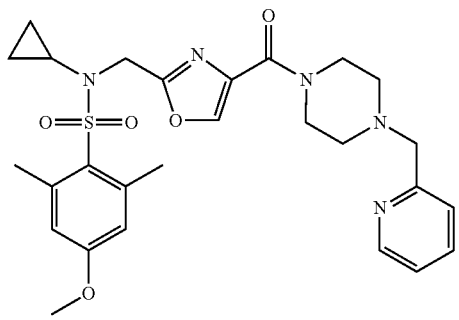 [SMILES: COc1cc(C)c(S(=O)(=O)N(Cc2nc(C(=O)N3CCN(Cc4ccccn4)CC3)co2)C2CC2)c(C)c1]

N-Cyclopropyl-4-methoxy-2,6-dimethyl-N-[(4-{[4-(pyridin-2-ylmethyl)piperazin-1-yl]carbonyl}-1,3-oxazol-2-yl)methyl]benzenesulfonamide trifluoroacetate Ex 227

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 μL, 0.52 mmol), 1-pyridin-2-ylmethylpiperazine (23 mg, 0.13 mmol) and DMF (1 mL). The resulting crude compound was purified by FCC eluting with 99:1 DCM:7N $NH_3$ in MeOH followed by purification using prep method D.

Yield: 4.8 mg, 7%.

LCMS method C: rt 3.19 min, 100%; m/z 540.31 ($MH^+$, 100%).

$^1$H NMR (500 MHz, $CDCl_3$): δ ppm 8.56-8.62 (1H, m), 8.14 (1H, s), 7.68 (1H, td, J 7.7, 1.8 Hz), 7.42 (1H, d, J=7.8 Hz), 7.15-7.24 (1H, m), 6.63 (2H), s, 4.64 (2H, s), 4.11 (2H, br. s), 3.83 (3H, s), 3.76-3.82 (2H, m), 3.71 (2H, s), 2.55-2.62 (11H, m), 0.49-0.55 (2H, m), 0.12-0.18 (2H, m).

Potency: A

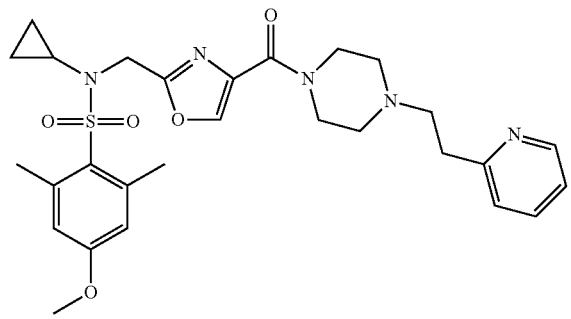 [SMILES: COc1cc(C)c(S(=O)(=O)N(Cc2nc(C(=O)N3CCN(CCc4ccccn4)CC3)co2)C2CC2)c(C)c1]

N-Cyclopropyl-4-methoxy-2,6-dimethyl-N-[(4-{[4-(2-pyridin-2-ylethyl)piperazin-1-yl]carbonyl}-1,3-oxazol-2-yl)methyl]benzenesulfonamide trifluoroacetate Ex 228

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 μL, 0.52 mmol), 1-(2-pyridin-2-yl-ethyl)piperazine (25 mg, 0.13 mmol) and DMF (1 mL). The resulting crude compound was purified by FCC eluting with 99:1 DCM:7N $NH_3$ in MeOH followed by purification using prep method D.

Yield: 14.7 mg, 21%.

LCMS method C: rt 3.10 min, 98%; m/z 554.35 ($MH^+$, 100%).

$^1$H NMR (500 MHz, $CDCl_3$) δ ppm 8.52 (1H, d, J=4.3 Hz), 8.14 (1H, s), 7.60 (1H, td, J 7.6, 1.8 Hz), 7.19 (1H, d, J=7.8 Hz), 7.12 (1H, dd, J 7.0, 5.2 Hz), 6.63 (2H, s), 4.64 (2H, s), 4.02-4.14 (2H, m), 3.82 (3H, s), 3.72-3.79 (2H, m), 2.95-3.06 (2H, m), 2.76-2.86 (2H, m), 2.52-2.65 (11H, m), 0.44-0.60 (2H, m), 0.16 (2H, dd, J 3.4, 1.9 Hz)

Potency: B

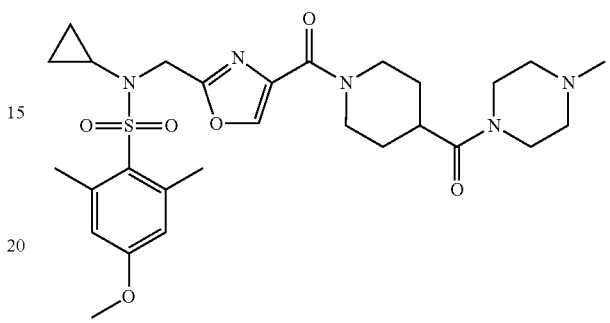

N-Cyclopropyl-4-methoxy-2,6-dimethyl-N-{[4-({4-[(4-methylpiperazin-1-yl)carbonyl]piperidin-1-yl}carbonyl)-1,3-oxazol-2-yl]methyl}benzenesulfonamide trifluoroacetate Ex 229

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 μL, 0.52 mmol), (4-methylpiperazin-1-yl)piperidin-4-yl-methanone (27 mg, 0.13 mmol) and DMF (1 mL). The resulting crude compound was purified by FCC eluting with 99:1 DCM:7N $NH_3$ in MeOH followed by purification using prep method D.

Yield: 11.4 mg, 15%.

LCMS method C: rt 3.05 min, 98%; m/z 574.32 ($MH^+$, 100%).

Potency: A

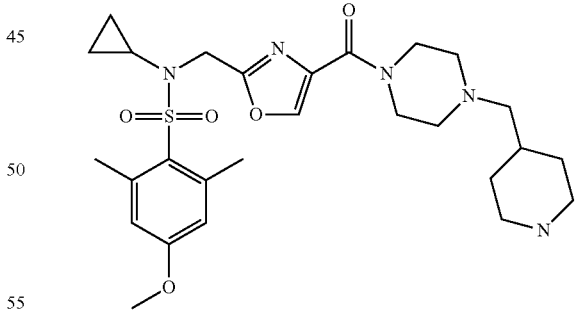

N-Cyclopropyl-4-methoxy-2,6-dimethyl-N-[(4-{[4-(piperidin-4-ylmethyl)piperazin-1-yl]carbonyl}-1,3-oxazol-2-yl)methyl]benzenesulfonamide trifluoroacetate Ex 230

To a stirred solution of N-cyclopropyl-4-methoxy-2,6-dimethyl-N-{[4-(piperazin-1-ylcarbonyl)-1,3-oxazol-2-yl]methyl}benzenesulfonamide (26 mg, 0.06 mmol) in DCE (1 mL) were added tert-butyl 4-formylpiperidine-1-carboxylate (12 mg, 0.06 μmol) and AcOH (4 μL, 0.06 μmol) and the reaction mixture was stirred for 1 h at ambient temperature. STAB (18 mg, 84 µmol) was added and the reaction was stirred for 16 h. The reaction mixture was quenched with H₂O (2 mL) and extracted with DCM (3×2 mL). The organic layer was dried over Na₂SO₄ and concentrated in vacuo. The resulting residue was purified using prep method D. The purified material was stirred in a 4:1 mixture of DCM:TFA (1 mL) at ambient temperature for 1 h and then concentrated in vacuo to afford the title compound as the TFA salt.

Yield: 9.7 mg, 29%

LCMS method C: rt 2.72 min, 96%; m/z 273.73 ([M+2H]²⁺, 100%), 546.42 (MH⁺, 30%)

Potency: C

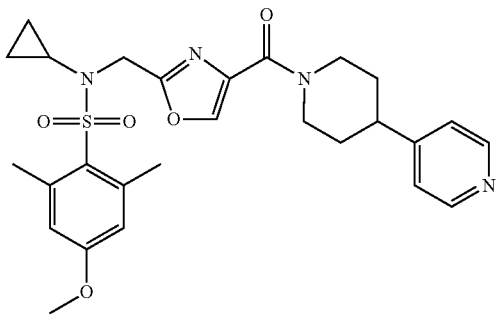 [SMILES: COc1cc(C)c(S(=O)(=O)N(Cc2nc(C(=O)N3CCC(c4ccncc4)CC3)co2)C2CC2)c(C)c1]

N-Cyclopropyl-4-methoxy-2,6-dimethyl-N-({4-[(4-pyridin-4-ylpiperidin-1-yl)carbonyl]-1,3-oxazol-2-yl}methyl)benzenesulfonamide Ex 231

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 µL, 0.52 mmol), 4-piperidin-4-ylpyridine (21 mg, 0.13 mmol) and DMF (1 mL). The resulting crude compound was purified by FCC eluting with 99:1 DCM:7N NH₃ in MeOH.

Yield: 6.6 mg, 7%.

LCMS method C: rt 3.22 min, 95%; m/z 525.32 (MH⁺, 100%).

Potency: B

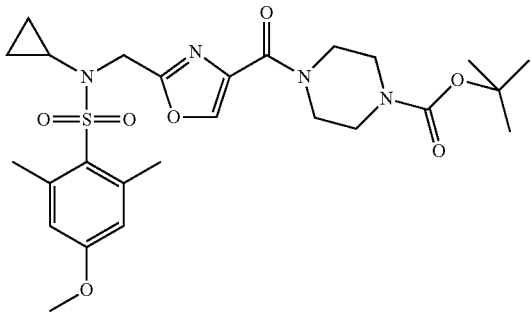 [SMILES: COc1cc(C)c(S(=O)(=O)N(Cc2nc(C(=O)N3CCN(C(=O)OC(C)(C)C)CC3)co2)C2CC2)c(C)c1]

tert-Butyl 4-{[2-({cyclopropyl[(4-methoxy-2,6-dimethylphenyl)sulfonyl]amino}methyl)-1,3-oxazol-4-yl]carbonyl}piperazine-1-carboxylate Int 245

The title compound was prepared according to general procedure AH using 2-({cyclopropyl[(4-methoxy-2,6-dimethylphenyl)sulfonyl]amino}methyl)-1,3-oxazole-4-carboxylic acid (300 mg, 0.79 mmol), EDCI (303 mg, 1.58 mmol), HOBt monohydrate (242 mg, 1.58 mmol), DIPEA (544 µL, 3.16 mmol), tert-butyl piperazine-1-carboxylate (147 mg, 0.79 mmol) and DMF (6 mL). The resulting crude compound was purified by FCC eluting with 99:1 DCM:7N NH₃ in MeOH.

Yield: 250 mg, 58%.

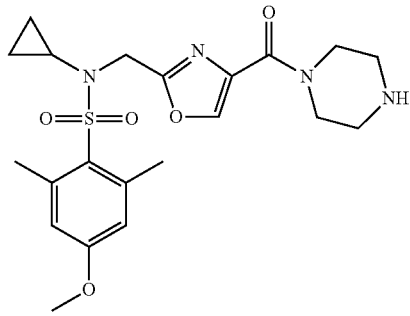 [SMILES: COc1cc(C)c(S(=O)(=O)N(Cc2nc(C(=O)N3CCNCC3)co2)C2CC2)c(C)c1]

N-Cyclopropyl-4-methoxy-2,6-dimethyl-N-{[4-(piperazin-1-ylcarbonyl)-1,3-oxazol-2-yl]methyl}benzenesulfonamide Int 246 tert-butyl 4-{[2-({cyclopropyl[(4-methoxy-2,6-dimethylphenyl)sulfonyl]amino}methyl)-1,3-oxazol-4-yl]carbonyl}piperazine-1-carboxylate (250 mg, 0.46 mmol) was stirred in a 4:1 mixture of DCM:TFA (10 mL) at ambient temperature for 1 h. The reaction was concentrated in vacuo to afford the title compound, which was used without further purification.

LCMS method C: rt 3.03 min, 99%; m/z 449.29 (MH⁺, 100%).

¹H NMR (500 MHz, CD₃OD) δ ppm 8.42 (1H, s), 6.76 (2H, s), 4.70 (2H, s), 4.39 (2H, br. s.), 3.95 (2H, br. s.), 3.84 (3H, s), 3.33-3.39 (4H, m), 2.68 (1H, tt, J 6.9, 3.6 Hz), 2.57 (6H, s), 0.52-0.61 (2H, m), 0.17-0.27 (2H, m)

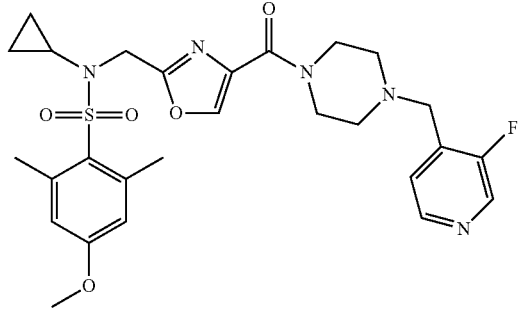 [SMILES: COc1cc(C)c(S(=O)(=O)N(Cc2nc(C(=O)N3CCN(Cc4ccncc4F)CC3)co2)C2CC2)c(C)c1]

N-Cyclopropyl-N-{[4-({4-[(3-fluoropyridin-4-yl)methyl]piperazin-1-yl}carbonyl)-1,3-oxazol-2-yl]methyl}-4-methoxy-2,6-dimethylbenzenesulfonamide trifluoroacetate Ex 232

To a stirred solution of N-cyclopropyl-4-methoxy-2,6-dimethyl-N-{[4-(piperazin-1-ylcarbonyl)-1,3-oxazol-2-yl]methyl}benzenesulfonamide (24 mg, 0.05 mmol) in DCE (1 mL) were added 3-fluoropyridine-4-carboxaldehyde (7 mg, 0.05 mmol) and AcOH (3 µL, 0.05 mmol) and the reaction mixture was stirred for 1 h at ambient temperature. STAB (16 mg, 0.08 mmol) was added and the reaction was stirred for 16 h. The reaction mixture was quenched with H₂O (2 mL) and extracted with DCM (3×2 mL). The organic layer was dried over Na₂SO₄ and concentrated in vacuo. The resulting residue was purified using prep method D to afford the title compound.

Yield: 6.2 mg, 21%

LCMS method C: rt 3.49 min, 98%; m/z 558.32 (MH⁺, 100%).

¹H NMR (500 MHz, CD₃OD) δ ppm 8.42 (1H, d, J=1.5 Hz), 8.37 (1H, d, J=4.9 Hz), 8.30 (1H, s), 7.61 (1H, t, J=5.6 Hz), 6.74 (2H, s), 4.66 (2H, s), 4.06 (2H, br. s.), 3.83 (3H, s), 3.75 (2H, br. s.), 3.72 (2H, s), 2.64 (1H, tt, J 6.8, 3.6 Hz), 2.55-2.61 (10H, m), 0.52-0.60 (2H, m), 0.19-0.26 (2H, m)
Potency: A

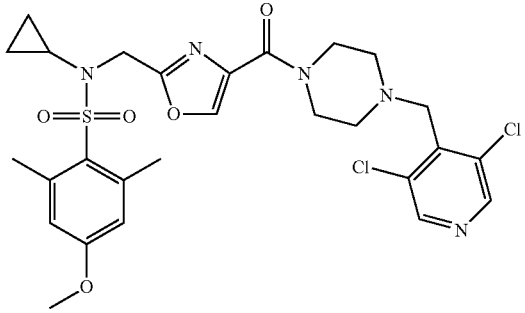 [SMILES: COc1cc(C)c(S(=O)(=O)N(Cc2nc(C(=O)N3CCN(Cc4c(Cl)cncc4Cl)CC3)co2)C2CC2)c(C)c1]

N-Cyclopropyl-N-{[4-({4-[(3,5-dichloropyridin-4-yl)methyl]piperazin-1-yl}carbonyl)-1,3-oxazol-2-yl]methyl}-4-methoxy-2,6-dimethylbenzenesulfonamide trifluoroacetate Ex 233

To a stirred solution of N-cyclopropyl-4-methoxy-2,6-dimethyl-N-{[4-(piperazin-1-ylcarbonyl)-1,3-oxazol-2-yl]methyl}benzenesulfonamide (24 mg, 0.05 mmol) in DCE (1 mL) were added 3,5-dichloro-4-pyridinecarboxaldehyde (10 mg, 0.05 mmol) and AcOH (3 μL, 0.05 mmol) and the reaction mixture was stirred for 1 h at ambient temperature. STAB (16 mg, 0.08 mmol) was added and the reaction was stirred for 16 h. The reaction mixture was quenched with H₂O (2 mL) and extracted with DCM (3×2 mL). The organic layer was dried over Na₂SO₄ and concentrated in vacuo. The resulting residue was purified using prep method D to afford the title compound.
Yield: 6.6 mg, 20%
LCMS method C: rt 4.62 min, 95%; m/z 608.26 (MH⁺, 100%).
Potency: B

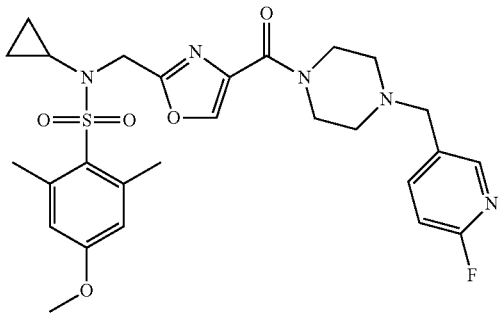 [SMILES: COc1cc(C)c(S(=O)(=O)N(Cc2nc(C(=O)N3CCN(Cc4ccc(F)nc4)CC3)co2)C2CC2)c(C)c1]

N-Cyclopropyl-N-{[4-({4-[(6-fluoropyridin-3-yl)methyl]piperazin-1-yl}carbonyl)-1,3-oxazol-2-yl]methyl}-4-methoxy-2,6-dimethylbenzenesulfonamide trifluoroacetate Ex 234

To a stirred solution of N-cyclopropyl-4-methoxy-2,6-dimethyl-N-{[4-(piperazin-1-ylcarbonyl)-1,3-oxazol-2-yl]methyl}benzenesulfonamide (24 mg, 0.05 mmol) in DCE (1 mL) were added 3-fluoropyridine-5-carboxaldehyde (7 mg, 0.05 mmol) and AcOH (3 μL, 0.05 mmol) and the reaction mixture was stirred for 1 h at ambient temperature. STAB (16 mg, 0.08 mmol) was added and the reaction was stirred for 16 h. The reaction mixture was quenched with H₂O (2 mL) and extracted with DCM (3×2 mL). The organic layer was dried over Na₂SO₄ and concentrated in vacuo. The resulting residue was purified using prep method D to afford the title compound.
Yield: 5.2 mg, 17%
LCMS method C: rt 3.35 min, 97%; m/z 558.32 (MH⁺, 100%).
¹H NMR (500 MHz, CD₃OD) δ ppm 8.38-8.41 (2H, m), 8.30 (1H, s), 7.70 (1H, d, J 9.3 Hz), 6.74 (2H, s), 4.66 (2H, s), 4.06 (2H, br. s.), 3.81-3.85 (3H, m), 3.72-3.80 (2H, m), 3.68 (2H, s), 2.64 (1H, tt, J 6.8, 3.5 Hz), 2.57 (10H, s), 0.53-0.58 (2H, m), 0.19-0.25 (2H, m)
Potency: A

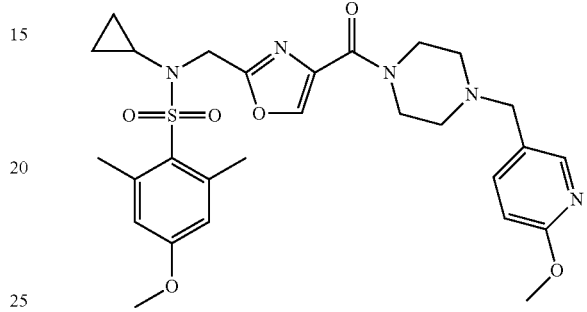

N-Cyclopropyl-4-methoxy-N-{[4-({4-[(6-methoxypyridin-3-yl)methyl]piperazin-1-yl}carbonyl)-1,3-oxazol-2-yl]methyl}-2,6-dimethylbenzenesulfonamide trifluoroacetate Ex 235

To a stirred solution of N-cyclopropyl-4-methoxy-2,6-dimethyl-N-{[4-(piperazin-1-ylcarbonyl)-1,3-oxazol-2-yl]methyl}benzenesulfonamide (24 mg, 0.05 mmol) in DCE (1 mL) were added 6-methoxy-3-pyridinecarboxaldehyde (8 mg, 0.05 mmol) and AcOH (3 μL, 0.05 mmol) and the reaction mixture was stirred for 1 h at ambient temperature. STAB (16 mg, 0.08 mmol) was added and the reaction was stirred for 16 h. The reaction mixture was quenched with H₂O (2 mL) and extracted with DCM (3×2 mL). The organic layer was dried over Na₂SO₄ and concentrated in vacuo. The resulting residue was purified using prep method D to afford the title compound.
Yield: 12.1 mg, 39%
LCMS method C: rt 3.30 min, 100%; m/z 570.35 (MH⁺, 100%).
Potency: C

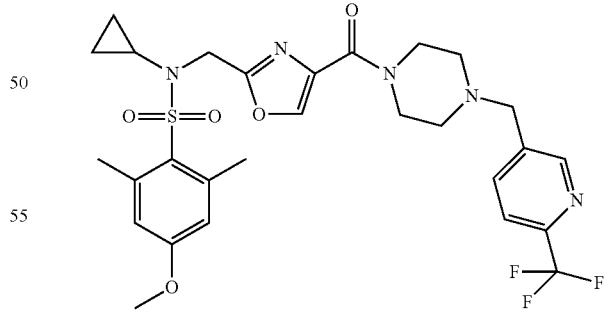

N-Cyclopropyl-4-methoxy-2,6-dimethyl-N-({4-[(4-{[6-(trifluoromethyl)pyridin-3-yl]methyl}piperazin-1-yl)carbonyl]-1,3-oxazol-2-yl}methyl)benzenesulfonamide trifluoroacetate Ex 236

To a stirred solution of N-cyclopropyl-4-methoxy-2,6-dimethyl-N-{[4-(piperazin-1-ylcarbonyl)-1,3-oxazol-2-yl]

methyl}benzenesulfonamide (24 mg, 0.05 mmol) in DCE (1 mL) were added 6-(trifluoromethyl)pyridine-3-carboxaldehyde (10 mg, 0.05 mmol) and AcOH (3 μL, 0.05 mmol) and the reaction mixture was stirred for 1 h at ambient temperature. STAB (16 mg, 0.08 mmol) was added and the reaction was stirred for 16 h. The reaction mixture was quenched with H₂O (2 mL) and extracted with DCM (3×2 mL). The organic layer was dried over Na₂SO₄ and concentrated in vacuo. The resulting residue was purified using prep method D to afford the title compound.

Yield: 17.2 mg, 52%

LCMS method C: rt 3.74 min, 99%; m/z 608.32 (MH⁺, 100%).

Potency: B

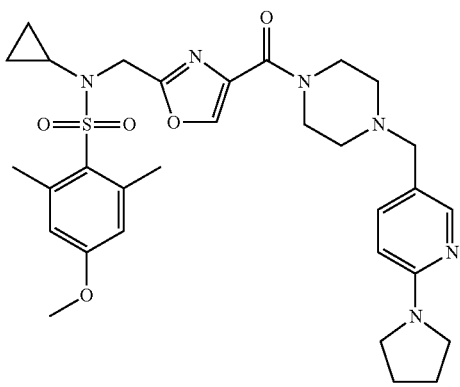 [SMILES: COc1cc(C)c(S(=O)(=O)N(Cc2nc(C(=O)N3CCN(Cc4ccc(N5CCCC5)nc4)CC3)co2)C2CC2)c(C)c1]

N-Cyclopropyl-4-methoxy-2,6-dimethyl-N-{[4-({4-[(6-pyrrolidin-1-ylpyridin-3-yl)methyl]piperazin-1-yl}carbonyl)-1,3-oxazol-2-yl]methyl}benzenesulfonamide trifluoroacetate Ex 237

To a stirred solution of N-cyclopropyl-4-methoxy-2,6-dimethyl-N-{[4-(piperazin-1-ylcarbonyl)-1,3-oxazol-2-yl]methyl}benzenesulfonamide (24 mg, 0.05 mmol) in DCE (1 mL) were added 6-(pyrrolidin-1-yl)pyridine-3-carbaldehyde (10 mg, 0.05 mmol) and AcOH (3 μL, 0.05 mmol) and the reaction mixture was stirred for 1 h at ambient temperature. STAB (16 mg, 0.08 mmol) was added and the reaction was stirred for 16 h. The reaction mixture was quenched with H₂O (2 mL) and extracted with DCM (3×2 mL). The organic layer was dried over Na₂SO₄ and concentrated in vacuo. The resulting residue was purified using prep method D to afford the title compound.

Yield: 14.2 mg, 43%

LCMS method C: rt 2.92 min, 100%; m/z 305.29 ([M+2H]²⁺, 100%), 609.39 (MH⁺, 20%).

¹H NMR (500 MHz, CD₃OD) δ ppm 8.29 (1H, s), 7.92 (1H, d, J=1.8 Hz), 7.53 (1H, dd, J 8.7, 2.1 Hz), 6.74 (2H, s), 6.50 (1H, d, J=8.7 Hz), 4.66 (2H, s), 4.02 (2H, br. s.), 3.83 (3H, s), 3.69-3.77 (2H, m), 3.45 (2H, s), 3.42 (4H, t, J=6.5 Hz), 2.63 (1H, dt, J 6.8, 3.3 Hz), 2.57 (6H, s), 2.52 (4H, br. s.), 1.99-2.07 (4H, m), 0.52-0.58 (2H, m), 0.17-0.29 (2H, m)

Potency: C

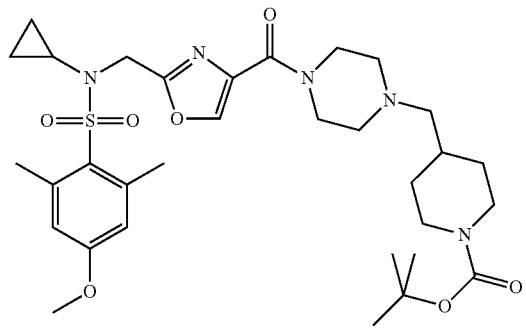 [SMILES: COc1cc(C)c(S(=O)(=O)N(Cc2nc(C(=O)N3CCN(CC4CCN(C(=O)OC(C)(C)C)CC4)CC3)co2)C2CC2)c(C)c1]

2-({Cyclopropyl[(4-methoxy-2,6-dimethylphenyl)sulfonyl]amino}methyl)-N-(2-piperidin-3-ylethyl)-1,3-oxazole-4-carboxamide trifluoroacetate Ex 238

To a stirred solution of N-cyclopropyl-4-methoxy-2,6-dimethyl-N-{[4-(piperazin-1-ylcarbonyl)-1,3-oxazol-2-yl]methyl}benzenesulfonamide (24 mg, 0.05 mmol) in DCE (1 mL) were added tert-butyl 4-formylpiperidine-1-carboxylate (11 mg, 0.05 mmol) and AcOH (3 μL, 0.05 mmol) and the reaction mixture was stirred for 1 h at ambient temperature. STAB (16 mg, 0.08 mmol) was added and the reaction was stirred for 16 h. The reaction mixture was quenched with H₂O (2 mL) and extracted with DCM (3×2 mL). The organic layer was dried over Na₂SO₄ and concentrated in vacuo. The resulting residue was purified using prep method D to afford the title compound.

Yield: 9.4 mg, 27%

LCMS method C: rt 3.52 min, 100%; m/z 646.43 (MH⁺, 100%).

Potency: A

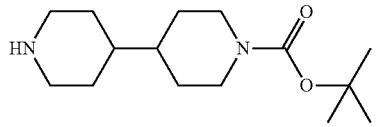 [SMILES: CC(C)(C)OC(=O)N1CCC(C2CCNCC2)CC1]

tert-butyl 4,4'-bipiperidine-1-carboxylate

Int 247

To a stirred solution of 4-4'-Bipiperidine (0.5 g, 3.0 mmol) in DCM (20 mL) were added TEA (2.5 mL, 18.0 mmol), DIPEA (10 mL) and MeOH (30 mL). Di-tert-butyl dicarbonate (0.33 g, 1.5 mmol) was added portionwise and the reaction stirred at ambient temperature for 16 h. The reaction mixture was concentrated in vacuo and the resulting residue was partitioned between H₂O (10 mL) and Et₂O (10 mL). The layers were separated and the aqueous phase basified to pH 14 with aqueous sodium hydroxide solution then extracted with Et₂O (2×25 mL). The organic phase was extracted with aqueous citric acid solution (10% w/v, 2×30 mL) and the acidic aqueous layer basified to pH 14 with aqueous sodium hydroxide solution. This basic aqueous layer was then extracted with Et₂O (3×25 mL) and the combined organic extracts dried over Na₂SO₄ and concentrated in vacuo to afford the title compound.

Yield: 268 mg, 33%

¹H NMR (500 MHz, CD₃OD) δ ppm 4.08 (2H, d, J=13.3 Hz), 3.03 (2H, d, J=12.5 Hz), 2.69 (2H, br. s.), 2.48-2.58 (2H, m), 1.71 (4H, d, J=11.9 Hz), 1.44 (9H, s), 0.99-1.33 (6H, m)

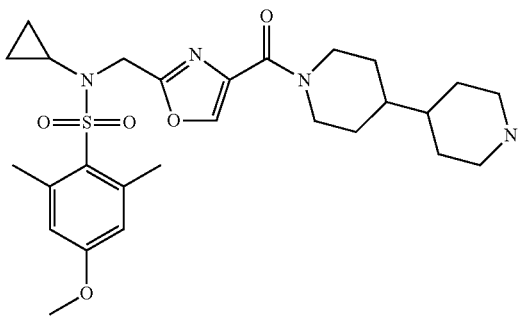 [SMILES: COc1cc(C)c(S(=O)(=O)N(Cc2nc(C(=O)N3CCC(C4CCNCC4)CC3)co2)C2CC2)c(C)c1]

N-{[4-(4,4'-Bipiperidin-1-ylcarbonyl)-1,3-oxazol-2-yl]methyl}-N-cyclopropyl-4-methoxy-2,6-dimethylbenzenesulfonamide trifluoroacetate Ex 239

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 μL, 0.52 mmol), tert-butyl 4,4'-bipiperidine-1-carboxylate (34 mg, 0.13 mmol) and DMF (1 mL). The resulting crude compound was purified by FCC eluting with 99:1 DCM:7N NH$_3$ in MeOH followed by purification using prep method D. The purified material was stirred in a 4:1 mixture of DCM:TFA (1 mL) at ambient temperature for 1 h and then concentrated in vacuo to afford the title compound as the TFA salt.

Yield: 1.8 mg, 3%.

LCMS method C: rt 3.24 min, 99%; m/z 531.40 (MH$^+$, 100%).

Potency: A

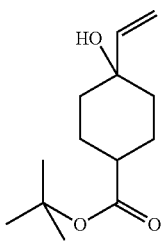

tert-Butyl 4-ethenyl-4-hydroxycyclohexanecarboxylate

Int 248 tert-butyl-4-oxo-1-piperidine carboxylate (1.0 g, 5 mmol) was dissolved in THF (10 mL) and cooled to 0° C. under a N$_2$ atmosphere. To this cooled solution was added vinyl magnesium chloride (1.6 M in THF, 3.0 mL). The reaction was warmed to ambient temperature and stirred for 16 h. The reaction mixture was quenched by addition of saturated aqueous NaHCO$_3$ (10 mL) and extracted with EtOAc (2×50 mL). The organic layer was washed with brine, dried over Na$_2$SO$_4$ and concentrated in vacuo. The resulting residue was purified by FCC eluting with 98:2 DCM:7N NH$_3$ in MeOH to afford the title compound.

Yield: 795 mg, 67%

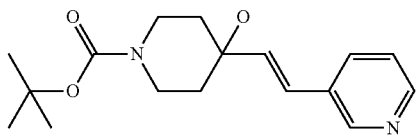 [SMILES: CC(C)(C)OC(=O)N1CCC(O)(/C=C/c2cccnc2)CC1]

tert-Butyl 4-hydroxy-4-[(E)-2-pyridin-3-ylethenyl]piperidine-1-carboxylate

Int 249

To a stirred solution of tert-butyl 4-ethenyl-4-hydroxycyclohexanecarboxylate (200 mg, 0.88 mmol) in MeCN (10 mL) was added DIPEA (315 μL, 1.83 mmol) and 2-bromopyridine (70 μL, 0.73 mmol). The resulting solution was degassed with N$_2$ for 30 min. Pd(OAc)$_2$ (16 mg, 0.073 mmol) and tri-o-tolylphosphine (44 mg, 0.15 mmol) were added and the reaction was stirred at reflux for 16 h under a N$_2$ atmosphere. The reaction mixture was concentrated in vacuo and the resulting residue was purified by FCC eluting with 99:1 to 95:5 DCM:7N NH$_3$ in MeOH to afford the title compound.

Yield: 67.5 mg, 25%

$^1$H NMR (500 MHz, CDCl$_3$) δ ppm 8.55 (1H, br. s.), 8.44 (1H, d, J=3.8 Hz), 7.69 (1H, d, J=7.9 Hz), 7.24 (1H, dd, J 7.8, 4.9 Hz), 6.63 (1H, d, J=16.2 Hz), 6.35 (1H, d, J=16.2 Hz), 3.88 (2H, br. s.), 3.26 (2H, br. s.), 2.48-2.75 (1H, m), 1.68-1.82 (2H, m), 1.55-1.68 (2H, m), 1.46 (9H, s).

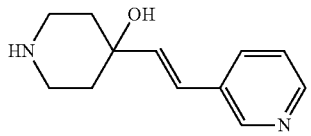

4-[(E)-2-(Pyridin-3-yl)ethenyl]piperidin-4-ol trifluoroacetate

Int 250 tert-butyl 4-hydroxy-4-[(E)-2-(pyridin-3-yl)ethenyl]piperidine-1-carboxylate (67.5 mg, 0.330 mmol) was stirred in a 4:1 mixture of DCM:TFA (1 mL) at ambient temperature for 1 h. The resulting solution was concentrated in vacuo to afford the title compound as a trifluoroacetate salt, which was used without any further purification.

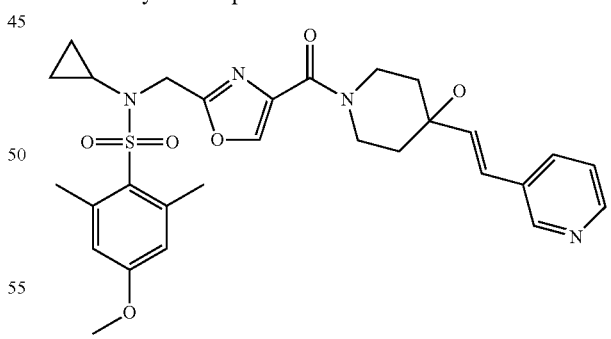

N-Cyclopropyl-N-{[4-({4-hydroxy-4-[(E)-2-pyridin-3-ylethenyl]piperidin-1-yl}carbonyl)-1,3-oxazol-2-yl]methyl}-4-methoxy-2,6-dimethylbenzenesulfonamide trifluoroacetate Ex 240

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 µL, 0.52 mmol), 4-[(E)-2-(pyridin-3-yl)ethenyl]piperidin-4-ol (27 mg, 0.13 mmol) and DMF (1 mL). The resulting crude compound was purified by FCC eluting with 99:1 DCM:7N NH$_3$ in MeOH followed by purification using prep method D.

Yield: 10.4 mg, 14%.

LCMS method C: rt 3.41 min, 96%; m/z 567.39 (MH$^+$, 100%).

$^1$H NMR (250 MHz, CD$_3$OD) δ ppm 8.52-8.60 (1H, m), 8.39 (1H, dd, J 4.9, 1.5 Hz), 8.31 (1H, s), 7.95 (1H, dt, J 8.1, 1.8 Hz), 7.40 (1H, dd, J 7.9, 4.7 Hz), 6.67-6.81 (3H, m), 6.56 (1H, d), 4.69 (2H, s), 4.30-4.63 (2H, m), 3.83 (3H, s), 3.52-3.74 (1H, m), 3.33-3.41 (1H, m), 2.61-2.72 (1H, m), 2.58 (6H, s), 1.81-2.03 (2H, m), 1.61-1.81 (2H, m), 0.46-0.65 (2H, m), 0.11-0.32 (2H, m)

Potency: B

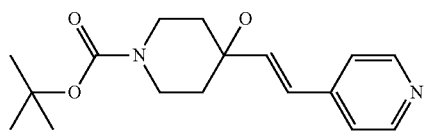

tert-Butyl 4-hydroxy-4-[(E)-2-pyridin-4-ylethenyl]piperidine-1-carboxylate

Int 251

To a stirred solution of tert-butyl 4-ethenyl-4-hydroxycyclohexanecarboxylate (200 mg, 0.88 mmol) in MeCN (10 mL) was added DIPEA (315 µL, 1.83 mmol) and 4-bromopyridine hydrochloride (142 mg, 0.73 mmol). The resulting solution was degassed with N$_2$ for 30 min. Pd(OAc)$_2$ (16 mg, 0.07 mmol) and tri-o-tolylphosphine (44 mg, 0.15 mmol) were added and the reaction was stirred at reflux for 16 h under a N$_2$ atmosphere. The reaction mixture was concentrated in vacuo and the resulting residue was purified by FCC eluting with 99:1 to 95:5 DCM:7N NH$_3$ in MeOH to afford the title compound.

Yield: 145 mg, 54%

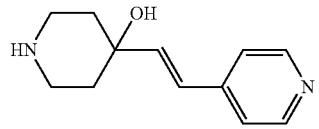 [SMILES: OC1(/C=C/c2ccncc2)CCNCC1]

4-[(E)-2-(Pyridin-4-yl)ethenyl]piperidin-4-ol trifluoroacetate

Int 252 tert-butyl 4-hydroxy-4-[(E)-2-(pyridin-4-yl)ethenyl]piperidine-1-carboxylate (145 mg, 0.71 mmol) was stirred in a 4:1 mixture of DCM:TFA (1 mL) at ambient temperature for 1 h. The resulting solution was concentrated in vacuo to afford the title compound as a TFA salt, which was used without any further purification.

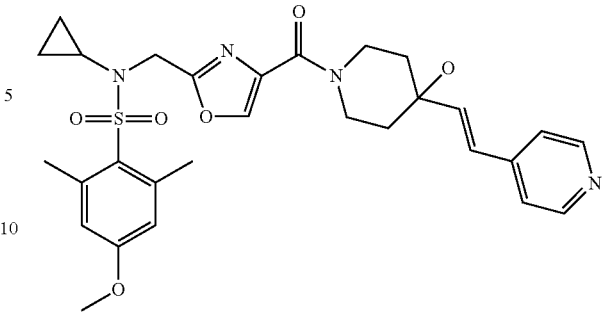

N-Cyclopropyl-N-{[4-({4-hydroxy-4-[(E)-2-pyridin-4-ylethenyl]piperidin-1-yl}carbonyl)-1,3-oxazol-2-yl]methyl}-4-methoxy-2,6-dimethylbenzenesulfonamide trifluoroacetate Ex 241

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 µL, 0.52 mmol), 4-[(E)-2-(pyridin-4-yl)ethenyl]piperidin-4-ol (27 mg, 0.13 mmol) and DMF (1 mL). The resulting crude compound was purified by FCC eluting with 99:1 DCM:7N NH$_3$ in MeOH followed by purification using prep method D.

Yield: 8.8 mg, 12%.

LCMS method C: rt 3.30 min, 100%; m/z 567.39 (MH$^+$, 100%).

$^1$H NMR (250 MHz, CD$_3$OD) δppm 8.39-8.48 (2H, m), 8.31 (1H, s), 7.47 (2H, dd, J 4.6, 1.6 Hz), 6.68-6.78 (4H, m), 4.69 (2H, s), 4.58 (1H, d, J=13.4 Hz), 4.41 (1H, d, J=14.5 Hz), 3.83 (3H, s), 3.52-3.72 (1H, m), 3.34-3.42 (1H, m), 2.65 (1H, td, J 6.8, 3.6 Hz), 2.58 (6H, s), 1.80-2.01 (2H, m), 1.60-1.80 (2H, m), 0.49-0.62 (2H, m), 0.16-0.27 (2H, m).

Potency: B

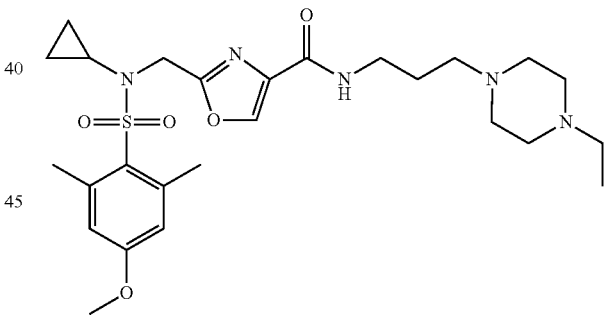

2-({Cyclopropyl[(4-methoxy-2,6-dimethylphenyl)sulfonyl]amino}methyl)-N-[3-(4-ethylpiperazin-1-yl)propyl]-1,3-oxazole-4-carboxamide trifluoroacetate Ex 242

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 µL, 0.52 mmol), 3-(4-ethyl-piperazin-1-yl)-propylamine (22 mg, 0.13 mmol) and DMF (1 mL). The resulting crude compound was purified by FCC eluting with 99:1 DCM:7N NH$_3$ in MeOH followed by purification using prep method D.

Yield: 3.6 mg, 5%.

LCMS method C: rt 2.88 min, 99%; m/z 534.39 (MH$^+$, 100%).

Potency: B

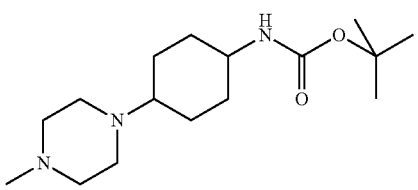 [SMILES: CN1CCN(C2CCC(NC(=O)OC(C)(C)C)CC2)CC1]

tert-Butyl[4-(4-methylpiperazin-1-yl)cyclohexyl]carbamate

Int 253

To a stirred solution of N-methylpiperazine (1.5 mL, 13.5 mmol) in MeOH (5 mL) were added tert-butyl (4-oxocyclohexyl)carbamate (0.6 g, 2.7 mmol) and AcOH (1.6 mL, 2.7 mmol) and the reaction mixture was stirred for 1 h at ambient temperature. STAB (1.14 g, 5.4 mmol) was added and the reaction was stirred for 2 h. The reaction mixture was basified to pH 9 with saturated aqueous $NaHCO_3$ and extracted with DCM (3×20 mL). The organic layer was dried over $Na_2SO_4$ and concentrated in vacuo. The resulting residue was purified by FCC eluting with 98:2 DCM:7N $NH_3$ in MeOH to afford the title compound.

Yield: 258 mg, 45%

$^1$H NMR (500 MHz, $CD_3OD$) δ ppm 3.62 (1H, br. s.), 2.36-2.78 (9H, m), 2.16-2.33 (5H, m), 1.96 (1H, d, J=10.4 Hz), 1.74-1.88 (1H, m), 1.61-1.72 (1H, m), 1.49-1.61 (2H, m), 1.44 (9H, s), 1.28-1.38 (1H, m), 1.15-1.26 (1H, m).

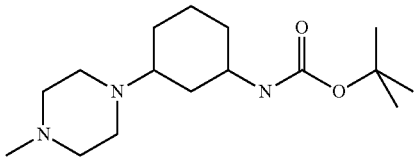 [SMILES: CN1CCN(C2CCCC(NC(=O)OC(C)(C)C)C2)CC1]

tert-Butyl[3-(4-methylpiperazin-1-yl)cyclohexyl]carbamate

Int 254

To a stirred solution of N-methylpiperazine (1.5 mL, 13.5 mmol) in MeOH (5 mL) were added tert-butyl (3-oxocyclohexyl)carbamate (0.6 g, 2.7 mmol) and AcOH (1.6 mL, 2.7 mmol) and the reaction mixture was stirred for 1 h at ambient temperature. STAB (1.14 g, 5.4 mmol) was added and the reaction was stirred for 2 h. The reaction mixture was basified to pH 9 with saturated aqueous $NaHCO_3$ and extracted with DCM (3×20 mL). The organic layer was dried over $Na_2SO_4$ and concentrated in vacuo. The resulting residue was purified by FCC eluting with 98:2 DCM:7N $NH_3$ in MeOH to afford the title compound.

Yield: 453 mg, 56%

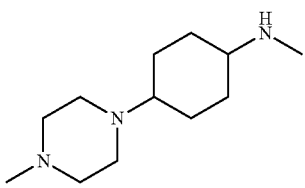

N-Methyl-4-(4-methylpiperazin-1-yl)cyclohexanamine

Int 255

A stirred solution of Lithium aluminium hydride (1.0 M in THF, 1.6 mL) under $N_2$ atmosphere was cooled to 0° C. A solution of tert-butyl[4-(4-methylpiperazin-1-yl)cyclohexyl]carbamate (157 mg, 0.53 mmol) in THF (2 mL) was added dropwise over 10 min. The reaction mixture was then heated to 75° C. for 2 h. The reaction mixture was cooled to 0° C. and quenched by slow addition of 1 M aqueous sodium hydroxide solution (1 mL), followed by $H_2O$ (1 mL). The resulting suspension was dried by addition of solid $Na_2SO_4$, the slurry was filtered and the solid was washed with THF. The combined filtrates were concentrated in vacuo to afford the title compound.

Yield: 39.7 mg, 36%

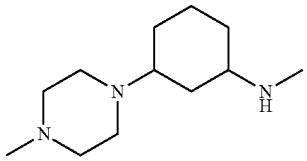

N-Methyl-3-(4-methylpiperazin-1-yl)cyclohexanamine

Int 256

A stirred solution of Lithium aluminium hydride (1.0 M in THF, 1.6 mL) under $N_2$ atmosphere was cooled to 0° C. A solution of tert-butyl[3-(4-methylpiperazin-1-yl)cyclohexyl]carbamate (157 mg, 0.53 mmol) in THF (2 mL) was added dropwise over 10 min. The reaction mixture was then heated to 75° C. for 2 h. The reaction mixture was cooled to 0° C. and quenched by slow addition of 1 M aqueous sodium hydroxide solution (1 mL) followed by $H_2O$ (1 mL). The resulting suspension was dried by addition of solid $Na_2SO_4$, the slurry was filtered and the solid was washed with THF. The combined filtrates were concentrated in vacuo to afford the title compound.

Yield: 39.7 mg, 36%

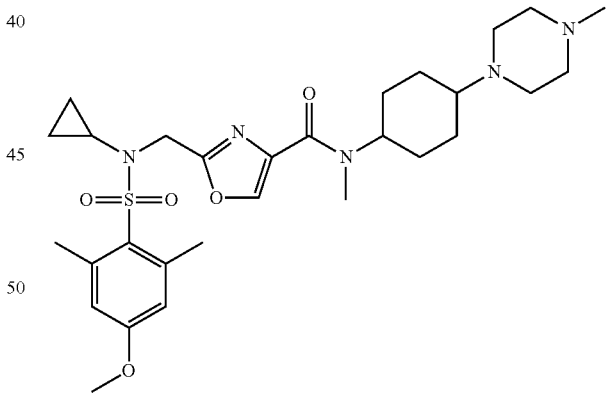

2-({Cyclopropyl[(4-methoxy-2,6-dimethylphenyl)sulfonyl]amino}methyl)-N-methyl-N-[4-(4-methylpiperazin-1-yl)cyclohexyl]-1,3-oxazole-4-carboxamide trifluoroacetate Ex 243

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 μL, 0.52 mmol), N-methyl-4-(4-methylpiperazin-1-yl)cyclohexanamine (27 mg, 0.13 mmol) and DMF (1 mL). The resulting crude compound was purified by FCC eluting with 99:1 DCM:7N NH$_3$ in MeOH followed by purification using prep method D.

Yield: 9.9 mg, 13%.

LCMS method C: rt 3.21 min, 98%; m/z 574.44 (MH$^+$, 100%).

Potency: B

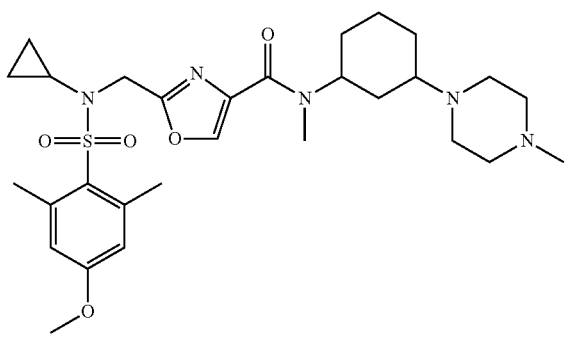 [SMILES: COc1cc(C)c(S(=O)(=O)N(Cc2nc(C(=O)N(C)C3CCCC(N4CCN(C)CC4)C3)co2)C2CC2)c(C)c1]

2-({Cyclopropyl[(4-methoxy-2,6-dimethylphenyl)sulfonyl]amino}methyl)-N-methyl-N-[3-(4-methylpiperazin-1-yl)cyclohexyl]-1,3-oxazole-4-carboxamide Ex 244

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 μL, 0.52 mmol), N-methyl-3-(4-methylpiperazin-1-yl)cyclohexanamine (27 mg, 0.13 mmol) and DMF (1 mL). The resulting crude compound was purified by FCC eluting with 99:1 DCM:7N NH$_3$ in MeOH followed by purification using prep method D.

Yield: 8.8 mg, 2%.

LCMS method C: rt 3.12 min, 89%; m/z 574.44 (MH$^+$, 100%).

Potency: C

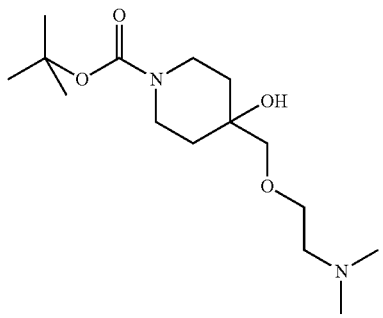 [SMILES: CN(C)CCOCC1(O)CCN(C(=O)OC(C)(C)C)CC1]

tert-Butyl 4-{[2-(dimethylamino)ethoxy]methyl}-4-hydroxypiperidine-1-carboxylate Int 262

N,N-dimethylaminoethanol (0.283 mL, 2.81 mmol) and NaH (60%, 113 mg, 2.82 mmol) were stirred in DMSO (2 mL) at ambient temperature for 30 mins. tert-Butyl 1-oxa-6-azaspiro[2.5]octane-6-carboxylate (200 mg, 0.94 mmol) was added to the mixture as a solution in DMSO (2 mL) and the reaction was heated to 60° C. for 3 h. The mixture was allowed to cool, quenched with H$_2$O (1 mL) and concentrated. The residue was purified using FCC, eluting with 98:2:1 DCM:MeOH:NH$_3$, to afford the title compound as a colourless oil.

Yield: 281 mg, 99%.

$^1$H NMR (500 MHz, CDCl$_3$): δ ppm 4.96 (1H, br s), 3.82 (2H, br s), 3.67 (2H, t, J=5.3 Hz), 3.38 (2H, s), 3.21 (2H, br s), 2.56 (2H, br s), 2.33 (6H, s), 1.61 (2H, d, J=14.0 Hz), 1.46 (9H, s), 1.38-1.46 (2H, m)

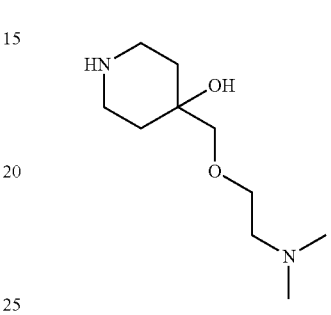

4-{[2-(Dimethylamino)ethoxy]methyl}piperidin-4-ol trifluoroacetate

Int 263 tert-butyl 4-{[2-(dimethylamino)ethoxy]methyl}-4-hydroxypiperidine-1-carboxylate (280 mg, 0.93 mmol) was stirred in DCM (10 mL) and trifluoroacetic acid (0.21 mL, 2.78 mmol) was added. The reaction was stirred at ambient temperature for 18 h, then concentrated afford the title compound as a TFA salt, which was used without further purification.

Yield: 329 mg, 82%.

$^1$H NMR (500 MHz, CD$_3$OD): δ ppm 3.76-3.81 (2H, m), 3.40 (2H, s), 3.31-3.36 (2H, m), 3.21-3.25 (4H, m), 2.89 (6H, s), 1.80 (4H, dd, J 7.3, 4.7 Hz)

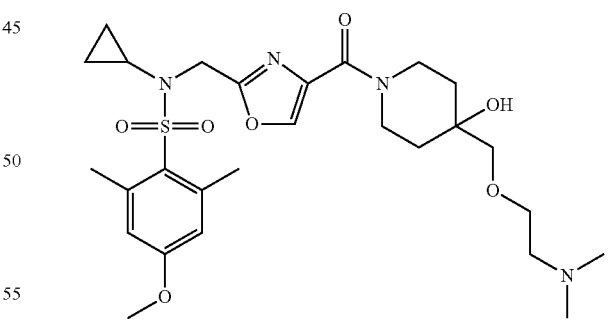

N-Cyclopropyl-N-({4-[(4-{[2-(dimethylamino)ethoxy]methyl}-4-hydroxypiperidin-1-yl)carbonyl]-1,3-oxazol-2-yl}methyl)-4-methoxy-2,6-dimethylbenzenesulfonamide trifluoroacetate Ex 246

The title compound was prepared according to general procedure AC using 2-({cyclopropyl[(4-methoxy-2,6-dimethylphenyl)sulfonyl]amino}methyl)-1,3-oxazole-4-carboxylic acid (30 mg, 0.08 mmol), EDCI (18 mg, 0.09 mmol), HOBt monohydrate (13 mg, 0.10 mmol), TEA (0.045 mL, 0.32 mmol) and 4-{[2-(dimethylamino)ethoxy]methyl}piperidin-4-ol.2TFA (70 mg, 0.16 mmol) in DMF (2 mL). The crude product was purified using prep method D, followed by prep method C, followed by prep method A.

LCMS Method C: rt 3.14 min, 97%; 565.40 (MH+, 100%)
$^1$H NMR (500 MHz, CD$_3$OD): δ ppm 8.26 (1H, s), 6.72 (2H, s), 4.64 (2H, d, J=2.6 Hz), 4.43-4.51 (1H, m), 4.26-4.34 (1H, m), 3.80 (3H, s), 3.75-3.79 (2H, m), 3.55 (1H, br s), 3.40 (2H, s), 3.31-3.36 (2H, m), 3.19-3.25 (1H, m), 2.89 (6H, s), 2.60 (1H, tt, J 6.8, 3.6 Hz), 2.54 (6H, s), 1.71-1.79 (1H, m), 1.59-1.71 (3H, m), 0.52 (2H, dd, J 6.9, 1.4 Hz), 0.15-0.22 (2H, m)

Potency: B

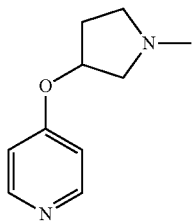

4-[(1-Methylpyrrolidin-3-yl)oxy]pyridine

Int 264

To a stirred solution of 4-chloropyridine hydrochloride (3.56 g, 23.80 mmol) and potassium tert-butoxide (8.0 g, 71.40 mmol) in DMSO (8 mL) was added 1-methylpyrrolidin-3-ol (2.4 g, 23.80 mmol). The reaction mixture was stirred at 90° C. for 12 h, cooled to ambient temperature and concentrated in vacuo. The resulting residue was purified by FCC eluting with 0-1% MeOH in DCM to afford the title compound as a pale yellow viscous liquid.

Yield: 650 mg, 16%.
$^1$H NMR (300 MHz, CDCl$_3$): δ 8.41-8.39 (m, 2H), 6.76 (m, 2H), 4.86 (m, 1H), 2.86-2.79 (m, 3H), 2.44-2.32 (m, 5H), 2.08-1.94 (m, 1H).

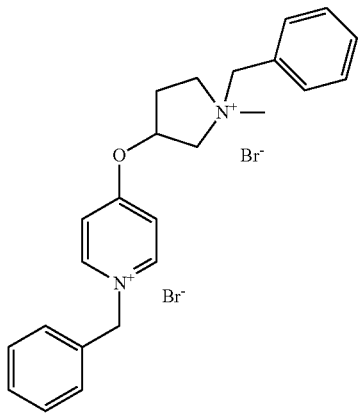 [SMILES: C[N+]1(Cc2ccccc2)CCC(Oc2cc[n+](Cc3ccccc3)cc2)C1 ; [Br-] ; [Br-]]

1-Benzyl-4-[(1-benzyl-1-methylpyrrolidinium-3-yl)oxy]pyridinium dibromide

Int 265

4-[(1-Methylpyrrolidin-3-yl)oxy]pyridine (1.0 g, 5.62 mmol) was dissolved in DCM (25 mL) and benzyl bromide (2.35 mL, 19.76 mmol) added. The reaction mixture was stirred at ambient temperature for 4 h. The solvent was removed in vacuo and the residue was dissolved in DCM (3 mL). Diethyl ether (15 mL) was added and the solution was stirred until a precipitate formed. The off-white semi solid formed was isolated by decanting the solvent mixture and used in the next step without further purification.

Yield: 1.96 g, 67%

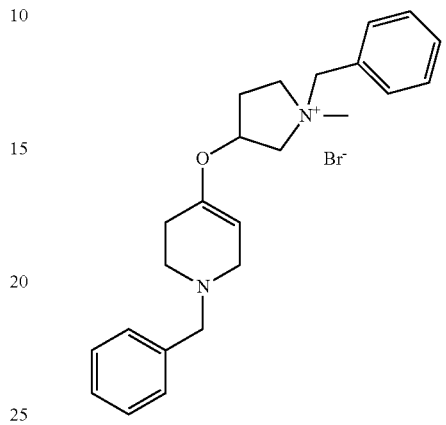

1-Benzyl-3-[(1-benzyl-1,2,3,6-tetrahydropyridin-4-yl)oxy]-1-methylpyrrolidinium bromide Int 266

1-benzyl-4-[(1-benzyl-1-methylpyrrolidinium-3-yl)oxy] pyridinium dibromide (1.6 g, 3.07 mmol) was stirred in methanol (20 mL) under argon and NaBH$_4$ (470 mg, 12.30 mmol) was added portionwise over 30 min. The reaction mixture was stirred for 45 min at ambient temperature. The solvent was removed in vacuo and the residue was purified by FCC eluting with 0-2% MeOH in DCM to afford the title compound as a light red semi solid.

Yield: 950 mg, 69%.

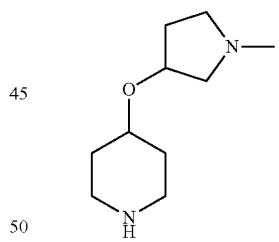

4-[(1-Methylpyrrolidin-3-yl)oxy]piperidine

Int 267

To a stirred solution of 1-benzyl-3-[(1-benzyl-1,2,3,6-tetrahydropyridin-4-yl)oxy]-1-methylpyrrolidinium bromide (950 mg, 2.14 mmol) in MeOH (25 mL) was added Pd/C (195 mg, 20% w/w). The resultant suspension was purge-filled with N$_2$ (3 cycles), then with hydrogen (3 cycles). Constant pressure of hydrogen (10 psi) was maintained and the mixture was stirred at ambient temperature for 3 h. The mixture was filtered through Celite and the filter cake was washed with MeOH (40 mL). The combined organic layers were concentrated in vacuo and the crude product was used in the next step without further purification.

Crude product: 900 mg.

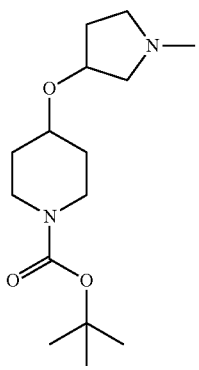 [SMILES: CN1CCC(OC2CCN(C(=O)OC(C)(C)C)CC2)C1]

tert-Butyl 4-[(1-methylpyrrolidin-3-yl)oxy]piperidine-1-carboxylate

Int 268

4-[(1-Methylpyrrolidin-3-yl)oxy]piperidine (900 mg, 4.88 mmol) as a crude was dissolved in DCM (20 mL) and di-tert-butyl-dicarbonate (1.2 g, 5.40 mmol) added. The reaction mixture was cooled to 0° C. prior to the addition of TEA (2.7 mL, 19.78 mmol) then stirred at ambient temperature for 4 h. The reaction was washed with water (2×10 mL) and the organic layer separated and dried over Na$_2$SO$_4$ and concentrated in vacuo. The resulting residue was purified by FCC eluting with 0-0.5% MeOH in DCM to afford the title compound as a colourless liquid.

Yield: 250 mg, 18%

$^1$H NMR (300 MHz, CDCl$_3$) δ ppm 4.13 (1H, m), 3.70 (2H, m), 3.44 (1H, m), 3.04 (2H, m), 2.71 (1H, m), 2.62 (1H, m), 2.47 (2H, m), 2.34 (3H, s), 2.09 (1H, m), 1.77 (2H, m), 1.15 (1H, m), 1.44 (9H, s).

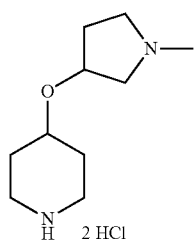

4-[(1-Methylpyrrolidin-3-yl)oxy]piperidine dihydrochloride

Int 269

To a stirred solution of tert-butyl 4-[(1-methylpyrrolidin-3-yl)oxy]piperidine-1-carboxylate (250 mg, 0.88 mmol) in Et$_2$O (5 mL) at 0° C. was added a solution of HCl in Et$_2$O (2 mL). The reaction mixture was stirred at ambient temperature for 15 min and then the solvent removed in vacuo and the residue was washed with n-pentane to afford the title compound.

Yield: 194 mg, 86%

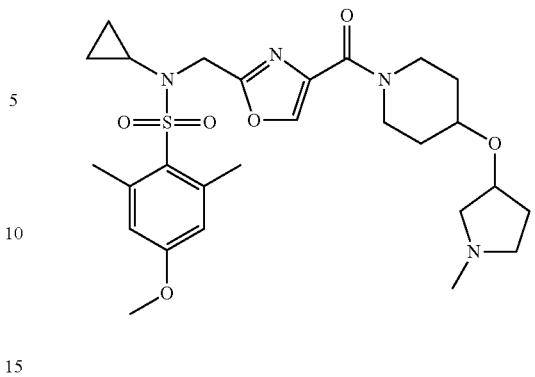

N-Cyclopropyl-4-methoxy-2,6-dimethyl-N-{[4-({4-[(1-methylpyrrolidin-3-yl)oxy]piperidin-1-yl}carbonyl)-1,3-oxazol-2-yl]methyl}benzenesulfonamide Ex 247

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 μL, 0.52 mmol), 4-[(1-methylpyrrolidin-3-yl)oxy]piperidine (24 mg, 0.13 mmol) and DMF (1 mL). The resulting crude compound was purified using prep method D.

Yield: 5.1 mg, 7%.

LCMS method C: rt 3.14 min, 88%; m/z 547.38 (MH$^+$, 100%).

Potency: A

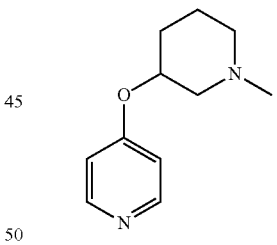

3-[(1-Methylpiperidin-3-yl)oxy]pyridine

Int 270

To a stirred solution of 4-chloropyridine hydrochloride (5.2 g, 34.66 mmol) and potassium tert-butoxide (11.7 g, 104 mmol) in DMSO (12 mL) was added 1-methylpiperidin-3-ol (4.0 g, 34.72 mmol). The reaction mixture was stirred at 90° C. for 12 h, cooled to ambient temperature and concentrated in vacuo. The resulting residue was purified by FCC eluting with 0-1% MeOH in DCM to afford the title compound as a pale yellow viscous liquid.

Yield: 2.25 g, 34%.

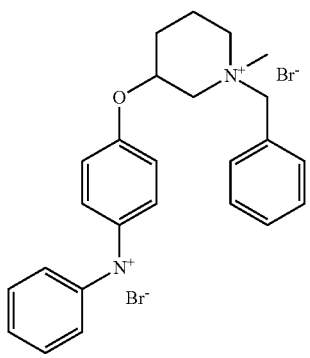 [SMILES: C[N+]1(Cc2ccccc2)CCCC(Oc2ccc([NH2+]c3ccccc3)cc2)C1 ; [Br-] ; [Br-]]

1-Benzyl-4-(1-benzyl-1-methylpiperidinium-3-yloxy)pyridinium dibromide

Int 271

4-[(1-methylpiperidin-4-yl)oxy]pyridine (2.5 g, 13.0 mmol) was dissolved in DCM (25 mL) and benzyl bromide (5.5 mL, 46.0 mmol) added. The reaction mixture was stirred at ambient temperature for 4 h. The solvent was removed in vacuo and the residue was dissolved in DCM (3 mL). Diethyl ether (15 mL) was added and the solution was stirred until a precipitate formed. The off-white semi solid formed was isolated by decanting the solvent mixture and used in the next step without further purification.

Yield: 5.5 g, 79%

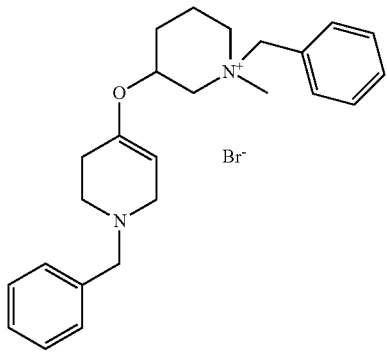 [SMILES: C[N+]1(Cc2ccccc2)CCCC(OC2=CCN(Cc3ccccc3)CC2)C1 ; [Br-]]

1-Benzyl-3-(1-benzyl-1,2,3,6-tetrahydropyridin-4-yloxy)-1-methylpiperidinium bromide Int 272

1-benzyl-4-(1-benzyl-1-methylpiperidinium-3-yloxy)pyridinium dibromide (5.5 g, 10.3 mmol) was stirred in methanol (25 mL) under argon and NaBH$_4$ (1.57 mg, 41.50 mmol) was added portionwise over 30 min. The reaction mixture was stirred for 45 min at ambient temperature. The solvent was removed in vacuo and the residue was purified by FCC eluting with 0-2% MeOH in DCM to afford the title compound as a white solid.

Yield: 4.0 g, 85%.

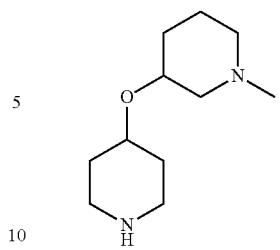

1-Methyl-3-(piperidin-4-yloxy)piperidine

Int 273

To a stirred solution of 1-benzyl-3-(1-benzyl-1,2,3,6-tetrahydropyridin-4-yloxy)-1-methylpiperidinium bromide (4.0 mg, 8.75 mmol) in MeOH (50 mL) was added Pd/C (800 mg, 20% w/w). The resultant suspension was purge-filled with N$_2$ (3 cycles), then with hydrogen (3 cycles). Constant pressure of hydrogen (10 psi) was maintained and the mixture was stirred at ambient temperature for 3 h. The mixture was filtered through Celite and the filter cake was washed with MeOH (160 mL). The combined organic layers were concentrated in vacuo and the crude product was used in the next step without further purification.

Crude yield: 2.5 g

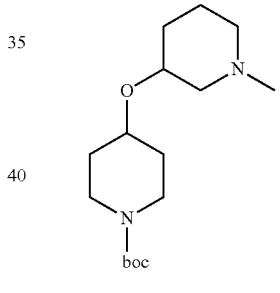

tert-Butyl 4-[(1-methyl piperidin-3-yl)oxy]piperidine-1-carboxylate

Int 274

1-Methyl-3-(piperidin-4-yloxy)piperidine (2.5 g, 12.60 mmol) as a crude was dissolved in DCM (25 mL) and di-tert-butyl-dicarbonate (3.03 g, 13.90 mmol) added. The reaction mixture was cooled to 0° C. prior to the addition of TEA (6.85 mL, 49.14 mmol) then stirred at ambient temperature for 4 h. The reaction was washed with water (2×10 mL), the organic layer separated and dried over Na$_2$SO$_4$ and concentrated in vacuo. The resulting residue was purified by FCC eluting with 0-0.5% MeOH in DCM to afford the title compound as a colourless liquid.

Yield: 450 mg, 12%

$^1$H NMR (300 MHz, CDCl$_3$) δ ppm 3.76 (2H, m), 3.55 (2H, m), 3.03 (2H, m), 2.87 (1H, m), 2.65 (1H, m), 2.27 (3H, s), 1.70-1.95 (7H, m), 1.51 (2H, m), 1.45 (9H, s), 1.25 (1H, m).

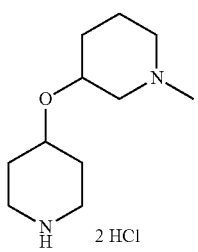

1-Methyl-3-(piperidin-4-yloxy)piperidine dihydrochloride

Int 275

To a stirred solution of tert-butyl 4-[(1-methyl piperidin-3-yl)oxy]piperidine-1-carboxylate (450 mg, 1.50 mmol) in Et$_2$O (3 mL) at 0° C. was added a solution of HCl in Et$_2$O (3 mL). The reaction mixture was stirred at ambient temperature for 15 min and then the solvent removed in vacuo and the residue was washed with n-pentane to afford the title compound.

Yield: 410 mg, 100%.

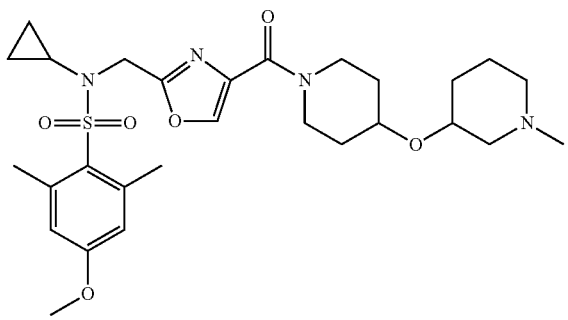 [SMILES: COc1cc(C)c(S(=O)(=O)N(Cc2nc(C(=O)N3CCC(OC4CCCN(C)C4)CC3)co2)C2CC2)c(C)c1]

N-Cyclopropyl-4-methoxy-2,6-dimethyl-N-{[4-({4-[(1-methylpiperidin-3-yl)oxy]piperidin-1-yl}carbonyl)-1,3-oxazol-2-yl]methyl}benzenesulfonamide trifluoroacetate Ex 248

The title compound was prepared according to general procedure AC using 2-({cyclopropyl[(4-methoxy-2,6-dimethylphenyl)sulfonyl]amino}methyl)-1,3-oxazole-4-carboxylic acid (30 mg, 0.08 mmol), EDCI (18 mg, 0.09 mmol), HOBt monohydrate (13 mg, 0.10 mmol), TEA (0.056 mL, 0.40 mmol) and 1-methyl-3-(piperidin-4-yloxy)piperidine 0.2HCl (44 mg, 0.16 mmol) in DMF (1 mL). A portion of the crude product was purified using prep method D.

LCMS Method C: rt 3.24 min, 99%; 561.41 (MH$^+$, 100%)

$^1$H NMR (500 MHz, CD$_3$OD): δ ppm 8.25 (1H, s), 6.72 (2H, s), 4.64 (2H, s), 4.22 (1H, br s), 3.98 (1H, br s), 3.81 (3H, s), 3.74-3.80 (1H, m), 3.61-3.70 (1H, m), 3.50-3.60 (1H, m), 3.37-3.46 (1H, m), 2.83 (1H, br s), 2.62 (2H, tt, J 6.8, 3.5 Hz), 2.55 (6H, s), 2.26 (3H, s), 2.00 (2H, br s), 1.83-1.94 (3H, m), 1.71-1.80 (1H, m), 1.47-1.64 (3H, m), 1.20-1.34 (1H, m), 0.49-0.57 (2H, m), 0.16-0.24 (2H, m)

Potency: B

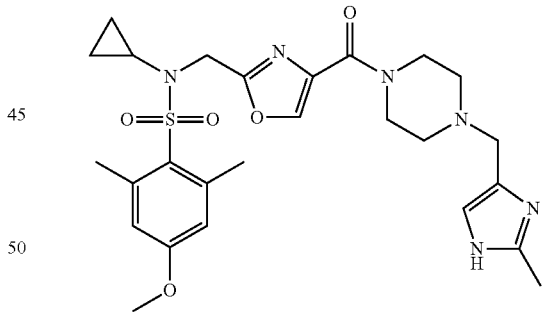

N-Cyclopropyl-N-[(4-{[4-(1H-imidazol-4-ylmethyl)piperazin-1-yl]carbonyl}-1,3-oxazol-2-yl)methyl]-4-methoxy-2,6-dimethylbenzenesulfonamide Ex 249

To a stirred solution of N-cyclopropyl-4-methoxy-2,6-dimethyl-N-{[4-(piperazin-1-ylcarbonyl)-1,3-oxazol-2-yl]methyl}benzenesulfonamide (30 mg, 0.07 mmol) in DCE (2 mL) were added 1-H-imidazole-4-carboxaldehyde (8 mg, 0.08 mmol) and AcOH (3 µL, 0.07 mmol) and the reaction mixture was stirred for 1 h at ambient temperature. STAB (20 mg, 0.09 mmol) was added and the reaction was stirred for 16 h. The reaction mixture was quenched with H$_2$O (2 mL) and extracted with DCM (3×2 mL). The organic layer was dried over Na$_2$SO$_4$ and concentrated in vacuo. The resulting residue was purified using prep method D to afford the title compound.

Yield: 5.6 mg, 16%

LCMS method C: rt 2.97 min, 99%; m/z 529.35 (MH$^+$, 100%).

$^1$H NMR (500 MHz, CDCl$_3$) δ ppm 8.14-8.22 (2H, m), 7.28 (1H, s), 6.64 (2H, s), 4.64 (2H, s), 4.32 (2H, br. s.), 3.97-4.05 (2H, m), 3.91 (2H, br. s.), 3.84 (3H, s), 2.87-3.00 (4H, m), 2.60-2.66 (1H, m), 2.58 (6H, s), 0.47-0.60 (2H, m), 0.10-0.19 (2H, m)

Potency: B

N-Cyclopropyl-4-methoxy-2,6-dimethyl-N-{[4-({4-[(2-methyl-1H-imidazol-4-yl)methyl]piperazin-1-yl}carbonyl)-1,3-oxazol-2-yl]methyl}benzenesulfonamide Ex 250

To a stirred solution of N-cyclopropyl-4-methoxy-2,6-dimethyl-N-{[4-(piperazin-1-ylcarbonyl)-1,3-oxazol-2-yl]methyl}benzenesulfonamide (30 mg, 0.07 mmol) in DCE (2 mL) were added 2-methyl-1H-imidazole-4-carboxaldehyde (9 mg, 0.08 mmol) and AcOH (3 µL, 0.07 mmol) and the reaction mixture was stirred for 1 h at ambient temperature. STAB (20 mg, 0.09 mmol) was added and the reaction was stirred for 16 h. The reaction mixture was quenched with H$_2$O (2 mL) and extracted with DCM (3×2 mL). The organic layer was dried over Na$_2$SO$_4$ and concentrated in vacuo. The resulting residue was purified using prep method D to afford the title compound.

Yield: 3.8 mg, 11%

LCMS method C: rt 2.93 min, 100%; m/z 272.25 ([M+2H]$^{2+}$, 100%), 543.40 (MH$^+$, 40%).

Potency: C

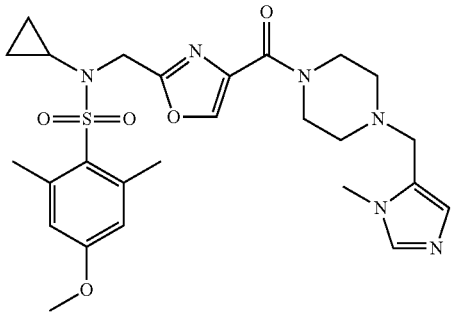 [SMILES: COc1cc(C)c(S(=O)(=O)N(Cc2nc(C(=O)N3CCN(Cc4cncn4C)CC3)co2)C2CC2)c(C)c1]

N-Cyclopropyl-4-methoxy-2,6-dimethyl-N-{[4-({4-[(1-methyl-1H-imidazol-5-yl)methyl]piperazin-1-yl}carbonyl)-1,3-oxazol-2-yl]methyl}benzenesulfonamide Ex 251

To a stirred solution of N-cyclopropyl-4-methoxy-2,6-dimethyl-N-{[4-(piperazin-1-ylcarbonyl)-1,3-oxazol-2-yl]methyl}benzenesulfonamide (30 mg, 0.07 mmol) in DCE (2 mL) were added 1-methyl-1H-imidazole-5-carboxaldehyde (9 mg, 0.08 mmol) and AcOH (3 μL, 0.07 mmol) and the reaction mixture was stirred for 1 h at ambient temperature. STAB (20 mg, 0.09 mmol) was added and the reaction was stirred for 16 h. The reaction mixture was quenched with H$_2$O (2 mL) and extracted with DCM (3×2 mL). The organic layer was dried over Na$_2$SO$_4$ and concentrated in vacuo. The resulting residue was purified using prep method D to afford the title compound.

Yield: 14.0 mg, 39%

LCMS method C: rt 3.11 min, 96%; m/z 543.38 (MH$^+$, 100%).

Potency: A

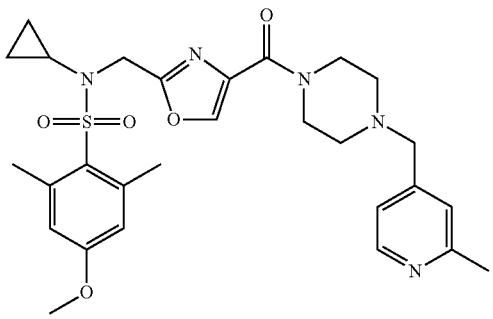 [SMILES: COc1cc(C)c(S(=O)(=O)N(Cc2nc(C(=O)N3CCN(Cc4ccnc(C)c4)CC3)co2)C2CC2)c(C)c1]

N-Cyclopropyl-4-methoxy-2,6-dimethyl-N-{[4-({4-[(2-methylpyridin-4-yl)methyl]piperazin-1-yl}carbonyl)-1,3-oxazol-2-yl]methyl}benzenesulfonamide Ex 252

To a stirred solution of N-cyclopropyl-4-methoxy-2,6-dimethyl-N-{[4-(piperazin-1-ylcarbonyl)-1,3-oxazol-2-yl]methyl}benzenesulfonamide (30 mg, 0.07 mmol) in DCE (2 mL) were added 6-methyl-4-pyridinecarboxaldehyde (10 mg, 0.08 mmol) and AcOH (3 μL, 0.07 mmol) and the reaction mixture was stirred for 1 h at ambient temperature. STAB (20 mg, 0.09 mmol) was added and the reaction was stirred for 16 h. The reaction mixture was quenched with H$_2$O (2 mL) and extracted with DCM (3×2 mL). The organic layer was dried over Na$_2$SO$_4$ and concentrated in vacuo. The resulting residue was purified using prep method D to afford the title compound.

Yield: 10.7 mg, 29%

LCMS method C: rt 3.16 min, 99%; m/z 554.35 (MH$^+$, 100%).

$^1$H NMR (500 MHz, CDCl$_3$) δ ppm 8.53 (1H, d, J=5.3 Hz), 8.16 (1H, s), 7.27-7.29 (1H, m), 7.25 (1H, d, J=5.0 Hz), 6.63 (2H, s), 4.64 (2H, s), 4.14 (2H, br. s.), 3.83 (3H, s), 3.80 (2H, br. s.), 3.58 (2H, s), 2.64 (3H, s), 2.51-2.62 (1H, m), 0.47-0.57 (2H, m), 0.08-0.21 (2H, m)

Potency: C

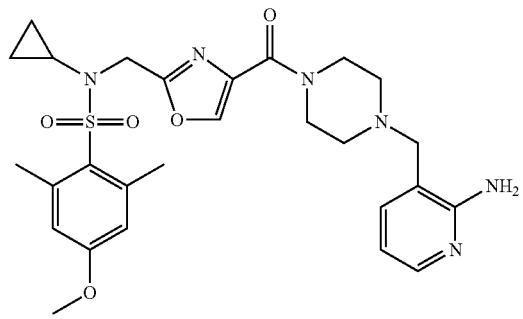 [SMILES: COc1cc(C)c(S(=O)(=O)N(Cc2nc(C(=O)N3CCN(Cc4cccnc4N)CC3)co2)C2CC2)c(C)c1]

N-{[4-({4-[(2-Aminopyridin-3-yl)methyl]piperazin-1-yl}carbonyl)-1,3-oxazol-2-yl]methyl}-N-cyclopropyl-4-methoxy-2,6-dimethylbenzenesulfonamide Ex 253

To a stirred solution of N-cyclopropyl-4-methoxy-2,6-dimethyl-N-{[4-(piperazin-1-ylcarbonyl)-1,3-oxazol-2-yl]methyl}benzenesulfonamide (30 mg, 0.07 mmol) in DCE (2 mL) were added 2-amino-3-pyridinecarboxaldehyde (10 mg, 0.08 mmol) and AcOH (3 μL, 0.07 mmol) and the reaction mixture was stirred for 1 h at ambient temperature. STAB (20 mg, 0.09 mmol) was added and the reaction was stirred for 16 h. The reaction mixture was quenched with H$_2$O (2 mL) and extracted with DCM (3×2 mL). The organic layer was dried over Na$_2$SO$_4$ and concentrated in vacuo. The resulting residue was purified using prep method D to afford the title compound.

Yield: 4.2 mg, 11%

LCMS method C: rt 3.21 min, 100%; m/z 555.36 (MH$^+$, 100%).

$^1$H NMR (500 MHz, CDCl$_3$) δ ppm 8.16 (1H, s), 7.96 (1H, dd, J 5.3, 1.4 Hz), 7.29-7.37 (1H, m), 6.55-6.66 (3H, m), 6.12 (2H, br. s.), 4.64 (2H, s), 4.10 (2H, br. s.), 3.83 (3H, s), 3.76 (2H, br. s.), 3.51 (2H, s), 2.55-2.66 (7H, m), 2.50 (4H, br. s.), 0.45-0.56 (2H, m), 0.08-0.20 (2H, m)

Potency: C

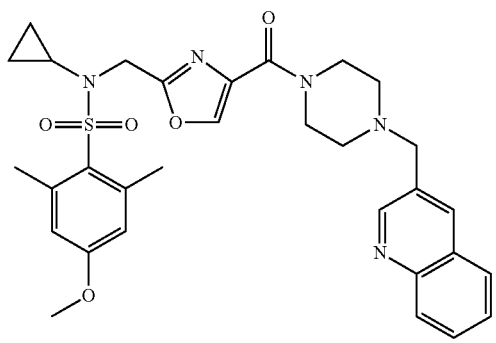 [SMILES: COc1cc(C)c(S(=O)(=O)N(Cc2nc(C(=O)N3CCN(Cc4cnc5ccccc5c4)CC3)co2)C2CC2)c(C)c1]

N-Cyclopropyl-4-methoxy-2,6-dimethyl-N-[(4-{[4-(quinolin-3-ylmethyl)piperazin-1-yl]carbonyl}-1,3-oxazol-2-yl)methyl]benzenesulfonamide Ex 254

To a stirred solution of N-cyclopropyl-4-methoxy-2,6-dimethyl-N-{[4-(piperazin-1-ylcarbonyl)-1,3-oxazol-2-yl]methyl}benzenesulfonamide (30 mg, 0.07 mmol) in DCE (2 mL) were added quinoline-3-carboxaldehyde (13 mg, 0.08 mmol) and AcOH (3 µL, 0.07 mmol) and the reaction mixture was stirred for 1 h at ambient temperature. STAB (20 mg, 0.09 mmol) was added and the reaction was stirred for 16 h. The reaction mixture was quenched with H$_2$O (2 mL) and extracted with DCM (3×2 mL). The organic layer was dried over Na$_2$SO$_4$ and concentrated in vacuo. The resulting residue was purified using prep method D to afford the title compound.

Yield: 9.3 mg, 24%

LCMS method C: rt 3.42 min, 96%; m/z 295.77 ([M+2H]$^{2+}$, 100%), 590.37 (MH$^+$, 40%).

Potency: C

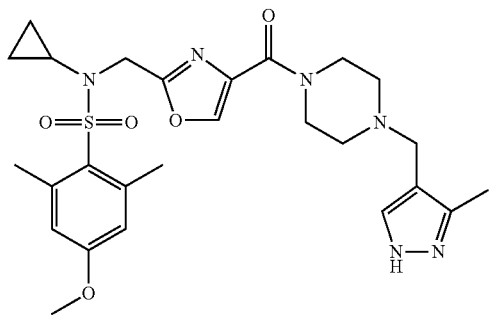 [SMILES: COc1cc(C)c(S(=O)(=O)N(Cc2nc(C(=O)N3CCN(Cc4c[nH]nc4C)CC3)co2)C2CC2)c(C)c1]

N-Cyclopropyl-4-methoxy-2,6-dimethyl-N-{[4-({4-[(3-methyl-1H-pyrazol-4-yl)methyl]piperazin-1-yl}carbonyl)-1,3-oxazol-2-yl]methyl}benzenesulfonamide Ex 255

To a stirred solution of N-cyclopropyl-4-methoxy-2,6-dimethyl-N-{[4-(piperazin-1-ylcarbonyl)-1,3-oxazol-2-yl]methyl}benzenesulfonamide (30 mg, 0.07 mmol) in DCE (2 mL) were added 3-methyl-1H-pyrazole-4-carboxaldehyde (9 mg, 0.08 mmol) and AcOH (3 µL, 0.07 mmol) and the reaction mixture was stirred for 1 h at ambient temperature. STAB (20 mg, 0.09 mmol) was added and the reaction was stirred for 16 h. The reaction mixture was quenched with H$_2$O (2 mL) and extracted with DCM (3×2 mL). The organic layer was dried over Na$_2$SO$_4$ and concentrated in vacuo. The resulting residue was purified using prep method D to afford the title compound.

Yield: 3.1 mg, 9%

LCMS method C: rt 3.13 min, 100%; m/z 543.33 (MH$^+$, 100%).

Potency: B

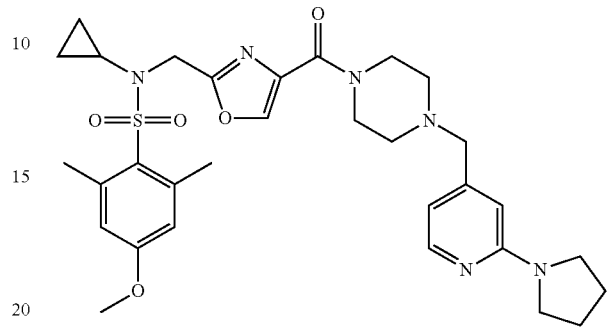

N-Cyclopropyl-4-methoxy-2,6-dimethyl-N-{[4-({4-[(2-pyrrolidin-1-ylpyridin-4-yl)methyl]piperazin-1-yl}carbonyl)-1,3-oxazol-2-yl]methyl}benzenesulfonamide Ex 256

To a stirred solution of N-cyclopropyl-4-methoxy-2,6-dimethyl-N-{[4-(piperazin-1-ylcarbonyl)-1,3-oxazol-2-yl]methyl}benzenesulfonamide (30 mg, 0.07 mmol) in DCE (2 mL) were added 2-pyrrolidin-1-ylisonicotinaldehyde (14 mg, 0.08 mmol) and AcOH (3 µL, 0.07 mmol) and the reaction mixture was stirred for 1 h at ambient temperature. STAB (20 mg, 0.09 mmol) was added and the reaction was stirred for 16 h. The reaction mixture was quenched with H$_2$O (2 mL) and extracted with DCM (3×2 mL). The organic layer was dried over Na$_2$SO$_4$ and concentrated in vacuo. The resulting residue was purified using prep method D to afford the title compound.

Yield: 4.2 mg, 10%

LCMS method C: rt 3.17 min, 99%; m/z 305.29 ([M+2H]$^{2+}$, 100%), 609.39 (MH$^+$, 20%).

Potency: A

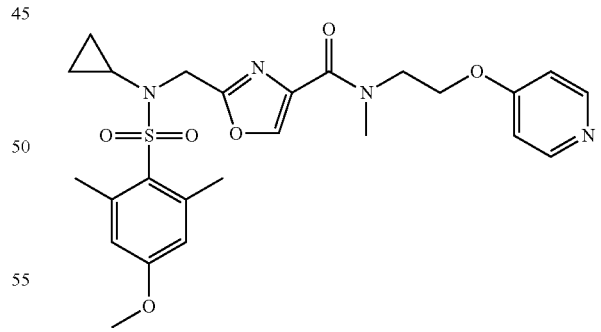

2-({Cyclopropyl[(4-methoxy-2,6-dimethylphenyl)sulfonyl]amino}methyl)-N-methyl-N-[2-(pyridin-4-yloxy)ethyl]-1,3-oxazole-4-carboxamide Ex 257

The title compound was prepared according to general procedure AH using 2-({cyclopropyl[(4-methoxy-2,6-dimethylphenyl)sulfonyl]amino}methyl)-1,3-oxazole-4-carboxylic acid (50 mg, 0.13 mmol), EDCI (50 mg, 0.26 mmol), HOBt monohydrate (40 mg, 0.26 mmol), DIPEA (90 µL, 0.52 mmol), N-methyl-2-(pyridin-4-yloxy)ethanamine (20 mg, 0.13 mmol) and DMF (1 mL). The resulting crude compound was purified using prep method D.

Yield: 4.8 mg, 7%.

LCMS method C: rt 3.21 min, 92%; m/z 515.31 (MH⁺, 100%).

Potency: A

Oxazole Synthesis

Scheme 9 describes the synthesis of an oxazole regioisomer (R1=cyclopropyl; $R^{1a}$=$R^{1b}$=H; $X^1$=O; $X^2$=CH; $X^3$=N)

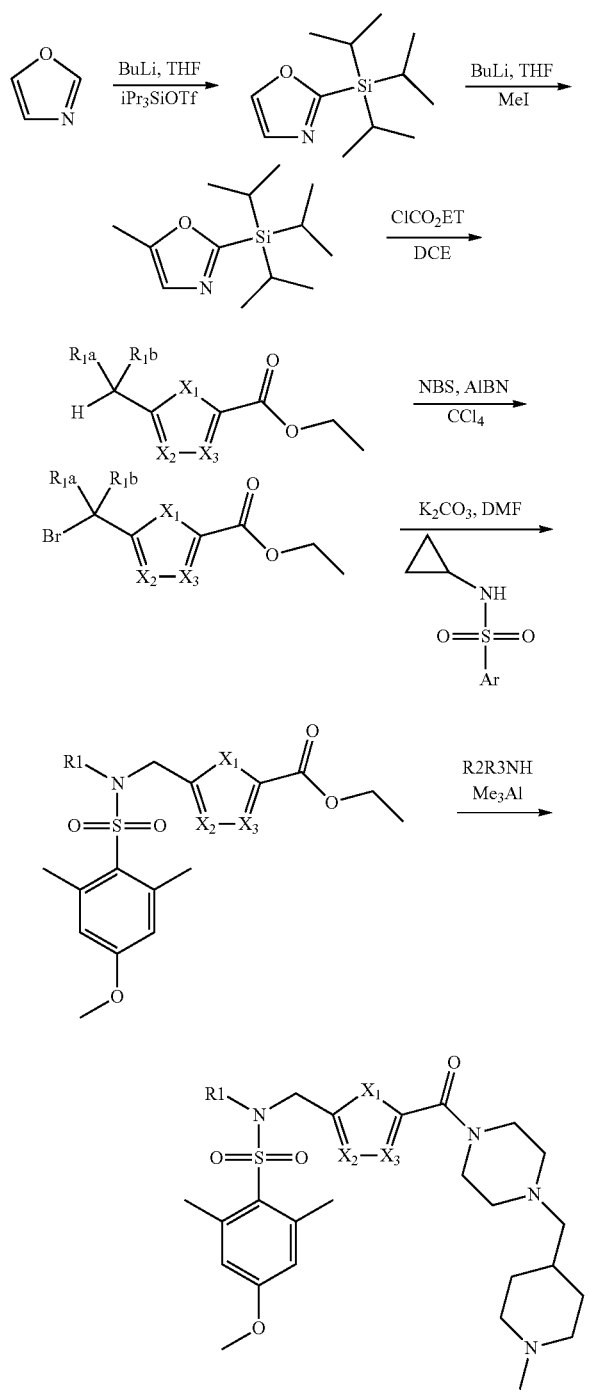

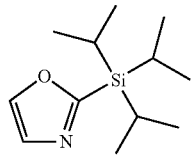

2-[Tris(1-methylethyl)silyl]-1,3-oxazole

Int 257

To a stirred solution of oxazole (0.2 g, 2.90 mmol), in THF (4 mL) at −10° C. under $N_2$ was added dropwise a solution of n-butyl lithium (1.6 M in THF, 1.99 mL). The mixture was stirred at −10° C. for 10 min prior to dropwise addition of triisopropylsilyl-trifluoromethanesulfonate (0.86 mL, 3.19 mmol) at −10° C. When the addition was complete, the flask and its contents were allowed to warm to ambient temperature and the reaction stirred for 1 h. The reaction mixture was quenched by dropwise addition of saturated aqueous NH₄Cl and extracted with EtOAc. The organic extract was dried over MgSO₄ and concentrated in vacuo to afford the title compound as a brown liquid. No further purification was required.

Yield: 0.665 g

Yield: assumed to be quantitative

LCMS Method B: rt 2.80 min, 100%; m/z 226.10 (MH⁺, 100%).

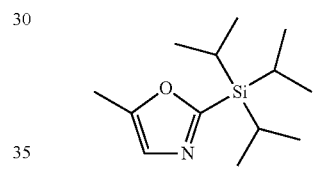

5-Methyl-2-[tris(1-methylethyl)silyl]-1,3-oxazole

Int 258

To a stirred solution of 2-[tris(1-methylethyl)silyl]-1,3-oxazole (3.0 g, 13 mmol), in THF (60 mL) at −30° C. under $N_2$ was added dropwise a solution of n-butyl lithium (1.6 M in THF, 9.15 mL). The mixture was stirred at −30° C. for 15 min prior to dropwise addition of methyliodide (0.91 mL, 15 mmol) at −30° C. Subsequent additions of n-butyl lithium (1.6 M in THF, 5 mL) and methyl iodide (0.5 mL) at −30° C. were needed to bring the reaction to 86% completion by LCMS. The reaction mixture was quenched by dropwise addition of 2M K₂CO₃ and extracted with EtOAc. The organic extract was dried over MgSO₄, and concentrated in vacuo. The residue was purified by FCC eluting with 2.5-5% EtOAc in heptane. This afforded the title compound as a colourless oil.

Yield: 2.14 g, 67%.

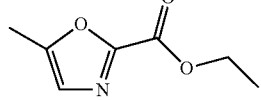

Ethyl 5-methyl-1,3-oxazole-2-carboxylate

Int 259

To a stirred solution of 5-methyl-2-[tris(1-methylethyl)silyl]-1,3-oxazole (1.6 g, 6.68 mmol), in toluene (16 mL) under $N_2$ was added dropwise ethyl chloroformate (12.78 mL, 0.133 mol). The mixture was stirred in a sealed vessel at 100° C. for 5 h. The reaction mixture was quenched by addition of saturated aqueous NaHCO₃ and extracted with EtOAc. The organic extract was dried over MgSO₄, and concentrated in vacuo. The residue was purified by FCC eluting with 20-30% EtOAc in heptane. This afforded the title compound as a colourless oil.

Yield: 0.126 g, 12%.

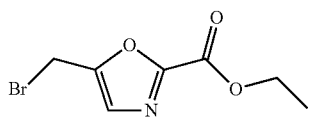

Ethyl 5-(bromomethyl)-1,3-oxazole-2-carboxylate

Int 260

To a stirred solution of ethyl 5-methyl-1,3-oxazole-2-carboxylate (0.05 g, 0.32 mmol), in carbon tetrachloride (5 mL) under N₂ was added NBS (0.063 g, 0.35 mmol) and AIBN (0.006 g, 0.04 mmol). The mixture was stirred in the dark at 70° C. for 2.5 h. The reaction mixture was filtered then washed with saturated aqueous NaHCO₃ and extracted with DCM. The organic extract was dried over MgSO₄, and concentrated in vacuo to afford the product as an orange oil. No further purification was required.

Yield: 0.086 g, 100%.

LCMS Method A: rt 1.10 min, 76%; m/z 235.80 (MH⁺, 100%).

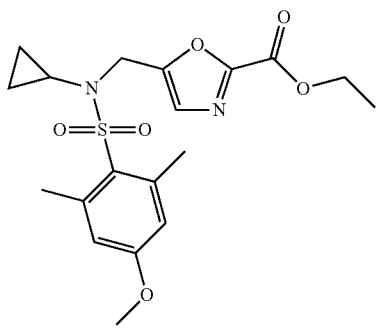 [SMILES: CCOC(=O)c1ncc(CN(C2CC2)S(=O)(=O)c2c(C)cc(OC)cc2C)o1]

Ethyl 5-({[(4-methoxy-2,6-dimethylphenyl)sulfonyl](cyclopropyl)amino}methyl)-1,3-oxazole-2-carboxylate Int 261

To a stirred solution of N-cyclopropyl-4-methoxy-2,6-dimethylbenzenesulfonamide (0.150 g, 0.59 mmol) in DMF (2 mL) was added K₂CO₃ (0.162 g, 1.18 mmol) followed by ethyl 5-(bromomethyl)-1,3-oxazole-2-carboxylate (0.137 g, 0.59 mmol). The mixture was stirred at 50° C. overnight. The reaction mixture was washed with water and extracted with DCM. The organic extract was dried over MgSO₄, and concentrated in vacuo. The residue was purified by FCC eluting with 10-30% EtOAc in heptane. This afforded the title compound as a colourless oil.

Yield: 0.027 g, 11%

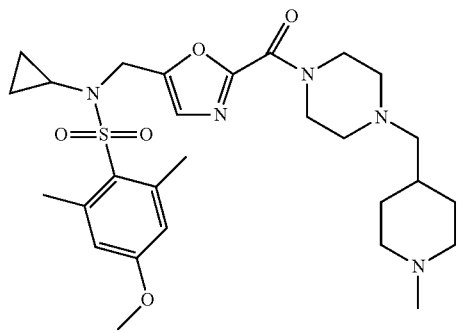 [SMILES: COc1cc(C)c(S(=O)(=O)N(Cc2cnc(C(=O)N3CCN(CC4CCN(C)CC4)CC3)o2)C2CC2)c(C)c1]

N-Cyclopropyl-4-methoxy-2,6-dimethyl-N-{[2-({4-[(1-methylpiperidin-4-yl)methyl]piperazin-1-yl}carbonyl)-1,3-oxazol-5-yl]methyl}benzenesulfonamide Ex 245

To a stirred solution of ethyl 5-({[(4-methoxy-2,6-dimethylphenyl)sulfonyl](cyclopropyl)amino}methyl)-1,3-oxazole-2-carboxylate (25 mg, 0.07 mmol) and 1-(N-methylpiperidin-4-yl-methyl)piperazine (26 mg, 0.13 mmol) in DCE (1 mL) was added trimethylaluminium 2M in toluene (65 μL, 0.13 mmol) and the mixture stirred at 60° C. for 1.5 h. The reaction mixture was washed with saturated aqueous NaHCO₃ and extracted with DCM. The organic extract was dried over MgSO₄, and concentrated in vacuo. The residue was purified by FCC eluting with 95:4.5:0.5 NH₃/MeOH/DCM. This afforded the title compound as a colourless oil.

Yield: δ 13.4 mg, 36%

LCMS Method C: rt 2.78 min, 99%; m/z 560.41 (MH⁺, 100%).

1H NMR (500 MHz, CDCl₃) δ ppm 7.27 (1H, s), 6.63 (2H, s), 4.63 (2H, s), 4.15 (2H, br. s.), 3.83 (3H, s), 3.78 (2H, br. s.), 2.90 (2H, d, J=10.7 Hz), 2.58 (6H, s), 2.42-2.53 (4H, m), 2.30 (3H, s), 2.22 (2H, d, J=7.0 Hz), 1.96 (3H, t, J=11.1 Hz), 1.76 (2H, d), 1.41-1.58 (1H, m), 1.31 (2H, q), 0.56 (2H, d, J=6.0 Hz), 0.18 (2H, br. s.)

Potency: A

Oxadiazole Synthesis

Scheme 10 describes the general synthesis of oxadiazole derivatives.

(R¹=Me, cyclopropyl; R¹ᵃ=R¹ᵇ=H; X¹=O; X²=X³=N; NR²R³=various amines)

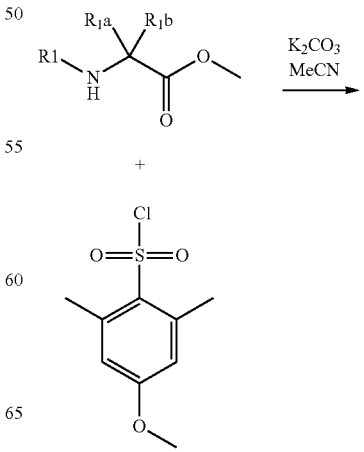

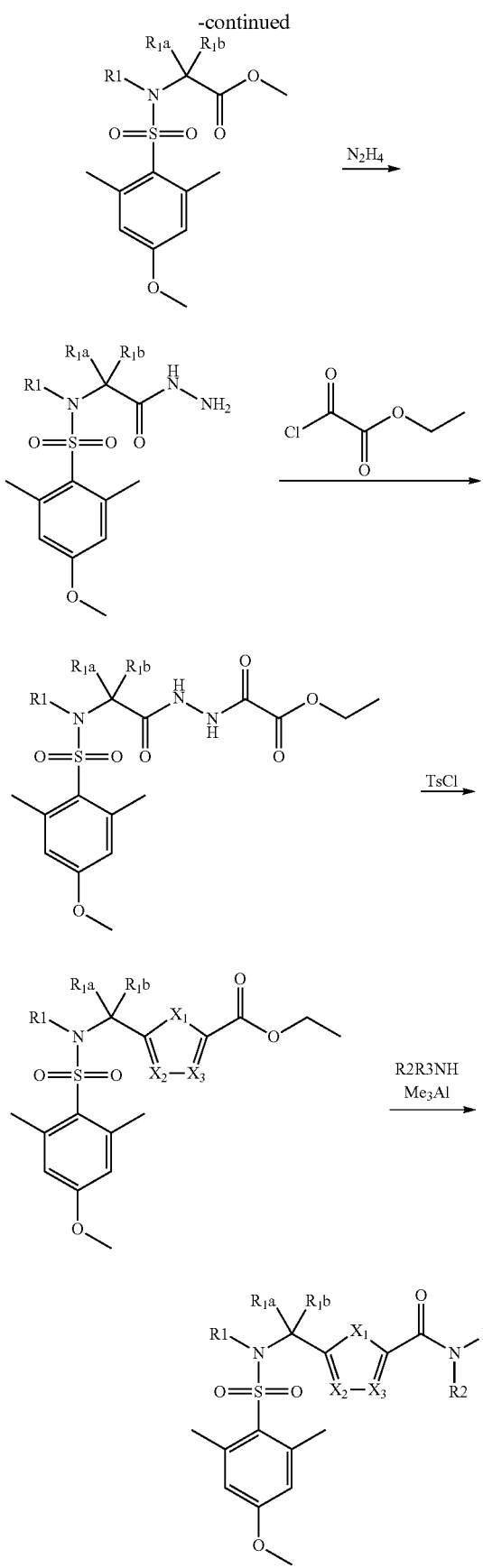

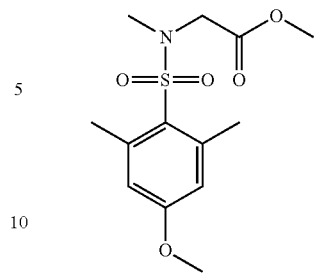

Methyl N-[(4-methoxy-2,6-dimethylphenyl)sulfonyl]-N-methylglycinate

Int 276

4-methoxy-2,6-dimethylbenzenesulfonyl chloride (7.8 g, 33 mmol), methyl N-methylglycinate hydrochloride (4.6 g, 333 mmol) and K$_2$CO$_3$ (9.1 g, 66 mmol) were stirred in MeCN (250 mL) at ambient temperature. After 1 h, the reaction was filtered and diluted with DCM (250 mL) and washed with aqueous HCl (1M, 2×250 mL), saturated aqueous NaHCO$_3$ (2×250 mL), dried over MgSO$_4$ and concentrated in vacuo. The crude product was purified by FCC, eluting with 1-2% MeCN in DCM to afford the title compound.

Yield: 5.7 g, 57%.

1H NMR (500 MHz, CDCl$_3$) δ ppm 6.65 (2H, s), 3.98 (2H, s), 3.82 (3H, s), 3.72 (3H, s), 2.81 (3H, s), 2.63 (6H, s).

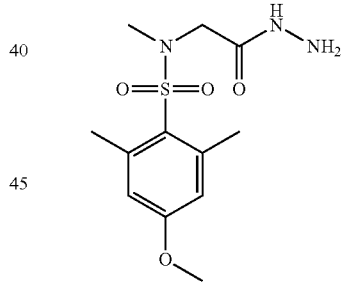

N-(2-Hydrazino-2-oxoethyl)-4-methoxy-N,2,6-trimethylbenzenesulfonamide

Int 277 methyl N-[(4-methoxy-2,6-dimethylphenyl)sulfonyl]-N-methylglycinate (2.4 g, 8 mmol) and hydrazine hydrate (1 mL, 20 mmol) were stirred in EtOH (5 mL) at 80° C. in a sealed tube. After 2.5 h the reaction was cooled to ambient temperature and the white solid collected by filtration. The crude product was recrystallised from MeOH to afford the title compound as white crystals.

Yield: 2.16 g, 89%

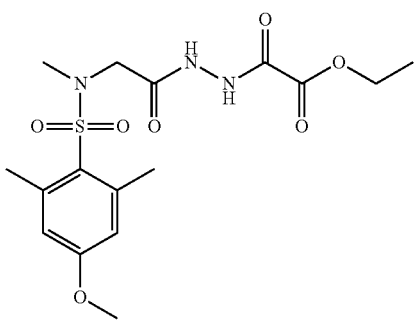 [SMILES: CCOC(=O)C(=O)NNC(=O)CN(C)S(=O)(=O)c1c(C)cc(OC)cc1C]

Ethyl[2-({[(4-methoxy-2,6-dimethylphenyl)sulfonyl](methyl)amino}acetyl)hydrazino](oxo)acetate Int 278

N-(2-hydrazino-2-oxoethyl)-4-methoxy-N,2,6-trimethylbenzenesulfonamide (2.16 g, 7.2 mmol) and TEA (1.5 mL, 10.8 mmol) were stirred in THF (25 mL) at 0-5° C. prior to dropwise addition of ethyl chloro(oxo)acetate (1.2 mL, 10.8 mmol). When addition was complete the reaction was warmed to ambient temperature and stirred for 16 h. The reaction was diluted with EtOAc (50 mL) and washed with saturated aqueous NaHCO$_3$ (50 mL). The aqueous phase was re-extracted with EtOAc (50 mL) and the combined organic extracts dried over MgSO$_4$ and concentrated in vacuo. The resultant crude product was used without any further purification.

$^1$H NMR (500 MHz, CDCl$_3$) δ ppm 8.93-9.33 (2H, m), 6.68 (2H, s), 4.30-4.45 (2H, m), 3.97 (2H, s), 3.84 (3H, s), 2.89 (3H, s), 2.63 (6H, s), 1.33-1.45 (3H, m)

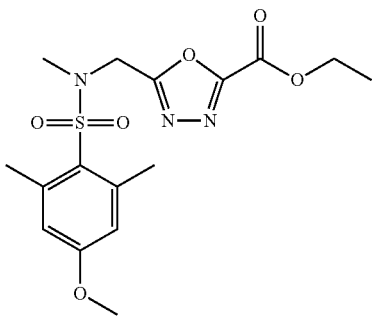 [SMILES: CCOC(=O)c1nnc(CN(C)S(=O)(=O)c2c(C)cc(OC)cc2C)o1]

Ethyl 5-({[(4-methoxy-2,6-dimethylphenyl)sulfonyl](methyl)amino}methyl)-1,3,4-oxadiazole-2-carboxylate Int 279 ethyl[2-({[(4-methoxy-2,6-dimethylphenyl)sulfonyl](methyl)amino}acetyl)hydrazino](oxo)acetate (2.89 g, 7.2 mmol) and TEA (3.0 mL, 21.6 mmol) were stirred in DCM (50 mL) at 0-5° C. prior to dropwise addition of a solution of TsCl (2.33 g, 12.2 mmol) in DCM (10 mL). When the addition was complete, the reaction was stirred at ambient temperature for 3 h and then filtered. The resultant white solid was recrystallised from IPA to afford the title compound as white crystals.

Yield: 1.53 g, 55%.

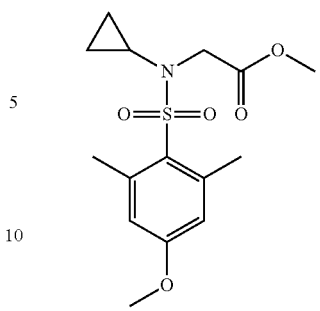

Methyl {cyclopropyl[(4-methoxy-2,6-dimethylphenyl)sulfonyl]amino}acetate

Int 280

NaH (60%, 610 mg 15.25 mmol) was stirred in anhydrous DMF (30 mL) at 0° C. and NaI (2.0 g) and N-cyclopropyl-4-methoxy-2,6-dimethylbenzenesulfonamide (3.0 g, 11.76 mmol) were added. After 20 min methyl chloroacetate (1.24 mL, 14.15 mmol) was added dropwise to the reaction mixture and the resulting solution was stirred and allowed to warm to ambient temperature over 18 h. The reaction mixture was then diluted with water (30 mL) and extracted with DCM (4×30 mL) and the combined organics were dried over MgSO$_4$ and concentrated in vacuo to afford the title compound as an orange oil, which was used without further purification.

Yield: 4.12 g.

$^1$H NMR (500 MHz, CDCl$_3$): δ ppm 6.64 (2H, s), 4.16 (2H, s), 3.84 (3H, s), 3.78 (3H, s), 2.82 (1H, tt, J 6.9, 3.6 Hz), 2.62 (6H, s), 0.51-0.56 (2H, m), 0.23-0.30 (2H, m)

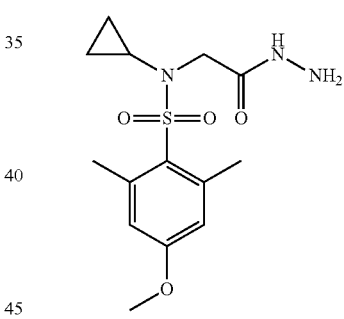

N-Cyclopropyl-N-(2-hydrazinyl-2-oxoethyl)-4-methoxy-2,6-dimethylbenzenesulfonamide Int 281 methyl {cyclopropyl[(4-methoxy-2,6-dimethylphenyl)sulfonyl]amino}acetate (11.76 mmol) was stirred in EtOH (10 mL) and hydrazine hydrate (0.73 mL, 15.02 mmol) was added. The reaction mixture heated to 80° C. for 2 h, a further portion of hydrazine hydrate (0.73 mL, 15.02 mmol) was added and the reaction was heated to 80° C. for 1 h, then allowed to cool to ambient temperature and stirred for 18 h. A further portion of hydrazine hydrate (0.35 mL, 7.20 mmol) was added and the reaction was heated to 80° C. for 3 h, then allowed to cool to ambient temperature and stirred for 18 h. The reaction mixture was then concentrated in vacuo to afford the title compound as an orange oil and crystals, which was used without further purification.

Yield: 4.71 g.

$^1$H NMR (250 MHz, CD$_3$OD): δ ppm 6.75 (2H, s), 4.00 (2H, s), 3.84 (3H, s), 2.64-2.72 (1H, m), 2.59 (6H, s), 0.46-0.57 (2H, m), 0.22-0.31 (2H, m)

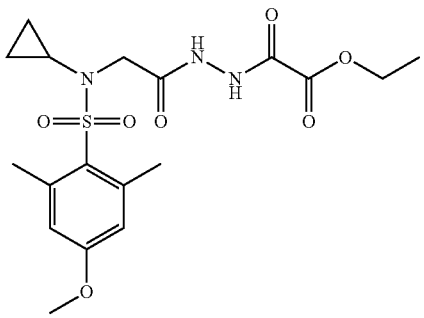 [SMILES: CCOC(=O)C(=O)NNC(=O)CN(C1CC1)S(=O)(=O)c1c(C)cc(OC)cc1C]

Ethyl[2-({cyclopropyl[(4-methoxy-2,6-dimethylphenyl)sulfonyl]amino}acetyl)hydrazino](oxo)acetate Int 282

N-cyclopropyl-N-(2-hydrazinyl-2-oxoethyl)-4-methoxy-2,6-dimethylbenzenesulfonamide (11.76 mmol) was stirred in DCM (30 mL) at 0° C. under N₂ and TEA (3.5 mL, 25.11 mmol) was added dropwise, followed by ethyl chloro(oxo)acetate (1.68 mL, 15.01 mmol). The reaction mixture stirred at ambient temperature for 2 h, a further portion of ethyl chloro(oxo)acetate (0.80 mL, 7.15 mmol) was added and the reaction was stirred at ambient temperature for a further 2 h. The reaction mixture was then partitioned between H₂O (50 mL) and DCM (4×50 mL) and the combined organic extracts were dried over MgSO₄ and concentrated in vacuo. The crude product was purified using FCC, eluting with 20% EtOAc in heptane, to afford the title compound as an orange oil.

Yield: 3.2 g, 64%.

¹H NMR (500 MHz, CDCl₃): δ ppm 9.24 (2H, br. s.,), 6.68 (2H, s), 4.41 (2H, q, J=7.2 Hz), 4.20 (2H, s), 4.14 (2H, q, J=7.2 Hz), 3.86 (3H, s), 2.74 (1H, dt, J 6.9, 3.3 Hz), 2.62 (6H, s), 1.42 (3H, t, J=7.2 Hz), 1.28 (3H, t, J=7.1 Hz), 0.58-0.63 (2H, m), 0.37-0.42 (2H, m)

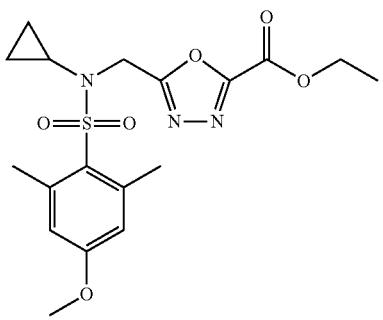

Ethyl 5-({cyclopropyl[(4-methoxy-2,6-dimethylphenyl)sulfonyl]amino}methyl)-1,3,4-oxadiazole-2-carboxylate Int 283

Ethyl[2-({cyclopropyl[(4-methoxy-2,6-dimethylphenyl)sulfonyl]amino}acetyl)hydrazino](oxo)acetate (2.2 g, 5.14 mmol) was stirred in DCM (30 mL) at 0° C. under N₂ and TEA (1.4 mL, 10.04 mmol) was added, followed by TsCl (1.2 g, 6.29 mmol). The reaction was stirred at ambient temperature for 3 h, then partitioned between H₂O (100 mL) and DCM (4×50 mL). The combined organic extracts were then dried over MgSO₄ and concentrated in vacuo. The crude product was then purified using FCC, eluting with 25% EtOAc in heptane to afford the title compound as a yellow solid.

Yield: 1.34 g, 64%.

¹H NMR (500 MHz, CDCl₃): δ ppm 6.64 (2H, s), 4.81 (2H, s), 4.52 (2H, q, J=7.2 Hz), 3.84 (3H, s), 2.67 (1H, dt, J 6.9, 3.3 Hz), 2.62 (6H, s), 1.47 (3H, t, J=7.2 Hz), 0.55-0.62 (2H, m), 0.19-0.26 (2H, m)

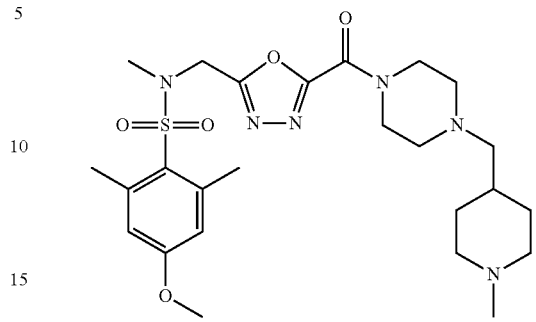

4-Methoxy-N,2,6-trimethyl-N-{[5-({4-[(1-methylpiperidin-4-yl)methyl]piperazin-1-yl}carbonyl)-1,3,4-oxadiazol-2-yl]methyl}benzenesulfonamide Ex 258

Ethyl 5-({[(4-methoxy-2,6-dimethylphenyl)sulfonyl](methyl)amino}methyl)-1,3,4-oxadiazole-2-carboxylate (1.0 g, 2.6 mmol) and 1-[(1-methylpiperidin-4-yl)methyl]piperazine (1.03 g, 5.2 mmol) were dissolved in DCE (5 mL) and stirred at 0° C. prior to degassing with N₂. Trimethylaluminium (2M in toluene, 2.6 mL) was added dropwise to this solution. Upon complete addition, the reaction was stirred for 1 h at 80° C. The reaction was cooled, diluted with DCM (30 mL) and washed with saturated aqueous NaHCO₃ (30 mL). The aqueous layer was extracted with DCM (2×30 mL) and the combined organic extracts dried over MgSO₄ and concentrated in vacuo. The resulting brown oil was purified by FCC, eluting with 98:2 DCM:7N NH₃ in MeOH to afford the title compound.

Yield: 1.29 g, 92%.

¹H NMR (500 MHz, CDCl₃): δ ppm 6.64 (2H, s), 4.60 (2H, s,), 3.96-4.14 (2H, m), 3.82 (3H, s), 3.74-3.80 (2H, m,), 2.88 (1H, br. s.), 2.86 (3H, s), 2.64 (6H, s), 2.49 (4H, t, J 4.3 Hz,), 2.28 (3H s,), 2.23 (2H, d, J=7.2 Hz), 1.93 (2H, t, J=11.5 Hz), 1.76 (2H, d, J=13.1 Hz), 1.21-1.52 ppm (4H, m).

LCMS method C: rt 2.52 min, 99%; m/z 535.20 (MH⁺, 100%).

Potency: C

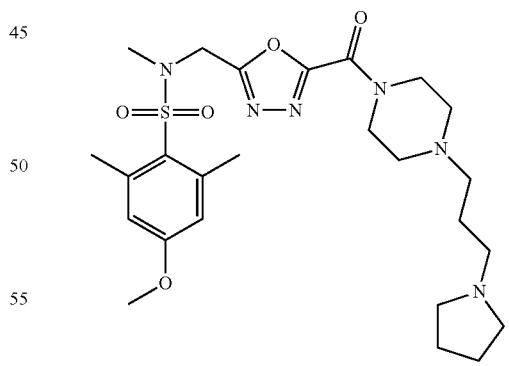

General Procedure BK

4-Methoxy-N,2,6-trimethyl-N-[(5-{[4-(3-pyrrolidin-1-ylpropyl)piperazin-1-yl]carbonyl}-1,3,4-oxadiazol-2-yl)methyl]benzenesulfonamide Ex 259

1-(3-Pyrrolidin-1-ylpropyl)piperazine (128 mg, 1.65 mmol) was dissolved in THF (5 mL) and the resulting solution was cooled to −40° C. prior to the addition of trimethylaluminium (2 M in toluene, 0.59 mL). The reaction was stirred for 15 min at −40° C. and a solution of methyl 5-({[(4-methoxy-2,6-dimethylphenyl)sulfonyl](methyl)amino}methyl)-1,3,4-oxadiazole-2-carboxylate (200 mg, 0.54 mmol) in THF (5 mL) was added dropwise. The reaction was stirred at ambient temperature for 18 h and MeOH (5 mL) was added. The solvents were removed in vacuo and the resulting residue was purified by FCC, eluting with 0-2% MeOH in DCM to afford the title compound as a pale yellow semi solid.

Yield: 80 mg, 29%.

LCMS method C: rt 2.55 min, 100%; m/z 535.85 (MH+, 100%).

Potency: B

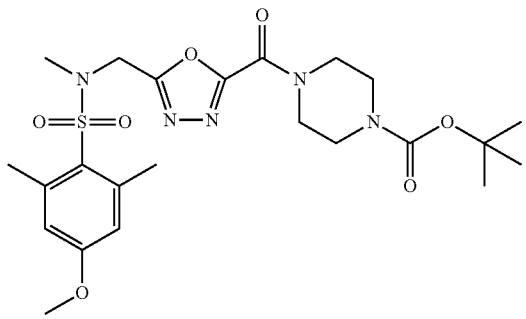 [SMILES: COc1cc(C)c(S(=O)(=O)N(C)Cc2nnc(C(=O)N3CCN(C(=O)OC(C)(C)C)CC3)o2)c(C)c1]

tert-Butyl 4-{[5-({[(4-methoxy-2,6-dimethylphenyl)sulfonyl](methyl)amino}methyl)-1,3,4-oxadiazol-2-yl]carbonyl}piperazine-1-carboxylate Int 284

The title compound was prepared according to general procedure CE using ethyl 5-({[(4-methoxy-2,6-dimethylphenyl)sulfonyl](methyl)amino}methyl)-1,3,4-oxadiazole-2-carboxylate (0.42 g, 1.1 mmol), tert-butyl piperazine-1-carboxylate (0.41 g, 2.2 mmol), DCE (2.0 mL) and trimethylaluminium (2.0 M in toluene, 1.1 mL). The crude product was triturated with heptane and recrystallised from IPA/Et$_2$O/heptane to afford the title compound as white crystals.

Yield: 0.47 g, 82%

$^1$H NMR (500 MHz, CDCL$_3$) δ ppm 6.65 (2H, s), 4.62 (2H, s), 4.09 (2H, br. s.), 3.83 (3H, s), 3.78 (2H, br. s.), 3.40-3.47 (2H, m), 3.18-3.28 (2H, m), 2.87 (3H, s), 2.65 (6H, s), 1.49 (9H, s).

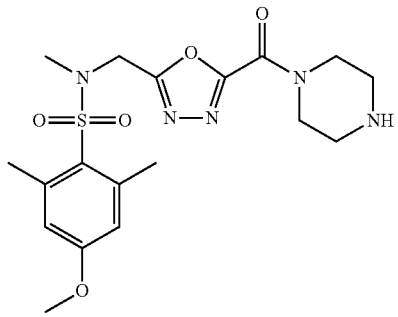 [SMILES: COc1cc(C)c(S(=O)(=O)N(C)Cc2nnc(C(=O)N3CCNCC3)o2)c(C)c1]

4-Methoxy-N,2,6-trimethyl-N-{[5-(piperazin-1-ylcarbonyl)-1,3,4-oxadiazol-2-yl]methyl}benzenesulfonamide Int 285

The title compound was prepared according to general procedure AN using tert-butyl 4-{[5-({[(4-methoxy-2,6-dimethylphenyl)sulfonyl](methyl)amino}methyl)-1,3,4-oxadiazol-2-yl]carbonyl}piperazine-1-carboxylate (0.46 g, 0.88 mmol), TFA (2.5 mL) and DCM (7.5 mL). The crude product was redissolved in DCM (20 mL) and washed with saturated aqueous NaHCO$_3$ (10 mL) and saturated brine (5 mL). The aqueous washes were re-extracted with DCM (5 mL) and the combined organic phases dried over Na$_2$SO$_4$. The solvent was removed in vacuo to afford the title compound.

Yield: 0.40 g, 100%.

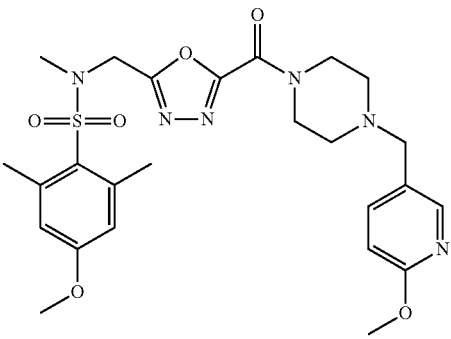 [SMILES: COc1cc(C)c(S(=O)(=O)N(C)Cc2nnc(C(=O)N3CCN(Cc4ccc(OC)nc4)CC3)o2)c(C)c1]

4-Methoxy-N-{[5-({4-[(6-methoxypyridin-3-yl)methyl]piperazin-1-yl}carbonyl)-1,3,4-oxadiazol-2-yl]methyl}-N,2,6-trimethylbenzenesulfonamide trifluoroacetate Ex 260

The title compound was prepared according to general procedure CD using 4-methoxy-N,2,6-trimethyl-N-{[5-(piperazin-1-ylcarbonyl)-1,3,4-oxadiazol-2-yl]methyl}benzenesulfonamide (28 mg, 0.066 mmol), 6-methoxypyridine-3-carbaldehyde (11 mg, 0.079 mmol), STAB (28 mg, 0.13 mmol), DCE (1 mL) and a few 4 Å molecular sieves. The crude product was purified using prep method A to afford the title compound.

Yield: 20 mg, 46%

LCMS method C: rt 3.21 min, 94%; m/z 545.35 (MH+, 100%).

$^1$H NMR (500 MHz, CD$_3$OD) δ ppm 8.25-8.34 (1H, m), 7.73-7.88 (1H, m), 6.88-6.96 (1H, m), 6.76 (2H, s), 4.69 (2H, s), 4.40 (2H, s), 3.95 (3H, s), 3.84 (3H, s), 3.46 (8H, br. s.), 2.86 (3H, s), 2.61 (6H, s)

Potency: B

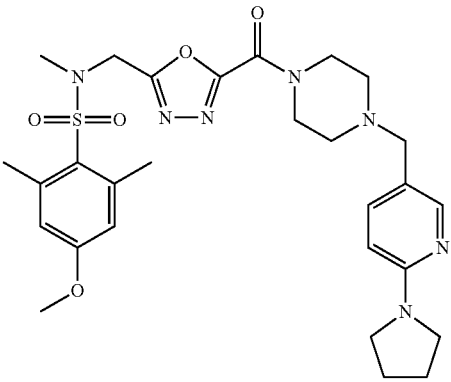 [SMILES: COc1cc(C)c(S(=O)(=O)N(C)Cc2nnc(C(=O)N3CCN(Cc4ccc(N5CCCC5)nc4)CC3)o2)c(C)c1]

4-Methoxy-N,2,6-trimethyl-N-{[5-({4-[(6-pyrrolidin-1-ylpyridin-3-yl)methyl]piperazin-1-yl}carbonyl)-1,3,4-oxadiazol-2-yl]methyl}benzenesulfonamide trifluoroacetate Ex 261

The title compound was prepared according to general procedure CD using 4-methoxy-N,2,6-trimethyl-N-{[5-(piperazin-1-ylcarbonyl)-1,3,4-oxadiazol-2-yl]methyl}benzenesulfonamide (28 mg, 0.066 mmol), 6-pyrrolidin-1-ylpyridine-3-carbaldehyde (14 mg, 0.079 mmol), STAB (28 mg, 0.13 mmol), DCE (1 mL) and a few 4 Å molecular sieves. The crude product was purified using prep method A to afford the title compound.

Yield: 20 mg, 43%

LCMS method C: rt 2.90 min, 99%; m/z 584.39 (MH$^+$, 100%).

$^1$H NMR (500 MHz, CD$_3$OD) δ ppm 7.96-8.08 (2H, m), 7.10-7.21 (1H, m), 6.75 (2H, s), 4.61-4.74 (2H, m), 4.39 (2H, br. s.), 4.22 (2H, s), 4.06 (2H, br. s.), 3.83 (3H, s), 3.62 (4H, br. s.), 2.86 (3H, s), 2.60 (6H, s), 2.06-2.25 (4H, m)

Potency: C

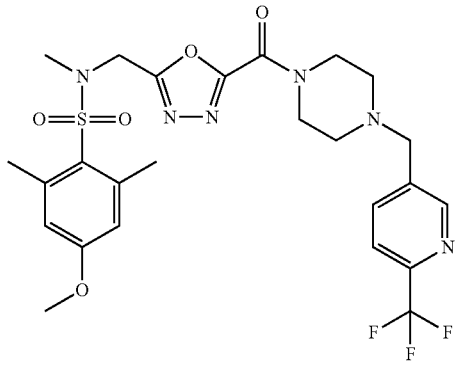 [SMILES: COc1cc(C)c(S(=O)(=O)N(C)Cc2nnc(C(=O)N3CCN(Cc4ccc(C(F)(F)F)nc4)CC3)o2)c(C)c1]

4-Methoxy-N,2,6-trimethyl-N-({5-[(4-{[6-(trifluoromethyl)pyridin-3-yl]methyl}piperazin-1-yl)carbonyl]-1,3,4-oxadiazol-2-yl}methyl)benzenesulfonamide trifluoroacetate Ex 262

The title compound was prepared according to general procedure CD using 4-methoxy-N,2,6-trimethyl-N-{[5-(piperazin-1-ylcarbonyl)-1,3,4-oxadiazol-2-yl]methyl}benzenesulfonamide (28 mg, 0.066 mmol), 6-(trifluoromethyl)pyridine-3-carbaldehyde (14 mg, 0.079 mmol), STAB (28 mg, 0.13 mmol), DCE (1 mL) and a few 4 Å molecular sieves. The crude product was purified using prep method A to afford the title compound.

Yield: 18 mg, 39%

LCMS method C: rt 3.84 min, 98%; m/z 583.32 (MH$^+$, 100%).

Potency: A

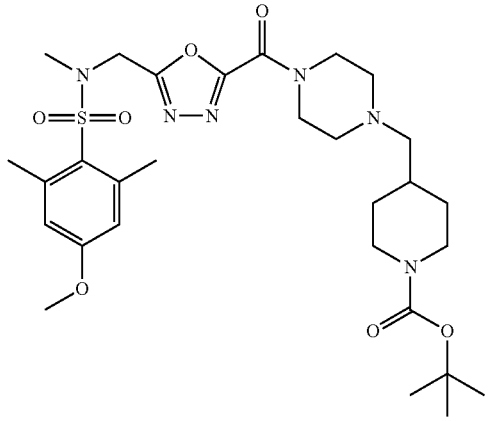 [SMILES: COc1cc(C)c(S(=O)(=O)N(C)Cc2nnc(C(=O)N3CCN(CC4CCN(C(=O)OC(C)(C)C)CC4)CC3)o2)c(C)c1]

tert-Butyl 4-[(4-{[5-({[(4-methoxy-2,6-dimethylphenyl)sulfonyl](methyl)amino}methyl)-1,3,4-oxadiazol-2-yl]carbonyl}piperazin-1-yl)methyl]piperidine-1-carboxylate Ex 263

4-Methoxy-N,2,6-trimethyl-N-{[5-(piperazin-1-ylcarbonyl)-1,3,4-oxadiazol-2-yl]methyl}benzenesulfonamide (0.2 g, 0.44 mmol) and tert-butyl 4-formylpiperidine-1-carboxylate (0.14 g, 0.66 mmol) were dissolved in DCE (4 mL) and a few 4 Å molecular sieves added. The reaction was stirred for 30 min at ambient temperature prior to addition of STAB (0.28 g, 1.3 mmol). The reaction was stirred for 18 h, diluted with MeOH (0.5 mL) and concentrated in vacuo. The residue was redissolved in DCM (5 mL) and filtered through Celite, washing with DCM. The DCM solution was treated with acetic anhydride (0.1 mL, 1.0 mmol) and stirred for 30 min at ambient temperature. The solvent was removed in vacuo and the residue redissolved in MeOH (2 mL) and the solution absorbed on to a 2 g SCX cartridge. The sorbent was washed with MeOH (10 mL) and the product eluted with 7 N NH$_3$ in MeOH (10 mL). The solvent was removed in vacuo to afford the title compound.

Yield: 280 mg, 100%.

LCMS method A: rt 1.23 min, 96%; m/z 521.20 ([M-Boc+H]$^+$, 100%), 643.25 (M+Na$^+$, 44%).

Potency: A

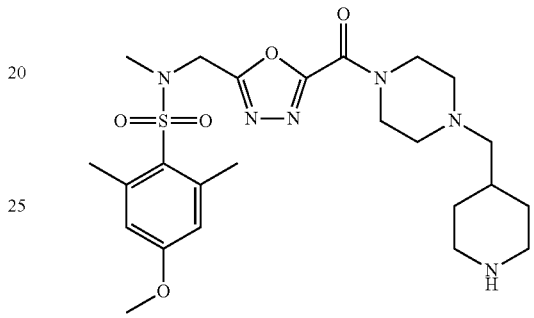

4-Methoxy-N,2,6-trimethyl-N-[(5-{[4-(piperidin-4-ylmethyl)piperazin-1-yl]carbonyl}-1,3,4-oxadiazol-2-yl)methyl]benzenesulfonamide Int 286

The title compound was prepared according to general procedure AN using tert-butyl 4-[(4-{[5-({[(4-methoxy-2,6-dimethylphenyl)sulfonyl](methyl)amino}methyl)-1,3,4-oxadiazol-2-yl]carbonyl}piperazin-1-yl)methyl]piperidine-1-carboxylate (0.28 g, 0.44 mmol), TFA (1.4 mL) and DCM (4.2 mL). The crude product was dissolved in MeOH (5 mL) and absorbed on to a 5 g SCX cartridge and the sorbent washed with MeOH (10 mL). The title compound was eluted with 7 N NH$_3$ in MeOH (10 mL) and the solvent removed in vacuo.

Yield: 0.15 g, 64%.

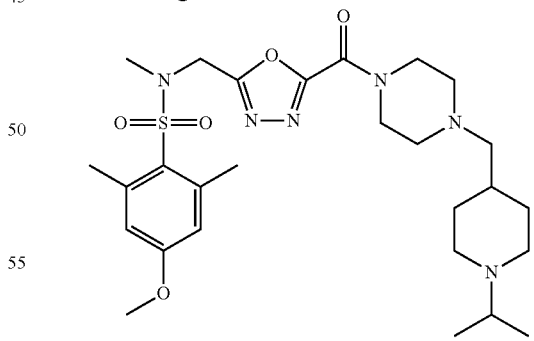

4-Methoxy-N,2,6-trimethyl-N-({5-[(4-{[1-(1-methylethyl)piperidin-4-yl]methyl}piperazin-1-yl)carbonyl]-1,3,4-oxadiazol-2-yl}methyl)benzenesulfonamide trifluoroacetate Ex 264

The title compound was prepared according to general procedure CD using 4-methoxy-N,2,6-trimethyl-N-[(5-{[4-

(piperidin-4-ylmethyl)piperazin-1-yl]carbonyl}-1,3,4-oxadiazol-2-yl)methyl]benzenesulfonamide (34 mg, 0.066 mmol), acetone (0.1 mL, 1.3 mmol), STAB (42 mg, 0.2 mmol) DCE (1 mL) and a few 4 Å molecular sieves. The crude product was purified using prep method A to afford the title compound.

LCMS method C: rt 2.67 min, 88%; m/z 563.46 (MH$^+$, 100%).

Potency: A

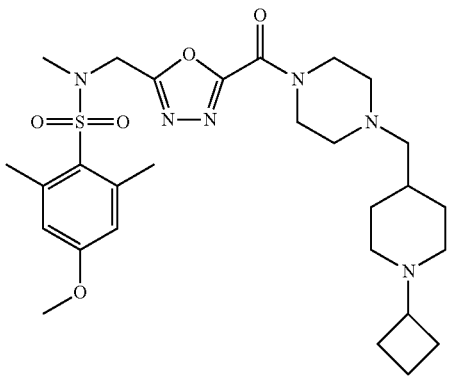 [SMILES: COc1cc(C)c(S(=O)(=O)N(C)Cc2nnc(C(=O)N3CCN(CC4CCN(C5CCC5)CC4)CC3)o2)c(C)c1]

N-{[5-({4-[(1-Cyclobutylpiperidin-4-yl)methyl]piperazin-1-yl}carbonyl)-1,3,4-oxadiazol-2-yl]methyl}-4-methoxy-N,2,6-trimethylbenzenesulfonamide trifluoroacetate Ex 265

The title compound was prepared according to general procedure CD using 4-methoxy-N,2,6-trimethyl-N-[(5-{[4-(piperidin-4-ylmethyl)piperazin-1-yl]carbonyl}-1,3,4-oxadiazol-2-yl)methyl]benzenesulfonamide (34 mg, 0.066 mmol), cyclobutanone (0.01 mL, 0.13 mmol), STAB (42 mg, 0.2 mmol) DCE (1 mL) and a few 4 Å molecular sieves. The crude product was purified using prep method A to afford the title compound.

LCMS method C: rt 2.71 min, 94%; m/z 575.45 (MH$^+$, 100%).

Potency: A

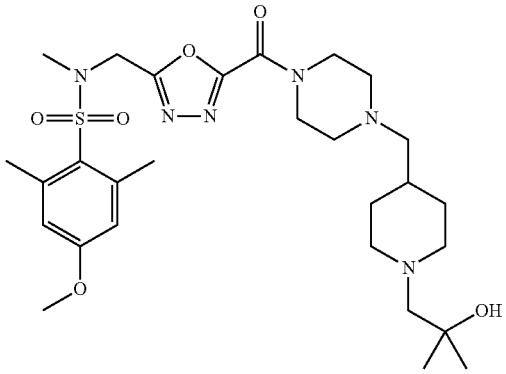 [SMILES: COc1cc(C)c(S(=O)(=O)N(C)Cc2nnc(C(=O)N3CCN(CC4CCN(CC(C)(C)O)CC4)CC3)o2)c(C)c1]

N-({5-[(4-{[1-(2-Hydroxy-2-methylpropyl)piperidin-4-yl]methyl}piperazin-1-yl)carbonyl]-1,3,4-oxadiazol-2-yl}methyl)-4-methoxy-N,2,6-trimethylbenzenesulfonamide Ex 266

4-methoxy-N,2,6-trimethyl-N-[(5-{[4-(piperidin-4-ylmethyl)piperazin-1-yl]carbonyl}-1,3,4-oxadiazol-2-yl)methyl]benzenesulfonamide (34 mg, 0.066 mmol) and 2,2-dimethyloxirane (1 mL, 13.8 mmol) were dissolved in DMF (1 mL) and the reaction heated to 70° C. in a sealed tube for 6 h. The reaction was cooled and concentrated in vacuo and the crude product purified using prep method B to afford the title compound.

LCMS method C: rt 2.58 min, 93%; m/z 593.46 (MH$^+$, 100%).

$^1$H NMR (500 MHz, CD$_3$OD) δ ppm 6.71 (2H, s), 4.63 (2H, s), 3.87-3.98 (2H, m), 3.80 (3H, s), 3.69-3.77 (2H, m), 2.90-3.02 (2H, m), 2.85 (3H, s), 2.57 (6H, s), 2.44-2.51 (4H, m), 2.26-2.35 (2H, m), 2.13-2.25 (3H, m), 2.00 (2H, s), 1.62-1.76 (2H, m), 1.53 (1H, br. s.), 1.19-1.32 (2H, m), 1.15 (6H, s)

Potency: A

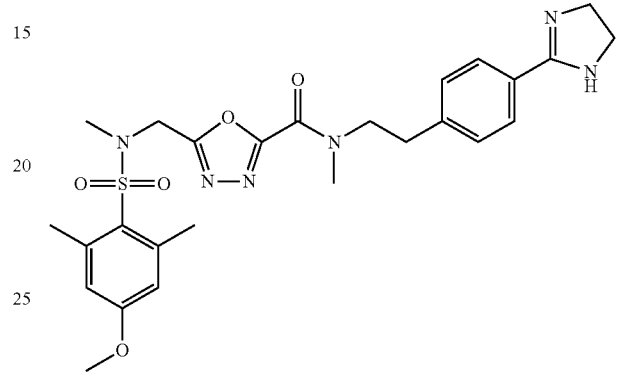

N-{2-[4-(4,5-Dihydro-1H-imidazol-2-yl)phenyl]ethyl}-5-({[(4-methoxy-2,6-dimethylphenyl)sulfonyl](methyl)amino}methyl)-N-methyl-1,3,4-oxadiazole-2-carboxamide Ex 267

The title compound was prepared according to general procedure AT using methyl 5-({[(4-methoxy-2,6-dimethylphenyl)sulfonyl](methyl)amino}methyl)-1,3,4-oxadiazole-2-carboxylate (50 mg, 0.135 mmol), 2-[4-(4,5-dihydro-1H-imidazol-2-yl)phenyl]-N-methylethanamine (110 mg, 0.54 mmol) and trimethylaluminium (2 M in toluene, 0.27 mL) in DCM (10 mL). A portion of the crude product was purified using prep method A, then prep method B.

LCMS Method C: rt 3.16 min, 100%; m/z 542.17 (MH$^+$, 100%)

Potency: C

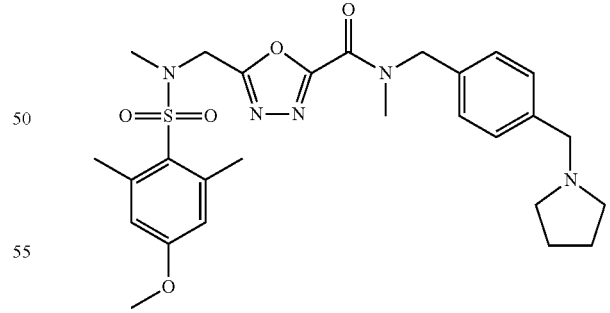

5-({[(4-Methoxy-2,6-dimethylphenyl)sulfonyl](methyl)amino}methyl)-N-methyl-N-[4-(pyrrolidin-1-ylmethyl)benzyl]-1,3,4-oxadiazole-2-carboxamide trifluoroacetate Ex 268

The title compound was prepared according to general procedure AT using methyl 5-({[(4-methoxy-2,6-dimethylphenyl)sulfonyl](methyl)amino}methyl)-1,3,4-oxadiazole-2-carboxylate (50 mg, 0.135 mmol), N-methyl 1-[4(pyrrolidinylmethyl)phenyl]methanamine (110 mg, 0.54 mmol) and trimethylaluminium (2 M in toluene, 0.27 mL) in DCM (10 mL). A portion of the crude product was purified using prep method A.

LCMS Method C: rt 3.21 min, 99%; m/z 542.23 (MH$^+$, 100%)

Potency: B

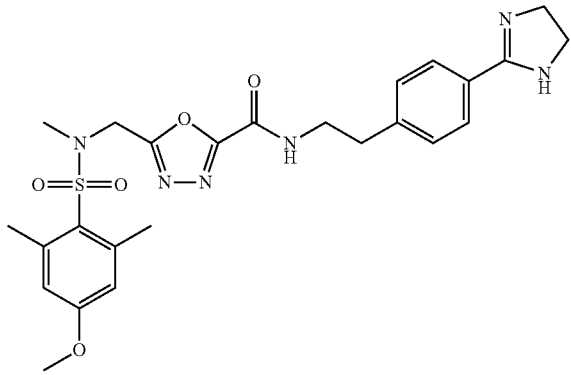

N-{2-[4-(4,5-Dihydro-1H-imidazol-2-yl)phenyl]ethyl}-5-({[(4-methoxy-2,6-dimethylphenyl)sulfonyl](methyl)amino}methyl)-1,3,4-oxadiazole-2-carboxamide trifluoroacetate Ex 269

The title compound was prepared according to general procedure AT using methyl 5-({[(4-methoxy-2,6-dimethylphenyl)sulfonyl](methyl)amino}methyl)-1,3,4-oxadiazole-2-carboxylate (50 mg, 0.135 mmol), 1-[4-(4,5-dihydro-1H-imidazol-2-yl)phenyl]ethanamine (100 mg, 0.53 mmol) and trimethylaluminium (2 M in toluene, 0.27 mL) in DCM (5 mL). A portion of the crude product was purified using prep method A.

LCMS Method C: rt 3.06 min, 99%; m/z 527.18 (MH$^+$, 100%)

$^1$H NMR (500 MHz, CD$_3$OD) δ ppm 7.81 (2H, d, J=8.39 Hz) 7.58 (2H, d, J=8.24 Hz) 6.77 (2H, s) 4.68 (2H, s) 4.10 (4H, s) 3.85 (3H, s) 3.71 (2H, t, J=7.10 Hz) 3.08 (2H, t, J=7.10 Hz) 2.89 (3H, s) 2.61 (6H, s)

Potency: C

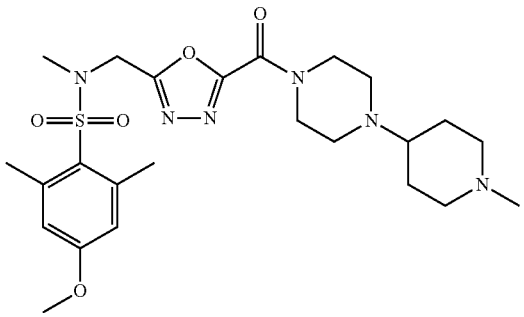

4-Methoxy-N,2,6-trimethyl-N-[(5-{[4-(1-methylpiperidin-4-yl)piperazin-1-yl]carbonyl}-1,3,4-oxadiazol-2-yl)methyl]benzenesulfonamide trifluoroacetamide Ex 270

The title compound was prepared according to general procedure AT using methyl 5-({[(4-methoxy-2,6-dimethylphenyl)sulfonyl](methyl)amino}methyl)-1,3,4-oxadiaz-ole-2-carboxylate (30 mg, 0.08 mmol), 1-(1-methylpiperidin-4-yl)piperazine (60 mg, 0.33 mmol) and trimethylaluminium (2 M in toluene, 0.16 mL) in DCM (5 mL). A portion of the product was purified using prep method C.

LCMS Method C: rt 2.59 min, 97%; m/z 521.19 (MH$^+$, 100%)

Potency: A

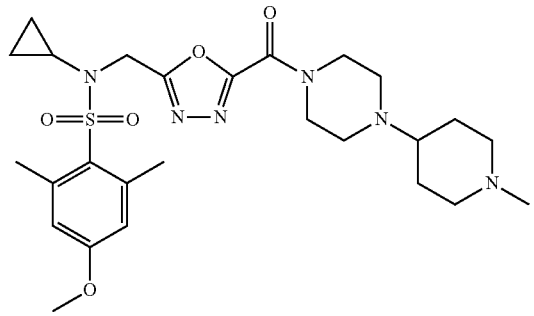 [SMILES: COc1cc(C)c(S(=O)(=O)N(Cc2nnc(C(=O)N3CCN(C4CCN(C)CC4)CC3)o2)C2CC2)c(C)c1]

N-Cyclopropyl-4-methoxy-2,6-dimethyl-N-[(5-{[4-(1-methylpiperidin-4-yl)piperazin-1-yl]carbonyl}-1,3,4-oxadiazol-2-yl)methyl]benzenesulfonamide Ex 271

The title compound was prepared according to general procedure AT using Ethyl 5-({cyclopropyl[(4-methoxy-2,6-dimethylphenyl)sulfonyl]amino}methyl)-1,3,4-oxadiazole-2-carboxylate (30 mg, 0.07 mmol), 1-(1-methylpiperidin-4-yl)piperazine (26 mg, 0.14 mmol) and trimethylaluminium (2 M in toluene, 0.07 mL) in DCE (5 mL). A portion of the crude product was purified using FCC, eluting with 95:4.5:0.5 DCM:MeOH:NH$_3$.

LCMS Method C: rt 2.78 min, 97%; m/z 547.21 (MH$^+$, 100%)

$^1$H NMR (500 MHz, CD$_3$OD): δ ppm 6.76 (2H, s), 4.84 (2H, s), 3.96-4.02 (2H, m), 3.85 (3H, s), 3.77-3.82 (2H, m), 2.95 (2H, d, J=12.1 Hz), 2.68-2.73 (4H, m), 2.64-2.68 (1H, m), 2.58 (6H, s), 2.32-2.40 (1H, m), 2.28 (3H, s), 2.08 (2H, t, J=11.1 Hz), 1.89 (2H, d, J=12.7 Hz), 1.59 (2H, qd, J 12.2, 3.6 Hz), 0.58-0.64 (2H, m), 0.25-0.31 (2H, m)

Potency: B

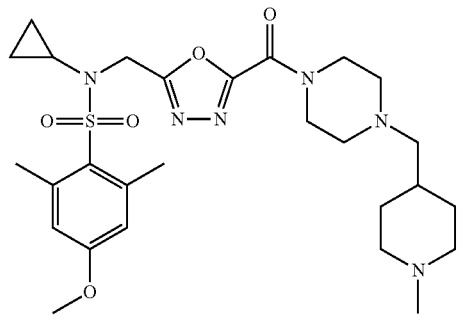 [SMILES: COc1cc(C)c(S(=O)(=O)N(Cc2nnc(C(=O)N3CCN(CC4CCN(C)CC4)CC3)o2)C2CC2)c(C)c1]

N-Cyclopropyl-4-methoxy-2,6-dimethyl-N-{[5-({4-[(1-methylpiperidin-4-yl)methyl]piperazin-1-yl}carbonyl)-1,3,4-oxadiazol-2-yl]methyl}benzenesulfonamide Ex 272

The title compound was prepared according to general procedure AT using Ethyl 5-({cyclopropyl[(4-methoxy-2,6-dimethylphenyl)sulfonyl]amino}methyl)-1,3,4-oxadiazole-2-carboxylate (30 mg, 0.07 mmol), 1-[(1-methylpiperidin-4- yl)methyl]piperazine (31 mg, 0.16 mmol) and trimethylaluminium (2 M in toluene, 0.07 mL) in DCE (5 mL). A portion of the crude product was purified using FCC, eluting with 95:4.5:0.5 DCM:MeOH:NH$_3$, to afford the title compound.

LCMS Method C: rt 2.71 min, 97%; m/z 281.20 ([M+2H]$^{2+}$, 100%), 561.22 (MH$^+$, 31%)
Potency: C

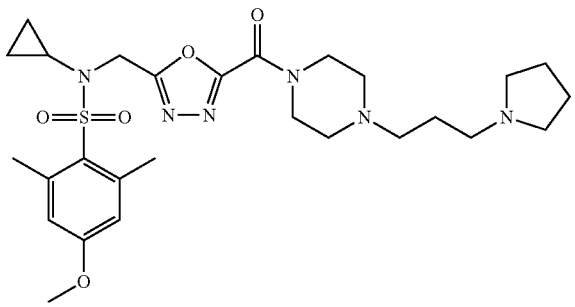 [SMILES: COc1cc(C)c(S(=O)(=O)N(Cc2nnc(C(=O)N3CCN(CCCN4CCCC4)CC3)o2)C2CC2)c(C)c1]

N-Cyclopropyl-4-methoxy-2,6-dimethyl-N-[(5-{[4-(3-pyrrolidin-1-ylpropyl)piperazin-1-yl]carbonyl}-1,3,4-oxadiazol-2-yl)methyl]benzenesulfonamide Ex 273

The title compound was prepared according to general procedure AT using ethyl 5-({cyclopropyl[(4-methoxy-2,6-dimethylphenyl)sulfonyl]amino}methyl)-1,3,4-oxadiazole-2-carboxylate (30 mg, 0.07 mmol), 1-[3-(pyrrolidin-1-yl)propyl]piperazine (31 mg, 0.16 mmol) and trimethylaluminium (2 M in toluene, 0.07 mL) in DCE (5 mL). A portion of the crude product was purified using FCC, eluting with 95:4.5:0.5 DCM:MeOH:NH$_3$, to afford the title compound.

LCMS Method C: rt 2.74 min, 97%; m/z 281.19 ([M+2H]$^{2+}$, 100%), 561.19 (MH$^+$, 47%)
Potency: C

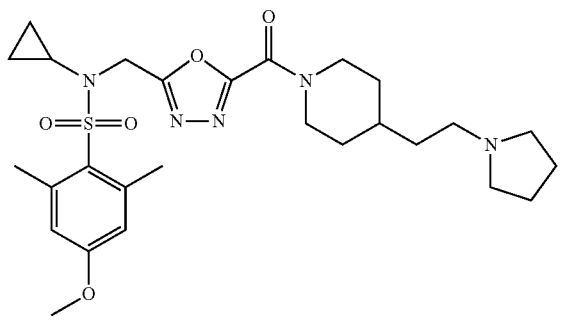 [SMILES: COc1cc(C)c(S(=O)(=O)N(Cc2nnc(C(=O)N3CCC(CCN4CCCC4)CC3)o2)C2CC2)c(C)c1]

N-Cyclopropyl-4-methoxy-2,6-dimethyl-N-[(5-{[4-(2-pyrrolidin-1-ylethyl)piperidin-1-yl]carbonyl}-1,3,4-oxadiazol-2-yl)methyl]benzenesulfonamide Ex 274

The title compound was prepared according to general procedure AT using ethyl 5-({cyclopropyl[(4-methoxy-2,6-dimethylphenyl)sulfonyl]amino}methyl)-1,3,4-oxadiazole-2-carboxylate (30 mg, 0.07 mmol), 14-[2-(pyrrolidin-1-yl)ethyl]piperidine (29 mg, 0.16 mmol) and trimethylaluminium (2 M in toluene, 0.07 mL) in DCE (5 mL). A portion of the crude product was purified using FCC, eluting with 95:4.5:0.5 DCM:MeOH:NH$_3$, to afford the title compound.

LCMS Method C: rt 3.24 min, 96%; m/z 546.20 (MH$^+$, 100%)
Potency: C

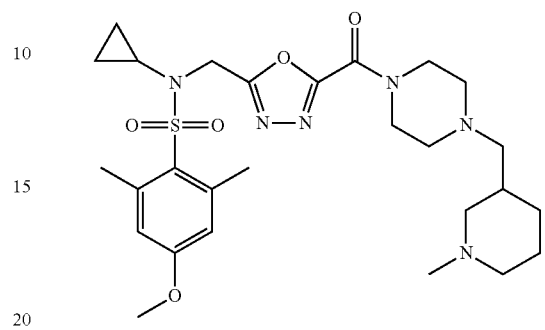

N-Cyclopropyl-4-methoxy-2,6-dimethyl-N-{[5-({4-[(1-methylpiperidin-3-yl)methyl]piperazin-1-yl}carbonyl)-1,3,4-oxadiazol-2-yl]methyl}benzenesulfonamide Ex 275

The title compound was prepared according to general procedure AT using ethyl 5-({cyclopropyl[(4-methoxy-2,6-dimethylphenyl)sulfonyl]amino}methyl)-1,3,4-oxadiazole-2-carboxylate (30 mg, 0.07 mmol), 1-[(1-methylpiperidin-3-yl)methyl]piperazine (31 mg, 0.16 mmol) and trimethylaluminium (2 M in toluene, 0.07 mL) in DCE (5 mL). The crude product was purified using FCC, eluting with 95:4.5:0.5 DCM:MeOH:NH$_3$, to afford the title compound.

Yield: 22.9 mg, 58%.
LCMS Method C: rt 2.82 min, 97%; m/z 281.25 ([M+2H]$^{2+}$, 100%), 561.25 (MH$^+$, 38%)
Potency: B

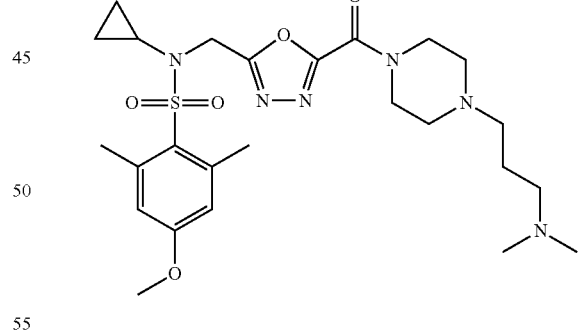

N-Cyclopropyl-N-{[5-({4-[3-(dimethylamino)propyl]piperazin-1-yl}carbonyl)-1,3,4-oxadiazol-2-yl]methyl}-4-methoxy-2,6-dimethylbenzenesulfonamide Ex 276

The title compound was prepared according to general procedure AT using ethyl 5-({cyclopropyl[(4-methoxy-2,6-dimethylphenyl)sulfonyl]amino}methyl)-1,3,4-oxadiazole-2-carboxylate (30 mg, 0.07 mmol), N,N-dimethyl-3-(piperazin-1-yl)propan-1-amine (27 mg, 0.16 mmol) and trimethylaluminium (2 M in toluene, 0.07 mL) in DCE (5 mL). The crude product was purified using FCC, eluting with 95:4.5:0.5 DCM:MeOH:NH$_3$, to afford the title compound.
Yield: 22.3 mg, 60%.
LCMS Method C: rt 2.69 min, 94%; m/z 268.24 ([M+2H]$^{2+}$, 100%), 535.24 (MH$^+$, 66%)
Potency: B

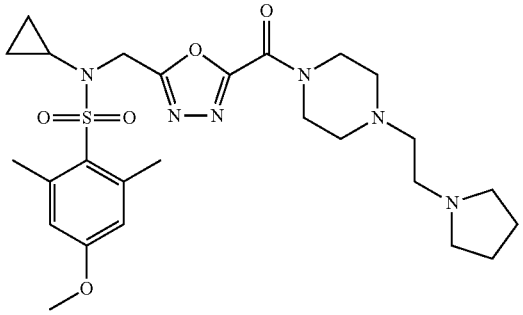 [SMILES: COc1cc(C)c(S(=O)(=O)N(Cc2nnc(C(=O)N3CCN(CCN4CCCC4)CC3)o2)C2CC2)c(C)c1]

N-Cyclopropyl-4-methoxy-2,6-dimethyl-N-[(5-{[4-(2-pyrrolidin-1-ylethyl)piperazin-1-yl]carbonyl}-1,3,4-oxadiazol-2-yl)methyl]benzenesulfonamide Ex 277
The title compound was prepared according to general procedure AT using ethyl 5-({cyclopropyl[(4-methoxy-2,6-dimethylphenyl)sulfonyl]amino}methyl)-1,3,4-oxadiazole-2-carboxylate (30 mg, 0.07 mmol), 1-[2-(pyrrolidin-1-yl)ethyl]piperazine (29 mg, 0.16 mmol) and trimethylaluminium (2 M in toluene, 0.07 mL) in DCE (5 mL). The crude product was purified using FCC, eluting with 95:4.5:0.5 DCM:MeOH:NH$_3$, to afford the title compound.
Yield: 27.9 mg, 73%.
LCMS Method C: rt 3.17 min, 95%; m/z 547.23 (MH$^+$, 100%)
Potency: B

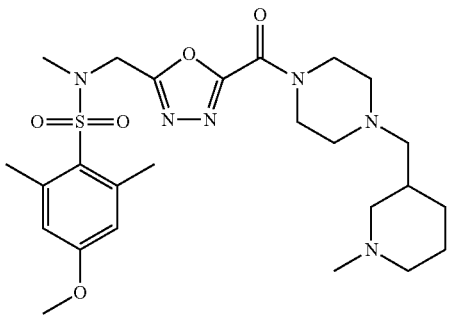 [SMILES: COc1cc(C)c(S(=O)(=O)N(C)Cc2nnc(C(=O)N3CCN(CC4CCCN(C)C4)CC3)o2)c(C)c1]

4-Methoxy-N,2,6-trimethyl-N-{[5-({4-[(1-methylpiperidin-3-yl)methyl]piperazin-1-yl}carbonyl)-1,3,4-oxadiazol-2-yl]methyl}benzenesulfonamide Ex 278
The title compound was prepared according to general procedure AT using methyl 5-({[(4-methoxy-2,6-dimethylphenyl)sulfonyl](methyl)amino}methyl)-1,3,4-oxadiazole-2-carboxylate (30 mg, 0.08 mmol), 1-[(1-methylpiperidin-3-yl)methyl]piperazine (31 mg, 0.16 mmol) and trimethylaluminium (2 M in toluene, 0.08 mL) in DCE (5 mL). The crude product was purified using FCC, eluting with 95:4.5:0.5 DCM:MeOH:NH$_3$, to afford the title compound.
Yield: 28.7 mg, 67%.
LCMS Method C: rt 2.63 min, 99%; m/z 268.24 ([M+2H]$^{2+}$, 100%), 535.24 (MH$^+$, 36%)
Potency: A

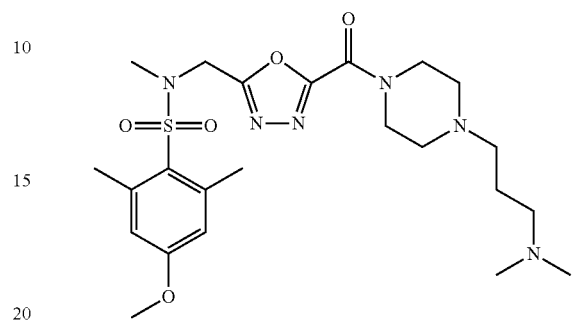

N-{[5-({4-[3-(Dimethylamino)propyl]piperazin-1-yl}carbonyl)-1,3,4-oxadiazol-2-yl]methyl}-4-methoxy-N,2,6-trimethylbenzenesulfonamide Ex 279
The title compound was prepared according to general procedure AT using methyl 5-({[(4-methoxy-2,6-dimethylphenyl)sulfonyl](methyl)amino}methyl)-1,3,4-oxadiazole-2-carboxylate (30 mg, 0.08 mmol), N,N-dimethyl-3-(piperazin-1-yl)propan-1-amine (27 mg, 0.16 mmol) and trimethylaluminium (2 M in toluene, 0.08 mL) in DCE (5 mL). The crude product was purified using FCC, eluting with 95:4.5:0.5 DCM:MeOH:NH$_3$, to afford the title compound.
Yield: 29.3 mg, 72%.
LCMS Method C: rt 2.58 min, 100%; m/z 255.21 ([M+2H]$^{2+}$, 100%), 509.22 (MH$^+$, 36%)
Potency: B

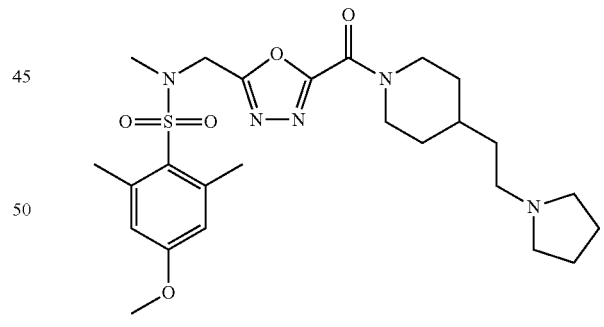

4-Methoxy-N,2,6-trimethyl-N-[(5-{[4-(2-pyrrolidin-1-ylethyl)piperidin-1-yl]carbonyl}-1,3,4-oxadiazol-2-yl)methyl]benzenesulfonamide Ex 280
The title compound was prepared according to general procedure AT using methyl 5-({[(4-methoxy-2,6-dimethylphenyl)sulfonyl](methyl)amino}methyl)-1,3,4-oxadiazole-2-carboxylate (30 mg, 0.08 mmol), 4-[2-(pyrrolidin-1-yl)ethyl]piperidine (29 mg, 0.16 mmol) and trimethylaluminium (2 M in toluene, 0.08 mL) in DCE (5 mL). The crude product was purified twice using FCC, eluting with 95:4.5:0.5 and 98:2:0.5 DCM:MeOH:NH₃, to afford the title compound.

Yield: 12.0 mg, 29%.

LCMS Method C: rt 3.06 min, 100%; m/z 520.40 (MH⁺, 100%)

Potency: B

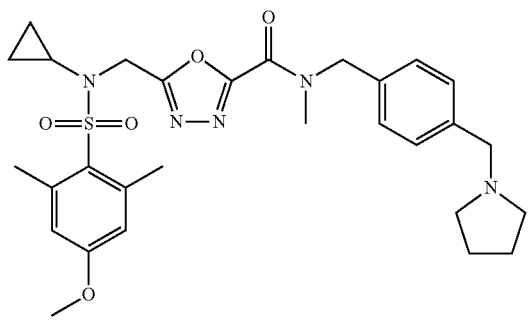 [SMILES: COc1cc(C)c(S(=O)(=O)N(Cc2nnc(C(=O)N(C)Cc3ccc(CN4CCCC4)cc3)o2)C2CC2)c(C)c1]

5-({Cyclopropyl[(4-methoxy-2,6-dimethylphenyl)sulfonyl]amino}methyl)-N-methyl-N-[4-(pyrrolidin-1-ylmethyl)benzyl]-1,3,4-oxadiazole-2-carboxamide Ex 281

The title compound was prepared according to general procedure AT using Ethyl 5-({cyclopropyl[(4-methoxy-2,6-dimethylphenyl)sulfonyl]amino}methyl)-1,3,4-oxadiazole-2-carboxylate (30 mg, 0.07 mmol), N-methyl-1-[4-(pyrrolidin-1-ylmethyl)phenyl]methanamine (30 mg, 0.15 mmol) and trimethylaluminium (2 M in toluene, 0.07 mL) in DCE (5 mL). The crude product was purified twice using FCC, eluting with 95:4.5:0.5, then 98:1:0.5 DCM:MeOH:NH₃, to afford the title compound.

Yield: 29.7 mg, 75%.

LCMS Method C: rt 3.29 min, 97%; m/z 568.33 (MH⁺, 100%)

Potency: C

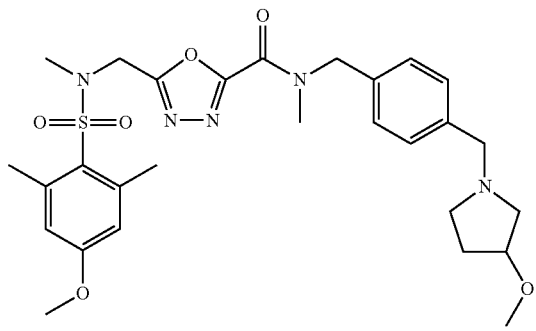 [SMILES: COc1cc(C)c(S(=O)(=O)N(C)Cc2nnc(C(=O)N(C)Cc3ccc(CN4CCC(OC)C4)cc3)o2)c(C)c1]

5-({[(4-Methoxy-2,6-dimethylphenyl)sulfonyl](methyl)amino}methyl)-N-{4-[(3-methoxypyrrolidin-1-yl)methyl]benzyl}-N-methyl-1,3,4-oxadiazole-2-carboxamide Ex 282

The title compound was prepared according to general procedure AT using methyl 5-({[(4-methoxy-2,6-dimethylphenyl)sulfonyl](methyl)amino}methyl)-1,3,4-oxadiazole-2-carboxylate (30 mg, 0.08 mmol), 1-{4-[(3-methoxypyrrolidin-1-yl)methyl]phenyl}-N-methylmethanamine (45 mg, 0.19 mmol) and trimethylaluminium (2 M in toluene, 0.08 mL) in DCE (5 mL). The crude product was purified using FCC, eluting with 95:4.5:0.5 DCM:MeOH:NH₃. The fraction collected was dissolved in DCM (5 mL) and shaken with PL-MIA resin for 2 h, and the beads were filtered and washed with DCM (10 mL). The combined filtrates were concentrated in vacuo and the residue purified using prep method D to afford the title compound.

Yield: 11.8 mg, 26%.

LCMS Method C: rt 3.23 min, 100%; m/z 572.36 (MH⁺, 100%)

Potency: A

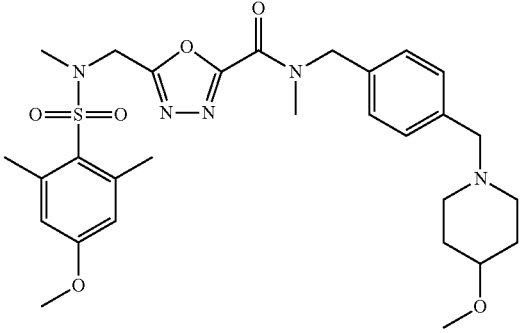 [SMILES: COc1cc(C)c(S(=O)(=O)N(C)Cc2nnc(C(=O)N(C)Cc3ccc(CN4CCC(OC)CC4)cc3)o2)c(C)c1]

5-({[(4-Methoxy-2,6-dimethylphenyl)sulfonyl](methyl)amino}methyl)-N-{4-[(4-methoxypiperidin-1-yl)methyl]benzyl}-N-methyl-1,3,4-oxadiazole-2-carboxamide Ex 283

The title compound was prepared according to general procedure AT using methyl 5-({[(4-methoxy-2,6-dimethylphenyl)sulfonyl](methyl)amino}methyl)-1,3,4-oxadiazole-2-carboxylate (30 mg, 0.08 mmol), 1-{4-[(4-methoxypiperidin-1-yl)methyl]phenyl}-N-methylmethanamine (35 mg, 0.14 mmol) and trimethylaluminium (2 M in toluene, 0.08 mL) in DCE (5 mL). The crude product was purified using FCC, eluting with 95:4.5:0.5 DCM:MeOH:NH₃. A portion of the fraction collected was further purified using prep method D to afford the title compound.

LCMS Method C: rt 3.27 min, 100%; m/z 586.34 (MH⁺, 100%)

Potency: B

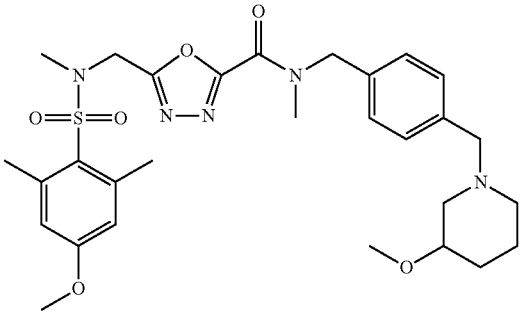 [SMILES: COc1cc(C)c(S(=O)(=O)N(C)Cc2nnc(C(=O)N(C)Cc3ccc(CN4CCCC(OC)C4)cc3)o2)c(C)c1]

5-({[(4-Methoxy-2,6-dimethylphenyl)sulfonyl](methyl)amino}methyl)-N-{4-[(3-methoxypiperidin-1-yl)methyl]benzyl}-N-methyl-1,3,4-oxadiazole-2-carboxamide Ex 284

The title compound was prepared according to general procedure AT using methyl 5-({[(4-methoxy-2,6-dimethylphenyl)sulfonyl](methyl)amino}methyl)-1,3,4-oxadiazole-2-carboxylate (30 mg, 0.08 mmol), 1-{4-[(3-methoxypiperidin-1-yl)methyl]phenyl}-N-methylmethanamine (40 mg, 0.16 mmol) and trimethylaluminium (2 M in toluene, 0.08 mL) in DCE (5 mL). The crude product was purified using FCC, eluting with 95:4.5:0.5 DCM:MeOH:NH$_3$. A portion of the fraction collected was further purified using prep method D to afford the title compound.

LCMS Method C: rt 3.28 min, 100%; m/z 586.34 (MH$^+$, 100%)

Potency: A

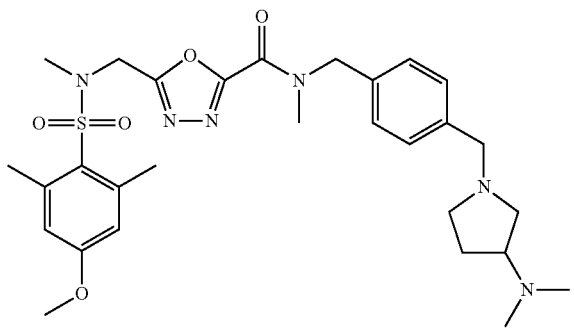

N-(4-{[3-(Dimethylamino)pyrrolidin-1-yl]methyl}benzyl)-5-({[(4-methoxy-2,6-dimethylphenyl)sulfonyl](methyl)amino}methyl)-N-methyl-1,3,4-oxadiazole-2-carboxamide Ex 285

The title compound was prepared according to general procedure AT using methyl 5-({[(4-methoxy-2,6-dimethylphenyl)sulfonyl](methyl)amino}methyl)-1,3,4-oxadiazole-2-carboxylate (30 mg, 0.08 mmol), N,N-dimethyl-1-{4-[(methylamino)methyl]benzyl}pyrrolidin-3-amine (32 mg, 0.13 mmol) and trimethylaluminium (2 M in toluene, 0.08 mL) in DCE (5 mL). A portion of the crude product was purified using prep method D to afford the title compound.

LCMS Method C: rt 2.83 min, 98%; m/z 293.25 ([M+2H]$^{2+}$, 100%), 585.34 (MH$^+$, 23%)

Potency: A

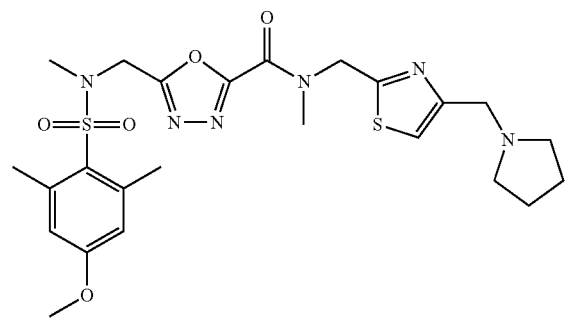 [SMILES: COc1cc(C)c(S(=O)(=O)N(C)Cc2nnc(C(=O)N(C)Cc3nc(CN4CCCC4)cs3)o2)c(C)c1]

5-({[(4-Methoxy-2,6-dimethylphenyl)sulfonyl](methyl)amino}methyl)-N-methyl-N-{[4-(pyrrolidin-1-ylmethyl)-1,3-thiazol-2-yl]methyl}-1,3,4-oxadiazole-2-carboxamide Ex 286

The title compound was prepared according to general procedure AT using methyl 5-({[(4-methoxy-2,6-dimethylphenyl)sulfonyl](methyl)amino}methyl)-1,3,4-oxadiazole-2-carboxylate (30 mg, 0.08 mmol), N-methyl-1-[4-(pyrrolidin-1-ylmethyl)-1,3-thiazol-2-yl]methanamine (30 mg, 0.14 mmol) and trimethylaluminium (2 M in toluene, 0.08 mL) in DCE (5 mL). A portion of the crude product was purified using prep method D to afford the title compound.

LCMS Method C: rt 3.17 min, 98%; m/z 549.25 (MH$^+$, 100%)

Potency: A

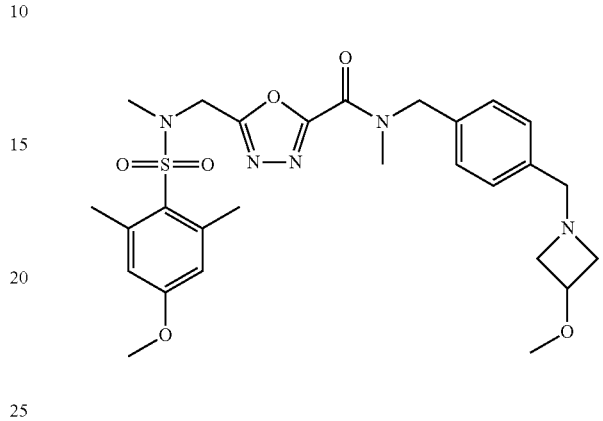

N-{4-[(3-Methoxyazetidin-1-yl)methyl]benzyl}-5-({[(4-methoxy-2,6-dimethylphenyl)sulfonyl](methyl)amino}methyl)-N-methyl-1,3,4-oxadiazole-2-carboxamide Ex 287

The title compound was prepared according to general procedure AT using methyl 5-({[(4-methoxy-2,6-dimethylphenyl)sulfonyl](methyl)amino}methyl)-1,3,4-oxadiazole-2-carboxylate (30 mg, 0.08 mmol), 1-{4-[(3-methoxyazetidin-1-yl)methyl]phenyl}-N-methylmethanamine (30 mg, 0.14 mmol) and trimethylaluminium (2 M in toluene, 0.08 mL) in DCE (5 mL). A portion of the crude product was purified using prep method D to afford the title compound.

LCMS Method C: rt 3.24 min, 100%; m/z 558.27 (MH$^+$, 100%)

Potency: A

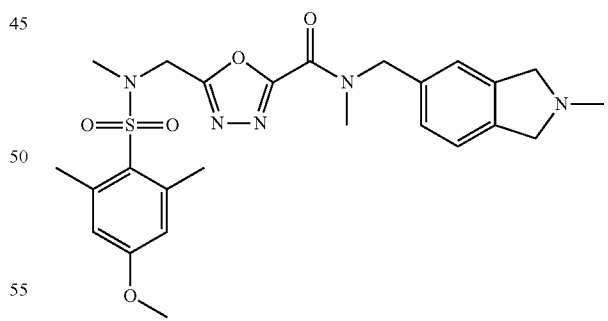

5-({[(4-Methoxy-2,6-dimethylphenyl)sulfonyl](methyl)amino}methyl)-N-methyl-N-[(2-methyl-2,3-dihydro-1H-isoindol-5-yl)methyl]-1,3,4-oxadiazole-2-carboxamide Ex 288

Ethyl 5-({[(4-methoxy-2,6-dimethylphenyl)sulfonyl](methyl)amino}methyl)-1,3,4-oxadiazole-2-carboxylate (30 mg, 0.081 mmol) and N-methyl-1-(2-methyl-2,3-dihydro-1H- isoindol-5-yl)methanamine (29 mg, 0.162 mmol) were dissolved in DCE (5 mL) and stirred at 0° C. prior to being degassed with N₂. Trimethylaluminium (2M in toluene, 80 µl) was added dropwise to this solution. Upon completion of addition, the reaction was heated to 60° C. and stirred for 1 h. The reaction was cooled, and saturated aqueous NaHCO₃ (10 mL) was added. The aqueous layer was extracted with DCM (3×10 mL) and the combined organic extracts dried over Na₂SO₄ and concentrated in vacuo. The resulting brown oil was purified by FCC, eluting with 99:1 DCM:7M NH₃ in MeOH followed by purification using prep method D to afford the title compound.

Yield: 2.5 mg, 6%.
LCMS method C: rt 3.10 min, 100%; m/z 514.27 (MH⁺, 100%).
Potency: A

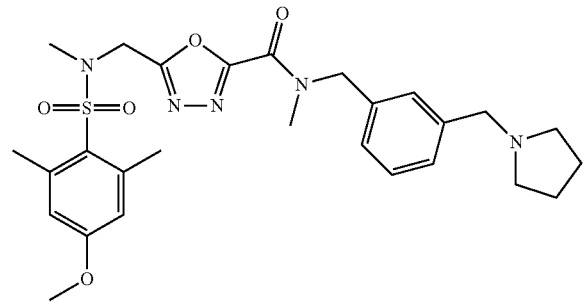 [SMILES: COc1cc(C)c(S(=O)(=O)N(C)Cc2nnc(C(=O)N(C)Cc3cccc(CN4CCCC4)c3)o2)c(C)c1]

5-({[(4-Methoxy-2,6-dimethylphenyl)sulfonyl](methyl)amino}methyl)-N-methyl-N-[3-(pyrrolidin-1-ylmethyl)benzyl]-1,3,4-oxadiazole-2-carboxamide Ex 289

The title compound was prepared according to general procedure BK using methyl 5-({[(4-methoxy-2,6-dimethylphenyl)sulfonyl](methyl)amino}methyl)-1,3,4-oxadiazole-2-carboxylate (150 mg, 0.41 mmol), methyl-(3-pyrrolidin-1-ylmethyl-benzyl)-amine (99 mg, 0.48 mmol), trimethylaluminium (2 M in toluene, 0.44 mL) and THF (15 mL).

Yield: 100 mg, 45%
LCMS method C: rt 3.28 min, 100%; m/z 584.25 ([MH+MeCN]⁺, 100%).
Potency: B

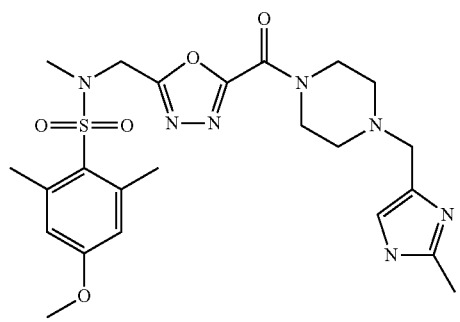

4-Methoxy-N,2,6-trimethyl-N-{[5-({4-[(2-methyl-1H-imidazol-4-yl)methyl]piperazin-1-yl}carbonyl)-1,3,4-oxadiazol-2-yl]methyl}benzenesulfonamide Ex 292

The title compound was prepared according to general procedure CD using 4-methoxy-N,2,6-trimethyl-N-{[5-(piperazin-1-ylcarbonyl)-1,3,4-oxadiazol-2-yl]methyl}benzenesulfonamide (42 mg, 0.10 mmol), 2-methyl-1H-imidazole-4-carbaldehyde (13 mg, 0.12 mmol), STAB (42 mg, 0.2 mmol) DCE (0.8 mL) and a few 4 Å molecular sieves. The crude product was purified using prep method D.

LCMS method C: rt 2.82 min, 88%; m/z 518.33 (MH⁺, 100%).
Potency: C

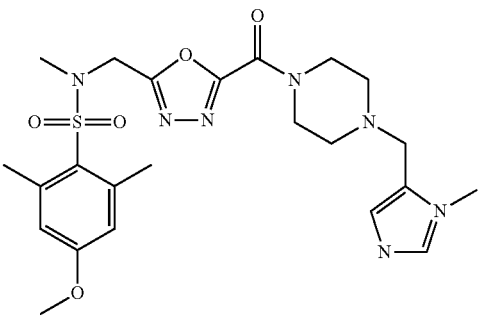

4-Methoxy-N,2,6-trimethyl-N-{[5-({4-[(1-methyl-1H-imidazol-5-yl)methyl]piperazin-1-yl}carbonyl)-1,3,4-oxadiazol-2-yl]methyl}benzenesulfonamide Ex 293

The title compound was prepared according to general procedure CD using 4-methoxy-N,2,6-trimethyl-N-{[5-(piperazin-1-ylcarbonyl)-1,3,4-oxadiazol-2-yl]methyl}benzenesulfonamide (42 mg, 0.10 mmol), 1-methyl-1H-imidazole-5-carbaldehyde (13 mg, 0.12 mmol), STAB (42 mg, 0.2 mmol) DCE (0.8 mL) and a few 4 Å molecular sieves. The crude product was purified using prep method D.

LCMS method C: rt 2.99 min, 85%; m/z 518.33 (MH⁺, 100%).
Potency: A

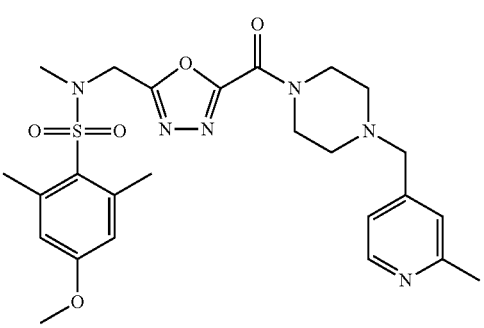

4-Methoxy-N,2,6-trimethyl-N-{[5-({4-[(2-methylpyridin-4-yl)methyl]piperazin-1-yl}carbonyl)-1,3,4-oxadiazol-2-yl]methyl}benzenesulfonamide Ex 294

The title compound was prepared according to general procedure CD using 4-methoxy-N,2,6-trimethyl-N-{[5-(piperazin-1-ylcarbonyl)-1,3,4-oxadiazol-2-yl]methyl}benzenesulfonamide (42 mg, 0.10 mmol), 2-methylpyridine-4-carbaldehyde (15 mg, 0.12 mmol), STAB (42 mg, 0.2 mmol) DCE (0.8 mL) and a few 4 Å molecular sieves. The crude product was purified using prep method D.

LCMS method C: rt 3.04 min, 85%; m/z 529.35 (MH⁺, 100%).

Potency: B

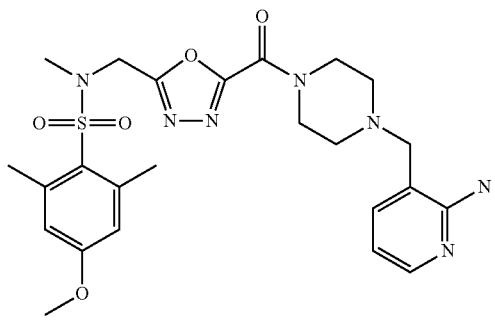 [SMILES: COc1cc(C)c(S(=O)(=O)N(C)Cc2nnc(C(=O)N3CCN(Cc4cccnc4N)CC3)o2)c(C)c1]

N-{[5-({4-[(2-Aminopyridin-3-yl)methyl]piperazin-1-yl}carbonyl)-1,3,4-oxadiazol-2-yl]methyl}-4-methoxy-N,2,6-trimethylbenzenesulfonamide Ex 295

The title compound was prepared according to general procedure CD using 4-methoxy-N,2,6-trimethyl-N-{[5-(piperazin-1-ylcarbonyl)-1,3,4-oxadiazol-2-yl]methyl}benzenesulfonamide (42 mg, 0.10 mmol), 2-aminopyridine-3-carbaldehyde (15 mg, 0.12 mmol), STAB (42 mg, 0.2 mmol) DCE (0.8 mL) and a few 4 Å molecular sieves. The crude product was purified using prep method D.

LCMS method C: rt 3.09 min, 87%; m/z 530.36 (MH$^+$, 100%).

Potency: C

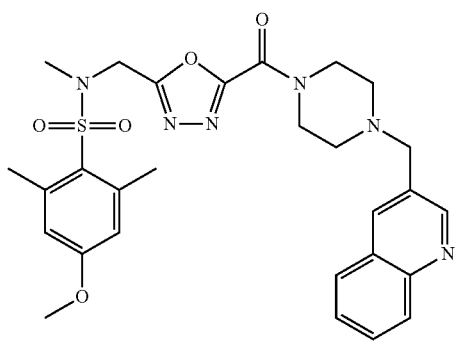 [SMILES: COc1cc(C)c(S(=O)(=O)N(C)Cc2nnc(C(=O)N3CCN(Cc4cnc5ccccc5c4)CC3)o2)c(C)c1]

4-Methoxy-N,2,6-trimethyl-N-[(5-{[4-(quinolin-3-ylmethyl)piperazin-1-yl]carbonyl}-1,3,4-oxadiazol-2-yl)methyl]benzenesulfonamide Ex 296

The title compound was prepared according to general procedure CD using 4-methoxy-N,2,6-trimethyl-N-{[5-(piperazin-1-ylcarbonyl)-1,3,4-oxadiazol-2-yl]methyl}benzenesulfonamide (42 mg, 0.10 mmol), quinoline-3-carbaldehyde (18 mg, 0.12 mmol), STAB (42 mg, 0.2 mmol) DCE (0.8 mL) and a few 4 Å molecular sieves. The crude product was purified using prep method D.

LCMS method C: rt 3.35 min, 92%; m/z 565.34 (MH$^+$, 100%).

Potency: C

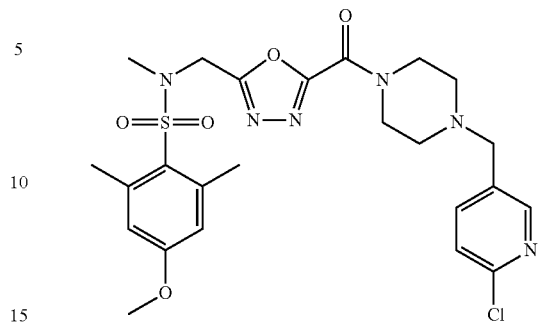

N-{[5-({4-[(6-Chloropyridin-3-yl)methyl]piperazin-1-yl}carbonyl)-1,3,4-oxadiazol-2-yl]methyl}-4-methoxy-N,2,6-trimethylbenzenesulfonamide Ex 297

The title compound was prepared according to general procedure CD using 4-methoxy-N,2,6-trimethyl-N-{[5-(piperazin-1-ylcarbonyl)-1,3,4-oxadiazol-2-yl]methyl}benzenesulfonamide (210 mg, 0.50 mmol), 6-chloropyridine-3-carbaldehyde (84 mg, 0.60 mmol), STAB (210 mg, 0.99 mmol) DCE (4.0 mL) and a few 4 Å molecular sieves. The crude product recrystallised from IPA/MeOH/DCM.

Yield: 212 mg, 77%
Potency: C
$^1$H NMR (500 MHz, CDCl$_3$) δ ppm 8.34 (1H, d, J=2.1 Hz), 7.61-7.73 (1H, m), 7.27 (1H, s), 6.65 (2H, s), 4.62 (2H, s), 4.08-4.16 (2H, m), 3.76-3.85 (5H, m), 3.55 (2H, s), 2.85 (3H, s), 2.64 (6H, s), 2.56 (4H, d).

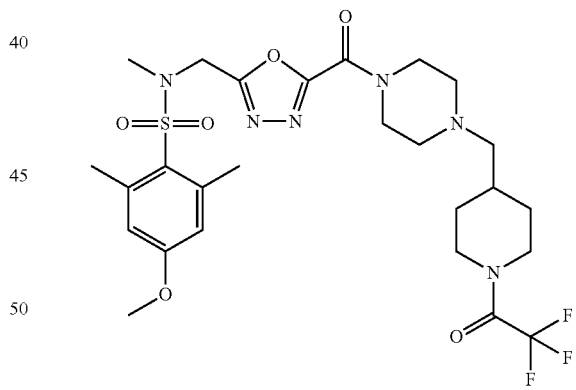

4-Methoxy-N,2,6-trimethyl-N-({5-[(4-{[1-(trifluoroacetyl)piperidin-4-yl]methyl}piperazin-1-yl)carbonyl]-1,3,4-oxadiazol-2-yl}methyl)benzenesulfonamide trifluoroacetate Ex 298

4-Methoxy-N,2,6-trimethyl-N-[(5-{[4-(piperidin-4-ylmethyl)piperazin-1-yl]carbonyl}-1,3,4-oxadiazol-2-yl)methyl]benzenesulfonamide (10 mg, 0.02 mmol) was dissolved in DMF (0.5 mL) prior to addition of trifluoroacetic anhydride (0.025 mL, 0.2 mmol). The reaction was stirred at ambient temperature for 75 min and concentrated in vacuo.

The crude product was purified by prep method A to afford the title compound as the trifluoroacetate salt.

LCMS method C: rt 3.29 min, 88%; m/z 617.45 (MH+, 100%).

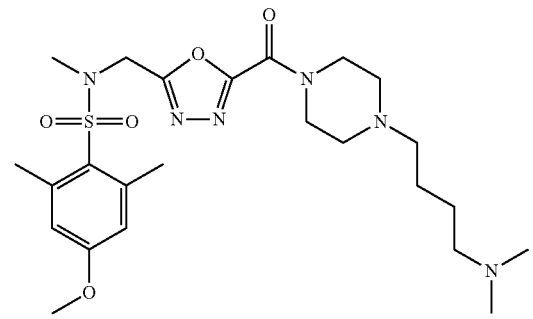

N-{5-({4-[4-(Dimethylamino)butyl]piperazin-1-yl}carbonyl)-1,3,4-oxadiazol-2-yl]methyl}-4-methoxy-N,2,6-trimethylbenzenesulfonamide trifluoroacetate Ex 299

The title compound was prepared according to general procedure CE using ethyl 5-({[(4-methoxy-2,6-dimethylphenyl)sulfonyl](methyl)amino}methyl)-1,3,4-oxadiazole-2-carboxylate (38 mg, 0.1 mmol), N,N-dimethyl-4-piperazin-1-ylbutan-1-amine (36 mg, 0.2 mmol), DCE (1.0 mL) and trimethylaluminium (2.0 M in toluene, 0.1 mL). The crude product was purified by prep method A.

LCMS method C: rt 2.59 min, 97%; m/z 262.25 ([M+2H]$^{2+}$], 100%), 523.37 (MH+, 31%).

Oxadiazoles Synthesis

Scheme 10 describes the general synthesis of oxadiazole derivatives.

(R$^1$=H, CD$_3$; R$^{1a}$=R$^{1b}$=H; X$^1$=O; X$^2$=X$^3$=N)

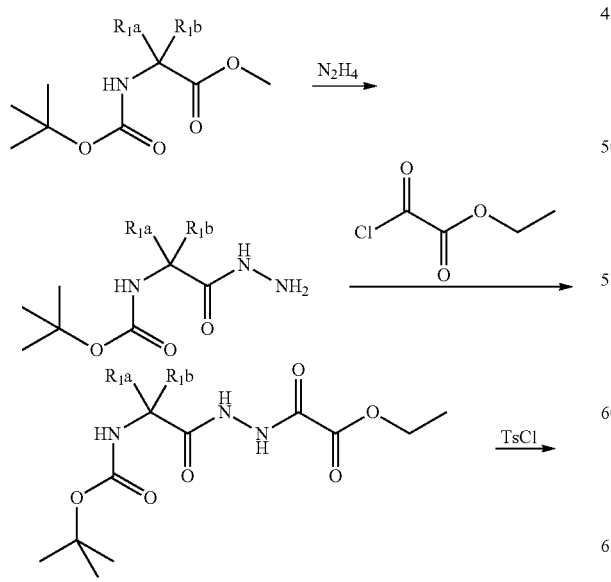

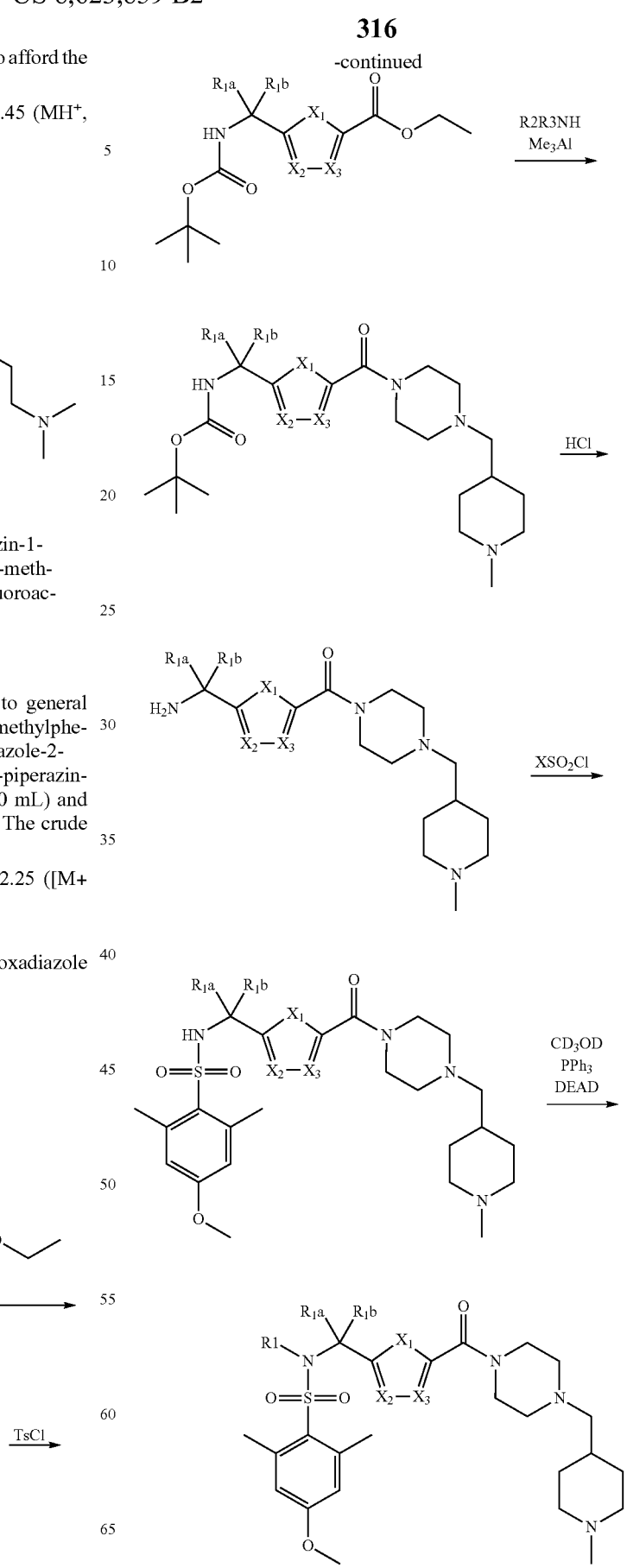

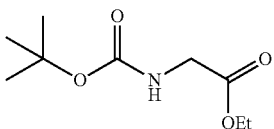

Ethyl[(tert-butoxycarbonyl)amino]acetate

Int 287

Ethyl Chloroformate (2.7 mL, 28.5 mmol) in MeCN (5 mL) was added to a solution of Boc glycine (5.0 g, 28.5 mmol) and TEA (3.9 mL, 28.5 mmol) in MeCN (15 mL) under N$_2$. After 5 minute a solution of DMAP (1.7 g, 14.25 mmol) in MeCN (14 mL) was added and the resultant yellow solution was stirred at ambient temperature for 16 h. The pale yellow suspension was concentrated in vacuo and the residue diluted with DCM (100 mL) and washed with saturated aqueous NaHCO$_3$ (50 mL) and aqueous HCl (0.1 M, 50 mL). The organics were dried over MgSO$_4$ and concentrated in vacuo to a pale yellow oil which was used without further purification.

Yield: 6.6 g.

$^1$H NMR (500 MHz, CDCl$_3$) δ ppm 4.95-5.09 (1H, m), 4.22-4.23 (1H, m), 4.20 (2H, q J 7.2 Hz), 3.86-3.93 (2H, m), 1.46 (9H, s), 1.28 (2H, t, J 7.2 Hz)

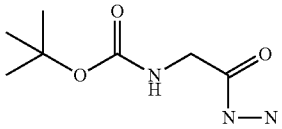

tert-Butyl (2-hydrazinyl-2-oxoethyl)carbamate

Int 288

Ethyl[(tert-butoxycarbonyl)amino]acetate (28.5 mmol), in EtOH (10 mL) was treated with hydrazine hydrate (4.2 mL, 85.6 mmol) and the resultant pale yellow solution was stirred at ambient temperature for 65 h.

The reaction mixture was concentrated in vacuo and the residue was diluted with EtOAc and washed with water followed by brine. The organics were dried over MgSO$_4$ and concentrated in vacuo. The solid was triturated with ether to give the title compound as a white solid (1.0 g, 19%). The aqueous was further extracted with DCM (×4) and the organics were dried over MgSO$_4$ and concentrated in vacuo to give the title compound as a white solid. (1.0 g, 19%)

Yield: 2.0 g, 38%.

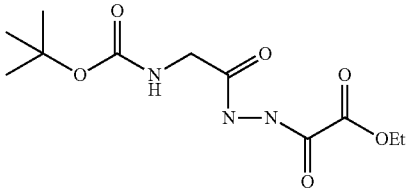 [SMILES: CCOC(=O)C(=O)NNC(=O)CNC(=O)OC(C)(C)C]

Ethyl (2-{[(tert-butoxycarbonyl)amino]acetyl}hydrazinyl)(oxo)acetate

Int 289

A suspension of tert-butyl (2-hydrazinyl-2-oxoethyl)carbamate (2.0 g, 10.6 mmol) and TEA (2.2 mL, 15.8 mmol) in THF (20 mL), under N$_2$, was cooled to −40° C. and treated with ethyl chloro(oxo)acetate (1.8 mL, 15.8 mmol). The mixture was allowed to slowly warm to ambient temperature and was stirred for 16 h.

The suspension was quenched with saturated aqueous NaHCO$_3$ (30 mL) and concentrated in vacuo. The residue was extracted with EtOAc (×4). The combined organic extracts were washed with brine, dried over MgSO$_4$ and concentrated in vacuo to afford the title compound as a beige foam.

LCMS Method A: rt 0.87 min, 46%; m/z 312.00 (M+Na$^+$, 100%).

Yield: 1.6 g, 53%.

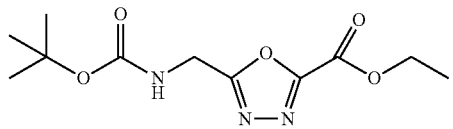 [SMILES: CCOC(=O)c1nnc(CNC(=O)OC(C)(C)C)o1]

Ethyl 5-{[(tert-butoxycarbonyl)amino]methyl}-1,3,4-oxadiazole-2-carboxylate

Int 290 p-Toluenesulfonyl chloride (1.3 g, 6.6 mmol) was added to a solution of ethyl (2-{[(tert-butoxycarbonyl)amino]acetyl}hydrazinyl)(oxo)acetate (1.6 g, 5.5 mmol) and TEA (1.5 mL, 11.0 mmol) in DCM (20 mL) at 0° C. under N$_2$. The solution was stirred and slowly allowed to warm to ambient temperature over 16 h. The reaction mixture was diluted with DCM and washed with saturated aqueous NaHCO$_3$. The organic layer was dried over MgSO$_4$ and concentrated in vacuo to a red gum.

The crude material was purified by FCC, eluting with 10% EtOAc in DCM to give the title compound as a gum.

Yield: 756 mg, 51%.

LCMS Method A: rt 1.26 min, 84%; m/z 215.90 (M+H-$^t$Bu$^+$, 100%), 293.95 (M+Na$^+$, 90%).

$^1$H NMR (500 MHz, CDCl$_3$) δ ppm 5.13-5.26 (1H, m), 4.61-4.70 (2H, m), 4.52 (2H, q J 7.2 Hz), 4.52 (9H, d), 1.40-1.53 (12H, m)

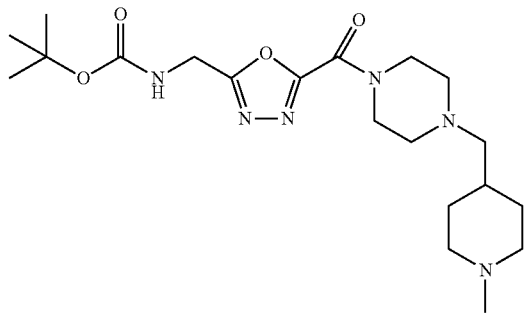 [SMILES: CN1CCC(CN2CCN(C(=O)c3nnc(CNC(=O)OC(C)(C)C)o3)CC2)CC1]

tert-Butyl {[5-({4-[(1-methylpiperidin-4-yl)methyl]piperazin-1-yl}carbonyl)-1,3,4-oxadiazol-2-yl]methyl}carbamate Int 291

The title compound was prepared according to general procedure AT using ethyl 5-{[(tert-butoxycarbonyl)amino]methyl}-1,3,4-oxadiazole-2-carboxylate (218 mg, 0.8 mmol), 1-(N-Methylpiperidin-4-yl-methyl)piperazine (316 mg, 1.6 mmol) and trimethylaluminium (2.0 M in toluene, 0.8 mL) in DCE (11 mL). The crude product was purified by FCC eluting with 7.5% NH$_3$ (2M in MeOH) in DCM to afford the title compound as a clear gum.

Yield: 183 mg, 54%.

LCMS Method A: rt 0.48 min, 100%; m/z 423.15 (MH$^+$, 100%)

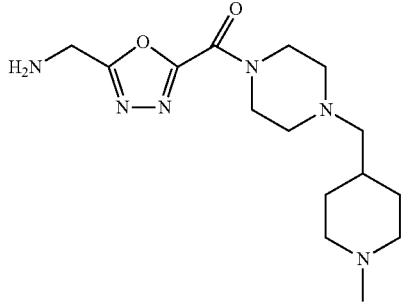 [SMILES: CN1CCC(CN2CCN(C(=O)c3nnc(CN)o3)CC2)CC1]

(5-Aminomethyl-1,3,4-oxadiazol-2-yl)-[4-(1-methyl-piperidin-4-ylmethyl)-piperazin-1-yl]-methanone trihydrochloride Int 292

A suspension of tert-butyl {[5-({4-[(1-methylpiperidin-4-yl)methyl]piperazin-1-yl}carbonyl)-1,3,4-oxadiazol-2-yl]methyl}carbamate (180 mg, 0.4 mmol) in EtOAc (5 mL) under N$_2$ was cooled to 0° C. and HCl (4.0 M in dioxane, 1.1 mL) was added. The resultant suspension was stirred at 0° C. for 30 min then at ambient temperature for 1 h. The suspension was concentrated in vacuo to afford the title compound as a white solid which was used without further purification.

Yield: 200 mg, 100%

LCMS Method A: rt 0.17 min, 100%; m/z 162.10 ([M+2H]$^{2+}$, 100%), 323.15 (MH$^+$, 50%)

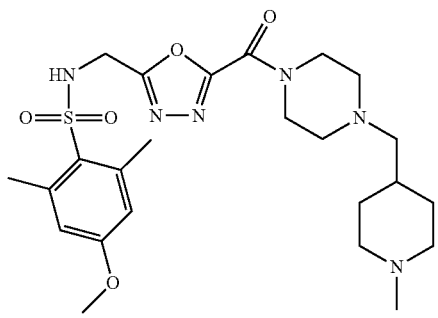 [SMILES: COc1cc(C)c(S(=O)(=O)NCc2nnc(C(=O)N3CCN(CC4CCN(C)CC4)CC3)o2)c(C)c1]

4-Methoxy-2,6-dimethyl-N-{5-[4-(1-methyl-piperidin-4-ylmethyl)-piperazine-1-carbonyl]-1,3,4-oxadiazol-2-ylmethyl}-benzenesulfonamide Ex 290

4-methoxy-2,6-dimethylbenzenesulfonyl chloride (118 mg, 0.5 mmol) was added to a suspension of (5-Amino methyl-1,3,4-oxadiazol-2-yl)-[4-(1-methyl-piperidin-4-ylmethyl)-piperazin-1-yl]-methanone trihydrochloride (200 mg, 0.43 mmol) in DCM, under N$_2$ and the mixture was cooled to −30° C. DIPEA (376 μL, 2.15 mmol) was added over about 3 min and the resultant pink solution was stirred at −30° C. for 30 min and then at ambient temperature for 16 h. The mixture was diluted with saturated aqueous NaHCO$_3$ and extracted with DCM (×2). The combined organic extracts were dried over MgSO$_4$ and concentrated in vacuo to a brown gum which was purified using FCC, eluting with 5% NH$_3$ (2.0 M in MeOH) in DCM, to give the title compound as a clear gum.

Yield: 150 mg, 67%.

LCMS Method C: rt 2.42 min, 92%; m/z 261.24 ([M+2H]$^2$ 100%), 521.41 (MH$^+$, 61%).

$^1$H NMR (500 MHz, CDCl$_3$) δ ppm 6.59 (2H, s), 4.45 (2H, s), 4.03 (2H, br. s.), 3.73-3.79 (2H, m), 2.89 (2H, d, J=11.3 Hz), 2.43-2.52 (4H, m), 2.29 (3H, s), 2.23 (2H, d, J=7.0 Hz), 1.94 (3H, t), 1.76 (2H, d, J=12.2 Hz), 1.43-1.54 (1H, m), 1.28 (2H, d)

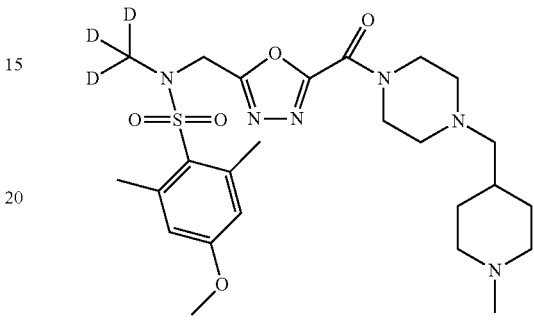

4-Methoxy-2,6-dimethyl-N-($^2$H$_3$)methyl-N-{[5-({4-[(1-methylpiperidin-4-yl)methyl]piperazin-1-yl}carbonyl)-1,3,4-oxadiazol-2-yl]methyl}benzenesulfonamide trifluoroacetate Ex 291

A solution of 4-methoxy-2,6-dimethyl-N-{5-[4-(1-methyl-piperidin-4-ylmethyl)-piperazine-1-carbonyl]-1,3,4-oxadiazol-2-ylmethyl}-benzenesulfonamide (21 mg, 0.04 mmol) in THF (1 mL), under N$_2$ was treated with CD$_3$OD (2 μL, 0.05 mmol) followed by triphenylphosphine (13 mg, 0.05 mmol). After 5 min diethylazodicarboxylate (11 μL, 0.05 mmol) was added and the red solution was stirred at ambient temperature for 16 h.

Additional CD$_3$OD (10 μL, 0.25 mmol) followed by triphenylphosphine (65 mg, 0.25 mmol) were added and after 5 min diethylazodicarboxylate (55 μL, 0.25 mmol) was added and the red solution was stirred at ambient temperature for 5 h.

The reaction mixture was absorbed on to a 2.0 g SCX cartridge and the sorbent washed with MeOH. The cartridge was eluted with NH$_3$ (7M in MeOH) and eluent concentrated in vacuo. The crude product was purified using FCC, eluting with 5% NH$_3$ (2M in MeOH) in DCM. This material was further purified using prep method A to afford the title compound as a clear gum.

Yield: 5.5 mg, 21%.

LCMS Method C: rt 0.86 min, 92%; m/z 270.0 ([M+2H]$^{2+}$ 100%), 538.42 (MH$^+$, 29%).

$^1$H NMR (500 MHz, CD$_3$OD) δ ppm 6.78 (2H, s), 4.72 (2H, s), 3.86 (3H, s), 3.56-3.63 (2H, m), 2.97-3.08 (4H, m), 2.90 (3H, s), 2.63 (6H, s), 2.66 (1H, s), 2.03-2.23 (3H, m), 1.50-1.62 (2H, m), 1.10-1.42 (1H, m)

Potency: A

Oxadiazole Synthesis

Scheme 11 describes the general synthesis of oxadiazole derivatives.

(R$^1$=Me, cyclopropyl; R$^{1a}$=R$^{1b}$=H; X=2,6-dimethyl-4-methoxybenzenesulfonyl; X$^1$=X$^2$=N; X$^3$=O; NR$^2$R$^3$=various amines)

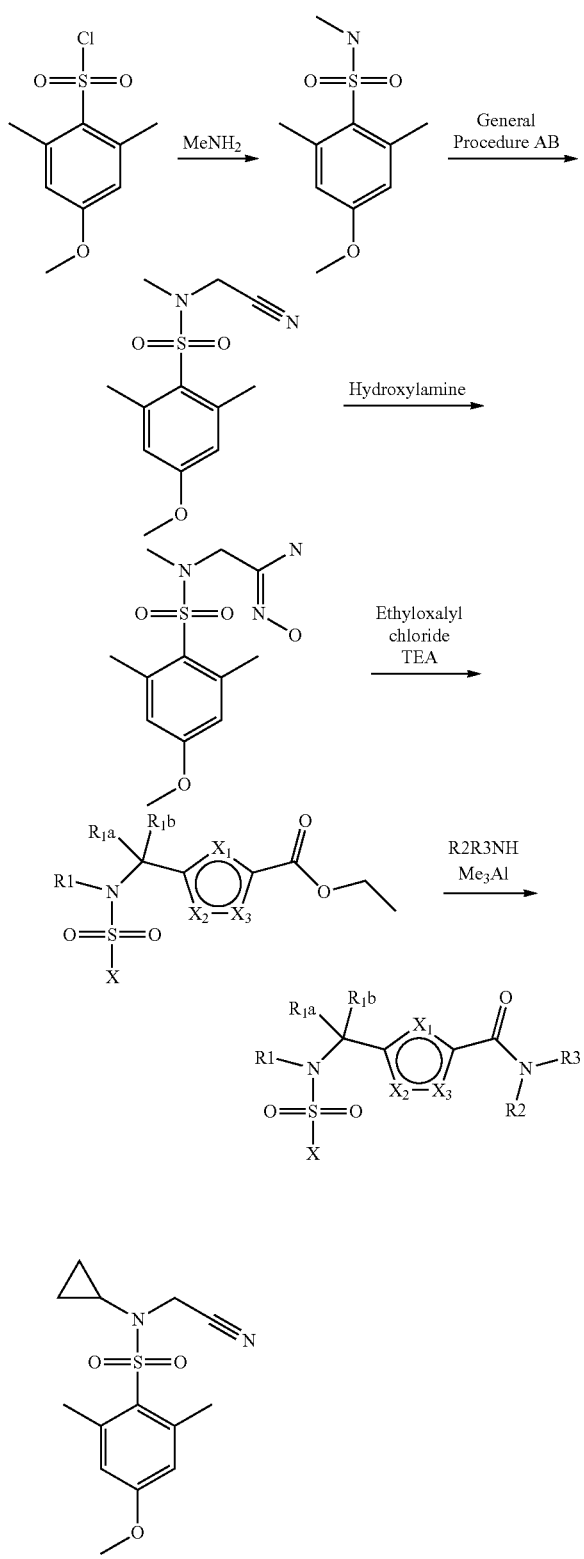

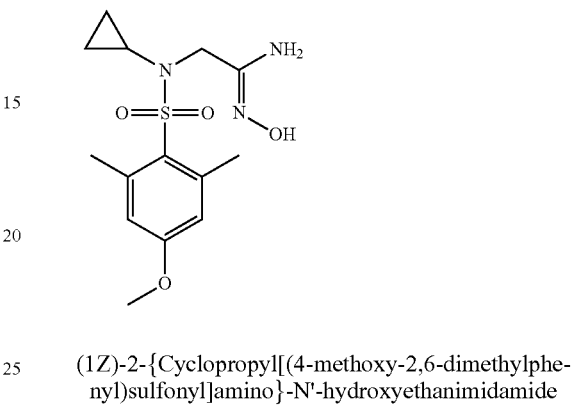

(1Z)-2-{Cyclopropyl[(4-methoxy-2,6-dimethylphenyl)sulfonyl]amino}-N'-hydroxyethanimidamide

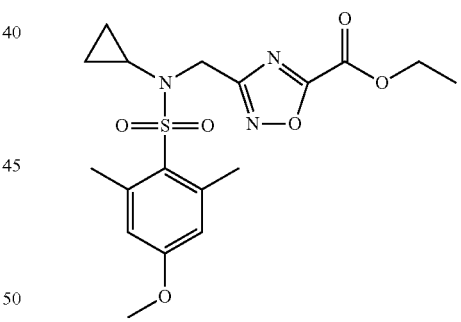

Ethyl 3-({cyclopropyl[(4-methoxy-2,6-dimethylphenyl)sulfonyl]amino}methyl)-1,2,4-oxadiazole-5-carboxylate N-(Cyanomethyl)-N-cyclopropyl-4-methoxy-2,6-dimethylbenzenesulfonamide Int 293
N-cyclopropyl-4-methoxy-2,6-dimethylbenzenesulfonamide (21 g, 82.24 mmol) and NaH (60%; 3.95 g, 98.69 mmol) were stirred in anhydrous THF (420 mL) for 30 min at 0° C. 2-Chloroacetonitrile (6.3 mL, 98.69 mmol) and NaI (2.1 g) were then added to the reaction mixture and the resulting solution was stirred at ambient temperature for 18 h. The reaction mixture was then partitioned between 1:1 brine: water (800 mL) and EtOAc (3×500 mL) and the combined organics were dried over $Na_2SO_4$ and concentrated in vacuo to afford the title compound as a brown solid, which was used without further purification.
Yield: 23.6 g, 98%.

Int 294
To a solution of N-(cyanomethyl)-N-cyclopropyl-4-methoxy-2,6-dimethylbenzenesulfonamide (23.6 g, 80.17 mmol) in anhydrous EtOH (200 mL) was added hydroxylamine (50% aq. solution; 14.7 mL, 240.5 mmol) and the resulting solution was then heated at 60° C. for 18 h. The reaction mixture was concentrated in vacuo to afford a brown solid that was then azeotroped with toluene and was concentrated in vacuo. This material was then used without further purification.
Yield: 28.17 g.

Int 295
TEA (26.4 mL, 189.3 mmol) and ethyl chloro(oxo)acetate (10.6 mL, 94.64 mmol) were added to a solution of (1Z)-2-{cyclopropyl[(4-methoxy-2,6-dimethylphenyl)sulfonyl]amino}-N'-hydroxyethanimidamide (28.17 g, 86.04 mmol) stirring in anhydrous DCE (500 mL). The resulting reaction mixture was then heated at 60° C. under $N_2$ for 18 h. The reaction mixture was then concentrated in vacuo and was then partitioned between saturated brine (500 mL) and EtOAc (4×500 mL). The combined organic extracts were then dried over $Na_2SO_4$ concentrated in vacuo to give an oily residue.

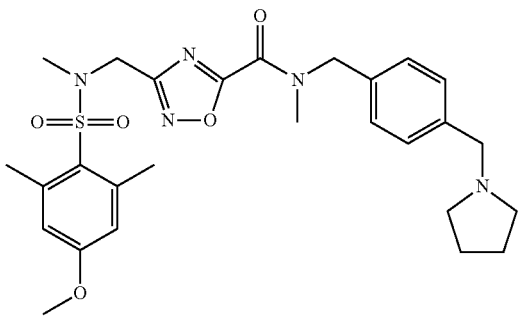 [SMILES: COc1cc(C)c(S(=O)(=O)N(C)Cc2noc(C(=O)N(C)Cc3ccc(CN4CCCC4)cc3)n2)c(C)c1]

3-({[(4-Methoxy-2,6-dimethylphenyl)sulfonyl](methyl)amino}methyl)-N-methyl-N-[4-(pyrrolidin-1-ylmethyl)benzyl]-1,2,4-oxadiazole-5-carboxamide trifluoroacetamide Ex 300

The title compound was prepared according to general procedure AT using Ethyl 3-({[(4-methoxy-2,6-dimethylphenyl)sulfonyl](methyl)amino}methyl)-1,2,4-oxadiazole-5-carboxylate (60 mg, 0.157 mmol), N-methyl 1-[4(pyrrolidinylmethyl)phenyl]methanamine (128 mg, 0.627 mmol) and trimethylaluminium (2 M in toluene, 0.32 mL) in DCM (5 mL). The crude product was purified using prep method C.

Yield: 34.5 mg, 41%.

LCMS Method C: rt 3.16 min, 99%; m/z 542.50 (MH+, 100%)

Potency: C

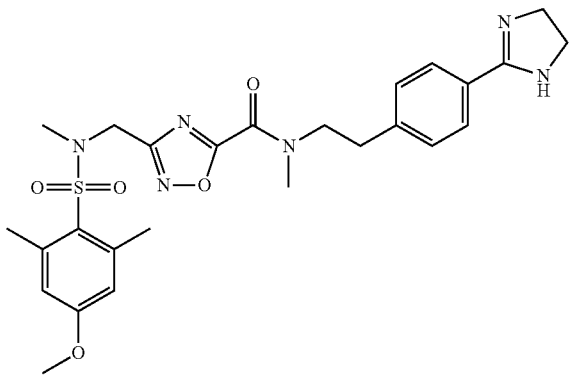 [SMILES: COc1cc(C)c(S(=O)(=O)N(C)Cc2noc(C(=O)N(C)CCc3ccc(C4=NCCN4)cc3)n2)c(C)c1]

N-{2-[4-(4,5-Dihydro-1H-imidazol-2-yl)phenyl]ethyl}-3-({[(4-methoxy-2,6-dimethylphenyl)sulfonyl](methyl)amino}methyl)-N-methyl-1,2,4-oxadiazole-5-carboxamide trifluoroacetamide Ex 301

The title compound was prepared according to general procedure AT using ethyl 3-({[(4-methoxy-2,6-dimethylphenyl)sulfonyl](methyl)amino}methyl)-1,2,4-oxadiazole-5-carboxylate (60 mg, 0.157 mmol), 2-[4-(4,5-dihydro-1H-imidazol-2-yl)phenyl]-N-methylethanamine dihydrochloride (127 mg, 0.463 mmol), TEA (0.175 mL, 1.23 mmol) and trimethylaluminium (2 M in toluene, 0.32 mL) in DCM (5 mL). A portion of the crude product was purified using prep method C.

LCMS Method C: rt 3.20 min, 100%; m/z 541.44 (MH+, 100%)

Potency: C

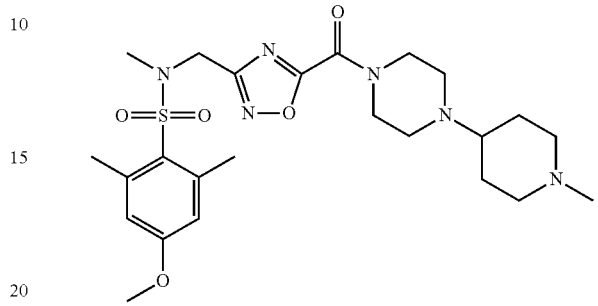

4-Methoxy-N,2,6-trimethyl-N-[(5-{[4-(1-methylpiperidin-4-yl)piperazin-1-yl]carbonyl}-1,2,4-oxadiazol-3-yl)methyl]benzenesulfonamide trifluoroacetate Ex 302

The title compound was prepared according to general procedure AT using ethyl 3-({[(4-methoxy-2,6-dimethylphenyl)sulfonyl](methyl)amino}methyl)-1,2,4-oxadiazole-5-carboxylate (50 mg, 0.13 mmol), 1-(1-methylpiperidin-4-yl)piperazine (95 mg, 0.52 mmol) and trimethylaluminium (2 M in toluene, 0.3 mL) in DCM (10 mL). The crude product was purified using prep method A.

Yield: 18.5 mg, 27%.

LCMS Method C: rt 2.66 min, 99%; m/z 521.12 (MH+, 100%)

¹H NMR (500 MHz, CD₃OD): δ ppm 6.79 (2H, s), 4.62 (2H, s), 4.31 (2H, br. s.), 4.08 (2H, br. s.), 3.86 (3H, s), 3.71 (2H, br. s.), 3.46 (1H, br. s.), 3.39-3.46 (4H, m), 3.14 (2H br. s.), 2.92 (3H, s), 2.82 (3H, s), 2.63 (6H, s), 2.44 (2H, br. s.), 2.03-2.16 (2H, m)

Potency: A

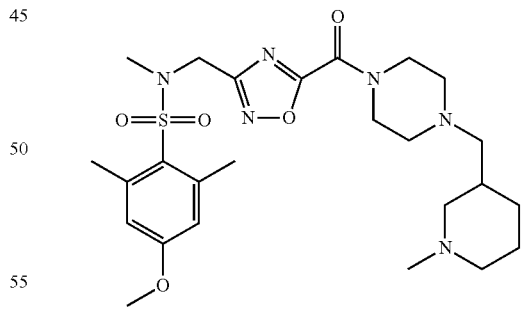

4-Methoxy-N,2,6-trimethyl-N-{[5-({4-[(1-methylpiperidin-3-yl)methyl]piperazin-1-yl}carbonyl)-1,2,4-oxadiazol-3-yl]methyl}benzenesulfonamide trifluoroacetamide Ex 303

The title compound was prepared according to general procedure AT using ethyl 3-({[(4-methoxy-2,6-dimethylphenyl)sulfonyl](methyl)amino}methyl)-1,2,4-oxadiazole-5- carboxylate (30 mg, 0.08 mmol), 1-[(1-methylpiperidin-3-yl)methyl]piperazine (63 mg, 0.32 mmol) and trimethylaluminium (2 M in toluene, 0.16 mL) in DCM (5 mL). A portion of the crude product was purified using prep method C.

LCMS Method C: rt 2.72 min, 99%; m/z 288.70 ([M+2H+MeCN]$^{2+}$, 100%), 535.22 (MH$^+$, 41%)

$^1$H NMR (500 MHz, CD$_3$OD): δ ppm 6.78 (2H, s), 4.61 (2H, s), 4.22 (2H, br. s.), 4.04 (2H, br. s.), 3.85 (3H, s), 3.69 (1H, br. s.), 3.53 (1H, br. s.), 3.14-3.30 (4H, m), 2.99-3.03 (1H, m), 2.92-2.99 (2H, m), 2.91 (3H, s), 2.83 (3H, s), 2.73-2.81 (1H, m), 2.63 (6H, s), 2.38 (1H, br. s.), 1.98-2.07 (2H, m), 1.91 (1H, br. s.), 1.26-1.38 (1H, m)

Potency: A

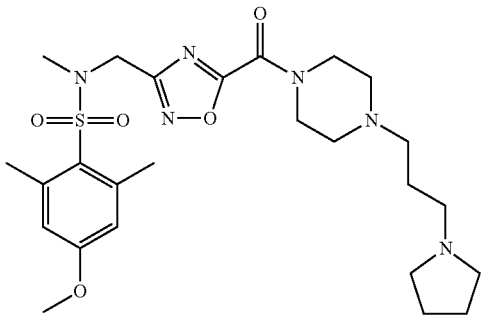 [SMILES: COc1cc(C)c(S(=O)(=O)N(C)Cc2noc(C(=O)N3CCN(CCCN4CCCC4)CC3)n2)c(C)c1]

4-Methoxy-N,2,6-trimethyl-N-[(5-{[4-(3-pyrrolidin-1-ylpropyl)piperazin-1-yl]carbonyl}-1,2,4-oxadiazol-3-yl)methyl]benzenesulfonamide trifluoroacetamide Ex 304

The title compound was prepared according to general procedure AT using ethyl 3-({[(4-methoxy-2,6-dimethylphenyl)sulfonyl](methyl)amino}methyl)-1,2,4-oxadiazole-5-carboxylate (30 mg, 0.08 mmol), 1-[3-(pyrrolidin-1-yl)propyl]piperazine (63 mg, 0.32 mmol) and trimethylaluminium (2 M in toluene, 0.16 mL) in DCM (5 mL). A portion of the crude product was purified using prep method C.

LCMS Method C: rt 2.73 min, 99%; m/z 288.69 ([M+2H+MeCN]$^{2+}$, 100%), 535.19 (MH$^+$, 25%)

Potency: A

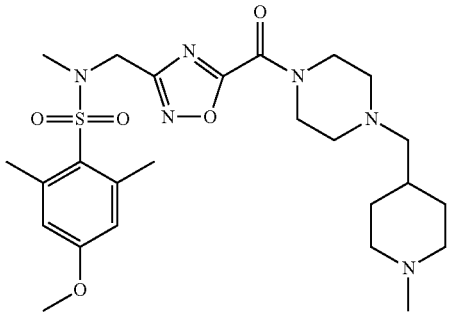 [SMILES: COc1cc(C)c(S(=O)(=O)N(C)Cc2noc(C(=O)N3CCN(CC4CCN(C)CC4)CC3)n2)c(C)c1]

4-Methoxy-N,2,6-trimethyl-N-{[5-({4-[(1-methylpiperidin-4-yl)methyl]piperazin-1-yl}carbonyl)-1,2,4-oxadiazol-3-yl]methyl}benzenesulfonamide trifluoroacetate Ex 305

The title compound was prepared according to general procedure AT using ethyl 3-({[(4-methoxy-2,6-dimethylphenyl)sulfonyl](methyl)amino}methyl)-1,2,4-oxadiazole-5-carboxylate (30 mg, 0.08 mmol), 1-[(1-methylpiperidin-4-yl)methyl]piperazine (31 mg, 0.16 mmol) and trimethylaluminium (2 M in toluene, 0.08 mL) in DCE (5 mL). The crude product was purified using prep method A, then FCC, eluting with 95:5:1 DCM:MeOH:NH$_3$.

Yield: 12.1 mg, 29%.

LCMS Method C: rt 2.63 min, 95%; m/z 268.19 ([M+2H]$^{2+}$, 100%), 535.18 (MH$^+$, 43%)

$^1$H NMR (500 MHz, CD$_3$OD): δ ppm 6.76 (2H, s), 4.55 (2H, s), 3.85 (3H, s), 3.74-3.81 (4H, m), 2.89-2.94 (2H, m), 2.87 (3H, s), 2.63 (6H, s), 2.54 (2H, t, J=5.1 Hz), 2.47-2.52 (2H, m), 2.30 (3H, s), 2.28 (2H, d, J=7.2 Hz), 2.07 (2H, t, J=11.1 Hz), 1.83 (2H, d, J=12.8 Hz), 1.61 (1H, ddd, J 11.1, 7.4, 3.9 Hz), 1.21-1.32 (2H, m)

Potency: C

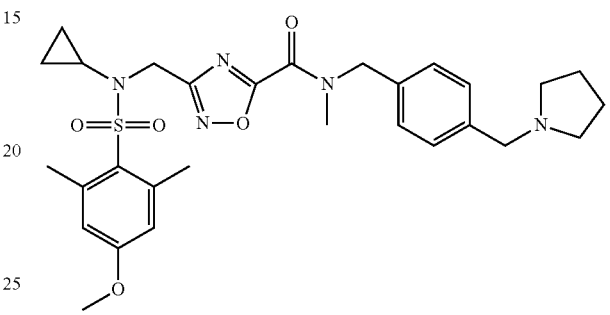

3-({Cyclopropyl[(4-methoxy-2,6-dimethylphenyl)sulfonyl]amino}methyl)-N-methyl-N-[4-(pyrrolidin-1-ylmethyl)benzyl]-1,2,4-oxadiazole-5-carboxamide trifluoroacetate Ex 306

The title compound was prepared according to general procedure AT using ethyl 3-({cyclopropyl[(4-methoxy-2,6-dimethylphenyl)sulfonyl]amino}methyl)-1,2,4-oxadiazole-5-carboxylate (30 mg, 0.07 mmol), N-methyl-1-[4-(pyrrolidin-1-ylmethyl)phenyl]methanamine (29 mg, 0.14 mmol) and trimethylaluminium (2 M in toluene, 0.07 mL) in DCE (5 mL). A portion of the crude product was purified using prep method A to afford the title compound.

LCMS Method C: rt 3.39 min, 100%; m/z 568.18 (MH$^+$, 100%)

Potency: C

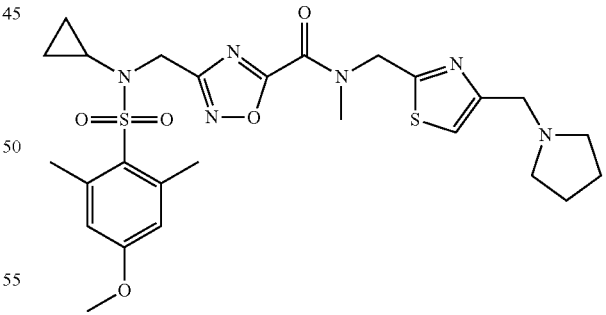

3-({Cyclopropyl[(4-methoxy-2,6-dimethylphenyl)sulfonyl]amino}methyl)-N-methyl-N-{[4-(pyrrolidin-1-ylmethyl)-1,3-thiazol-2-yl]methyl}-1,2,4-oxadiazole-5-carboxamide trifluoroacetate Ex 307

The title compound was prepared according to general procedure AT using ethyl 3-({cyclopropyl[(4-methoxy-2,6-dimethylphenyl)sulfonyl]amino}methyl)-1,2,4-oxadiazole-5-carboxylate (30 mg, 0.07 mmol), N-methyl-1-[4-(pyrrolidin-1-ylmethyl)-1,3-thiazol-2-yl]methanamine (30 mg, 0.14 mmol) and trimethylaluminium (2 M in toluene, 0.07 mL) in DCE (5 mL). A portion of the crude product was purified using prep method A to afford the title compound.

LCMS Method C: rt 3.34 min, 96%; m/z 575.16 (MH+, 100%)

Potency: B

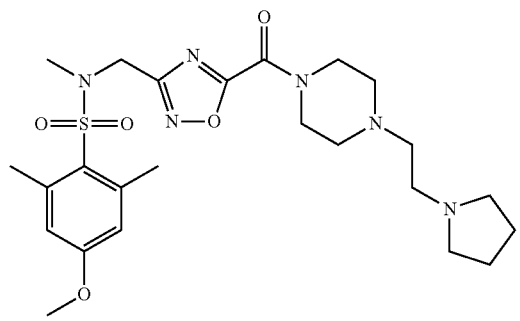 [SMILES: COc1cc(C)c(S(=O)(=O)N(C)Cc2noc(C(=O)N3CCN(CCN4CCCC4)CC3)n2)c(C)c1]

4-Methoxy-N,2,6-trimethyl-N-[(5-{[4-(2-pyrrolidin-1-ylethyl)piperazin-1-yl]carbonyl}-1,2,4-oxadiazol-3-yl)methyl]benzenesulfonamide Ex 308

The title compound was prepared according to general procedure AT using ethyl 3-({[(4-methoxy-2,6-dimethylphenyl)sulfonyl](methyl)amino}methyl)-1,2,4-oxadiazole-5-carboxylate (30 mg, 0.08 mmol), 1-[2-(pyrrolidin-1-yl)ethyl]piperazine (29 mg, 0.16 mmol) and trimethylaluminium (2 M in toluene, 0.08 mL) in DCE (5 mL). The crude product was purified using FCC, eluting with 95:4.5:0.5 DCM:MeOH:NH$_3$, to afford the title compound.

Yield: 32.3 mg, 77%.

LCMS Method C: rt 3.11 min, 99%; m/z 521.19 (MH+, 100%)

$^1$H NMR (500 MHz, CD$_3$OD): δ ppm 6.77 (2H, s), 4.55 (2H, s), 3.85 (3H, s), 3.77-3.83 (4H, m), 2.87 (3H, s), 2.69-2.75 (2H, m), 2.60-2.67 (14H, m), 2.57-2.60 (2H, m), 1.81-1.88 (4H, m)

Potency: A

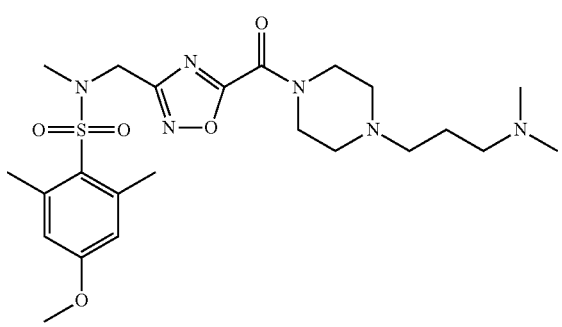

N-{[5-({4-[3-(Dimethylamino)propyl]piperazin-1-yl}carbonyl)-1,2,4-oxadiazol-3-yl]methyl}-4-methoxy-N,2,6-trimethylbenzenesulfonamide Ex 309

The title compound was prepared according to general procedure AT using ethyl 3-({[(4-methoxy-2,6-dimethylphenyl)sulfonyl](methyl)amino}methyl)-1,2,4-oxadiazole-5-carboxylate (30 mg, 0.08 mmol), N,N-dimethyl-3-(piperazin-1-yl)propan-1-amine (27 mg, 0.16 mmol) and trimethylaluminium (2 M in toluene, 0.08 mL) in DCE (5 mL). The crude product was purified using FCC, eluting with 95:4.5:0.5 DCM:MeOH:NH$_3$, to afford the title compound.

Yield: 11.9 mg, 30%.

LCMS Method C: rt 2.62 min, 94%; m/z 255.18 ([M+2H]$^{2+}$, 100%), 509.17 (MH+, 53%)

Potency: B

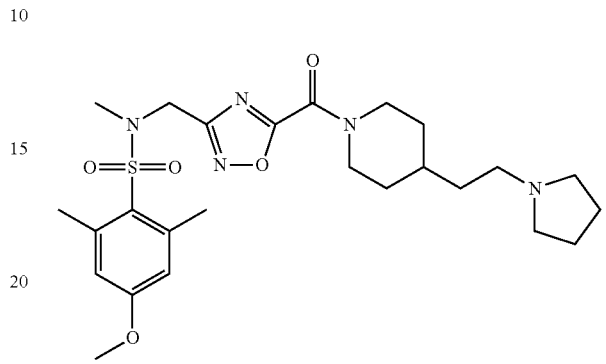

4-Methoxy-N,2,6-trimethyl-N-[(5-{[4-(2-pyrrolidin-1-ylethyl)piperidin-1-yl]carbonyl}-1,2,4-oxadiazol-3-yl)methyl]benzenesulfonamide Ex 310

The title compound was prepared according to general procedure AT using ethyl 3-({[(4-methoxy-2,6-dimethylphenyl)sulfonyl](methyl)amino}methyl)-1,2,4-oxadiazole-5-carboxylate (30 mg, 0.08 mmol), 4-[2-(pyrrolidin-1-yl)ethyl]piperidine (29 mg, 0.16 mmol) and trimethylaluminium (2 M in toluene, 0.08 mL) in DCE (5 mL). The crude product was purified using FCC, eluting with 95:4.5:0.5 DCM:MeOH:NH$_3$, to afford the title compound.

Yield: 29.7 mg, 73%.

LCMS Method C: rt 3.17 min, 95%; m/z 520.19 (MH+, 100%)

Potency: C

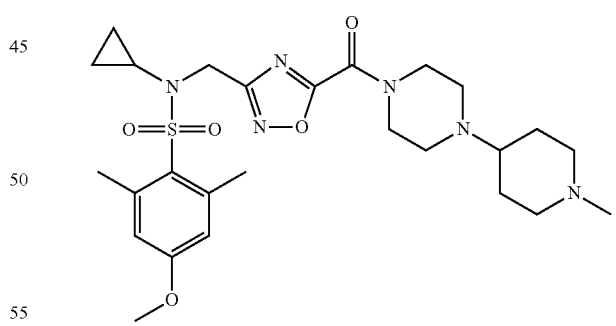

N-Cyclopropyl-4-methoxy-2,6-dimethyl-N-[(5-{[4-(1-methylpiperidin-4-yl)piperazin-1-yl]carbonyl}-1,2,4-oxadiazol-3-yl)methyl]benzenesulfonamide Ex 311

The title compound was prepared according to general procedure AT using ethyl 3-({cyclopropyl[(4-methoxy-2,6-dimethylphenyl)sulfonyl]amino}methyl)-1,2,4-oxadiazole-5-carboxylate (30 mg, 0.07 mmol), 1-(1-methylpiperidin-4-yl)piperazine (26 mg, 0.14 mmol) and trimethylaluminium (2

M in toluene, 0.07 mL) in DCE (5 mL). A portion of the crude product was purified using FCC, eluting with 95:4.5:0.5 DCM:MeOH:NH$_3$, to afford the title compound.

LCMS Method C: rt 2.84 min, 100%; m/z 274.20 ([M+2H]$^{2+}$, 100%), 547.21 (MH$^+$, 60%)

$^1$H NMR (500 MHz, CD$_3$OD): δ ppm 6.77 (2H, s), 4.76 (2H, s), 3.86 (3H, s), 3.78-3.85 (4H, m), 2.96 (2H, d, J=12.1 Hz), 2.65-2.75 (5H, m), 2.61 (6H, s), 2.33-2.43 (1H, m), 2.29 (3H, s), 2.09 (2H, t, J=11.3 Hz), 1.90 (2H, d, J=12.5 Hz), 1.52-1.67 (2H, m), 0.55-0.64 (2H, m), 0.24-0.34 (2H, m)

Potency: C

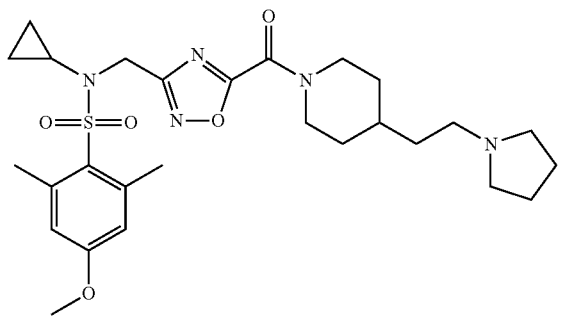 [SMILES: COc1cc(C)c(S(=O)(=O)N(Cc2noc(C(=O)N3CCC(CCN4CCCC4)CC3)n2)C2CC2)c(C)c1]

N-Cyclopropyl-4-methoxy-2,6-dimethyl-N-[(5-{[4-(2-pyrrolidin-1-ylethyl)piperidin-1-yl]carbonyl}-1,2,4-oxadiazol-3-yl)methyl]benzenesulfonamide Ex 312

The title compound was prepared according to general procedure AT using ethyl 3-({cyclopropyl[(4-methoxy-2,6-dimethylphenyl)sulfonyl]amino}methyl)-1,2,4-oxadiazole-5-carboxylate (30 mg, 0.07 mmol), 4-[2-(pyrrolidin-1-yl)ethyl]piperidine (29 mg, 0.14 mmol) and trimethylaluminium (2 M in toluene, 0.07 mL) in DCE (5 mL). A portion of the crude product was purified using FCC, eluting with 95:4.5:0.5 DCM:MeOH:NH$_3$, to afford the title compound.

LCMS Method C: rt 3.30 min, 100%; m/z 546.20 (MH$^+$, 100%)

Potency: C

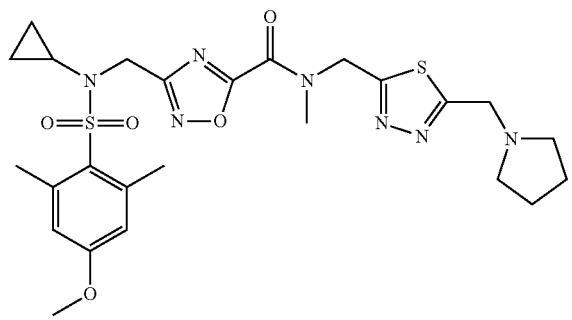 [SMILES: COc1cc(C)c(S(=O)(=O)N(Cc2noc(C(=O)N(C)Cc3nnc(CN4CCCC4)s3)n2)C2CC2)c(C)c1]

3-({Cyclopropyl[(4-methoxy-2,6-dimethylphenyl)sulfonyl]amino}methyl)-N-methyl-N-{[5-(pyrrolidin-1-ylmethyl)-1,3,4-thiadiazol-2-yl]methyl}-1,2,4-oxadiazole-5-carboxamide Ex 313

The title compound was prepared according to general procedure AT using ethyl 3-({cyclopropyl[(4-methoxy-2,6-dimethylphenyl)sulfonyl]amino}methyl)-1,2,4-oxadiazole-5-carboxylate (30 mg, 0.07 mmol), N-methyl-1-[5-(pyrrolidin-1-ylmethyl)-1,3,4-thiadiazol-2-yl]methanamine (34 mg, 0.14 mmol) and trimethylaluminium (2 M in toluene, 0.07 mL) in DCE (5 mL). A portion of the crude product was purified using prep method D to afford the title compound.

LCMS Method C: rt 3.26 min, 98%; m/z 576.12 (MH$^+$, 100%)

Potency: C

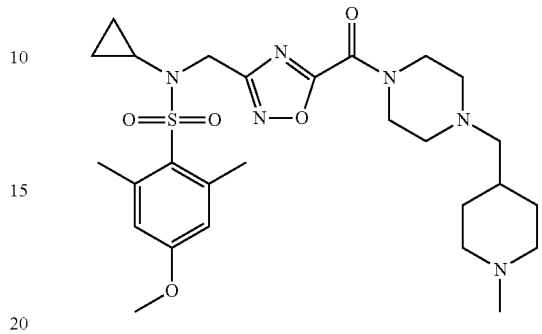

N-Cyclopropyl-4-methoxy-2,6-dimethyl-N-{[5-({4-[(1-methylpiperidin-4-yl)methyl]piperazin-1-yl}carbonyl)-1,2,4-oxadiazol-3-yl]methyl}benzenesulfonamide Ex 314

The title compound was prepared according to general procedure AT using ethyl 3-({cyclopropyl[(4-methoxy-2,6-dimethylphenyl)sulfonyl]amino}methyl)-1,2,4-oxadiazole-5-carboxylate (30 mg, 0.07 mmol), 1-[(1-methylpiperidin-4-yl)methyl]piperazine (31 mg, 0.14 mmol) and trimethylaluminium (2 M in toluene, 0.07 mL) in DCE (5 mL). A portion of the crude product was purified using prep method C, then FCC, eluting with 95:4.5:0.5 DCM:MeOH:NH$_3$, to afford the title compound.

LCMS Method C: rt 2.76 min, 100%; m/z 281.20 ([M+2H]$^{2+}$, 100%), 561.21 (MH$^+$, 35%)

$^1$H NMR (500 MHz, CD$_3$OD): δ ppm 6.77 (2H, s), 4.76 (2H, s), 3.86 (3H, s), 3.76-3.84 (4H, m), 2.91 (2H, d, J=11.6 Hz), 2.69 (1H, dt, J 6.9, 3.3 Hz), 2.60 (6H, s), 2.54 (4H, dt, J 14.0, 5.1 Hz), 2.30 (3H, s), 2.28 (2H, d, J=7.2 Hz), 2.02-2.11 (2H, m), 1.84 (2H, d, J=13.1 Hz), 1.61 (1H, dd, J 7.6, 3.6 Hz), 1.20-1.33 (2H, m), 0.55-0.62 (2H, m), 0.26-0.33 (2H, m)

Potency: C

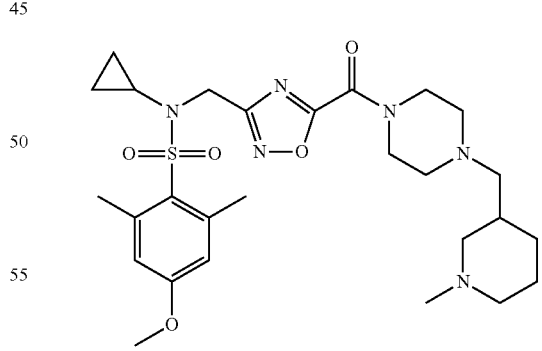

N-Cyclopropyl-4-methoxy-2,6-dimethyl-N-{[5-({4-[(1-methylpiperidin-3-yl)methyl]piperazin-1-yl}carbonyl)-1,2,4-oxadiazol-3-yl]methyl}benzenesulfonamide Ex 315

The title compound was prepared according to general procedure AT using ethyl 3-({cyclopropyl[(4-methoxy-2,6- dimethylphenyl)sulfonyl]amino}methyl)-1,2,4-oxadiazole-5-carboxylate (30 mg, 0.07 mmol), 1-[(1-methylpiperidin-3-yl)methyl]piperazine (31 mg, 0.14 mmol) and trimethylaluminium (2 M in toluene, 0.07 mL) in DCE (5 mL). A portion of the crude product was purified using prep method C, then FCC, eluting with 95:4.5:0.5 DCM:MeOH:NH$_3$, to afford the title compound.

LCMS Method C: rt 2.83 min, 100%; m/z 281.23 ([M+2H]$^{2+}$, 100%), 561.20 (MH$^+$, 78%)

Potency: B

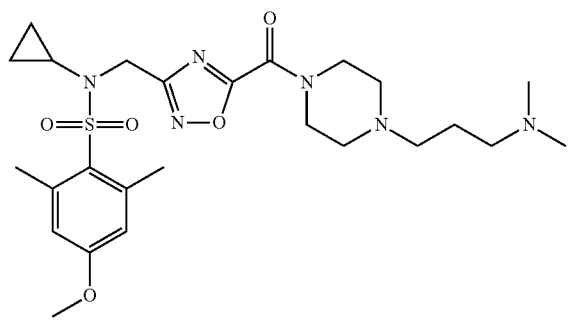 [SMILES: COc1cc(C)c(S(=O)(=O)N(Cc2noc(C(=O)N3CCN(CCCN(C)C)CC3)n2)C2CC2)c(C)c1]

N-Cyclopropyl-N-{[5-([4-[3-(dimethylamino)propyl]piperazin-1-yl]carbonyl)-1,2,4-oxadiazol-3-yl]methyl}-4-methoxy-2,6-dimethylbenzenesulfonamide Ex 316

The title compound was prepared according to general procedure AT using ethyl 3-({cyclopropyl[(4-methoxy-2,6-dimethylphenyl)sulfonyl]amino}methyl)-1,2,4-oxadiazole-5-carboxylate (30 mg, 0.07 mmol), N,N-dimethyl-3-(piperazin-1-yl)propan-1-amine (27 mg, 0.14 mmol) and trimethylaluminium (2 M in toluene, 0.07 mL) in DCE (5 mL). A portion of the crude product was purified using FCC, eluting with 95:4.5:0.5 DCM:MeOH:NH$_3$, to afford the title compound.

LCMS Method C: rt 2.79 min, 94%; m/z 268.17 ([M+2H]$^{2+}$, 100%), 535.19 (MH$^+$, 50%)

Potency: B

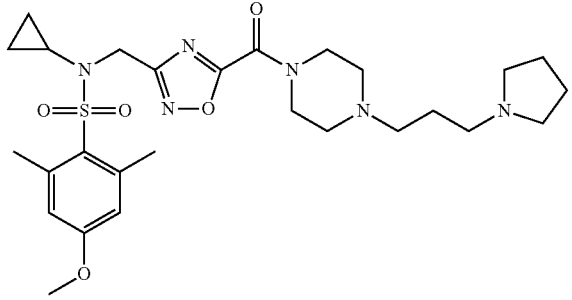 [SMILES: COc1cc(C)c(S(=O)(=O)N(Cc2noc(C(=O)N3CCN(CCCN4CCCC4)CC3)n2)C2CC2)c(C)c1]

N-Cyclopropyl-4-methoxy-2,6-dimethyl-N-[(5-{[4-(3-pyrrolidin-1-ylpropyl)piperazin-1-yl]carbonyl}-1,2,4-oxadiazol-3-yl)methyl]benzenesulfonamide Ex 317

The title compound was prepared according to general procedure AT using ethyl 3-({cyclopropyl[(4-methoxy-2,6-dimethylphenyl)sulfonyl]amino}methyl)-1,2,4-oxadiazole-5-carboxylate (30 mg, 0.07 mmol), 1-[3-(pyrrolidin-1-yl)propyl]piperazine (31 mg, 0.16 mmol) and trimethylaluminium (2 M in toluene, 0.07 mL) in DCE (3 mL). The crude product was purified using prep method C, then FCC, eluting with 95:4.5:0.5 DCM:MeOH:NH$_3$, to afford the title compound.

Yield: 11.9 mg, 30%.

LCMS Method C: rt 2.81 min, 99%; m/z 281.20 ([M+2H]$^{2+}$, 100%), 561.22 (MH$^+$, 38%)

Potency: C

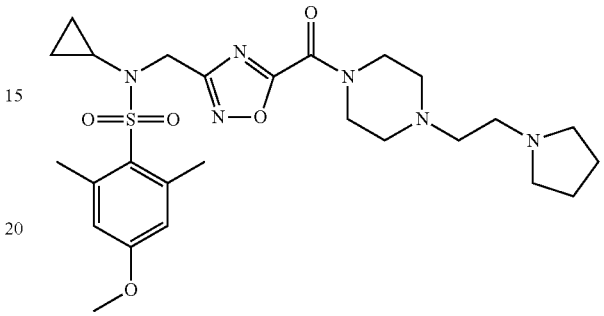

N-Cyclopropyl-4-methoxy-2,6-dimethyl-N-[(5-{[4-(2-pyrrolidin-1-ylethyl)piperazin-1-yl]carbonyl}-1,2,4-oxadiazol-3-yl)methyl]benzenesulfonamide Ex 318

The title compound was prepared according to general procedure AT using ethyl 3-({cyclopropyl[(4-methoxy-2,6-dimethylphenyl)sulfonyl]amino}methyl)-1,2,4-oxadiazole-5-carboxylate (30 mg, 0.07 mmol), 1-[2-(pyrrolidin-1-yl)ethyl]piperazine (29 mg, 0.16 mmol) and trimethylaluminium (2 M in toluene, 0.07 mL) in DCE (3 mL). The crude product was purified using prep method C, then FCC, eluting with 95:4.5:0.5 DCM:MeOH:NH$_3$, to afford the title compound.

Yield: 10.8 mg, 28%.

LCMS Method C: rt 3.25 min, 99%; m/z 547.21 (MH$^+$, 100%)

Potency: B

General Procedure CE

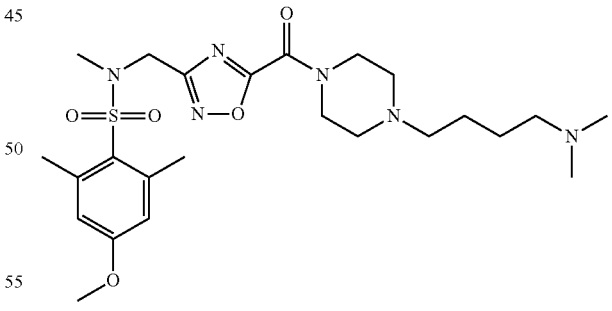

N-{[5-({4-[4-(Dimethylamino)butyl]piperazin-1-yl}carbonyl)-1,2,4-oxadiazol-3-yl]methyl}-4-methoxy-N,2,6-trimethylbenzenesulfonamide trifluoroacetate Ex 319

Ethyl 3-({[(4-methoxy-2,6-dimethylphenyl)sulfonyl](methyl)amino}methyl)-1,2,4-oxadiazole-5-carboxylate (38 mg, 0.1 mmol) and N,N-dimethyl-4-piperazin-1-ylbutan-1-amine (27 mg, 0.15 mmol) were dissolved in DCE (1 mL) and the solution degassed under N$_2$. The solution was cooled to 0° C. and trimethylaluminium (2.0 M in toluene, 0.075 mL) was added. The reaction was stirred in a sealed vessel at 60° C. for 1 h. The reaction was cooled and diluted with DCM (2 mL) and washed with saturated aqueous NaHCO$_3$ (1 mL). The organic layer was dried over MgSO$_4$ and concentrated in vacuo. The crude product was purified using prep method A to afford the title compound.

Yield: 25 mg, 47%

LCMS method C: rt 2.59 min, 97%; m/z 523.37 (MH$^+$, 100%).

$^1$H NMR (500 MHz, CD$_3$OD) δ ppm 6.75 (2H, s), 4.58 (2H, s), 3.82 (3H, s), 3.34-3.60 (4H, m), 3.23-3.28 (2H, m), 3.14-3.20 (2H, m), 2.88 (6H, s), 2.78 (3H, s), 2.59 (6H, s), 1.75-1.91 (4H, m).

Potency: A

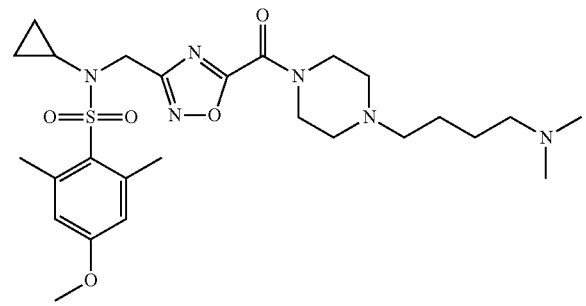 [SMILES: COc1cc(C)c(S(=O)(=O)N(Cc2noc(C(=O)N3CCN(CCCCN(C)C)CC3)n2)C2CC2)c(C)c1]

N-Cyclopropyl-N-{[5-({4-[4-(dimethylamino)butyl]piperazin-1-yl}carbonyl)-1,2,4-oxadiazol-3-yl]methyl}-4-methoxy-2,6-dimethylbenzenesulfonamide trifluoroacetate Ex 320

The title compound was prepared according to general procedure CE using 3 ethyl 3-({cyclopropyl[(4-methoxy-2,6-dimethylphenyl)sulfonyl]amino}methyl)-1,2,4-oxadiazole-5-carboxylate (41 mg, 0.1 mmol), N,N-dimethyl-4-piperazin-1-ylbutan-1-amine (27 mg, 0.15 mmol), DCE (1 mL) and trimethylaluminium (2.0 M in toluene, 0.075 mL). The crude product was purified using prep method A to afford the title compound.

Yield: 37 mg, 67%

LCMS method C: rt 2.71 min, 98%; m/z 549.38 (MH$^+$, 100%).

$^1$H NMR (500 MHz, CD$_3$OD) δ ppm 6.73 (2H, s), 4.74 (2H, s), 3.81 (3H, s), 3.34-3.66 (4H, m), 3.20-3.28 (2H, m), 3.07-3.20 (2H, m), 2.87 (6H, s), 2.56-2.59 (1H, m), 2.55 (6H, s), 1.82 (4H, br. s.), 0.39-0.63 (2H, m), 0.07-0.31 (2H, m)

Potency: A

Scheme 12 describes the general synthesis of oxadiazole derivatives.

(R$^1$=Me; R$^{1a}$=R$^{1b}$=H; X$^1$=X$^3$=N; X$^2$=O; NR$^2$R$^3$=various amines)

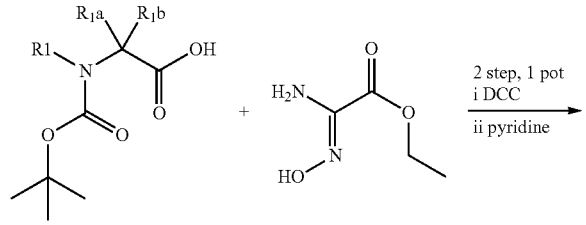

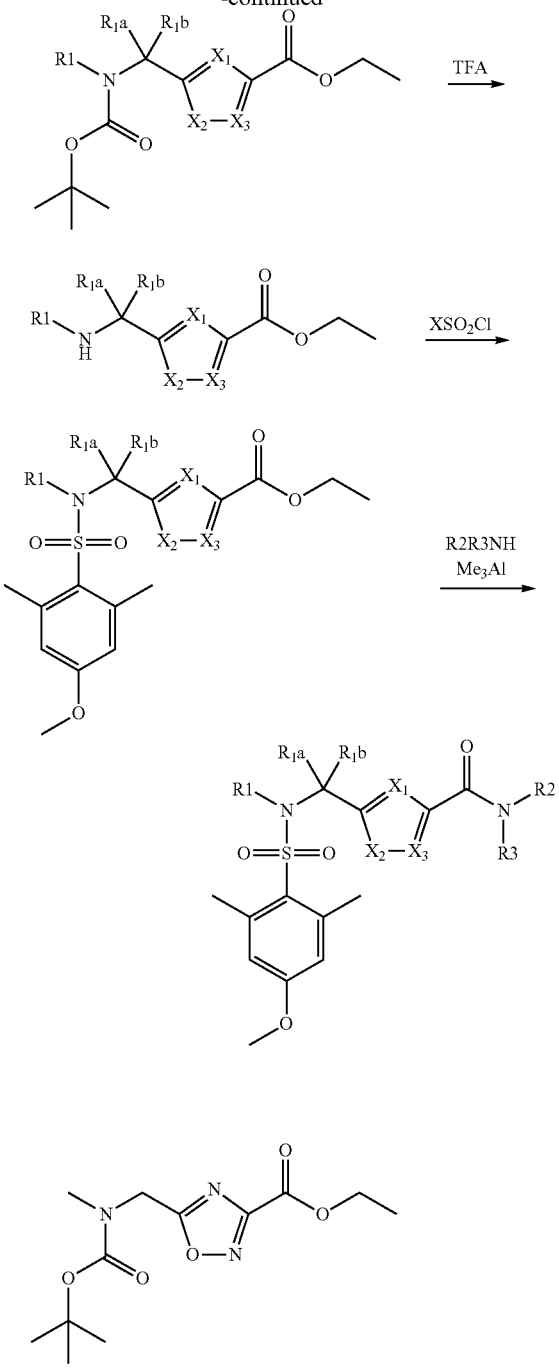

Ethyl 5-{[(tert-butoxycarbonyl)(methyl)amino]methyl}-1,2,4-oxadiazole-3-carboxylate Int 296

Boc sarcosine (500 mg, 2.64 mmol) and DCC (270 mg, 1.31 mmol) were stirred together in DCM (10 mL) at 0° C. for 1 h. The mixture was filtered to remove a white precipitate of DCU, concentrated in vacuo and dissolved in pyridine (4 mL). To this solution was added ethyl 2-oximinooxamate (173 mg, 1.31 mmol) as a solution in pyridine (2 mL) and the reaction was heated to 120° C. for 3 h, then stirred at ambient temperature for 18 h. The reaction was quenched with H$_2$O (2 mL), then concentrated in vacuo and the residue partitioned between H₂O (10 mL) and DCM (3×10 mL). The combined organic extracts were washed with saturated aqueous NaHCO₃ (10 mL), aqueous HCl (0.1 M, 10 mL) and brine (10 mL), dried over MgSO₄ and concentrated in vacuo to afford the title compound.

Yield: 304 mg, 81%.

LCMS Method A: rt 1.27 min, 69%; m/z 308.00 (MNa⁺, 100%)

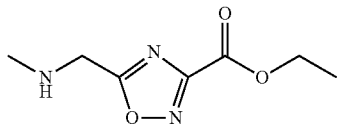

Ethyl 5-[(methylamino)methyl]-1,2,4-oxadiazole-3-carboxylate

Int 297

The title compound was prepared according to general procedure AN using ethyl 5-{[(tert-butoxycarbonyl)(methyl)amino]methyl}-1,2,4-oxadiazole-3-carboxylate (300 mg, 1.06 mmol), TFA (0.816 mL, 10.60 mmol) and DCM (5 mL), stirring at ambient temperature for 2 h, then at 40° C. for 2 h prior to concentration in vacuo. The crude product was used without further purification.

¹H NMR (500 MHz, CD₃OD): δ ppm 4.71 (2H, s), 4.46 (2H, q, J=7.1 Hz), 2.88 (3H, s), 1.37 (3H, t, J=7.2 Hz)

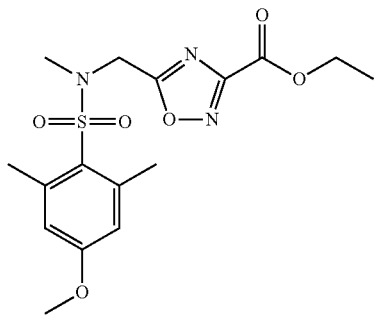

Ethyl 5-({[(4-methoxy-2,6-dimethylphenyl)sulfonyl](methyl)amino}methyl)-1,2,4-oxadiazole-3-carboxylate Int 298

Ethyl 5-[(methylamino)methyl]-1,2,4-oxadiazole-3-carboxylate (0.77 mmol), 4-methoxy-2,6-dimethylbenzenesulfonyl chloride (200 mg, 0.85 mmol) and TEA (0.236 mL, 1.70 mmol) were stirred together in DCM (10 mL) at ambient temperature for 2 h, then concentrated in vacuo. The residue was partitioned between saturated aqueous NaHCO₃ (20 mL) and DCM (3×15 mL) and the combined organic extracts were dried over MgSO₄ and concentrated in vacuo. The crude product was purified using FCC, eluting with 10% EtOAc in heptane, to afford the title compound.

Yield: 192 mg, 65%.

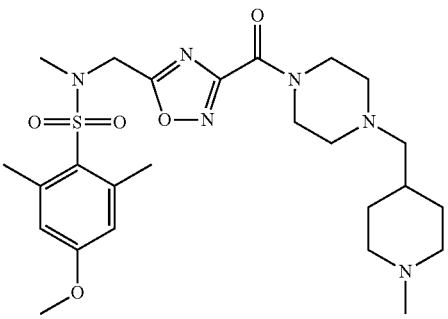 [SMILES: COc1cc(C)c(S(=O)(=O)N(C)Cc2nc(C(=O)N3CCN(CC4CCN(C)CC4)CC3)no2)c(C)c1]

4-Methoxy-N,2,6-trimethyl-N-{[3-({4-[(1-methylpiperidin-4-yl)methyl]piperazin-1-yl}carbonyl)-1,2,4-oxadiazol-5-yl]methyl}benzenesulfonamide Ex 321

The title compound was prepared according to general procedure AT using ethyl 5-({[(4-methoxy-2,6-dimethylphenyl)sulfonyl](methyl)amino}methyl)-1,2,4-oxadiazole-3-carboxylate (35 mg, 0.09 mmol), 1-[(1-methylpiperidin-4-yl)methyl]piperazine (34 mg, 0.17 mmol) and trimethylaluminium (2 M in toluene, 0.08 mL) in DCE (3 mL). A portion of the crude product was purified using prep method D.

LCMS Method C: rt 2.71 min, 100%; m/z 268.24 ([M+2H]²⁺, 100%), 535.40 (MH⁺, 31%)

Potency: A

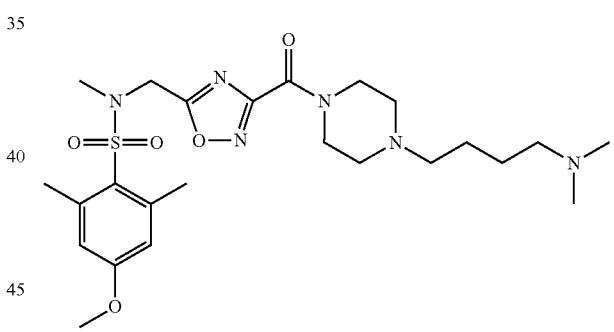

N-{[3-({4-[4-(Dimethylamino)butyl]piperazin-1-yl}carbonyl)-1,2,4-oxadiazol-5-yl]methyl}-4-methoxy-N,2,6-trimethylbenzenesulfonamide trifluoroacetate Ex 322

The title compound was prepared according to general procedure AT using ethyl 5-({[(4-methoxy-2,6-dimethylphenyl)sulfonyl](methyl)amino}methyl)-1,2,4-oxadiazole-3-carboxylate (27 mg, 0.07 mmol), N,N-dimethyl-4-(piperazin-1-yl)butan-1-amine (40 mg, 0.22 mmol) and trimethylaluminium (2 M in toluene, 0.08 mL) in DCE (2 mL). A portion of the crude product was purified using prep method D, then prep method A.

LCMS Method C: rt 2.60 min, 100%; m/z 198.99 (ArSO₂⁺, 100%), 262.25 ([M+2H]²⁺, 94%), 325.32 (M+2H—ArSO₂, 90%), 523.42 (MH⁺, 33%)

Potency: A

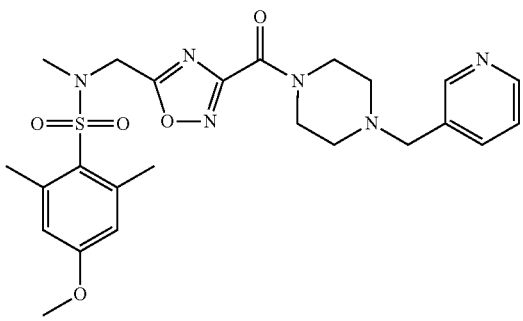 [SMILES: COc1cc(C)c(S(=O)(=O)N(C)Cc2nc(C(=O)N3CCN(Cc4cccnc4)CC3)no2)c(C)c1]

4-Methoxy-N,2,6-trimethyl-N-[(3-{[4-(pyridin-3-ylmethyl)piperazin-1-yl]carbonyl}-1,2,4-oxadiazol-5-yl)methyl]benzenesulfonamide Ex 323

The title compound was prepared according to general procedure AT using ethyl 5-({[(4-methoxy-2,6-dimethylphenyl)sulfonyl](methyl)amino}methyl)-1,2,4-oxadiazole-3-carboxylate (27 mg, 0.07 mmol), 1-(pyridin-3-ylmethyl)piperazine (40 mg, 0.23 mmol) and trimethylaluminium (2 M in toluene, 0.08 mL) in DCE (2 mL). A portion of the crude product was purified using prep method D.

LCMS Method C: rt 3.14 min, 100%; m/z 515.36 (MH+, 100%)

Potency: A

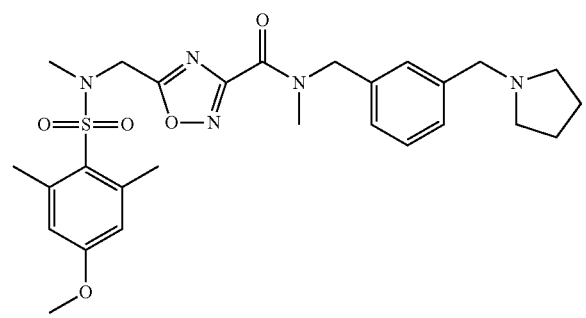 [SMILES: COc1cc(C)c(S(=O)(=O)N(C)Cc2nc(C(=O)N(C)Cc3cccc(CN4CCCC4)c3)no2)c(C)c1]

5-({[(4-Methoxy-2,6-dimethylphenyl)sulfonyl](methyl)amino}methyl)-N-methyl-N-[3-(pyrrolidin-1-ylmethyl)benzyl]-1,2,4-oxadiazole-3-carboxamide trifluoroacetate Ex 324

The title compound was prepared according to general procedure AT using ethyl 5-({[(4-methoxy-2,6-dimethylphenyl)sulfonyl](methyl)amino}methyl)-1,2,4-oxadiazole-3-carboxylate (27 mg, 0.07 mmol), N-methyl-1-[3-(pyrrolidin-1-ylmethyl)phenyl]methanamine (40 mg, 0.20 mmol) and trimethylaluminium (2 M in toluene, 0.08 mL) in DCE (2 mL). A portion of the crude product was purified using prep method D, then prep method A.

LCMS Method C: rt 3.27 min, 99%; m/z 542.39 (MH+, 100%)

Potency: B

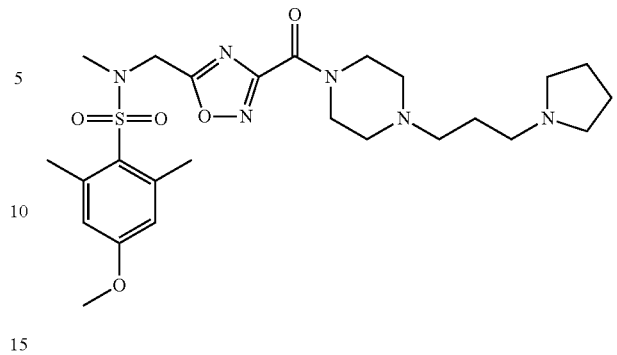

4-Methoxy-N,2,6-trimethyl-N-[(3-{[4-(3-pyrrolidin-1-ylpropyl)piperazin-1-yl]carbonyl}-1,2,4-oxadiazol-5-yl)methyl]benzenesulfonamide Ex 325

The title compound was prepared according to general procedure AT using ethyl 5-({[(4-methoxy-2,6-dimethylphenyl)sulfonyl](methyl)amino}methyl)-1,2,4-oxadiazole-3-carboxylate (27 mg, 0.07 mmol), 1-[3-(pyrrolidin-1-yl)propyl]piperazine (40 mg, 0.20 mmol) and trimethylaluminium (2 M in toluene, 0.08 mL) in DCE (2 mL). A portion of the crude product was purified using prep method D.

LCMS Method C: rt 2.72 min, 100%; m/z 198.99 (ArSO$_2^+$, 100%), 337.29 ([M+2H—ArSO$_2$]$^+$, 93%), 268.24 ([M+2H]$^{2+}$, 46%), 535.40 (MH+, 37%)

$^1$H NMR (500 MHz, CD$_3$OD): δ ppm 6.79 (2H, s), 4.74 (2H, s), 3.86 (3H, s), 3.80-3.84 (2H, m), 3.60-3.64 (2H, m), 2.87-3.03 (7H, m,), 2.63 (6H, s), 2.60 (2H, t, J=5.2 Hz), 2.49-2.56 (4H, m), 1.98 (4H, br. s.), 1.83-1.90 (2H, m), 1.31-1.36 (2H, m)

Potency: B

Scheme 13 describes the general synthesis of thiadiazole derivatives.

(R$^1$=Me, cyclopropyl; R$^{1a}$=R$^{1b=H}$; $X^1$=S, $X^2$=X$^3$=N; NR2R3=various amines)

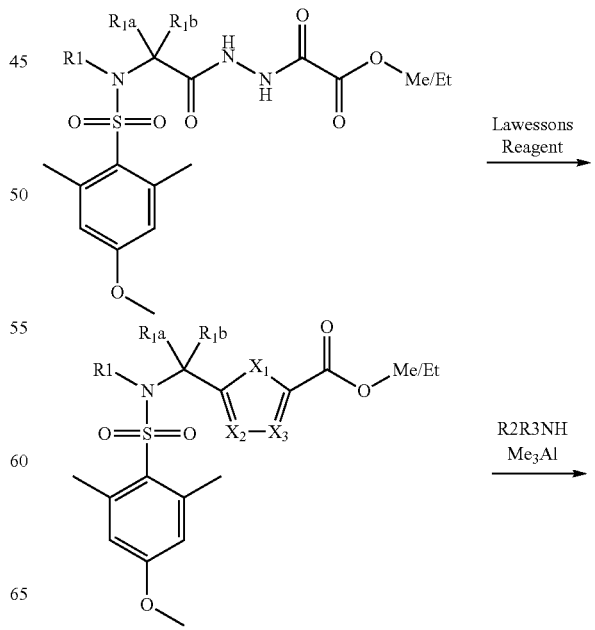

-continued

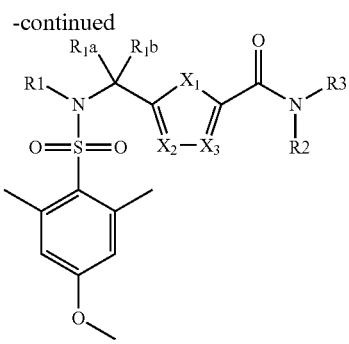

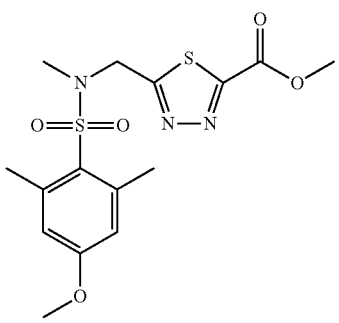

Methyl 5-({[(4-methoxy-2,6-dimethylphenyl)sulfonyl](methyl)amino}methyl)-1,3,4-thiadiazole-2-carboxylate Int 299

Methyl[2-({[(4-methoxy-2,6-dimethylphenyl)sulfonyl](methyl)amino}acetyl) hydrazino(oxo) acetate (1.6 g, 4.13 mmol) was dissolved in THF (25 mL) and Lawesson's reagent (2.0 g, 4.96 mmol) added. The reaction was heated to reflux for 2 h, cooled to ambient temperature and concentrated in vacuo. The resulting residue was purified by FCC, eluting with 0-30% EtOAc in hexane to afford the title compound as a pale yellow semi solid.

Yield: 800 mg, 53%.

$^1$H NMR (300 MHz, CDCl$_3$): δ ppm 6.66 (2H, s), 4.79 (2H, s), 4.03 (3H, s), 3.82 (3H, s), 2.74 (3H, s), 2.63 (6H, s).

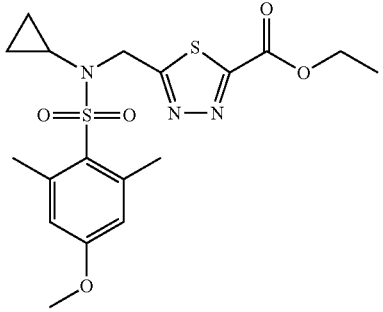 [SMILES: CCOC(=O)c1nnc(CN(C2CC2)S(=O)(=O)c2c(C)cc(OC)cc2C)s1]

Ethyl 5-({cyclopropyl[(4-methoxy-2,6-dimethylphenyl)sulfonyl]amino}methyl)-1,3,4-thiadiazole-2-carboxylate Int 300

Ethyl[2-({cyclopropyl[(4-methoxy-2,6-dimethylphenyl)sulfonyl]amino}acetyl)hydrazino](oxo)acetate (1 g, 2.34 mmol) was stirred in anhydrous THF (20 mL) under N$_2$ and Lawesson's reagent (1.13 g, 2.79 mmol) was added. The reaction was heated to 80° C. for 1 h, then allowed to cool and partitioned between 1:1 saturated brine:H$_2$O (100 mL) and DCM (4×50 mL). The combined organic extracts were then dried over MgSO$_4$ and concentrated in vacuo. The crude product was then purified twice using FCC, eluting with 25% EtOAc in heptane, then 20% EtOAc in heptane, to afford the title compound as a yellow solid.

Yield: 370 mg, 37%.

$^1$H NMR (500 MHz, CDCl$_3$): δ ppm 6.66 (2H, s), 5.04 (2H, s), 4.53 (2H, q, J=7.2 Hz), 3.85 (3H, s), 2.61 (6H, s), 2.49 (1H, dt, J 6.9, 3.2 Hz), 1.47 (3H, t, J=7.2 Hz), 0.57-0.63 (2H, m), 0.25-0.30 (2H, m)

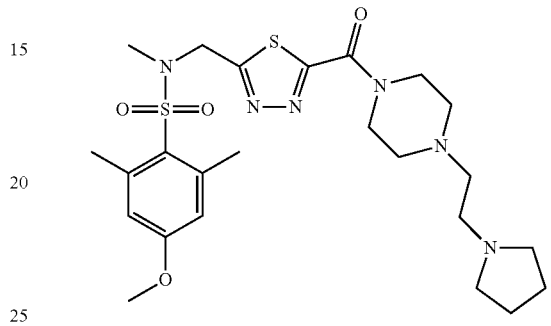

4-Methoxy-N,2,6-trimethyl-N-[(5-{[4-(2-pyrrolidin-1-ylethyl)piperazin-1-yl]carbonyl}-1,3,4-thiadiazol-2-yl)methyl]benzenesulfonamide Ex 326

The title compound was prepared according to general procedure BK using methyl 5-({[(4-methoxy-2,6-dimethylphenyl)sulfonyl](methyl)amino}methyl)-1,3,4-thiadiazole-2-carboxylate (125 mg, 0.32 mmol), 1-(2-pyrrolidin-1-yl-ethyl)-piperazine (71 mg, 0.39 mmol), trimethylaluminium (2 M in toluene, 0.35 mL) and THF (10 mL).

Yield: 22 mg, 13%

LCMS method C: rt 3.08 min, 95%; m/z 537.13 (MH$^+$, 100%).

Potency: A

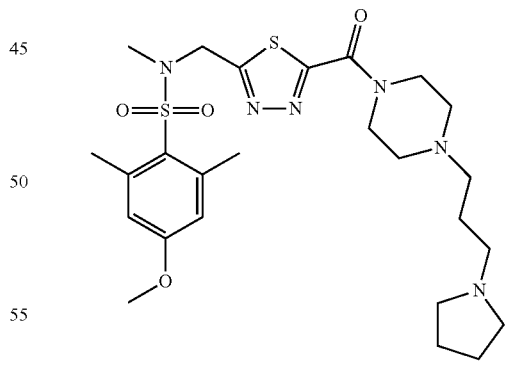

4-Methoxy-N,2,6-trimethyl-N-[(5-{[4-(3-pyrrolidin-1-ylpropyl)piperazin-1-yl]carbonyl}-1,3,4-thiadiazol-2-yl)methyl]benzenesulfonamide Ex 327

The title compound was prepared according to general procedure BK using methyl 5-({[(4-methoxy-2,6-dimethylphenyl)sulfonyl](methyl)amino}methyl)-1,3,4-thiadiazole-2-carboxylate (200 mg, 0.50 mmol), 1-(3-pyrrolidin-1- ylpropyl)piperazine (118 mg, 0.60 mmol), THF (10 mL) and trimethylaluminium (2.0 M in toluene, 0.55 mL). The crude product was purified by FCC, eluting with 0-2% MeOH in DCM to afford the title compound as a white solid.

Yield: 90 mg, 34%

LCMS method C: rt 2.64 min, 96%; m/z 551.18 (MH$^+$, 100%).

Potency: A

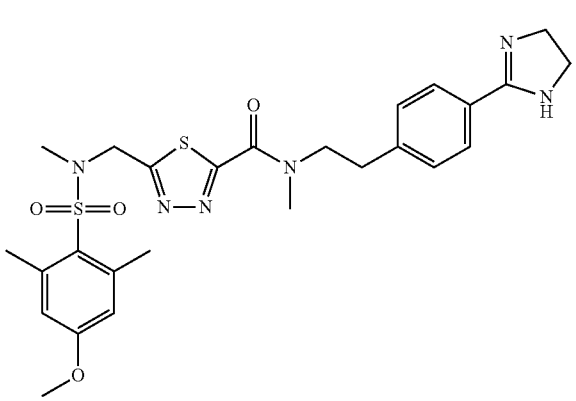

N-{2-[4-(4,5-Dihydro-1H-imidazol-2-yl)phenyl] ethyl}-5-({[(4-methoxy-2,6-dimethylphenyl)sulfonyl](methyl)amino}methyl)-N-methyl-1,3,4-thiadiazole-2-carboxamide Ex 328

The title compound was prepared according to general procedure AT using methyl 5-({[(4-methoxy-2,6-dimethylphenyl)sulfonyl](methyl)amino}methyl)-1,3,4-thiadiazole-2-carboxylate (50 mg, 0.13 mmol), 2-[4-(4,5-dihydro-1H-imidazol-2-yl)phenyl]-N-methylethanamine (110 mg, 0.54 mmol) and trimethylaluminium (2 M in toluene, 0.27 mL) in DCM (10 mL). A portion of the crude product was purified using prep method A, then prep method B.

LCMS Method C: rt 3.22 min, 100%; m/z 557.16 (MH$^+$, 86%), 558.17 (MH$^+$, 100%)

Potency: C

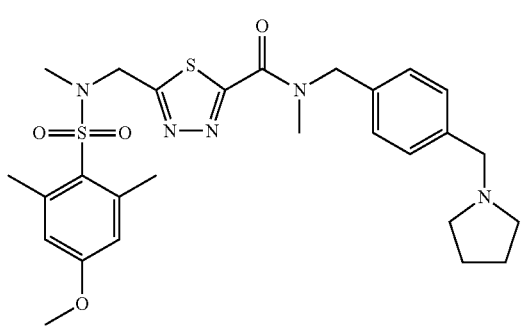

5-({[(4-Methoxy-2,6-dimethylphenyl)sulfonyl](methyl)amino}methyl)-N-methyl-N-[4-(pyrrolidin-1-ylmethyl)benzyl]-1,3,4-thiadiazole-2-carboxamide Ex 329

The title compound was prepared according to general procedure AT using methyl 5-({[(4-methoxy-2,6-dimethylphenyl)sulfonyl](methyl)amino}methyl)-1,3,4-thiadiazole-2-carboxylate (50 mg, 0.13 mmol), N-methyl 1-[4(pyrrolidinylmethyl)phenyl]methanamine (110 mg, 0.54 mmol) and trimethylaluminium (2 M in toluene, 0.27 mL) in DCM (10 mL). A portion of the crude product was purified using prep method B.

LCMS Method C: rt 3.26 min, 99%; m/z 558.17 (MH$^+$, 100%)

Potency: A

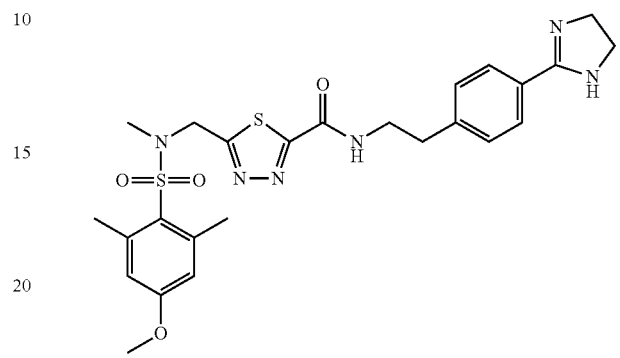

N-{2-[4-(4,5-Dihydro-1H-imidazol-2-yl)phenyl] ethyl}-5-({[(4-methoxy-2,6-dimethylphenyl)sulfonyl](methyl)amino}methyl)-1,3,4-thiadiazole-2-carboxamide trifluoroacetamide Ex 330

The title compound was prepared according to general procedure AT using methyl 5-({[(4-methoxy-2,6-dimethylphenyl)sulfonyl](methyl)amino}methyl)-1,3,4-thiadiazole-2-carboxylate (50 mg, 0.13 mmol), 1-[4-(4,5-dihydro-1H-imidazol-2-yl)phenyl]ethanamine (100 mg, 0.53 mmol) and trimethylaluminium (2 M in toluene, 0.27 mL) in DCM (5 mL). A portion of the crude product was purified using prep method C.

LCMS Method C: rt 3.20 min, 100%; m/z 543.17 (MH$^+$, 100%)

Potency: C

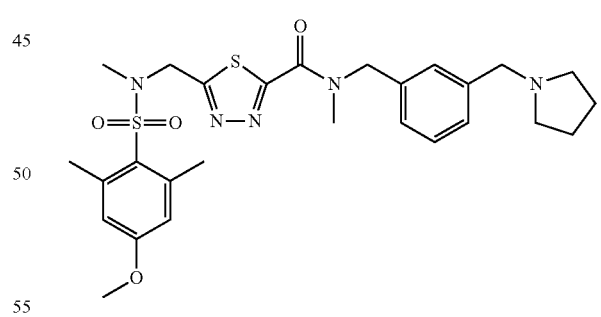

5-({[(4-Methoxy-2,6-dimethylphenyl)sulfonyl](methyl)amino}methyl)-N-methyl-N-[3-(pyrrolidin-1-ylmethyl)benzyl]-1,3,4-thiadiazole-2-carboxamide trifluoroacetate Ex 331

The title compound was prepared according to general procedure AT using methyl 5-({[(4-methoxy-2,6-dimethylphenyl)sulfonyl](methyl)amino}methyl)-1,3,4-thiadiazole-2-carboxylate (50 mg, 0.13 mmol), N-methyl-1-[3-(pyrrolidin-1-ylmethyl)phenyl]methanamine (110 mg, 0.54 mmol) and trimethylaluminium (2 M in toluene, 0.27 mL) in DCM (10 mL). A portion of the product was purified using prep method A.

LCMS Method C: rt 3.31 min, 97%; m/z 558.21 (MH+, 100%)
Potency: B

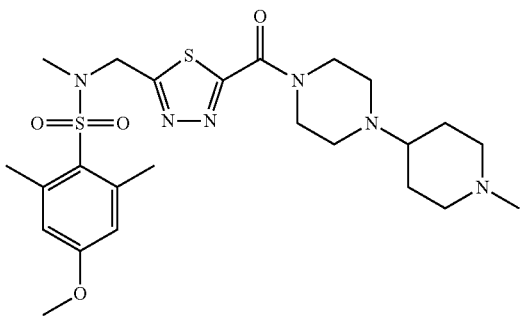

4-Methoxy-N,2,6-trimethyl-N-[(5-{[4-(1-methylpip-eridin-4-yl)piperazin-1-yl]carbonyl}-1,3,4-thiadia-zol-2-yl)methyl]benzenesulfonamide trifluoroaceta-mide Ex 332

The title compound was prepared according to general procedure AT using methyl 5-({[(4-methoxy-2,6-dimeth-ylphenyl)sulfonyl](methyl)amino}methyl)-1,3,4-thiadiaz-ole-2-carboxylate (30 mg, 0.08 mmol), 1-(1-methylpiperi-din-4-yl)piperazine (60 mg, 0.33 mmol) and trimethylaluminium (2 M in toluene, 0.16 mL) in DCM (5 mL). A portion of the product was purified using prep method C.

LCMS Method C: rt 2.62 min, 99%; m/z 537.19 (MH+, 100%)

$^1$H NMR (500 MHz, CD$_3$OD): δ ppm 6.80 (2H, s), 4.83 (2H, s), 4.62 (2H, br. s.), 4.10 (2H, br. s.), 3.86 (3H, s), 3.71 (2H, br. s.), 3.53-3.60 (1H, m), 3.49 (4H, br. s.), 3.14 (2H, br. s.), 2.92 (3H, s), 2.82 (3H, s), 2.64 (6H, s), 2.46 (2H, br. s.), 2.07-2.18 (2H, m)
Potency: A

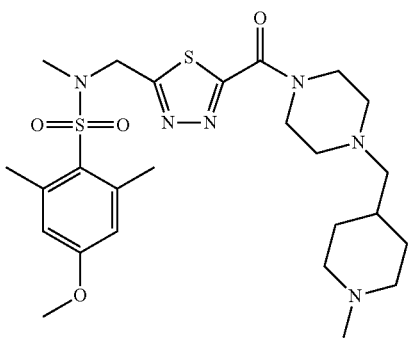 [SMILES: COc1cc(C)c(S(=O)(=O)N(C)Cc2nnc(C(=O)N3CCN(CC4CCN(C)CC4)CC3)s2)c(C)c1]

4-Methoxy-N,2,6-trimethyl-N-{[5-({4-[(1-methylpi-peridin-4-yl)methyl]piperazin-1-yl}carbonyl)-1,3,4-thiadiazol-2-yl]methyl}benzenesulfonamide Ex 333

The title compound was prepared according to general procedure BK using methyl 5-({[(4-methoxy-2,6-dimeth-ylphenyl)sulfonyl](methyl)amino}methyl)-1,3,4-thiadiaz-ole-2-carboxylate (100 mg, 0.26 mmol), 1-(1-methyl-piperi-din-4-ylmethyl)-piperazine (61 mg, 0.31 mmol), trimethylaluminium (2 M in toluene, 0.28 mL) and THF (10 mL).

Yield: 56 mg, 40%
LCMS method C: rt 2.59 min, 100%; m/z 276.19 ([M+2H]$^{2+}$, 100%), 551.18 (MH+, 59%).
Potency: A

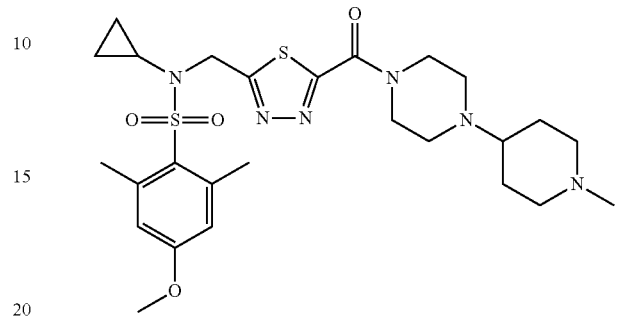

N-Cyclopropyl-4-methoxy-2,6-dimethyl-N-[(5-{[4-(1-methylpiperidin-4-yl)piperazin-1-yl]carbonyl}-1,3,4-thiadiazol-2-yl)methyl]benzenesulfonamide Ex 334

The title compound was prepared according to general procedure AT using ethyl 5-({cyclopropyl[(4-methoxy-2,6-dimethylphenyl)sulfonyl]amino}methyl)-1,3,4-thiadiazole-2-carboxylate (30 mg, 0.07 mmol), 1-(1-methylpiperidin-4-yl)piperazine (26 mg, 0.14 mmol) and trimethylaluminium (2 M in toluene, 0.07 mL) in DCE (5 mL). The crude product was purified using FCC, eluting with 95:4.5:0.5 DCM:MeOH:NH$_3$, to afford the title compound.

Yield: 12.4 mg, 32%.
LCMS Method C: rt 2.80 min, 100%; m/z 282.21 ([M+2H]$^{2+}$, 100%), 563.21 (MH+, 58%)
Potency: C

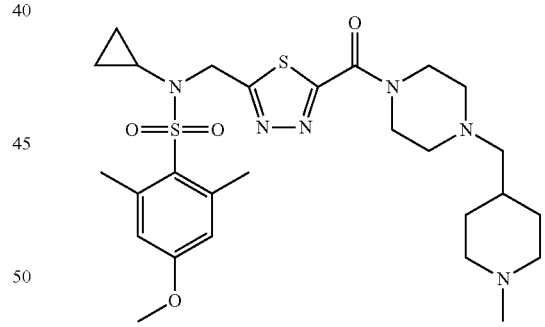

N-Cyclopropyl-4-methoxy-2,6-dimethyl-N-{[5-({4-[(1-methylpiperidin-4-yl)methyl]piperazin-1-yl}carbonyl)-1,3,4-thiadiazol-2-yl]methyl}benzenesulfonamide Ex 335

The title compound was prepared according to general procedure AT using ethyl 5-({cyclopropyl[(4-methoxy-2,6-dimethylphenyl)sulfonyl]amino}methyl)-1,3,4-thiadiazole-2-carboxylate (30 mg, 0.07 mmol), 1-[(1-methylpiperidin-4-yl)methyl]piperazine (31 mg, 0.16 mmol) and trimethylaluminium (2 M in toluene, 0.07 mL) in DCE (5 mL). The crude product was purified using FCC, eluting with 95:4.5:0.5 DCM:MeOH:NH$_3$, to afford the title compound.

Yield: 17.0 mg, 42%.

LCMS Method C: rt 2.77 min, 100%; m/z 289.23 ([M+2H]$^{2+}$, 100%), 577.19 (MH$^+$, 24%)

$^1$H NMR (500 MHz, CD$_3$OD): δ ppm 6.79 (2H, s), 5.03 (2H, s), 4.13-4.20 (2H, m), 3.86 (3H, s), 3.80-3.84 (2H, m), 2.92 (2H, d, J=11.7 Hz), 2.61 (6H, s), 2.52-2.59 (5H, m), 2.31 (3H, s), 2.29 (2H, d, J=7.3 Hz), 2.08 (2H, t, J=11.1 Hz), 1.83 (2H, br. s.), 1.62 (1H, ddd, J 11.1, 7.3, 3.7 Hz), 1.22-1.34 (2H, m), 0.59-0.66 (2H, m), 0.29-0.35 (2H, m)

Potency: C

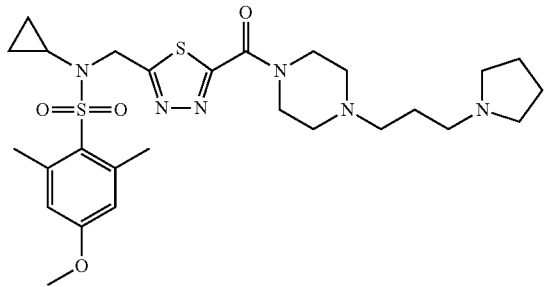

N-Cyclopropyl-4-methoxy-2,6-dimethyl-N-[(5-{[4-(3-pyrrolidin-1-ylpropyl)piperazin-1-yl]carbonyl}-1,3,4-thiadiazol-2-yl)methyl]benzenesulfonamide Ex 336

The title compound was prepared according to general procedure AT using ethyl 5-({cyclopropyl[(4-methoxy-2,6-dimethylphenyl)sulfonyl]amino}methyl)-1,3,4-thiadiazole-2-carboxylate (30 mg, 0.07 mmol), 1-[3-(pyrrolidin-1-yl)propyl]piperazine (31 mg, 0.16 mmol) and trimethylaluminium (2 M in toluene, 0.07 mL) in DCE (5 mL). The crude product was purified using FCC, eluting with 95:4.5:0.5 DCM:MeOH:NH$_3$, to afford the title compound.

Yield: 28.8 mg, 71%.

LCMS Method C: rt 2.90 min, 100%; m/z 289.21 ([M+2H]$^{2+}$, 100%), 577.25 (MH$^+$, 37%)

Potency: B

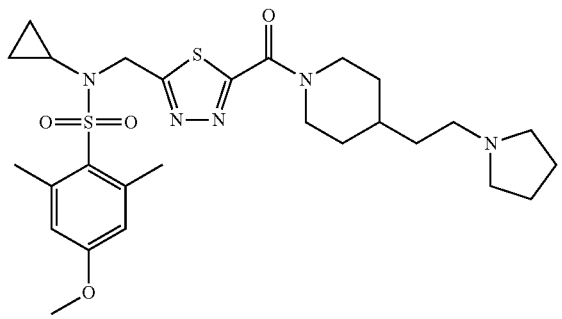 [SMILES: COc1cc(C)c(S(=O)(=O)N(Cc2nnc(C(=O)N3CCC(CCN4CCCC4)CC3)s2)C2CC2)c(C)c1]

N-Cyclopropyl-4-methoxy-2,6-dimethyl-N-[(5-{[4-(2-pyrrolidin-1-ylethyl)piperidin-1-yl]carbonyl}-1,3,4-thiadiazol-2-yl)methyl]benzenesulfonamide Ex 337

The title compound was prepared according to general procedure AT using ethyl 5-({cyclopropyl[(4-methoxy-2,6-dimethylphenyl)sulfonyl]amino}methyl)-1,3,4-thiadiazole-2-carboxylate (30 mg, 0.07 mmol), 4-[2-(pyrrolidin-1-yl)ethyl]piperidine (29 mg, 0.16 mmol) and trimethylaluminium (2 M in toluene, 0.07 mL) in DCE (5 mL). The crude product was purified using FCC, eluting with 95:4.5:0.5 DCM:MeOH:NH$_3$, to afford the title compound.

Yield: 30.6 mg, 78%.

LCMS Method C: rt 3.37 min, 98%; m/z 562.25 (MH$^+$, 100%)

Potency: C

Scheme 14 describes the general synthesis of triazole derivative.

(R$^1$=Me; R$^{1a}$=R$^{1b}$=H; X$^1$=X$^2$=X$^3$=N)

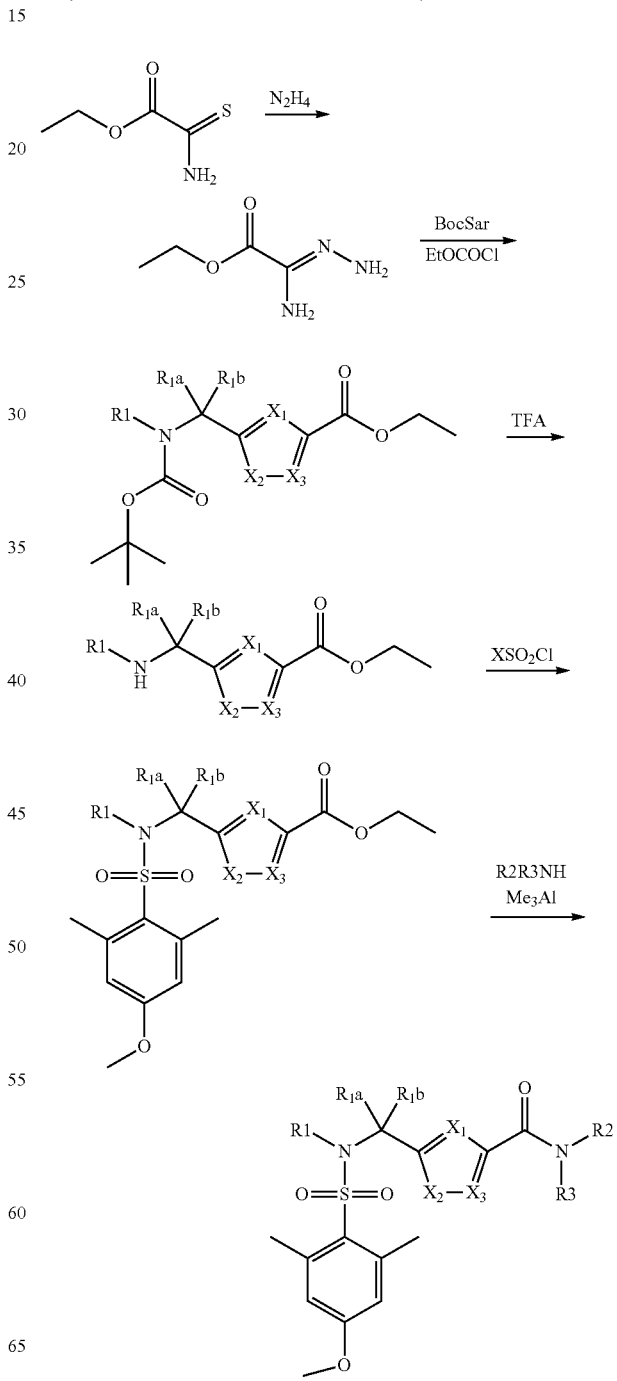

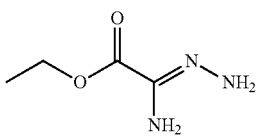

Ethyl (2Z)-amino(hydrazinylidene)ethanoate

Int 301

Ethyl thiooxamate (300 mg, 2.25 mmol) was stirred in anhydrous EtOH (2 mL) under N₂ at ambient temperature and hydrazine (1 M in anhydrous THF, 2.25 mL) was added dropwise. The reaction was stirred at ambient temperature for 2 h, then concentrated in vacuo to afford the title compound as a yellow solid, which was used without further purification.

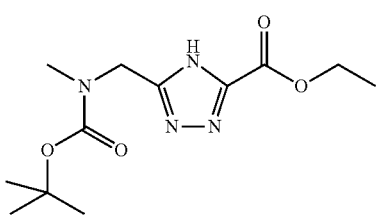 [SMILES: CCOC(=O)c1nnc(CN(C)C(=O)OC(C)(C)C)[nH]1]

Ethyl 5-{[(tert-butoxycarbonyl)(methyl)amino]methyl}-4H-1,2,4-triazole-3-carboxylate Int 302

Boc sarcosine (300 mg, 1.58 mmol) was stirred in anhydrous THF (3 mL) under N₂ and the slurry was cooled to −5° C. Ethyl chloroformate (0.24 mL, 2.51 mmol) was added dropwise, followed by TEA (0.296 mL, 2.12 mmol). The mixture was allowed to warm to ambient temperature over 1 h, then filtered to remove a white precipitate of TEA hydrochloride. To the filtrate was added ethyl (2Z)-amino(hydrazinylidene)ethanoate (1.69 mmol) as a solution in anhydrous THF (8 mL) and the reaction was stirred at ambient temperature for 18 h, then concentrated in vacuo. The residue was stirred in p-xylene (10 mL) at 140° C. for 4 h, then concentrated in vacuo and the crude product purified by FCC, eluting with 25% EtOAc in heptane, to afford the title compound as an opaque oil that solidified on standing.

Yield: 273 mg, 57%.

¹H NMR (500 MHz, CD₃OD): δ ppm 4.60 (2H, s), 4.45 (2H, q, J=7.1 Hz), 3.01 (3H, br. s.), 1.33-1.56 (12H, m)

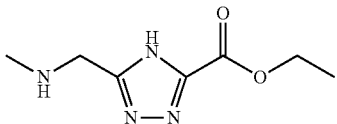

Ethyl 5-[(methylamino)methyl]-4H-1,2,4-triazole-3-carboxylate

Int 303

The title compound was prepared according to general procedure AN using ethyl 5-{[(tert-butoxycarbonyl)(methyl)amino]methyl}-4H-1,2,4-triazole-3-carboxylate (273 mg, 0.93 mmol), TFA (2.2 mL, 28.56 mmol) and DCM (5 mL). The crude product was used without further purification.

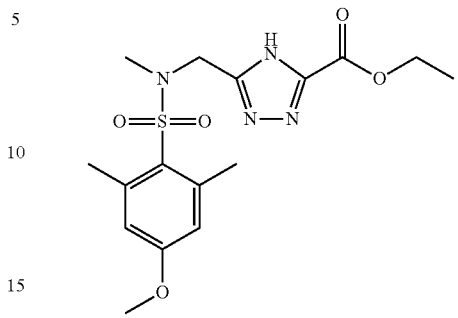

Ethyl 5-({[(4-methoxy-2,6-dimethylphenyl)sulfonyl](methyl)amino}methyl)-4H-1,2,4-triazole-3-carboxylate Int 304

Ethyl 5-[(methylamino)methyl]-4H-1,2,4-triazole-3-carboxylate (0.32 mmol) was stirred in DCM (3 mL) at ambient temperature and 4-methoxy-2,6-dimethylbenzenesulfonyl chloride (75 mg, 0.32 mmol) was added as a solution in DCM (2 mL). TEA (0.134 mL, 0.96 mmol) was then added and the reaction was stirred at ambient temperature for 1 h, then partitioned between saturated aqueous NaHCO₃ (10 mL) and DCM (3×10 mL). The combined organic extracts were dried over MgSO₄ and concentrated in vacuo. The crude product was purified using FCC, eluting with 20% EtOAc in heptane, to afford the title compound.

Yield: 33 mg, 27%.

LCMS Method A: rt 1.26 min, 69%; m/z 405.00 (MNa⁺, 100%)

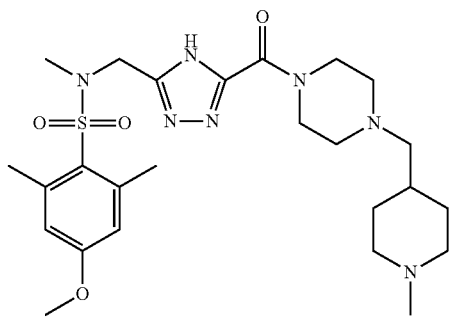 [SMILES: COc1cc(C)c(S(=O)(=O)N(C)Cc2nnc(C(=O)N3CCN(CC4CCN(C)CC4)CC3)[nH]2)c(C)c1]

4-Methoxy-N,2,6-trimethyl-N-{[5-({4-[(1-methylpiperidin-4-yl)methyl]piperazin-1-yl}carbonyl)-4H-1,2,4-triazol-3-yl]methyl}benzenesulfonamide Ex 338

The title compound was prepared according to general procedure AT using ethyl 5-({[(4-methoxy-2,6-dimethylphenyl)sulfonyl](methyl)amino}methyl)-4H-1,2,4-triazole-3-carboxylate (30 mg, 0.08 mmol), 1-[(1-methylpiperidin-4-yl)methyl]piperazine (31 mg, 0.16 mmol) and trimethylaluminium (2 M in toluene, 0.08 mL) in DCE (5 mL). A portion of the crude product was purified using prep method B.

LCMS Method C: rt 2.42 min, 100%; m/z 267.73 ([M+2H]$^{2+}$, 100%), 534.39 (MH$^+$, 12%)

$^1$H NMR (500 MHz, CD$_3$OD): δ ppm 6.76 (2H, s), 4.43 (2H, br. s.), 3.94 (2H, br. s.), 3.85 (3H, s), 3.74-3.81 (2H, m), 3.00 (2H, br. s.), 2.76 (3H, br. s.), 2.63 (6H, s), 2.52 (2H, br. s.), 2.44-2.50 (2H, m), 2.39 (3H, s), 2.28 (2H, d, J=7.2 Hz), 2.18-2.26 (2H, m), 1.87 (2H, br. s.), 1.66 (1H, br. s.), 1.31 (2H, br. s.)

Potency: A

The invention claimed is:

1. A compound of formula (I)

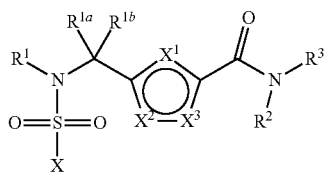

or a pharmaceutically acceptable salt, or prodrug thereof, wherein

X is phenyl, is substituted with R$^4$ and is optionally substituted with one or more R$^5$, which are the same or different;

R$^4$ and R$^5$ are independently selected from the group consisting of halogen, CN, C(O)OR$^6$, OR$^6$, C(O)N(R$^6$R$^{6a}$), S(O)$_2$N(R$^6$R$^{6a}$), S(O)N(R$^6$R$^{6a}$), S(O)$_2$R$^6$, N(R$^6$)S(O)$_2$N(R$^{6a}$R$^{6b}$), SR$^6$, N(R$^6$R$^{6a}$), NO$_2$, OC(O)R$^6$, N(R$^6$)C(O)R$^{6a}$, N(R$^6$)S(O)$_2$R$^{6a}$, N(R$^6$)S(O)R$^{6a}$, N(R$^6$)C(O)N(R$^{6a}$R$^{6b}$), N(R$^6$)C(O)OR$^{6a}$, OC(O)N(R$^6$R$^{6a}$), C(O)R$^6$, C$_{1-6}$ alkyl, C$_{2-6}$ alkenyl, C$_{2-6}$ alkynyl, and T, wherein C$_{1-6}$ alkyl, C$_{2-6}$ alkenyl, and C$_{2-6}$ alkynyl are optionally substituted with one or more R$^7$, which are the same or different; Optionally, R$^4$ and R$^5$ or two adjacent R$^5$ are joined together with the atoms to which they are attached to form benzo, or a 5- or 6-membered aromatic heterocyle, wherein benzo and the 5- or 6-membered aromatic heterocyle are optionally substituted with one or more R$^8$, which are the same or different;

R$^8$ is halogen, CN, C(O)OR$^6$, OR$^6$, C(O)N(R$^6$R$^{6a}$), S(O)$_2$N(R$^6$R$^{6a}$), S(O)N(R$^6$R$^{6a}$), S(O)$_2$R$^6$, N(R$^6$)S(O)$_2$N(R$^{6a}$R$^{6b}$), SR$^6$, N(R$^6$R$^{6a}$), NO$_2$, OC(O)R$^6$, N(R$^6$)C(O)R$^{6a}$, N(R$^6$)S(O)$_2$R$^{6a}$; N(R$^6$)S(O)R$^{6a}$, N(R$^6$)C(O)N(R$^{6a}$R$^{6b}$), N(R$^6$)C(O)OR$^{6a}$, OC(O)N(R$^6$R$^{6a}$), C(O)R$^6$, C$_{1-6}$ alkyl, C$_{2-6}$ alkenyl, C$_{2-6}$ alkynyl, or T, wherein C$_{1-6}$ alkyl, C$_{2-6}$ alkenyl, and C$_{2-6}$ alkynyl are optionally substituted with one or more R$^7$, which are the same or different;

R$^6$, R$^{6a}$, R$^{6b}$ are independently selected from the group consisting of H, T, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are optionally substituted with one or more R$^9$, which are the same or different;

R$^7$, R$^9$ are independently selected from the group consisting of halogen, C(O)R$^{10}$, CN, C(O)OR$^{10}$, OR$^{10}$, C(O)N(R$^{10}$R$^{10a}$), S(O)$_2$N(R$^{10}$R$^{10a}$), S(O)N(R$^{10}$R$^{10a}$), S(O)$_2$R$^{10}$, N(R$^{10}$)S(O)$_2$N(R$^{10a}$R$^{10b}$), SR$^{10}$, N(R$^{10}$R$^{10a}$), NO$_2$, OC(O)R$^{10}$, N(R$^{10}$)C(O)R$^{10a}$, N(R$^{10}$)S(O)$_2$R$^{10a}$, N(R$^{10}$)S(O)R$^{10a}$, N(R$^{10}$)C(O)N(R$^{10a}$R$^{10b}$), N(R$^{10}$)C(O)OR$^{10a}$, OC(O)N(R$^{10}$R$^{10a}$), and T$^1$;

R$^{10}$, R$^{10a}$, R$^{10b}$ are independently selected from the group consisting of H, T$^1$, C$_{1-6}$ alkyl, C$_{2-6}$ alkenyl, and C$_{2-6}$ alkynyl, wherein C$_{1-6}$ alkyl, C$_{2-6}$ alkenyl; and C$_{2-6}$ alkynyl are optionally substituted with one or more R$^{11}$, which are the same or different;

R$^{11}$ is halogen, C(O)R$^{12}$, CN, C(O)OR$^{12}$, OR$^{12}$, C(O)N(R$^{12}$R$^{12a}$), S(O)$_2$N(R$^{12}$R$^{12a}$), S(O)N(R$^{12}$R$^{12a}$), S(O)$_2$R$^{12}$, N(R$^{12}$)S(O)$_2$N(R$^{12a}$R$^{12b}$), SR$^{12}$, N(R$^{12}$R$^{12a}$), NO$_2$, OC(O)R$^{12}$, N(R$^{12}$)C(O)R$^{12a}$, N(R$^{12}$)S(O)$_2$R$^{12a}$, N(R$^{12}$)S(O)R$^{12a}$, N(R$^{12}$)C(O)N(R$^{12a}$R$^{12b}$), N(R$^{12}$)C(O)OR$^{12a}$, or OC(O)N(R$^{12}$R$^{12a}$);

R$^{12}$, R$^{12a}$, R$^{12b}$ are independently selected from the group consisting of H, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are optionally substituted with one or more halogen, which are the same or different;

T, T$^1$ are independently selected from the group consisting of phenyl, naphthyl, indenyl, indanyl, tetralinyl, decalinyl, adamantyl, C$_{3-7}$ cycloalkyl, 4 to 7 membered heterocyclyl, and 8 to 11 membered heterobicyclyl, wherein T, T$^1$ are optionally substituted with one or more R$^{13}$, which are the same or different;

R$^{13}$ is halogen, CN, C(O)R$^{14}$, COOR$^{14}$, OR$^{14}$, C(O)N(R$^{14}$R$^{14a}$), S(O)$_2$N(R$^{14}$R$^{14a}$), S(O)N(R$^{14}$R$^{14a}$), S(O)$_2$R$^{14}$, N(R$^{14}$)S(O)$_2$N(R$^{14a}$R$^{14b}$), SR$^{14}$, N(R$^{14}$R$^{14a}$), NO$_2$, OC(O)R$^{14}$, N(R$^{14}$)C(O)R$^{14a}$, N(R$^{14}$)S(O)$_2$R$^{14a}$, N(R$^{14}$)S(O)R$^{14a}$, N(R$^{14}$)C(O)N(R$^{14a}$R$^{14b}$), N(R$^{14}$)C(O)OR$^{14a}$, OC(O)N(R$^{14}$R$^{14a}$), oxo (=O), where the ring is at least partially saturated, C$_{1-6}$ alkyl, C$_{2-6}$ alkenyl, or C$_{2-6}$ alkynyl, wherein C$_{1-6}$ alkyl, C$_{2-6}$ alkenyl, and C$_{2-6}$ alkynyl are optionally substituted with one or more halogen, which are the same or different;

R$^{14}$, R$^{14a}$, R$^{14b}$ are independently selected from the group consisting of H, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are optionally substituted with one or more halogen, which are the same or different;

R$^1$ is H and C$_{1-8}$ alkyl wherein C$_{1-8}$ alkyl is optionally substituted with one or more R$^{15}$, which are the same or different;

R$^{15}$ is halogen, C(O)R$^{16}$, CN, C(O)OR$^{16}$, OR$^{16}$, C(O)N(R$^{16}$R$^{16a}$), S(O)$_2$N(R$^{16}$R$^{16a}$), S(O)N(R$^{16}$R$^{16a}$), S(O)$_2$R$^{16}$, N(R$^{16}$)S(O)$_2$N(R$^{16a}$R$^{16b}$), SR$^{16}$, N(R$^{16}$R$^{16a}$), NO$_2$, OC(O)R$^{16}$, N(R$^{16}$)C(O)R$^{16a}$, N(R$^{16}$)S(O)$_2$R$^{16a}$, N(R$^{16}$)S(O)R$^{16a}$, N(R$^{16}$)C(O)N(R$^{16a}$R$^{16b}$), N(R$^{16}$)C(O)OR$^{16a}$, OC(O)N(R$^{16}$R$^{16a}$), or cyclopropyl;

R$^{16}$, R$^{16a}$, R$^{16b}$ are independently selected from the group consisting of H, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are optionally substituted with one or more halogen, which are the same or different;

R$^{1a}$, R$^{1b}$ are independently selected from the group consisting of H; C$_{1-4}$ alkyl, wherein C$_{1-4}$ alkyl is optionally substituted with one or more halogen, which are the same or different;

X$^1$ is O or CR$^{1c}$, X$^2$ is O, and X$^3$ is CR$^{1c}$;

R$^{1c}$ is H; or CH$_3$;

R$^2$, R$^3$ are joined to form, together with the nitrogen atom to which they are attached, a ring, wherein the ring is a saturated 4 to 7 membered heterocycle; wherein the ring contains said nitrogen atom and optionally one or more further heteroatoms, which are the same or different, and, wherein the ring is optionally substituted with one or more R$^{20}$, which are the same or different;

R$^{20}$ is selected from the group consisting of halogen, CN, C(O)OR$^{23}$, OR$^{23}$, C(O)N(R$^{23}$R$^{23a}$), C(NR$^{23b}$)N(R$^{23}$R$^{23a}$), C(NR$^{23b}$)N(R$^{23}$)OR$^{23a}$, S(O)$_2$N(R$^{23}$R$^{23a}$), S(O)N(R$^{23}$R$^{23a}$), S(O)$_2$R$^{23}$, N(R$^{23}$)S(O)$_2$N(R$^{23a}$R$^{23b}$), SR$^{23}$, N(R$^{23}$R$^{23a}$), NO$_2$, OC(O)R$^{23}$, N(R$^{23}$)C(O)R$^{23a}$, N(R$^{23}$)S(O)$_2$R$^{23a}$, N(R$^{23}$)S(O)R$^{23a}$, N(R$^{23}$)C(O)

$NR^{23a}R^{23b}$), $N(R^{23})C(NR^{23c})N(R^{23a}R^{23b})$, $N(R^{23})C(O)OR^{23a}$, $OC(O)N(R^{23}R^{23a})$, oxo (=O), where the ring is at least partially saturated, $C(O)R^{23}$, $C_{1-10}$ alkyl, $C_{2-10}$ alkenyl, $C_{2-10}$ alkynyl, and $T^4$, wherein $C_{1-10}$ alkyl, $C_{2-10}$ alkenyl, and $C_{2-10}$ alkynyl are optionally substituted with one or more $R^{24}$, which are the same or different;

$R^{23}$, $R^{23a}$, $R^{23b}$, $R^{23c}$ are independently selected from the group consisting of H, $T^4$, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more $R^{25}$, which are the same or different;

$R^{24}$, $R^{25}$ are independently selected from the group consisting of halogen, CN, $C(O)R^{26}$, $C(O)OR^{26}$, $OR^{26}$, $C(O)R^{26}$, $C(O)N(R^{26}R^{26a})$, $S(O)_2N(R^{26}R^{26a})$, $S(O)N(R^{26}R^{26a})$, $S(O)_2R^{26}$, $N(R^{26})S(O)_2N(R^{26a}R^{26b})$, $SR^{26}$, $N(R^{26}R^{26a})$, $OC(O)R^{26}$, $N(R^{26})C(O)R^{26a}$, $N(R^{26})SO_2R^{26a}$, $N(R^{26})S(O)R^{26a}$, $N(R^{26})C(O)N(R^{26a}R^{26b})$, $N(R^{26})C(O)OR^{26a}$, $OC(O)N(R^{26}R^{26a})$, $C_{1-6}$ alkyl, $C_{2-6}$ alkenyl, $C_{2-6}$ alkynyl and $T^4$, wherein $C_{1-6}$ alkyl, $C_{2-6}$ alkenyl, and $C_{2-6}$ alkynyl are optionally substituted with one or more $R^{27}$, which are the same or different;

$R^{26}$, $R^{26a}$, $R^{26b}$ are independently selected from the group consisting of H, $T^4$, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more $R^{28}$, which are the same or different;

$R^{27}$, $R^{28}$ are independently selected from the group consisting of halogen, CN, $C(O)OR^{29}$, $OR^{29}$, $C(O)R^{29}$, $C(O)N(R^{29}R^{29a})$, $S(O)_2N(R^{29}R^{29a})$, $S(O)N(R^{29}R^{29a})$, $S(O)_2R^{29}$, $N(R^{29})S(O)_2N(R^{29a}R^{29b})$, $SR^{29}$, $N(R^{29}R^{29a})$, $NO_2$, $OC(O)R^{29}$, $N(R^{29})C(O)R^{29a}$, $N(R^{29})SO_2R^{29a}$, $N(R^{29})S(O)R^{29a}$, $N(R^{29})C(O)N(R^{29a}R^{29b})$, $N(R^{29})C(O)OR^{29a}$, $OC(O)N(R^{29}R^{29a})$, $C_{1-6}$ alkyl, $C_{2-6}$ alkenyl, $C_{2-6}$ alkynyl, and $T^4$, wherein $C_{1-6}$ alkyl, $C_{2-6}$ alkenyl, and $C_{2-6}$ alkynyl are optionally substituted with one or more $R^{30}$, which are the same or different;

$R^{29}$, $R^{29a}$, $R^{29b}$ are independently selected from the group consisting of H, $C_{1-6}$ alkyl, $C_{2-6}$ alkenyl, $C_{2-6}$ alkynyl, and $T^4$, wherein $C_{1-6}$ alkyl, $C_{2-6}$ alkenyl, and $C_{2-6}$ alkynyl are optionally substituted with one or more $R^{31}$, which are the same or different;

$T^4$ is phenyl, naphthyl, indenyl, indanyl, tetralinyl, decalinyl, adamantyl, $C_{3-7}$ cycloalkyl, 4 to 7 membered heterocyclyl, or 8 to 11 membered heterobicyclyl, wherein $T^4$ is optionally substituted with one or more $R^{32}$, which are the same or different;

$R^{32}$ is halogen, CN, $C(O)OR^{33}$, $OR^{33}$, $C(O)N(R^{33}R^{33a})$, $C(NR^{33b})N(R^{33}R^{33a})$, $C(NR^{33b})N(R^{33})OR^{33a}$, $S(O)_2N(R^{33}R^{33a})$, $S(O)N(R^{33}R^{33a})$, $S(O)_2R^{33}$, $N(R^{33})S(O)_2N(R^{33a}R^{33b})$, $SR^{33}$, $N(R^{33}R^{33a})$, $NO_2$, $OC(O)R^{33}$, $N(R^{33})C(O)R^{33a}$, $N(R^{33})S(O)_2R^{33a}$, $N(R^{33})S(O)R^{33a}$, $N(R^{33})C(O)N(R^{33a}R^{33b})$, $N(R^{33})C(NR^{33c})N(R^{33a}R^{33b})$, $N(R^{33})C(O)OR^{33a}$, $OC(O)N(R^{33}R^{33a})$, oxo (=O), where the ring is at least partially saturated, $C(O)R^{33}$, $T^5$, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more $R^{34}$, which are the same or different;

$R^{33}$, $R^{33a}$, $R^{33b}$, $R^{33c}$ are independently selected from the group consisting of H, $T^5$, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same or different;

$R^{30}$; $R^{31}$; $R^{34}$ are independently selected from the group consisting of halogen, CN, $C(O)OR^{35}$, $OR^{35}$, $C(O)R^{35}$, $C(O)N(R^{35}R^{35a})$, $S(O)_2N(R^{35}R^{35a})$, $S(O)N(R^{35}R^{35a})$, $S(O)_2R^{35}$, $N(R^{35})S(O)_2N(R^{35a}R^{35b})$, $SR^{35}$, $N(R^{35}R^{35a})$, $NO_2$, $OC(O)R^{35}$, $N(R^{35})C(O)R^{35a}$, $N(R^{35})SO_2R^{35a}$, $N(R^{35})S(O)R^{35a}$, $N(R^{35})C(O)N(R^{35a}R^{35b})$, $N(R^{35})C(O)OR^{35a}$, $OC(O)N(R^{35}R^{35a})$, $T^5$, $C_{1-6}$ alkyl, $C_{2-6}$ alkenyl, $C_{2-6}$ alkynyl, wherein $C_{1-6}$ alkyl, $C_{2-6}$ alkenyl, and $C_{2-6}$ alkynyl are optionally substituted with one or more halogen, which are the same of different;

$R^{35}$, $R^{35a}$, $R^{35b}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same of different;

$T^5$ is phenyl, $C_{3-7}$ cycloalkyl, or 4 to 7 membered heterocyclyl, wherein $T^5$ is optionally substituted with one or more $R^{36}$, which are the same or different;

$R^{36}$ is independently selected from the group consisting of halogen, CN, $C(O)OR^{37}$, $OR^{37}$, $C(O)N(R^{37}R^{37a})$, $C(NR^{37b})N(R^{37}R^{37a})$, $C(NR^{37b})N(R^{37})OR^{37a}$, $S(O)_2N(R^{37}R^{37a})$, $S(O)N(R^{37}R^{37a})$, $S(O)_2R^{37}$, $N(R^{37})S(O)_2N(R^{37a}R^{37b})$, $SR^{37}$, $N(R^{37}R^{37a})$, $NO_2$, $OC(O)R^{37}$, $N(R^{37})C(O)R^{37a}$, $N(R^{37})S(O)_2R^{37a}$, $N(R^{37})S(O)R^{37a}$, $N(R^{37})C(O)N(R^{37a}R^{37b})$, $N(R^{37})C(NR^{37c})N(R^{37a}R^{37b})$, $N(R^{37})C(O)OR^{37a}$, $OC(O)N(R^{37}R^{37a})$, oxo (=O), where the ring is at least partially saturated, $C(O)R^{37}$, $C_{1-6}$ alkyl, $C_{2-6}$ alkenyl, or $C_{2-6}$ alkynyl, wherein $C_{1-6}$ alkyl, $C_{2-6}$ alkenyl, and $C_{2-6}$ alkynyl are optionally substituted with one or more halogen, which are the same or different; and $R^{37}$, $R^{37a}$, $R^{37b}$, $R^{37c}$ are independently selected from the group consisting of H, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are optionally substituted with one or more halogen, which are the same of different.

2. The compound of claim 1, wherein two adjacent $R^5$ are joined together with the atoms to which they are attached to form benzo and wherein benzo is optionally substituted with one or more $R^8$, which are the same or different.

3. The compound of claim 1, wherein X is substituted in 2-position relative to the sulfonamide group in formula (I) with $R^4$ and is optionally substituted with one or more $R^5$, which are the same or different.

4. The compound of claim 1, wherein $R^4$, $R^5$, $R^8$ are independently selected from the group consisting of $CH_3$; $CF_3$; $CH_2CH_3$; $CH_2OH$; $OCH_3$; Cl; Br; and phenyl.

5. The compound of claim 1, wherein $R^1$ is methyl; ethyl; isopropyl; or cyclopropylmethyl.

6. The compound of claim 1, wherein $R^{1a}$, $R^{1b}$ are independently selected from the group consisting of H; and methyl.

7. The compound of claim 1 of one of the formulae (Ia) or (Ie)

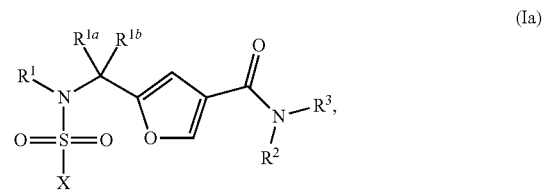

(Ia)

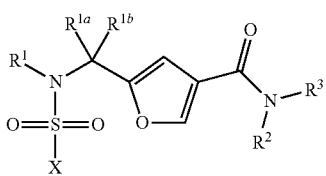

(Ie)

wherein X, $R^1$, $R^{1a}$, $R^{1b}$, $R^2$, $R^3$ have the meaning as indicated in claim 1.

8. The compound of claim 1, wherein $R^2$, $R^3$ are joined to form a ring selected from the group consisting of piperidine; piperazine; morpholine; pyrrolidine; and diazepane, wherein the ring is optionally substituted with one or more $R^{20}$, which are the same or different.

9. The compound of claim 1, wherein $R^{20}$ is selected from the group consisting of CN, C(O)N($R^{23}R^{23a}$), C($NR^{23b}$)N ($R^{23}R^{23a}$), C($NR^{23b}$)N($R^{23}$)O$R^{23a}$, N($R^{23}R^{23a}$), N($R^{23}$)C(O) N($R^{23a}R^{23b}$), C(O)$R^{23}$, N($R^{23}$)C($NR^{23c}$)N($R^{23a}R^{23b}$), $C_{1-6}$ alkyl, and $T^4$, wherein $C_{1-6}$ alkyl is optionally substituted with one or more $R^{24}$, which are the same or different.

10. The compound of claim 1, wherein one of $R^{23}$, $R^{23a}$, $R^{23b}$, $R^{23c}$ is $T^4$.

11. The compound of claim 1, wherein $R^{24}$ is $T^4$.

12. The compound of claim 1, wherein $T^4$ is selected from the group consisting of pyrrole, pyrrolidine, imidazole, 4,5-dihydroimidazole, oxazolidine, tetrahydrofuran, pyridine, piperidine, morpholine, pyrimidine, and 3,4,5,6-tetrahydropyrimidine, and wherein $T^4$ is optionally substituted with one or more $R^{32}$, which are the same or different.

13. The compound of claim 1, wherein $R^{32}$ is $C_{1-4}$ alkyl, oxo (=O), where the ring is at least partially saturated, $NH_2$, F, or C(O)$CF_3$.

14. A compound selected from the group consisting of
   4-Methoxy-N,2,6-trimethyl-N-[(4-{[4-(1-methylpiperidin-4-yl)piperazin-1-yl]carbonyl}furan-2-yl)methyl]benzenesulfonamide,
   4-bromo-2-ethyl-N-methyl-N-[(4-{[4-(3-pyrrolidin-1-yl-propyl)-1,4-diazepan-1-yl]carbonyl}furan-2-yl)methyl]benzenesulfonamide,
   2,6-dichloro-N-methyl-N-{[4-({4-[(1-methylpiperidin-4-yl)methyl]piperazin-1-yl}carbonyl)furan-2-yl]methyl}benzenesulfonamide,
   2,6-dichloro-N-methyl-N-[(4-{[4-(2-pyridin-4-ylethyl)piperazin-1-yl]carbonyl}furan-2-yl)methyl]benzenesulfonamide,
   N-{[4-({3-[4-(4,5-dihydro-1H-imidazol-2-yl)phenyl]piperidin-1-yl}carbonyl)furan-2-yl]methyl}-4-methoxy-N,2,6-trimethylbenzenesulfonamide,
   4-methoxy-N,2,6-trimethyl-N-{[4-({4-[(1-methylpiperidin-3-yl)methyl]piperazin-1-yl}carbonyl)furan-2-yl]methyl}benzenesulfonamide,
   4-methoxy-N,2,6-trimethyl-N-{[4-({4-[(1-methylpiperidin-4-yl)methyl]piperazin-1-yl}carbonyl)furan-2-yl]methyl}benzenesulfonamide,
   4-methoxy-N,2,6-trimethyl-N-[(4-{[4-(2-pyridin-4-ylethyl)piperazin-1-yl]carbonyl}furan-2-yl)methyl]benzenesulfonamide,
   4-methoxy-N,2,6-trimethyl-N-[(4-{[4-(pyridin-4-ylmethyl)piperazin-1-yl]carbonyl}furan-2-yl)methyl]benzenesulfonamide,
   4-methoxy-N,2,6-trimethyl-N-[(4-{[4-(2-morpholin-4-ylethyl)piperazin-1-yl]carbonyl}furan-2-yl)methyl]benzenesulfonamide,
   4-methoxy-N,2,6-trimethyl-N-[(4-{[4-(2-pyrrolidin-1-ylethyl)piperazin-1-yl]carbonyl}furan-2-yl)methyl]benzenesulfonamide,
   4-methoxy-N,2,6-trimethyl-N-[(4-{[4-(pyrrolidin-1-ylmethyl)piperidin-1-yl]carbonyl}furan-2-yl)methyl]benzenesulfonamide, and
   4-Methoxy-N,2,6-trimethyl-N-{[4-({3-[4-(pyrrolidin-1-ylmethyl)phenyl]piperidin-1-yl}carbonyl)furan-2-yl]methyl}benzenesulfonamide trifluoroacetamide.

15. A pharmaceutical composition comprising a compound or a pharmaceutically acceptable salt thereof according to claim 1 together with a pharmaceutically acceptable carrier, optionally in combination with one or more other pharmaceutical compositions.

16. A pharmaceutical composition comprising a compound or a pharmaceutically acceptable salt thereof according to claim 1 together with a pharmaceutically acceptable carrier and comprising one or more additional compounds or pharmaceutically acceptable salts thereof selected from the group consisting of compounds according to claim 1 and not being the first compound; or other Bradykinin B1 antagonists.

17. A method for the preparation of a compound according to claim 1, comprising the step of
   reacting a compound of formula (II)

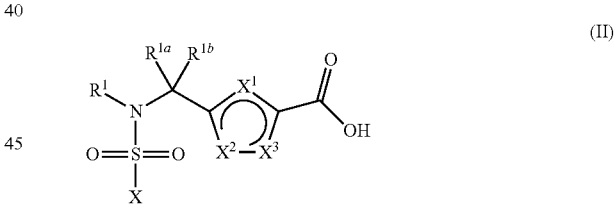

(II)

with a compound of formula HN($R^2$)$R^3$ to yield a compound of formula (I).

* * * * *